US012599593B2

(12) United States Patent
Saha et al.

(10) Patent No.: US 12,599,593 B2
(45) Date of Patent: Apr. 14, 2026

(54) METHODS AND COMPOSITIONS FOR TREATING NON-ERK MAPK PATHWAY INHIBITOR-RESISTANT CANCERS

(71) Applicant: BIOMED VALLEY DISCOVERIES, INC., Kansas City, MO (US)

(72) Inventors: Saurabh Saha, Wellesley Hills, MA (US); Dean Welsch, Parkville, MO (US); Gary Decrescenzo, Parkville, MO (US); Jeffrey Roix, Boston, MA (US)

(73) Assignee: Biomed Valley Discoveries, Inc., Kansas City, MO (US)

( * ) Notice: Subject to any disclaimer, the term of this patent is extended or adjusted under 35 U.S.C. 154(b) by 1047 days.

(21) Appl. No.: 17/561,076

(22) Filed: Dec. 23, 2021

(65) Prior Publication Data

US 2022/0117950 A1 Apr. 21, 2022

Related U.S. Application Data

(63) Continuation of application No. 16/302,955, filed as application No. PCT/US2017/033843 on May 22, 2017, now Pat. No. 11,246,859, which is a continuation of application No. 15/161,137, filed on May 20, 2016, now abandoned, which is a continuation-in-part of application No. PCT/US2014/071749, filed on Dec. 19, 2014.

(60) Provisional application No. 61/919,551, filed on Dec. 20, 2013.

(51) Int. Cl.

| | |
|---|---|
| ***A61K 31/4439*** | (2006.01) |
| ***A61K 31/506*** | (2006.01) |
| ***A61K 31/519*** | (2006.01) |
| ***A61K 45/06*** | (2006.01) |
| ***C12Q 1/6886*** | (2018.01) |
| ***G01N 33/574*** | (2006.01) |

(52) U.S. Cl.

CPC ........ *A61K 31/4439* (2013.01); *A61K 31/506* (2013.01); *A61K 31/519* (2013.01); *A61K 45/06* (2013.01); *C12Q 1/6886* (2013.01); *G01N 33/57484* (2013.01); *C12Q 2600/106* (2013.01); *C12Q 2600/156* (2013.01)

(58) Field of Classification Search

CPC .............. A61K 31/4439; A61K 31/506; A61K 31/519; A61K 45/06; C12Q 1/6886; C12Q 2600/106; C12Q 2600/156; G01N 33/57484

USPC ........................................................ 514/264.1

See application file for complete search history.

(56) References Cited

U.S. PATENT DOCUMENTS

| | | | | |
|---|---|---|---|---|
| 9,670,177 | B2 * | 6/2017 | DeCrescenzo et al. | |
| 9,676,746 | B2 * | 6/2017 | DeCrescenzo et al. | |
| 9,951,041 | B2 * | 4/2018 | DeCrescenzo et al. | |
| 10,183,927 | B2 * | 1/2019 | DeCrescenzo et al. | |
| 10,881,646 | B2 * | 1/2021 | Saha | A61P 37/04 |
| 11,246,859 | B2 * | 2/2022 | Saha | A61P 43/00 |
| 2006/0106069 | A1 * | 5/2006 | Botella et al. | |
| 2009/0306020 | A1 | 12/2009 | Scheuring et al. | |
| 2021/0038587 | A1 * | 2/2021 | DeCrescenzo et al. | |

FOREIGN PATENT DOCUMENTS

| | | |
|---|---|---|
| JP | 2015-531763 A | 11/2015 |
| JP | 2016-509045 A | 3/2016 |
| JP | 2016-513097 A | 5/2016 |
| WO | 2015/095834 A1 | 6/2015 |
| WO | 2015095819 | 6/2015 |
| WO | 2015095833 | 6/2015 |
| WO | 2015095842 | 6/2015 |
| WO | 2016025649 | 2/2016 |

OTHER PUBLICATIONS

Marks et al.,"Novel MEK1 Mutation Identified by Mutational Analysis of Epidermal Growth Factor Receptor Signaling Pathway Genes in Lung Adenocarcinoma", Cancer Res. Jul. 15, 2008;68(14):5524-5528. doi: 10.1158/0008-5472.CAN-08-0099; (Year: 2008).*

Cagnol et al. "Oncogenic KRAS and BRAF Activation of the MEK/ERK Signaling Pathway Promotes Expression of Dual-Specificity Phosphatase 4 (DUSP4/MKP2) Resulting in Nuclear ERK1/2 Inhibition", Oncogene, Jan. 31, 2013;32(5):564-76. doi: 10.1038/onc.2012.88. Epub Mar. 19, 2012; (Year: 2013).*

Reinersman et al. "Frequency of EGFR and KRAS Mutations in Lung Adenocarcinomas in African-Americans", J Thorac Oncol. Jan. 2011;6(1):28-31. doi: 10.1097/JTO.0b013e3181fb4fe2. (Year: 2011).*

Morris et al. "Discovery of a novel ERK inhibitor with activity in models of acquired resistance to BRAF and MEK inhibitors", Cancer Discov., Jul. 3, 2013, vol. 3, No. 7, pp. 742-750 (Year: 2013).*

Jin et al., "Exploration of N-(2-aminoethyl)piperidine-4-carboxamide as a potential scaffold for development of VEGFR-2, ERK-2 and Abl-1 multikinase inhibitor", Bioorg Med Chem., Sep. 15, 2013, vol. 21, Issue No. 18, pp. 5694-5706. (Year: 2013).*

(Continued)

*Primary Examiner* — Jeffrey H Murray
*Assistant Examiner* — Grace Ching Hsu
(74) *Attorney, Agent, or Firm* — Bryan Cave Leighton Paisner LLP

(57) ABSTRACT

The present invention provides, inter alia, methods, pharmaceutical compositions, and kits for treating or ameliorating the effects of a cancer in a subject, which cancer is refractory or resistant to non-ERK MAPK pathway inhibitor therapy. Also provided are methods for identifying a subject having cancer who would benefit from therapy with an ERK inhibitor and methods for inhibiting phosphorylation of RSK in a cancer cell that is refractory or resistant to a non-ERK MAPK pathway inhibitor.

8 Claims, 145 Drawing Sheets

Specification includes a Sequence Listing.

(56) References Cited

OTHER PUBLICATIONS

Ivy et al., "Approaches to phase 1 clinical trial design focused on safety, efficiency, and selected patient populations: a report from the clinical trial design task force of the national cancer institute investigational drug steering committee", Clin Cancer Res, Mar. 15, 2010;16: p. 1726-1736. (Year: 2010).*
Marks et al., "Novel MEK1 Mutation Identified by Mutational Analysis of Epidermal Growth Factor Receptor Signaling Pathway Genes in Lung Adenocarcinoma", Cancer Res. Jul. 15, 2008;68(14):5524-5528. (Year: 2008).*
Cagnol et al. "Oncogenic KRAS and BRAF Activation of the MEK/ERK Signaling Pathway Promotes Expression of Dual-Specificity Phosphatase 4 (DUSP4/MKP2) Resulting in Nuclear ERK1/2 Inhibition", Oncogene, Jan. 31, 2013;32(5):564-76. doi: 10.1038/onc.2012.88. (Year: 2013).*
Reinersman et al. "Frequency of EGFR and KRAS Mutations in Lung Adenocarcinomas in African-Americans", J Thorac Oncol. Jan. 2011;6(1):28-31. (Year: 2011).*
Nazarian, R., et al. Melanomas acquire resistance to B-RAF (V600E) inhibition by RTK or N-RAS upregulation. Nature. 2010; 468(7326):973-977.
Nikolaev Si, et al. Exome sequencing identifies recurrent somatic MAP2K1 and MAP2K2 mutations in melanoma. Nat Genet 2012;44:133-9.
Nilsson, M., et al. Padlock probes: circularizing oligonucleotides for localized DNA detection. Science. 1994, No. 265, p. 2085-2088.
O'Hara AJ, et al. The genomics and genetics of endometrial cancer. Adv Genomics Genet 2012;2012:33-47.
Ojesina AI, et al. Landscape of genomic alterations in cervical carcinomas. Nature 2014;506:371-5.
Ota et al., Single nucleotide polymorphism detection by polymerase chain reaction-restriction fragment length polymorphism. Nat Protoc. 2007;2(11):2857-64.
Paraiso KHT, et al. Recovery of phospho-ERK activity allows melanoma cells to escape from BRAF inhibitor therapy. Br J Cancer 2010; 102:1724-30.
Patgiri A, et al. An orthosteric inhibitor of the Ras-Sos interaction. Nat Chem Biol. 2011;7:585-587.
Pennycuick A, et al. Routine EGFR and KRAS mutation analysis using COLD-PCR in non-small cell lung cancer. Int J Clin Pract 2012;66:748-52.
Porter SB, et al. Inhibition of the CaaX proteases Rce1p and Ste24p by peptidyl (acyloxy)methyl ketones. Biochim Biophys Acta. 2007;1773(6):853-862.
Poulikakos PI, et al. RAF inhibitor resistance is mediated by dimerization of aberrantly spliced BRAF(V600E). Nature 2011;480:387-90.
Queirolo P, et al. Combined BRAF and MEK inhibition for the treatment of BRAF-mutated metastatic melanoma. Cancer Treat Rev 2015;41:519-26.
Rasola A, et al. Activation of mitochondria! ERK protects cancer cells from death through inhibition of the permeability transition. Proc Natl Acad Sci U S A 2010;107:726-31.
Rizos H, et al. BRAF inhibitor resistance mechanisms in metastatic melanoma: spectrum and clinical impact. Clin Cancer Res 2014;20:1965-77.
Robert C, et al. Improved overall survival in melanoma with combined dabrafenib and trametinib. N Engl J Med 2015;372:30-9.
Romeo Y, et al. Regulation and function of the RSK family of protein kinases. Biochem J 2012;441:553-69.
Rudolph J, et al. Slow inhibition and conformation selective properties of extracellular signal-regulated kinase 1 and 2 inhibitors. Biochemistry 2015;54:22-31.
Shaul YD, et al. The MEK/ERK cascade: from signaling specificity to diverse functions. Biochim Biophys Acta 2007;1773:1213-26.
Shi H, et al. Acquired resistance and clonal evolution in melanoma during BRAF inhibitor therapy. Cancer Discov 2014;4:80-93.
Shima, F, et al. In silico discovery of small-molecule Ras inhibitors that display antitumor activity by blocking the Ras- effector interaction. PNAS. 2013;110(20):8182-7.
Schubbert S, et al. Hyperactive Ras in developmental disorders and cancer. Nat Rev Cancer 2007;7:295-308.
Sun C, et al. Intrinsic resistance to MEK inhibition in KRAS mutant lung and colon cancer through transcriptional induction of ERBB3. Cell Rep 2014;7:86-93.
Taflinar [package insert]. Research Triangle Park, NC: GlaxoSmithKline; 2014.
Trunzer K, et al. Pharmacodynamic effects and mechanisms of resistance to vemurafenib in patients with metastatic melanoma. J Clin Oncol 2013;31:1767-74.
Villanueva, J., et al. Acquired resistance to BRAF inhibitors mediated by a RAF kinase switch in melanoma can be overcome by cotargeting MEK and IGF-1R/PI3K. Cancer Cell. 2010;18:683-695.
Wagle, N., et al. Dissecting therapeutic resistance to RAF inhibition in melanoma by tumor genomic profiling. Journal of Clinical Oncology 2011;29(22):3085-3096.
Wagle N, et al. MAP kinase pathway alterations in BRAF-mutant melanoma patients with acquired resistance to combined RAF/MEK inhibition. Cancer Discov 2014;4:61-8.
Wainstein E, et al. The dynamic subcellular localization of ERK: mechanisms of translocation and role in various organelles. Curr Opin Cell Biol 2016;39:15-20.
Wang, H., et al. Identification of the MEK1(F129L) activating mutation as a potential mechanism of acquired resistance to MEK inhibition in human cancers carrying the B-RAF V600E mutation. Cancer Res (2011);71 (16):5535-45.
Yang W, et al. Genomics of Drug Sensitivity in Cancer (GDSC): a resource for therapeutic biomarker discovery in cancer cells. Nucleic Acids Res 2013;41:D955-D961.
Mekinist [package insert]. Research Triangle Park, NC: GlaxoSmithKline; 2014.
Yao Z, et al. BRAF Mutants Evade ERK-Dependent Feedback by Different Mechanisms that Determine Their Sensitivity to Pharmacologic Inhibition. Cancer Cell 2015;28:370-83.
Yohe S. Molecular genetic markers in acute myeloid leukemia. J Clin Med 2015;4:460-78.
Zelboraf [package insert]. South San Francisco, CA: Genentech USA, Inc.; 2015.
Fofaria, et al. "Overexpression of Mcl-1 confers resistance to BRAFV600E inhibitors alone and in combination with MEK1/2 inhibitors in melanoma," Oncotarget, Dec. 1, 2015 vol. 6, No. 38, pp. 40535-40556.
Li, et al. "First-in-class oral ERK 1/2 inhibitor Ulixertinib (BVD-523) in patients with advanced solid tumors: Final results of a phase 1 dose escalation and expansion study," Journal of Clinical Oncology, May 1, 2017 vol. 35, No. 15 pp. 2508-2508.
Morris et al. (Cancer Discov., Jul. 2013, vol. 3, No. 7, pp. 742-750).
Jin et al. (Bioorg Med Chem., Sep. 15, 2013, vol. 21, No. 18, pp. 5694-5706).
Ivy et al. (Clin Cancer Res 2010;16: p. 1726-1736).
Infante, "Dose escalation stage of a first-in-class phase I study of the novel oral ERK 1/2 kinase inhibitor BVD-523 (ulixertinib) in patients with advanced solid tumors", Journal of Clinical Oncology, vol. 33, Issue 15_suppl, Published online May 20, 2015, https://ascopubs.org/doi/10.1200/jco.2015.33.15_suppl.2506.
History of Changes for Study: NCT01781429, U.S. National Library of Medicine, ClinicalTrials.gov archive, submitted Jul. 31, 2014.
Botton, "Recurrent BRAF kinase fusions in melanocytic tumors offer an opportunity for targeted therapy", Pigment Cell Melanoma Res., Nov. 2013, vol. 26, No. 6.
Populo, "GNAQ and BRAF mutations show differential activation of gthe mTOR pathway in human transformed cells", Peer J (2013).
Notice of Reasons for Rejection, Japanese Patent Application No. 2018-560887, dated May 17, 2023.
International Search Report and ISR Written Opinion for PCT/US2014/071749.
PCT/US2017/033843 Search Report dated Aug. 4, 2017.

(56) References Cited

OTHER PUBLICATIONS

Sullivan, et al. "Activity of ERK 1/2 Inhibitor Ulixertinib (BVD-523) in Patients with BRAF and NRAS Mutant Melanoma," 2017 American Association of Cancer Research Annual Meeting Apr. 2, 2017 pp. 1-18.
Absalan, F et al. (2008). Molecular Inversion Probe Assay. Methods in Molecular Biology 396. Humana Press. pp. 315-330.
Ahronian LG, et al. Clinical acquired resistance to RAF inhibitor combinations in BRAF-mutant colorectal cancer through MAPK pathway alterations. Cancer Discov 2015;5:358-67.
Arcila ME, et al. MAP2K1 (MEK1) mutations define a distinct subset of lung adenocarcinoma associated with smoking. Clin Cancer Res 2015;21:1935-43.
Aronov AM, et al. Flipped out: structure-guided design of selective pyrazolylpyrrole ERK inhibitors. J Med Chem 2007;50:1280-7.
Aronov AM, et al. Structure-guided design of potent and selective pyrimidylpyrrole inhibitors of extracellular signal-conformational J Med Chem 2009;52:6362-8.
Arrington AK, et al. Prognostic and predictive roles of KRAS mutation in colorectal cancer. Int J Mol Sci 2012;13:12153-68.
Cargnello M, et al. Activation and function of the MAPKs and their substrates, the MAPK-activated protein kinases. Microbiol Mol Biol Rev 2011;75:50-83.
Carlino MS, et al. Preexisting MEK1P124 mutations diminish response to BRAF inhibitors in metastatic melanoma patients. Clin Cancer Res 2015;21:98-105.
Chapman PB, et al. Improved survival with vemurafenib in melanoma with BRAF V600E mutation. N Engl J Med 2011;364:2507-16.
Corcoran, R.B., et al. BRAF gene amplification can promote acquired resistance to MEK inhibitors in cancer cells harboring the BRAF V600E mutation. Sci Signal (2010);3(149): ra84.
Dai, B., et al. STAT3 mediates resistance to MEK inhibitor through microRNA miR-17. Cancer Res (2011);71:3658-3668.
Davies H, et al. Mutations of the BRAF gene in human cancer. Nature 2002;417:949-54.
Deschenes-Simard X, et al. ERKs in cancer: friends or foes? Cancer Res 2014;74:412-9.
Dobrzycka B, et al. Mutations in the KRAS gene in ovarian tumors. Folia Histochem Cytobiol 2009;47:221-4.
Emery, C.M., et al. MEK1 mutations confer resistance to MEK and B-RAF inhibition. PNAS (2009); 106(48):20411-6.
Fedorov O et al. Kinase inhibitor selectivity profiling using differential scanning fluorimetry. Methods Mol Biol 2012;795:109-18.
Fernandez-Medarde A, et al. Ras in cancer and developmental diseases. Genes Cancer 2011;2:344-58.
Flaherty KT, et al. Combined BRAF and MEK inhibition in melanoma with BRAF V600 mutations. N Engl J Med 2012;367:1694-703.
Goetz EM, et al. ERK mutations confer resistance to mitogen-activated protein kinase pathway inhibitors. Cancer Res 2014;74:7079-89.
Gollob JA, et al. Role of Raf kinase in cancer: therapeutic potential of targeting the Raf/MEK/ERK signal transduction pathway. Semin Oncol 2006;33:392-406.
Greger, J G., et al. Combinations of BRAF, MEK, and PI3K/mTOR inhibitors overcome acquired resistance to the BRAF inhibitor GSK2118436 dabrafenib, mediated by NRAS or MEK mutations. Molecular cancer therapeutics 11.4 (2012): 909-920.
Groenendijk FH, et al. Drug resistance to targeted therapies: deja vu all over again. Mol Oncol 2014;8:1067-83.
Hall RD, et al. BRAF mutations: signaling, epidemiology, and clinical experience in multiple malignancies. Cancer Control 2014;21:221-30.
Hardenbol, P., et al. Multiplexed genotyping with sequence-tagged molecular inversion probes. Nat. Biotechnol. 2003, No. 21 , p. 673-678.
Hatzivassiliou, G, et al. RAF inhibitors prime wild-type RAF to activate the MAPK pathway and enhance growth. Nature 464.7287 (2010): 431-435.
Hatzivassiliou G, et al. ERK inhibition overcomes acquired resistance to MEK inhibitors. Mol Cancer Ther 2012;11:1143-54.
Hauschild A, et al. Dabrafenib in BRAF-mutated metastatic melanoma: a multicentre, open-label, phase 3 randomised controlled trial. Lancet 2012;380:358-65.
Hayes TK, et al. Long-Term ERK Inhibition in KRAS-Mutant Pancreatic Cancer is Associated with MYC Degradation and Senescence-like Growth Suppression. Cancer Cell 2016;29:75-89.
Hezel AF, et al. Phase II study of gemcitabine, oxaliplatin in combination with panitumumab in KRAS wild-type unresectable or metastatic biliary tract and gallbladder cancer. Br J Cancer 2014;111:430-6.
Jha S, et al. Dissecting therapeutic resistance to ERK inhibition. Mol Cancer Ther 2016;15:548-59.
Johannessen, C.M., et al. COT/MAP3K8 drives resistance to RAF inhibition through MAP kinase pathway reactivation. Nature (2010);468(7326):968-972.
Johnson DB, et al. Acquired BRAF inhibitor resistance: A multicenter meta-analysis of the spectrum and frequencies, clinical behaviour, and phenotypic associations of resistance mechanisms. Eur J Cancer 2015;51:2792-9.
Kanda M, et al. Presence of somatic Mutations in most early-stage pancreatic intraepithelial neoplasia. Gastroenterology 2012;142:730-733.
Khattak M, et al. Targeted therapy and immunotherapy in advanced melanoma: an evolving paradigm. Ther Adv Med Oncol 2013;5:105-18.
King, Alastair J., et al. Dabrafenib; preclinical characterization, increased efficacy when combined with trametinib, while BRAF/MEK tool combination reduced skin lesions. PloS one 8.7 (2013): e67583.
Larkin J, et al. Combined vemurafenib and cobimetinib in BRAF-mutated melanoma. N Engl J Med 2014;371:1867-76.
Little, A.S., et al., Amplification of the Driving Oncogene, KRAS or BRAF, Underpins Acquired Resistance to MEK1/2 Inhibitors in Colorectal Cancer Cells. Sci. Signal. 4, ra17 (2011).
Liu, Dingxie, et al. BRAF V600E maintains proliferation, transformation, and tumorigenicity of BRAF-mutant papillary thyroid cancer cells. Journal of Clinical Endocrinology & Metabolism 92.6 (2007): 2264-2271.
Liu B, et al. Computational design, chemical synthesis, and biological evaluation of a novel ERK inhibitor (BL-E1001) with apoptosis-inducing mechanisms in breast cancer. Oncotarget 2015;6:6762-75.
Long GV, et al. Increased MAPK reactivation in early resistance to dabrafenib/trametinib combination therapy of BRAF-mutant metastatic melanoma. Nat Commun 2014;5:5694.
Long GV, et al. Dabrafenib and trametinib versus dabrafenib and placebo for Val600 BRAF-mutant melanoma: a multicentre, double-blind, phase 3 randomised controlled trial. Lancet 2015;386:444-51.
Manandhar SP, et al. Small-molecule inhibitors of the Rce1p CaaX protease. J Biomol Screen. 2007;12(7):983-993.
Massey PR, et al. Multiplying therapies and reducing toxicity in metastatic melanoma. Cancer Biol Ther 2015;16:1014-8.
Maurer, T, et al. Small-molecule ligands bind to a distinct pocket in Ras and inhibit SOS-mediated nucleotide exchange activity. PNAS. 2012;109(14):5299-304.
McArthur GA, et al. Safety and efficacy of vemurafenib in BRAFv600Eand BRAFv600K mutation-positive melanoma (BRIM-3): extended follow-up of a phase 3, randomised, open-label study. Lancet Oncol 2014;15:323-32.
Metzker, Emerging technologies in DNA sequencing Genome Res. 2005. 15: 1767-1776.
Mittal, Rohit et al. The acetyltransferase activity of the bacterial toxin YopJ of Yersinia is activated by eukaryotic host cell inositol hexakisphosphate. Journal of Biological Chemistry 285.26 (2010): 19927-19934.

* cited by examiner

FIG. 11A

% Inhibition:

| Trametinib (nM) \ Dabrafenib (μM) | 0 | 0.001 | 0.003 | 0.01 | 0.03 | 0.1 | 0.3 | 1 | 3 | 10 |
|---|---|---|---|---|---|---|---|---|---|---|
| 10000 | 85 | 85 | 85 | 85 | 84 | 84 | 86 | 93 | 95 | 83 |
| 1000 | 72 | 74 | 73 | 73 | 72 | 74 | 76 | 84 | 89 | 76 |
| 100 | 74 | 74 | 73 | 73 | 74 | 75 | 77 | 84 | 88 | 75 |
| 10 | 67 | 66 | 67 | 68 | 68 | 70 | 72 | 80 | 86 | 77 |
| 1 | 46 | 49 | 50 | 57 | 61 | 64 | 69 | 77 | 83 | 76 |
| 0.1 | -6 | -6 | 12 | 31 | 48 | 58 | 66 | 75 | 80 | 72 |
| 0.01 | 5 | -4 | 1 | 18 | 42 | 54 | 63 | 72 | 79 | 68 |
| 0 | 0 | -3 | -2 | 16 | 40 | 53 | 61 | 70 | 78 | 69 |

A375: Trametinib single agent (CellTiter-Glo)

$IC_{50} = 1nM$

Log [M] Trametinib

% of Control

A375: Dabrafenib single agent (CellTiter-Glo)

$IC_{50} = 28nM$

Log [M] Dabrafenib

% of Control

FIG. 13A

% Inhibition:

| BVD-0523 (µM) | | | | | | | | | | |
|---|---|---|---|---|---|---|---|---|---|---|
| 10 | 78 | 79 | 79 | 81 | 81 | 81 | 83 | 86 | 89 | 79 |
| 3 | 80 | 80 | 81 | 82 | 81 | 82 | 85 | 87 | 91 | 81 |
| 1 | 68 | 69 | 71 | 74 | 75 | 75 | 79 | 84 | 89 | 80 |
| 0.3 | 28 | 35 | 41 | 53 | 61 | 66 | 70 | 76 | 82 | 75 |
| 0.1 | 4 | 11 | 21 | 39 | 51 | 60 | 66 | 75 | 80 | 74 |
| 0.03 | -4 | -3 | 12 | 32 | 50 | 58 | 64 | 73 | 79 | 71 |
| 0.01 | -2 | -4 | 4 | 26 | 47 | 57 | 63 | 72 | 78 | 71 |
| 0 | 0 | -3 | -2 | 24 | 44 | 54 | 62 | 70 | 78 | 70 |
| | 0 | 0.001 | 0.003 | 0.01 | 0.03 | 0.1 | 0.3 | 1 | 3 | 10 |

Dabrafenib (µM)

Excess over Bliss:

| BVD-0523 (μM) \ Dabrafenib (μM) | 0 | 0.001 | 0.003 | 0.01 | 0.03 | 0.1 | 0.3 | 1 | 3 | 10 |
|---|---|---|---|---|---|---|---|---|---|---|
| 10 | 0.00 +/-0.00 | 0.01 +/-0.00 | 0.02 +/-0.01 | -0.02 +/-0.01 | -0.07 +/-0.01 | -0.09 +/-0.02 | -0.09 +/-0.01 | -0.07 +/-0.01 | -0.06 +/-0.01 | -0.14 +/-0.02 |
| 3 | 0.00 +/-0.00 | 0.01 +/-0.02 | 0.01 +/-0.01 | -0.03 +/-0.00 | -0.08 +/-0.02 | -0.09 +/-0.02 | -0.08 +/-0.01 | -0.07 +/-0.01 | -0.05 +/-0.01 | -0.13 +/-0.02 |
| 1 | 0.00 +/-0.00 | 0.02 +/-0.01 | 0.04 +/-0.01 | -0.02 +/-0.01 | -0.08 +/-0.02 | -0.11 +/-0.01 | -0.09 +/-0.01 | -0.07 +/-0.01 | -0.04 +/-0.01 | -0.11 +/-0.01 |
| 0.3 | 0.00 +/-0.00 | 0.10 +/-0.05 | 0.14 +/-0.04 | 0.07 +/-0.00 | 0.01 +/-0.02 | -0.01 +/-0.01 | -0.03 +/-0.01 | -0.02 +/-0.01 | -0.02 +/-0.01 | -0.03 +/-0.01 |
| 0.1 | 0.00 +/-0.00 | 0.10 +/-0.11 | 0.19 +/-0.13 | 0.12 +/-0.06 | 0.05 +/-0.06 | 0.04 +/-0.08 | 0.02 +/-0.03 | 0.03 +/-0.03 | 0.02 +/-0.01 | 0.03 +/-0.03 |
| 0.03 | 0.00 +/-0.00 | 0.04 +/-0.13 | 0.18 +/-0.14 | 0.11 +/-0.06 | 0.08 +/-0.06 | 0.06 +/-0.05 | 0.03 +/-0.02 | 0.04 +/-0.04 | 0.03 +/-0.01 | 0.02 +/-0.03 |
| 0.01 | 0.00 +/-0.00 | 0.01 +/-0.14 | 0.08 +/-0.13 | 0.04 +/-0.05 | 0.04 +/-0.05 | 0.03 +/-0.04 | 0.01 +/-0.03 | 0.02 +/-0.03 | 0.01 +/-0.01 | 0.01 +/-0.04 |
| 0 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 |

A375: BVD-0523 single agent (CellTiter-Glo)

IC$_{50}$ = 0.41 µM

% of Control

Log [M] BVD-0523

A375: Dabrafenib single agent

IC$_{50}$ = 21 nM

% of Control

Log [M] Dabrafenib

FIG. 14A

% Inhibition:

| BVD-0523 (μM) \ Trametinib (nM) | 0 | 0.0001 | 0.001 | 0.01 | 0.1 | 1 | 10 | 100 | 1000 | 10000 |
|---|---|---|---|---|---|---|---|---|---|---|
| 10 | 88 | 88 | 88 | 90 | 89 | 90 | 89 | 89 | 89 | 94 |
| 3 | 89 | 86 | 89 | 90 | 89 | 89 | 90 | 89 | 90 | 94 |
| 1 | 81 | 82 | 84 | 83 | 82 | 86 | 89 | 89 | 89 | 93 |
| 0.3 | 41 | 43 | 49 | 46 | 49 | 72 | 85 | 86 | 86 | 93 |
| 0.1 | -3 | -7 | 1 | -4 | 2 | 59 | 82 | 88 | 86 | 93 |
| 0.03 | -35 | -35 | -29 | -27 | -30 | 47 | 81 | 87 | 86 | 92 |
| 0.01 | -19 | -33 | -36 | -33 | -37 | 34 | 78 | 86 | 86 | 93 |
| 0 | 0 | -10 | -14 | -1 | -30 | 41 | 81 | 89 | 89 | 95 |

A375: BVD-0523 single agent (Alamar Blue)

$IC_{50} = 0.28\mu M$

Log [M] BVD-0523

% of Control

A375: Trametinib single agent (Alamar Blue)

$IC_{50} = 1nM$

Log [M] Trametinib

% of Control

FIG. 15A

% Inhibition:

| BVD-0523 (µM) \ Trametinib (nM) | 0 | 0.0001 | 0.001 | 0.01 | 0.1 | 1 | 10 | 100 | 1000 | 10000 |
|---|---|---|---|---|---|---|---|---|---|---|
| 10 | 74 | 75 | 75 | 77 | 75 | 76 | 75 | 75 | 74 | 86 |
| 3 | 77 | 72 | 78 | 80 | 78 | 78 | 80 | 79 | 79 | 88 |
| 1 | 64 | 65 | 66 | 67 | 62 | 70 | 76 | 74 | 77 | 87 |
| 0.3 | 18 | 20 | 23 | 20 | 21 | 48 | 69 | 74 | 70 | 87 |
| 0.1 | -9 | -12 | -11 | -11 | -11 | 28 | 62 | 71 | 70 | 86 |
| 0.03 | -21 | -22 | -20 | -17 | -26 | 13 | 58 | 69 | 68 | 84 |
| 0.01 | -4 | -15 | -12 | -15 | -23 | 7 | 57 | 71 | 67 | 85 |
| 0 | 0 | -5 | -12 | -4 | -26 | 4 | 57 | 70 | 69 | 86 |

FIG. 15B
1 (Synergy)
0 (Additivity)
-1 (Antagonism)

Excess over Bliss:

| BVD-0523 (μM) \ Trametinib (nM) | 0 | 0.0001 | 0.001 | 0.01 | 0.1 | 1 | 10 | 100 | 1000 | 10000 |
|---|---|---|---|---|---|---|---|---|---|---|
| 10 | 0.00 +/-0.00 | 0.02 +/-0.05 | 0.04 +/-0.03 | 0.04 +/-0.04 | 0.07 +/-0.03 | 0.01 +/-0.03 | -0.14 +/-0.02 | -0.17 +/-0.01 | -0.18 +/-0.03 | -0.11 +/-0.02 |
| 3 | 0.00 +/-0.00 | -0.04 +/-0.11 | 0.04 +/-0.02 | 0.03 +/-0.04 | 0.06 +/-0.02 | 0.00 +/-0.00 | -0.11 +/-0.01 | -0.15 +/-0.01 | -0.14 +/-0.03 | -0.09 +/-0.02 |
| 1 | 0.00 +/-0.00 | 0.03 +/-0.06 | 0.06 +/-0.02 | 0.04 +/-0.02 | 0.07 +/-0.02 | 0.04 +/-0.03 | -0.09 +/-0.01 | -0.15 +/-0.01 | -0.12 +/-0.01 | -0.08 +/-0.00 |
| 0.3 | 0.00 +/-0.00 | 0.05 +/-0.10 | 0.15 +/-0.09 | 0.05 +/-0.12 | 0.23 +/-0.11 | 0.27 +/-0.09 | 0.04 +/-0.03 | -0.02 +/-0.04 | -0.05 +/-0.03 | -0.02 +/-0.02 |
| 0.1 | 0.00 +/-0.00 | 0.02 +/-0.16 | 0.11 +/-0.08 | 0.01 +/-0.15 | 0.25 +/-0.09 | 0.33 +/-0.12 | 0.09 +/-0.04 | 0.04 +/-0.04 | 0.04 +/-0.07 | 0.01 +/-0.01 |
| 0.03 | 0.00 +/-0.00 | 0.05 +/-0.15 | 0.16 +/-0.13 | 0.08 +/-0.23 | 0.27 +/-0.22 | 0.30 +/-0.12 | 0.11 +/-0.05 | 0.06 +/-0.06 | 0.06 +/-0.08 | 0.00 +/-0.04 |
| 0.01 | 0.00 +/-0.00 | -0.06 +/-0.12 | 0.05 +/-0.12 | -0.07 +/-0.11 | 0.08 +/-0.09 | 0.07 +/-0.11 | 0.02 +/-0.05 | 0.02 +/-0.03 | 0.00 +/-0.07 | -0.01 +/-0.05 |
| 0 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 |

A375: BVD-0523 single agent (CellTiter-Glo)

$IC_{50} = 0.44\,\mu M$

% of Control

Log [M] BVD-0523

A375: Trametinib single agent (CellTiter-Glo)

$IC_{50} = 4\,nM$

% of Control

Log [M] Trametinib

FIG. 19

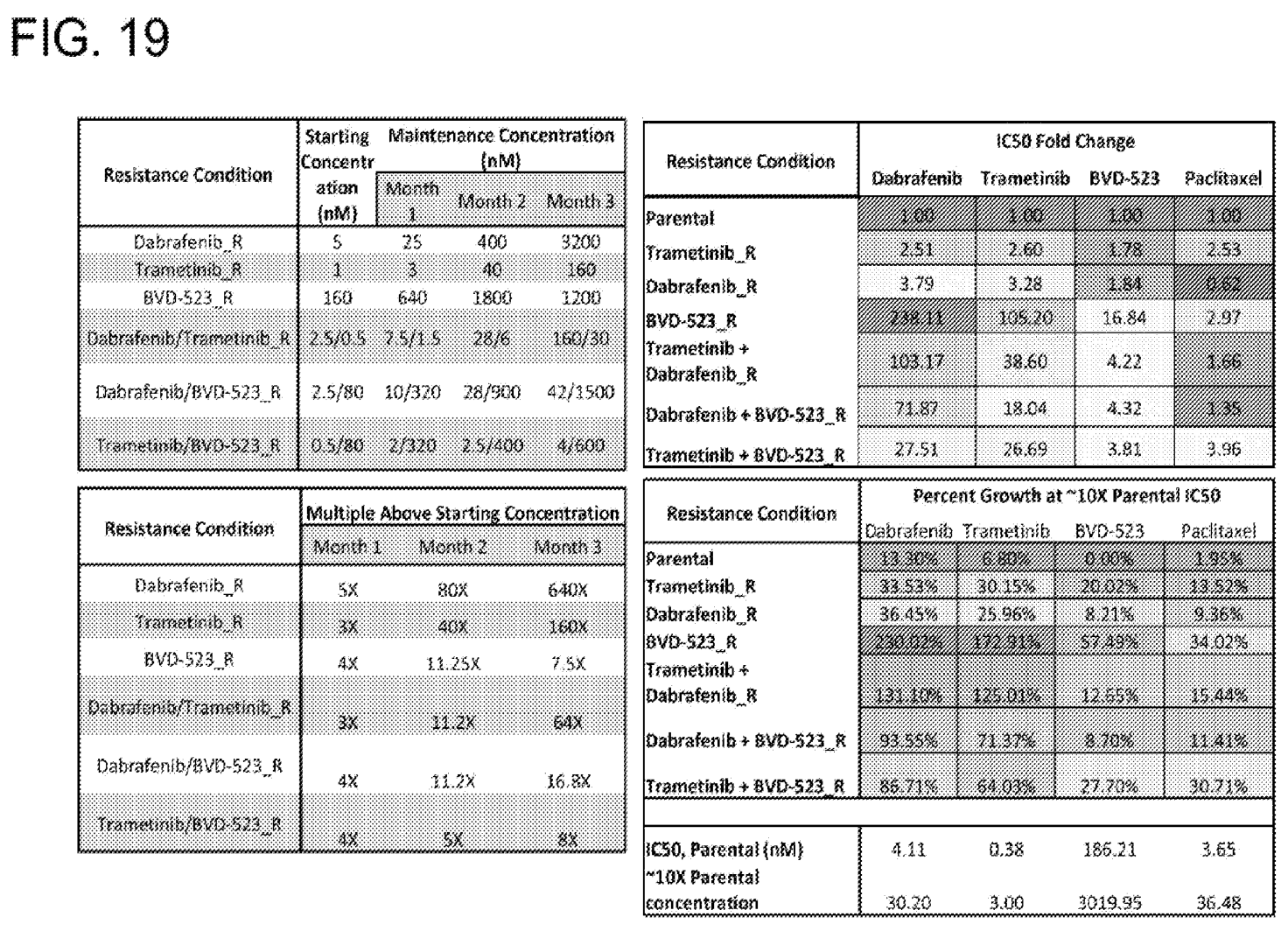

| Resistance Condition | Starting Concentration (nM) | Maintenance Concentration (nM) | | |
|---|---|---|---|---|
| | | Month 1 | Month 2 | Month 3 |
| Dabrafenib_R | 5 | 25 | 400 | 3200 |
| Trametinib_R | 1 | 3 | 40 | 160 |
| BVD-523_R | 160 | 640 | 1800 | 1200 |
| Dabrafenib/Trametinib_R | 2.5/0.5 | 7.5/1.5 | 28/6 | 160/30 |
| Dabrafenib/BVD-523_R | 2.5/80 | 10/320 | 28/900 | 42/1500 |
| Trametinib/BVD-523_R | 0.5/80 | 2/320 | 2.5/400 | 4/600 |

| Resistance Condition | Multiple Above Starting Concentration | | |
|---|---|---|---|
| | Month 1 | Month 2 | Month 3 |
| Dabrafenib_R | 5X | 80X | 640X |
| Trametinib_R | 3X | 40X | 160X |
| BVD-523_R | 4X | 11.25X | 7.5X |
| Dabrafenib/Trametinib_R | 3X | 11.2X | 64X |
| Dabrafenib/BVD-523_R | 4X | 11.2X | 16.8X |
| Trametinib/BVD-523_R | 4X | 5X | 8X |

| Resistance Condition | IC50 Fold Change | | | |
|---|---|---|---|---|
| | Dabrafenib | Trametinib | BVD-523 | Paclitaxel |
| Parental | 1.00 | 1.00 | 1.00 | 1.00 |
| Trametinib_R | 2.51 | 2.60 | 1.78 | 2.53 |
| Dabrafenib_R | 3.79 | 3.28 | 1.84 | 0.62 |
| BVD-523_R | 238.11 | 105.20 | 16.84 | 2.97 |
| Trametinib + Dabrafenib_R | 103.17 | 38.60 | 4.22 | 1.66 |
| Dabrafenib + BVD-523_R | 71.87 | 18.04 | 4.32 | 1.35 |
| Trametinib + BVD-523_R | 27.51 | 26.69 | 3.81 | 3.96 |

| Resistance Condition | Percent Growth at ~10X Parental IC50 | | | |
|---|---|---|---|---|
| | Dabrafenib | Trametinib | BVD-523 | Paclitaxel |
| Parental | 13.30% | 6.80% | 0.00% | 1.35% |
| Trametinib_R | 33.53% | 30.15% | 20.02% | 13.52% |
| Dabrafenib_R | 36.45% | 25.96% | 8.21% | 9.36% |
| BVD-523_R | 230.02% | 172.91% | 57.49% | 34.02% |
| Trametinib + Dabrafenib_R | 131.10% | 125.01% | 12.65% | 15.44% |
| Dabrafenib + BVD-523_R | 93.55% | 71.37% | 8.70% | 11.41% |
| Trametinib + BVD-523_R | 86.71% | 64.03% | 27.70% | 30.71% |
| | | | | |
| IC50, Parental (nM) | 4.11 | 0.38 | 186.21 | 3.65 |
| ~10X Parental concentration | 30.20 | 3.00 | 3019.95 | 36.48 |

- Vehicle; BID to end
- Temozolomide, 75 mg/kg; QD x 5
- Temozolomide, 175 mg/kg; QD x 5
- BVD-523, 5 mg/kg; BID to end
- BVD-523, 25 mg/kg; BID to end
- BVD-523, 50 mg/kg; BID to end
- BVD-523, 100 mg/kg; BID to end

- ● Vehicle, 1% CMC
- BVD-523, 25 mg/kg; BID
- BVD-523, 50 mg/kg; BID
- BVD-523, 75 mg/kg; BID
- BVD-523, 100 mg/kg; BID
- CPT-11, 100 mg/kg; Q4D × 2

FIG. 34C
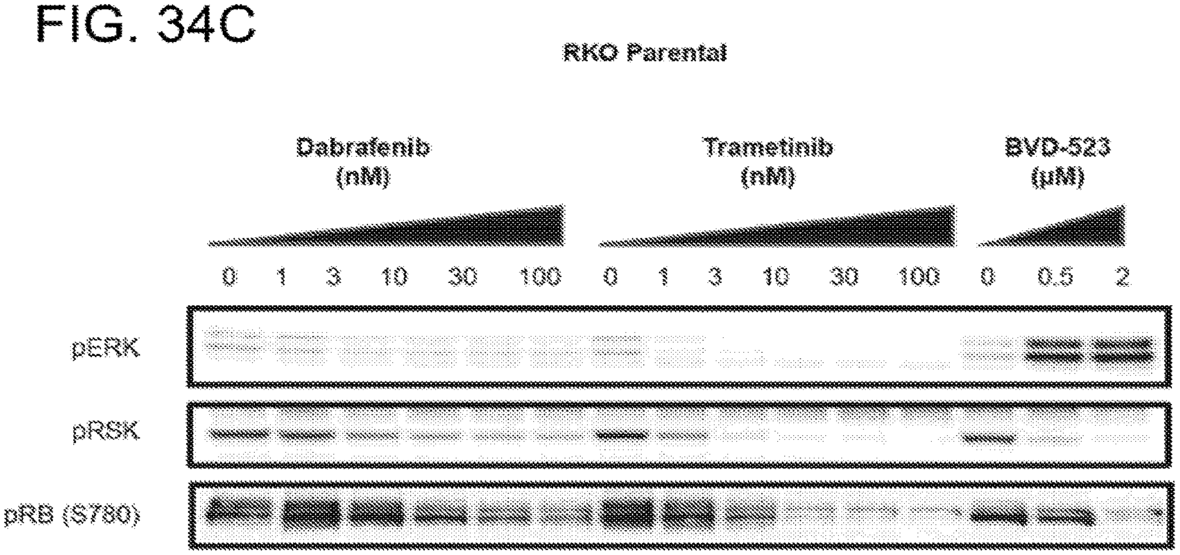
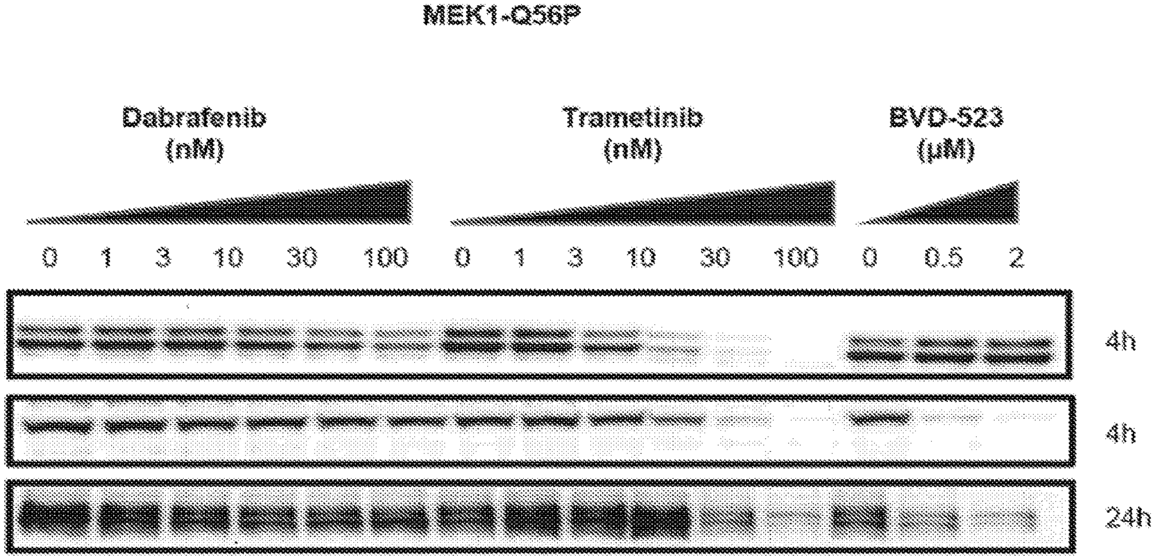

- G1: Vehicle; QD to end
- G2: Dabrafenib, 50 mg/kg + BVD-523, 50 mg/kg
- G3: Dabrafenib, 50 mg/kg + BVD-523, 100 mg/kg
- G4: Dabrafenib, 100 mg/kg + BVD-523, 50 mg/kg
- G5: Dabrafenib, 100 mg/kg + BVD-523, 100 mg/kg
- G6: Dabrafenib, 50 mg/kg orally; QD to end
- G7: Dabrafenib, 100 mg/kg orally; QD to end
- G8: BVD-523, 50 mg/kg orally; BID to end
- G9: BVD-523, 100 mg/kg orally; BID to end
- G10: Temozolomide, 150 mg/kg orally; QD x 5

G1: Vehicle; po; BID to end

G2: BVD-523, 100 mg/kg orally; BID x 41

G3: Dabrafenib, 50 mg/kg orally; BID x 41

G4: Dabrafenib, 25 mg/kg + BVD-523, 50 mg/kg

G5: Dabrafenib, 50 mg/kg + BVD-523, 100 mg/kg

METHODS AND COMPOSITIONS FOR TREATING NON-ERK MAPK PATHWAY INHIBITOR-RESISTANT CANCERS

CROSS REFERENCE TO RELATED APPLICATIONS

The present application is a continuation of U.S. patent application Ser. No. 16/302,955, file Nov. 19, 2018, which is the National Stage of International Application No. PCT/US2017/033843, filed May 22, 2017, which claims benefit to U.S. patent application Ser. No. 15/161,137, filed on May 20, 2016, which is a continuation in part of PCT international application no. PCT/US2014/071749, filed Dec. 19, 2014, which claims benefit of U.S. Patent Application Ser. No. 61/919,551, filed on Dec. 20, 2013, all of which are incorporated by reference in their entireties as if recited in full herein.

FIELD OF INVENTION

The present invention provides, inter alia, methods, pharmaceutical compositions, and kits for treating or ameliorating the effects of a cancer in a subject, which cancer is refractory or resistant to non-ERK MAPK pathway inhibitor therapy.

INCORPORATION BY REFERENCE OF SEQUENCE LISTING

This application contains references to amino acids and/or nucleic acid sequences that have been filed concurrently herewith as sequence listing text file "0398850pct.txt", file size of 351 KB, created on May 20, 2016. The aforementioned sequence listing is hereby incorporated by reference in its entirety pursuant to 37 C.F.R. § 1.52(e)(5).

BACKGROUND OF THE INVENTION

Drug inhibitors that target components of the mitogen-activated protein kinases (MAPK) signaling pathway show clinical efficacy in a variety of cancers, particularly those bearing mutations in the BRAF protein kinase. Both RAF and MEK inhibitors are approved for single-agent use in advanced metastatic BRAF mutant melanoma. Either alone or in combination, BRAF and MEK inhibitor activity is unpredictable in other cancers, with promising efficacy in BRAF mutant thyroid and lung cancer, but only marginal activity in BRAF mutant colorectal cancer.

As with other targeted therapies, patterns of disease response to RAF and MEK inhibitors appear to be influenced by the intrinsic genetic heterogeneity present in the cancers where the drugs are used. For instance, it has been shown that certain genetic alterations, including PTEN and other changes that activate the PI3K cell growth signaling pathway, may predict a poor initial response, and/or relatively rapid progression, in BRAF mutant melanoma treated with the RAF inhibitor vemurafenib. Likewise, direct mutations in MEK gene loci appear to emerge in tumors that have progressed following either BRAF, MEK, or combined drug treatment. Several additional examples, from RAS and RAF gene amplification and splicing mutations, suggest that acquired drug resistance is produced when oncogenic pleiotropy encounters the selective pressure of targeted drug treatment.

In view of the foregoing, there is a need for novel targeted agents that would ideally inhibit diverse nodes of oncogenic pathways, and also be effective in combinations by inducing a burden of selective pressures that exceeds the adaptive capacity of diverse cancer genomes. The present application is directed to meeting these and other needs.

SUMMARY OF THE INVENTION

One embodiment of the present invention is a method for treating or ameliorating the effects of a cancer in a subject, which cancer is refractory or resistant to non-ERK MAPK pathway inhibitor therapy. The method comprises administering to the subject an effective amount of BVD-523 or a pharmaceutically acceptable salt thereof.

Another embodiment of the present invention is a method for treating or ameliorating the effects of a cancer in a subject. The method comprises:

(a) identifying a subject with cancer that has become refractory or resistant to BRAF inhibitor therapy, MEK inhibitor therapy, or BRAF and MEK inhibitor therapy; and (b) administering to the subject with said refractory or resistant cancer an effective amount of an ERK inhibitor, which is BVD-523 or a pharmaceutically acceptable salt thereof.

A further embodiment of the present invention is a method for treating or ameliorating the effects of cancer in a subject, which cancer is refractory or resistant to BRAF inhibitor therapy, MEK inhibitor therapy, or both. The method comprises administering to the subject an effective amount of BVD-523 or a pharmaceutically acceptable salt thereof.

Another embodiment of the present invention is a method for identifying a subject having cancer who would benefit from therapy with an ERK inhibitor. The method comprises:

(a) obtaining a biological sample from the subject; and (b) screening the sample to determine whether the subject has one or more of the following markers:

(i) a switch between RAF isoforms, (ii) upregulation of receptor tyrosine kinase (RTK) or NRAS signaling, (iii) reactivation of mitogen activated protein kinase (MAPK) signaling, (iv) the presence of a MEK activating mutation, (v) amplification of mutant BRAF, (vi) STAT3 upregulation, (vii) mutations in the allosteric pocket of MEK that directly block binding of inhibitors to MEK or lead to constitutive MEK activity, wherein the presence of one or more of the markers confirms that the subject's cancer is refractory or resistant to BRAF and/or MEK inhibitor therapy and that the subject would benefit from therapy with an ERK inhibitor, which is BVD-523 or a pharmaceutically acceptable salt thereof.

A further embodiment of the present invention is a pharmaceutical composition for treating or ameliorating the effects of a cancer in a subject, which cancer is refractory or resistant to non-ERK MAPK pathway therapy. The composition comprises a pharmaceutically acceptable carrier or diluent and an effective amount of BVD-523 or a pharmaceutically acceptable salt thereof.

Another embodiment of the present invention is a kit for treating or ameliorating the effects of a cancer in a subject, which cancer is refractory or resistant to non-ERK MAPK pathway therapy. The kit comprises any of the pharmaceutical compositions according to the present invention packaged together with instructions for its use.

Another embodiment of the present invention is a method for inhibiting phosphorylation of RSK in a cancer cell that is refractory or resistant to a non-ERK MAPK pathway inhibitor. The method comprises contacting the cancer cell with an effective amount of BVD-523 or a pharmaceutically acceptable salt thereof for a period of time sufficient for phosphorylation of RSK in the cancer cell to be inhibited.

Another embodiment of the present invention is a method of treating a subject having an unresectable or metastatic BRAF600 mutation-positive melanoma comprising administering to the subject 600 mg BID of BVD-523 or a pharmaceutically acceptable salt thereof.

Another embodiment of the present invention is a composition for treating a subject having an unresectable or metastatic BRAF600 mutation-positive melanoma, the composition comprising 600 mg of BVD-523 or a pharmaceutically acceptable salt thereof and optionally a pharmaceutically acceptable carrier, adjuvant, or vehicle.

BRIEF DESCRIPTION OF THE DRAWINGS

FIG. 2A, FIG. 2C and FIG. 2G are normalized to control, whereas FIG. 2D, FIG. 2F and FIG. 2H show the raw data.

FIG. 4A, FIG. 4C and FIG. 4G are normalized to control, whereas FIG. 4D, FIG. 4F and FIG. 4H show the raw data.

FIG. 5A, FIG. 5C and FIG. 5G are normalized to control, whereas FIG. 5D, FIG. 5F and FIG. 5H show the raw data.

FIG. 11A is a dose matrix showing % inhibition of the trametinib/dabrafenib combination in A375 cells using the CellTiter-Glo cell viability assay.

FIG. 13A is a dose matrix showing % inhibition of the BVD-523/dabrafenib combination in A375 cells using the CellTiter-Glo cell viability assay.

FIG. 14A is a dose matrix showing % inhibition of the trametinib/BVD-523 combination in A375 cells using the Alamar Blue cell viability assay.

FIG. 15A is a dose matrix showing % inhibition of the trametinib/BVD-523 combination in A375 cells using the CellTiter-Glo cell viability assay.

FIG. 16A and FIG. 16B show results from duplicate samples. Similarly, FIG. 16C and FIG. 16D also show results from duplicate samples. In FIG. 16A and FIG. 16B, pRSK1 had a relatively weak signal in A375 cells compared to other markers. A different pRSK1-S380 antibody from Cell Signaling (cat. #11989) was tested but did not give a detectable signal (data not shown). In FIG. 16C and FIG. 16D, pCRAF-338 gave a minimal signal.

FIG. 17A and FIG. 17B show results from duplicate samples. Similarly, FIG. 17C and FIG. 17D also show results from duplicate samples. In FIG. 17A and FIG. 17B, pRSK1 levels appear to be very low in HCT116 cells, and in FIG. 17C and FIG. 17D, pCRAF-338 signal was also very weak.

FIG. 18A and FIG. 18B show results from duplicate samples. Similarly, FIG. 18C and FIG. 18D also show results from duplicate samples. In FIG. 18A and FIG. 18B, no band of a size corresponding to cleaved PARP (89 kDa) was apparent.

FIG. 19 shows that BVD-523 can treat acquired resistance to targeted drugs in-vivo. A patient-derived line, ST052C, was isolated from a BRAFV600E melanoma patient that progressed following 10 months of therapy with MAPK-pathway directed therapies. Treated ex vivo, ST052C exhibited acquired cross-resistance to dabrafenib at 50 mg/kg BID. Meanwhile, BVD-523 was effective in ST052C as a single-agent at 100 mg/kg BID.

FIG. 23A shows a dose matrix showing inhibition (%) for the combination in RKO parental cells. FIG. 23O shows Bliss excess for the combination in FIG. 23K.

FIG. 24A shows a dose matrix showing inhibition (%) for the combination in RKO parental cells. FIG. 24O shows Bliss excess for the combination in FIG. 24K.

FIG. 25A shows a dose matrix showing inhibition (%) for the combination in RKO parental cells. FIG. 25O shows Bliss excess for the combination in FIG. 25K.

FIG. 27A shows increased signaling in RKO MEK1 (Q56P/+) cells. FIG. 27B-FIG. 27C show the results of a 4 hour treatment in Experiment 1 (See, Example 7) in RKO Parental (27B) and RKO MEK1 (Q56P/+) (27C) cells. FIG. 27D-FIG. 27E show the results of a 4 hour treatment in Experiment 2 (See, Example 7) in RKO Parental (27D) and RKO MEK1 (Q56P/+) (27E) cells. FIG. 27F-FIG. 27G show the results of a 4 hour treatment in Experiment 2 (See, Example 7) in RKO Parental (27F) and RKO MEK1 (Q56P/+) (27G) cells. FIG. 27H-FIG. 27I show a summary of results in RKO Parental (27H) and RKO MEK1 (Q56P/+) (27I) cells.

FIG. 28A shows a dose matrix showing inhibition (%) for the combination in A375 cells. FIG. 28B-FIG. 28C show the results of single agent proliferation assays for the combination in FIG. 28A. FIG. 28D shows Loewe excess for the combination in FIG. 28A and FIG. 28E shows Bliss excess for the combination in FIG. 28A.

FIG. 29A shows that BVD-523 demonstrates inhibition in a reversible ATP-competitive manner. This is demonstrated by a linear increase in $IC_{50}$ values for inhibition of ERK2 with increasing ATP concentration as shown in FIG. 29B. FIG. 29C shows a representative plot of the dose-response curve and FIG. 29D shows a plot of $IC_{50}$ over time. FIG. 29E shows BVD-523 binding to ERK2 and phospho-ERK2 (pERK2), compared with negative control protein p38. FIG. 29F shows BVD-523 binding to ERK2 compared with the ERK inhibitors SCH772984 and pyrazolylpyrrole.

FIG. 30A shows that BVD-523 demonstrates preferential activity in cells with MAPK pathway mutations, as defined by the presence of mutations in RAS family members and RAF. In addition, as shown in FIG. 30B, BVD-523 blocks sensitive cell lines in the G1 phase of the cell cycle. FIG. 30C shows that BVD-523 induced a concentration- and time-dependent increase in caspase activity in the A375, WM266, and LS411N cancer cell lines after 72 hours of exposure. FIG. 30D shows that the MAPK pathway and effector proteins are modulated by acute (4-hour) and prolonged (24-hour) BVD-523 treatment in $BRAF^{V600E}$-mutant A375 cells.

FIG. 31C shows that in Colo205 xenografts, increased ERK1/2 phosphorylation correlates with BVD-523 concentration.

FIG. 34A-FIG. 34D show that BVD-523 demonstrates activity in models of resistance to BRAF/MEK inhibition. The appearance of resistance to BVD-523, dabrafenib, or trametinib in $BRAF^{V600E}$ A375 cells following exposure to increasing concentrations of drug is indicated. A strict set of "criteria" was applied to determine when the dose could be increased in order to ensure that the kinetics of the acquisition of resistance between treatments was comparable. See, Example 1. Time is shown against multipliers of $IC_{50}$; each point on the plotted line represents a change of medium or cell split. FIG. 34A shows that adapting cells to growth in the presence of BVD-523 was more challenging than with either dabrafenib or trametinib. FIG. 34B shows that BVD-523 sensitivity is retained in A375 cells cultured to acquire resistance to combined BRAF (dabrafenib)+MEK (trametinib) inhibition. In FIG. 34C, cells were treated with compound for 96 h and viability was assessed using CellTiter-Glo®. BVD-523 activity is retained in $BRAF^{V600E}$ RKO cells cross-resistant to BRAF (dabrafenib) and MEK (trametinib) inhibitors due to endogenous heterozygous knock-in of $MEK1^{Q56P}$. FIG. 34D shows that BVD-523 inhibition of pRSK in $BRAF^{V600E}$-mutant cell line RKO is maintained in the presence of $MEK1^{Q56P}$, which confers resistance to MEK and BRAF inhibition. Knock-in of KRAS mutant alleles into SW48 cell lines significantly diminishes sensitivity to the MEK inhibitors trametinib and selumetinib, while comparatively sensitivity to BVD-523 is retained.

FIG. 36A-FIG. 36B show that the combination of BVD-523 plus dabrafenib exhibited superior antitumor activity compared with treatment with either agent alone in a A375 $BRAF^{V600E}$-mutant melanoma cell line xenograft model with a tumor start volume of 75-144 $mm^3$. FIG. 36C-FIG. 36D show similar data from the same model with an enlarged tumor volume (700-800 $mm^3$) at the start of dosing. Plots of mean tumor growth (left panels) and Kaplan-Meier survival (right panels) are presented for each study. Abbreviations: BID, twice daily; QD, once daily.

DETAILED DESCRIPTION OF THE INVENTION

One embodiment of the present invention is a method for treating or ameliorating the effects of a cancer in a subject, which cancer is refractory or resistant to non-ERK MAPK pathway inhibitor therapy. The method comprises administering to the subject an effective amount of BVD-523 or a pharmaceutically acceptable salt thereof.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

Figures 18A, 18B:
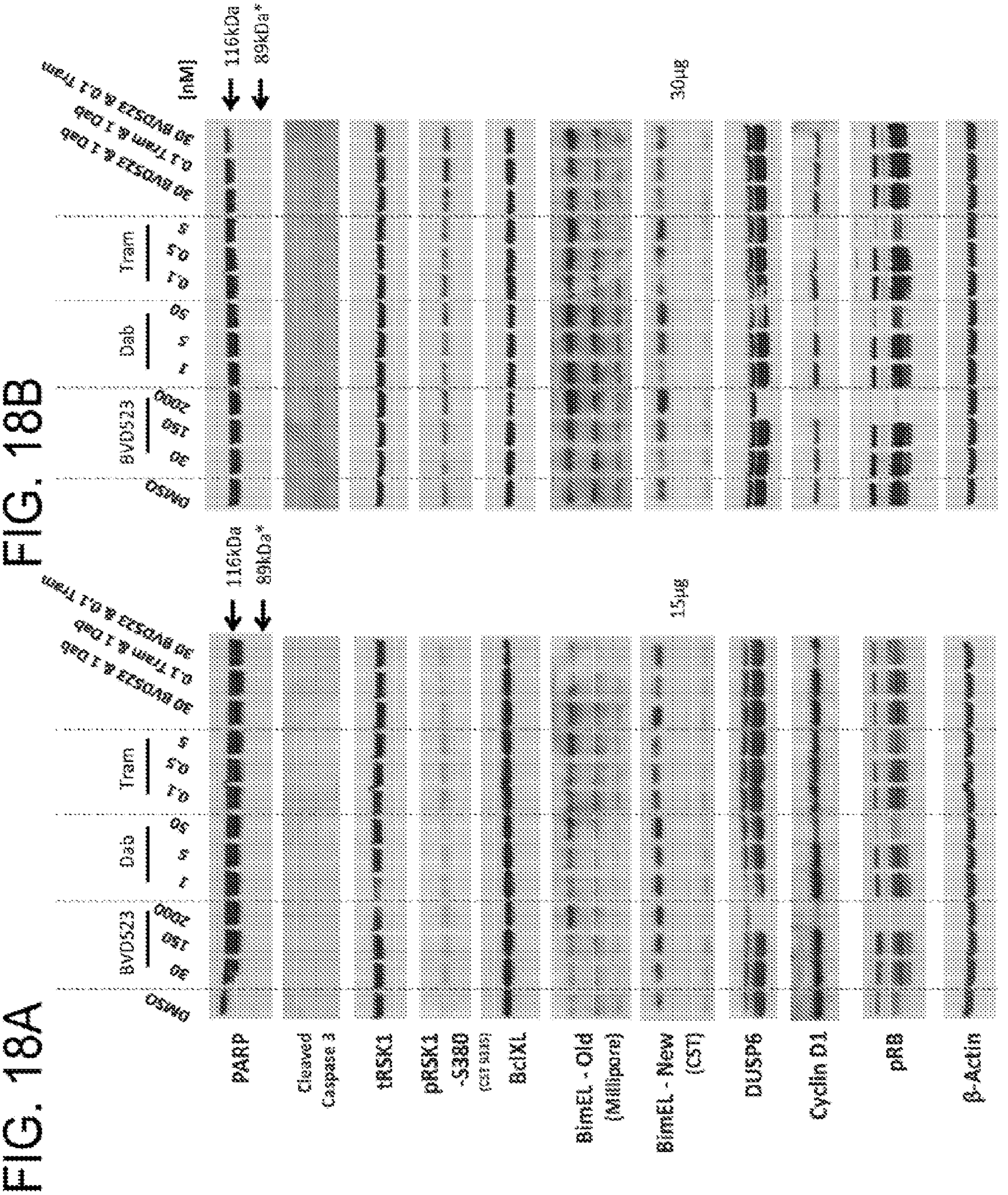
FIG. 18A-FIG. 18D are a set of images showing Western blot analysis of cell cycle and apoptosis signaling in A375 melanoma cells after a 24 hour treatment with various concentrations (in nM) of BVD-523 ("BVD523"), trametinib ("tram") and/or dabrafenib ("Dab") as labelled. 50 μg of total protein was loaded in each lane except where indicated otherwise. In this experiment, duplicate samples were collected.
Figure 18D:
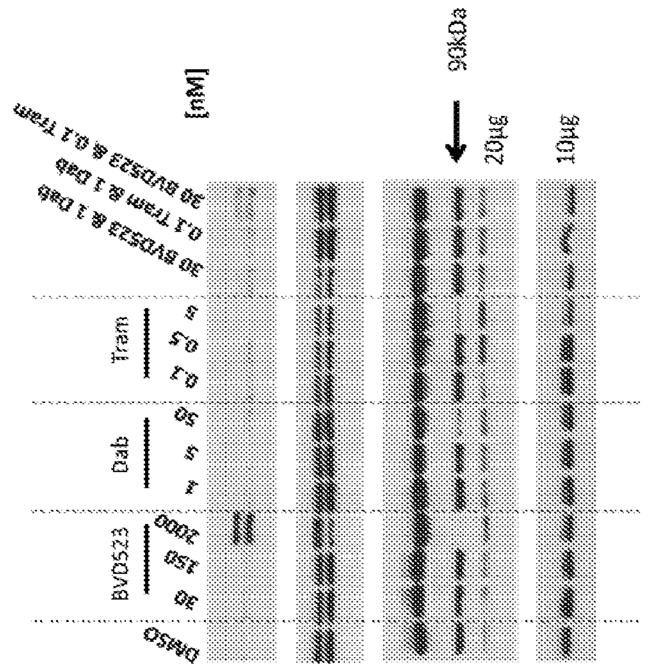
Figure 18C:
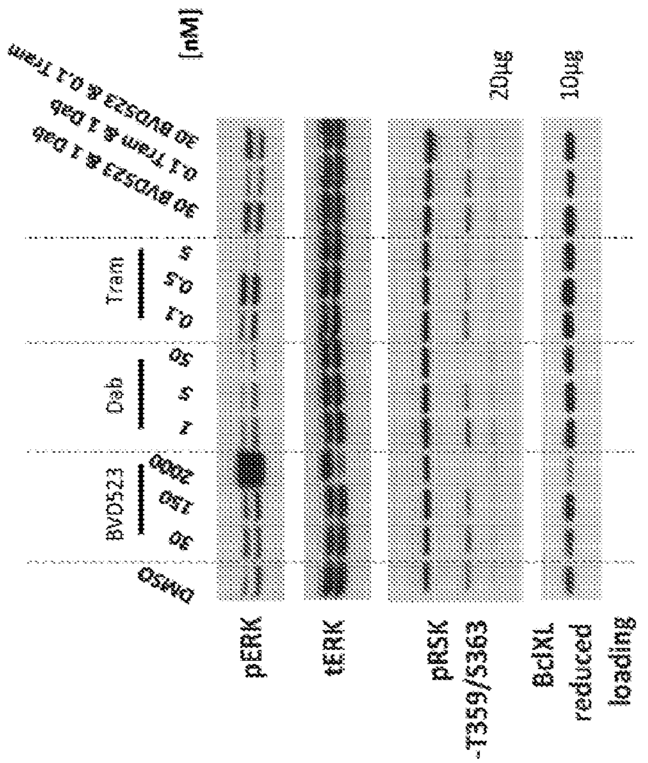

In the present invention, BVD-523 corresponds to a compound according to formula (I):

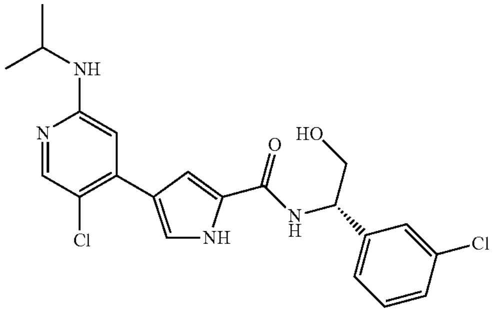 [SMILES: CC(C)Nc1cc(-c2c[nH]c(C(=O)N[C@H](CO)c3cccc(Cl)c3)c2)c(Cl)cn1]

and pharmaceutically acceptable salts thereof. BVD-523 may be synthesized according to the methods disclosed, e.g., in U.S. Pat. No. 7,354,939. Enantiomers and racemic mixtures of both enantiomers of BVD-523 are also contemplated within the scope of the present invention. BVD-523 is an ERK1/2 inhibitor with a mechanism of action that is believed to be, e.g., unique and distinct from certain other ERK1/2 inhibitors, such as SCH772984 and the pyrimidinal structure used by Hatzivassiliou et al. (2012). For example, other ERK1/2 inhibitors, such as SCH772984, inhibit autophosphorylation of ERK (Morris et al., 2013), whereas BVD-523 allows for the autophosphorylation of ERK while still inhibiting ERK. (See, e.g., FIG. 18).

As used herein, the words "resistant" and "refractory" are used interchangeably. Being "resistant" to non-ERK MAPK pathway inhibitor therapy treatments means that non-ERK MAPK inhibitors have reduced efficacy in treating cancer.

As used herein, a "non-ERK MAPK inhibitor" means any substance that reduces the activity, expression or phosphorylation of proteins or other members of the MAPK pathway that results in a reduction of cell growth or an increase in cell death, with the exception of ERK1/2 inhibitors. As used herein, an "ERK1/2 inhibitor" means those substances that (i) directly interact with ERK1 and/or ERK2, e.g., by binding to ERK1/2 and (ii) decrease the expression or the activity of ERK1 and/or ERK2 protein kinases. Therefore, inhibitors that act upstream of ERK1/2, such as MEK inhibitors and RAF inhibitors, are not ERK1/2 inhibitors according to the present invention (but they are non-ERK MAPK inhibitors). Non-limiting examples of ERK1/2 inhibitors according to the present invention include AEZS-131 (Aeterna Zentaris), AEZS-136 (Aeterna Zentaris), BVD-523 (BioMed Valley Discoveries, Inc.), SCH-722984 (Merck & Co.), SCH-772984 (Merck & Co.), SCH-900353 (MK-8353) (Merck & Co.), pharmaceutically acceptable salts thereof, and combinations thereof.

Figure 21:
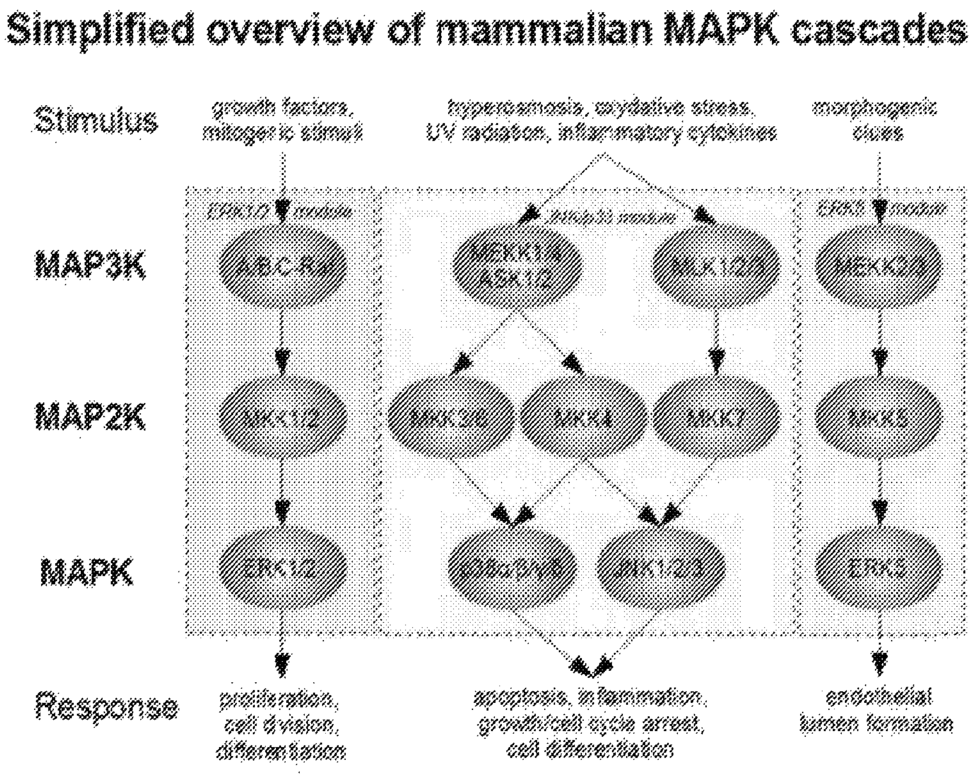
FIG. 21 shows a schematic of the mitogen-activated protein kinases (MAPK) pathway.
Figure 22A:
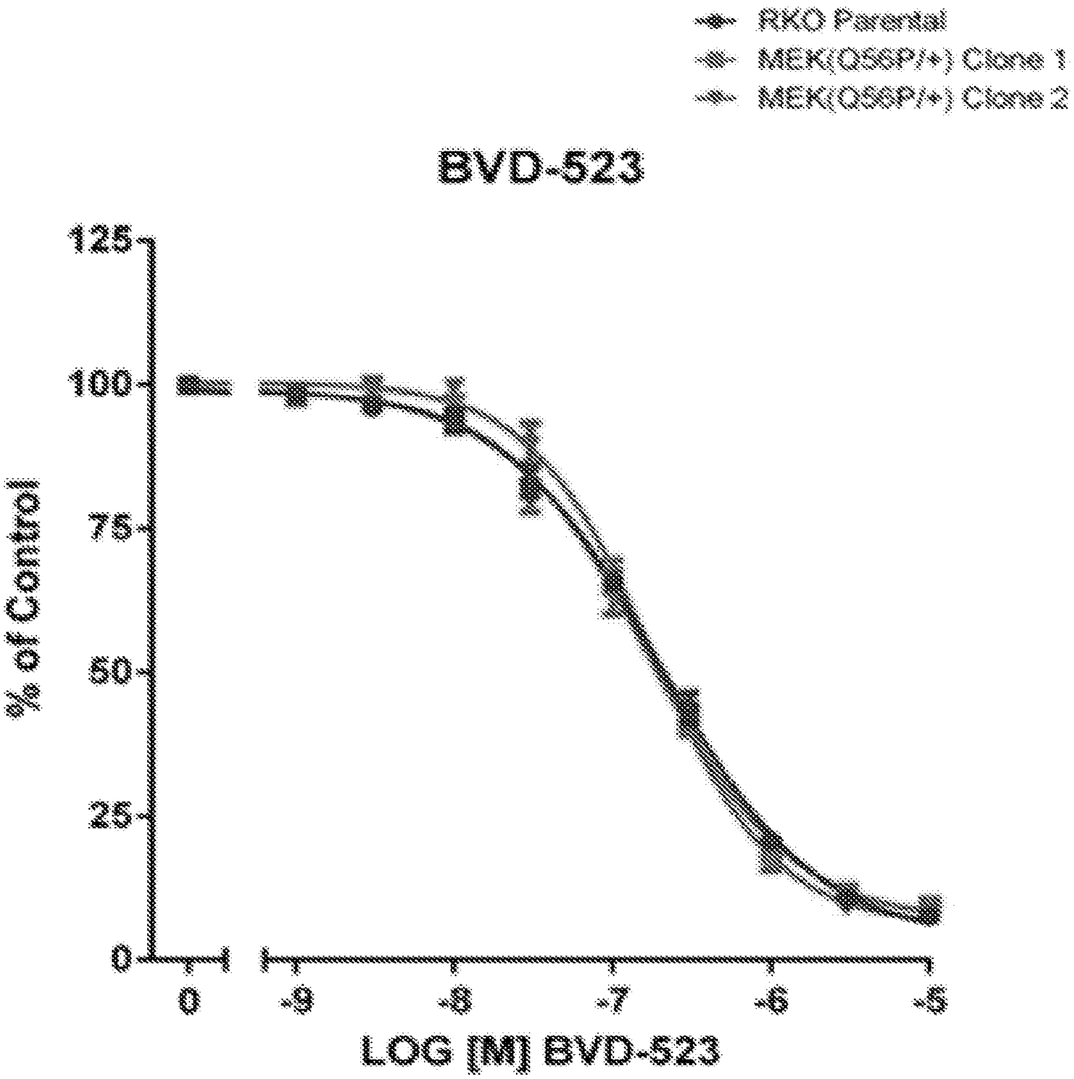
FIG. 22A-FIG. 22E show the results of single agent proliferation assays. Proliferation results are shown for treatment with BVD-523 (FIG. 22A), SCH772984 (FIG. 22B), Dabrafenib (FIG. 22C), Trametinib (FIG. 22D), and Paclitaxel (FIG. 22E).
Figure 22B:
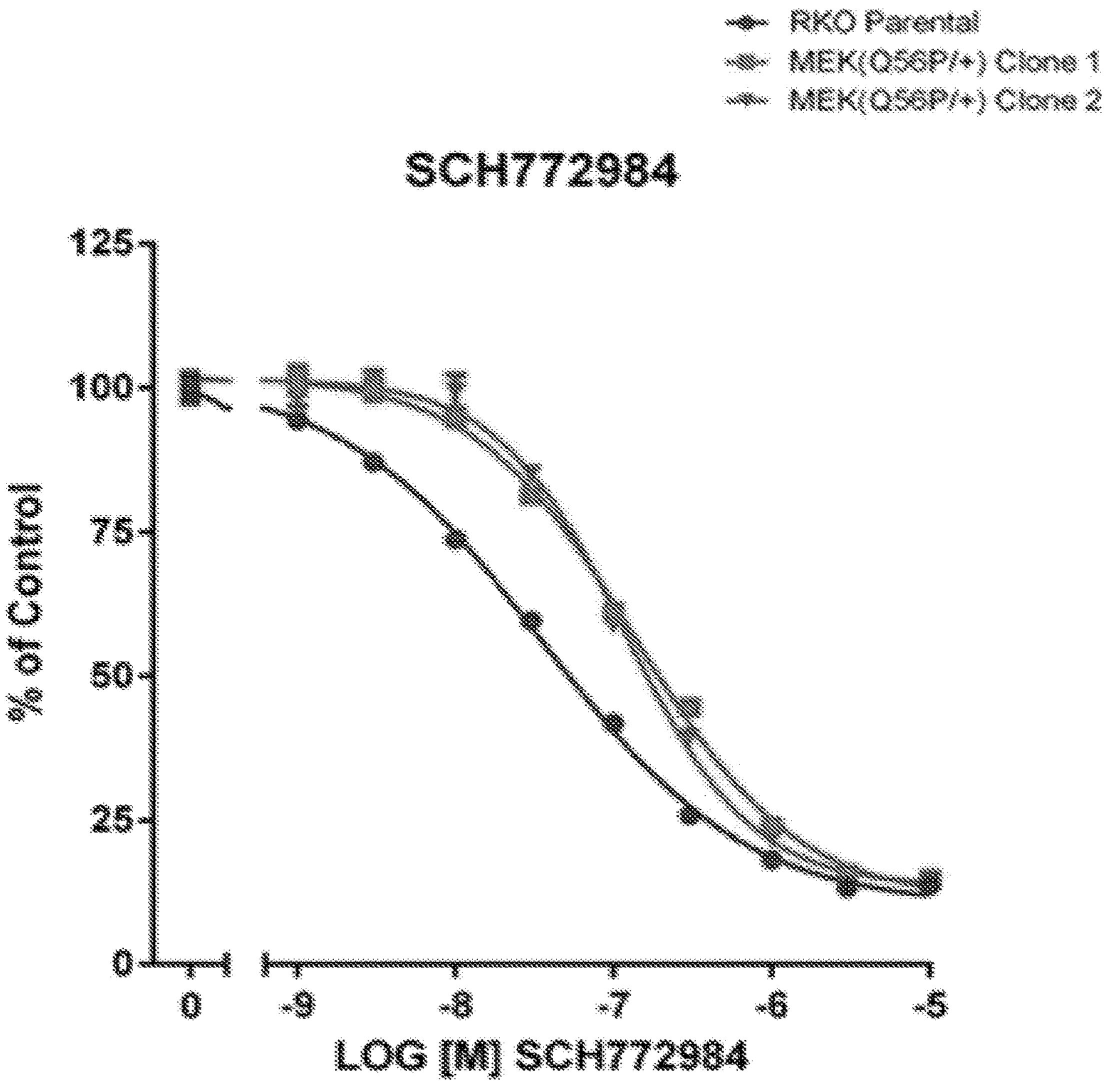
Figure 22C:
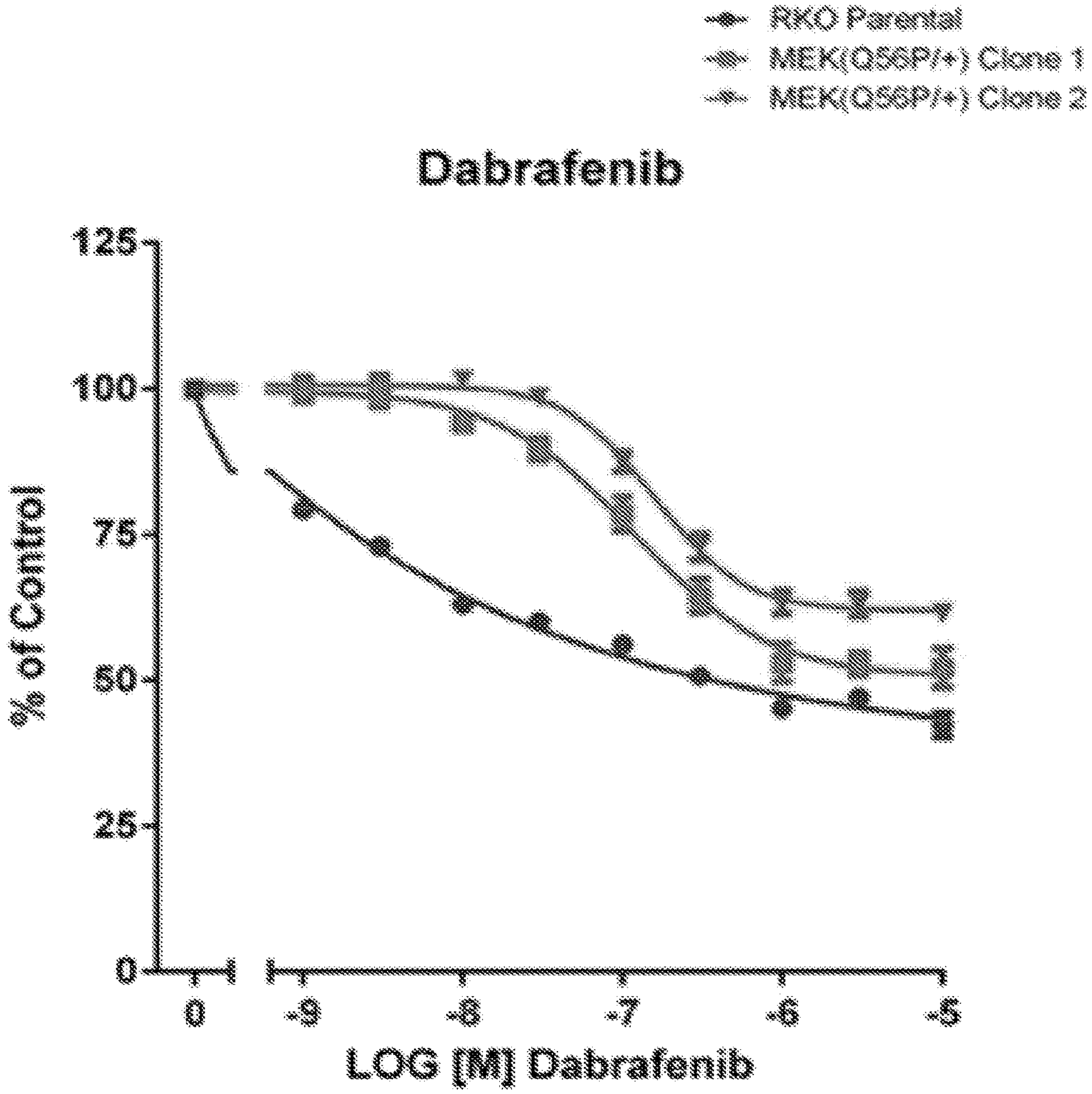
Figure 22D:
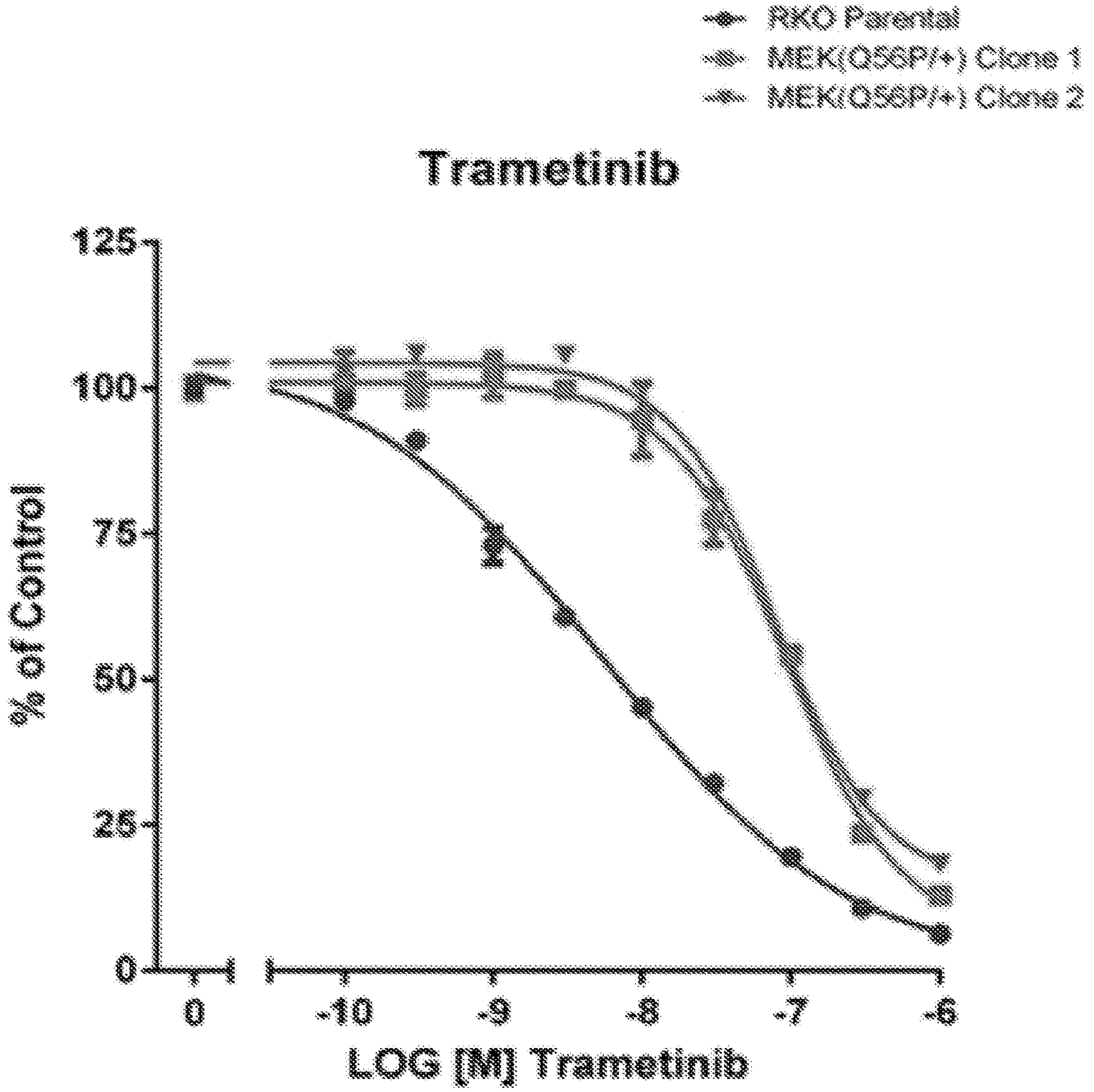
Figure 22E:
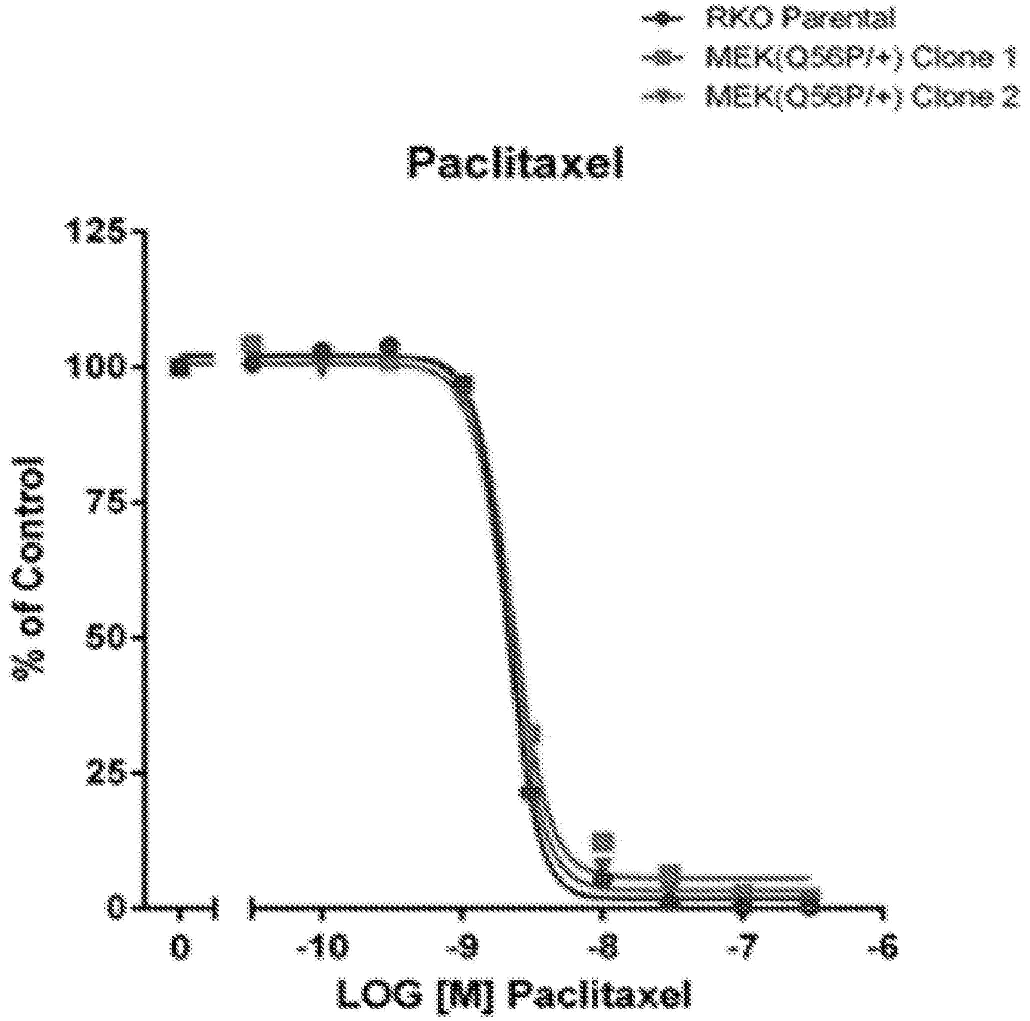
Figure 23A:
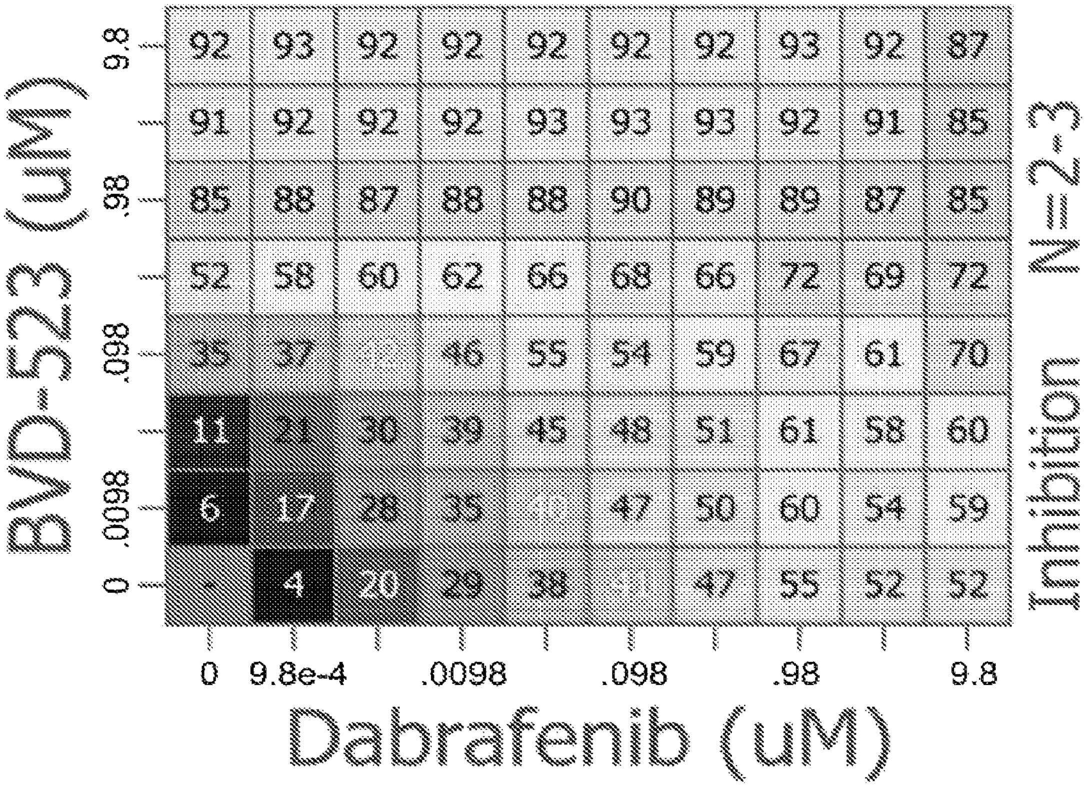
FIG. 23A-FIG. 23O show the results of the combination of BVD-523 and Dabrafenib.
Figure 23B:
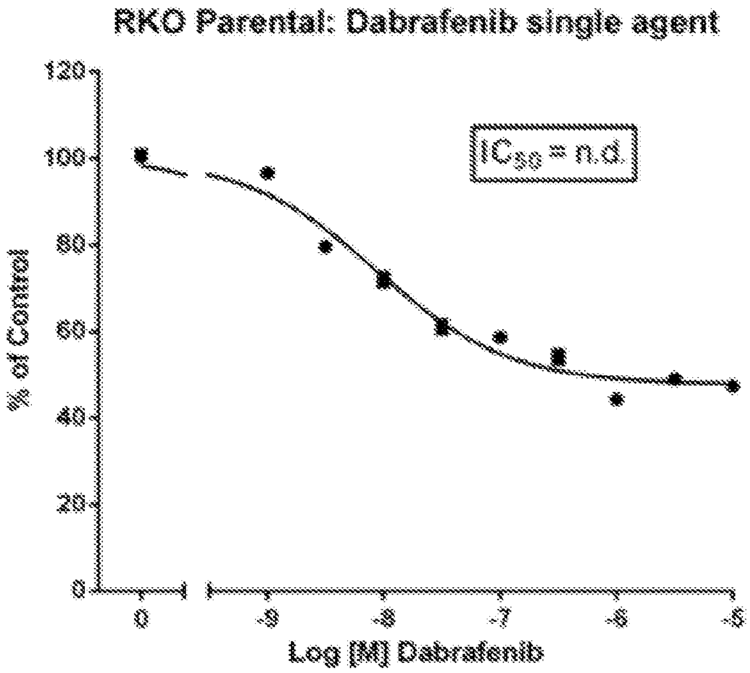
FIG. 23B-FIG. 23C show the results of single agent proliferation assays for the combination in FIG. 23A.
Figure 23C:
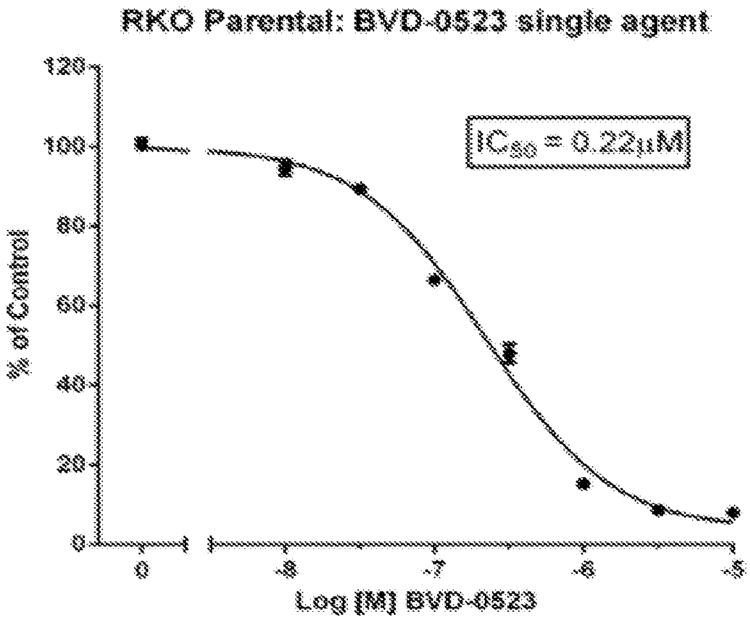
Figure 23E:
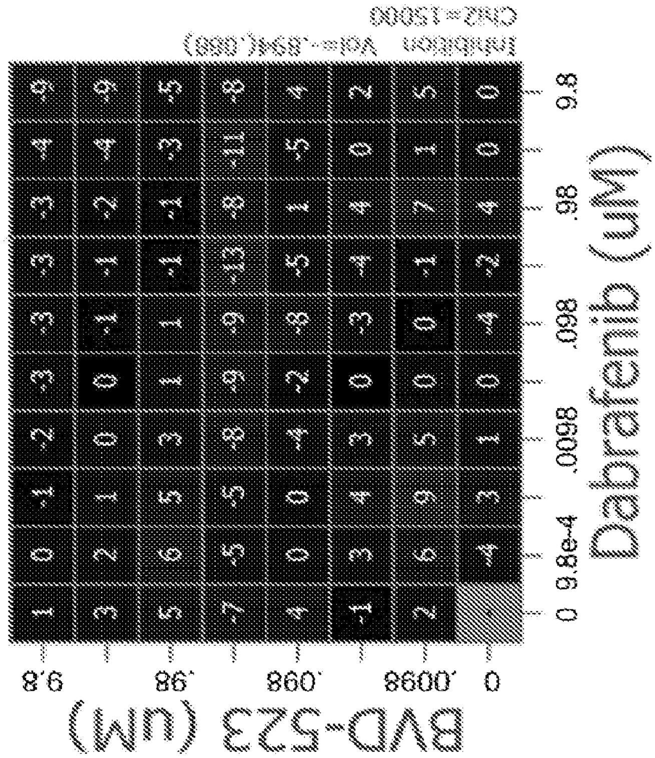
FIG. 23E shows Bliss excess for the combination in FIG. 23A.
Figure 23D:
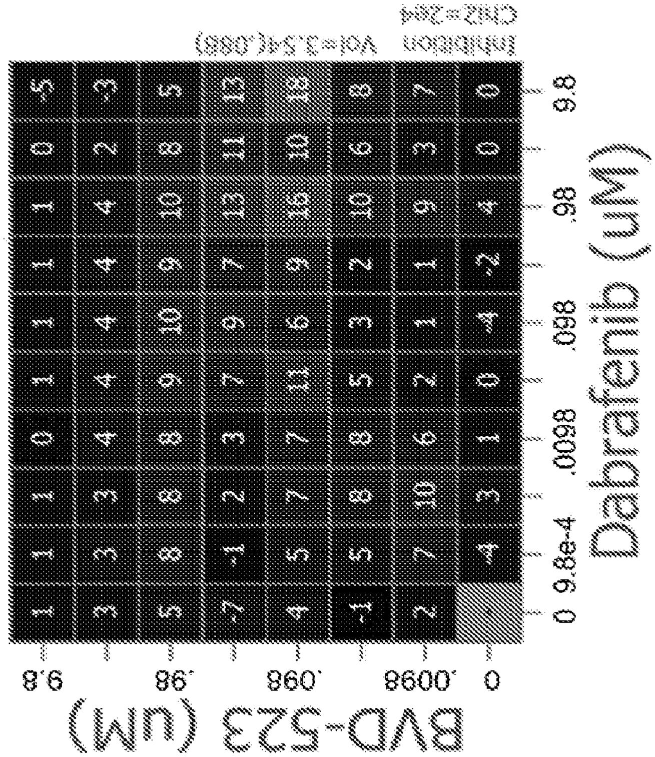
FIG. 23D shows Loewe excess for the combination in FIG. 23A
Figure 23F:
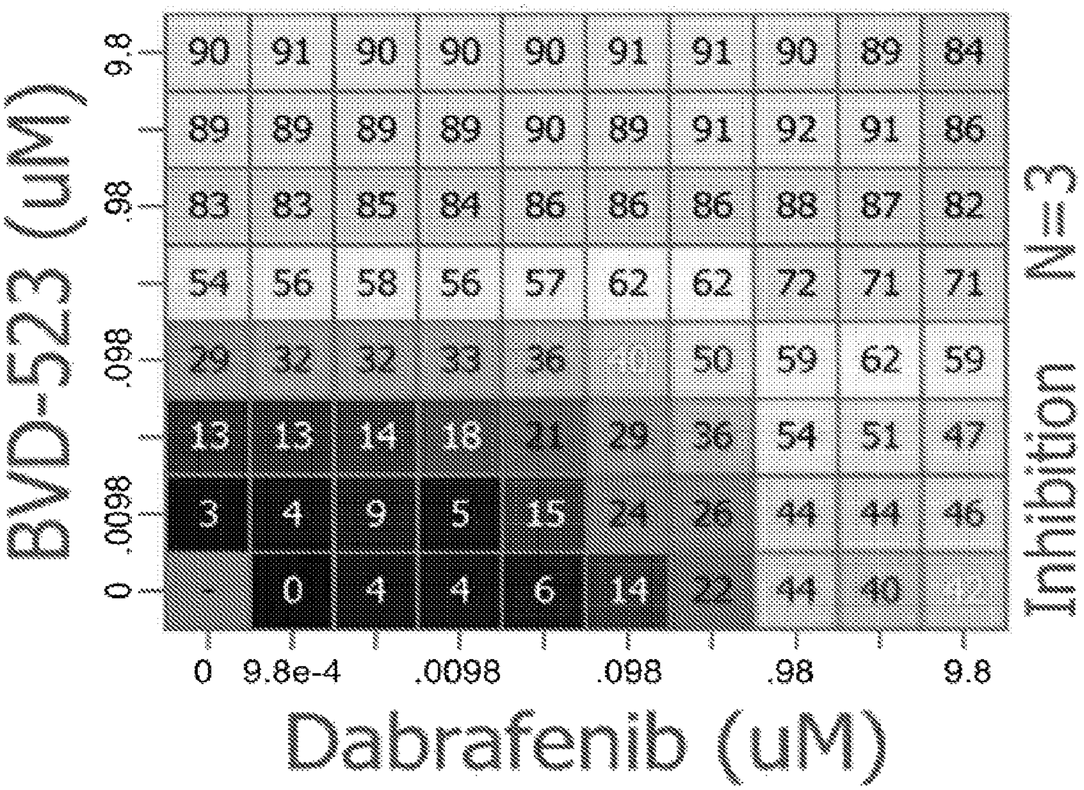
FIG. 23F shows a dose matrix showing inhibition (%) for the combination in RKO MEK1 (Q56P/+)— clone 1 cells.
Figure 23G:
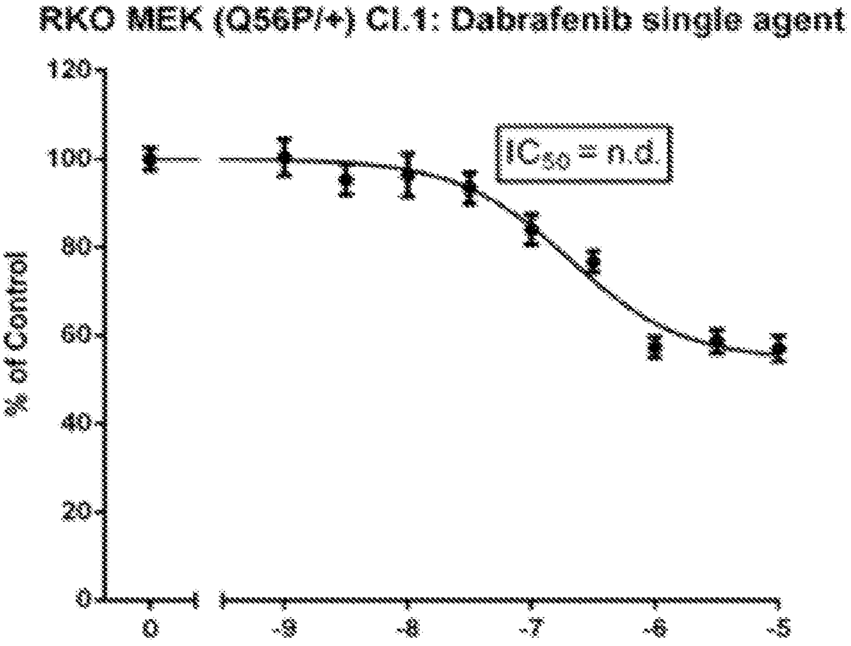
FIG. 23G-FIG. 23H show the results of single agent proliferation assays for the combination in FIG. 23F.
Figure 23H:
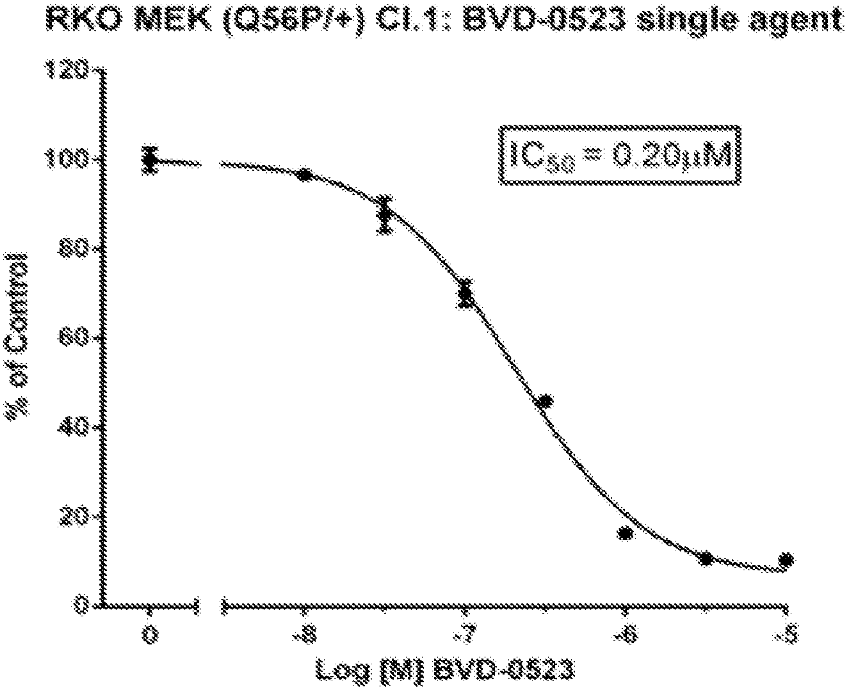
Figure 23I:
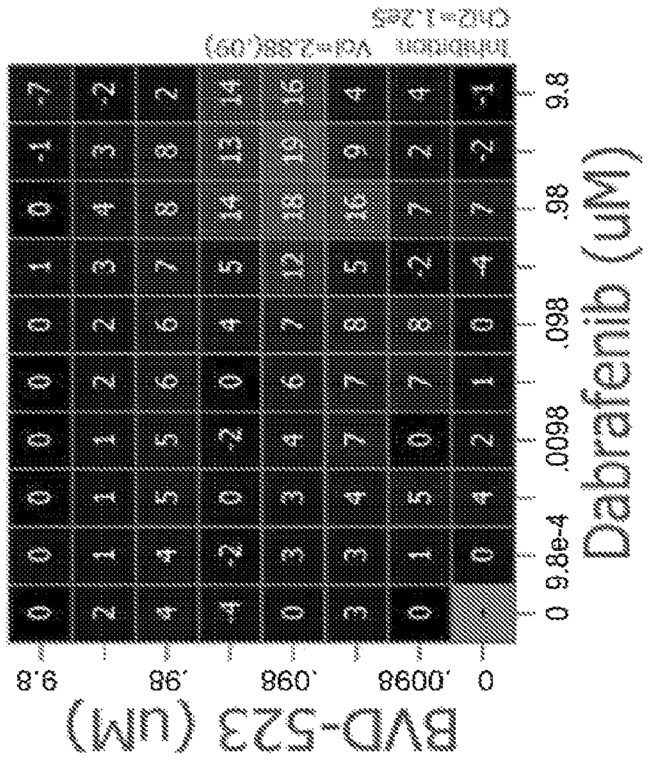
FIG. 23I shows Loewe excess for the combination in FIG. 23F
Figure 23J:
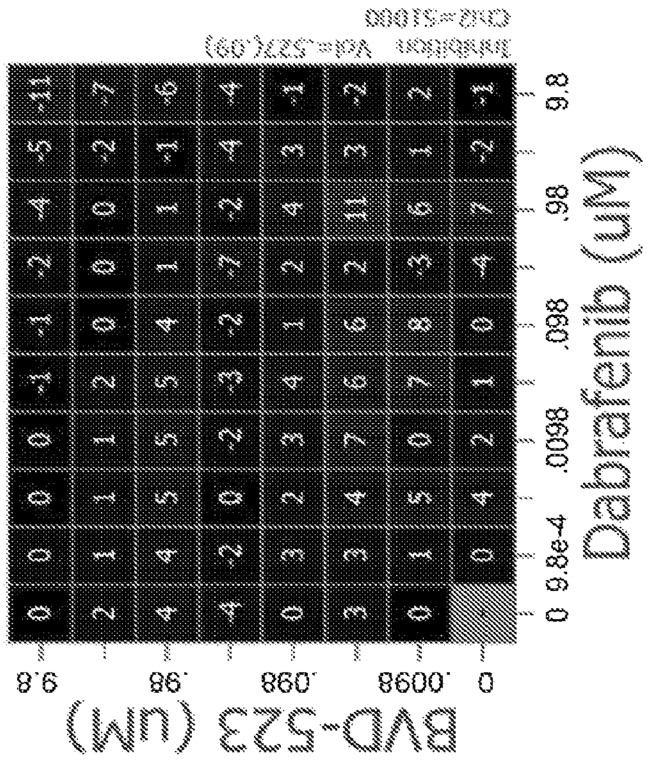
FIG. 23J shows Bliss excess for the combination in FIG. 23F.
Figure 23K:
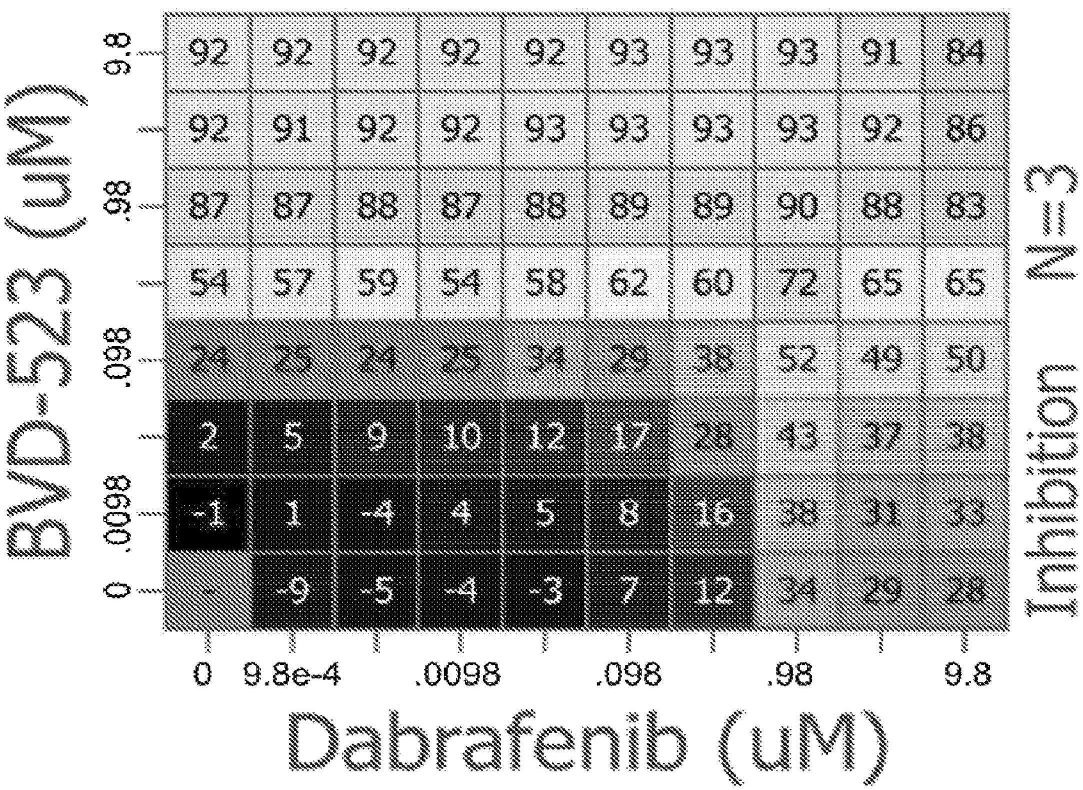
FIG. 23K shows a dose matrix showing inhibition (%) for the combination in RKO MEK1 (Q56P/+)—clone 2 cells.
Figure 23L:
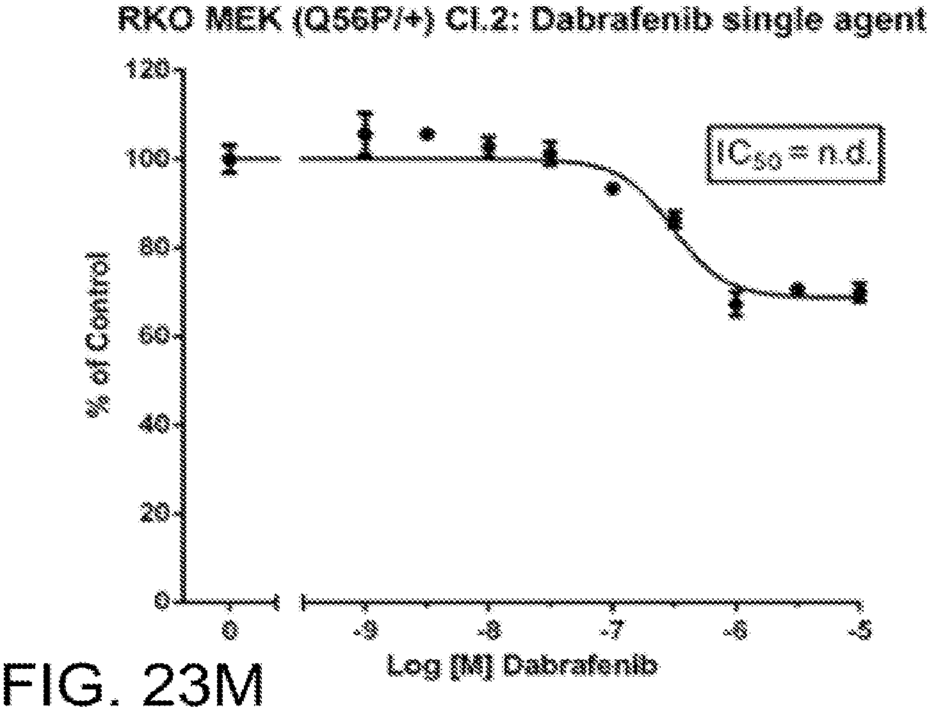
FIG. 23L-FIG. 23M show the results of single agent proliferation assays for the combination in FIG. 23K.
Figure 23M:
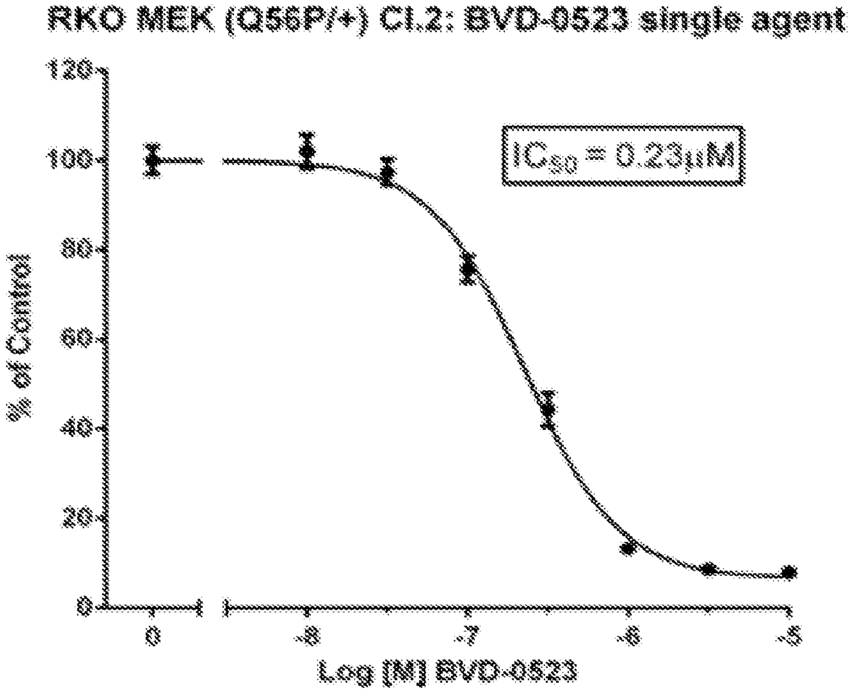
Figure 23N:
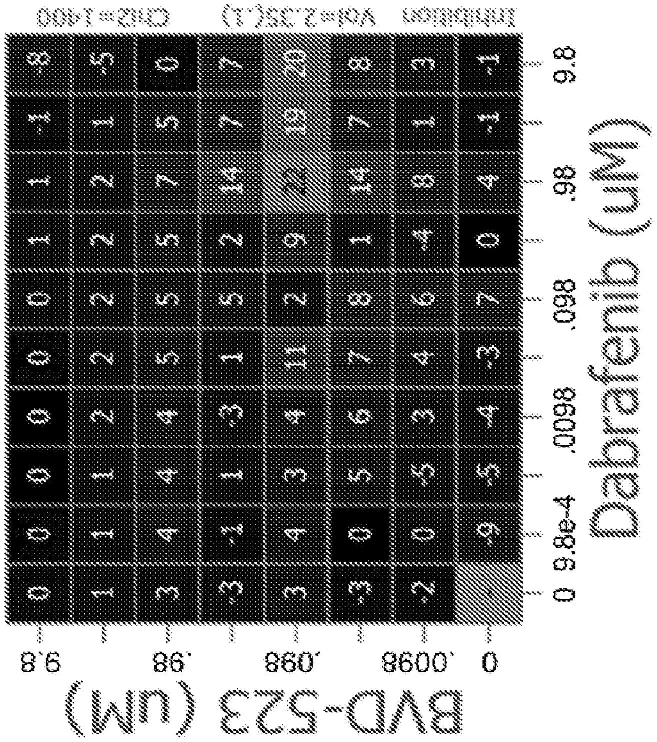
FIG. 23N shows Loewe excess for the combination in FIG. 23K
Figure 23O:
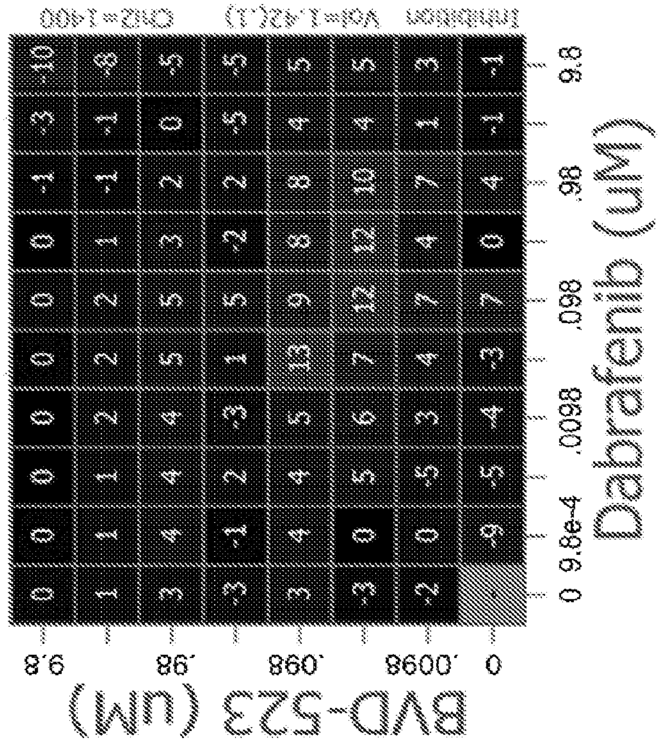
Figure 24A:
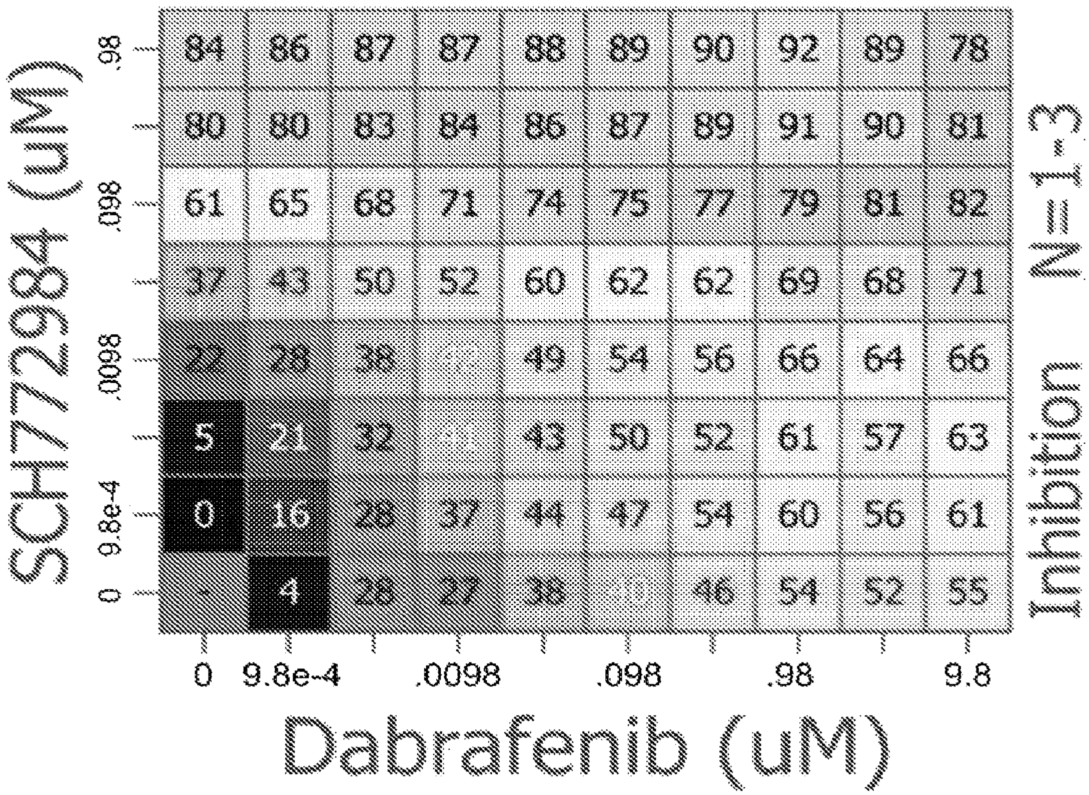
FIG. 24A-FIG. 24O show the results of the combination of SCH772984 and Dabrafenib.
Figure 24B:
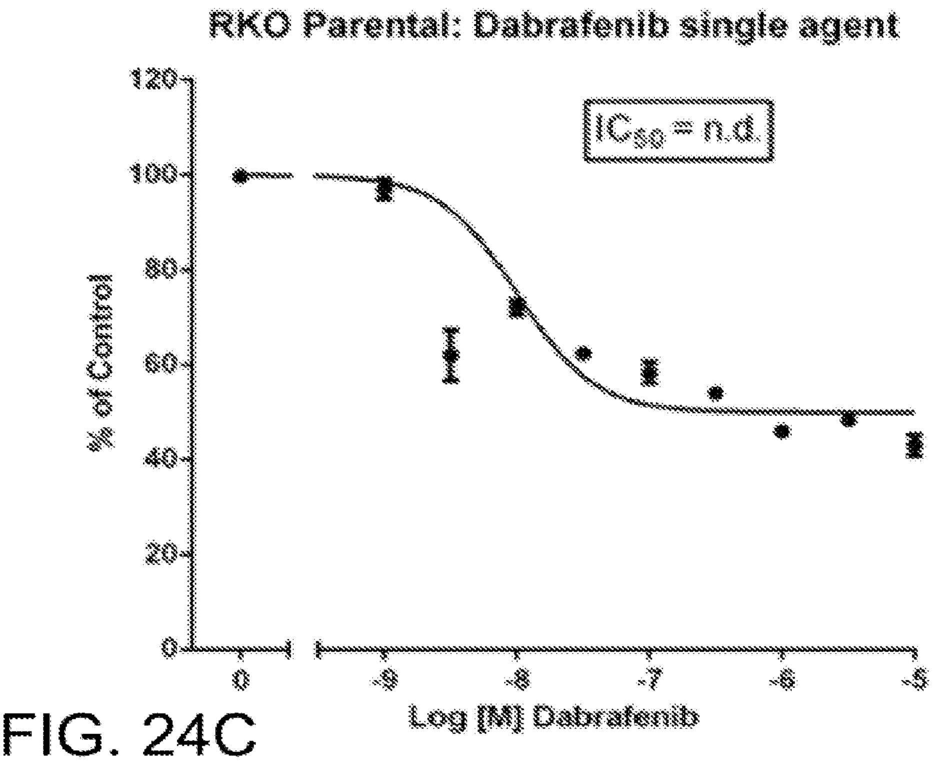
FIG. 24B-FIG. 24C show the results of single agent proliferation assays for the combination in FIG. 24A.
Figure 24C:
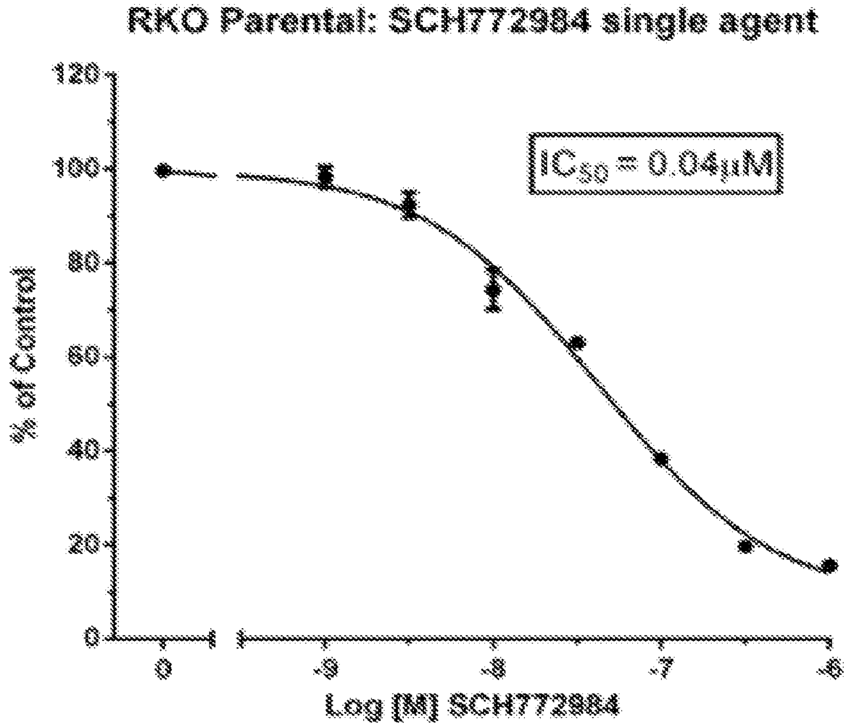
Figure 24E:
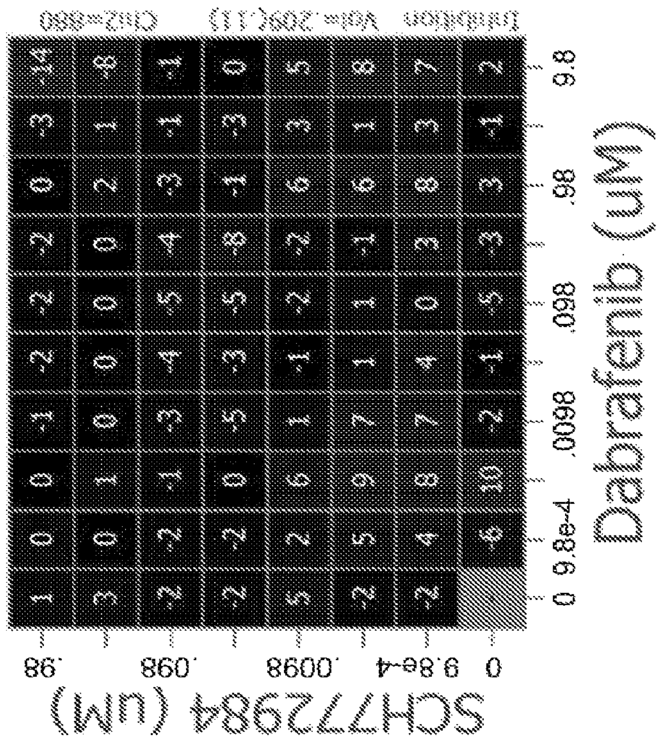
FIG. 24E shows Bliss excess for the combination in FIG. 24A.
Figure 24D:
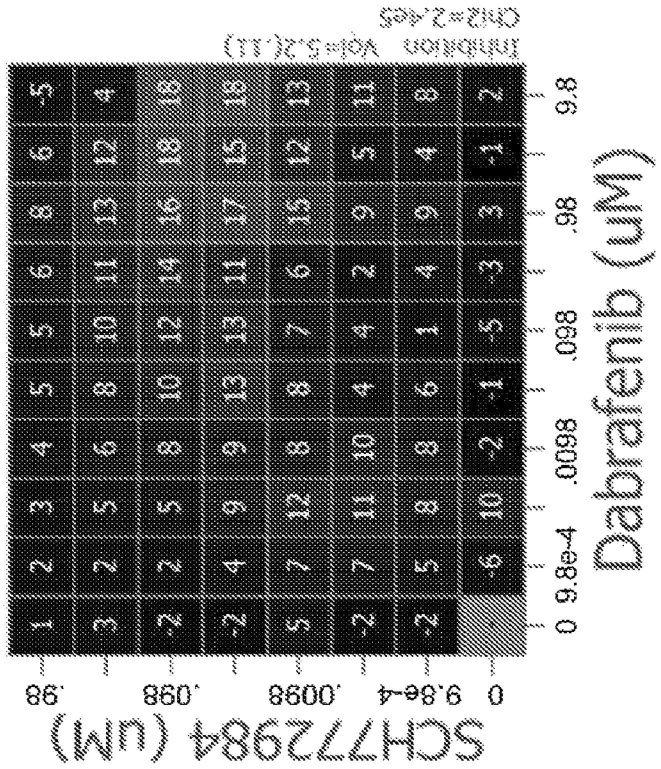
FIG. 24D shows Loewe excess for the combination in FIG. 24A
Figure 24F:
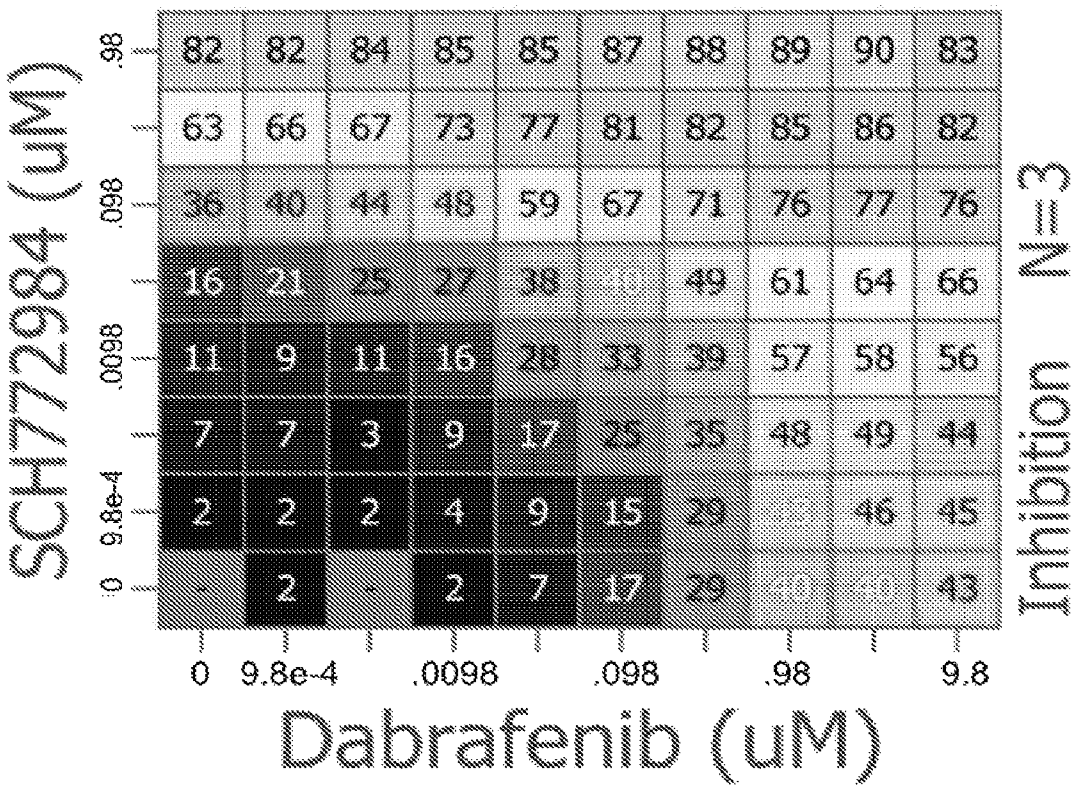
FIG. 24F shows a dose matrix showing inhibition (%) for the combination in RKO MEK1 (Q56P/+)—clone 1 cells.
Figure 24G:
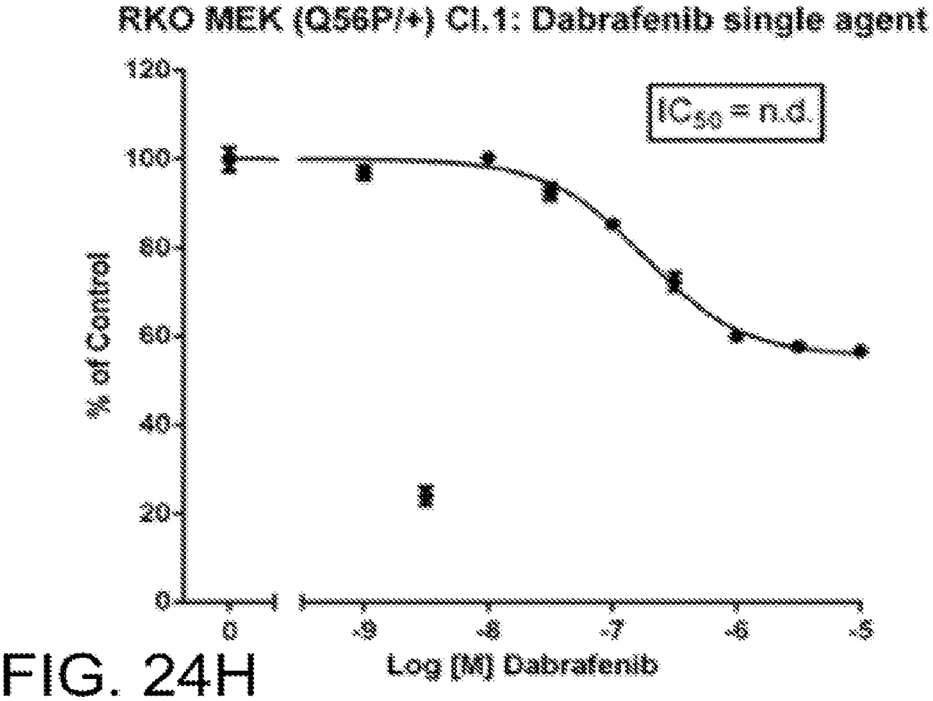
FIG. 24G-FIG. 24H show the results of single agent proliferation assays for the combination in FIG. 24F.
Figure 24H:
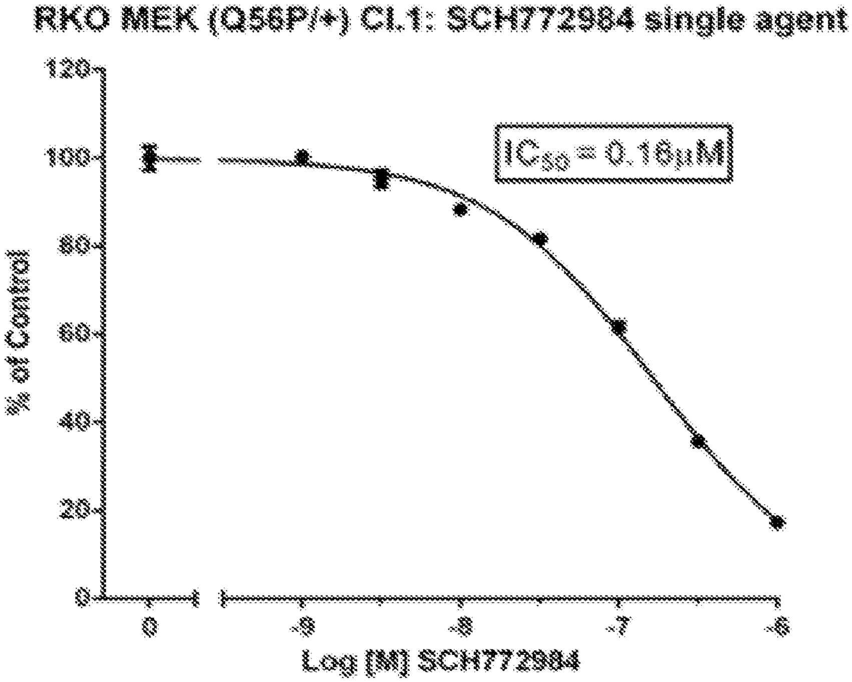
Figure 24J:
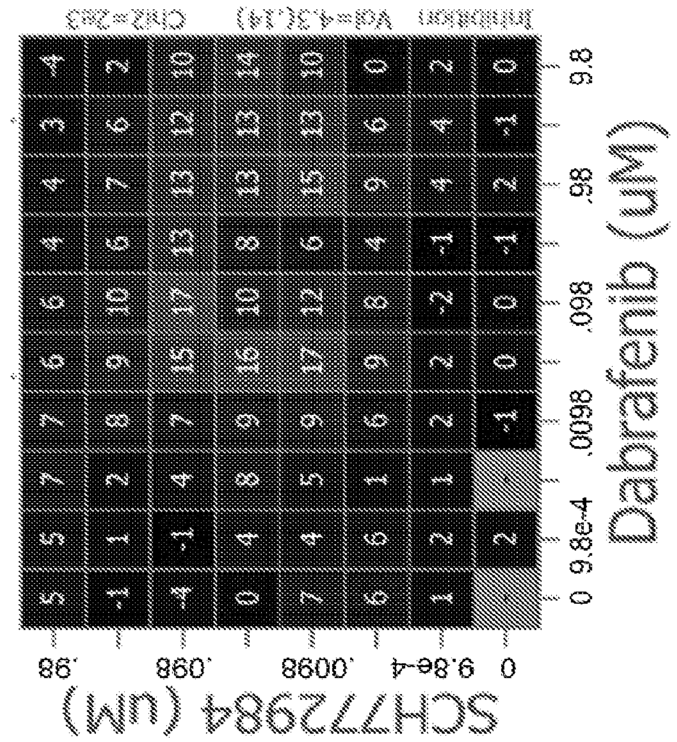
FIG. 24J shows Bliss excess for the combination in FIG. 24F.
Figure 24I:
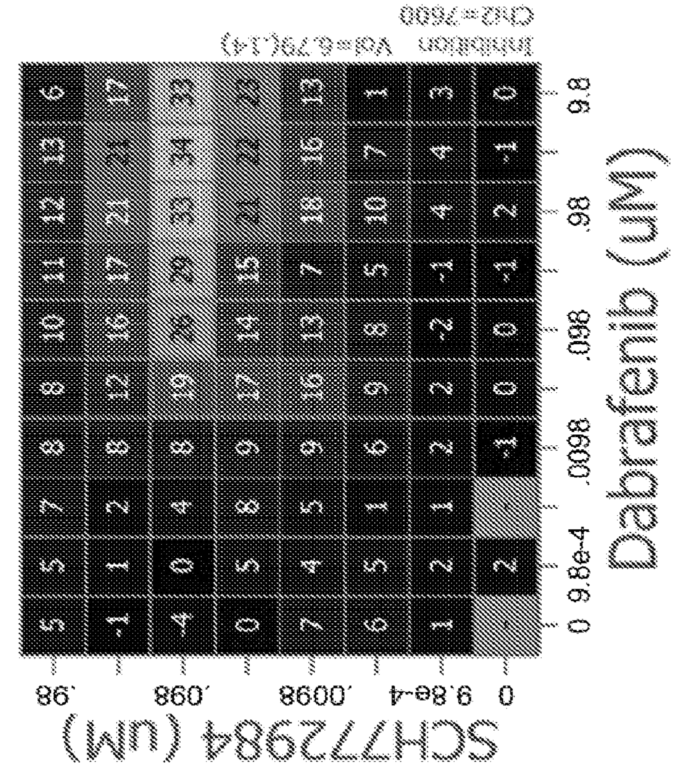
FIG. 24I shows Loewe excess for the combination in FIG. 24F
Figure 24K:
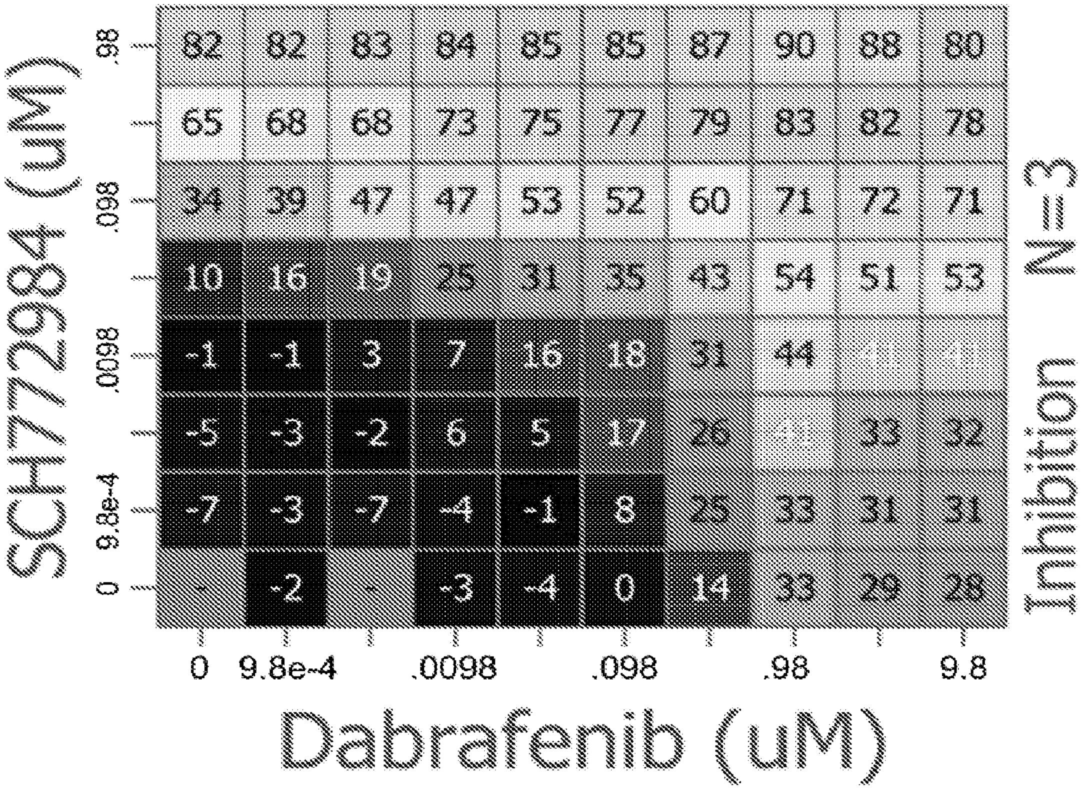
FIG. 24K shows a dose matrix showing inhibition (%) for the combination in RKO MEK1 (Q56P/+)—clone 2 cells.
Figure 24L:
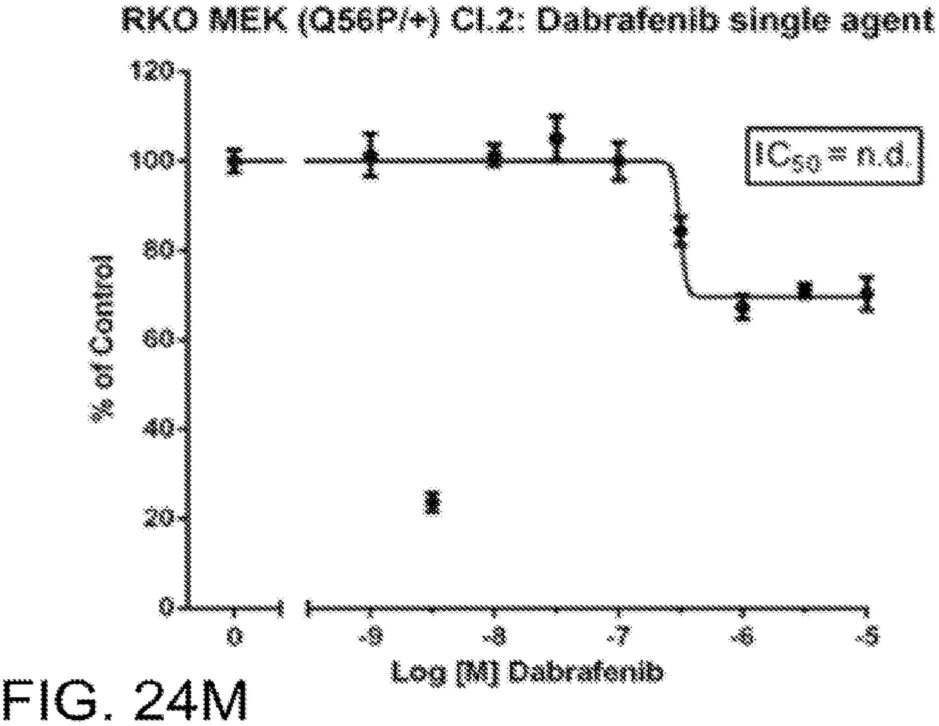
FIG. 24L-FIG. 24M show the results of single agent proliferation assays for the combination in FIG. 24K.
Figure 24M:
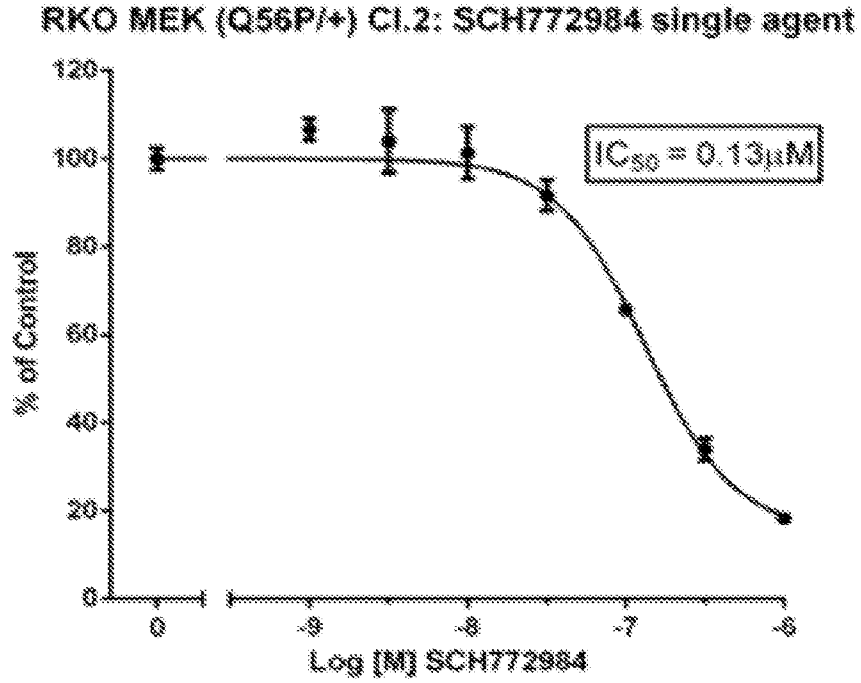
Figure 24N:
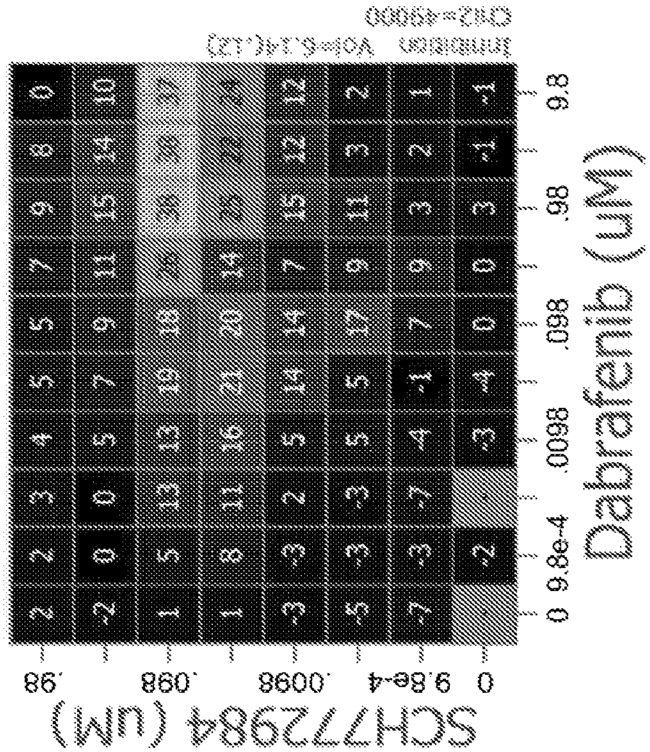
FIG. 24N shows Loewe excess for the combination in FIG. 24K
Figure 24O:
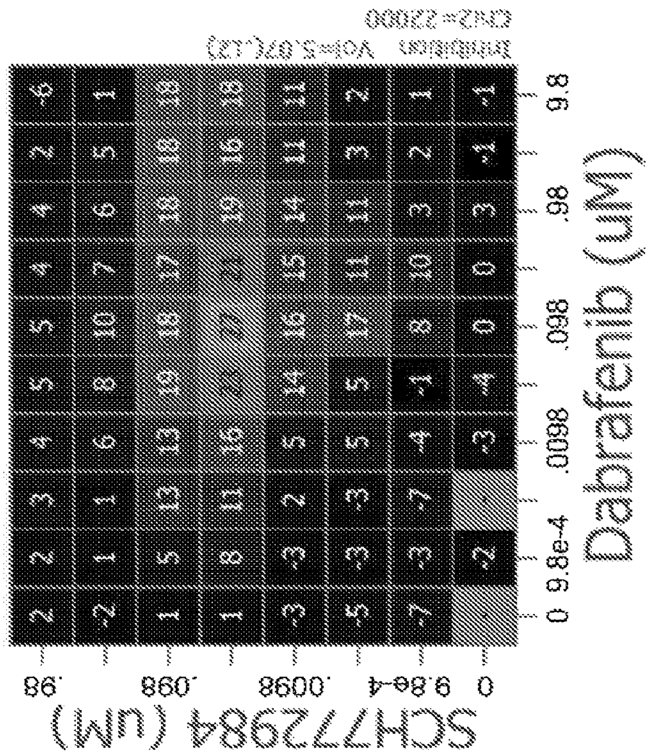

An overview of the mammalian MAPK cascades is shown in FIG. 21. The MAPK pathway is reviewed in e.g., Akinleye et al., 2013. Briefly, with respect to the ERK1/2 module in FIG. 21 (light purple box), the MAPK 1/2 signaling cascade is activated by ligand binding to receptor tyrosine kinases (RTK). The activated receptors recruit and phosphorylate adaptor proteins Grb2 and SOS, which then interact with membrane-bound GTPase Ras and cause its activation. In its activated GTP-bound form, Ras recruits and activates RAF kinases (A-RAF, B-RAF, and C-RAF/RAF-1). The activated RAF kinases activate MAPK 1/2 (MKK1/2), which in turn catalyzes the phosphorylation of threonine and tyrosine residues in the activation sequence Thr-Glu-Tyr of ERK1/2. With respect to the JNK/p38 module (yellow box in FIG. 21), upstream kinases, MAP3Ks, such as MEKK1/4, ASK1/2, and MLK1/2/3, activate MAP2K3/6 (MKK3/6), MAP2K4 (MKK4), and MAP2K7 (MKK7). These MAP2K's then activate JNK protein kinases, including JNK1, JNK2, and JNK3, as well as p38 α/β/γ/δ. To execute their functions, JNKs activate several transcription factors, including c-Jun, ATF-2, NF-ATc1, HSF-1 and STAT3. With respect to the ERK5 module (blue box in FIG. 21), the kinases upstream of MAP2K5 (MKK5) are MEKK2 and MEKK3. The best characterized downstream target of MEK5 is ERK5, also known as big MAP kinase 1 (BMK1) because it is twice the size of other MAPKs.

Non-limiting examples of non-ERK MAPK pathway inhibitors according to the present invention include RAS inhibitors, RAF inhibitors (such as, e.g., inhibitors of A-RAF, B-RAF, C-RAF (RAF-1)), MEK inhibitors, and combinations thereof. Preferably, the non-ERK MAPK pathway inhibitors are BRAF inhibitors, MEK inhibitors, and combinations thereof.

As used herein, a "RAS inhibitor" means those substances that (i) directly interact with RAS, e.g., by binding to RAS and (ii) decrease the expression or the activity of RAS. Non-limiting exemplary RAS inhibitors include, but are not limited to, farnesyl transferase inhibitors (such as, e.g., tipifarnib and lonafarnib), farnesyl group-containing small molecules (such as, e.g., salirasib and TLN-4601), DCAI, as disclosed by Maurer (Maurer et al., 2012), Kobe0065 and and Kobe2602, as disclosed by Shima (Shima et al., 2013), HBS 3 (Patgiri et al., 2011), and AIK-4 (Allinky).

As used herein, a "RAF inhibitor" means those substances that (i) directly interact with RAF, e.g., by binding to RAF and (ii) decrease the expression or the activity of RAF, such as, e.g., A-RAF, B-RAF, and C-RAF (RAF-1). Non-limiting exemplary RAF inhibitors, including BRAF inhibitors, include:

Compound 7

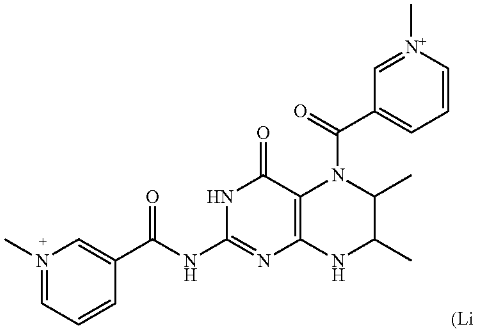

(Li et al.),

Compound 9

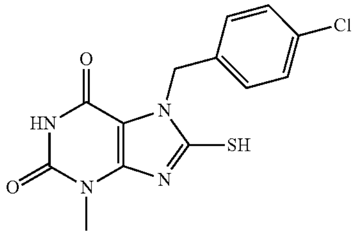

(Id.),

Compound 10

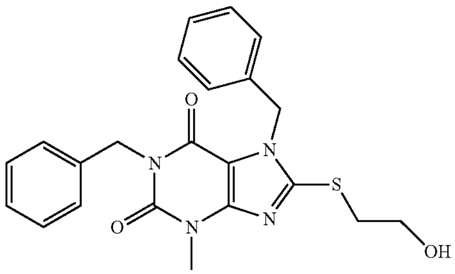

(Id.),

Compound 13

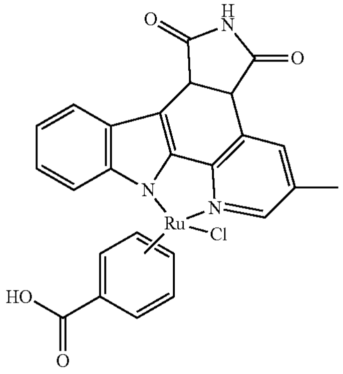

(Id.),

Compound 14

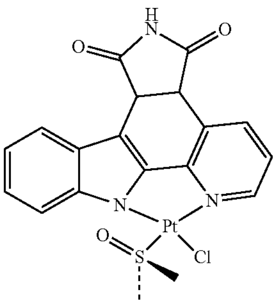

(Id.),

-continued
Compound 15
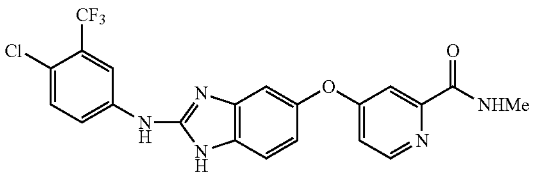
(Id.),
Compound 16
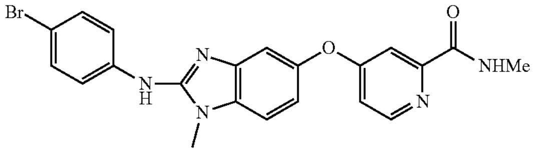
(Id.),
Compound 18
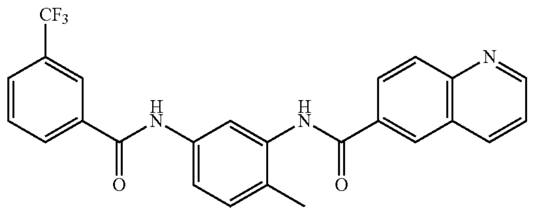
(Id.),
Compound 19
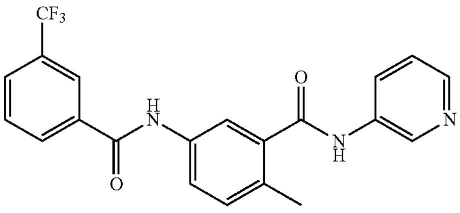
(Id.),
Compound 20
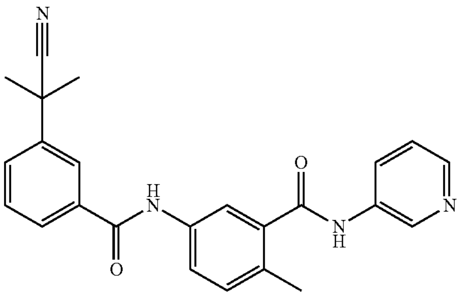
(Id.),
Compound 21
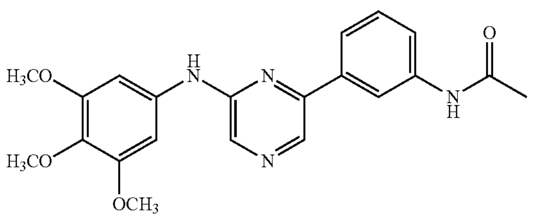
(Id.),
-continued
Compound 22
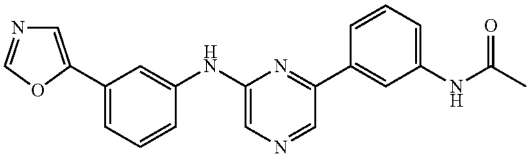
(Id.),
Compound 23
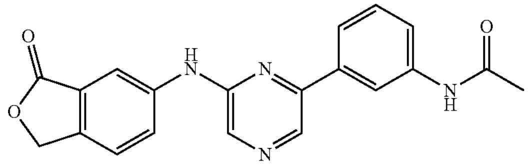
(Id.),
Compound 24
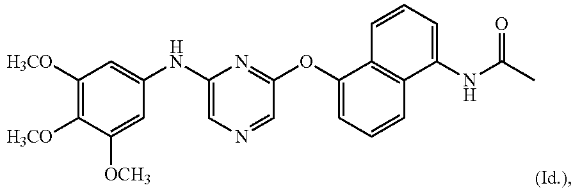
(Id.),
Compound 25
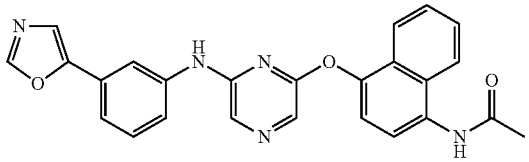
(Id.),
Compound 26
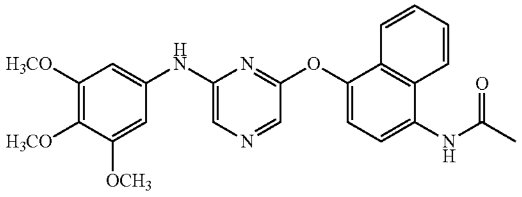
(Id.),
Compound 27
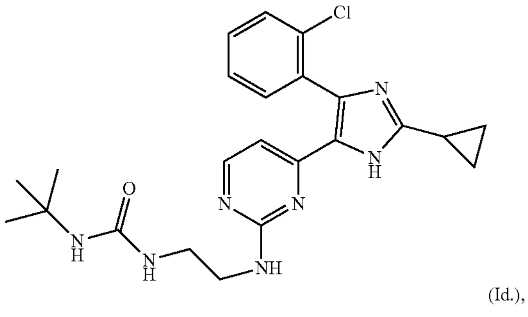
(Id.), Compound 28
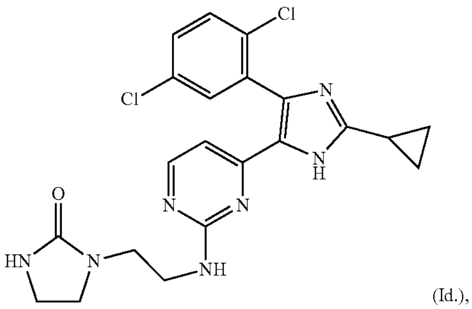
(Id.),
Compound 30
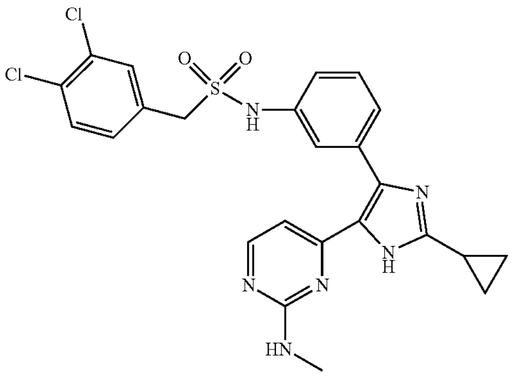
(Id.),
Compound 31
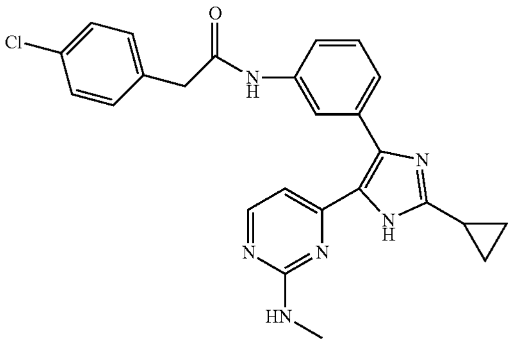
(Id.),
Compound 32
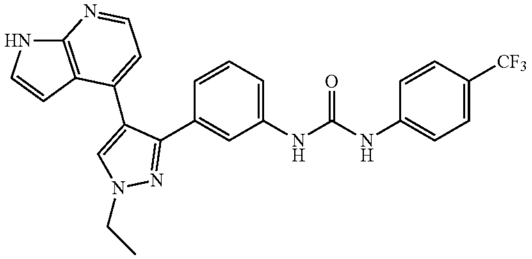
(Id.),
Compound 33
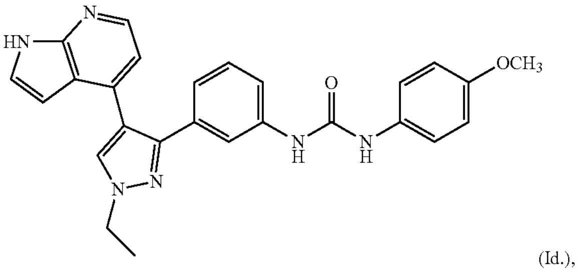
(Id.),
Compound 34
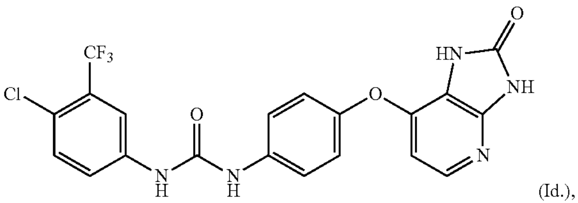
(Id.),
Compound 35
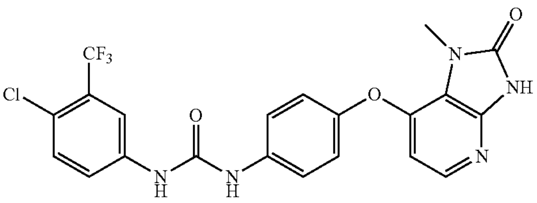
(Id.),
Compound 36
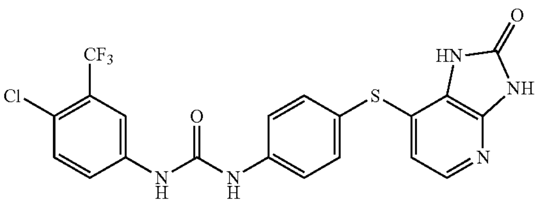
(Id.),
Compound 37
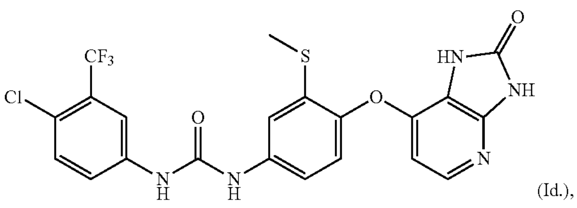
(Id.),
Compound 38
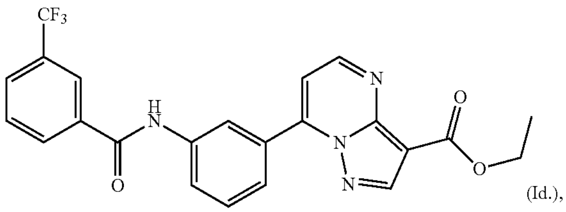
(Id.), -continued Compound 39

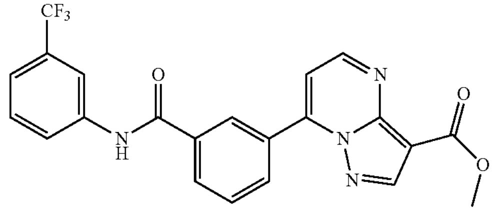

(Id.),

Compound 40

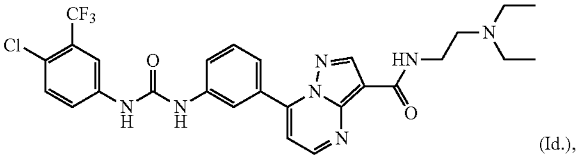

(Id.),

AAL881 (Novartis); AB-024 (Ambit Biosciences), ARQ-736 (ArQule), ARQ-761 (ArQule), AZ628 (Axon Medchem BV), BeiGene-283 (BeiGene), BIIB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 523 (cctatcgttagagtcttcctg) (Liu et al., 2007), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), RAF-265 (Novartis), RAF-365 (Novartis), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

As used herein, a "MEK inhibitor" means those substances that (i) directly interact with MEK, e.g., by binding to MEK and (ii) decrease the expression or the activity of MEK. Thus, inhibitors that act upstream of MEK, such as RAS inhibitors and RAF inhibitors, are not MEF inhibitors according to the present invention. Non-limiting examples of MEK inhibitors include anthrax toxin, antroquinonol (Golden Biotechnology), ARRY-142886 (6-(4-bromo-2-chloro-phenylamino)-7-fluoro-3-methyl-3H-benzoimidazole-5-carboxylic acid (2-hydroxy-ethoxy)-amide) (Array BioPharma), ARRY-438162 (Array BioPharma), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxyphenyl)-oxanaphthalen-4-one) (Pfizer), PD 184352 (CI-1040) (Pfizer), PD-0325901 (Pfizer), pimasertib (Santhera Pharmaceuticals), RDEA119 (Ardea Biosciences/Bayer), refametinib (AstraZeneca), RG422 (Chugai Pharmaceutical Co.), RO092210 (Roche), RO4987655 (Hoffmann-La Roche), RO5126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio)butadiene) (Sigma), WX-554 (Wilex), YopJ polypeptide (Mittal et al., 2010), pharmaceutically acceptable salts thereof, and combinations thereof.

In one aspect of this embodiment, substantially all phosphorylation of ribosomal s6 kinase (RSK) is inhibited after administration of BVD-523 or a pharmaceutically acceptable salt thereof. As used herein in the context of RSK phosphorylation, "substantially all" means a reduction of greater than 50% reduction, preferably greater than 55%, 60%, 65%, 70%, 75%, 80%, 85%, 90%, 91%, 92%, 93%, 94%, 95%, 96%, 97%, 98%, or 99% reduction.

In another aspect of this embodiment, the cancer has MAPK activity. As used herein, having "MAPK activity" means that proteins downstream of ERK are still active, even if proteins upstream of ERK may not be active. Such a cancer may be a solid tumor cancer or a hematologic cancer.

In the present invention, cancers include both solid and hematologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver tumor/cancer, lung tumor/cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms.

Preferably, the cancer is selected from the group consisting of a cancer of the large intestine, breast cancer, pancreatic cancer, skin cancer, and endometrial cancers. More preferably, the cancer is melanoma.

In another aspect of this embodiment, the method further comprises administering to the subject at least one additional therapeutic agent effective for treating or ameliorating the effects of the cancer. The additional therapeutic agent may be selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', $F(ab')_2$, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Cetuximab (Erbitux), bevacizumab (Avastin), and Ibritumomab (Zevalin).

Cytotoxic agents according to the present invention include DNA damaging agents, antimetabolites, anti-microtubule agents, antibiotic agents, etc. DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and pemetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation vinca alkaloids, paclitaxel (Taxol®), docetaxel (Taxotere®), and ixabepilone (Ixempra®). Antibiotic agents include without limitation actinomycin, anthracyclines, valrubicin, epirubicin, bleomycin, plicamycin, mitomycin, pharmaceutically acceptable salts thereof, prodrugs, and combinations thereof.

Cytotoxic agents according to the present invention also include an inhibitor of the PI3K/Akt pathway. Non-limiting examples of an inhibitor of the PI3K/Akt pathway include A-674563 (CAS #552325-73-2), AGL 2263, AMG-319 (Amgen, Thousand Oaks, CA), AS-041164 (5-benzo[1,3] dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, CA), BML-257 (CAS #32387-96-5), CAL-120 (Gilead Sciences, Foster City, CA), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, MA), perifosine, PHT-427 (CAS #1191951-57-1), PI3 kinase delta inhibitor, Merck KGaA (Merck & Co., Whitehouse Station, NJ), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, CA), PI3-delta inhibitors, Cellzome (Cellzome AG, Heidelberg, Germany), PI3-delta inhibitors, Intellikine (Intellikine Inc., La Jolla, CA), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, NY), SF-1126 (Semafore Pharmaceuticals, Indianapolis, IN), SH-5, SH-6, Tetrahydro Curcumin, TG100-115 (Targegen Inc., San Diego, CA), Triciribine, X-339 (Xcovery, West Palm Beach, FL), XL-499 (Evotech, Hamburg, Germany), pharmaceutically acceptable salts thereof, and combinations thereof.

In the present invention, the term "toxin" means an antigenic poison or venom of plant or animal origin. An example is diphtheria toxin or portions thereof.

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, I-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In the present invention, the term "photoactive therapeutic agent" means compounds and compositions that become active upon exposure to light. Certain examples of photoactive therapeutic agents are disclosed, e.g., in U.S. Patent Application Serial No. 2011/0152230 A1, "Photoactive Metal Nitrosyls For Blood Pressure Regulation And Cancer Therapy."

In the present invention, the term "radiosensitizing agent" means a compound that makes tumor cells more sensitive to radiation therapy. Examples of radiosensitizing agents include misonidazole, metronidazole, tirapazamine, and trans sodium crocetinate.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, lipotropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostatin, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an "anti-angiogenesis" agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

Another embodiment of the present invention is a method for treating or ameliorating the effects of a cancer in a subject. The method comprises:

(a) identifying a subject with cancer that has become refractory or resistant to BRAF inhibitor therapy, MEK inhibitor therapy, or BRAF and MEK inhibitor therapy; and (b) administering to the subject with said refractory or resistant cancer an effective amount of an ERK inhibitor, which is BVD-523 or a pharmaceutically acceptable salt thereof.

Suitable and preferred subjects are as disclosed herein. In this embodiment, the methods may be used to treat the cancers disclosed above. In accordance with the present invention, the cancer may have MAPK activity.

In one aspect of this embodiment, identifying a subject with cancer that is refractory or resistant to BRAF and/or MEK inhibitor therapy comprises:

(a) obtaining a biological sample from the subject; and (b) screening the sample to determine whether the subject has become resistant to an inhibitor therapy selected from the group consisting of BRAF inhibitor therapy, MEK inhibitor therapy, and combinations thereof.

In the present invention, biological samples include, but are not limited to, blood, plasma, urine, skin, saliva, and biopsies. Biological samples are obtained from a subject by routine procedures and methods which are known in the art.

Preferably, screening for a cancer that is refractory or resistant to BRAF inhibitor therapy may comprise, e.g., identifying (i) a switch between RAF isoforms, (ii) upregulation of RTK or NRAS signaling, (iii) reactivation of mitogen activated protein kinase (MAPK) signaling, (iv) the presence of a MEK activating mutation, and combinations thereof.

A switch between RAF isoforms may occur in subjects having acquired resistance to BRAF inhibitor therapy. To detect such a switch, BRAF inhibitor-resistant tumor cells may be retrieved from a patient and analyzed via Western blotting for ERK and phospho-ERK levels in the presence of a BRAF inhibitor. Comparison with BRAF inhibitor-sensitive cells treated with a BRAF inhibitor may reveal higher levels of phospho-ERK in BRAF inhibitor-resistant tumor cells, implying that a switch has taken place in which another RAF isoform phosphorylates ERK in place of BRAF. Confirmation of which RAF isoform has taken over may involve sh/siRNA-mediated knockdown of ARAF and CRAF individually in BRAF inhibitor-resistant cells exposed to a BRAF inhibitor, followed by subsequent Western blotting for ERK and phospho-ERK levels. If, for example, ARAF knockdown in BRAF inhibitor-resistant cells exposed to a BRAF inhibitor still results in high levels of phospho-ERK, it would indicate that CRAF has taken over phosphorylating ERK. Likewise, if CRAF was knocked down in BRAF inhibitor-resistant cells exposed to BRAF inhibitor and ERK was still highly phosphorylated, it would mean that ARAF has taken over ERK phosphorylation. RAF isoform switching may also involve simultaneous knockdown of ARAF and CRAF in BRAF inhibitor-resistant cells in the presence of BRAF inhibitor, effectively blocking all RAF-mediated phosphorylation. A resulting decrease in ERK phosphorylation would indicate that the BRAF inhibitor-resistant cells have the capacity to switch between RAF isoforms in order to phosphorylate ERK (Villanueva, et al., 2010).

Upregulation of RTK or NRAS signaling may also be a cause of BRAF inhibitor resistance. Detection may, e.g., first involve using Western blotting protocols with phospho-specific antibodies to analyze the activation of the downstream RAF effectors MEK1/2 and ERK1/2. If BRAF inhibitor-resistant cells show high activation levels of these proteins in the presence of a BRAF inhibitor, RTK or NRAS upregulation may be the cause. Gene expression profiling (or other related methods) of BRAF inhibitor-resistant cells in the presence of a BRAF inhibitor may reveal higher expression levels of KIT, MET, EGFR, and PDGFRβ RTKs as compared to BRAF inhibitor-sensitive cells. Real-time quantitative polymerase chain reaction experiments, or other similar procedures, focusing on any of these genes may confirm higher expression levels while phospho-RTK arrays (R&D Systems, Minneapolis, MN) may show elevated activation-associated tyrosine phosphorylation. Alternatively, NRAS activation may be detected by various gene sequencing protocols. Activating mutations in NRAS, particularly Q61K, may indicate that B-RAF signaling has been bypassed. In melanoma cells, activated NRAS uses C-RAF to signal to MEK-ERK. Thus, activated NRAS may enable a similar bypass pathway in BRAF inhibitor-resistant cells exposed to BRAF inhibitor. Further confirmation of these mechanisms in a given BRAF inhibitor-resistant sample may be accomplished, for example, using sh/siRNA-mediated knockdown of upregulated RTKs or activated NRAS in the presence of BRAF inhibitor. Any significant levels of growth inhibition may indicate that upregulation of RTK or NRAS signaling is the cause of BRAF inhibition in that particular sample (Nazarian, et al., 2010).

Detecting reactivation of MAPK signaling in BRAF inhibitor-resistant cells may indicate another bypass mechanism for BRAF inhibitor resistance. COT and C-RAF have been shown to be upregulated in a BRAF V600E background exposed to BRAF inhibitor. Quantitative real-time RT-PCR, e.g., may reveal increased COT expression in BRAF inhibitor-resistant cells in the presence of BRAF inhibitor. Furthermore, sh/siRNA-mediated knockdown of COT in BRAF inhibitor-resistant cells in the presence of BRAF inhibitor may reduce the viability of BRAF inhibitor-resistant cells, indicating that these particular cells may be sensitive to COT inhibition and/or combination BRAF inhibitor/MEK inhibitor treatments (Johannessen, et al., 2010).

Reactivation of MAPK signaling may also be accomplished in a BRAF inhibitor-resistant background by activating mutations in MEK1. Targeted, massively parallel sequencing of genomic DNA from a BRAF inhibitor-resistant tumor may reveal activating mutations in MEK1, such as C121S, G128D, N122D, and Y130, among others. Other, undocumented mutations in MEK1 may be analyzed by, for example, expressing the particular mutation in a BRAF inhibitor-sensitive cell line such as A375. Determining levels of growth inhibition in these cells upon exposure to BRAF inhibitor may indicate if the MEK1 mutation is causing resistance to BRAF inhibitory therapy. To confirm such a finding, Western blotting for elevated levels of phospho-ERK1/2 in cells ectopically expressing the MEK1 mutation may indicate that the MEK1 mutation is allowing the BRAF inhibitor-resistant tumor to bypass BRAF and promote phosphorylation of ERK through MEK1 (Wagle, et al., 2011).

In accordance with the present invention, screening for a cancer that is refractory or resistant to MEK inhibitor therapy may comprise, e.g., identifying (i) amplification of mutant BRAF, (ii) STAT3 upregulation, (iii) mutations in the allosteric pocket of MEK that directly block binding of inhibitors to MEK or lead to constitutive MEK activity, and combinations thereof.

Amplification of mutant BRAF may cause MEK inhibitor resistance. MEK inhibitor resistance is typically associated with high levels of phosphorylated ERK and MEK in the presence of a MEK inhibitor, which may be assessed via, for example, Western blotting. Amplification of mutant BRAF in MEK inhibitor-resistant cell lines may be detected by, for example, fluorescence in situ hybridization (FISH) or quantitative PCR from genomic DNA of the resistant cell lines. Confirmation that BRAF amplification is a primary cause of MEK inhibitor resistance may entail using BRAF-targeted sh/siRNAs in resistant cells. If a significant decrease in MEK or ERK phosphorylation is observed, BRAF amplification may be a suitable target for further therapeutic approaches. (Corcoran, et al., 2010).

Identifying STAT3 upregulation may indicate that a particular tumor sample is resistant to MEK inhibitor therapy. Genome-wide expression profiling may reveal the STAT3 pathway to be upregulated in a tumor. Other techniques, such as Western blotting for phospho-STAT3 and real-time qPCR for the STAT pathway-associated genes JAK1 and IL6ST may reveal upregulated STAT3. Further confirmation that STAT3 upregulation causes MEK inhibitor resistance in a particular sample may comprise the use of sh/siRNAs against STAT3 in the sample followed by appropriate Western blotting for MEK and ERK activation as well as phospho-STAT3 and total STAT3. Growth inhibition studies may show that STAT3 knockdown sensitizes previously MEK inhibitor-resistant cells to MEK inhibition. A similar effect may be seen if the sample were exposed to a STAT3 inhibitor such as JSI-124. Additional confirmation that STAT3 upregulation is the cause of MEK inhibitor resistance in a particular tumor could arise from Western blotting for BIM expression, including BIM-EL, BIM-L, and BIM-SL. BIM expression leads to MEK inhibitor-induced apoptosis, thus STAT3 upregulation may lower BIM levels. STAT3 is known to regulate the expression of miR 17-92, which suppresses BIM expression. Upregulated STAT3 may lead to higher levels of miR 17-92, which will lower BIM levels and promote resistance to MEK inhibition. Thus, real-time qPCR of miR 17-92 levels may also assist in assessing whether STAT3 upregulation is causing MEK inhibition resistance in a particular sample. (Dai, et al., 2011).

Mutations in the allosteric pocket of MEK that can directly block binding of inhibitors to MEK or lead to constitutive MEK activity may be detected by methods disclosed below. Such mutations have been identified previously by Emery and colleagues (Emery, et al., 2009) as well as Wang and colleagues (Wang et al., 2011). Other mutations may affect MEK1 codons located within or abutting the N-terminal negative regulatory helix, such as P124L and Q56P. (Id.).

Methods for identifying mutations in nucleic acids, such as the above identified MEK genes, are known in the art. Nucleic acids may be obtained from biological samples. In the present invention, biological samples include, but are not limited to, blood, plasma, urine, skin, saliva, and biopsies. Biological samples are obtained from a subject by routine procedures and methods which are known in the art.

Non-limiting examples of methods for identifying mutations include PCR, sequencing, hybrid capture, in-solution capture, molecular inversion probes, fluorescent in situ hybridization (FISH) assays, and combinations thereof.

Various sequencing methods are known in the art. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

PCR-based methods for detecting mutations are known in the art and employ PCR amplification, where each target sequence in the sample has a corresponding pair of unique, sequence-specific primers. For example, the polymerase chain reaction-restriction fragment length polymorphism (PCR-RFLP) method allows for rapid detection of mutations after the genomic sequences are amplified by PCR. The mutation is discriminated by digestion with specific restriction endonucleases and is identified by electrophoresis. See, e.g., Ota et al., 2007. Mutations may also be detected using real time PCR. See, e.g., International Application publication No. WO2012046981.

Hybrid capture methods are known in the art and are disclosed in e.g., U.S. Patent Publication No. 20130203632 and U.S. Pat. Nos. 8,389,219 and 8,288,520. These methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture).

Molecular Inversion Probe (MIP) techniques are known in the art and are disclosed in e.g., Absalan et al., 2008. This method uses MIP molecules, which are special "padlock" probes (Nilsson et al, 1994) for genotyping. A MIP molecule is a linear oligonucleotide that contains specific regions, universal sequences, restriction sites and a Tag (index) sequence (16-22 bp). A MIP hybridizes directly around the genetic marker/SNP of interest. The MIP method may also use a number of "padlock" probe sets that hybridize to genomic DNA in parallel (Hardenbol et al., 2003). In case of a perfect match, genomic homology regions are ligated by undergoing an inversion in configuration (as suggested by the name of the technique) and creating a circular molecule. After the first restriction, all molecules are amplified with universal primers. Amplicons are restricted again to ensure short fragments for hybridization on a microarray. Generated short fragments are labeled and, through a Tag sequence, hybridized to a cTag (complementary strand for index) on an array. After the formation of Tag-cTag duplex, a signal is detected.

The following Tables 1, 2, and 3 show the SEQ ID Nos. of representative nucleic acid and amino acid sequences of wild type BRAF, N-RAS, and MEK1 from various animals in the sequence listing. These sequences may be used in methods for identifying subjects with mutant BRAF, N-RAS, and MEK1 genotypes.

TABLE 1

BRAF sequences

| SEQ ID NO. | polypeptide or nucleic acid sequence | Organism | Other information |
|---|---|---|---|
| 1 | nucleic acid | human | |
| 2 | polypeptide | human | |
| 3 | nucleic acid | rat (*Rattus norvegicus*) | |
| 4 | polypeptide | rat (*Rattus norvegicus*) | |
| 5 | nucleic acid | mouse, *Mus musculus* | |

TABLE 1-continued

BRAF sequences

| SEQ ID NO. | polypeptide or nucleic acid sequence | Organism | Other information |
|---|---|---|---|
| 6 | polypeptide | mouse, *Mus musculus* | |
| 7 | nucleic acid | rabbit, *Oryctolagus cuniculus* | |
| 8 | polypeptide | rabbit, *Oryctolagus cuniculus* | |
| 9 | nucleic acid | guinea pig, *Cavia porcellus* | |
| 10 | polypeptide | guinea pig, *Cavia porcellus* | |
| 11 | nucleic acid | dog, *Canis lupus familiaris* | variant x1 |
| 12 | polypeptide | dog, *Canis lupus familiaris* | variant x1 |
| 13 | nucleic acid | dog, *Canis lupus familiaris* | variant x2 |
| 14 | polypeptide | dog, *Canis lupus familiaris* | variant x2 |
| 15 | nucleic acid | cat, *Felis catus* | |
| 16 | polypeptide | cat, *Felis catus* | |
| 17 | nucleic acid | cow, *Bos taurus* | variant X1 |
| 18 | polypeptide | cow, *Bos taurus* | variant X1 |
| 19 | nucleic acid | cow, *Bos taurus* | variant X2 |
| 20 | polypeptide | cow, *Bos taurus* | variant X2 |
| 21 | nucleic acid | cow, *Bos taurus* | variant X3 |
| 22 | polypeptide | cow, *Bos taurus* | variant X3 |
| 23 | nucleic acid | cow, *Bos taurus* | variant X4 |
| 24 | polypeptide | cow, *Bos taurus* | variant X4 |
| 25 | nucleic acid | cow, *Bos taurus* | variant X5 |
| 26 | polypeptide | cow, *Bos taurus* | variant X5 |
| 27 | nucleic acid | cow, *Bos taurus* | variant X6 |
| 28 | polypeptide | cow, *Bos taurus* | variant X6 |
| 29 | nucleic acid | cow, *Bos taurus* | variant X7 |
| 30 | polypeptide | cow, *Bos taurus* | variant X7 |
| 31 | nucleic acid | cow, *Bos taurus* | variant X8 |
| 32 | polypeptide | cow, *Bos taurus* | variant X8 |
| 33 | nucleic acid | cow, *Bos taurus* | variant X9 |
| 34 | polypeptide | cow, *Bos taurus* | variant X9 |
| 35 | nucleic acid | cow, *Bos taurus* | variant X10 |
| 36 | polypeptide | cow, *Bos taurus* | variant X10 |
| 37 | nucleic acid | cow, *Bos taurus* | variant X11 |
| 38 | polypeptide | cow, *Bos taurus* | variant X11 |
| 39 | nucleic acid | cow, *Bos taurus* | variant 2 |
| 40 | polypeptide | cow, *Bos taurus* | variant 2 |
| 41 | nucleic acid | horse, *Equus caballus* | |
| 42 | polypeptide | horse, *Equus caballus* | |
| 43 | nucleic acid | chicken, *Gallus gallus* | |
| 44 | polypeptide | chicken, *Gallus gallus* | |

TABLE 2

N-RAS sequences

| SEQ ID NO. | polypeptide or nucleic acid sequence | Organism | Other information |
|---|---|---|---|
| 45 | nucleic acid | human | |
| 46 | polypeptide | human | |
| 47 | nucleic acid | rat (*Rattus norvegicus*) | |
| 48 | polypeptide | rat (*Rattus norvegicus*) | |
| 49 | nucleic acid | mouse, *Mus musculus* | |
| 50 | polypeptide | mouse, *Mus musculus* | |
| 51 | nucleic acid | guinea pig, *Cavia porcellus* | |
| 52 | polypeptide | guinea pig, *Cavia porcellus* | |
| 53 | nucleic acid | guinea pig, *Cavia porcellus* | variant X1 |

TABLE 2-continued

N-RAS sequences

| SEQ ID NO. | polypeptide or nucleic acid sequence | Organism | Other information |
|---|---|---|---|
| 54 | polypeptide | guinea pig, *Cavia porcellus* | variant X1 |
| 55 | nucleic acid | dog, *Canis lupus familiaris* | |
| 56 | polypeptide | dog, *Canis lupus familiaris* | |
| 57 | nucleic acid | cat, *Felis catus* | |
| 58 | polypeptide | cat, *Felis catus* | |
| 59 | nucleic acid | cow, *Bos taurus* | |
| 60 | polypeptide | cow, *Bos taurus* | |
| 61 | nucleic acid | chicken, *Gallus gallus* | |
| 62 | polypeptide | chicken, *Gallus gallus* | |

TABLE 3

MEK1 sequences

| SEQ ID NO. | polypeptide or nucleic acid sequence | Organism |
|---|---|---|
| 63 | nucleic acid | human |
| 64 | polypeptide | human |
| 65 | nucleic acid | rat (*Rattus norvegicus*) |
| 66 | polypeptide | rat (*Rattus norvegicus*) |
| 67 | nucleic acid | mouse, *Mus musculus* |
| 68 | polypeptide | mouse, *Mus musculus* |
| 69 | nucleic acid | rabbit, *Oryctolagus cuniculus* |
| 70 | polypeptide | rabbit, *Oryctolagus cuniculus* |
| 71 | nucleic acid | guinea pig, *Cavia porcellus* |
| 72 | polypeptide | guinea pig, *Cavia porcellus* |
| 73 | nucleic acid | dog, *Canis lupus familiaris* |
| 74 | polypeptide | dog, *Canis lupus familiaris* |
| 75 | nucleic acid | cat, *Felis catus* |
| 76 | polypeptide | cat, *Felis catus* |
| 77 | nucleic acid | cow, *Bos taurus* |
| 78 | polypeptide | cow, *Bos taurus* |
| 79 | nucleic acid | horse, *Equus caballus* |
| 80 | polypeptide | horse, *Equus caballus* |
| 81 | nucleic acid | chicken, *Gallus gallus* |
| 82 | polypeptide | chicken, *Gallus gallus* |

In another aspect of this embodiment, the method further comprises administering at least one additional therapeutic agent, preferably an inhibitor of the PI3K/Akt pathway, as disclosed herein.

A further embodiment of the present invention is a method for treating or ameliorating the effects of cancer in a subject, which cancer is refractory or resistant to BRAF inhibitor therapy, MEK inhibitor therapy, or both. The method comprises administering to the subject an effective amount of BVD-523 or a pharmaceutically acceptable salt thereof.

Suitable and preferred subjects are as disclosed herein. In this embodiment, the methods may be used to treat the cancers disclosed above, including those cancers with the mutational backgrounds, resistance profiles, and MAPK activity identified above. Methods of identifying such mutations are also as set forth above.

In a further aspect of this embodiment, the method further comprises administering to the subject at least one additional therapeutic agent, preferably an inhibitor of the PI3K/Akt pathway, as disclosed herein.

Another embodiment of the present invention is a method for identifying a subject having cancer who would benefit from therapy with an ERK inhibitor. The method comprises:

(a) obtaining a biological sample from the subject; and (b) screening the sample to determine whether the subject has one or more of the following markers:

(i) a switch between RAF isoforms, (ii) upregulation of RTK or NRAS signaling, (iii) reactivation of mitogen activated protein kinase (MAPK) signaling, (iv) the presence of a MEK activating mutation, (v) amplification of mutant BRAF, (vi) STAT3 upregulation, (vii) mutations in the allosteric pocket of MEK that directly block binding of inhibitors to MEK or lead to constitutive MEK activity, wherein the presence of one or more of the markers confirms that the subject's cancer is refractory or resistant to BRAF and/or MEK inhibitor therapy and that the subject would benefit from therapy with an ERK inhibitor, which is BVD-523 or a pharmaceutically acceptable salt thereof.

Suitable and preferred subjects are as disclosed herein. In this embodiment, the methods may be used to identify a subject having cancers disclosed above, including those cancers with the mutational backgrounds, resistance profiles, and MAPK activity identified above. Methods of identifying such mutations are also as set forth above.

In one aspect of this embodiment, the method further comprises administering BVD-523 or a pharmaceutically acceptable salt thereof to a subject having one or more of the markers. Preferably, the method additionally comprises administering to the subject having one or more of the markers at least one additional therapeutic agent, preferably an inhibitor of the PI3K/Akt pathway, as disclosed herein.

An additional embodiment of the present invention is a pharmaceutical composition for treating or ameliorating the effects of a cancer in a subject, which cancer is refractory or resistant to non-ERK MAPK pathway therapy. The composition comprises a pharmaceutically acceptable carrier or diluent and an effective amount of BVD-523 or a pharmaceutically acceptable salt thereof.

Suitable and preferred subjects and types of non-ERK MAPK pathway inhibitor therapy are as disclosed herein. In this embodiment, the pharmaceutical composition may be used to treat the cancers disclosed above, including those cancers with the mutational backgrounds, resistance profiles, and MAPK activity identified above. Methods of identifying such mutations are also as set forth above.

In one aspect of this embodiment, the pharmaceutical composition further comprises at least one additional therapeutic agent, preferably an inhibitor of the PI3K/Akt pathway, as disclosed herein.

Another embodiment of the present invention is a kit for treating or ameliorating the effects of a cancer in a subject, which cancer is refractory or resistant to non-ERK MAPK pathway therapy. This kit comprises any pharmaceutical composition according to the present invention packaged together with instructions for its use.

The kits may also include suitable storage containers, e.g., ampules, vials, tubes, etc., for each pharmaceutical composition and other reagents, e.g., buffers, balanced salt solutions, etc., for use in administering the pharmaceutical compositions to subjects. The pharmaceutical compositions and other reagents may be present in the kits in any convenient form, such as, e.g., in a solution or in a powder form. The kits may further include a packaging container, optionally having one or more partitions for housing the pharmaceutical composition and other optional reagents.

Suitable and preferred subjects and types of non-ERK MAPK pathway inhibitor therapy are as disclosed herein. In this embodiment, the kit may be used to treat the cancers disclosed above, including those cancers with the mutational backgrounds, resistance profiles, and MAPK activity identified herein. Methods of identifying such mutations are as set forth above.

In one aspect of this embodiment, the kit further comprises at least one additional therapeutic agent, preferably an inhibitor of the PI3K/Akt pathway, as disclosed herein.

Another embodiment of the present invention is a method for inhibiting phosphorylation of RSK in a cancer cell that is refractory or resistant to a non-ERK MAPK pathway inhibitor. The method comprises contacting the cancer cell with an effective amount of BVD-523 or a pharmaceutically acceptable salt thereof for a period of time sufficient for phosphorylation of RSK in the cancer cell to be inhibited. In this embodiment, "contacting" means bringing BVD-523 or a pharmaceutically acceptable salt thereof and optionally one or more additional therapeutic agents into close proximity to the cancer cells. This may be accomplished using conventional techniques of drug delivery to mammals, or in the in vitro situation by, e.g., providing BVD-523 or a pharmaceutically acceptable salt thereof and optionally other therapeutic agents to a culture media in which the cancer cells are located. In the ex vivo situation, contacting may be carried out by, e.g., providing BVD-523 or a pharmaceutically acceptable salt thereof and optionally other therapeutic agents to a cancerous tissue.

Suitable and preferred types of non-ERK MAPK pathway inhibitors are as disclosed herein. In this embodiment, effecting cancer cell death may be accomplished in cancer cells having various mutational backgrounds, resistance profiles, and MAPK activity as disclosed above. Methods of identifying such mutations are also as set forth above.

The methods of this embodiment, which may be carried out in vitro, ex vivo, or in vivo, may be used to effect cancer cell death, by e.g., killing cancer cells, in cells of the types of cancer disclosed herein.

In one aspect of this embodiment, greater than 50% of RSK phosphorylation is inhibited. In another aspect of this embodiment, greater than 75% of RSK phosphorylation is inhibited. In an additional aspect of this embodiment, greater than 90% of RSK phosphorylation is inhibited. In a further aspect of this embodiment, greater than 95% of RSK phosphorylation is inhibited. In another aspect of this embodiment, greater than 99% of RSK phosphorylation is inhibited. In an additional aspect of this embodiment, 100% of RSK phosphorylation is inhibited.

In a further aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

In a further aspect of this embodiment, the contacting step comprises administering BVD-523 or a pharmaceutically acceptable salt to a subject from whom the cancer cell was obtained.

In the present invention, an "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a compound or composition according to the invention will be that amount of the composition, which is the lowest dose effective to produce the desired effect. The effective dose of a compound or composition of the present invention may be administered as two, three, four, five, six or more sub-doses, administered separately at appropriate intervals throughout the day.

A suitable, non-limiting example of a dosage of a BVD-523 and other anti-cancer agents disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of BVD-523 and other anti-cancer agents disclosed herein, may be administered as two, three, four, five, six or more sub-doses, administered separately at appropriate intervals throughout the day.

The BVD-523, other inhibitors, and various other anti-cancer agents disclosed herein, or a pharmaceutical composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, BVD-523, other inhibitors, and various other anti-cancer agents disclosed herein, or a pharmaceutical composition of the present invention may be administered in conjunction with other treatments. BVD-523, other inhibitors, and various other anti-cancer agents disclosed herein, or a pharmaceutical composition of the present invention may be encapsulated or otherwise protected against gastric or other secretions, if desired.

The pharmaceutical compositions of the invention comprise one or more active ingredients in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, PA.).

Pharmaceutically acceptable diluents or carriers are well known in the art (see, e.g., Remington, The Science and Practice of Pharmacy ($21^{st}$ Edition, Lippincott Williams and Wilkins, Philadelphia, PA.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The present invention provides treatment of cancer which is refractory or resistant to non-ERK MAPK pathway inhibitor therapy and discloses combinations shown to enhance the effects of ERK inhibitors. Herein, applicants have also shown that the combination of different ERK inhibitors is likewise synergistic. Therefore, it is contemplated that the effects of the combinations described herein can be further improved by the use of one or more additional ERK inhibitors. Accordingly, some embodiments of the present invention include one or more additional ERK inhibitors.

The present invention also provides a method of treating a subject having an unresectable or metastatic BRAF600 mutation-positive melanoma comprising administering to the subject 600 mg BID of BVD-523 or a pharmaceutically acceptable salt thereof.

In some embodiments of the invention, the mutation is a $BRAF^{V600E}$ mutation.

The present invention also provides a composition for treating a subject having an unresectable or metastatic BRAF600 mutation-positive melanoma, the composition comprising 600 mg of BVD-523 or a pharmaceutically acceptable salt thereof and optionally a pharmaceutically acceptable carrier, adjuvant, or vehicle.

The following examples are provided to further illustrate the methods of the present invention. These examples are illustrative only and are not intended to limit the scope of the invention in any way.

EXAMPLES

Example 1

Materials and Methods

Cancer cell lines were maintained in cell culture under standard media and serum conditions. For dose escalation studies, A375 cells were split, grown to about 40-60% confluence, and then treated with the initial dose of the specified drug. Table 4 shows a summary of drug treatments that were escalated.

TABLE 4

Summary of Treatments Being Escalated

| Treatment | Inhibitor |
|---|---|
| 1 | Trametinib (MEKi) |
| 2 | Dabrafenib (BRAFi) |
| 3 | BVD-523 (ERKi) |
| 4 | Dabrafenib (BRAFi) + Trametinib (MEKi) |
| 5 | Dabrafenib (BRAFi) + BVD-523 (ERKi) |
| 6 | Trametinib (MEKi) + BVD-523 (ERKi) |

Figure 20:
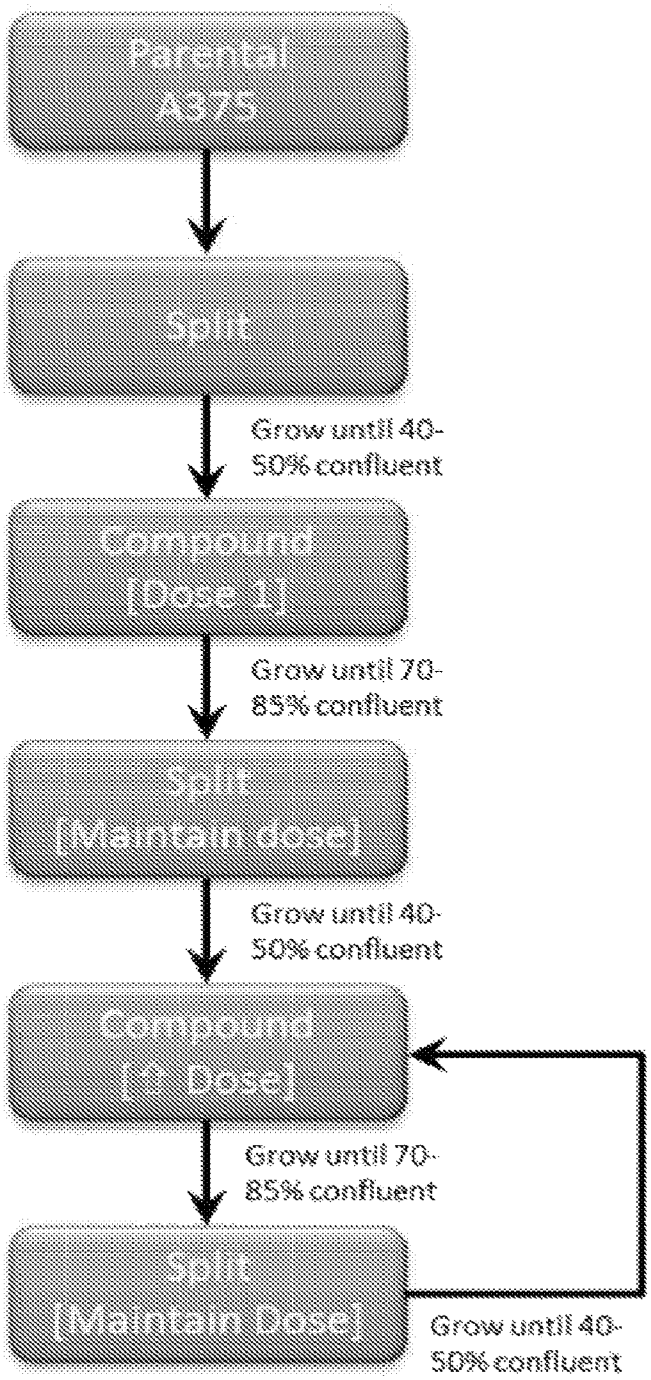
FIG. 20 is a flowchart showing the dose escalation protocol used herein.

Single agent dose escalations were performed based on Little et al., 2011 and are outlined in FIG. 20. Cells were then allowed to grow until 70-90% confluence and split. Split ratios were kept as "normal" as possible and reasonably consistent between treatments (e.g. a minimum of 50% of the normal split ratio of the parentals). Medium was refreshed every 3-4 days. When cells again reached about 40-60% confluence, the dose was escalated. In the event that the 40-60% window was missed, the cells were split again and dosed once they reached 40-60% confluence. Again, medium was refreshed every 3-4 days. The process was repeated as required (FIG. 20).

For single agent treatments, starting concentrations and dose increases were conducted by starting with the approximate $IC_{50}$, escalating in small increments or, gently, for the initial 4-5 doses, doubling the dose, increasing by the same increment for the next 4 doses, then moving to 1.5-fold increases in concentration for subsequent doses.

For combination treatments, starting concentrations and dose increases were conducted by starting with half of the approximate $IC_{50}$ of each compound (combination assay suggests this will result in about 40-70% inhibition range), escalating as per single agents (i.e. doing an initial doubling and then increasing by the same increment for the next 4 doses, then moving to 1.5-fold increases in concentration). Table 5 shows the projected dose increases using these schemes.

TABLE 5

Projected Dose Increases - Month 1

| Dose | Tram (nM) | Dab (nM) | BVD-523 (µM) | Dab/Tram Dab (nM) | Dab/Tram Tram (nM) | Dab/523 Dab (nM) | Dab/523 523 (µM) | Tram/523 Tram (nM) | Tram/523 523 (µM) |
|---|---|---|---|---|---|---|---|---|---|
| 1 | 1 | 5 | 0.16 | 2.5 | 0.5 | 2.5 | 0.08 | 0.5 | 0.08 |
| 2 | 2 | 10 | 0.32 | 5 | 1 | 5 | 0.16 | 1 | 0.16 |
| 3 | 3 | 15 | 0.48 | 7.5 | 1.5 | 7.5 | 0.24 | 1.5 | 0.24 |
| 4 | 4 | 20 | 0.64 | 10 | 2 | 10 | 0.32 | 2 | 0.32 |
| 5 | 5 | 25 | 0.80 | 12.5 | 2.5 | 12.5 | 0.40 | 2.5 | 0.40 |
| 6 | 8 | 38 | 1.2 | 19 | 4 | 19 | 0.6 | 4 | 0.6 |
| 7 | 11 | 56 | 1.8 | 28 | 6 | 28 | 0.9 | 6 | 0.9 |
| 8 | 17 | 84 | 2.7 | 42 | 8 | 42 | 1.4 | 8 | 1.4 |
| 9 | 25 | 127 | 4.1 | 63 | 13 | 63 | 2.0 | 13 | 2.0 |
| 10 | 38 | 190 | 6.1 | 95 | 19 | 95 | 3.0 | 19 | 3.0 |
| 11 | 57 | 285 | 9.1 | 142 | 28 | 142 | 4.6 | 28 | 4.6 |
| 12 | 85 | 427 | 13.7 | 214 | 43 | 214 | 6.8 | 43 | 6.8 |
| 13 | 128 | 641 | 20.5 | 320 | 64 | 320 | 10.3 | 64 | 10.3 |
| 14 | 192 | 961 | 30.8 | 481 | 96 | 481 | 15.4 | 96 | 15.4 |
| 15 | 288 | 1442 | 46.1 | 721 | 144 | 721 | 23.1 | 144 | 23.1 |
| 16 | 432 | 2162 | 69.2 | 1081 | 216 | 1081 | 34.6 | 216 | 34.6 |
| 17 | 649 | 3244 | 103.8 | 1622 | 324 | 1622 | 51.9 | 324 | 51.9 |
| 18 | 973 | 4865 | 155.7 | 2433 | 487 | 2433 | 77.8 | 487 | 77.8 |
| 19 | 1460 | 7298 | 233.5 | 3649 | 730 | 3649 | 116.8 | 730 | 116.8 |
| 20 | 2189 | 10947 | 350.3 | 5474 | 1095 | 5474 | 175.2 | 1095 | 175.2 |

Clonal resistant cell populations were derived from resistant cell pools by limiting dilution.

Proliferation assays were used to track changes in sensitivity to the escalated agent(s) at appropriate time intervals (e.g. each month, although the timing is dependent on adequate cell numbers being available). For proliferation assays, cells were seeded in 96-well plates at 3000 cells per well in drug-free DMEM medium containing 10% FBS and allowed to adhere overnight prior to addition of compound or vehicle control. Compounds were prepared from DMSO stocks to give a final concentration range as shown in FIG. 2A-FIG. 2H. The final DMSO concentration was constant at 0.1%. Test compounds were incubated with the cells for 96 hours at 37° C. and 5% $CO_2$ in a humidified atmosphere. Alamar Blue 10% (v/v) was then added and incubated for 4 hours and fluorescent product was detected using a BMG FLUOstar plate reader. The average media only background value was deducted and the data analyzed using a 4-parameter logistic equation in GraphPad Prism. Paclitaxel was used as a positive control.

Proliferation assays for month 1 were initiated at day 28 using cells growing in the concentrations of each agent indicated in Table 6.

TABLE 6

Initial Concentrations of Drugs Used in Proliferation Assays—Month 1

| Line | Dab | Tram | BVD-523 |
|---|---|---|---|
| Parental | — | — | — |
| Tram | — | 2 nM | — |
| Dab | 15 nM | — | — |
| BVD-523 | — | — | 0.48 µM |
| Tram + Dab | 5 nM | 1 nM | — |
| Dab + BVD-523 | 7.5 nM | — | 0.24 µM |
| Tram + BVD-523 | — | 1 nM | 0.16 µM |

Proliferation assays for month 2 were initiated at day 56 using cells growing in the concentrations of each agent indicated in Table 7.

TABLE 7

Initial Concentrations of Drugs Used in Proliferation Assays—Month 2

| Line | Dab | Tram | BVD-523 |
|---|---|---|---|
| Parental | — | — | — |
| Tram | — | 8 nM | — |
| Dab | 127 nM | — | — |
| BVD-523 | — | — | 0.8 µM |
| Tram + Dab | 10 nM | 2 nM | — |
| Dab + BVD-523 | 12.5 nM | — | 0.4 µM |
| Tram + BVD-523 | — | 2 nM | 0.32 µM |

At the end of the 3 month escalation period, cultures were maintained at the top concentration for 2 weeks prior to the final round of proliferation assays and potential single cell cloning. As the proliferation assays/single cell cloning required actively proliferating cells, for treatments where cells were proliferating very slowly at the top concentration or that were only recently escalated, a backup culture was also maintained at a lower concentration (Table 8). For the BVD-523 treatment, where cells appeared to have almost completely stopped growing and looked particularly fragile at the top concentration (1.8 µM), cultures were maintained at a lower concentration for the 2 week period.

TABLE 8

Details of Treatments Being Cultured at a Fixed Concentration for 2 Weeks

| Treatment | Inhibitor | Culture 1 | Backup Culture |
|---|---|---|---|
| 1 | Tram | 160 nM | 80 nM |
| 2 | Dab | 3.2 pM | — |
| 3 | BVD-523 | 1.2 pM | 0.8 µM |
| 4 | Dab + Tram | D: 160 nM<br>T: 30 nM | D: 80 nM<br>T: 16 nM |

TABLE 8-continued

| Details of Treatments Being Cultured at a Fixed Concentration for 2 Weeks | | | |
|---|---|---|---|
| Treatment | Inhibitor | Culture 1 | Backup Culture |
| 5 | Dab + BVD-523 | D: 42 nM<br>523: 1.4 μM | D: 28 nM<br>523: 0.9 μM |
| 6 | Tram + BVD-523 | T: 4 nM<br>523: 0.6 μM | T: 2.5 nM<br>523: 0.4 μM |

Proliferation assays for month 3 used cells growing in the concentrations of each agent indicated in Table 9.

TABLE 9

| Initial Concentrations of Drugs Used in Proliferation Assays—Month 3 | | | |
|---|---|---|---|
| Line | Dab | Tram | BVD-523 |
| Parental | — | — | — |
| Tram | — | 160 nM | — |
| Dab | 3.2 pM | — | — |
| BVD-523 | — | — | 1.2 pM |
| Tram + Dab | 80 nM | 16 nM | — |
| Dab + BVD-523 | 28 nM | — | 0.9 μM |
| Tram + BVD-523 | — | 2.5 nM | 0.4 μM |

For combination studies, A375 cells (ATCC) were seeded into triplicate 96-well plates at a cell density of 3000 cells/well in DMEM plus 10% FBS and allowed to adhere overnight prior to addition of test compound or vehicle control. Combinations were tested using a 10×8 dose matrix with a final DMSO concentration of 0.2%. A 96 hour assay incubation period followed, with subsequent addition of Alamar Blue 10% (v/v) and 4 hours incubation prior to reading on a fluorescent plate reader. After reading Alamar Blue, the medium/Alamar Blue mix was flicked off and 100 μl of CellTiter-Glo/PBS (1:1) added and the plates processed as per the manufacturers instructions (Promega). Media only background values were subtracted before the data was analysed. The Bliss additivity model was then applied.

In brief, predicted fractional inhibition values for combined inhibition were calculated using the equation $C_{bliss}$=A+B−(A×B) where A and B are the fractional inhibitions obtained by drug A alone or drug B alone at specific concentrations. $C_{bliss}$ is the fractional inhibition that would be expected if the combination of the two drugs were exactly additive. $C_{bliss}$ values are subtracted from the experimentally observed fractional inhibition values to give an 'excess over Bliss' value. Excess over Bliss values greater than 0 indicate synergy, whereas values less than 0 indicate antagonism. Excess over Bliss values are plotted as heat maps ±SD.

The single and combination data are also presented as dose-response curves generated in GraphPad Prism (plotted using % viability relative to DMSO only treated controls).

For focused combination studies, the Alamar Blue viability assays were performed as described above for combination studies. Additionally, Caspase-Glo 3/7 assays were performed. In brief, HCT116 cells were seeded in triplicate in white 96-well plates at a cell density of 5000 cells/well in McCoy's 5A plus 10% FBS. A375 cells were seeded at a density of 5000 cells/well in DMEM plus 10% FBS. Cells were allowed to adhere overnight prior to addition of test compound or vehicle control. The final concentration of DMSO was 0.2%, and 800 nM staurosporine was included as a positive control. 24 and 48 hour assay incubation periods were used. Then, Caspase-Glo® 3/7 50% (v/v) was added, plates were mixed for 5 minutes on an orbital shaker and incubated for 1 hour at room temperature prior to reading on a luminescent plate reader. Media only background values were subtracted before the data was analysed.

For Differential Scanning Fluorimetry, SYPRO orange (5,000× solution, Invitrogen) was diluted (1:1,000) in buffer solution (10 mM HEPES, 150 mM NaCl, pH 7.5). HisX6 tagged proteins included inactive ERK2, active ERK2 (ppERK2), or p38α at a final concentration of 1 μM. The protein/dye solution and compounds in 100% DMSO were added to wells (2% v/v final DMSO concentration) to achieve the desired final concentrations, mixed, and placed into an RT-PCR instrument. Next, a melting curve was run from 25-95° C. at a rate of 1° C. per minute and the melting temperature (Tm) was determined for each protein in the absence or presence of compounds. The change in Tm (ΔTm) in the presence of various drug concentrations is presented.

For Ki determination of ERK1, activated ERK1 (10 nM) was incubated with various concentrations of the compounds in 2.5% (v/v) DMSO for 10 minutes at 30° C. in 0.1 M HEPES buffer (pH 7.5), 10 mM $MgCl_2$, 2.5 mM phosphoenolpyruvate, 200 μM nicotinamide adenine dinucleotide (NADH), 150 μg/mL pyruvate kinase, 50 μg/mL lactate dehydrogenase, and 200 μM Erktide peptide. The reaction was initiated by the addition of 65 μM of ATP. Decreased absorbance rate (340 nm) was monitored and the $IC_{50}$ was determined as a function of inhibitor concentration.

For Ki determination of ERK2, the inhibitory activity of BVD-523 against ERK2 was determined using a radiometric assay, with final concentration of the components being 100 mM HEPES (pH 7.5), 10 mM $MgCl_2$, 1 mM dithiothreitol (DTT), 0.12 nM ERK2, 10 μM myelin basic protein (MBP), and 50 μM $^{33}$P-γ-ATP. All reaction components, with the exception of ATP and MBP, were premixed and aliquoted (33 μL) into a 96-well plate. A stock solution of compound in DMSO was used to make up to 500-fold dilutions, a 1.5-μL aliquot of DMSO or inhibitor in DMSO was added to each well. The reaction was initiated by adding the substrates $^{33}$P-γ-ATP and MBP (33 μL). After 20 minutes the reaction was quenched with 20% (w/v) tricholoracetic acid (TCA) (55 μL) containing 4 mM ATP, transferred to the GF/B filter plates, and washed 3 times with 5% (w/v) TCA). Following the addition of Ultimate Gold™ scintillant (50 μL), the samples were counted in a Packard TopCount. From the activity versus concentration titration curve, the Ki value was determined by fitting the data to an equation for competitive tight binding inhibition kinetics using Prism software, version 3.0.

For $IC_{50}$ determination of ERK2, activity was assayed by a standard coupled-enzyme assay. The final concentrations were as follows: 0.1 M HEPES (pH 7.5), 10 mM $MgCl_2$, 1 mM DTT, 2.5 mM phosphoenolpyruvate, 200 μM NADH, 50 μg/mL pyruvate kinase, 10 μg/mL lactate dehydrogenase, 65 μM ATP, and 800 μM peptide (ATGPLSPGPFGRR). All of the reaction components except ATP were premixed with ERK and aliquoted into assay-plate wells. BVD-523 in DMSO was introduced into each well, keeping the concentration of DMSO per well constant. BVD-523 concentrations spanned a 500-fold range for each titration. The assay-plate was incubated at 30° C. for 10 minutes in the plate reader compartment of the spectrophotometer (molecular devices) before initiating the reaction by adding ATP. The absorbance change at 340 nm was monitored as a function of time, the initial slope corresponds to the rate of the reaction. The rate versus concentration of the BVD-523 titration curve was fitted either to an equation for competitive tight-binding inhibition kinetics to determine a value for Ki or to a 3-parameter fit to determine the $IC_{50}$ using Prism software, version 3.0.

For apoptosis assays, cells were plated at $2\times10^4$ cells per well in a 96-well plate and allowed to attach overnight or grow to 50% confluency. Cells were treated with a serial dilution of BVD-523 in media (final volume 200 µL, concentration ranges 4-0.25 µM) and incubated for 48 hours in a 37° C. $CO_2$ incubator. Cells were washed with 100 µL of PBS, and 60 µL of radioimmunoprecipitation assay buffer was added (50 mM Tris-HCl, pH 8.0, 150 mM NaCl, 1.0% [w/v] NP-40, 0.5% [w/v] sodium deoxycholate, 1% [w/v] SDS), then incubated for 10 minutes at 4° C. to lyse the cells. A 30-µL lysate aliquot was added to 100 µL of caspase assay buffer (120 mM HEPES, 12 mM EDTA, 20 mM dithiothreitol, 12.5 µg/mL AC-DEVD-AMC caspase substrate) and incubated at RT from 4 hours to overnight. The plate was read in a fluorimeter (excitation wavelength 360 nm, emission wavelength 460 mm). The remaining 30 µL of lysate was analyzed for total protein content using the BioRad Protein Assay Kit (sample-to-working reagent ratio of 1:8). Final normalized caspase activity was derived as fluorescence units per µg protein and converted to a fold increase in caspase activity when compared with DMSO controls.

For measurement of antitumor activity in A375 xenografts, xenografts were initiated with A375 cells maintained by serial subcutaneous transplantation in female athymic nude mice. Each test mouse received an A375 tumor fragment (1 $mm^3$) implanted subcutaneously in the right flank. Once tumors reached target size (80-120 $mm^3$), animals were randomized into treatment and control groups, and drug treatment was initiated.

To evaluate BVD-523 monotherapy, BVD-523 in 1% (w/v) carboxymethylcellulose (CMC) was administered orally, per os (p.o.), BID at doses of 5, 25, 50, 100, or 150 mg/kg. Oral temozolomide was administered as a positive reference compound at 75 or 175 mg/kg once daily (QD) for a total of five treatments (QD×5).

The efficacy of BVD-523 in combination with dabrafenib was evaluated in mice randomized into 9 groups of 15 and 1 group of 10 (Group 10). Dabrafenib was administered p.o. at 50 or 100 mg/kg QD and BVD-523 was administered p.o. at 50 or 100 mg/kg BID, alone and in combination, until study end, vehicle-treated and temozolomide-treated (150 mg/kg QD×5) control groups were also included. Combination dosing was stopped on Day 20 to monitor for tumor regrowth. Animals were monitored individually and euthanized when each tumor reached an endpoint volume of 2000 $mm^3$, or the final day (Day 45), whichever came first, and median time to endpoint (TTE) calculated. The combination was also evaluated in an upstaged A375 model where larger tumors in the range 228-1008 $mm^3$ were evaluated. Here, mice were randomized into 1 group (Group 1) of 14 and 4 groups (Groups 2-5) of 20. Dosing was initiated on Day 1 with dabrafenib plus BVD-523 (25 mg/kg dabrafenib+50 mg/kg BVD-523 or 50 mg/kg dabrafenib+100 mg/kg BVD-523), with each agent given p.o. BID until study end. The study included 50-mg/kg dabrafenib and 100-mg/kg BVD-523 monotherapy groups as well as a vehicle-treated control group. Tumors were measured twice weekly. Combination dosing was stopped on Day 42 to monitor for tumor regrowth through study end (Day 60). Treatment outcome was determined from % TGD, defined as the percent increase in median TTE for treated versus control mice, with differences between groups analyzed via log rank survival analysis. For TGI analysis, % TGI values were calculated and reported for each treatment (T) group versus the control (C) using the initial (i) and final (f) tumor measurements based on the following formula: % TGI=1−Tf−Ti/Cf−C. Mice were also monitored for CR and PR responses. Animals with a CR at the end of the study were additionally classified as TFS.

For measurement of BVD-523 activity in Colo205 xenografts, human Colo205 cells were cultured in RPMI 1640 supplemented with 10% (v/v) fetal bovine serum (FBS), 100 units/mL penicillin, 100 µg/mL streptomycin (Invitrogen), and 2 mM L-glutamine. Cells were cultured for fewer than four passages prior to implantation. Female athymic nude mice (19-23 g) were injected subcutaneously with $2\times10^6$ Colo205 cells into the right dorsal axillary region on Day 0.

Mice with an approximate tumor volume of 200 $mm^3$ were randomized into 6 experimental groups. Vehicle control, 1% CMC (w/v), was prepared weekly. BVD-523 was suspended in 1% (w/v) CMC at the desired concentration and homogenized on ice at 6,500 rpm for 50 minutes. BVD-523 suspensions were prepared weekly and administered p.o. BID at total daily doses of 50, 100, 150, and 200 mg/kg (n=12/group) on an 8- or 16-hour dosing schedule for 13 days. The vehicle control (n=12) was administered using the same dosing regimen. CPT-11 was administered as a positive reference compound (n=12). Each 1 mL of CPT-11 injection contained 20 mg irinotecan, 45 mg sorbitol, and 0.9 mg lactic acid. CPT-11 was administered at 100 mg/kg/day intraperitoneally every 4 days for 2 consecutive doses.

For measurement of ERK1/2 Isotope-Tagged Internal Standard (ITIS) Mass Spectrometry in Colo205 Xenografts, frozen tumors were lysed in 10 volumes of ice cold lysis buffer (10 mM TRIS-HCl, pH 8.0, 10 mM $MgCl_2$, 1% (v/v) Triton X-100, Complete™ Protease Inhibitor Cocktail [Roche, cat. No. 1836170], Phosphatase Inhibitor Cocktail I [Sigma, cat. No. P-2850], Phosphatase Inhibitor Cocktail II [Sigma cat. No. 5726], and benzonase [Novagen cat. No. 70664]). Lysates were clarified by centrifugation (100,000×g for 60 minutes at 4° C.) and the supernatants adjusted to 2 mg/mL with lysis buffer. ERK1 was immunoprecipitated using agarose-coupled and pan-anti-ERK1 (Santa Cruz Biotechnology cat. No. sc-93ac) antibodies. Immunoprecipitated proteins were resolved by SDS-PAGE and stained with SYPRO Ruby (Invitrogen), and the ERK bands excised via razor. Gel slices were washed in 300 µL of 20 mM $NH_4HCO_3$, diced into small pieces, and placed in Page Eraser Tip (The Nest Group cat no. SEM0007). Gel fragments were reduced and alkylated prior to trypsin digestion. Tryptic fragments were isolated in 75 µL of 50% (v/v) Acetonitrile, 0.2% (v/v) trifluoroacetic acid and the resulting sample concentrated to 0-10 µL in a SpeedVac.

For ITIS analysis, digested samples were spiked with heavy-atom labeled peptide standards and fractional phosphorylation was quantified by coupled liquid chromatography-tandem mass spectrometry (MS). Nanocapillary chromatography was performed using a Rheos 2000 binary pump from Flux Instruments delivering nanoscale flow after 1:750 splitting, an LC Packings Inertsil nano-precolumn (C18, 5 mm, 100 Å, 30 mm ID×1 mm), and a New Objective PicoFrit AQUASIL resolving column (C18, 5 mm, 75/15 mm ID×10 cm), which also served as an electrospray ionization (ESI) emitter. An Applied Biosystem API 3000 mass spectrometer coupled with a nano-ESI source was used for MS analysis. An in-house-made gas nozzle connected to a nebulizing gas source was used to help steady nano-flow spray. Data were acquired in a multiple reaction monitoring (MRM) mode: nebulizing gas at 3; curtain gas at 7; collision gas at 5; ion spray voltage at 2150 volts, exit potential at 10 volts; Q1/Q3 resolution Low/Unit; and dwell time of 65 msec for all MRM channels. All raw MS data were processed using a combination of the Analyst software suite from Applied Biosystem and custom tools.

For assessment of drug sensitivity in cell-line models of acquired resistance, drug sensitivity of dose-escalated A375 cells and isogenic RKO cells was assessed in 96-hour proliferation assays. RKO isogenic cells (McCoy's 5A containing 10% [v/v] FBS) or dose-escalated A375 cells (DMEM containing 10% FBS were seeded into 96-well plates and allowed to adhere overnight prior to addition of compound or vehicle control. Note that the dose-escalated A375 cells were seeded in the absence of inhibitor. Compounds were prepared from 0.1% (v/v) DMSO stocks to give a final concentration as indicated. Test compounds were incubated with the cells for 96 hours at 37° C. in a 5% $CO_2$ humidified atmosphere. For the RKO cells, CellTiter-Glo® reagent (Promega) was added according to manufacturer's instructions and luminescence detected using a BMG FLUOstar plate reader. For the A375 assays Alamar blue (ThermoFisher) 10% (v/v) was added and incubated for 4 h, and fluorescent product was then detected using a BMG FLUOstar. The average media only background value was deducted and the data analyzed using a 4-parameter logistic equation in GraphPad Prism.

$IC_{50}$ Determination of ERK1 was measured in a final reaction volume of 25 μL. ERK1 (human) (5-10 mU) was incubated with 25 mM Tris (pH 7.5), 0.02 mM ethyleneglycoltetracetic acid, 250 μM peptide, 10 mM Mg acetate, and γ-$^{33}$P-ATP (specific activity approximately 500 cpm/pmol, concentration as required). Adding Mg ATP initiated the reaction. After incubation for 40 minutes at room temperature (RT), the reaction was stopped by adding 5 μL of a 3% (w/v) phosphoric acid solution. Then, 10 μL of the reaction was spotted onto a P30 filtermat, and washed 3 times for 5 minutes in 75 mM of phosphoric acid then once in methanol before drying and scintillation counting.

RKO MEK1 Q56P Isogenic cells were produced by Horizon Discovery (Cambridge, UK; #HD 106-019) using a recombinant AAV-mediated gene targeting strategy. Briefly, rAAV virus was generated following transfection of the appropriate targeting vector and helper vectors in HEK293T cells, purified using an AAV purification kit (Virapur, San Diego, USA) and titrated using qPCR. Parental homozygous RKO cells (homozygous wild type for MEK1) were then infected with rAAV virus and clones that had integrated the selection cassette were identified by G418 selection and expanded. Correctly targeted clones that were heterozygous for knock-in of the MEK1 Q56P point mutation into a single allele were identified by PCR and sequencing.

Isogenic SW48 cell lines heterozygous for knock-in of mutant KRAS (De Roock et al 2010, JAMA, 304, 1812-1820) were obtained from Horizon Discovery (Catalogue numbers; HD 103-002, HD 103-006 HD 103-007, HD 103-009, HD 103-010, HD 103-011, HD 103-013). For proliferation assay, cells were seeded into 96-well plates in McCoy's 5A medium supplemented with 10% FBS and allowed to adhere overnight prior to addition of compound or vehicle control. Test compounds were incubated with the cells for 96 hours at 37° C. in a 5% $CO_2$ atmosphere. Viability was then assessed using Alamar blue.

The proprietary KinaseProfiler assay was conducted at Upstate Discovery and employed radiometric detection similar to that employed by Davies et al, was used to profile the selectivity of BVD-523 against a panel of 70 kinases.

A drug sensitivity analysis was carried out as part of The Genomics of Drug Sensitivity in Cancer Project using high-throughput screening, as previously described (Yang et al. 2013).

For Western blot analysis, A375 cells were seeded onto 10 cm dishes in Dulbecco's Modified Eagle's Medium plus 10% (v/v) FBS. Cells were allowed to adhere overnight prior to the addition of test compound or vehicle. For experiments with RKO cells, these cells were seeded in 6-well plates or 10 cm dishes with McCoy's 5A+10% (v/v) FBS. Cells were then treated at the desired concentration and duration. Cells were harvested by trypsinization, pelleted, and snap frozen. Lysates were prepared with RIPA buffer supplemented with protease and phosphatase inhibitor cocktails (Roche), clarified by centrifugation at 11,000 rpm for 10 minutes, and quantitated by bicinchoninic acid assay. Samples were resolved by SDS-PAGE, blotted onto polyvinylidene difluoride membranes, and probed using antibodies (i.e., pRB [Ser780], cat. no. 9307; CCND1, cat. no. ab6152; BCL-xL, cat. no. 2762; PARP, cat. no. 9542; DUSP6, cat. no. 3058S) directed to the indicated targets.

For Reverse Phase Protein Analysis (RPPA), A375, MIAPaCa-2, HCT116, Colo205, HT-29, and AN3Ca cells (ATCC) were plated at 80% confluence, allowed to recover overnight (MIAPaCa-2 cells were plated at 30% confluence and allowed to recover for 3 days), then treated with 10 μM of each compound (i.e., BVD-523, SCH722984, GDC-0994, or Vx-11e) for 6 hours at 37° C. Control wells were treated with DMSO at 0.1% (v/v) for 6 hours prior to cell lysate generation. Samples were then analyzed using reverse-phase protein microarray technology (Theranostics Health).

For analysis of pERK IHC in Colo205 xenografts, xenograft tumors were processed overnight in 70% through 100% graded ethanols, cleared in two changes of xylene, infiltrated with paraffin, and embedded into paraffin blocks. Then, 5-μm sections were cut and placed onto positively charged glass slides and baked for at least 30 minutes, but not longer than 1 hour, at 60° C. A single section from each animal and dose group was probed with anti-phospho p42/p44 MAPK antibody (pERK [1:100], CST; Cat no. 9101; Lot no. 16), counterstained with hematoxylin, and then analyzed microscopically using a Zeiss Axioplan 2 microscope. An isotype control (rabbit, Zymed laboratories, catalog no. 08-6199, lot no. 40186458) was run as a negative control.

For FACS analysis, cells were scraped and pelleted at 1,500 rpm for 5 minutes, then re-suspended in 1 mL of buffer and frozen at −70° C. The frozen cells were thawed and centrifuged again, followed by 10 minutes of re-suspension in 0.25 mL of Buffer A (trypsin in spermine tetrahydrochloride detergent buffer) to disaggregate cell clumps and digest cell membranes and cytoskeletons. Buffer B (trypsin inhibitor and Ribonuclease I in buffer, 0.2 mL) was added for 10 minutes in the dark. The resulting DNA-stained nuclei were filtered and analyzed by FACS. The histograms were analyzed to establish the proportion of cells in the G1, S, and G2/M phases of the cell cycle based on the presence of n and 2n DNA (or higher) content.

For measurement of in vitro combination activity, five thousand G-361 cells were seeded into triplicate 96-well plates containing McCoy's 5A with 10% (v/v) FBS and allowed to adhere overnight. The vemurafenib/BVD-523 combination was tested using a 10×8 dose matrix. Compounds were incubated with the cells for 72 hours at 37° C. in a 5% $CO_2$ humidified atmosphere. CellTiter-Glo reagent was added according to manufacturer's instructions and luminescence detected using a MBG FLUOstar plate reader.

The interactions across the dose matrix were determined by the Loewe Additivity and Bliss independence models using Horizon's Chalice Combination Analysis Software.

For generating compound resistance in vitro by dose escalation, A375 parental cells (ATCC CRL-1619) were grown to ~40-60% confluence in Dulbecco's Modified Eagle's Medium (DMEM) supplemented with 10% heat-inactivated FBS and penicillin/streptomycin, then treated with initial doses of BVD-523, trametinib, or dabrafenib either alone or in combination at or slightly below each compound's $IC_{50}$; for combination studies, initial dosing was half of each compound's $IC_{50}$. Cells were allowed to grow until ~70-90% confluence and split; medium was refreshed every 3-4 days. When cells again reached ~40-60% confluence, the dose was escalated by the same increment (equivalent to the starting concentration) then moved to 1.5-fold increases in concentration followed by a further move to 2-fold increases if the cells continued to adapt rapidly (e.g., the first six doses of the dabrafenib escalation were: 5, 10, 15, 20, 25, and 37.5 nM). This process was repeated as required.

Figure 30A:
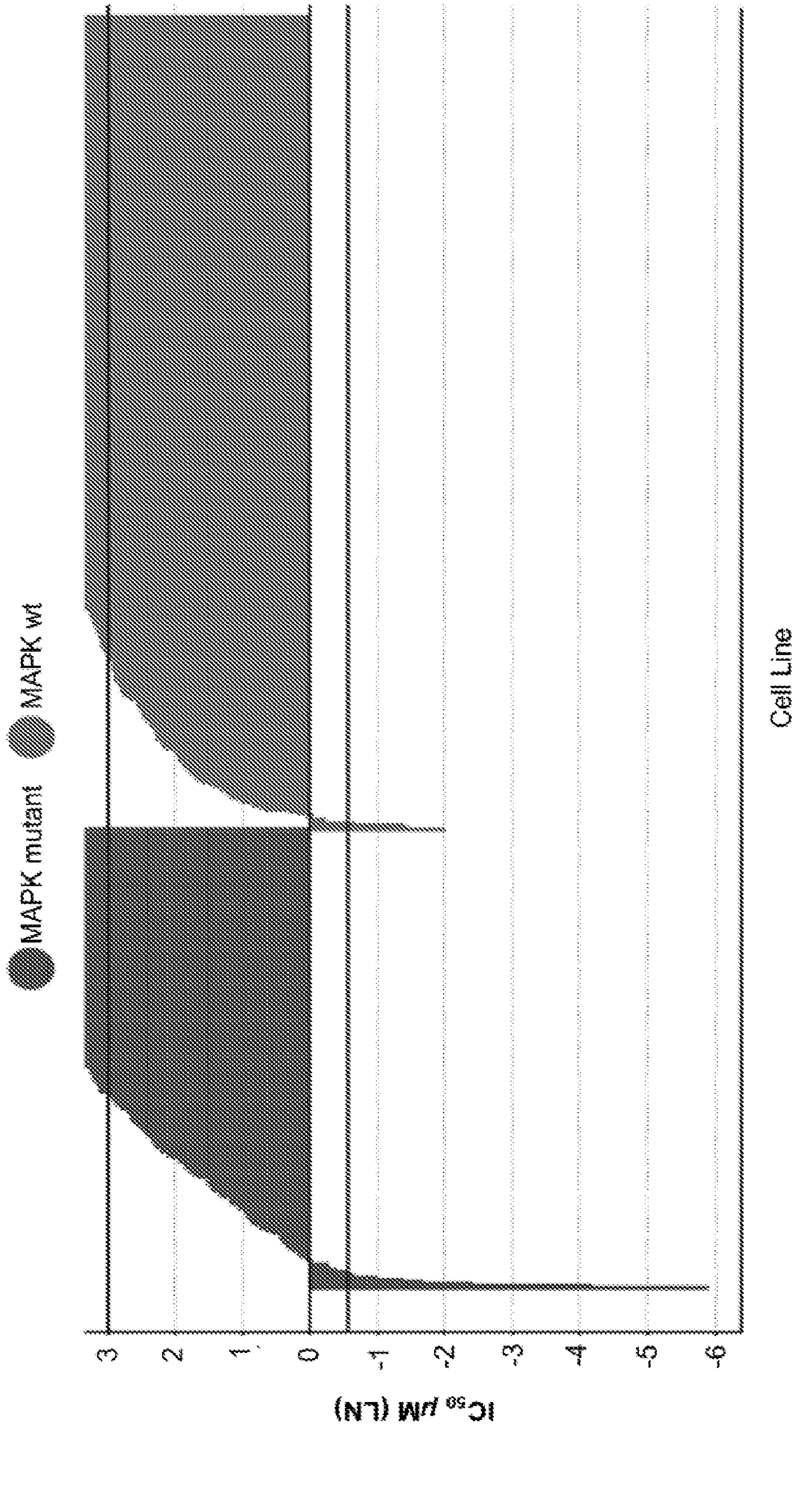
FIG. 30A-FIG. 30D show that BVD 523 inhibits cellular proliferation and enhances caspase 3 and caspase 7 activity in vitro.

Cell viability assays for FIG. 30A were performed by a Resazurin (Alamar Blue) metabolic assay after 5 days in drug in full serum under high glucose conditions. Cells were seeded in 384-well microplates at ~15%-50% confluence in medium with 10% FBS and penicillin/streptavidin plus high glucose (18-25 mM). The optimal cell number for each cell line was determined to optimize growth during drugging. For adherent cell lines, after overnight incubation cells were treated with 9 concentrations of each compound (2-fold dilutions series) using liquid handling robotics, and returned to the incubator for assay at a 96-h time point. For suspension cell lines, cells were treated with compound immediately after plating and returned to the incubator for a 96-h time point. Cells were then stained with 55 μg/ml Resazurin (Sigma) prepared in glutathione-free media for 4 hours. Quantitation of fluorescent signal intensity was performed using a fluorescent plate reader at excitation and emission wavelengths of 535/595 nm for Resazurin. All screening plates were subjected to stringent quality control measures. Effects on cell viability were measured and a curve-fitting algorithm was applied to the raw dataset to derive a multi-parameter description of drug response, including the half maximal inhibitory concentration ($IC_{50}$). $IC_{50}$ is expressed in natural log of the $IC_{50}$ in μM ($LN\_IC_{50}$; EXP returns $IC_{50}$ in μM). Extrapolation of the $IC_{50}$ was allowed for where it yielded very high values. If desired the data was restricted to the tested concentration range by capping $IC_{50}$ values at the maximum tested concentration (and the minimum tested concentration for low values).

For efficacy testing of BVD-523 in a patient-derived xenograft (AT052C) representing melanoma from a $BRAF^{V600E}$ patient that had become clinically refractory to vemurafenib. Tumor fragments were harvested from host animals and implanted into immune-deficient mice. The study was initiated at a mean tumor volume of approximately 170 $mm^3$, at which point the animals were randomized into four groups including a control (1% [v/v] CMC p.o., BID×31) and three treatment groups (BVD-523 [100 mg/kg], dabrafenib [50 mg/kg], or BVD-523/dabrafenib [100/50 mg/kg], n=10/group); All treatment drugs were administered p.o. on a BID×31 schedule.

For $IC_{50}$ determination for the inhibition of PMA-stimulated RSK1 phosphorylation by BVD-523 in human whole blood samples, $IC_{50}$ values for the inhibition of PMA stimulated RSK1 phosphorylation by BVD-523 were determined for 10 healthy donors (aged 22-61 years) using an 8-point concentration curve ranging from 10 μM to 5 nM of BVD-523. Controls consisted of 3 unstimulated samples and 3 PMA-stimulated samples for each donor. Both phosphor-RSK (pRSK) and total RSK levels were determined and data were calculated using pRSK/RSK levels for each sample.

Thirty milliliters of blood was drawn from each donor into sodium heparin vacutainers. One mL of whole blood was added to each of twenty-two 2-mL microtubes per donor. The microtubes tubes were labeled with the donor number (1 through 10) and the subsequent treatment designation: "A" for PMA stimulation only (maximum), "B" for BVD-523-containing samples that received PMA stimulation; and "C" for the unstimulated samples (minimum). Dimethyl sulfoxide (DMSO) was added to all tubes in groups A and C to a final concentration of 0.1%. Samples were then rocked gently at room temperature.

BVD-523 (10 mM in 100% DMSO) was serially diluted with 3-fold dilutions into 100% DMSO. These serially diluted BVD-523 samples in 100% DMSO were then diluted 10-fold in Dulbecco's Modified Eagle Medium containing 10% fetal bovine serum and penicillin/streptomycin/glutamine, and 10 μL of each of these working solutions was added per mL of blood for each designated BVD-523 concentration. Each concentration of BVD-523 was run in duplicate, two 1-mL blood samples each, yielding 16 total samples for the full 8-point concentration curve. Samples were then rocked gently at room temperature for a minimum of 2 hours but not longer than 3 hours.

Human whole blood samples in groups A and B for all donors were stimulated with PMA at a final concentration of 100 nM for 20 minutes at room temperature. Samples in group C were not treated with PMA but were rocked and handled as all other samples.

Upon completion of PMA treatment for each sample, peripheral blood mononuclear cells were isolated from the human whole blood. One mL of blood from each sample was gently layered onto 0.75 mL of room-temperature Histopaque 1077 in a 2-mL microcentrifuge tube. The samples were centrifuged for 2 minutes at 16,000×g in an Eppendorf microcentrifuge. The interface and upper layers were removed and added to tubes containing 1 mL of cold Dulbecco's phosphate-buffered saline (DPBS). These samples were then centrifuged for 30 seconds at 16,000×g to pellet the cells. The buffer supernatant was removed by aspiration and the pellets were re-suspended in 1 mL of cold DPBS. The pellets from each sample were then re-pelleted as above. The buffer was removed by aspiration and the pellets were lysed as indicated below.

Complete lysis buffer consisted of Meso Scale Discovery Tris lysis buffer, 1× Halt Protease inhibitor cocktail, 1× Phosphatase inhibitor cocktail 2, 1× Phosphatase inhibitor cocktail 3, 2 mM phenylmethanesulfonyl fluoride, and 0.1% sodium dodecyl sulfate. Lysis buffer was kept on ice and made fresh for each sample group. Final cell pellets were lysed by the addition of 120 μL of complete lysis buffer. Samples were vortexed until the cell pellet disappeared and then flash frozen on dry ice. Samples were stored at −20° C. prior to measurement of pRSK and total RSK by ELISA.

For the pRSK ELISA (PathScan), thawed lysates were combined 1:1 with sample diluent (provided in ELISA kit): 120 μL of lysate added to 120 μL of sample diluent in a round bottom 96-well plate. This combination was then transferred to the pRSK microwells at 100 μL per well. For the total RSK ELISA (PathScan), 20 μL of the lysate already diluted 1:1 in sample diluent was further diluted in 200 μL of sample diluent in a round bottom 96-well plate. This combination was then transferred to the total RSK microwells at 100 μL per well. The plates were sealed with a plate seal and incubated 16 to 18 hours at 4° C., a time that was shown to yield the best detection of the target protein. Both ELISAs were developed according to the kit instructions.

Patients aged ≥18 years were eligible for participation if they had noncurable, histologically confirmed metastatic or advanced stage malignant tumors; an ECOG performance status of 0 or 1; adequate renal, hepatic, bone marrow, and cardiac function; and a life expectancy 23 months. Patients may have received up to 2 prior lines of chemotherapy for their metastatic disease. Exclusion criteria were known uncontrolled brain metastases; gastrointestinal conditions which could impair absorption of study medication; history or current evidence/risk of retinal vein occlusion or central serous retinopathy; and concurrent therapy with drugs known to be strong inhibitors of CYP1A2, CYP2D6, and CYP3A4 or strong inducers of CYP3A4. All participants provided informed consent prior to initiation of any study procedures.

Patients that received at least one dose of BVD-523 were included in the analysis using SAS (version 9.3) software. The data cutoff was Dec. 1, 2016. This study is registered with ClinicalTrials.gov, number NCT01781429.

The present invention presents data from an open-label, multicenter phase I study to assess the safety, pharmacokinetics, and pharmacodynamics of escalating doses of BVD-523 in patients with advanced malignancies. The dosing regimen combined both accelerated titration and standard cohort 3+3 dose escalation schema, which were used jointly to identify the MTD and RP2D of BVD-523 in patients with advanced solid tumors. One to 6 patients per treatment cohort were assigned to receive sequentially higher oral doses of BVD-523 on a BID schedule (12-hour intervals) in 21-day cycles, starting at a dose of 10 mg BID. BVD-523 was administered BID continuously in 21-day cycles at the following doses: 10 mg (n=1); 20 mg (n=1); 40 mg (n=1); 75 mg (n=1); 150 mg (n=1); 300 mg (n=4); 600 mg (n=7); 750 mg (n=4); and 900 mg (n=7).

Patients received BID oral doses until disease progression, unacceptable toxicity, or a clinical observation satisfying another withdrawal criterion. Dose escalations occurred in up to 100% increments in single-patient cohorts until 1 patient experienced a ≥Grade 2 toxicity (excluding alopecia or diarrhea). Cohorts were then expanded to at least 3 patients each and subsequent dose-escalation increments were reduced from up to 100% to a maximum of 50%. When at least 1 patient in a 3-patient cohort experienced a DLT, up to 3 additional patients were treated at this dose level. When more than 1 DLT occurred in 56 patients, this dose level was defined as the nontolerated dose and dose escalation was stopped. Intrapatient dose escalation was allowed, provided the patients receiving the highest current dose had been observed for at least 3 weeks and dose-limiting side effects were reported in fewer than 2 of 6 patients assigned to a given dose. Patients experiencing DLTs or unacceptable toxicity had their treatment interrupted until the toxicity returned to ≤Grade 1. Resumption of BVD-523 treatment was then initiated at the next lower dose level tested or at a 20% to 30% dose decrease, aligning with capsule dosage.

The primary objective of the phase I study was to define the safety and tolerability of BVD-523 by determining the dose-limiting toxicities, the MTD, and the RP2D. The secondary objectives included the determination of the pharmacokinetic profile of BVD-523 in patients with advanced malignancies and the investigation of any preliminary clinical effects on tumor response, as assessed by physical or radiologic exam using RECIST v1.1. The exploratory objectives included evaluation of pharmacodynamic marker (biomarker) measures and investigation of preliminary clinical effects on tumor response assessed by $^{18}$F-FDG-PET as indicated.

For determination of MTD, DLT, and RP2D, MTD was defined as the highest dose cohort at which 533% of patients experienced BVD-523-related DLTs in the first 21 days of treatment. DLT was defined as a BVD-related toxicity in the first 21 days of treatment that resulted in ≥Grade 4 hematologic toxicity for >1 day; Grade 3 hematologic toxicity with complications (e.g., thrombocytopenia with bleeding); ≥Grade 3 nonhematologic toxicity, except untreated nausea, vomiting, constipation, pain, and rash (these become DLTs if the AE persisted despite adequate treatment); or a treatment interruption exceeding 3 days in Cycle 1 (or the inability to being in Cycle 2 for >7 days) due to BVD-523-related toxicity.

The RP2D could be as high as the MTD and was determined in discussion with the clinical investigators, the medical monitor, and the sponsor. Observations related to pharmacokinetics, pharmacodynamics, and any cumulative toxicity observed after multiple cycles were included in the rationale supporting the RP2D.

With regard to safety assessments, AEs were defined as any untoward medical occurrence in a patient who was administered a medicinal product that does not necessarily have a causal relationship with BVD-523, and was coded using the MedDRA coding dictionary. An SAE was any untoward medical occurrence that occurred at any dose that resulted in death, was life-threatening, required inpatient hospitalization or prolongation of existing hospitalization, or resulted in persistent or significant disability/incapacity or a congenital anomaly/birth defect. The severity of AEs were graded according to the National Cancer Institute Common Terminology Criteria for Adverse Events, Grading Scale, version 4.

Safety evaluations were conducted at baseline, on Days 8, 15, 22, 29, 36, and 43, and, in patients who continued treatment, every 3 weeks or if clinically indicated thereafter. Each evaluation included a physical examination and clinical laboratory studies. Electrocardiograms were repeated if clinically significant and at the discretion of the investigator. The investigators made judgments regarding whether or not AEs were related to study drug and followed up until resolution or stabilization, or the AE was judged to be no longer clinically significant.

For pharmacokinetic analysis, the pharmacokinetic population consisted of patients who received at least one dose of BVD-523 and had evaluable pharmacokinetic data for plasma and/or urine. Blood samples were collected prior to dosing, and then at 0.5 (±5 min), 1 (±5 min), 2 (±10 min), 4 (±10 min), 6 (±10 min), 8 (±10 min), and 12 (±2 hr) hours on Day 1 (Visit 2; baseline/initiation of treatment) and Day 15 (Visit 4; at steady state) after the morning dose. On Day 22, prior to dose administration, a final blood sample was collected for pharmacokinetic analyses. Urine samples were collected predose and at the 1- to 6-hour and 6- to 12-±2-hour intervals postdose on Days 1 and 15. Plasma and urine samples were analyzed for BVD-523 and metabolites using validated LC/MS/MS methods. Standard pharmacokinetic parameters were obtained using Phoenix WinNonlin (Pharsight) with a noncompartmental method. Relationship between dose and exposure was calculated using standard least-squares regression analysis.

For pharmacodynamic confirmation of target inhibition by BVD-523, targeted ERK inhibition by BVD-523 was determined by examining pRSK as a target biomarker in human whole blood samples obtained from patients with advanced solid tumors (N=27) who had received different doses of BVD-523 (10-900 mg BID) during the phase I study. The activity of BVD-523 from 4 timepoints (baseline predose, baseline 4 hours postdose, Day 15 predose, and Day 15 4 hours postdose) was expressed as a percent activity (pRSK) of PMA-stimulated blood incubated with BVD-523.

For measurement of antitumor response, tumor measurements based on physical examination occurred at baseline and on the first day of each treatment cycle. CT and other assessments were made every 2 to 3 cycles. Findings were assessed in accordance with RECIST v1.1: CR was defined as disappearance of all target lesions; PR was defined as a ≥30% decrease in the sum of the longest diameters of target lesions, taking baseline measurements as reference; stable disease was defined as being of neither sufficient shrinkage to qualify for PR nor sufficient increase to qualify for progressive disease, taking as reference the baseline measurement. Metabolic response was assessed by visualizing tumor uptake of $^{18}$F-glucose via $^{18}$F-FDG-PET scanning prior to receiving the first dose of BVD-523 and at Day 15 (Visit 4).

Example 2

Dose Escalation and Proliferation Assays—Month 1

Dose Escalation Progress—Month 1

Figure 1A:
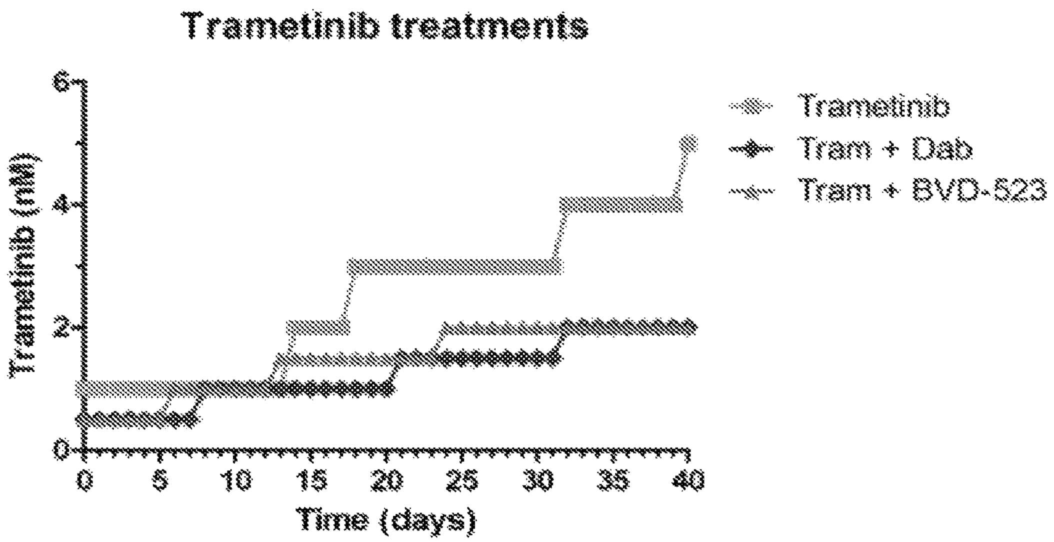
FIG. 1A-FIG. 1C show the progress of a dose escalation study in a human malignant melanoma cell line (A375 cells) for month 1. Various treatments (trametinib (a type 2 MEK inhibitor), dabrafenib (a BRAF inhibitor), and BVD-523 (an ERK1/2 inhibitor)) are as labeled.
Figure 1B:
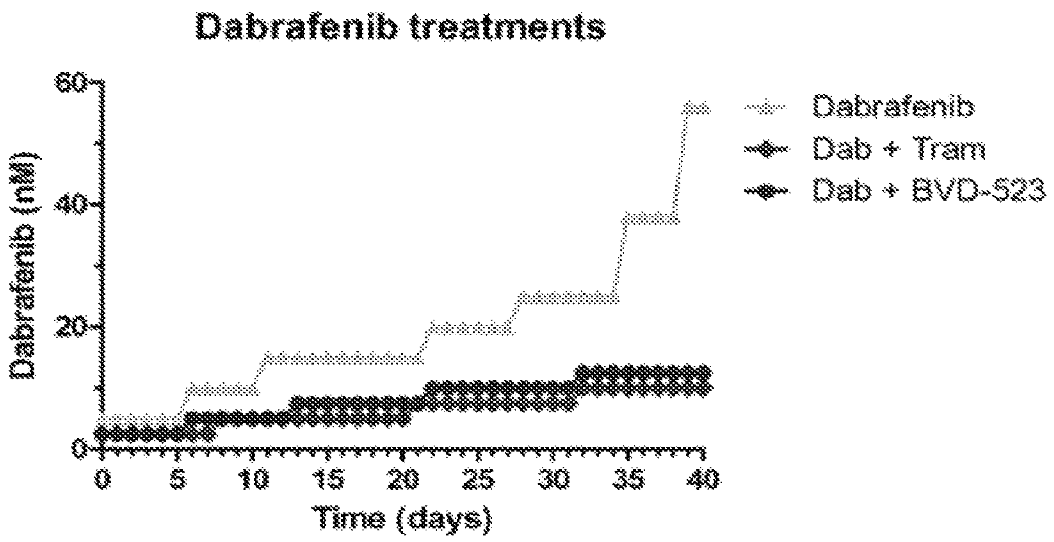
Figure 1C:
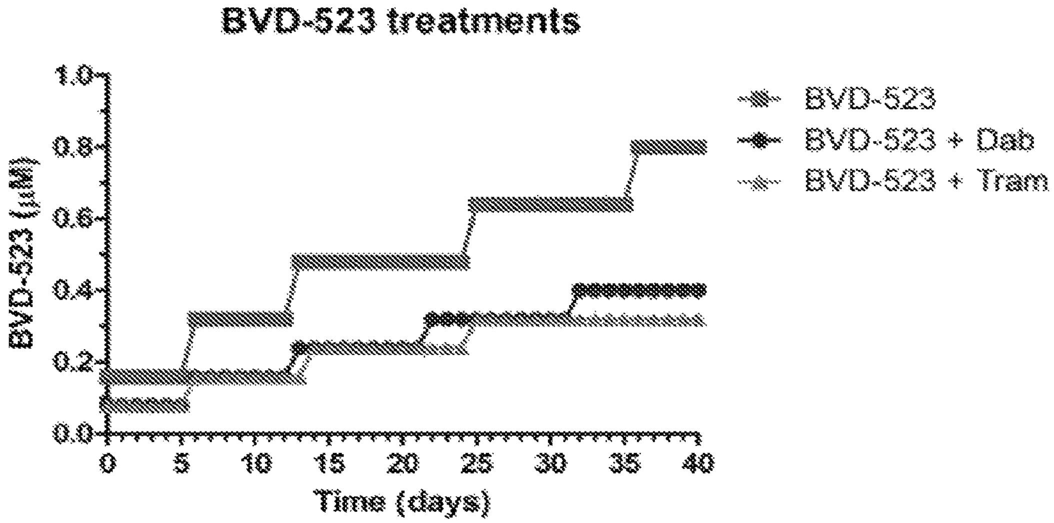
Figure 2A:
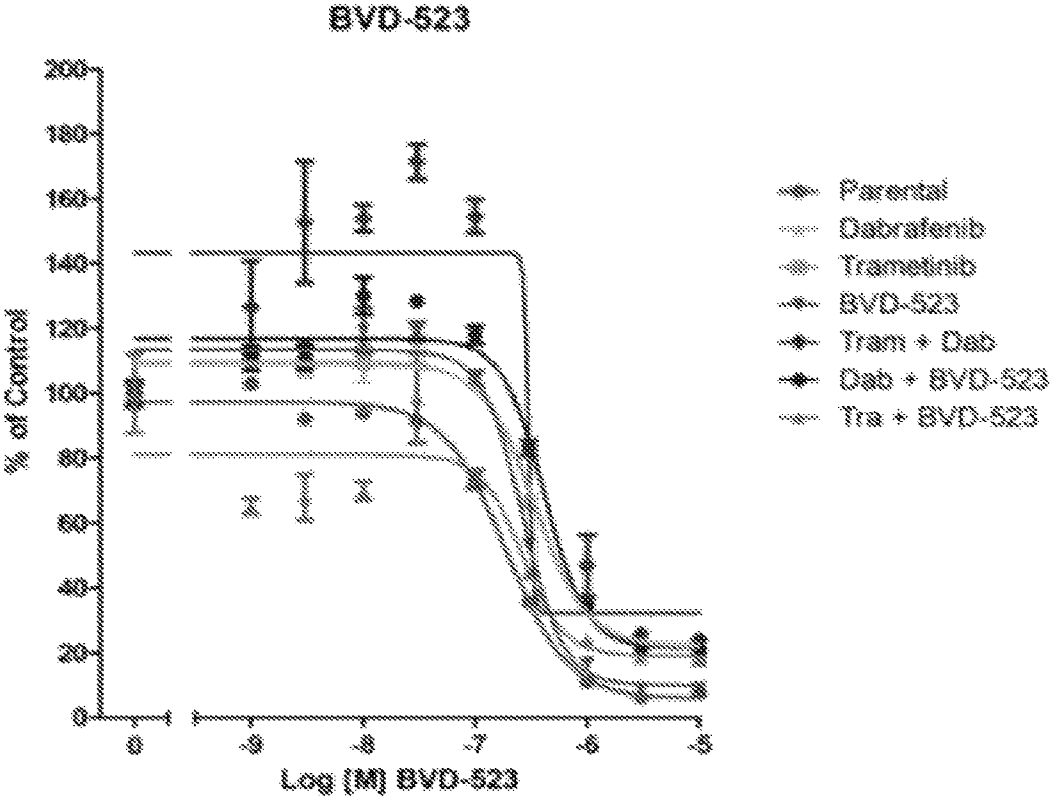
FIG. 2A-FIG. 2H show the results of a proliferation assay that tracks changes in sensitivity to the escalated agent(s) at month 1. Various treatments (trametinib, dabrafenib, BVD-523, and paclitaxel) are as labeled on the top of the graph. The caption to the right of the graph shows the various types of cells generated from the dose escalation study. For example, "dabrafenib" refers to the cells that have been treated with the highest dose of dabrafenib from month 1 of the dose escalation study. Parental refers to the control cells that have not been treated with drugs.
Figure 2B:
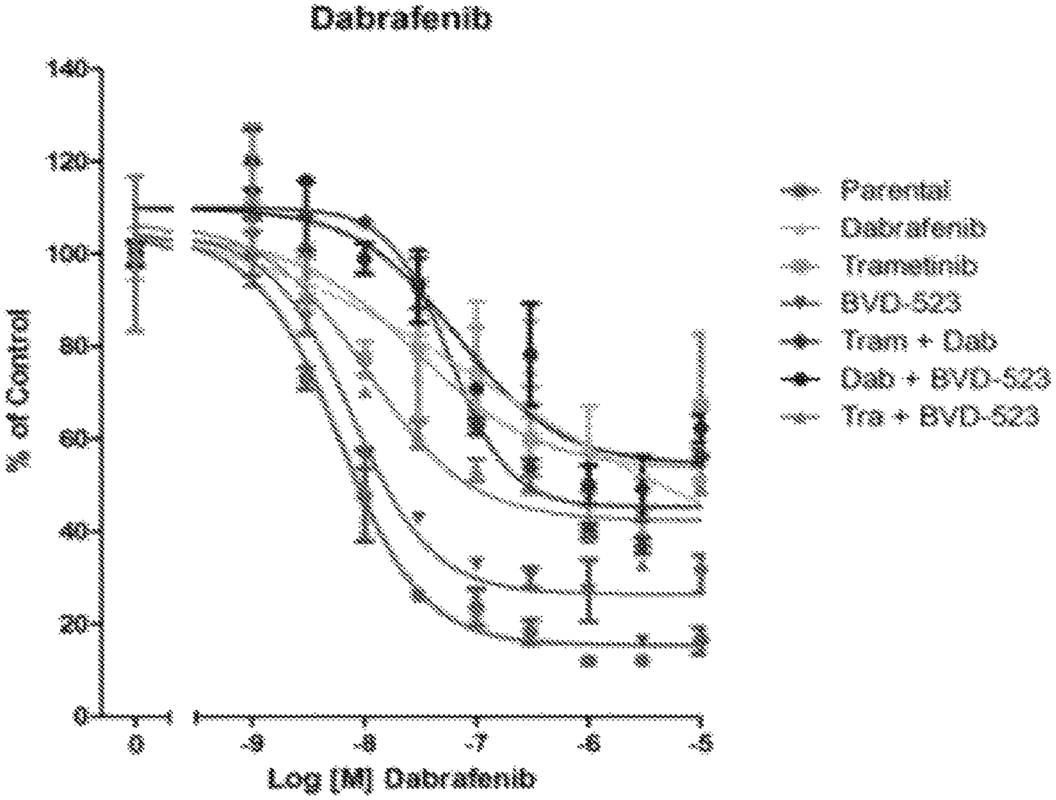
Figure 2C:
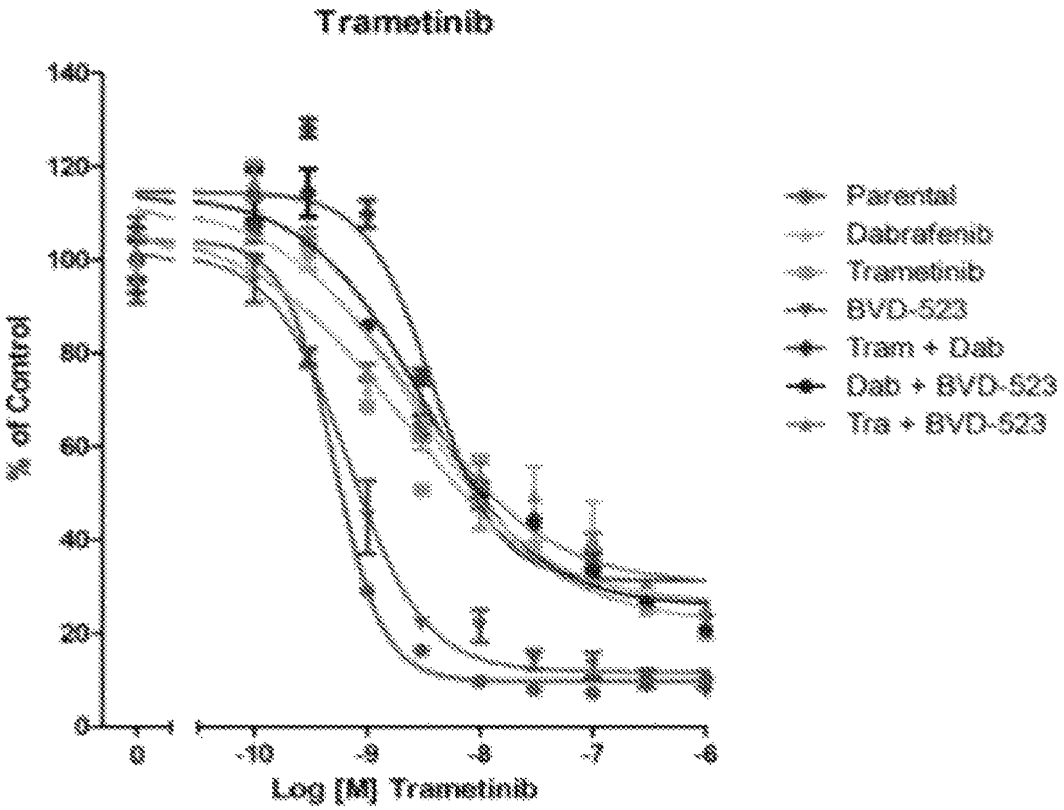
Figure 2D:
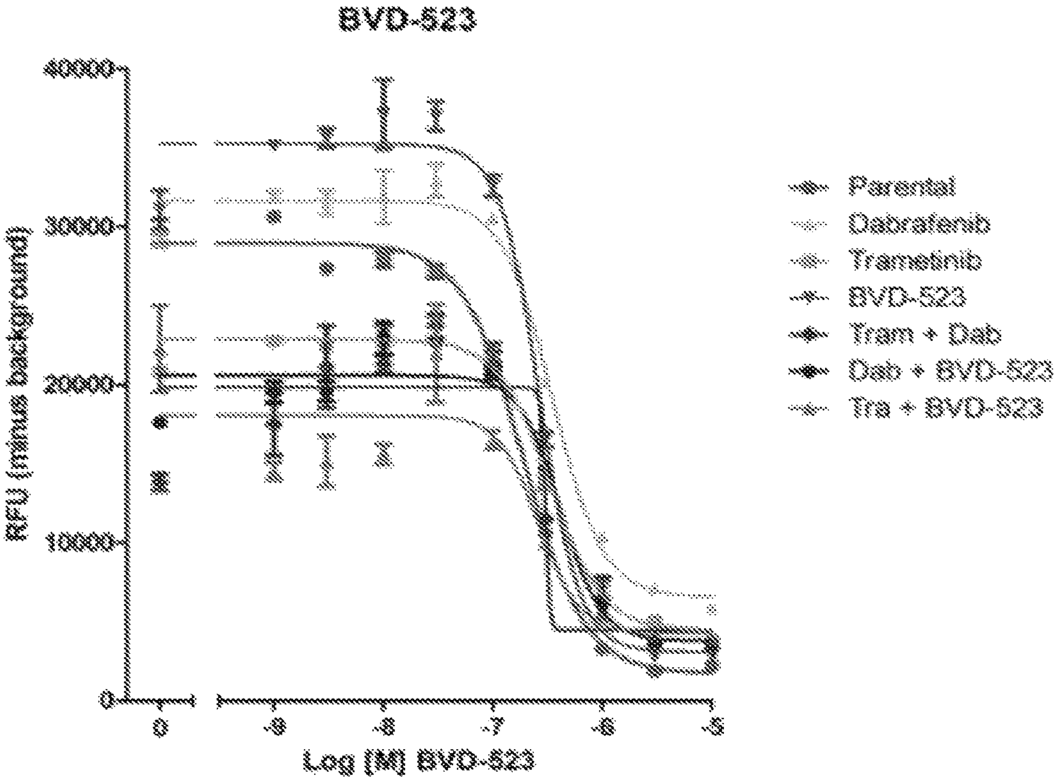
Figure 2E:
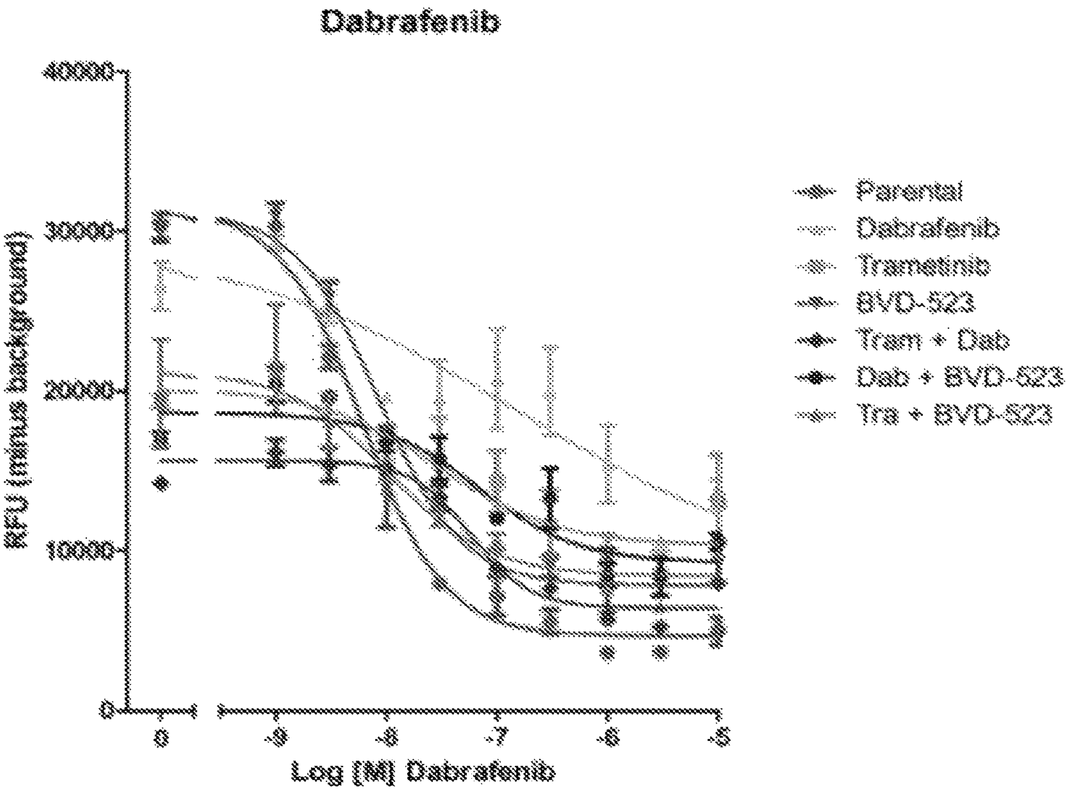
Figure 2F:
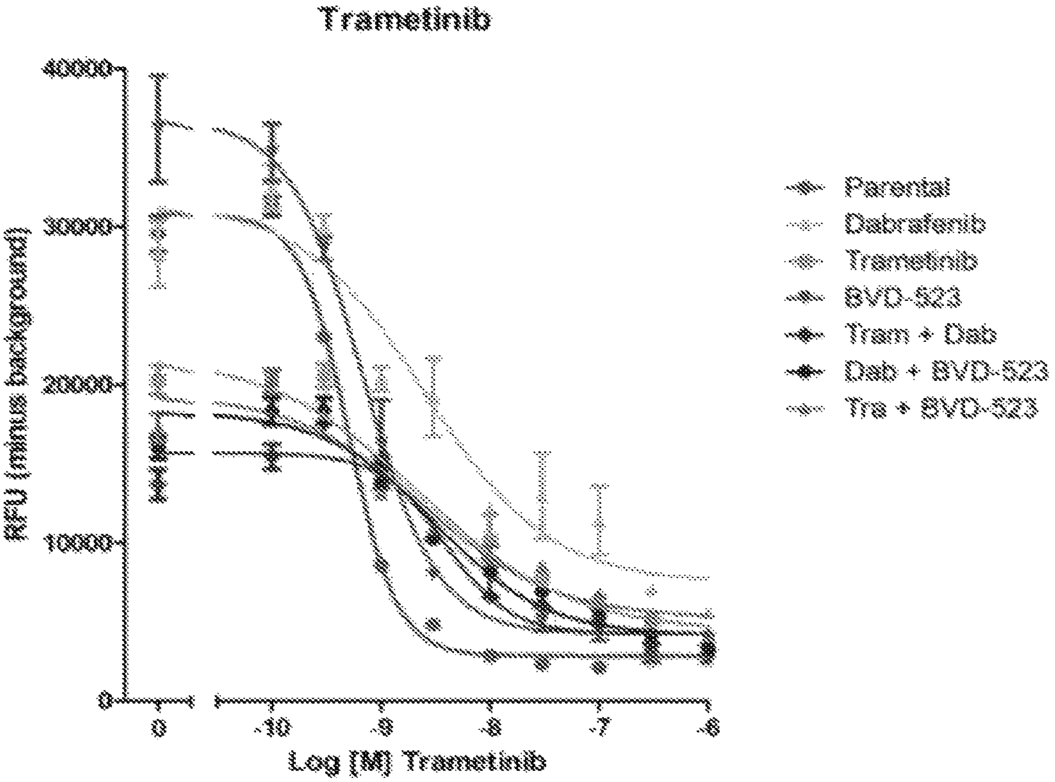
Figure 2G:
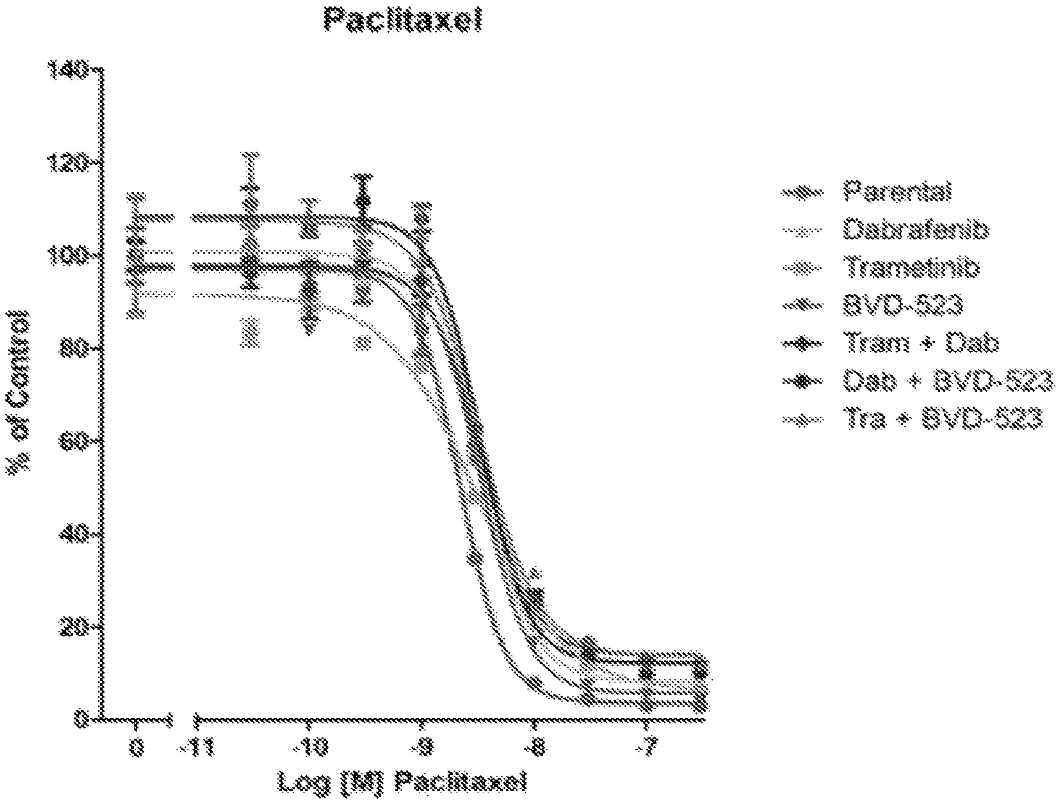
Figure 2H:
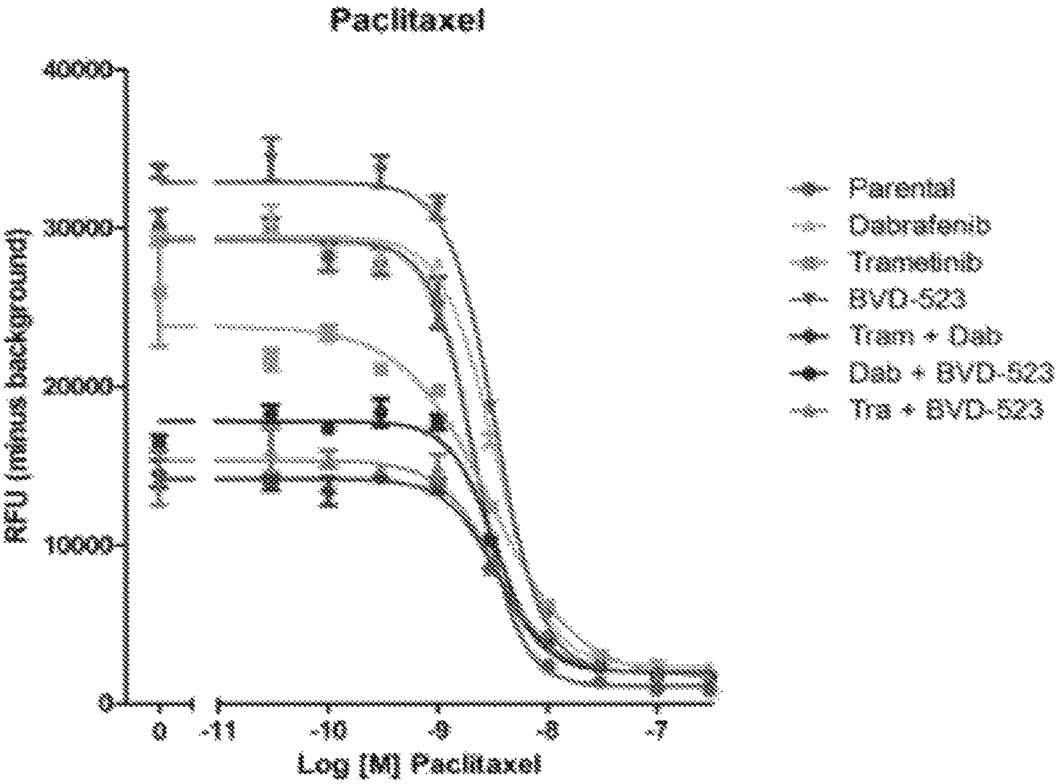

A375 cells were dose escalated using BVD-523, dabrafenib, and trametinib either as single agents or in combination. Doses were increased in small increments during the first month. Other than a marked reduction in growth rate, cells generally tolerated the escalations well and the doses were planned to be more aggressively escalated using larger increments in month 2. FIG. 1A-FIG. 1C show month 1 progress for the dose escalation studies.

Proliferation Assay Results—Month 1

Proliferation assays were performed to assess the response of the escalated cells lines vs. parental cell line, to BVD-523, dabrafenib, and trametinib treatments.

FIG. 2A-FIG. 2H show normalized and raw proliferation assay results from month 1 of the studies. Note that differences in max signals in DMSO controls between different treatments (FIG. 2D, FIG. 2F, and FIG. 2H) suggest differential growth rates between treatments. These differences may influence the responses of lines to inhibitors in the proliferation assays.

Table 10 shows $IC_{50}$ data for month 1 of the studies.

TABLE 10

$IC_{50}$ Data - Month 1

| | Cell Line, Relative $IC_{50}$ (nM) | | | | | | |
|---|---|---|---|---|---|---|---|
| Compound | Par* | Tram | Dab | BVD-523 | Dab/Tram | Dab/523 | Tram/523 |
| Dabrafenib | 6 | 29 | about 161 | 8 | 58 | 68 | 11 |
| Trametinib | 0.5 | 2.2 | 2.5 | 0.7 | 3.9 | 3.1 | 2.5 |
| BVD-523 | 189 | 335 | 350 | 268 | 300 | 412 | 263 |
| Paclitaxel | 2.2 | 3.0 | 3.3 | 3.4 | 3.5 | 3.4 | 3.4 |

There were early hints that cells grown in the presence of escalating doses of dabrafenib or trametinib, either as single agents or in combinations, were exhibiting decreased responses to these two agents in proliferation assays.

In the early stages of month 2, the growth rate of cells in the dabrafenib only treatment notably increased relative to the early stages of month 1. This enabled an increased rate of progression and suggested that resistance was becoming apparent.

Example 3

Dose Escalation and Proliferation Assays—Month 2

Dose Escalation Progress—Month 2

Figure 3A:
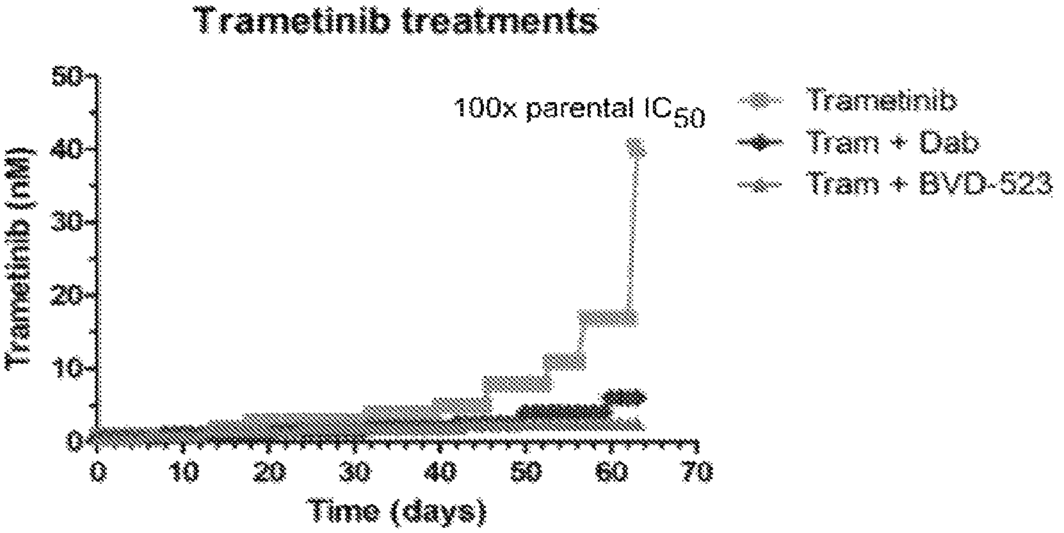
FIG. 3A-FIG. 3D show the progress of a dose escalation study in A375 cells for month 2. Various treatments (trametinib, dabrafenib, and BVD-523) are as labeled.
Figure 3B:
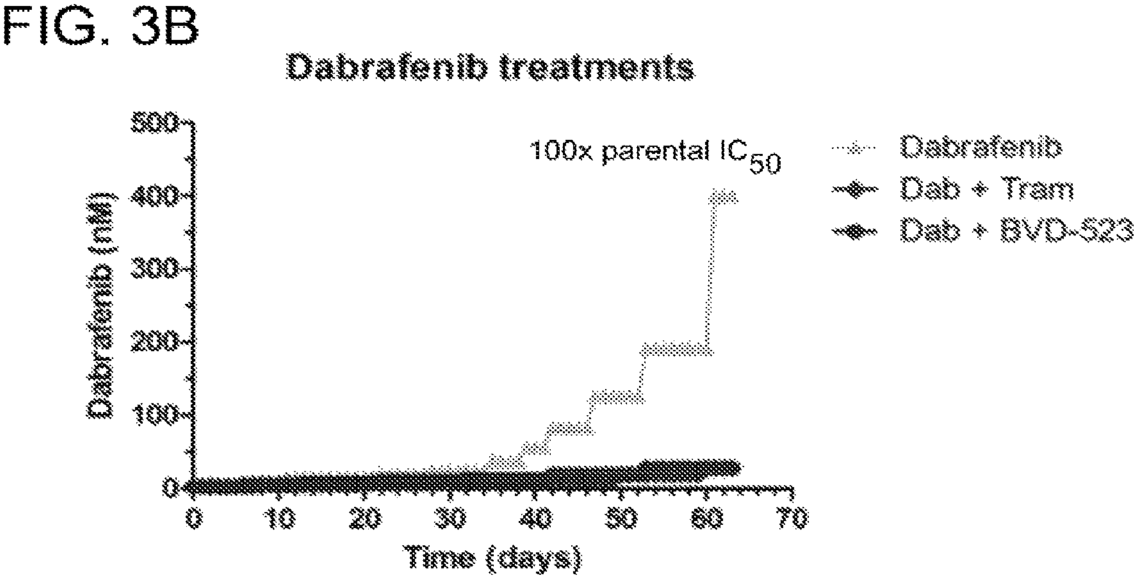
Figure 3C:
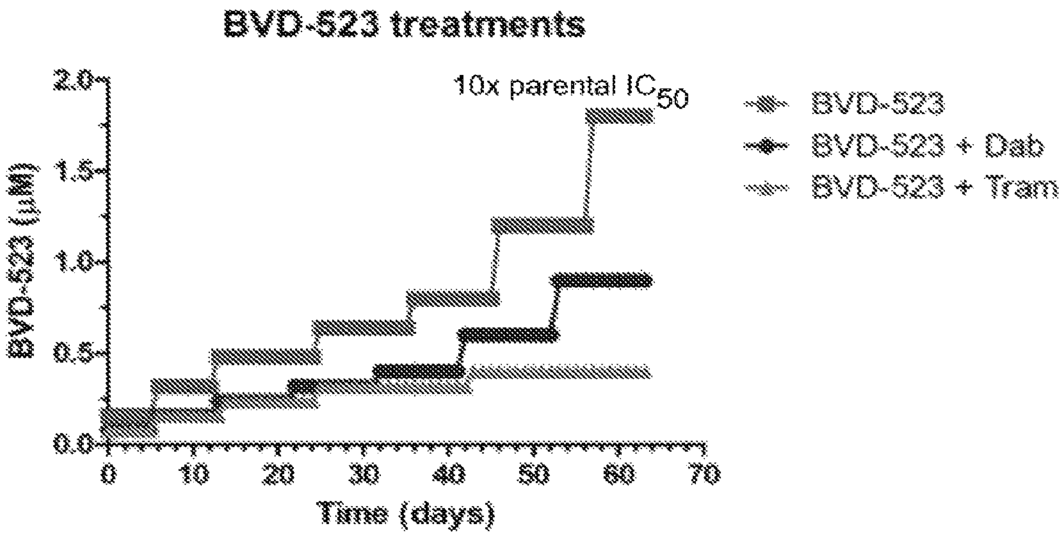
Figure 3D:
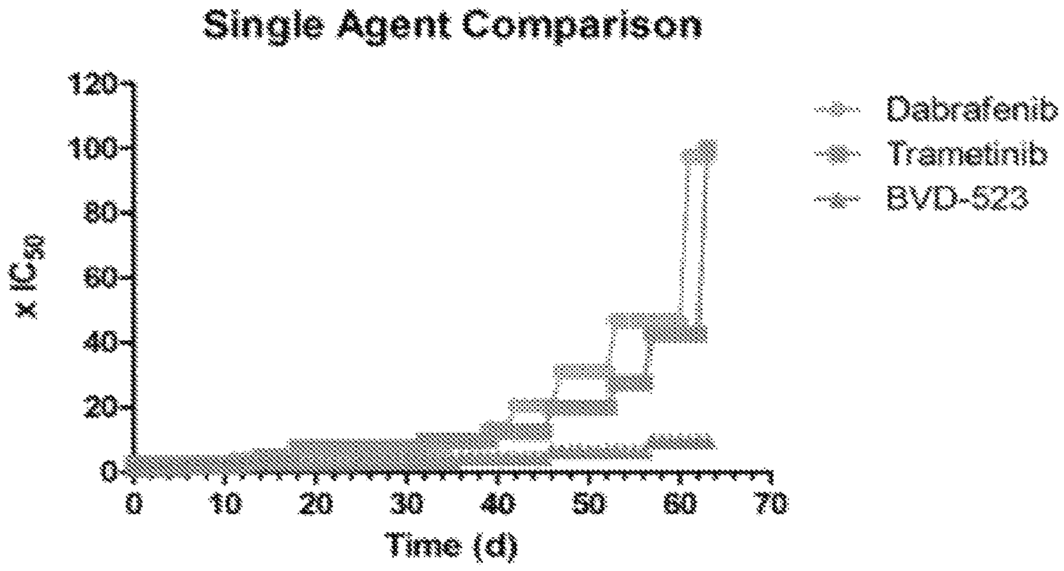
Figure 4A:
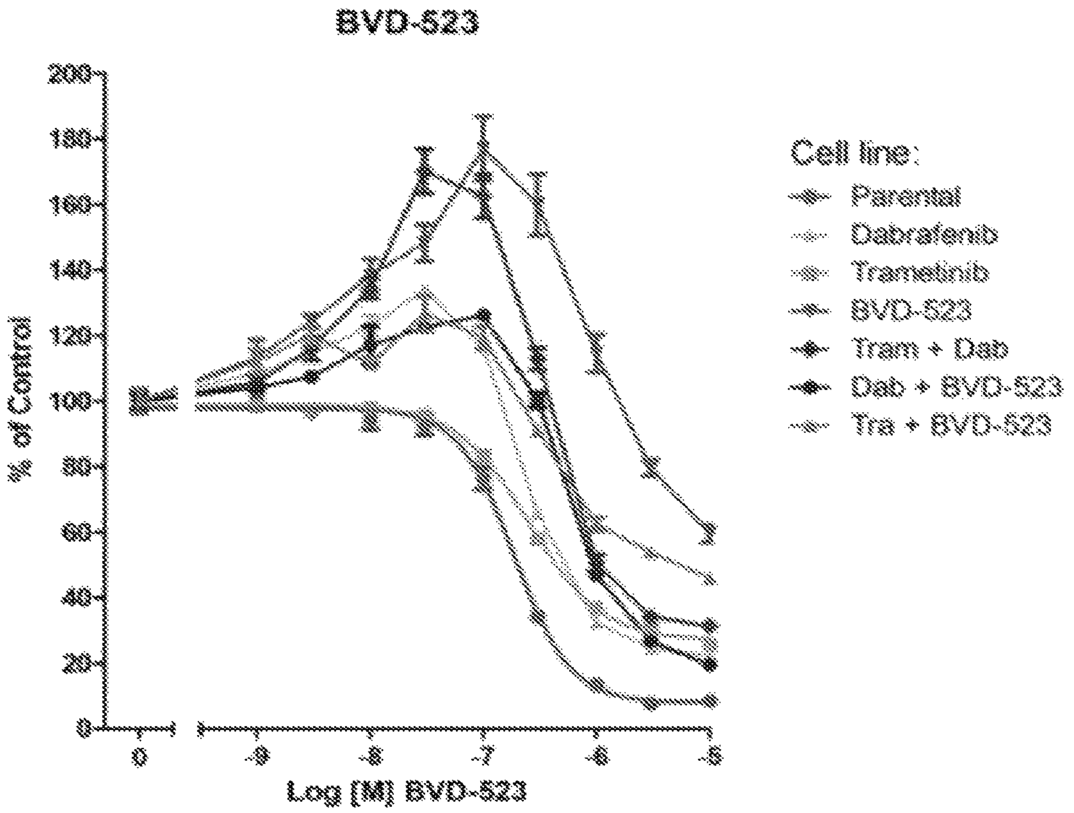
FIG. 4A-FIG. 4H show the results of a proliferation assay that tracks changes in sensitivity to the escalated agent(s) at month 2. Various treatments (trametinib, dabrafenib, BVD-523, and paclitaxel) are as labeled on the top of the graph. The caption to the right of the graph shows the various types of cells generated from the dose escalation study. For example, "dabrafenib" refers to the cells that have been treated with the highest dose of dabrafenib from month 2 of the dose escalation study. Parental refers to the control cells that have not been treated with drugs.
Figure 4B:
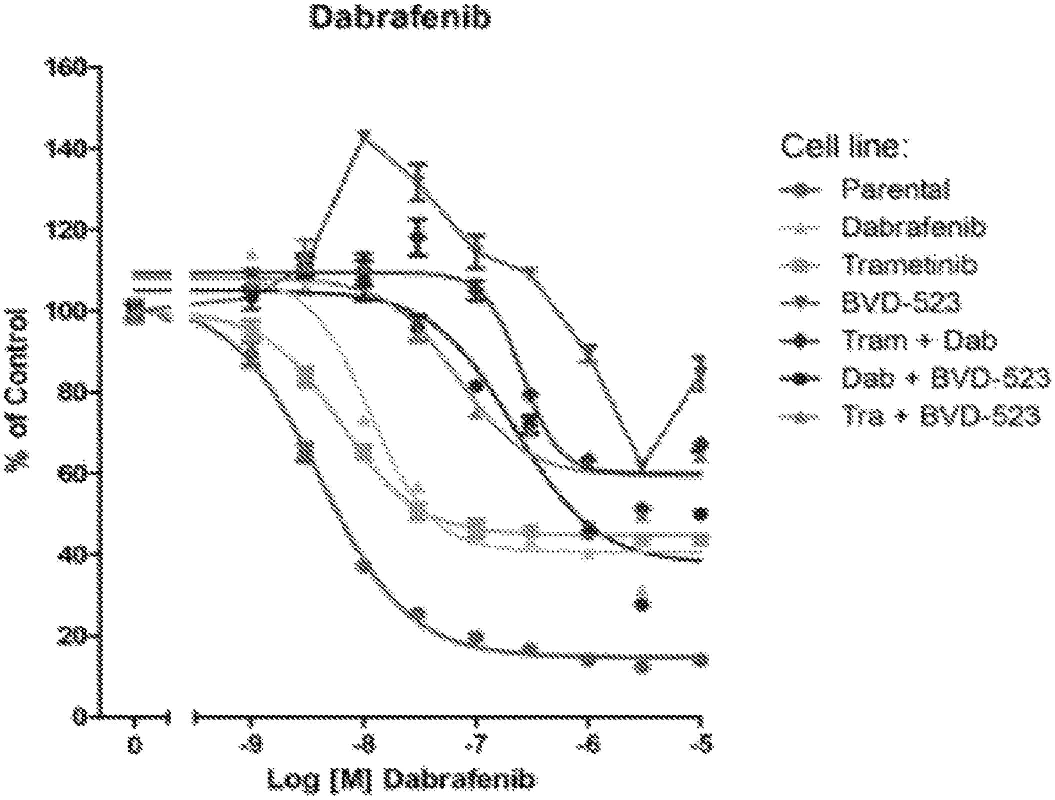
Figure 4C:
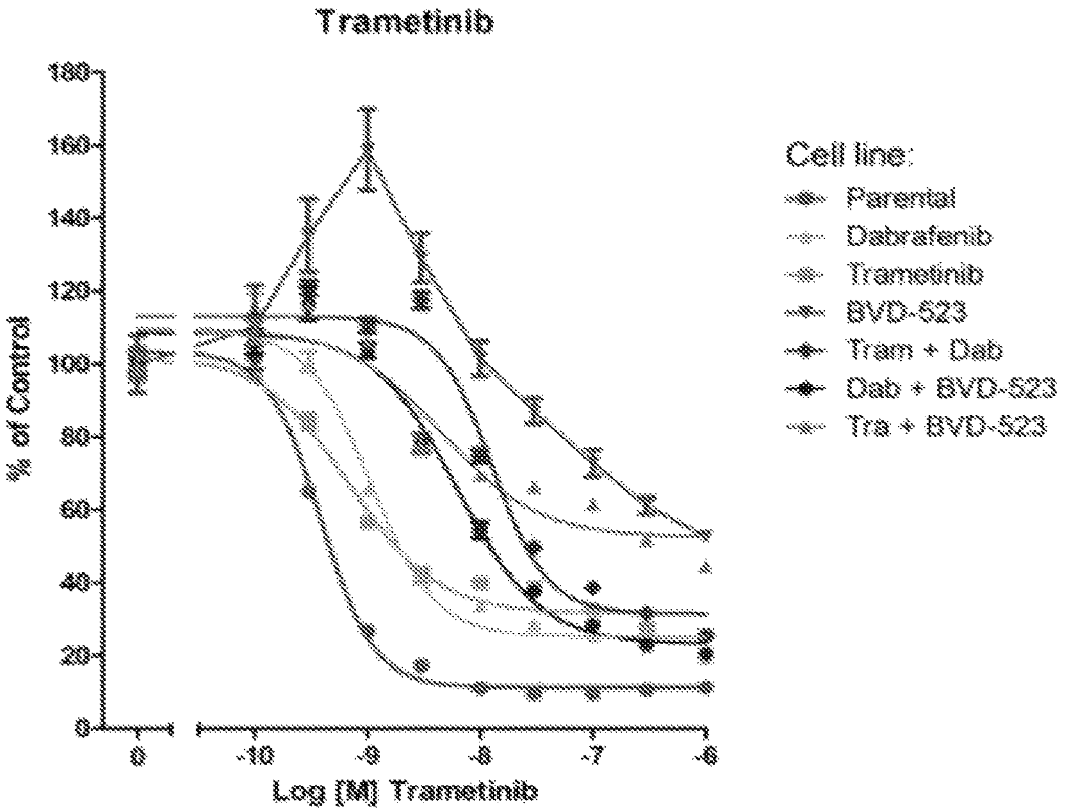
Figure 4D:
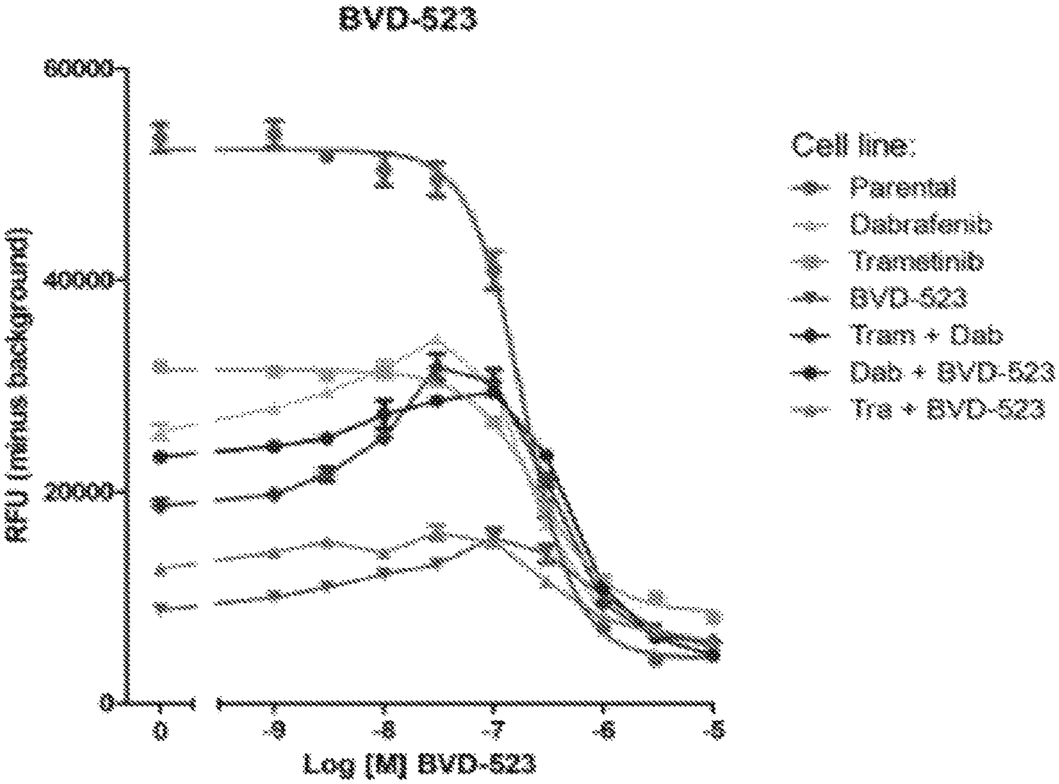
Figure 4E:
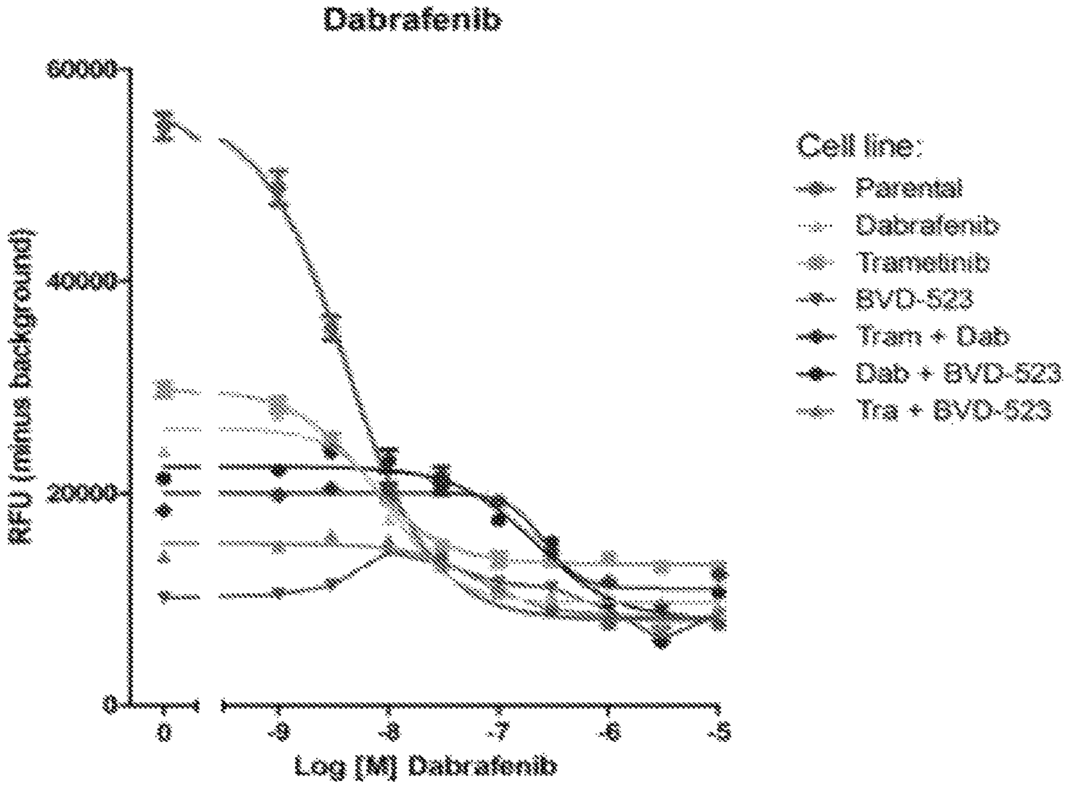
Figure 4F:
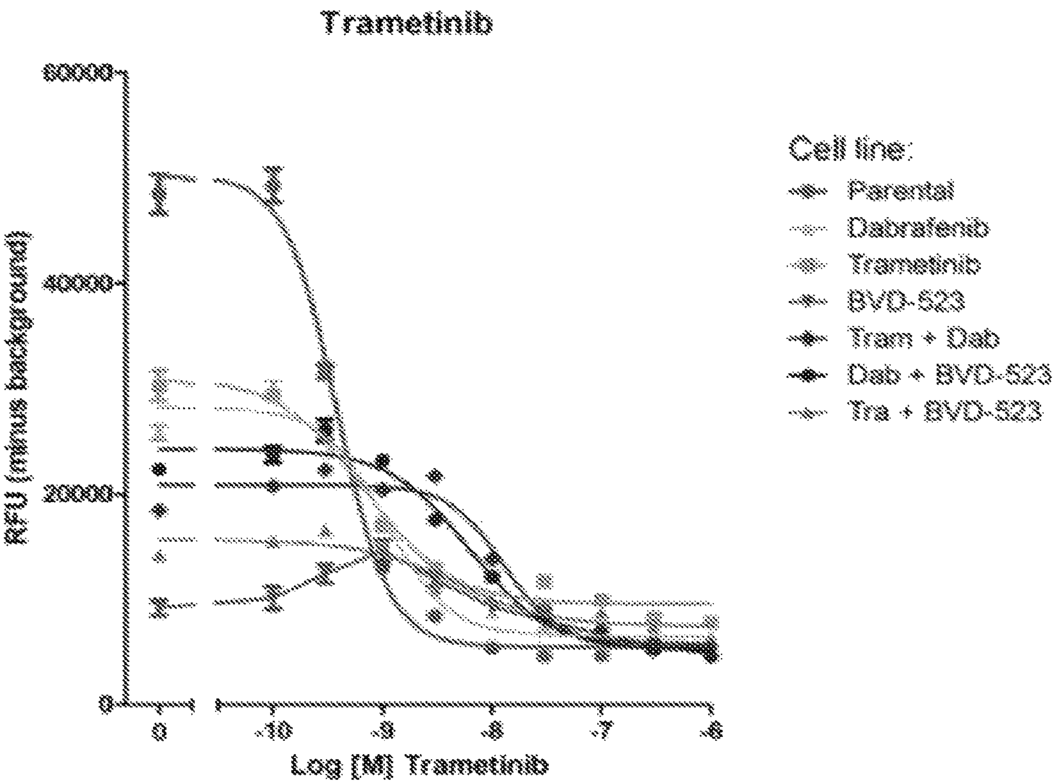
Figure 4G:
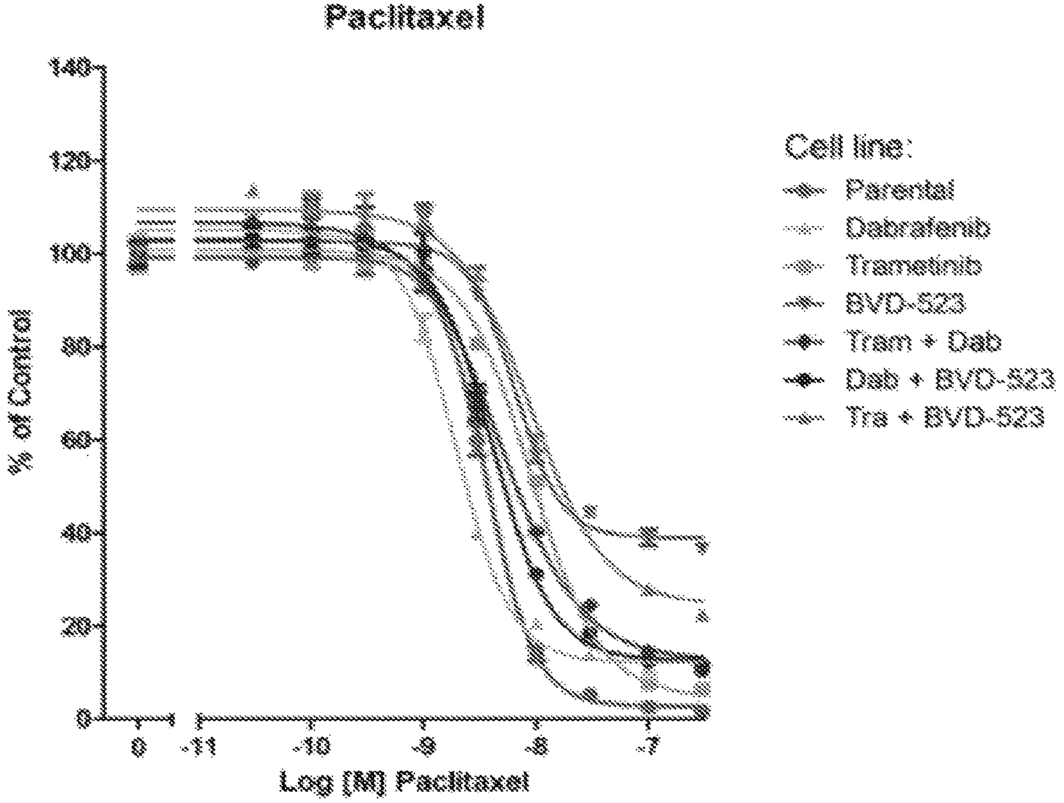
Figure 4H:
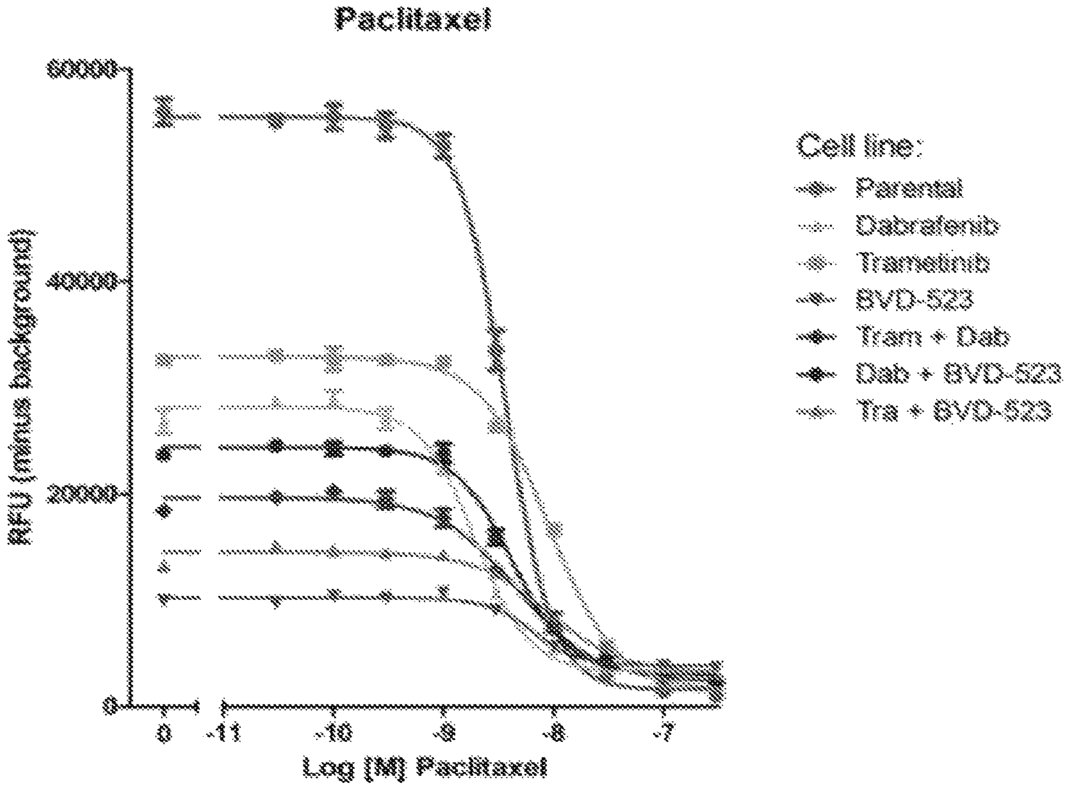
Figure 5A:
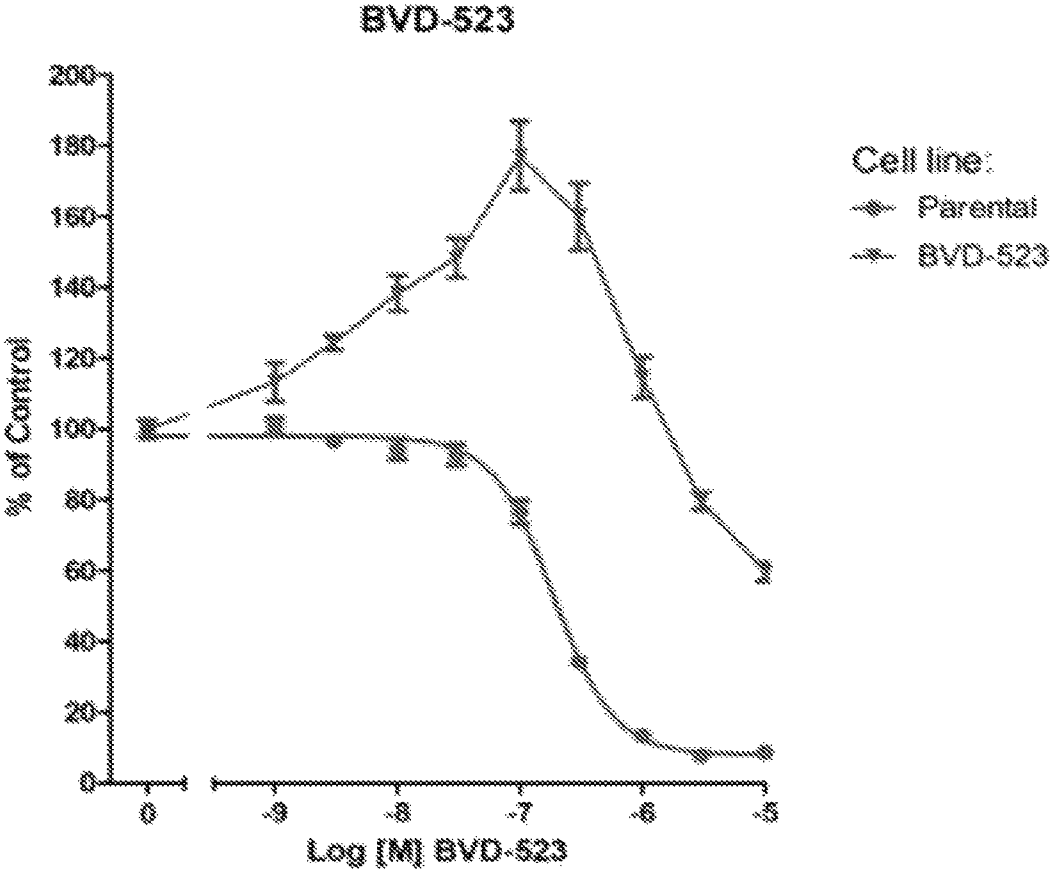
FIG. 5A-FIG. 5H show only the parental and BVD-523 cell line data from FIG. 4A-FIG. 4H. Various treatments (trametinib, dabrafenib, BVD-523, and paclitaxel) are as labeled.
Figure 5B:
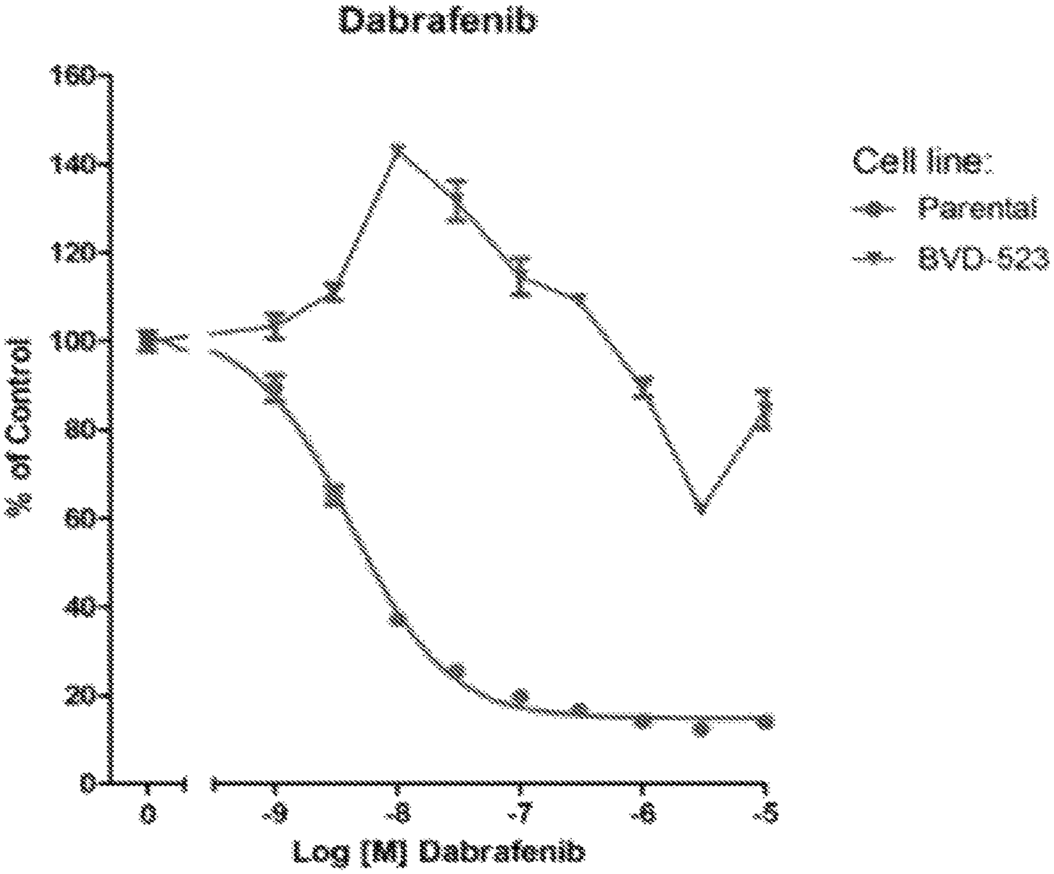
Figure 5C:
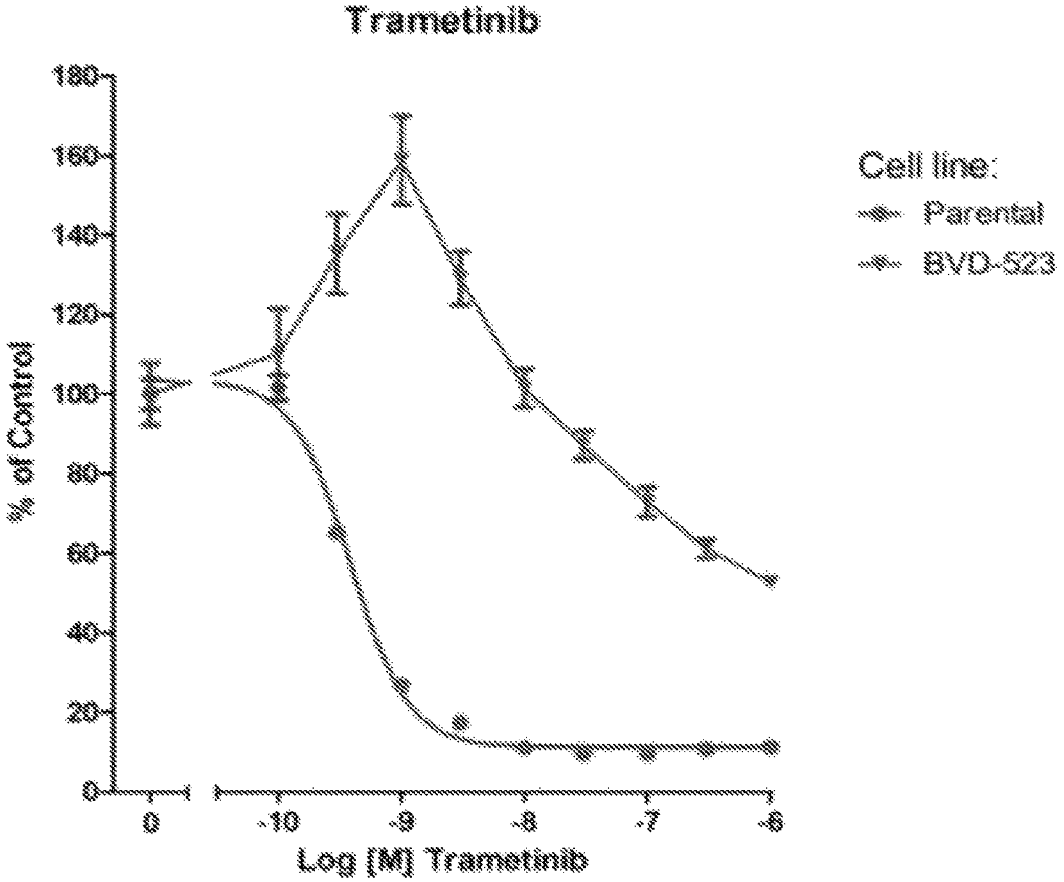
Figure 5D:
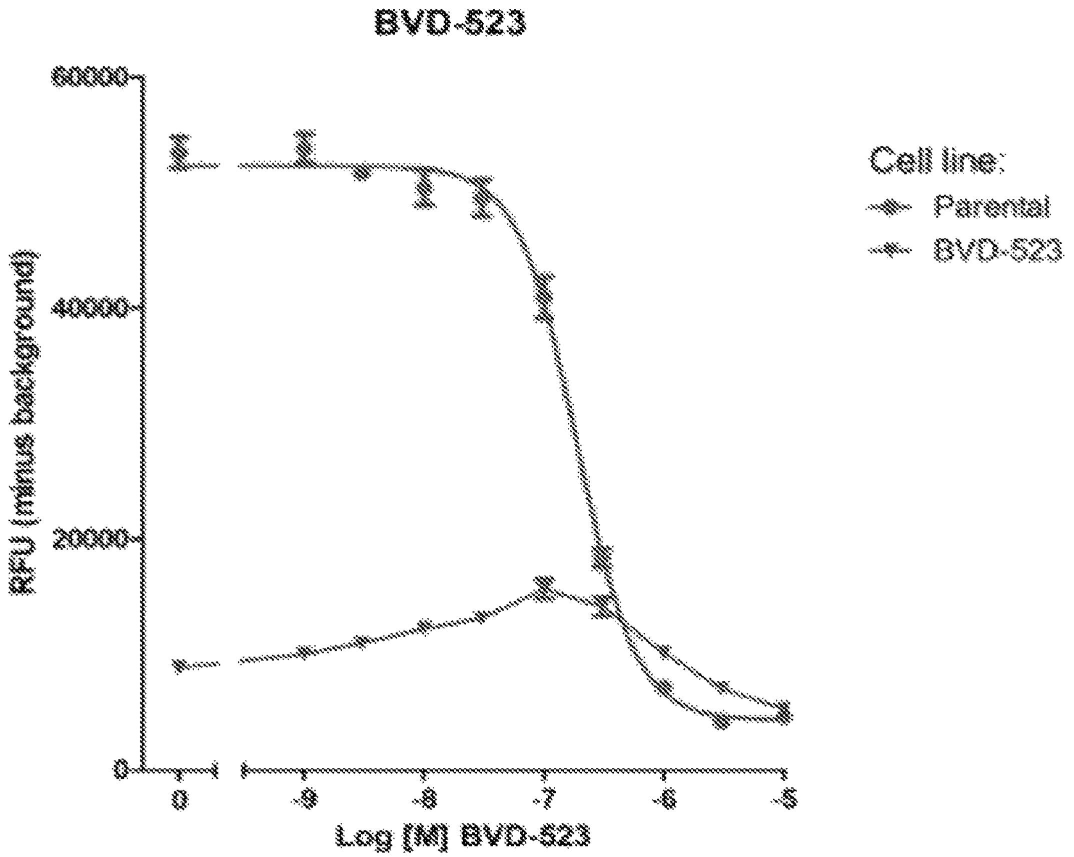
Figure 5E:
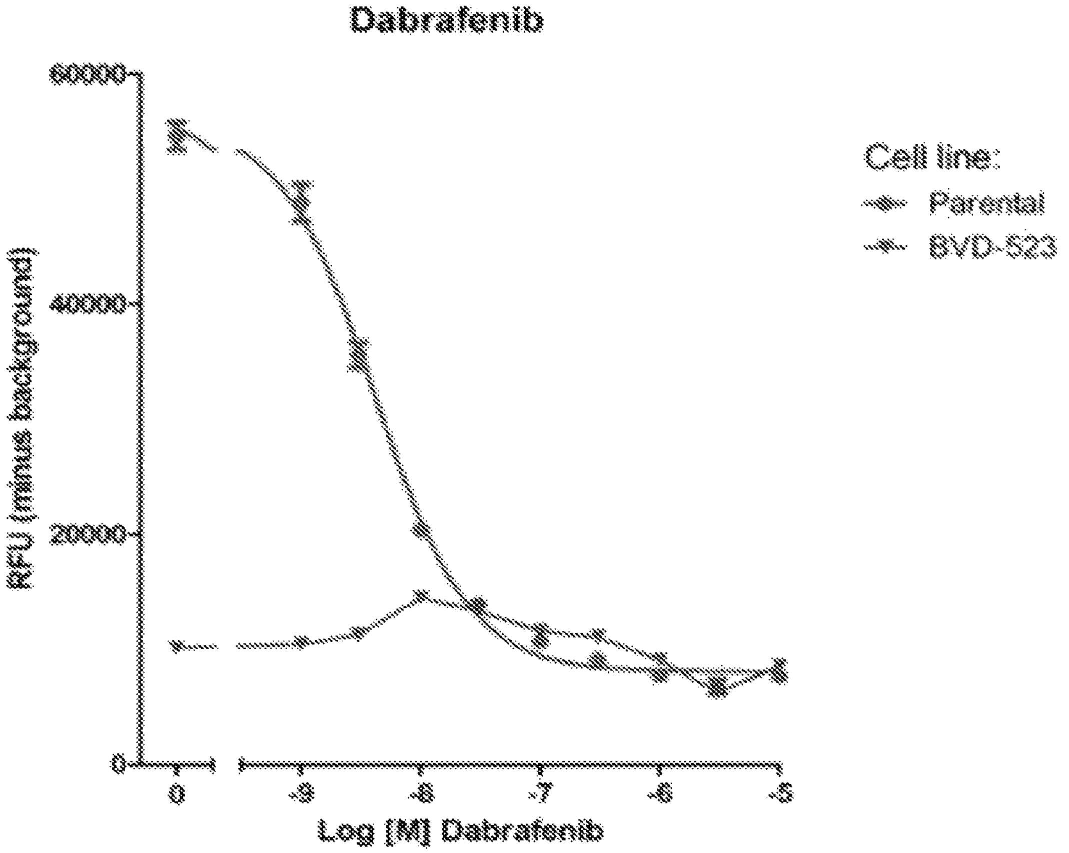
Figure 5F:
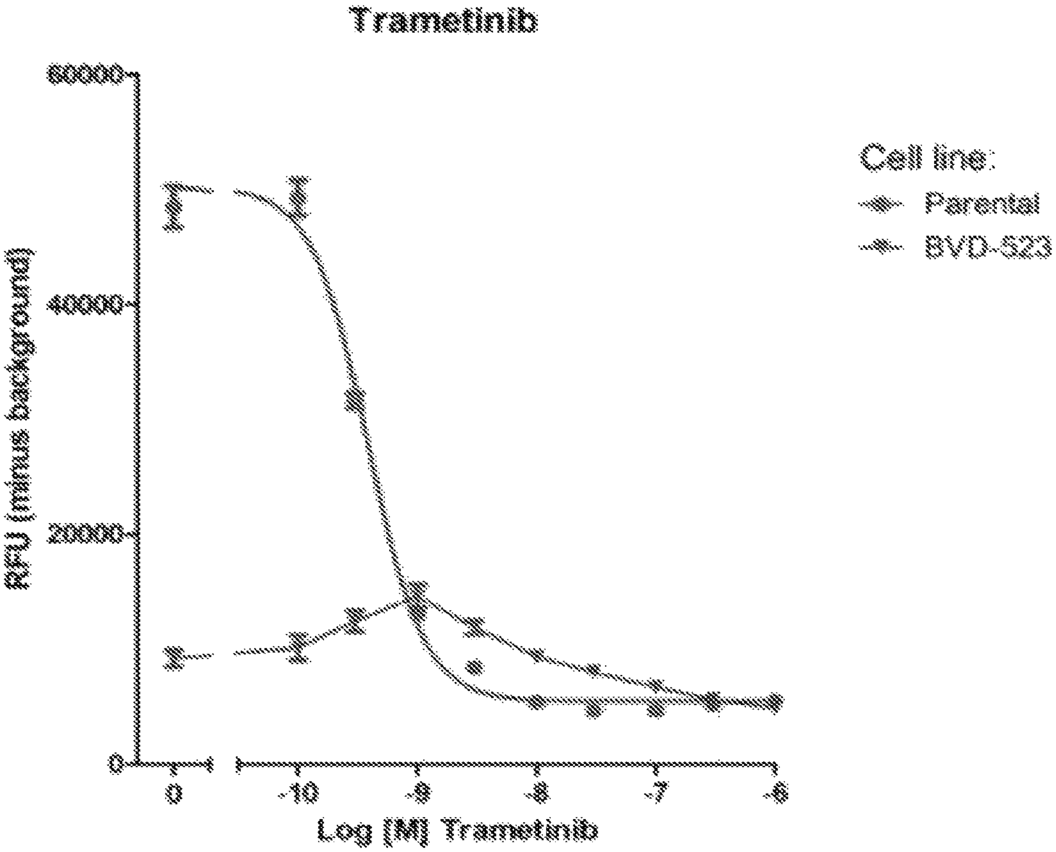
Figure 5G:
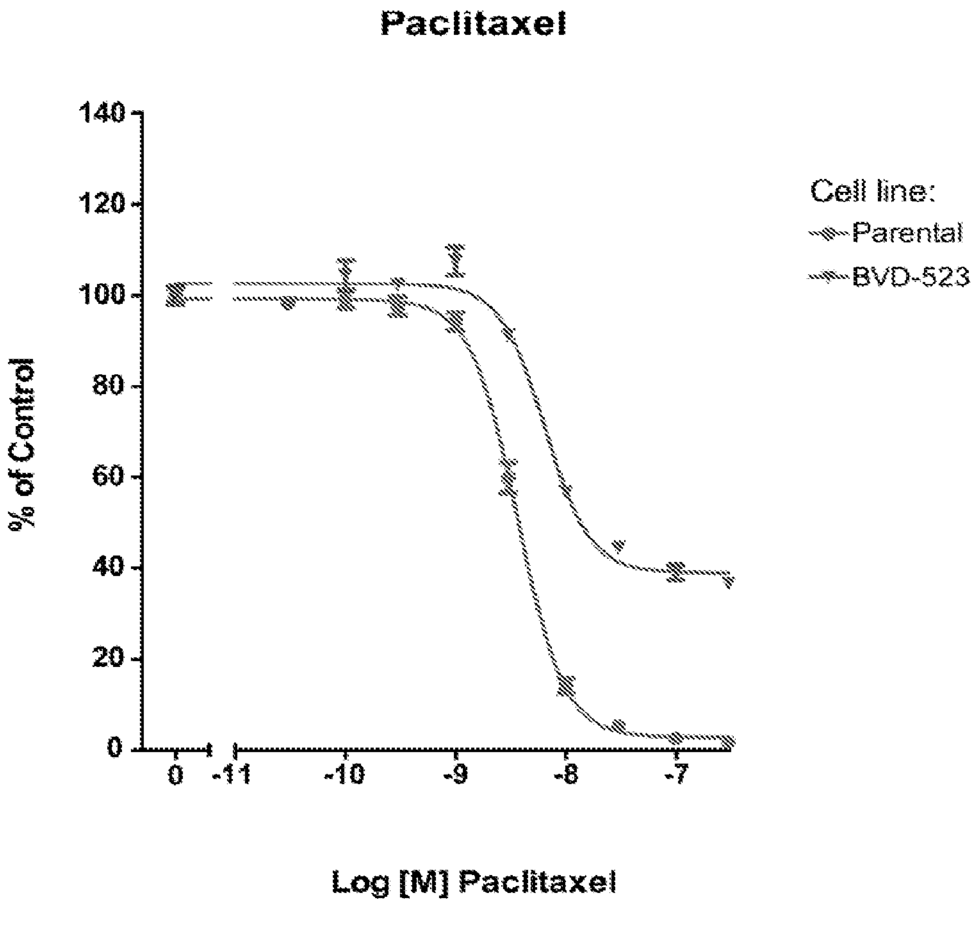
Figure 5H:
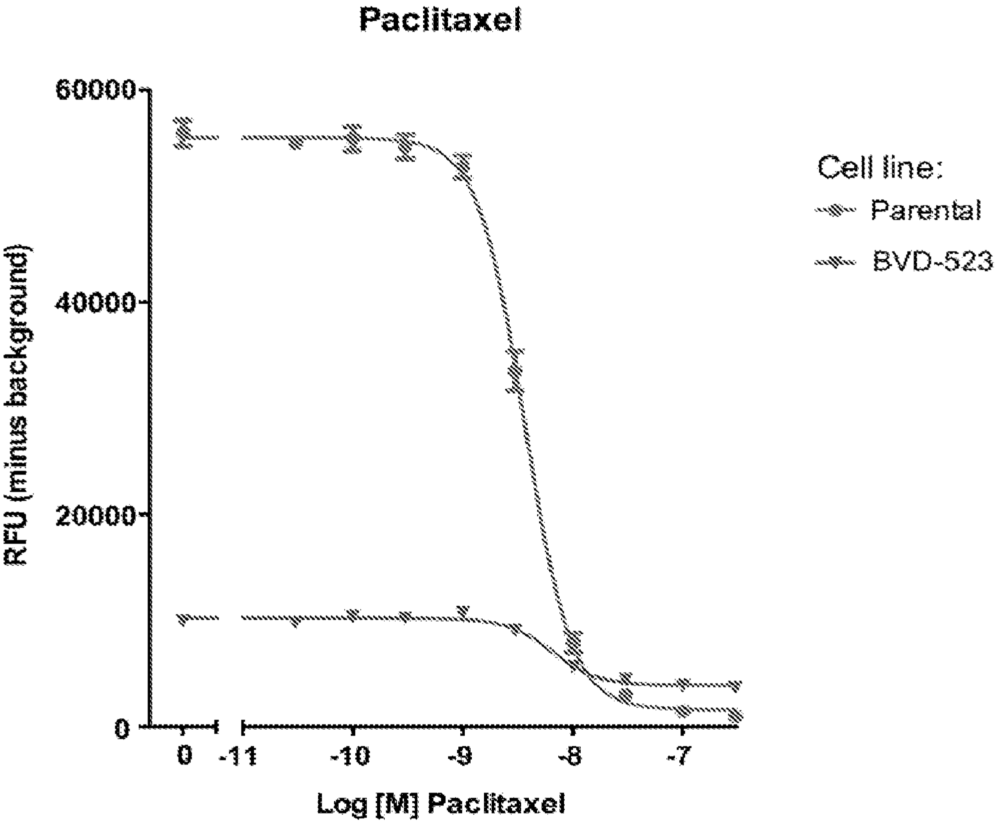

The second month of studies saw most treatments move into a phase where doses were increased in greater increments (1.5-fold) compared to the initial gentle escalation phase. The single agent escalation of dabrafenib and trametinib was quickest, with cells growing in concentrations equivalent to 100× parental cell $IC_{50}$ (FIG. 3A and FIG. 3B). The single agent escalation of BVD-523 progressed more slowly compared to dabrafenib and trametinib (FIG. 3C). See FIG. 3D for a comparison of the single agent escalations. BVD-523 escalated cells had a more "fragile" appearance and there was a greater number of floating cells compared to the dabrafenib and trametinib escalated populations.

The combined agent escalations progressed more slowly than the single agent treatments. The BVD-523/trametinib combination was particularly effective in preventing cells from progressing.

Proliferation Assay Results—Month 2

Proliferation assays on single agent escalated dabrafenib and trametinib cell populations revealed modest shifts in the dose response curves, suggesting that an additional period of escalation would be beneficial to further enrich for resistant cells. Interestingly, in the proliferations assay, there was evidence to suggest that cells exposed to BVD-523 grew less well upon inhibitor withdrawal, perhaps indicating a level of addiction.

FIG. 4A-FIG. 4H show normalized and raw proliferation assay results from month 2 of the studies. Note that differences in max signals in DMSO controls between different treatments (FIG. 4D, FIG. 4F, and FIG. 4H) suggest differential growth rates between treatments. These differences may influence the responses of lines to inhibitors in the proliferation assays.

FIG. 5A-FIG. 5H show normalized and raw proliferation assay results from month 2 of the studies with a focus on parental and BVD-523 line data only.

Table 11 shows $IC_{50}$ data for month 2 of the studies. Relative $IC_{50}$s were determined from 4-parameter curve fits in Prism.

TABLE 11

$IC_{50}$ Data - Month 2

| | Cell Line, Relative $IC_{50}$ (nM) | | | | | | |
|---|---|---|---|---|---|---|---|
| Compound | Par* | Tra | Dab | BVD-523 | Dab/Tram | Dab/523 | Tram/523 |
| Dabrafenib | 4.1 | 6.2 | 11.5 | 697 | 256 | 218 | 68 |
| Trametinib | 0.4 | 0.7 | 1.1 | 24.3 | 12.6 | 6.2 | 4.6 |
| BVD-523 | 187 | 252 | 284 | 1706 | 561 | 678 | 435 |
| Paclitaxel | 3.7 | 8.9 | 1.9 | 6.5 | 4.7 | 4.2 | 8.9 |

*Par = Parental cell line

Example 4

Dose Escalation and Proliferation Assays—Month 3

Dose Escalation Progress—Month 3

Figure 6A:
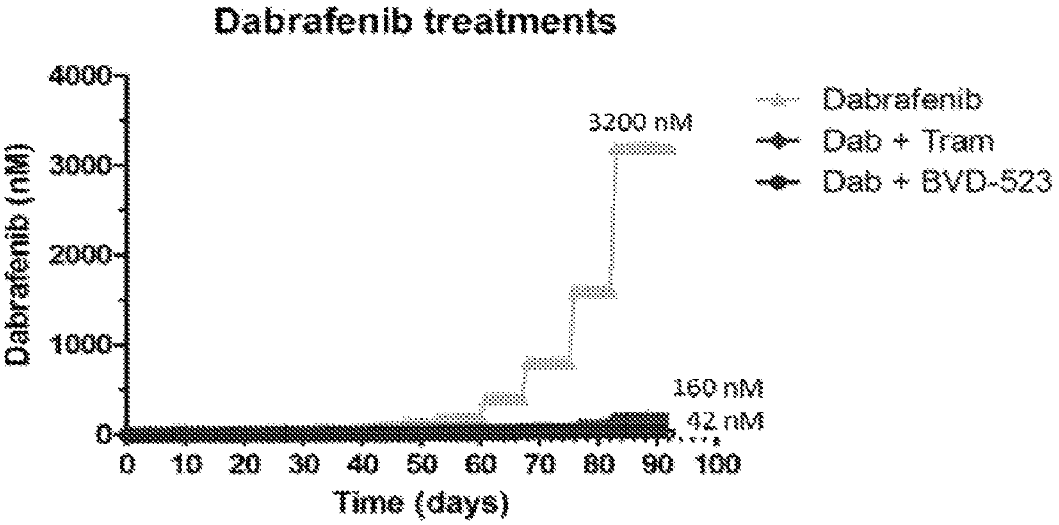
FIG. 6A-FIG. 6D show the progress of the dose escalation study in a human malignant cell line (A375 cells) for month 3. Various treatments (trametinib, dabrafenib, and BVD-523) are as labeled.
Figure 6B:
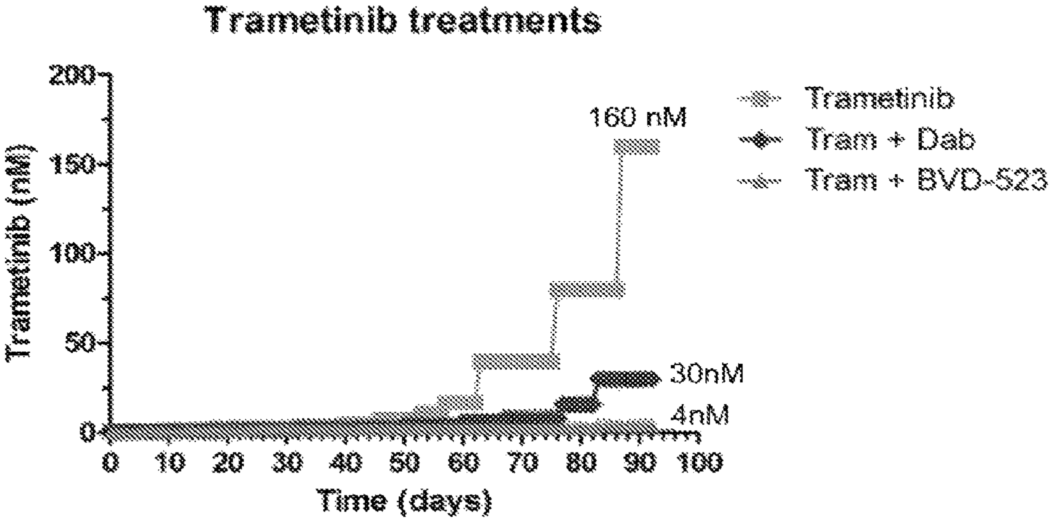
Figure 6C:
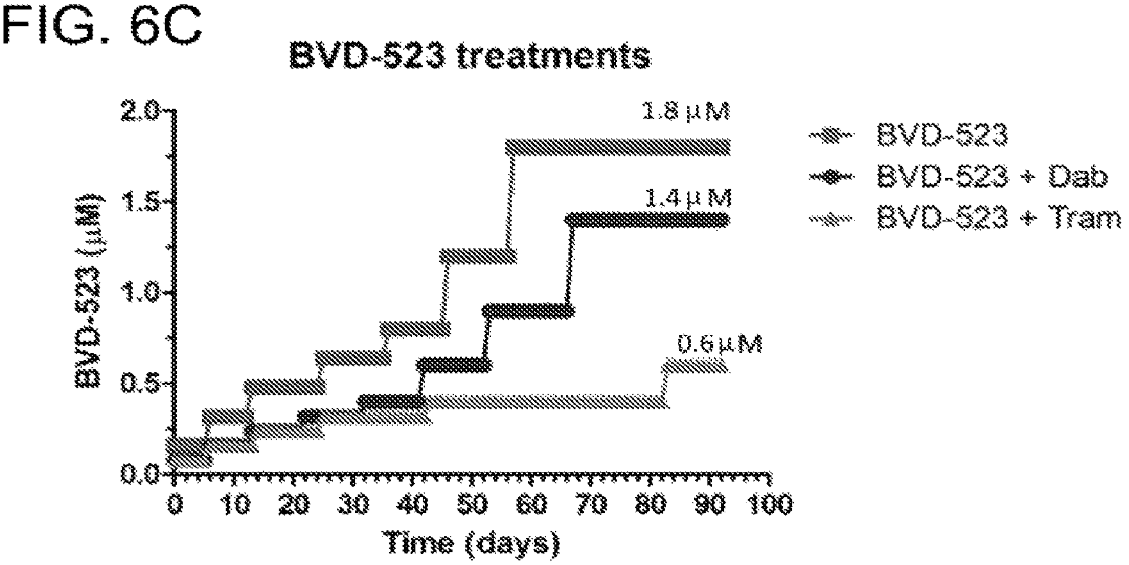
Figure 6D:
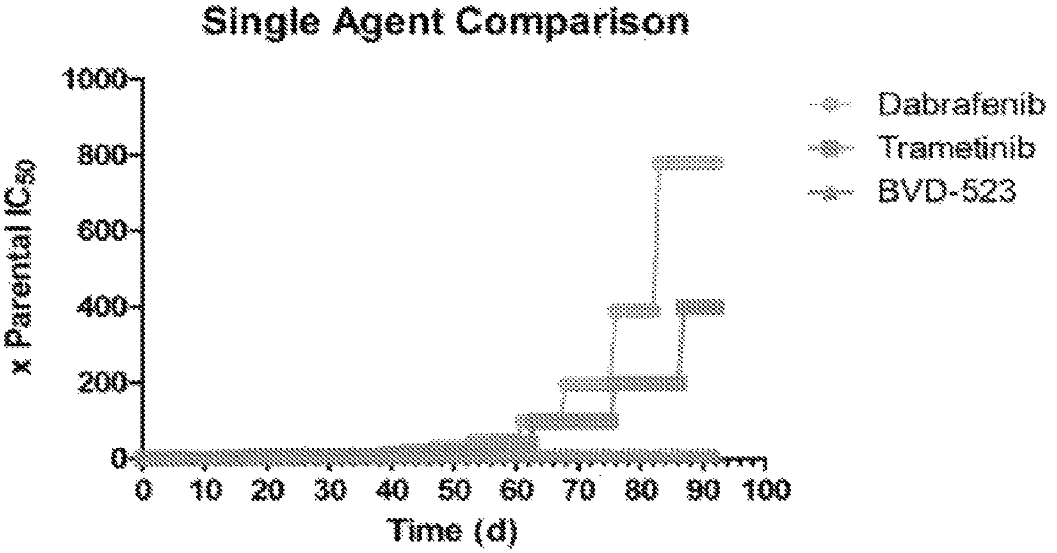

FIG. 6A-FIG. 6C show single and combination agent escalation for month 3 of the studies. FIG. 6D shows a comparison of single agent escalations.

Proliferation Assay Results—Month 3

Figure 7:
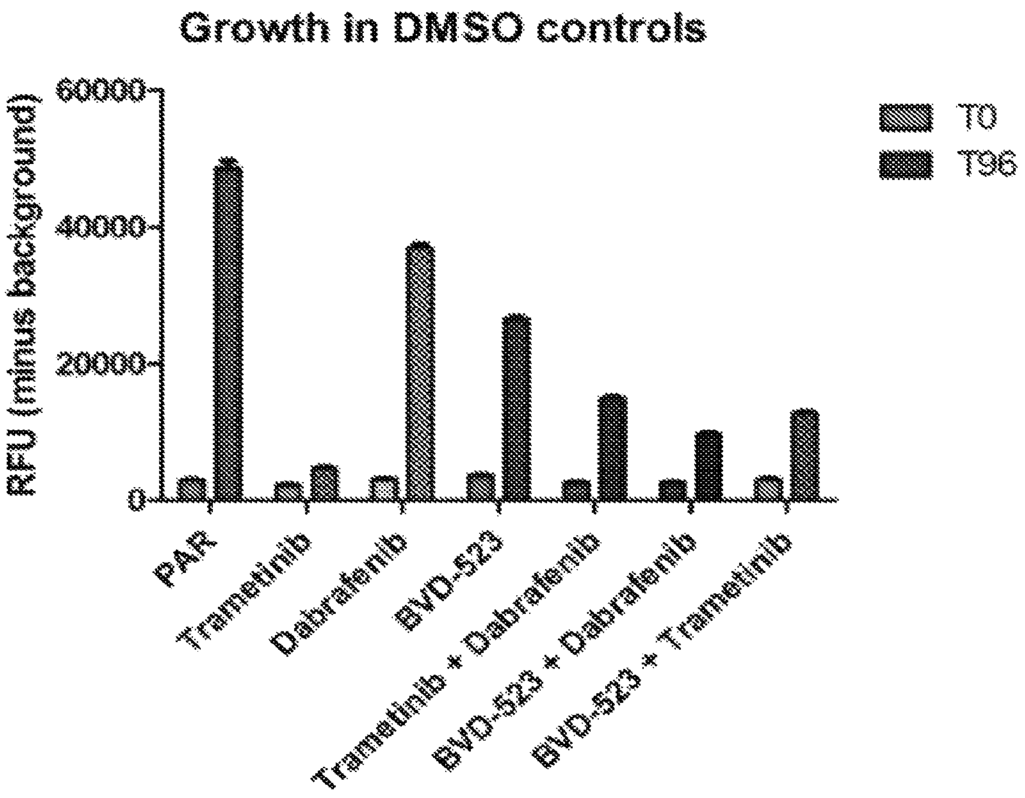
FIG. 7 is a histogram showing the results of a proliferation assay as applied to cells grown in the DMSO control wells from the dose escalation assay.
Figure 8A:
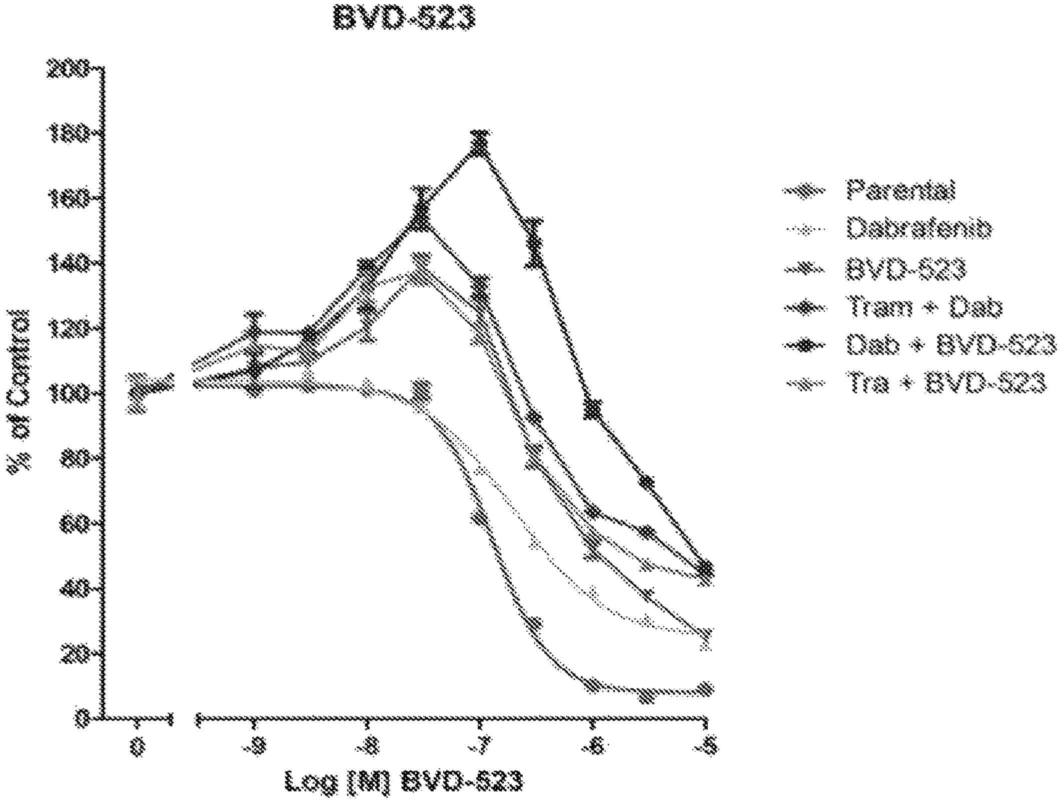
FIG. 8A-FIG. 8D are a set of line graphs showing proliferation assays for month 3 of the study. Various treatments (trametinib, dabrafenib, BVD-523, and paclitaxel) are as labeled on the top of the graph. The caption to the right of the graph shows the various types of cells generated from the dose escalation study. For example, "dabrafenib" refers to the cells that have been treated with the highest dose of dabrafenib from month 3 of the dose escalation study. Parental refers to the control cells that have not been treated with drugs.
Figure 8B:
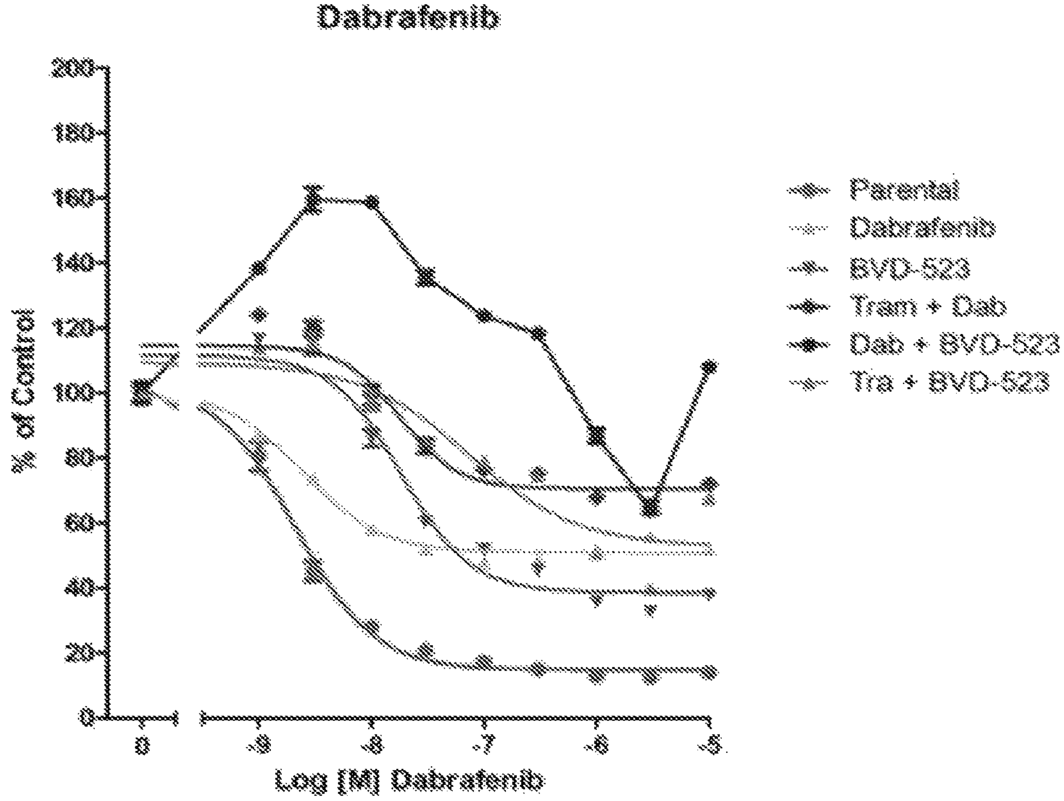
Figure 8C:
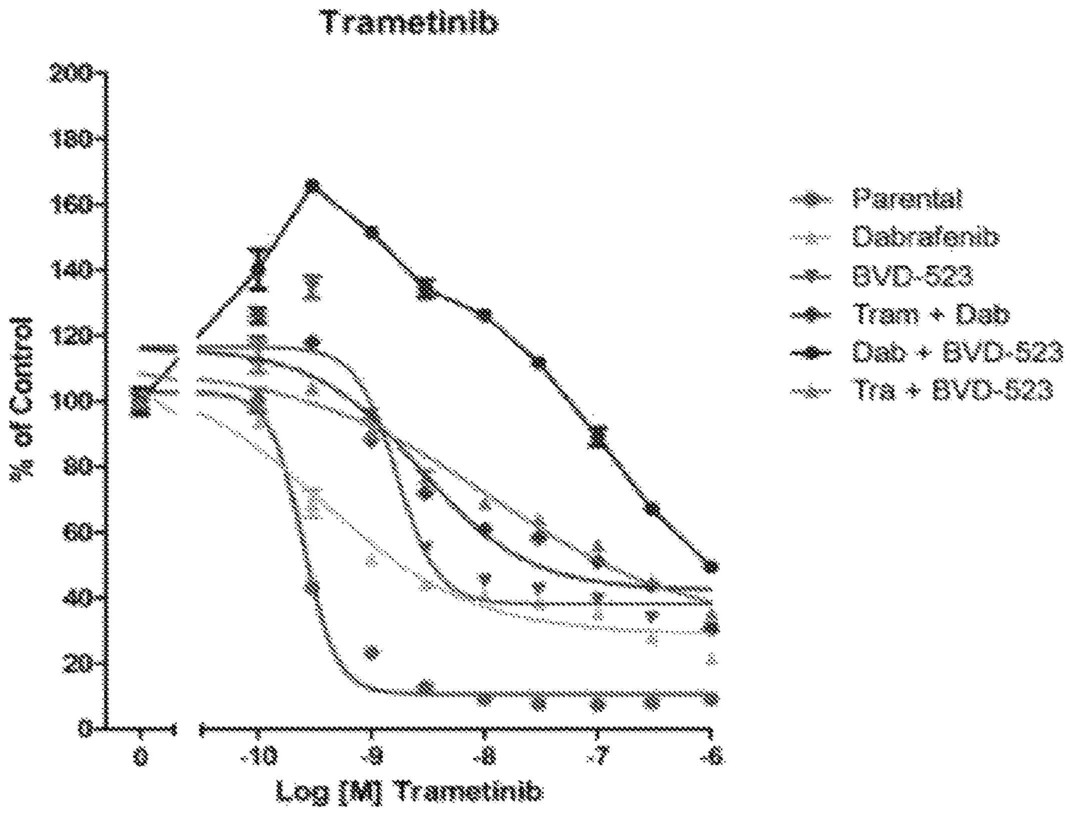
Figure 8D:
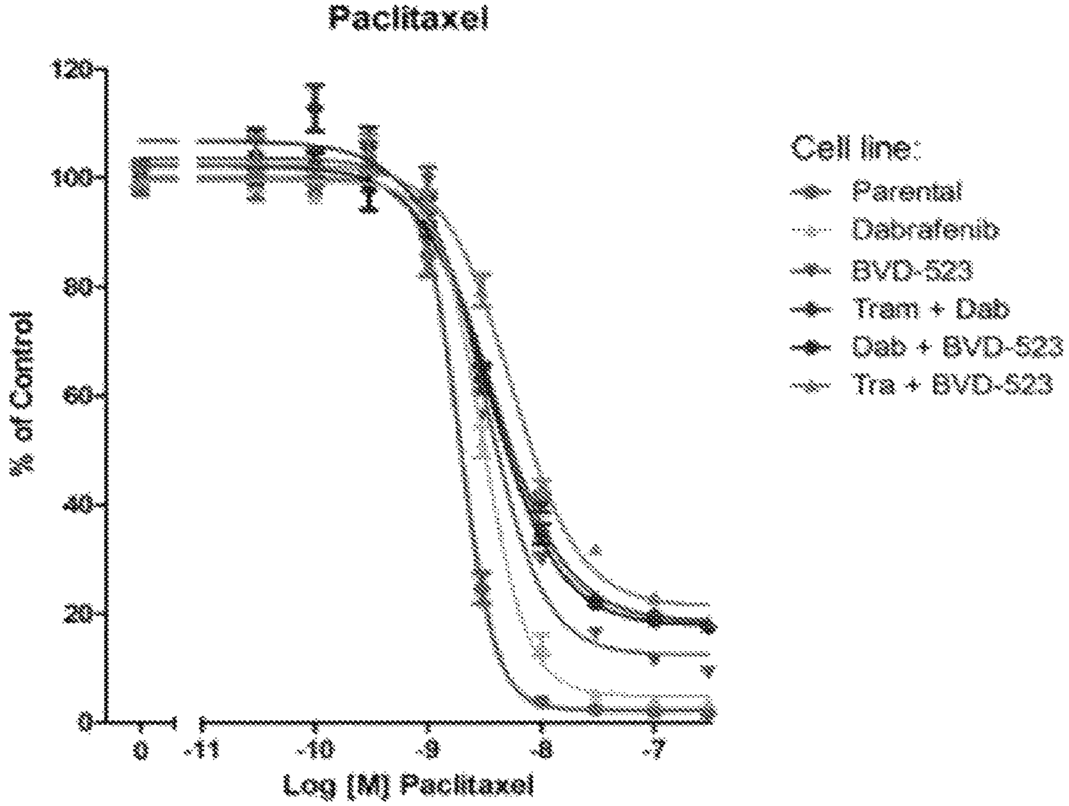
Figure 9A:
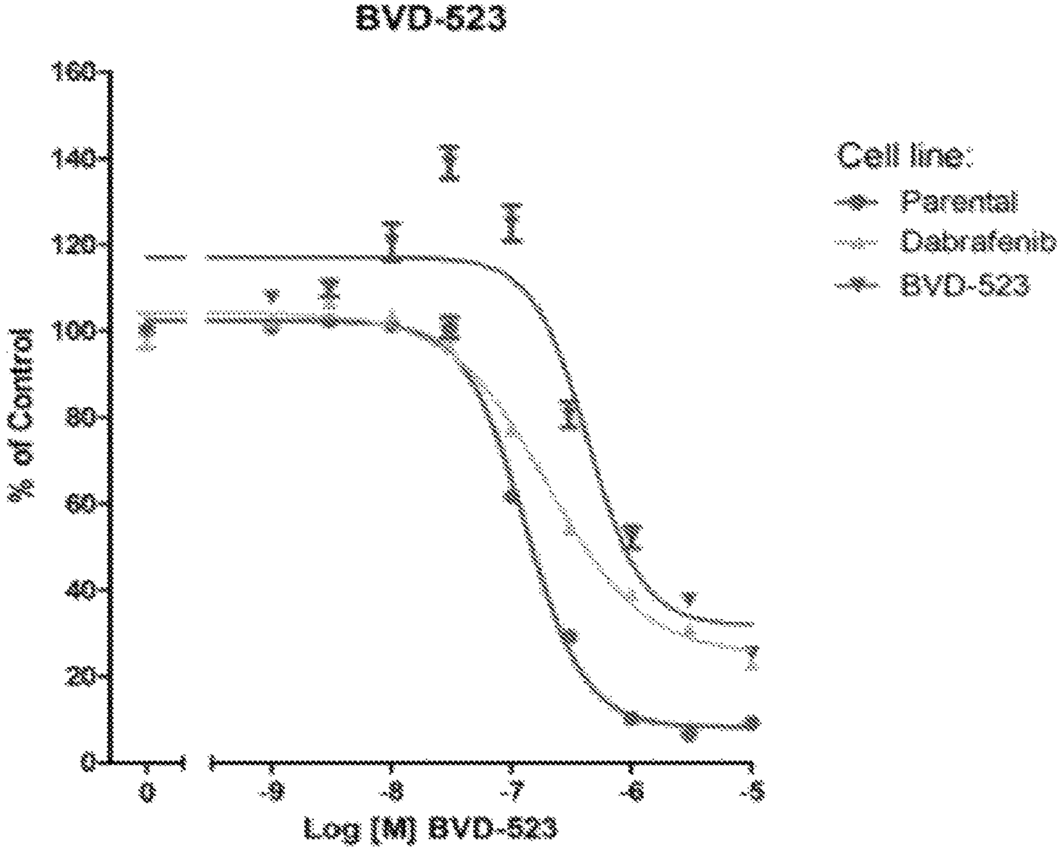
FIG. 9A-FIG. 9D show only the parental, dabrafenib, and BVD-523 cell line data from FIG. 8A-FIG. 8D.
Figure 9B:
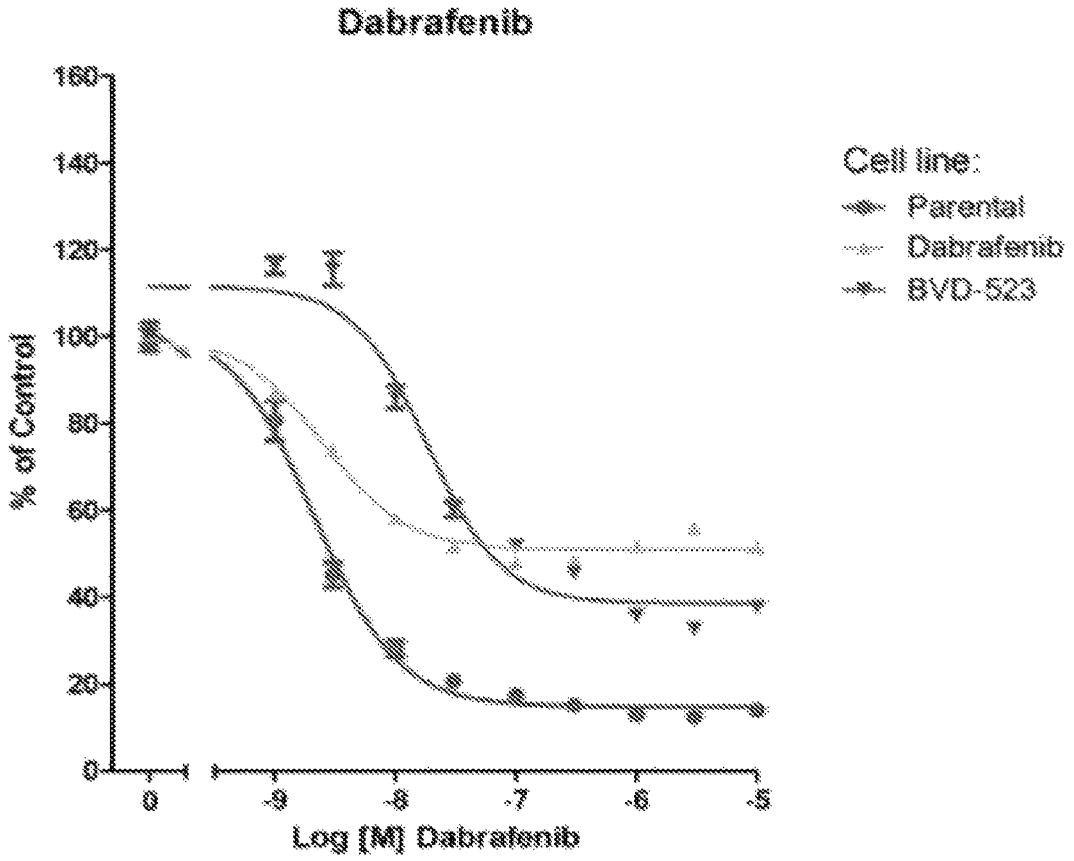
Figure 9C:
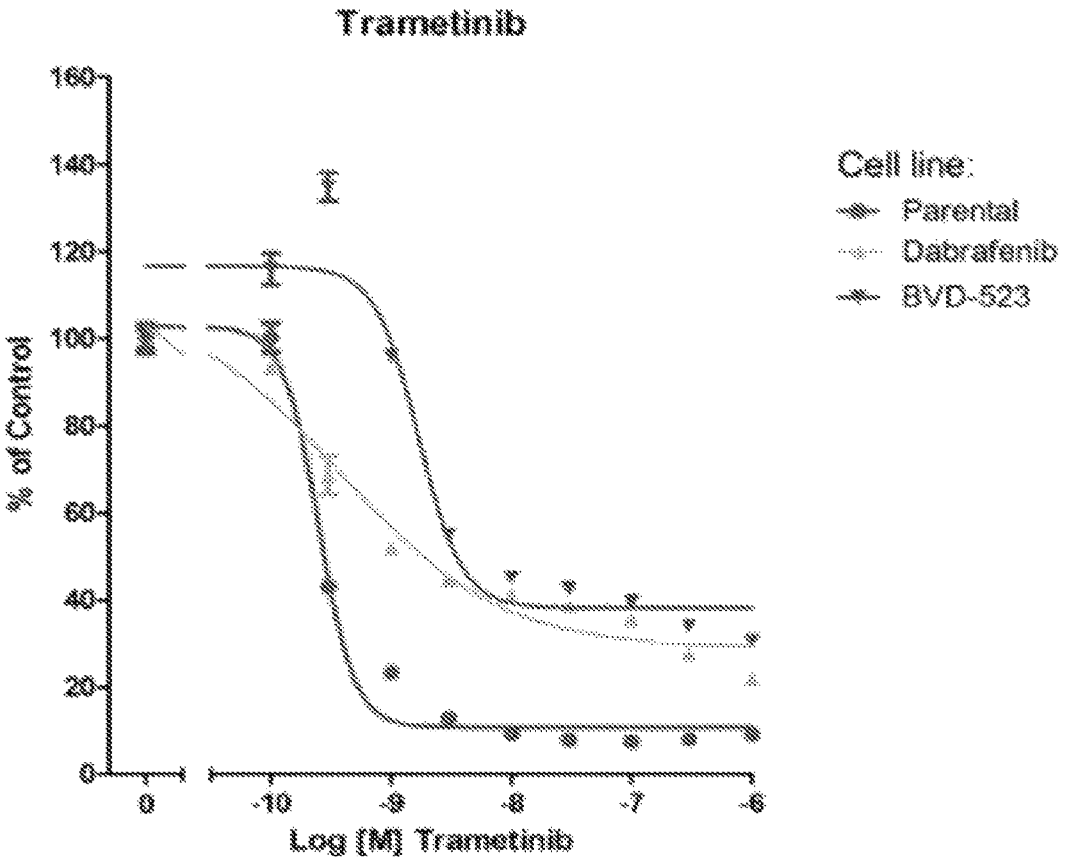
Figure 9D:
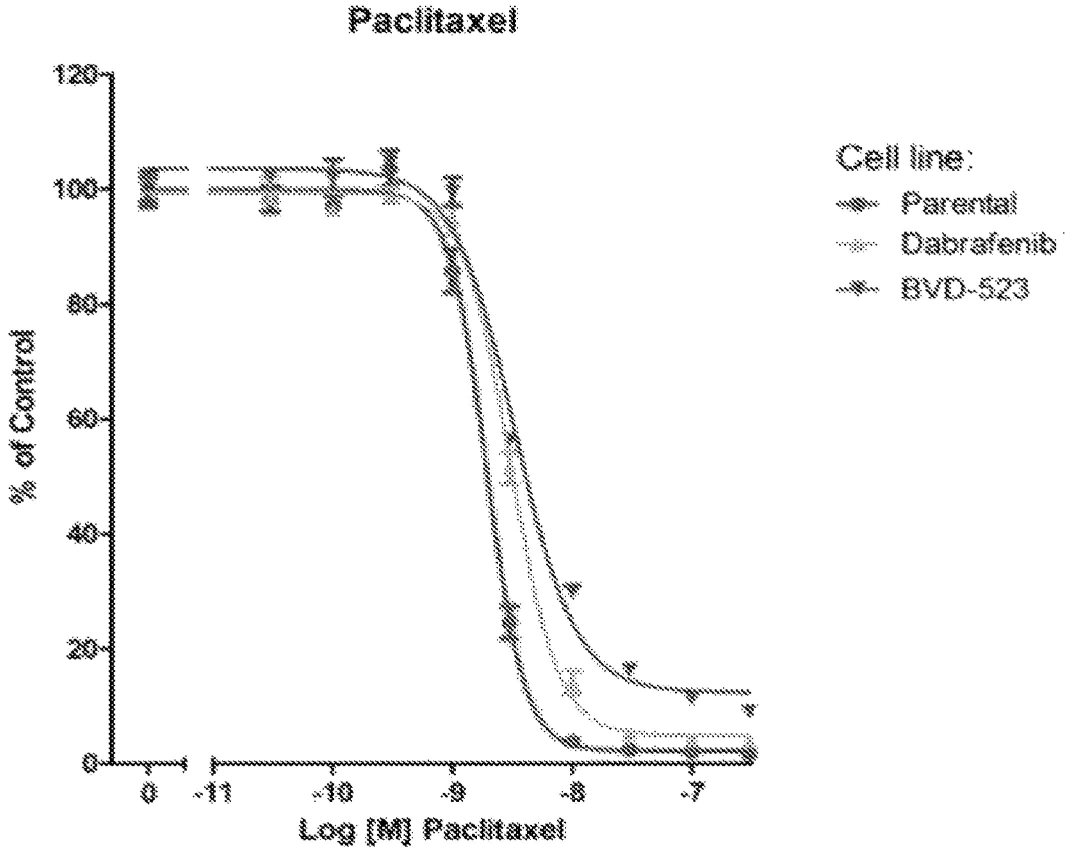
Figure 10A:
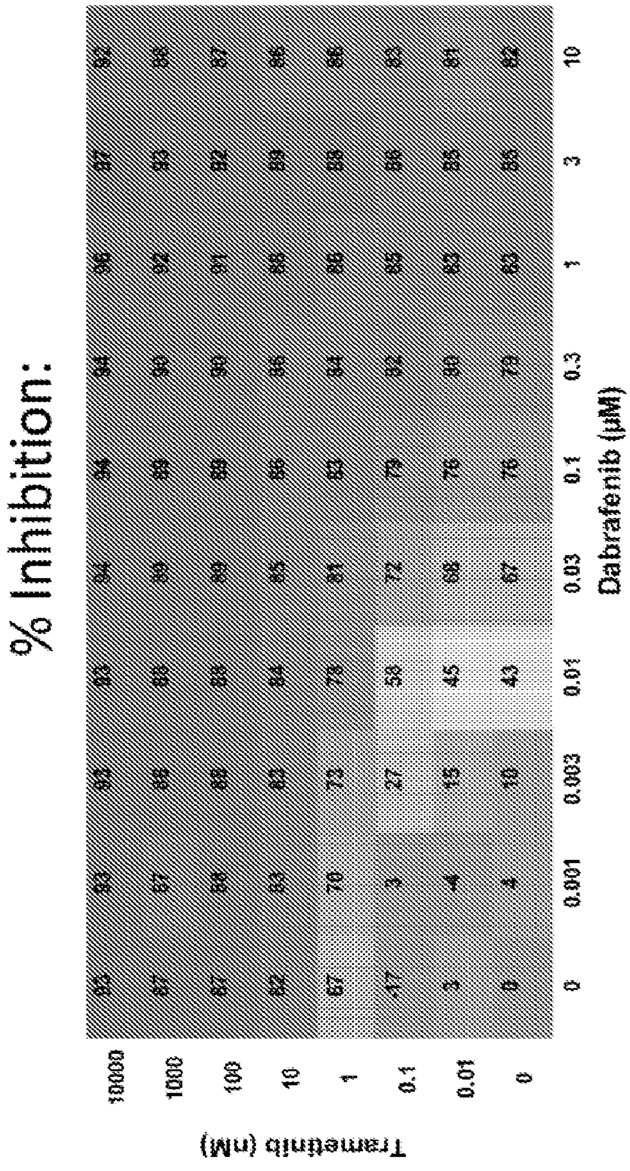
FIG. 10A is a dose matrix showing % inhibition of the trametinib/dabrafenib combination in A375 cells using the Alamar Blue cell viability assay.
Figure 10B:
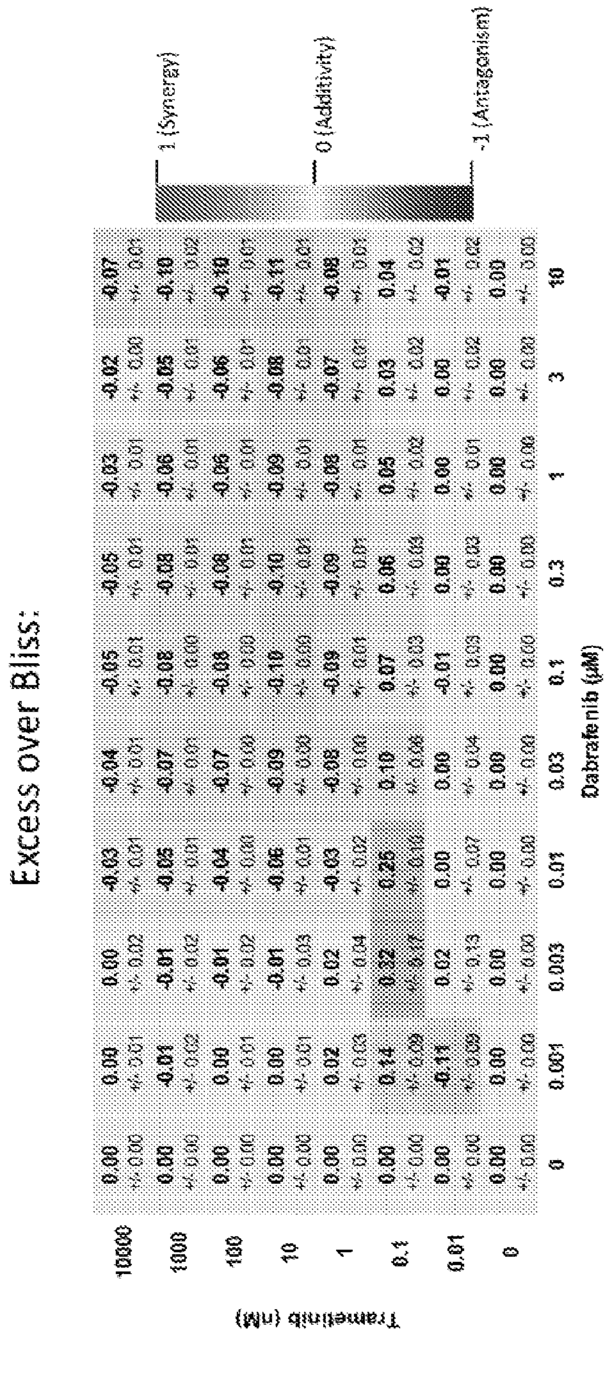
FIG. 10B is a dose matrix showing excess over Bliss for the trametinib/dabrafenib combination.
Figure 10C:
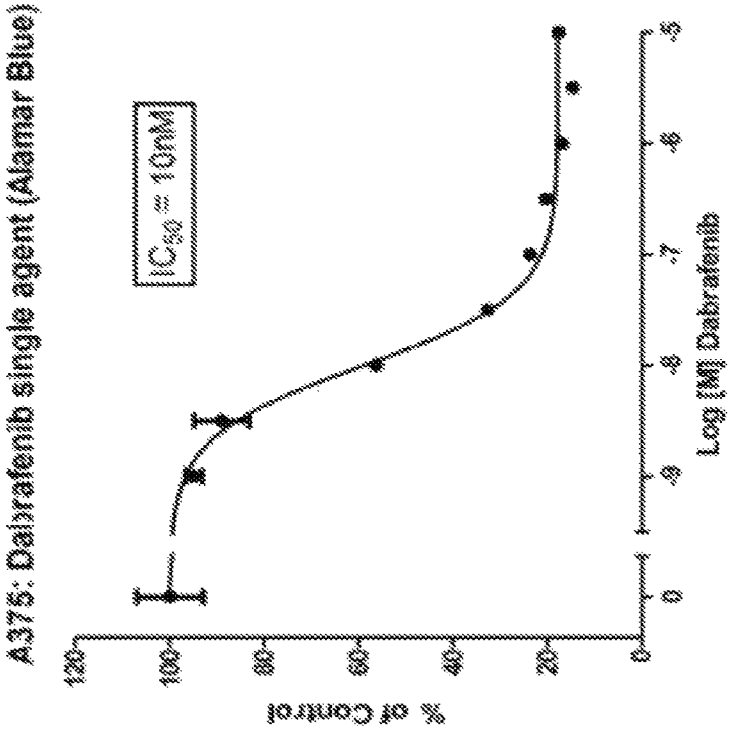
FIG. 10C and FIG. 10D show % viability relative to DMSO only treated controls for dabrafenib and trametinib single agent treatments in A375 cells using the Alamar Blue cell viability assay.
Figure 10D:
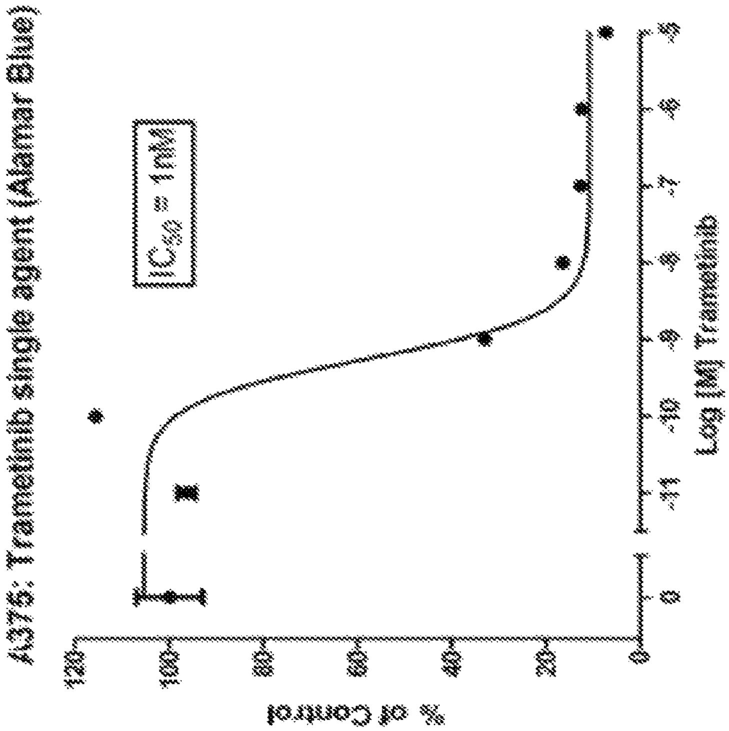
Figure 10E:
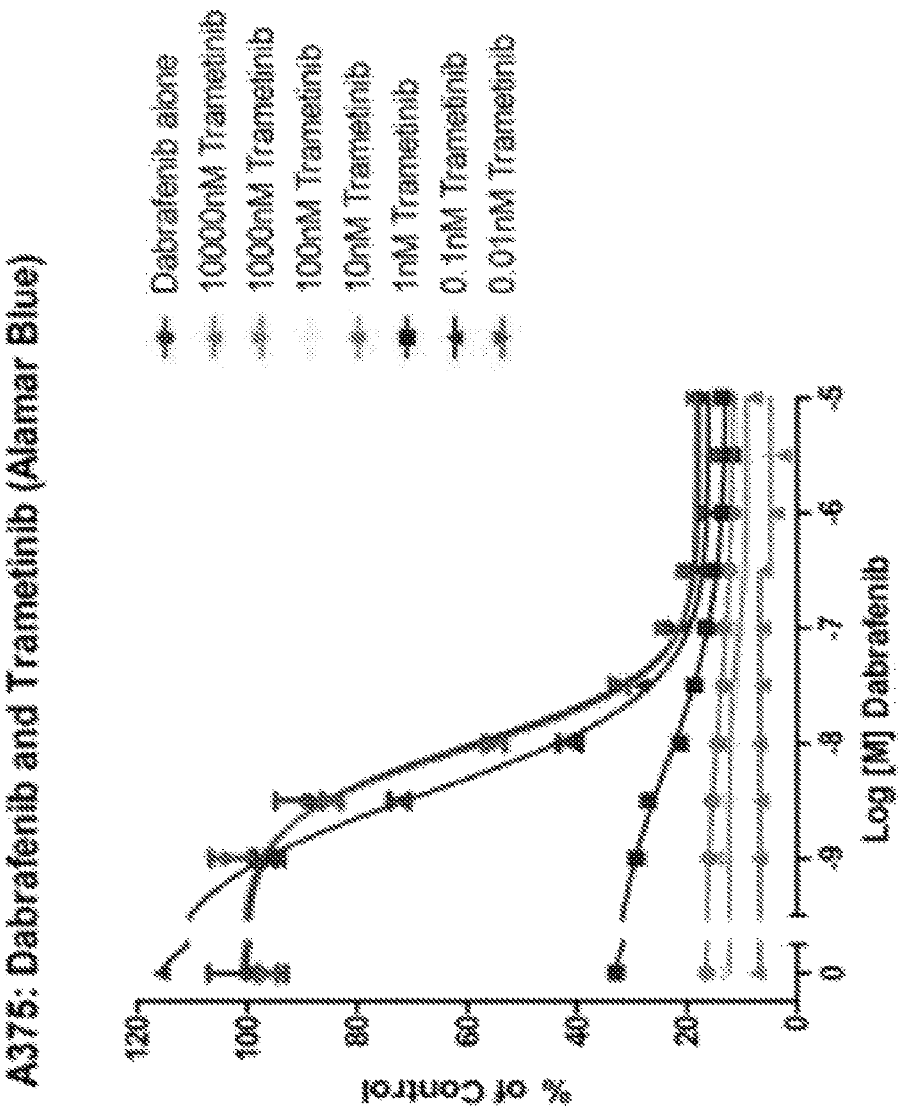
FIG. 10E shows % viability relative to DMSO only treated controls for dabrafenib and trametinib combination treatments in A375 cells using the Alamar Blue cell viability assay.
Figure 11B:
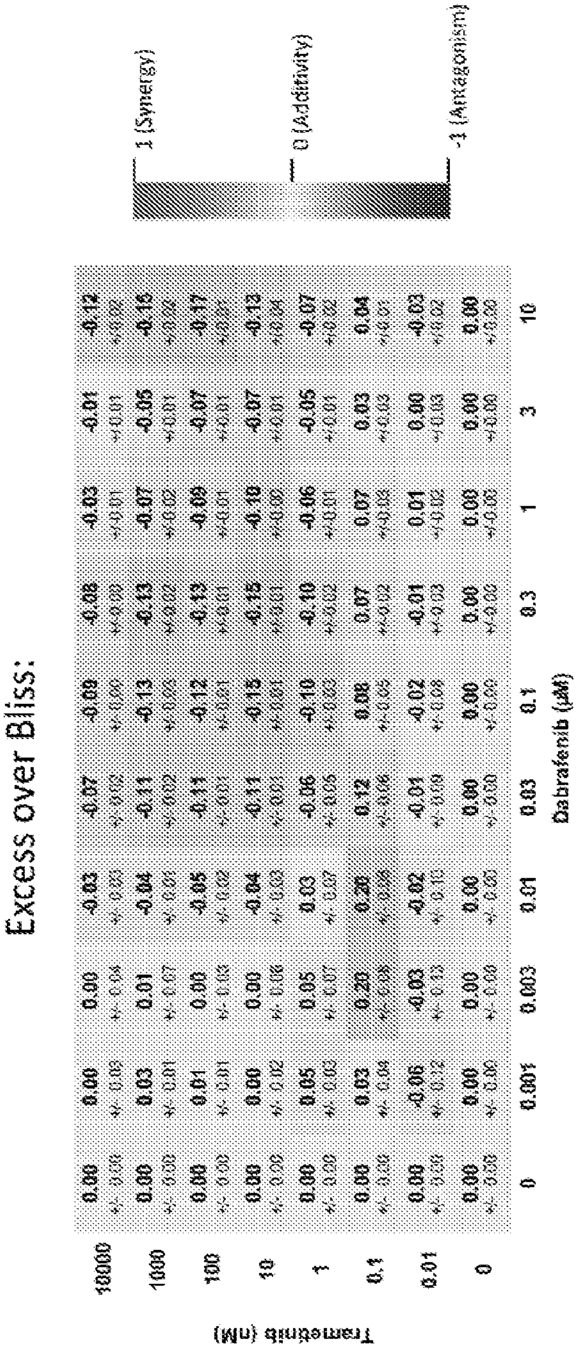
FIG. 11B is a dose matrix showing excess over Bliss for the trametinib/dabrafenib combination.
Figure 11C:
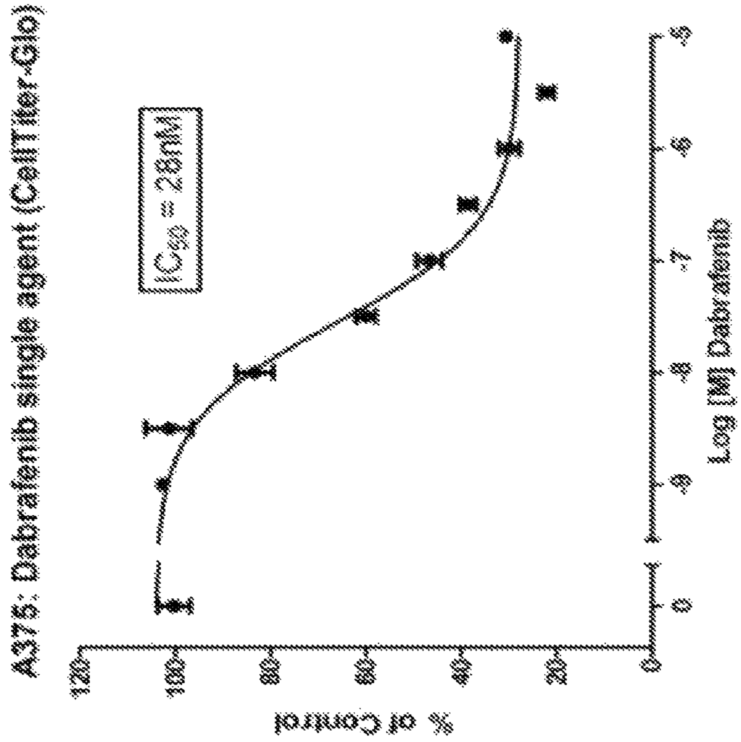
FIG. 11C and FIG. 11D show % viability relative to DMSO only treated controls for dabrafenib and trametinib single agent treatments in A375 cells using the CellTiter-Glo cell viability assay.
Figure 11D:
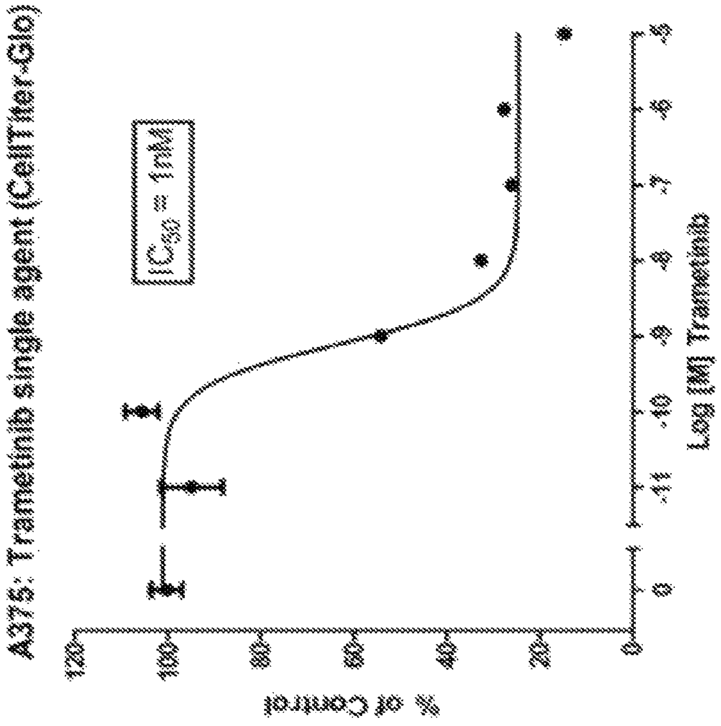
Figure 11E:
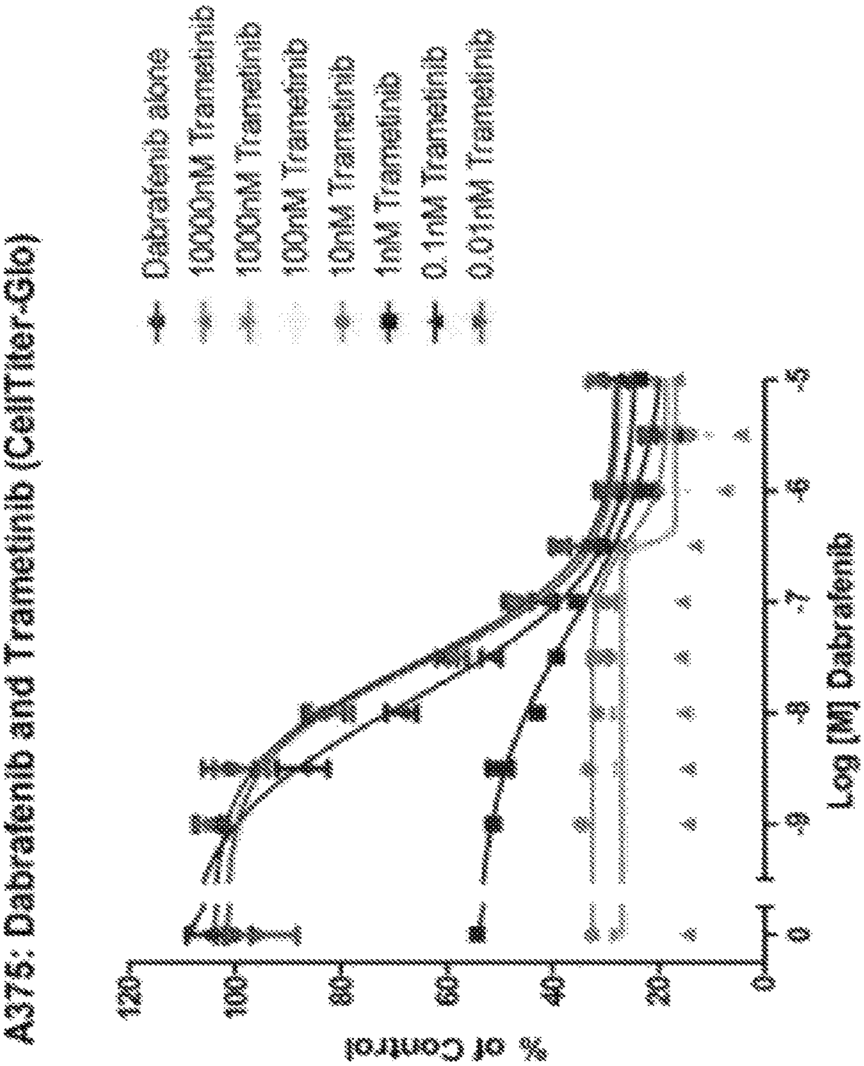
FIG. 11E shows % viability relative to DMSO only treated controls for dabrafenib and trametinib combination treatments in A375 cells using the CellTiter-Glo cell viability assay.
Figure 12A:
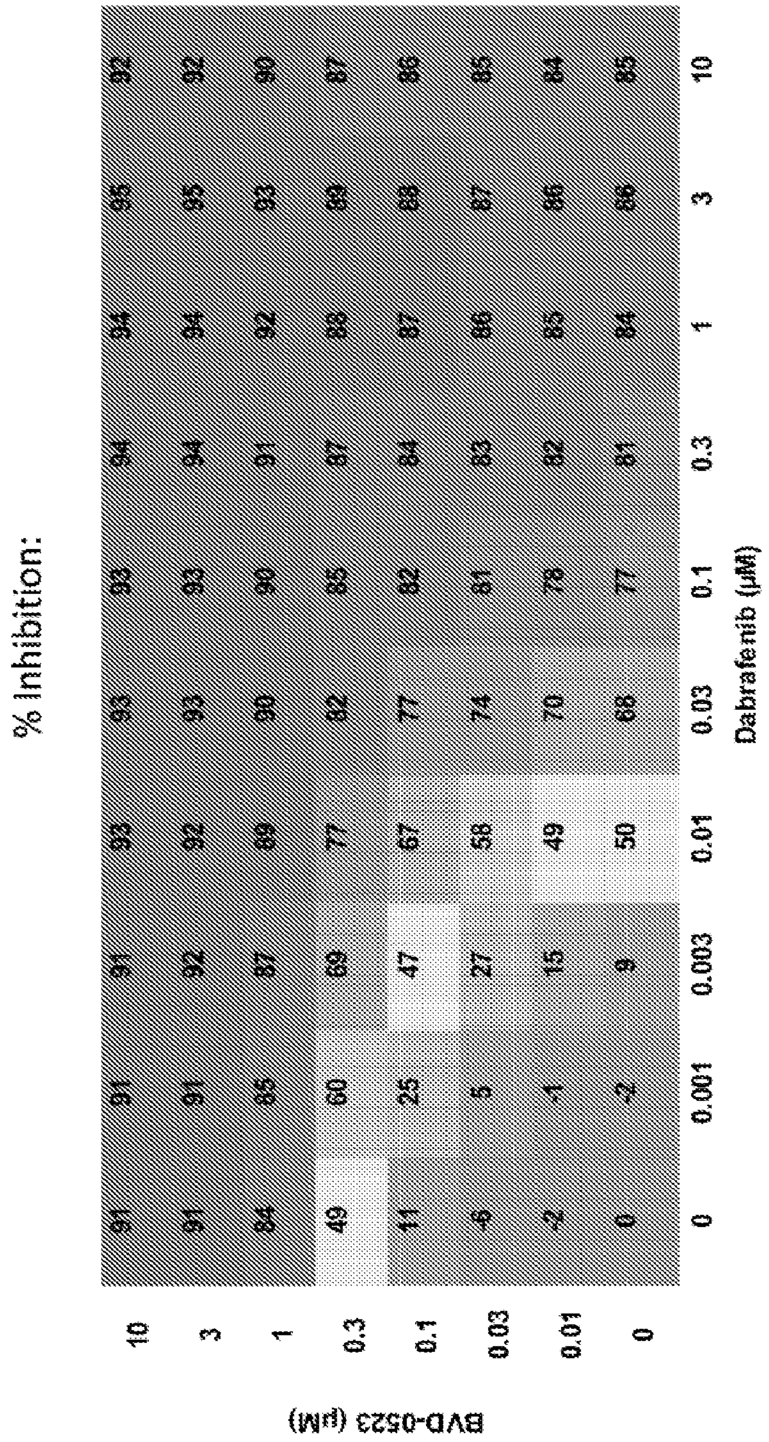
FIG. 12A is a dose matrix showing % inhibition of the BVD-523/dabrafenib combination in A375 cells using the Alamar Blue cell viability assay.
Figure 12B:
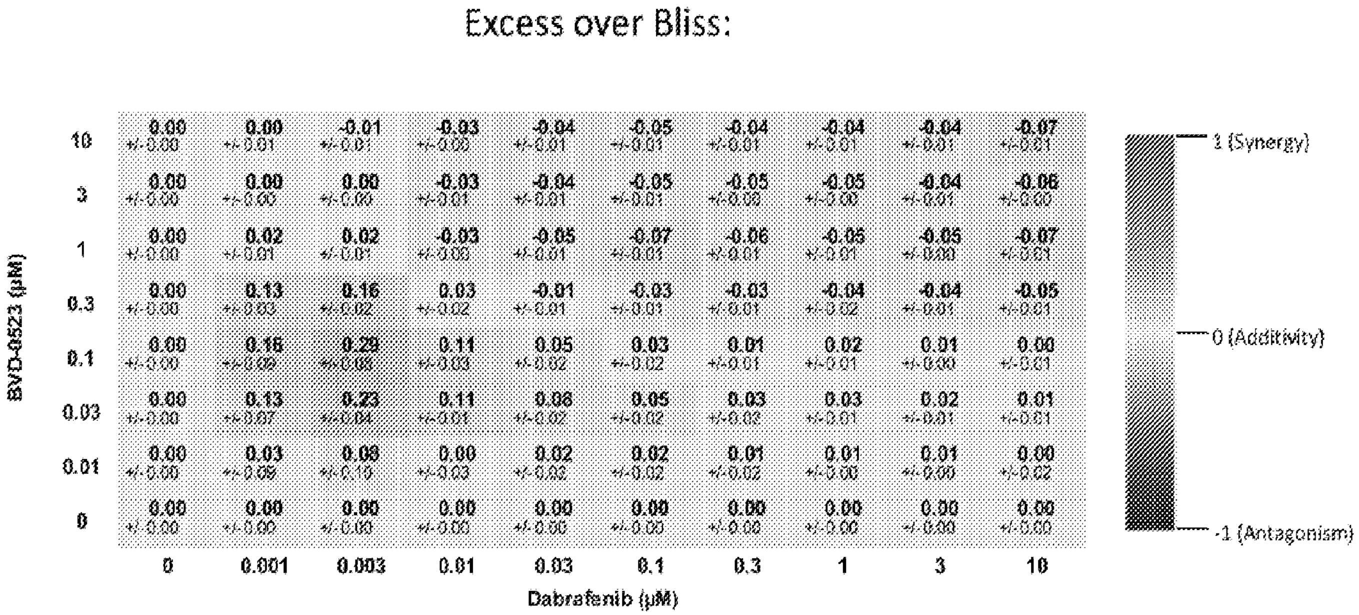
FIG. 12B is a dose matrix showing excess over Bliss for the BVD-523/dabrafenib combination.
Figure 12D:
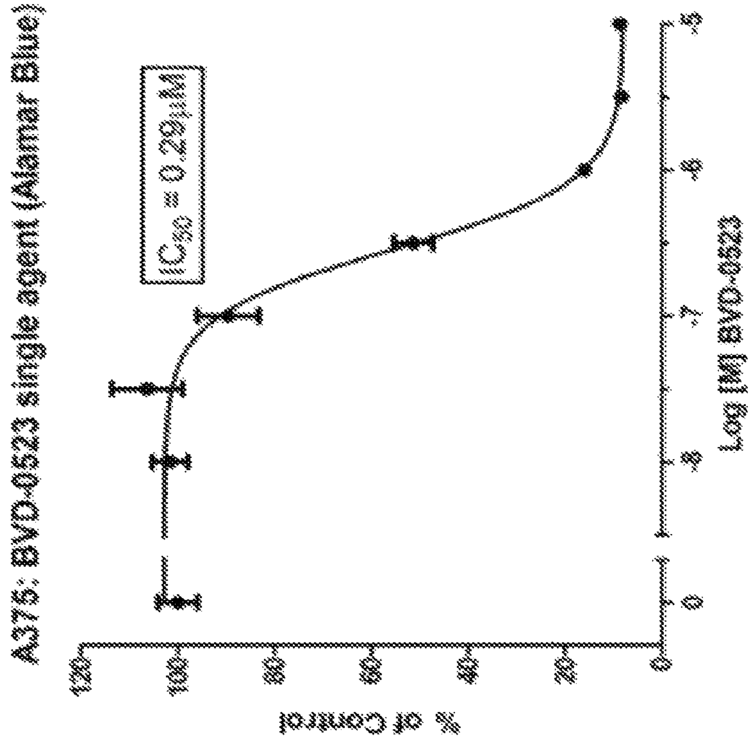
FIG. 12C and FIG. 12D show % viability relative to DMSO only treated controls for dabrafenib and BVD-523 single agent treatments in A375 cells using the Alamar Blue cell viability assay.
Figure 12C:
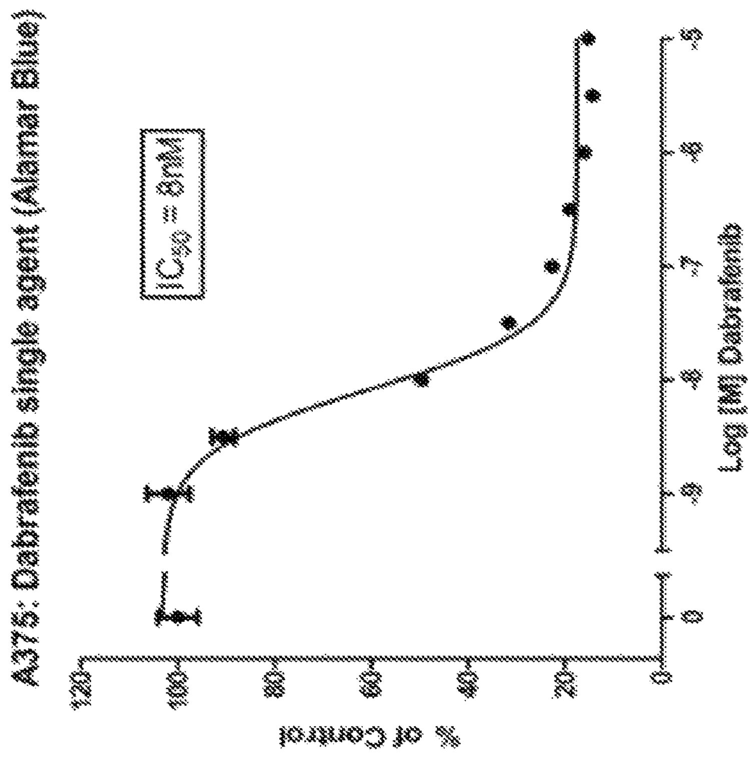
Figure 12E:
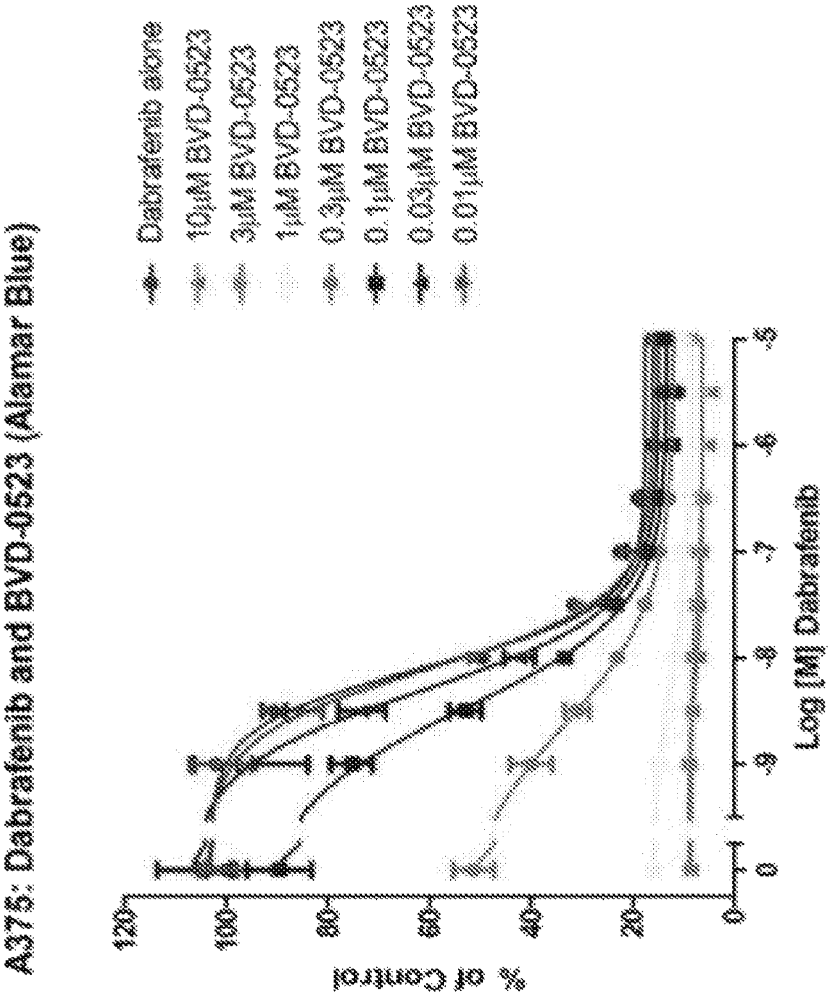
FIG. 12E shows % viability relative to DMSO only treated controls for dabrafenib and BVD-523 combination treatments in A375 cells using the Alamar Blue cell viability assay.
Figure 13B:
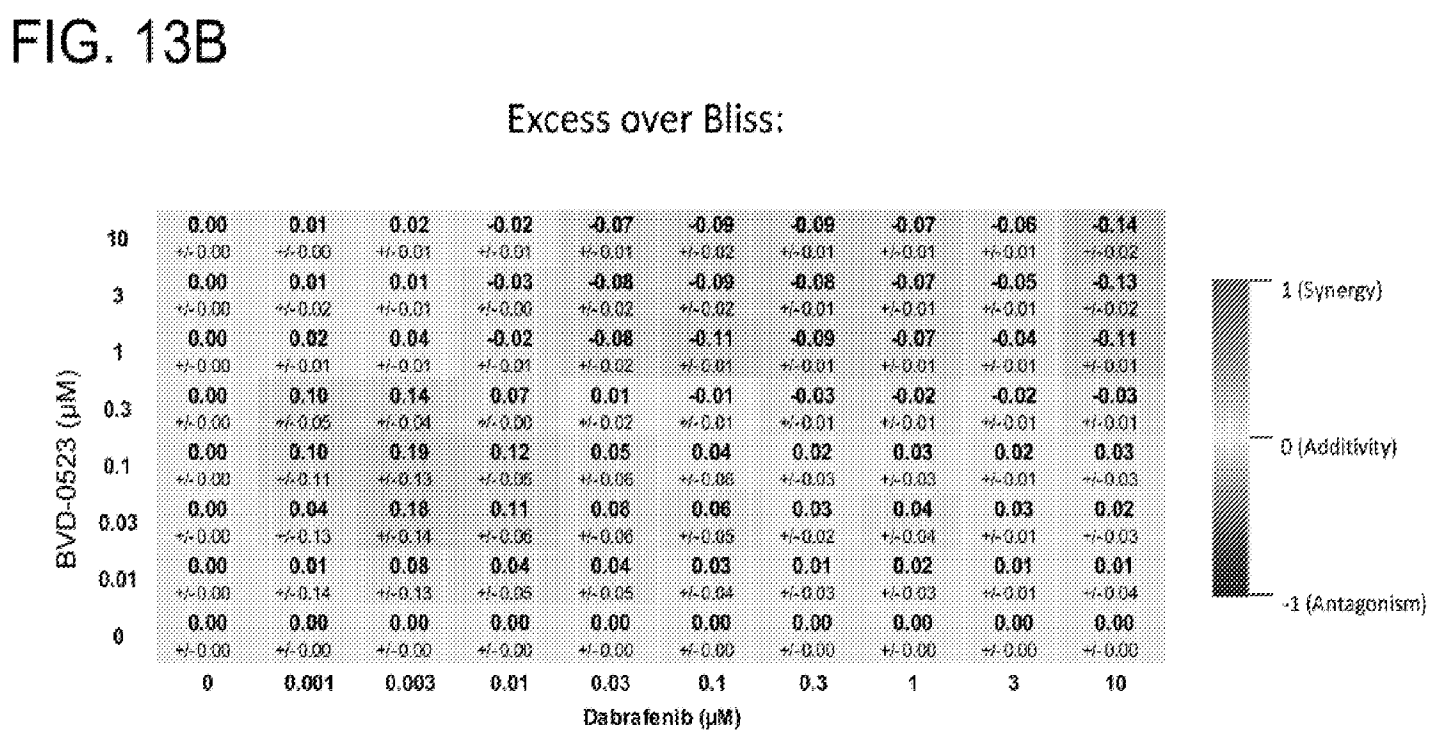
FIG. 13B is a dose matrix showing excess over Bliss for the BVD-523/dabrafenib combination.
Figure 13D:
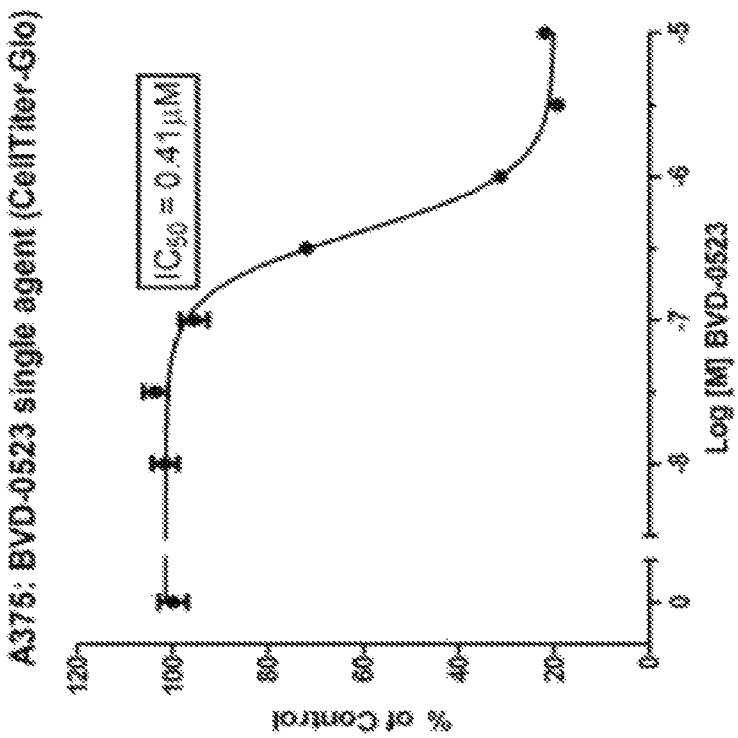
FIG. 13C and FIG. 13D show % viability relative to DMSO only treated controls for dabrafenib and BVD-523 single agent treatments in A375 cells using the CellTiter-Glo cell viability assay.
Figure 13C:
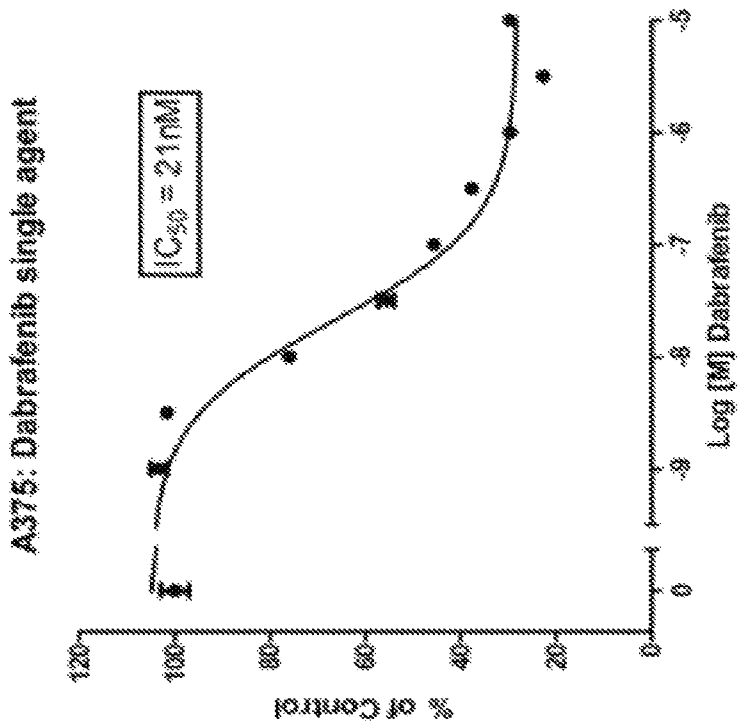
Figure 13E:
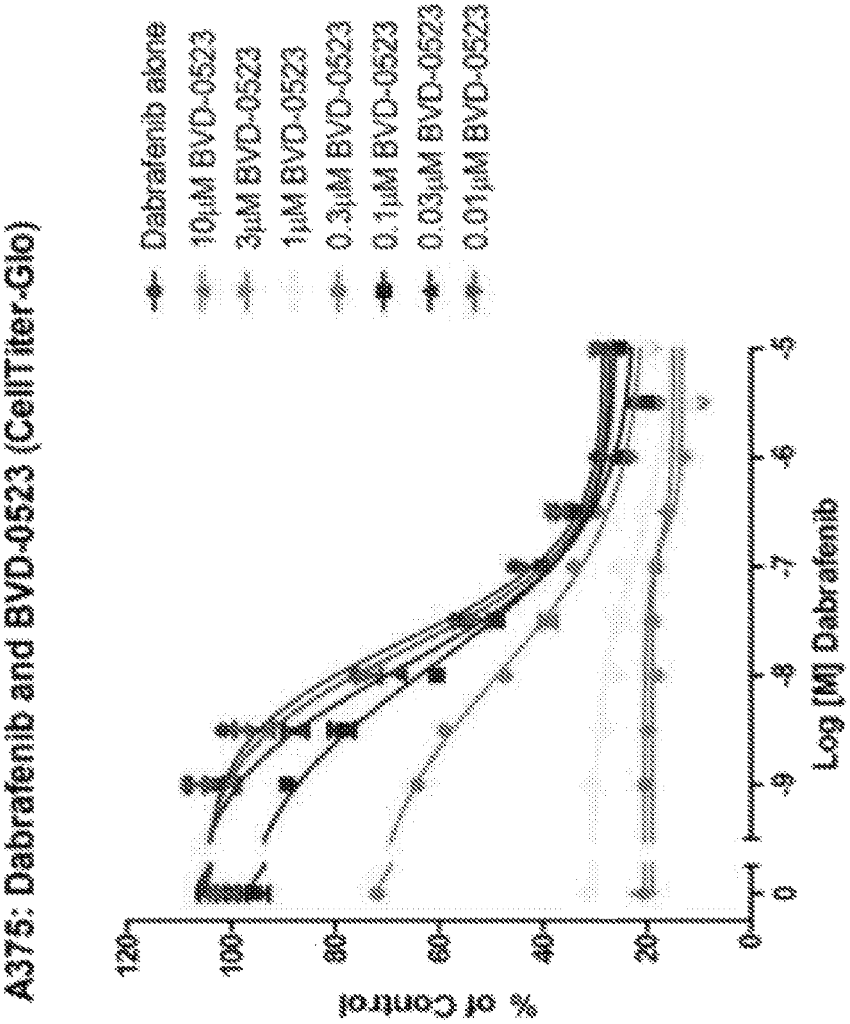
FIG. 13E shows % viability relative to DMSO only treated controls for dabrafenib and BVD-523 combination treatments in A375 cells using the CellTiter-Glo cell viability assay.
Figure 14B:
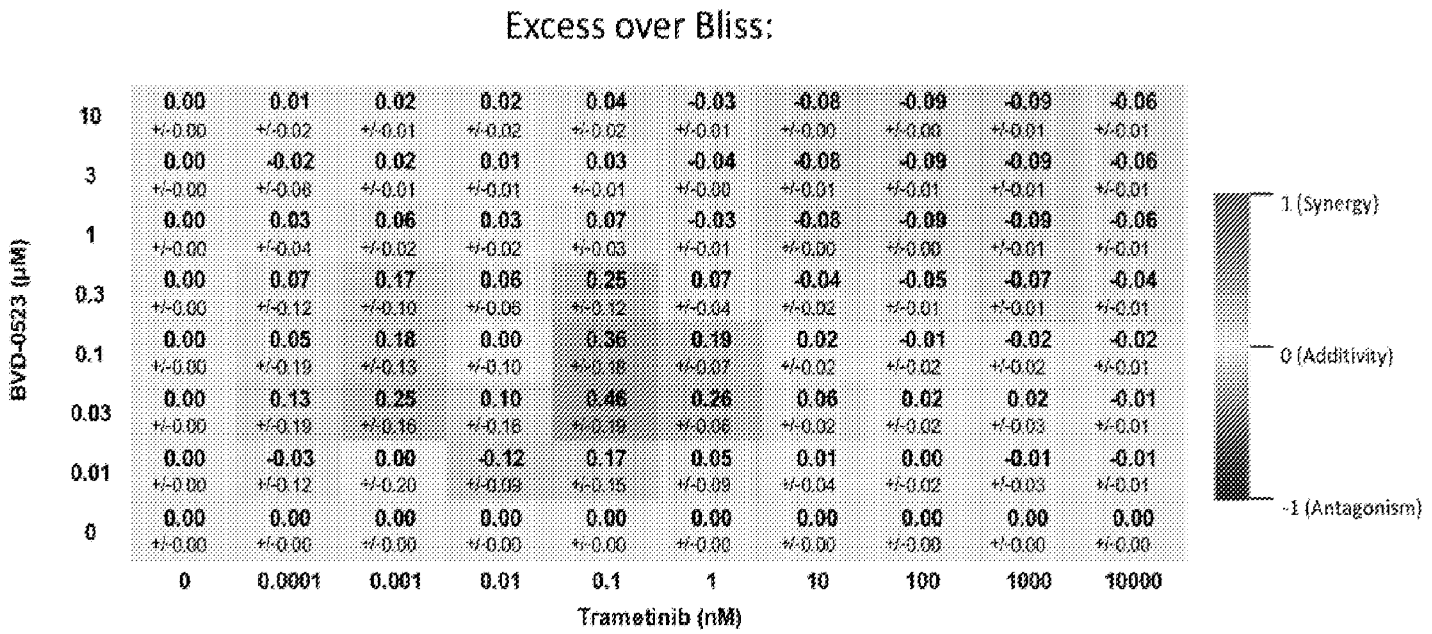
FIG. 14B is a dose matrix showing excess over Bliss for the trametinib/BVD-523 combination.
Figure 14C:
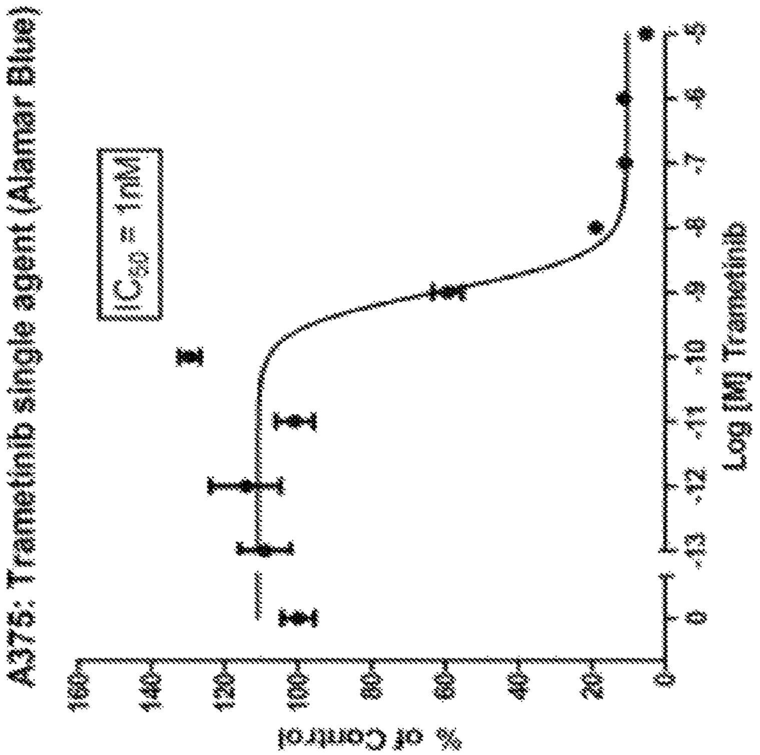
FIG. 14C and FIG. 14D show % viability relative to DMSO only treated controls for BVD-523 and trametinib single agent treatments in A375 cells using the Alamar Blue cell viability assay.
Figure 14D:
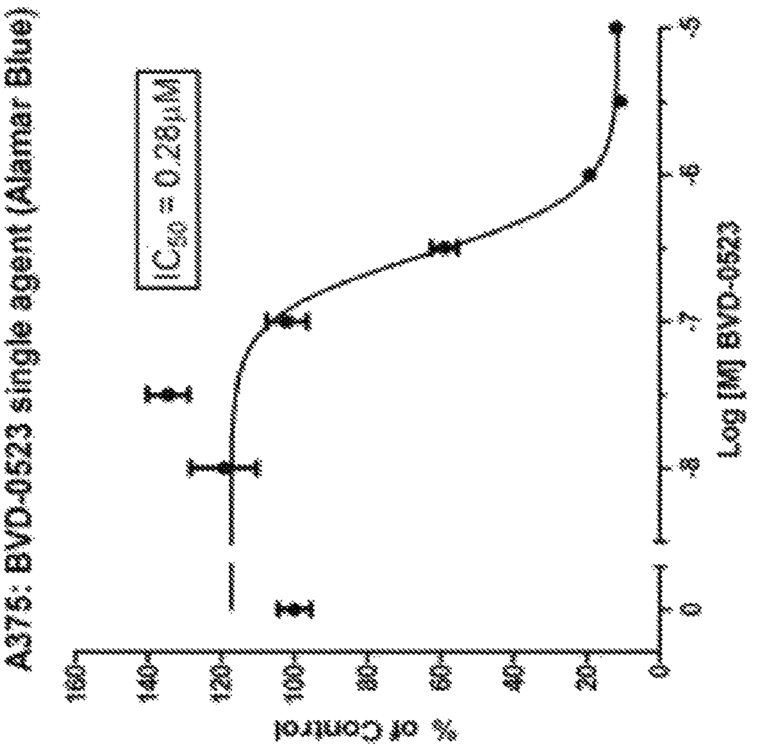
Figure 14E:
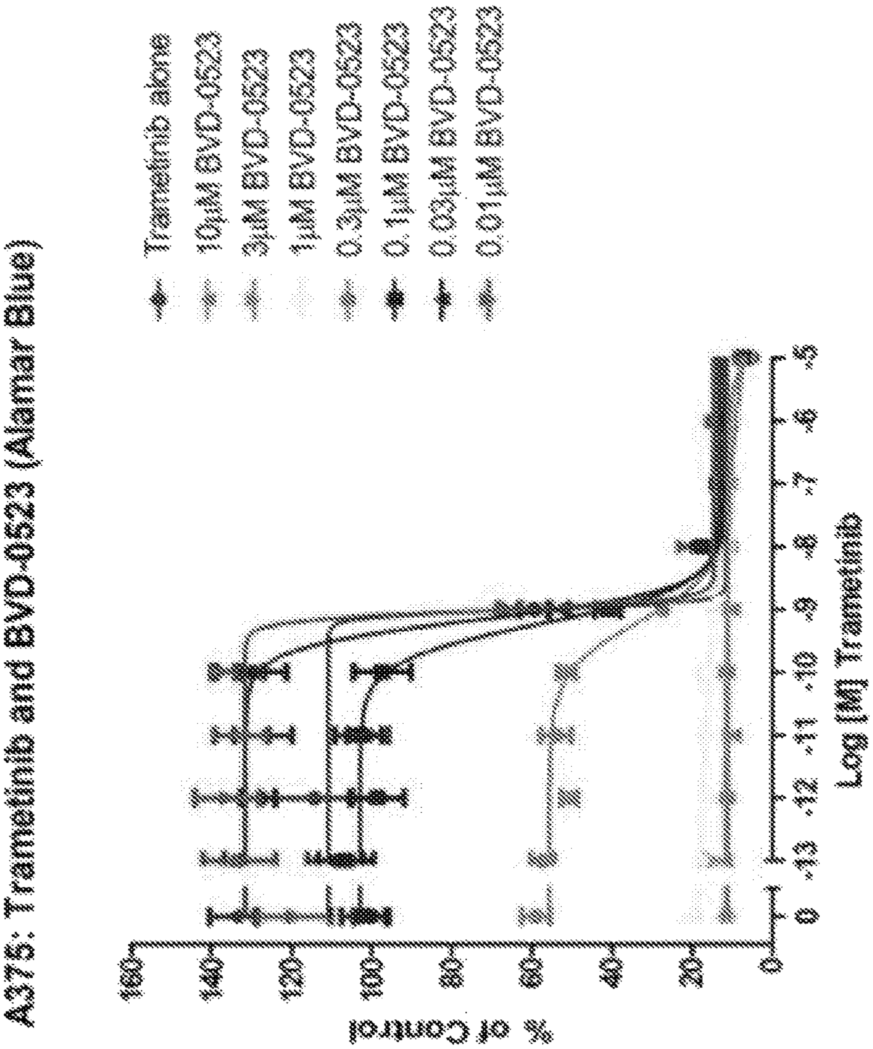
FIG. 14E shows % viability relative to DMSO only treated controls for BVD-523 and trametinib combination treatments in A375 cells using the Alamar Blue cell viability assay.
Figure 15B:
FIG. 15B is a dose matrix showing excess over Bliss for the trametinib/BVD-523 combination.
Figure 15C:
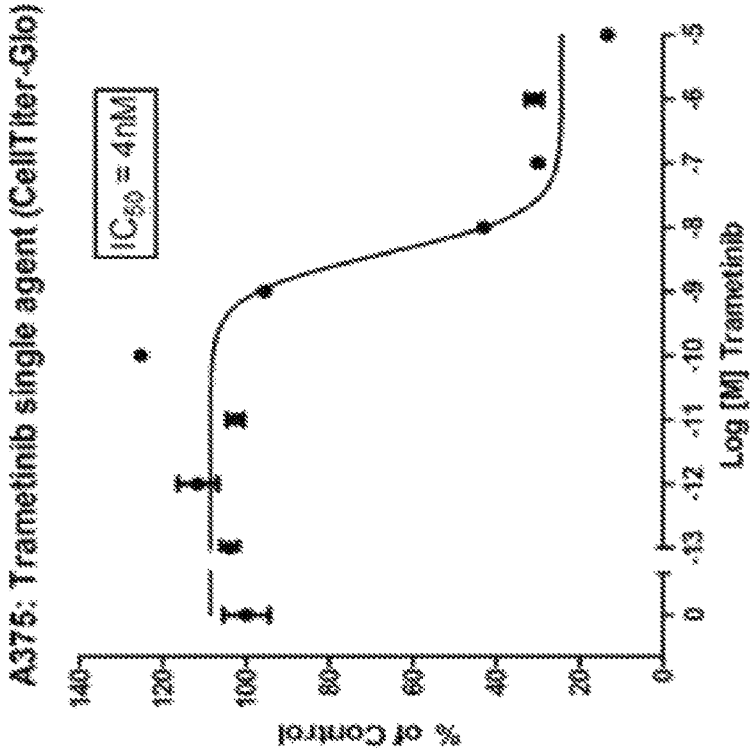
FIG. 15C and FIG. 15D show % viability relative to DMSO only treated controls for BVD-523 and trametinib single agent treatments in A375 cells using the CellTiter-Glo cell viability assay.
Figure 15D:
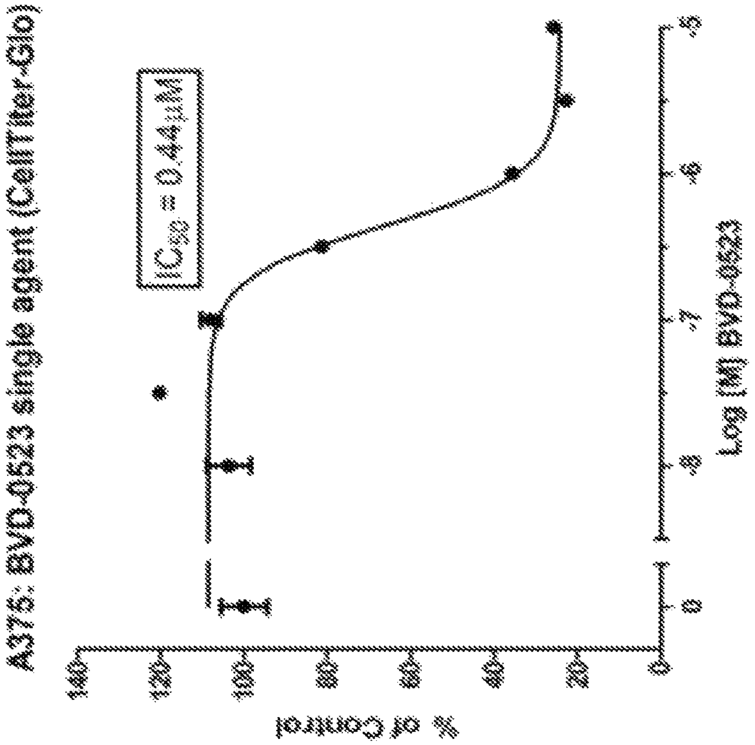
Figure 15E:
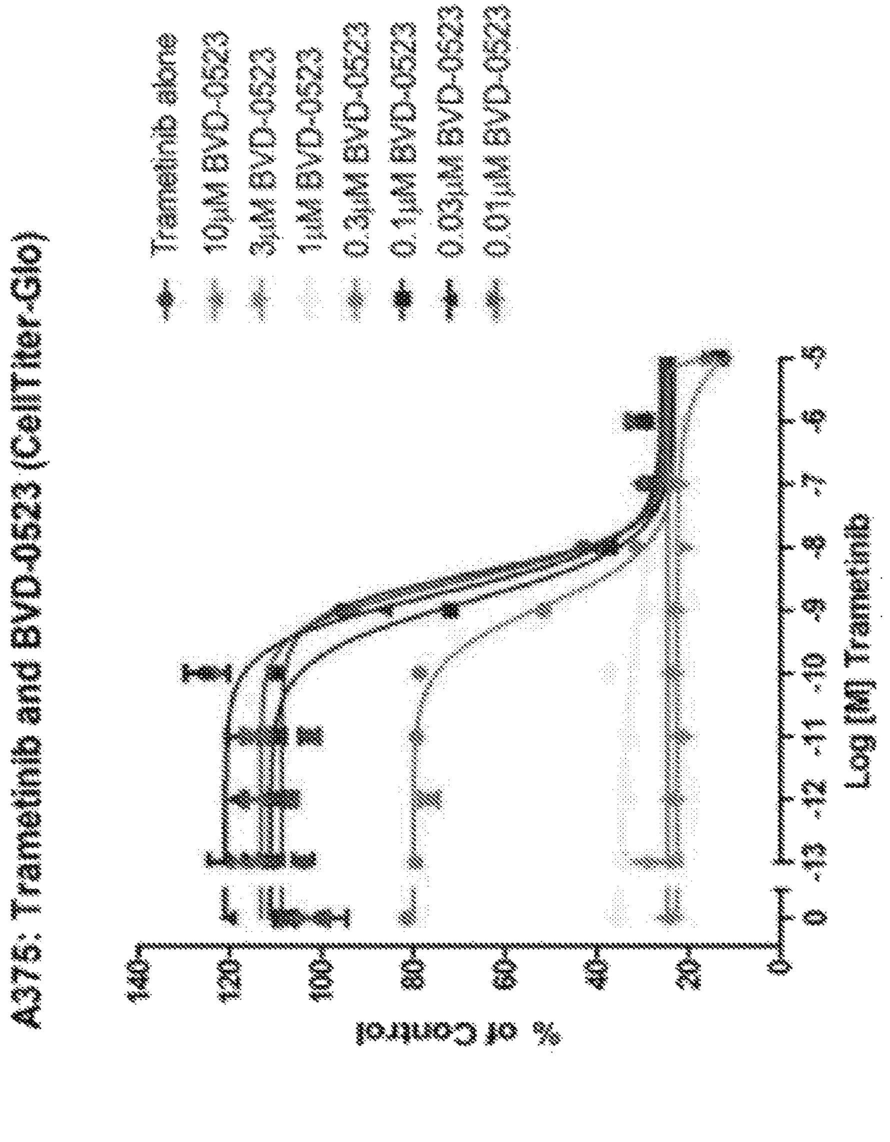
FIG. 15E shows % viability relative to DMSO only treated controls for BVD-523 and trametinib combination treatments in A375 cells using the CellTiter-Glo cell viability assay.
Figure 16B:
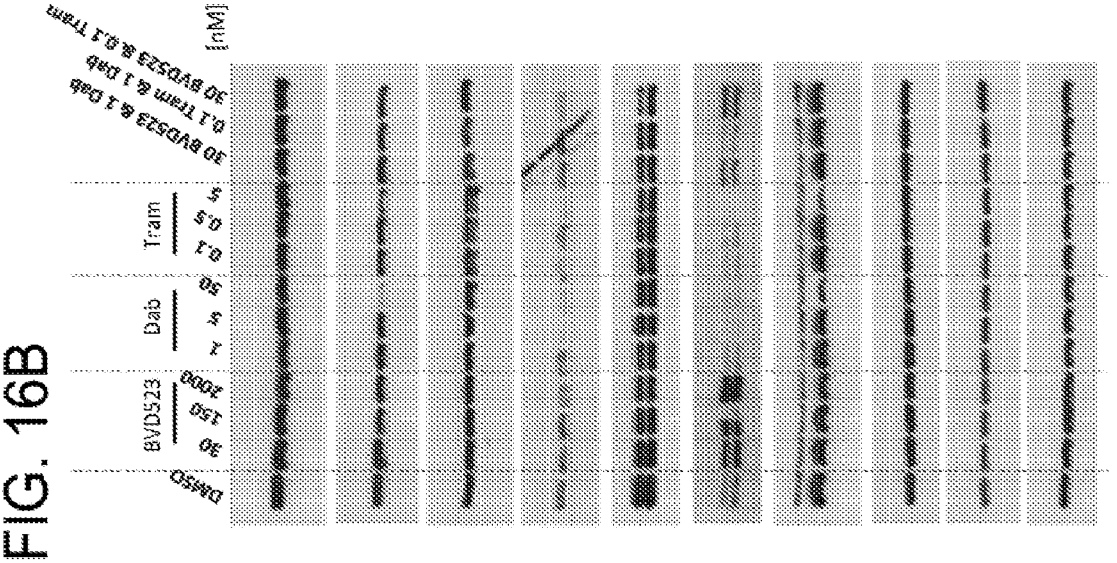
FIG. 16A-FIG. 16D are a set of images showing Western blot analysis of MAPK signaling in A375 cells after a 4 hour treatment with various concentrations (in nM) of BVD-523, dabrafenib (Dab), and Trametinib (Tram). 40 μg of total protein was loaded in each lane except where indicated otherwise. In this experiment, duplicate samples were collected.
Figure 16A:
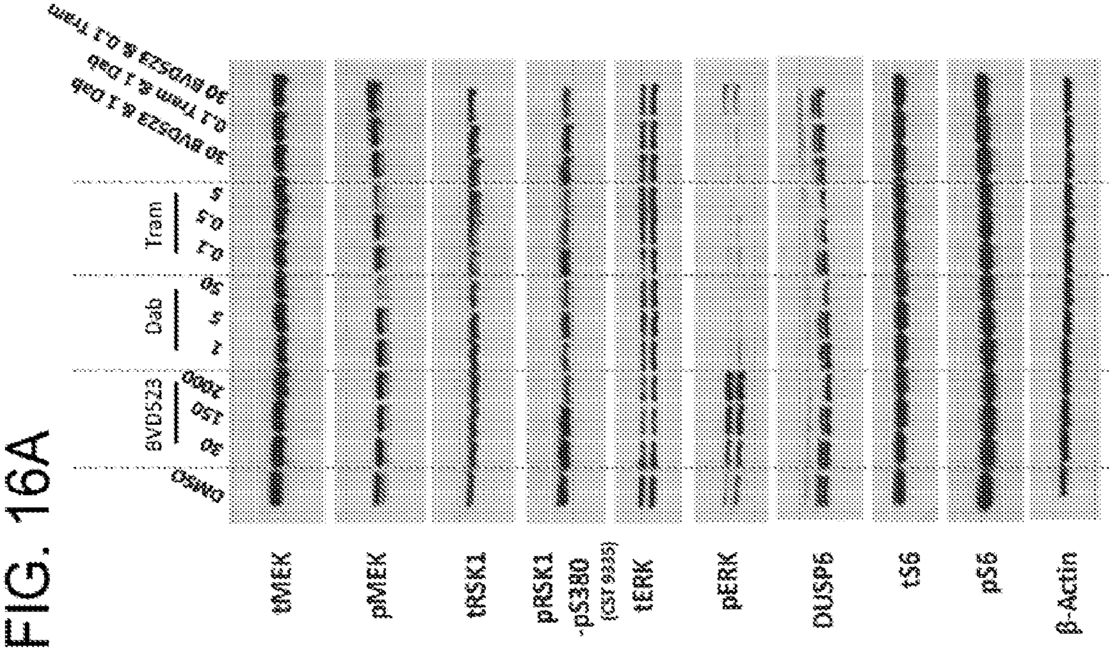
Figure 16D:
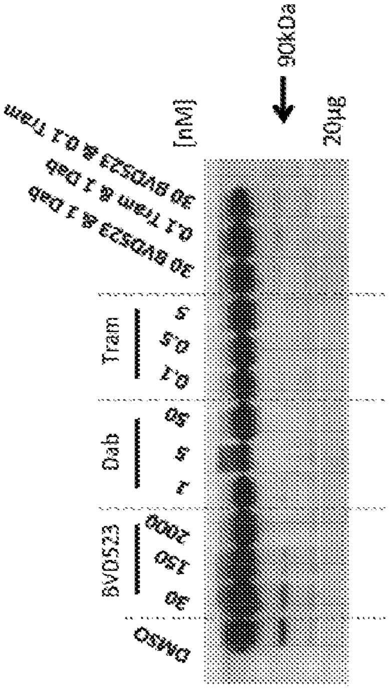
Figure 16C:
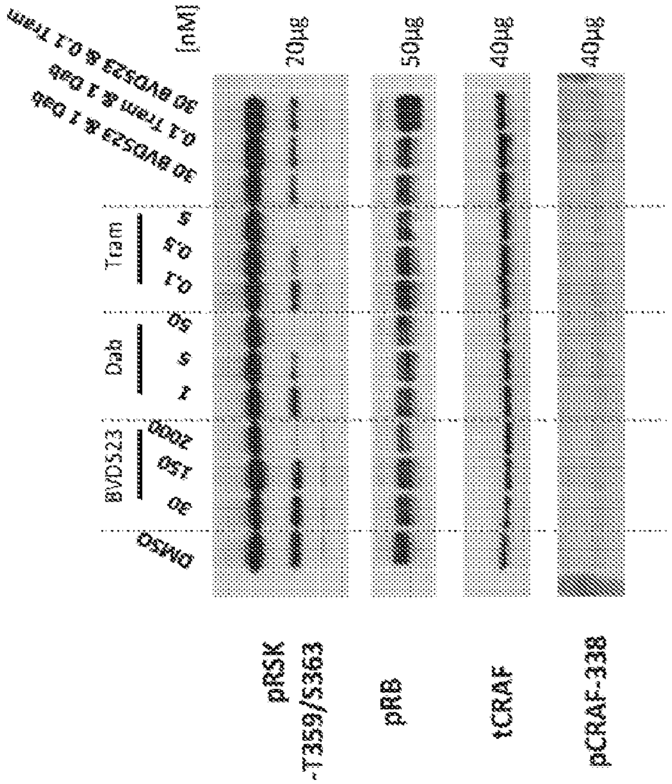
Figure 17B:
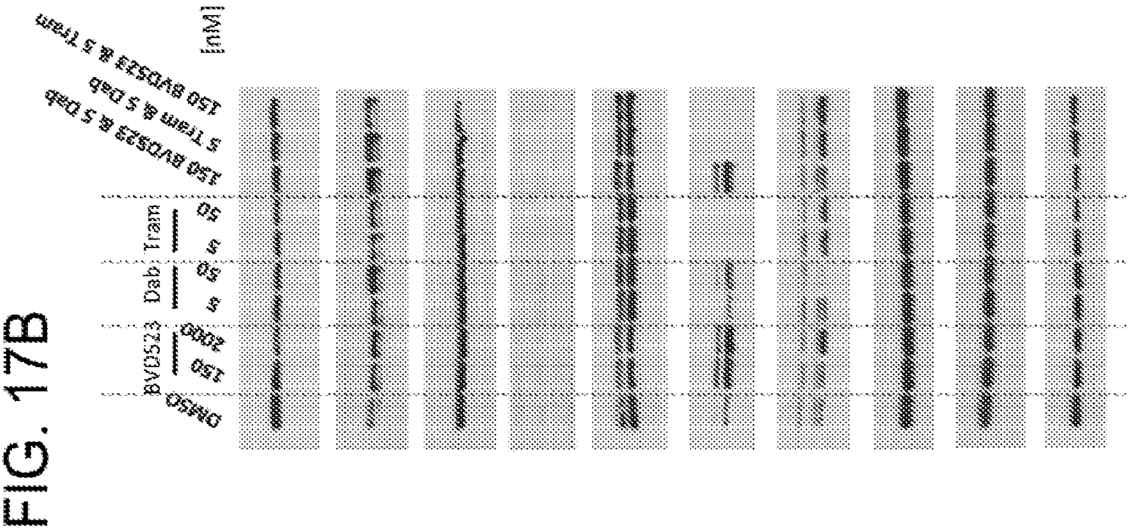
FIG. 17A-FIG. 17D are a set of images showing Western blot analysis of MAPK signaling in a human colorectal carcinoma cell line (HCT116 cells) after a 4 hour treatment with various concentrations (in nM) of BVD-523, dabrafenib (Dab), and Trametinib (Tram). 40 μg of total protein was loaded in each lane except where indicated otherwise. In this experiment, duplicate samples were collected.
Figure 17A:
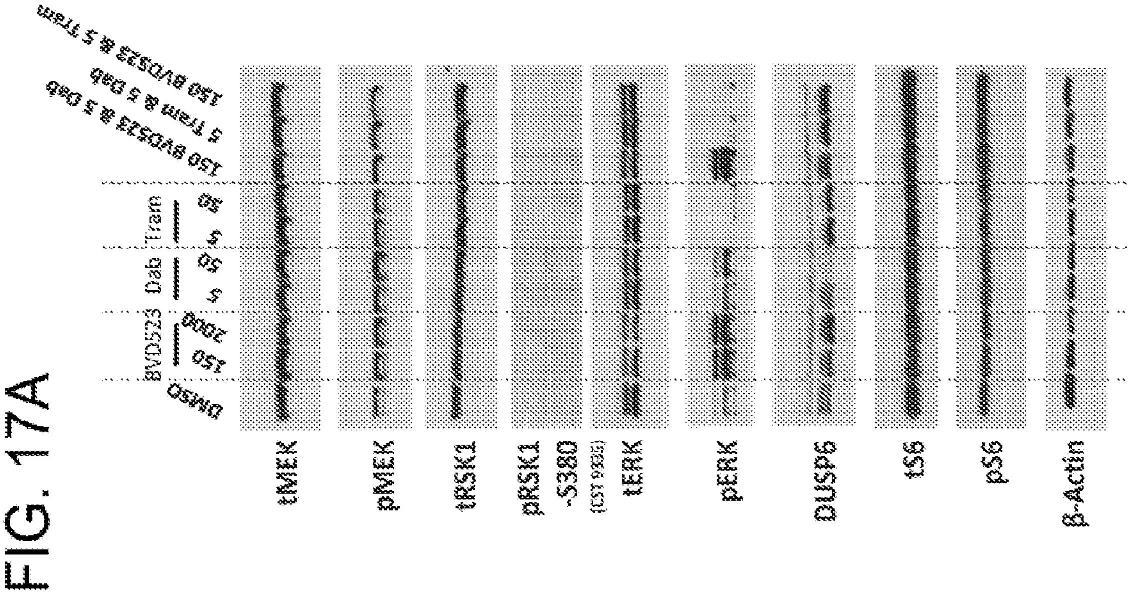
Figure 17D:
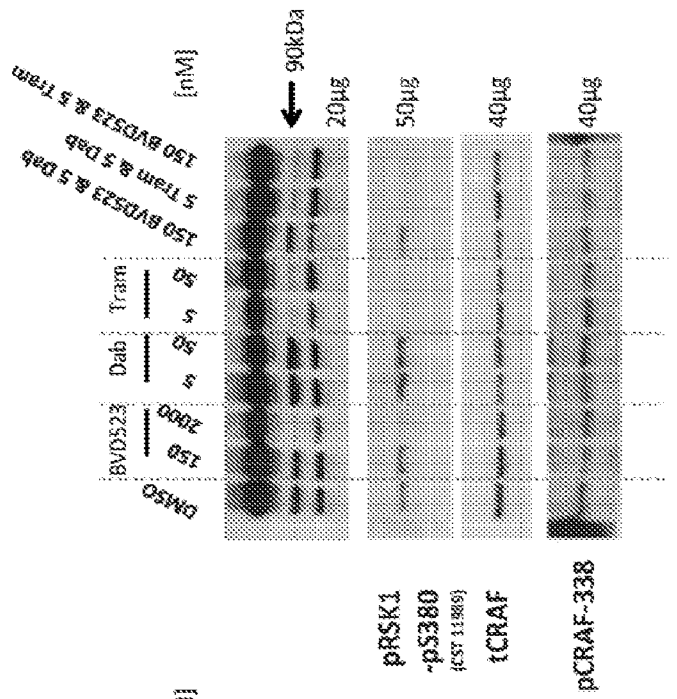
Figure 17C:
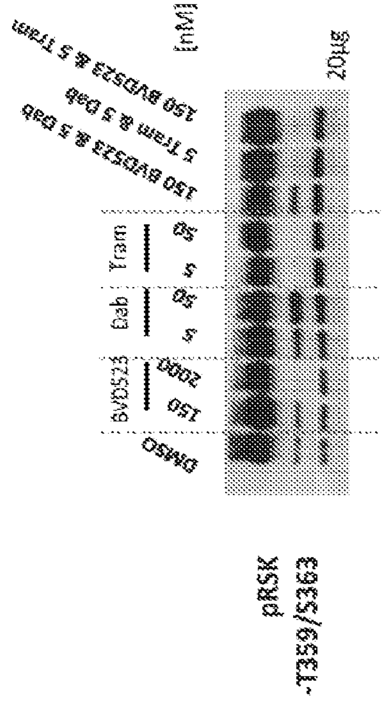

FIG. 7 shows an assessment of growth during the proliferation assay in DMSO control wells. FIG. 8A-FIG. 8D show results from month 3 of the studies. FIG. 9A-FIG. 9D show results from month 3 of the studies with a focus on single treatment cell lines.

Table 12 shows $IC_{50}$ data for month 3 of the studies. Relative $IC_{50}$s were determined from 4-parameter curve fits in Prism. $IC_{50}$ values were not determined for the cell line escalated with trametinib due to a lack of growth during the assay (ND: not done).

TABLE 12

| $IC_{50}$ Data - Month 3 | | | | | | | |
|---|---|---|---|---|---|---|---|
| | Cell Line, Relative $IC_{50}$ (nM) | | | | | | |
| Compound | Par* | Tram | Dab | BVD-523 | Dab/Tram | Dab/523 | Tram/523 |
| Dabrafenib | 2.1 | ND | 2.5 | 18.4 | 17.9 | 337 | 73 |
| Trametinib | 0.2 | ND | 0.4 | 1.7 | 2.7 | 90 | 11.2 |
| BVD-523 | 129 | ND | 198 | 433 | 323 | 1151 | 296 |
| Paclitaxel | 1.9 | ND | 1.9 | 6.5 | 4.7 | 4.2 | 8.9 |

*Par = Parental cell line

FIG. 19 shows single and combination agent escalation for month 3 of the studies. Cell line variants were obtained that could grow in the presence of dabrafenib or trametinib at concentrations greater than 100 times the $IC_{50}$ of these agents in parental A375 cell. In comparison, cell lines resistant to BVD-523 could only be maintained in less than 10× of parental $IC_{50}$ concentration. Sensitivity testing suggested dabrafenib and trametinib-resistant cell lines remained relatively sensitive to BVD-523; the increased $IC_{50}$ "shift" for BVD-523 in resistant cell lines was more modest than those corresponding $IC_{50}$ increases following dabrafenib or trametinib treatment. Likewise, compared to dabrafenib or trametinib treatment, more complete inhibition of cell growth was observed when resistant cell lines were treated with BVD-523 at concentrations 10-fold above its $IC_{50}$ in the parental A375 line. In total, patterns of resistance and cross-sensitivity suggest BVD-523 may remain effective in settings of acquired resistance.

Example 5

Combination Study Results

As expected, A375 cells, which carry a BRAF (V600E) mutation, were sensitive to dabrafenib. Single agent $IC_{50}$ values calculated using Alamar Blue (FIG. 10A-FIG. 10E, FIG. 12A-FIG. 12E, and FIG. 14A-FIG. 14E) were generally slightly lower for Dabrafenib and BVD-523 compared to those derived using CellTiter-Glo (FIG. 11A-FIG. 11E, FIG. 13A-FIG. 13E, and FIG. 15A-FIG. 15E). Published $IC_{50}$ values for Dabrafenib and Trametinib in a 72 hour CellTiter-Glo assay were 28±16 nM and 5±3 nM respectively (Greger et al., 2012; King et al., 2013)—the single agent results reported here are consistent with these values. There was some evidence for a window of synergy in all treatments. Variation between triplicates was low, however, there was some evidence of edge effects that likely explains the apparent enhanced growth observed in some treatments versus the no drug control (e.g. particularly apparent in the Trametinib/BVD-523 combination). This makes the interpretation of the Bliss analysis more challenging as in some treatments it may have resulted in the artefactual enhancement in the level of synergy.

The combination assays were repeated for A375 cells. Single agent BVD-523, Trametinib and Dabrafenib potencies were consistent with those reported in the previous studies disclosed herein.

In sum, taken together the data show that MEK and BRAF resistant cells could be overcome by treatment with the ERK inhibitor, BVD-523.

Example 6

BVD-523 Altered Markers of MAPK Kinase Activity and Effector Function

For Western blot studies, HCT116 cells ($5\times10^6$) were seeded into 10 cm dishes in McCoy's 5A plus 10% FBS. A375 cells ($2.5\times10^6$) were seeded into 10 cm dishes in DMEM plus 10% FBS. Cells were allowed to adhere overnight prior to addition of the indicated amount of test compound (BVD-523) or vehicle control. Cells were treated for either 4 or 24 hours before isolation of whole-cell protein lysates, as specified below. Cells were harvested by trypsinisation, pelleted and snap frozen. Lysates were prepared with RIPA (Radio-Immunoprecipitation Assay) buffer, clarified by centrifugation and quantitated by bicinchoninic acid assay (BCA) assay. 20-50 μg of protein was resolved by SDS-PAGE electrophoresis, blotted onto PVDF membrane and probed using the antibodies detailed in Table 13 (for the 4-hour treatment) and Table 14 (for the 24-hour treatment) below.

TABLE 13

| Antibody Details | | | | | | |
|---|---|---|---|---|---|---|
| Antigen | Size (kDa) | Supplier | Cat No | Dilution | Incubation/Block Conditions | Secondary |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |

TABLE 13-continued

| Antibody Details | | | | | | |
|---|---|---|---|---|---|---|
| Antigen | Size (kDa) | Supplier | Cat No | Dilution | Incubation/ Block Conditions | Secondary |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| pMEK1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| pS6-pS235 | 32 | Cell Signaling | 2211S | 1:3000 | o/n 4° C. 5% milk | anti-rabbit |
| Total S6 | 32 | Cell Signaling | 2217 | 1:2000 | o/n 4° C. 5% milk | anti-rabbit |
| DUSP6 | 48 | Cell Signaling | 3058S | 1:1000 | o/n 4° C. 5% BSA | anti-rabbit |
| Total CRAF | 73 | BD Bio-sciences | 610152 | 1:2000 | o/n 4° C. 5% milk | anti-mouse |
| pCRAF-Ser338 | 73 | Cell Signaling | 9427 | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| β-Actin | 42 | Sigma | A5441 | 1:500,000 | o/n 4° C. 5% milk | anti-mouse |

TABLE 14

| Antibody details | | | | | | |
|---|---|---|---|---|---|---|
| Antigen | Size (kDa) | Supplier | Cat No | Dilution | Incubation/ Block Conditions | Secondary |
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| Bim-EL | 23 | Millipore | AB17003 | 1:1000 | o/n 4° C. 5% BSA | anti-rabbit |
| Bim-EL | 23 | Cell Signaling | 2933 | 1:1000 | o/n 4° C. 5% BSA | anti-rabbit |
| BCL-xL | 30 | Cell Signaling | 2762 | 1:2000 | o/n 4° C. 5% BSA | anti-rabbit |
| PARP | 116/89 | Cell Signaling | 9542 | 1:1000 | o/n 4° C. 5% milk | anti-rabbit |
| Cleaved Caspase 3 | 17, 19 | Cell Signaling | 9664X | 1:1000 | o/n 4° C. 5% milk | anti-rabbit |
| DUSP6 | 48 | Cell Signaling | 3058S | 1:1000 | o/n 4° C. 5% BSA | anti-rabbit |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| B-Actin | 42 | Sigma | A5441 | 1:500,000 | o/n 4° C. 5% milk | anti-mouse |

FIG. 16A-FIG. 16D, FIG. 17A-FIG. 17D, and FIG. 18A-FIG. 18D show Western blot analyses of cells treated with BVD-523 at various concentrations for the following: 1) MAPK signaling components in A375 cells after 4 hours; 2) cell cycle and apoptosis signaling in A375 24 hours treatment with various amounts of BVD-523; and 3) MAPK signaling in HCT-116 cells treated for 4 hours. The results show that acute and prolonged treatment with BVD-523 in RAF and RAS mutant cancer cells in-vitro affects both substrate phosphorylation and effector targets of ERK kinases. The concentrations of BVD-523 required to induce these changes is typically in the low micromolar range.

Changes in several specific activity markers are noteworthy. First, the abundance of slowly migrating isoforms of ERK kinase increase following BVD-523 treatment; modest changes can be observed acutely, and increase following prolonged treatment. While this could indicate an increase in enzymatically active, phosphorylated forms of ERK, it remains noteworthy that multiple proteins subject to both direct and indirect regulation by ERK remain "off" following BVD-523 treatment. First, RSK1/2 proteins exhibit reduced phosphorylation at residues that are strictly dependent on ERK for protein modification (T359/S363). Second, BVD-523 treatment induces complex changes in the MAPK feedback phosphatase, DUSP6: slowly migrating protein isoforms are reduced following acute treatment, while total protein levels are greatly reduced following prolonged BVD-523 treatment. Both of these findings are consistent with reduced activity of ERK kinases, which control DUSP6 function through both post-translational and transcriptional mechanisms. Overall, despite increases in cellular forms of ERK that are typically thought to be active, it appears likely that cellular ERK enzyme activity is fully inhibited following either acute or prolonged treatment with BVD-523.

Consistent with these observations, effector genes that require MAPK pathway signaling are altered following treatment with BVD-523. The G1/S cell-cycle apparatus is regulated at both post-translational and transcriptional levels by MAPK signaling, and cyclin-D1 protein levels are greatly reduced following prolonged BVD-523 treatment. Similarly, gene expression and protein abundance of apoptosis effectors often require intact MAPK signaling, and total levels of Bim-EL increase following prolonged BVD-523 treatment. As noted above, however, PARP protein cleavage and increased apoptosis were not noted in the A375 cell background, this suggests that additional factors may influence whether changes in BVD-523/ERK-dependent effector signaling are translated into definitive events such as cell death and cell cycle arrest.

Consistent with the cellular activity of BVD-523, marker analysis suggests that ERK inhibition alters a variety of molecular signaling events in cancer cells, making them susceptible to both decreased cell proliferation and survival.

In sum, FIG. 16A-FIG. 16D, FIG. 17A-FIG. 17D, and FIG. 18A-FIG. 18D show that BVD-523 inhibits the MAPK signaling pathway and may be more favorable compared to RAF or MEK inhibition in this setting.

Finally, properties of BVD-523 may make this a preferred agent for use as an ERK inhibitor, compared to other agents with a similar activity. It is known that kinase inhibitor drugs display unique and specific interactions with their enzyme targets, and that drug efficacy is strongly influenced by both the mode of direct inhibition, as well as susceptibility to adaptive changes that occur following treatment. For example, inhibitors of ABL, KIT, EGFR and ALK kinases are effective only when their cognate target is found in active or inactive configurations. Likewise, certain of these inhibitors are uniquely sensitive to either secondary genetic mutation, or post-translational adaptive changes, of the protein target. Finally, RAF inhibitors show differential potency to RAF kinases present in certain protein complexes and/or subcellular localizations. In summary, as ERK kinases are similarly known to exist in diverse, variable, and complex biochemical states, it appears likely that BVD-523 may interact with and inhibit these targets in a fashion that is distinct and highly preferable to other agents.

Example 7

Effects of BVD-523 and Benchmark ERK BRAF and MEK Inhibitors on Viability and MAPK Signalling Single Agent Proliferation Assay Cells were seeded in 96-well plates at the densities indicated in Table 15 in McCoy's 5A containing 10% FBS and allowed to adhere overnight prior to addition of compound or vehicle control. Compounds were prepared from DMSO stocks to give the desired final concentrations. The final DMSO concentration was constant at 0.1%. Test compounds were incubated with the cells for 96 h at 37° C., 5% $CO_2$ in a humidified atmosphere. CellTiter-Glo® reagent (Promega, Madison, WI) was added according to manufacturer's instructions and luminescence detected using the BMG FLUOstar plate reader (BMG Labtech, Ortenberg, Germany). The average media only background value was deducted and the data analysed using a 4-parameter logistic equation in GraphPad Prism (GraphPad Software, La Jolla, CA).

Combination Proliferation Assay

Cells were seeded into triplicate 96-well plates at the densities indicated in Table 15 in McCoy's 5A containing 10% FBS and allowed to adhere overnight prior to addition of test compound or vehicle control. Combinations were tested using a 10×8 dose matrix. The final DMSO concentration was constant at 0.2%.

Test compounds were incubated with the cells for 96 h at 37° C., 5% $CO_2$ in a humidified atmosphere. Cells were stained with Hoechst stain and fluorescence detected as described above. The average media only background value was deducted and the data analysed.

Combination interactions across the dose matrix were determined by the Loewe Additivity and Bliss independence models using Chalice™ Combination Analysis Software (Horizon Discovery Group, Cambridge, MA) as outlined in the user manual (available at chalice.horizondiscovery.com/chalice-portal/documentation/analyzer/home.jsp). Synergy is determined by comparing the experimentally observed level of inhibition at each combination point with the value expected for additivity, which is derived from the single-agent responses along the edges of the matrix. Potential synergistic interactions were identified by displaying the calculated excess inhibition over that predicted as being additive across the dose matrix as a heat map, and by reporting a quantitative 'Synergy Score' based on the Loewe model. The single agent data derived from the combination assay plates were presented as dose-response curves generated in Chalice™.

TABLE 15

Cell Line Seeding Density

| | Seeding density (cell/well) | | |
|---|---|---|---|
| Cell Line | 96-well Prolifer-ation | 6-Well Western | 10 cm dish Westerns |
| RKO Parental | 1000 | $1 \times 10^6$ | $2.9 \times 10^6$ |
| RKO MEK1 (Q56P/+) Clone 1 | 1250 | Not tested | Not tested |
| RKO MEK1 (Q56P/+) Clone 2 | 1000 | $7.5 \times 10^5$ | $2 \times 10^6$ |

Western Blotting

Cells were seeded into 6-well plates (Experiment 1) or 10 cm dishes (Experiment 2) at the densities indicated in Table 15 in McCoy's 5A containing 10% FBS and allowed to adhere overnight prior to addition of compound or vehicle control. Test compounds were added and incubated with the cells for 4 or 24 h at 37° C., 5% $CO_2$ in a humidified atmosphere. Cells were harvested by trypsinisation, pelleted by centrifugation and snap frozen on dry ice.

Lysates were prepared using RIPA buffer (50 mM Tris-hydrochloride, pH 8.0; 150 mM sodium chloride; 1.0% Igepal CA-630 (NP-40); 0.5% sodium deoxycholate; 0.1% sodium dodecyl sulphate; 1× complete EDTA-free protease inhibitor cocktail (Roche, Nutley, NJ; cat 05 892 791 001); 1×phosSTOP phosphatase inhibitor cocktail (Roche Nutley, NJ; cat. 04 906 837 001)) and clarified by centrifugation at 11,000 rpm for 10 min in a bench-top centrifuge.

Total protein in the lysates was quantitated by BCA assay according to the manufacturer's instructions (Pierce™ BCA Protein Assay Kit; Thermo Scientific, Waltham, MA; cat. 23225), boiled in sample buffer (NuPAGE LDS Sample Buffer; (Invitrogen, Carlsbad, CA; cat. NP0007)) and stored at −80° C.

Equal amounts of protein (40 μg) were resolved on NuPAGE 4-12% Bis-Tris gels (Invitrogen, Carlsbad, CA; cat. WG1402BOX) and blotted onto PVDF membranes using iBlot gel transfer stacks (Invitrogen, Carlsbad, CA; cat. IB4010-01) on an iBlot gel transfer device (Invitrogen Carlsbad, CA) according to the manufacturer's instructions.

Blots were probed using the antibodies and block conditions detailed in Table 16. Western blots were developed using Pierce™ ECL2 Western blotting substrate (Thermo Scientific, Waltham, MA; cat. 80196) and imaged using a FluorChem M Western blot imager (ProteinSimple, San Jose, CA).

TABLE 16

Antibodies and Western Blotting Conditions

| Antigen | Size (kDa) | Supplier | Cat No | Dilution | Incubation/ block Conditions | Secondary |
|---|---|---|---|---|---|---|
| pRSK-T359/S363 | 90 | Millipore | 04-419 | 1:20000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| pMEK1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| DUSP6 | 48 | Cell Signaling | 3058S | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| B-Actin | 42 | Sigma | A5441 | 1:100,000 | o/n 4° C. 5% milk | anti-mouse |
| Anti-rabbit HRP-conjugated secondary | — | Cell Signaling | 7074S | 1:2000 | 1 h room temp; Block matched to primary Antibody | — |
| Anti-mouse HRP-conjugated secondary | — | Cell Signaling | 7076 | 1:5000 | 1 h room temp; Block matched to primary Antibody | — |

The MEK1 (Q56P) mutation exemplifies a class of clinically relevant MEK1/2 activating mutations known to upregulate the MAPK pathway and drive acquired resistance to BRAF or MEK inhibitors.

This study used a pair of RKO BRAF(V600E) cell lines that are isogenic for the presence or absence of a MEK1 (Q56P) activating mutation, to assess the effect that activating MEK mutations have in response to the novel ERK inhibitor BVD-523 versus other benchmark MAPK inhibitors.

Effects of on cell viability were assessed by quantitating cellular ATP levels using CellTiter-Glo® after 96 h. Single agent assays demonstrated that the double mutant BRAF (V600E)::MEK1(Q56P) cells displayed a markedly reduced sensitivity to inhibition with benchmark clinical BRAF (exemplified by Dabrafenib) or MEK (exemplified by Trametinib) inhibitors relative to the parental BRAF(V600E) cells, which demonstrates the suitability of this isogenic model for recapitulating the acquired resistance known to be associated with this class of mutation in the clinic (Table 17).

TABLE 17

Single Agent 1050 Values

| Compound | RKO Parental | RKO MEK1 Q56P/+ CI.1 | RKO MEK1 Q56P/+ CI.2 |
|---|---|---|---|
| BVD-523 | 0.20 | 0.17 | 0.18 |
| SCH772984 | 0.04 | 0.14 | 0.12 |
| Dabrafenib | n.d. | n.d. | n.d. |
| Trametinib | 0.006 | 0.093 | 0.080 |
| Paclitaxel | 0.002 | 0.002 | 0.002 |

n.d.—not determined, only a partial dose response achieved

In contrast, response to BVD-523 was identical in both the parental and double mutant cells, indicating that BVD-523 is not susceptible to this mechanism of acquired resistance.

These results were identical in two independently derived double mutant BRAF(V600E)::MEK1(Q56P) cell line clones confirming that these differences in response versus the parental cells were specifically related to the presence of the MEK1 mutation rather than an unrelated clonal artifact (FIG. 22A-FIG. 22E). Similar results were also observed with a second mechanistically distinct benchmark ERK inhibitor (SCH772984), which supports the notion that these observations are specifically related to inhibition of ERK and not due to an off-target effect.

The effect of combining BVD-523 with a BRAF inhibitor (exemplified by Dabrafenib) was also assessed in these cell lines across a matrix of concentrations using the Loewe Addivity or Bliss Independence models with Horizon's Chalice™ combination analysis software (FIG. 23-FIG. 23O and FIG. 24A-FIG. 24O). The presence of potentially synergistic interactions was then assessed by displaying the calculated excess inhibition over that predicted as being additive across the dose matrix as a heat map, and by calculating a 'Volume Score' that shows whether the overall response to a combination is synergistic (positive values), antagonistic (negative values) or additive (~0).

Figure 25A:
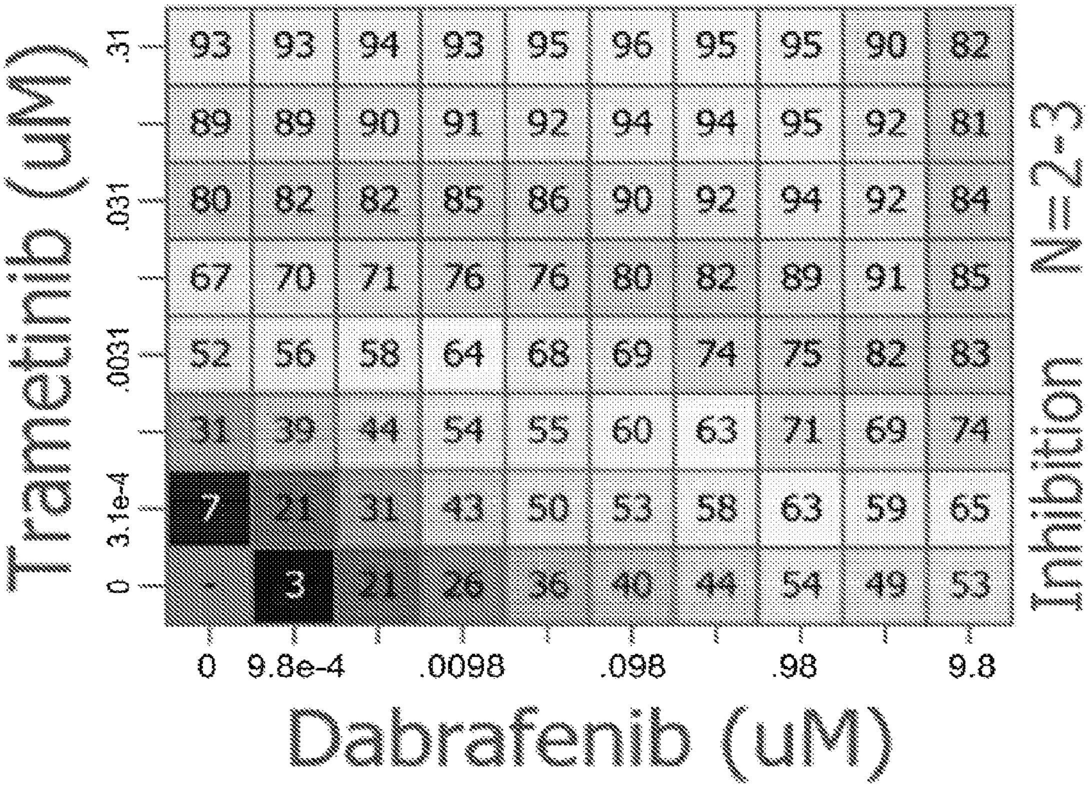
FIG. 25A-FIG. 25O show the results of the combination of Trametinib and Dabrafenib.
Figure 25B:
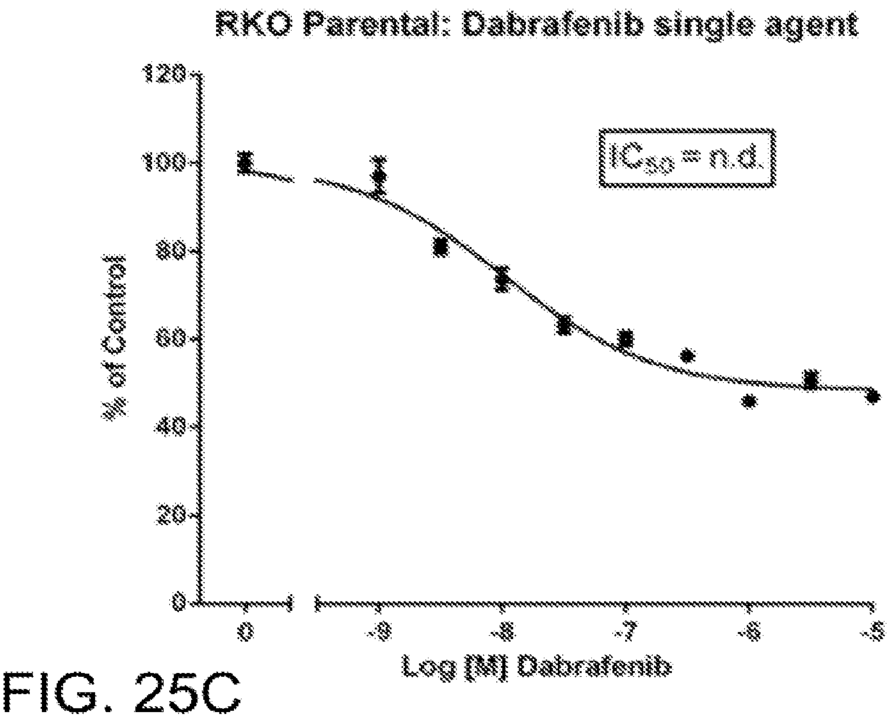
FIG. 25B-FIG. 25C show the results of single agent proliferation assays for the combination in FIG. 25A.
Figure 25C:
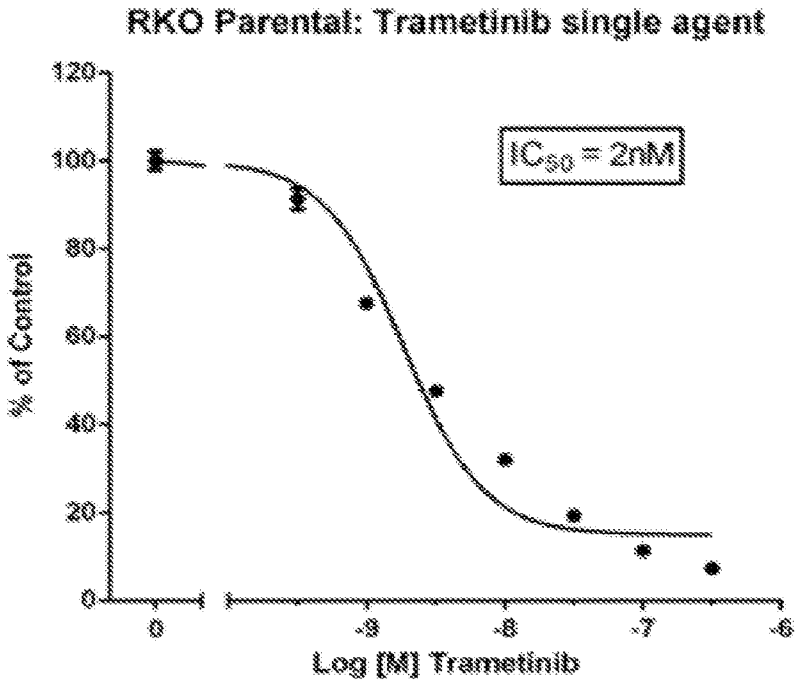
Figure 25E:
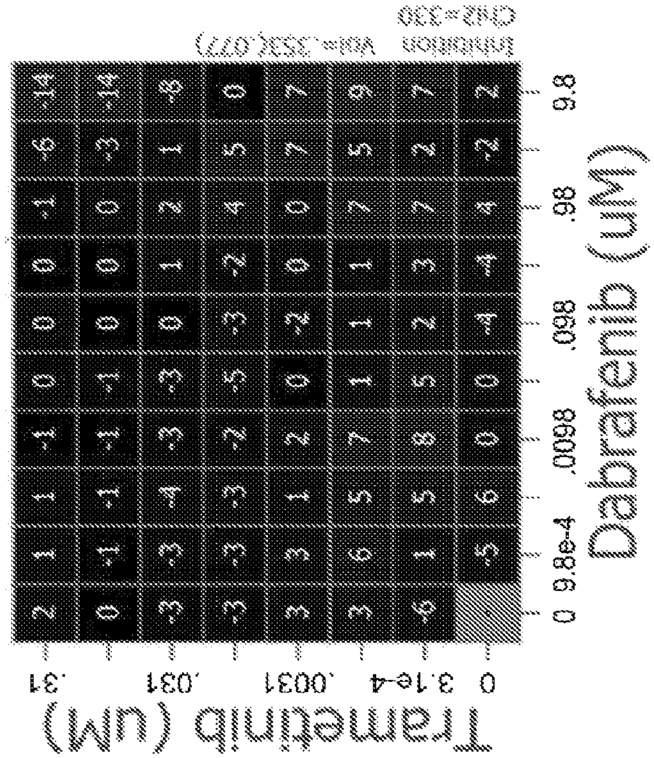
FIG. 25E shows Bliss excess for the combination in FIG. 25A.
Figure 25D:
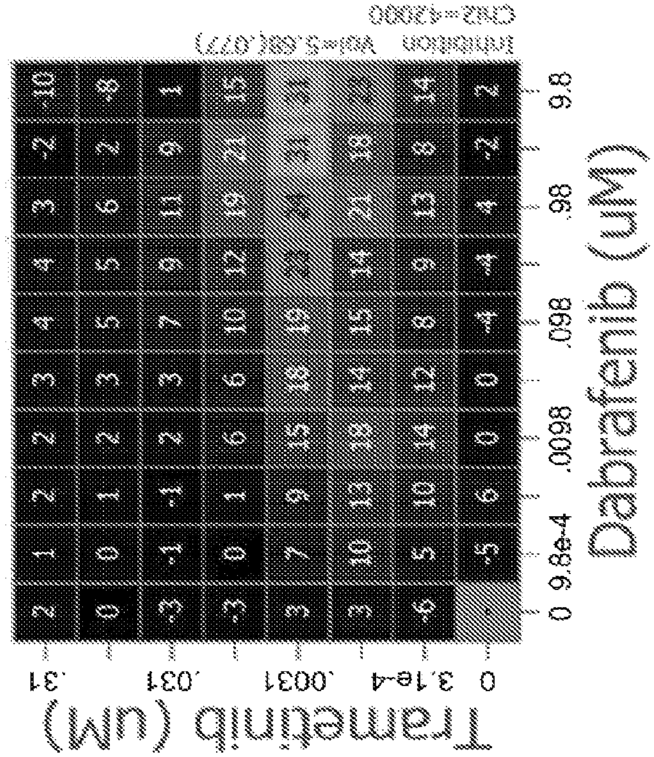
FIG. 25D shows Loewe excess for the combination in FIG. 25A
Figure 25F:
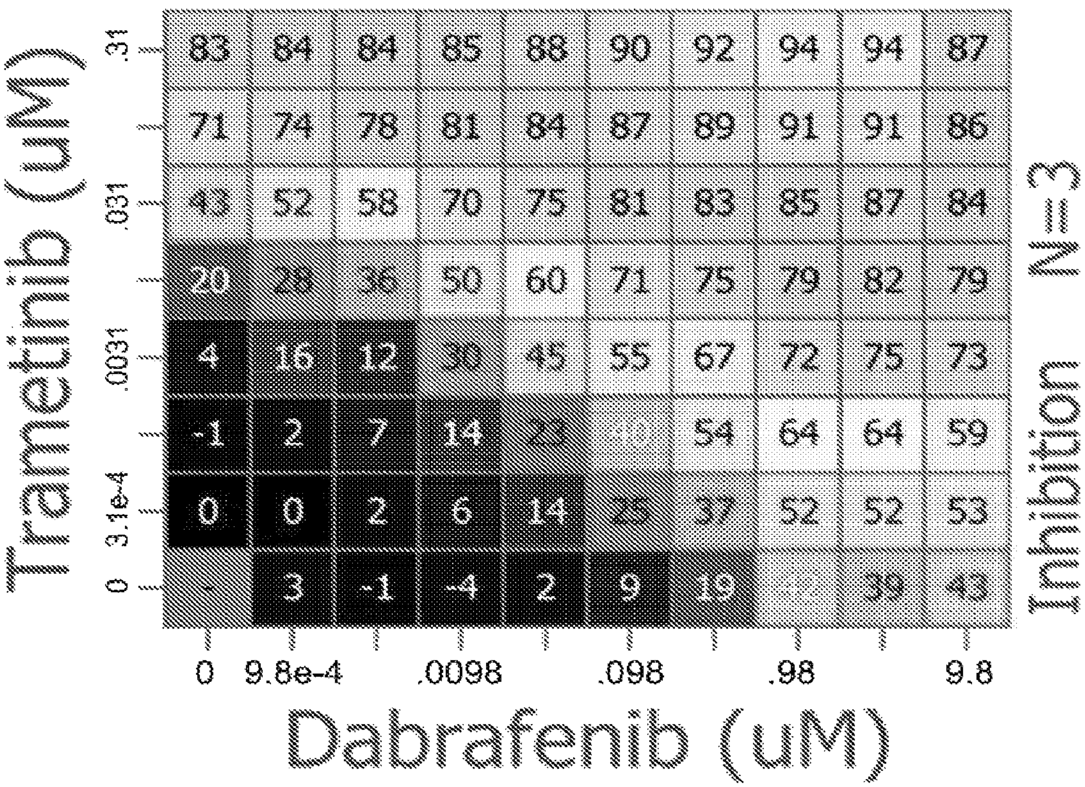
FIG. 25F shows a dose matrix showing inhibition (%) for the combination in RKO MEK1 (Q56P/+)—clone 1 cells.
Figure 25G:
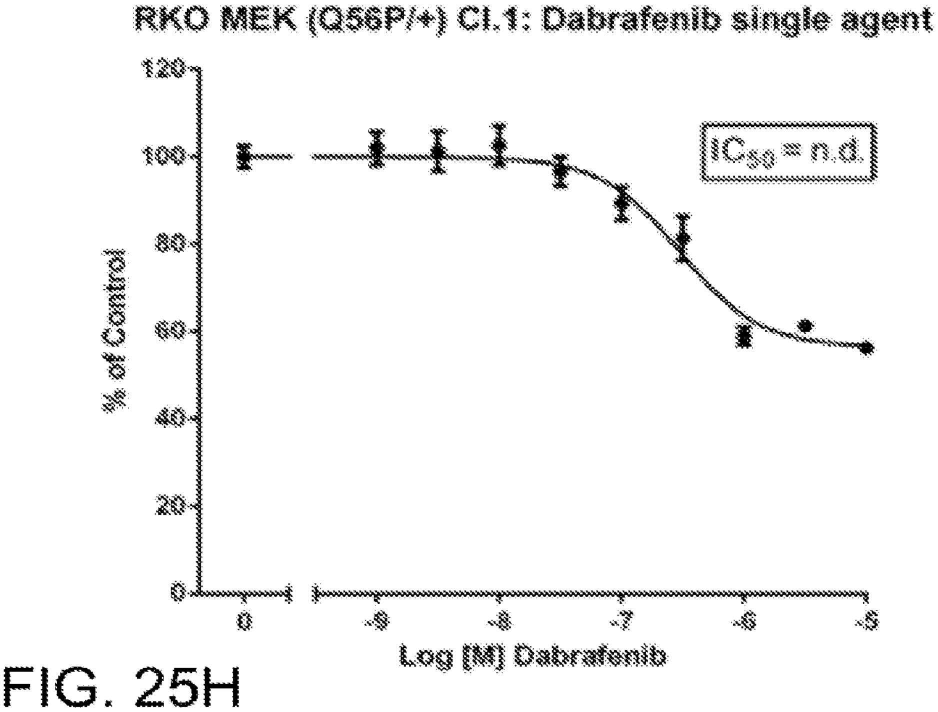
FIG. 25G-FIG. 25H show the results of single agent proliferation assays for the combination in FIG. 25F.
Figure 25H:
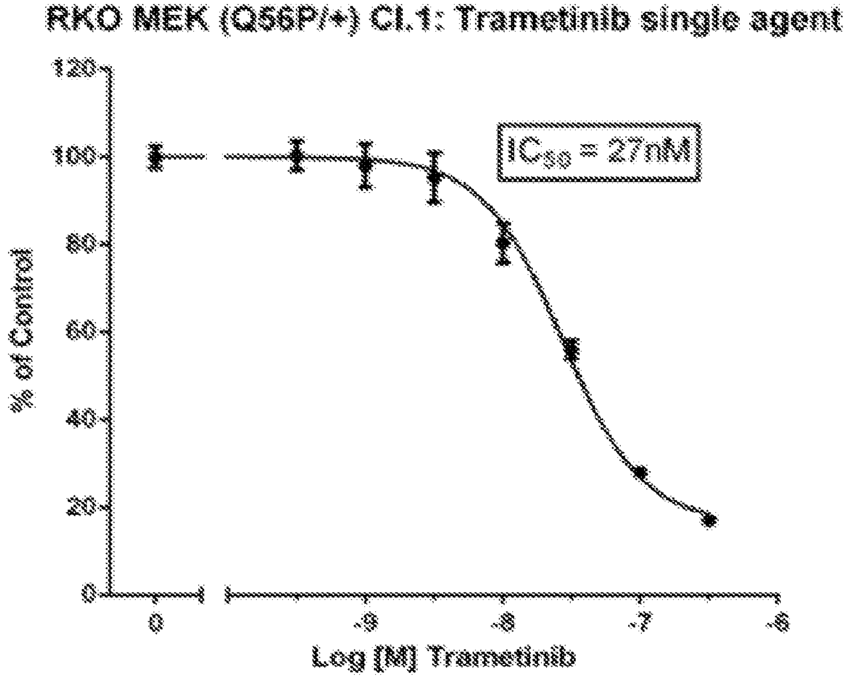
Figure 25J:
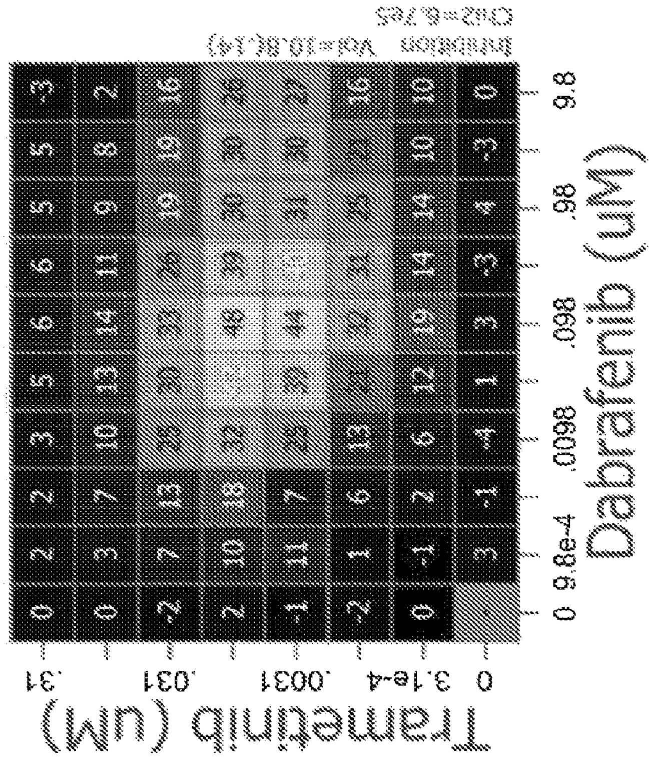
FIG. 25J shows Bliss excess for the combination in FIG. 25F.
Figure 25I:
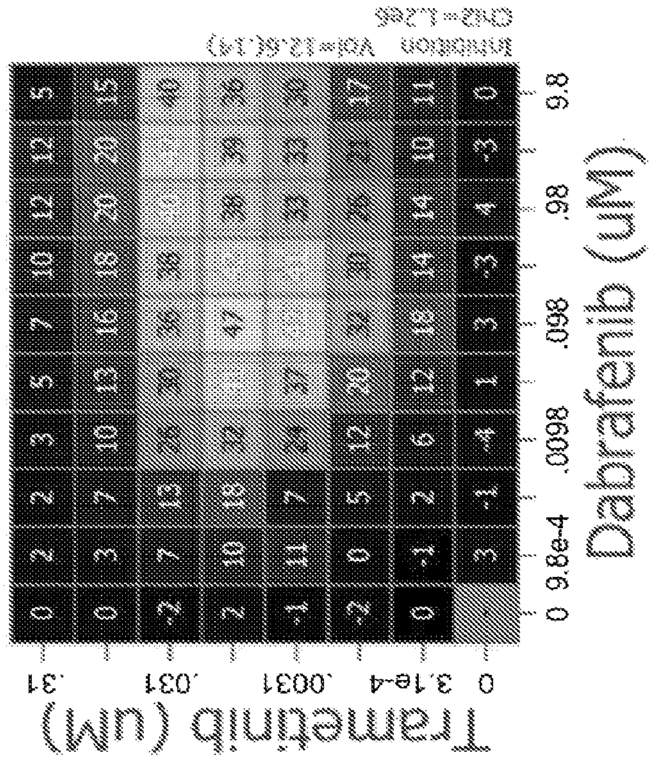
FIG. 25I shows Loewe excess for the combination in FIG. 25F
Figure 25K:
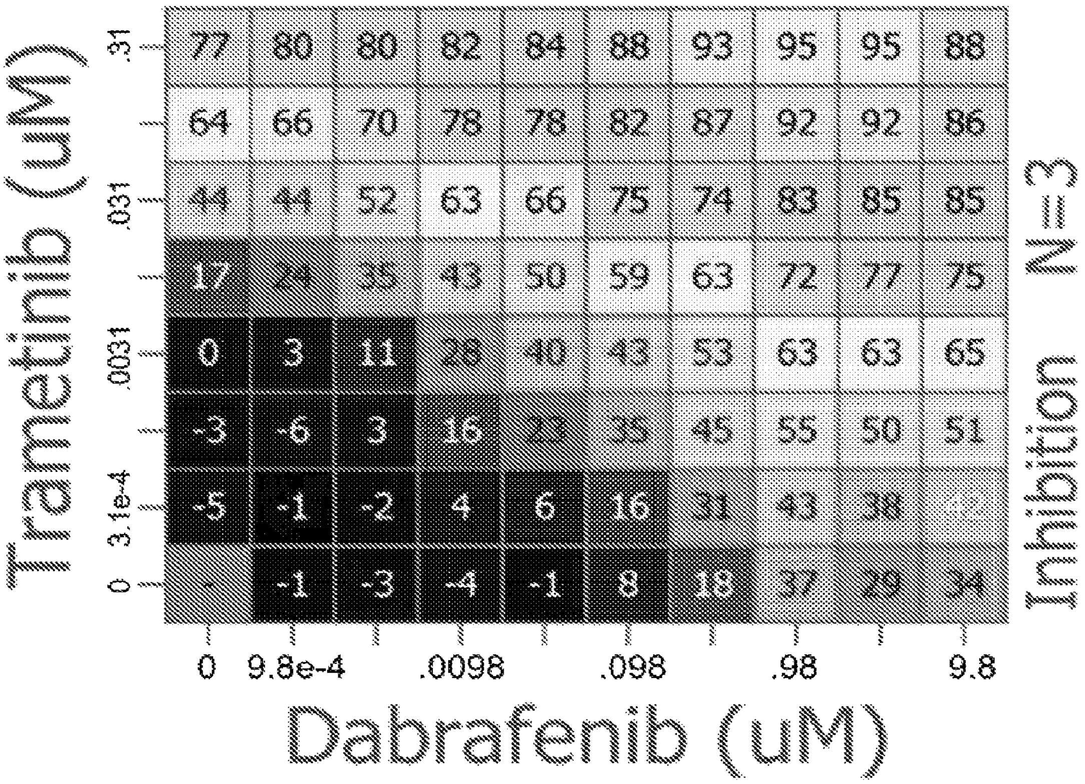
FIG. 25K shows a dose matrix showing inhibition (%) for the combination in RKO MEK1 (Q56P/+)—clone 2 cells.
Figure 25L:
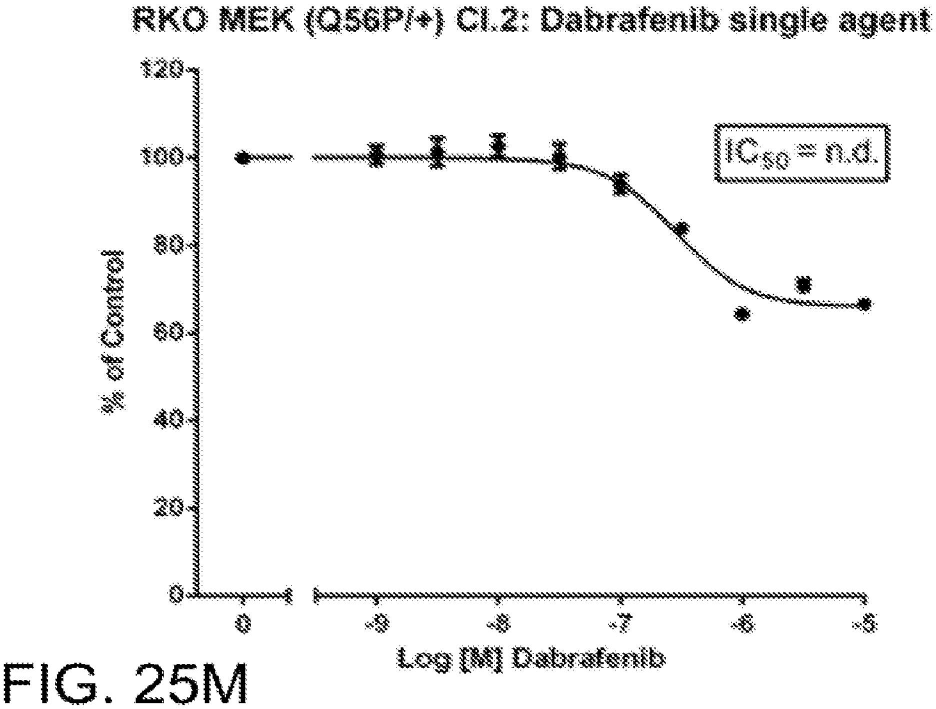
FIG. 25L-FIG. 25M show the results of single agent proliferation assays for the combination in FIG. 25K.
Figure 25M:
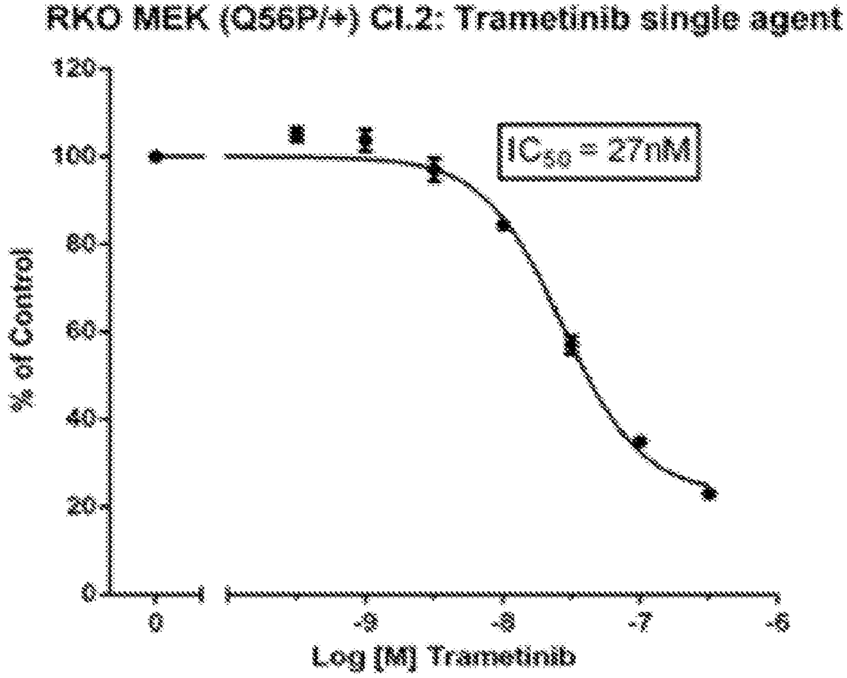
Figure 25O:
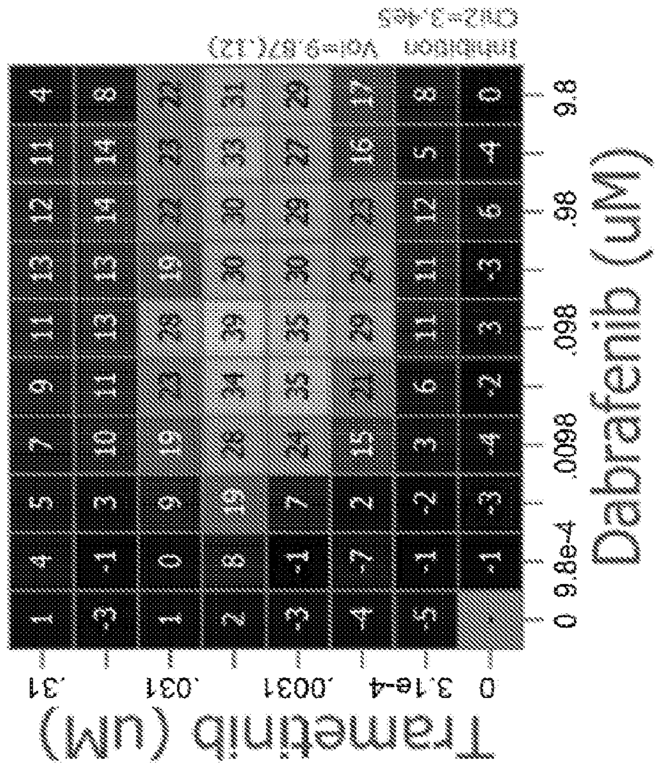
Figure 25N:
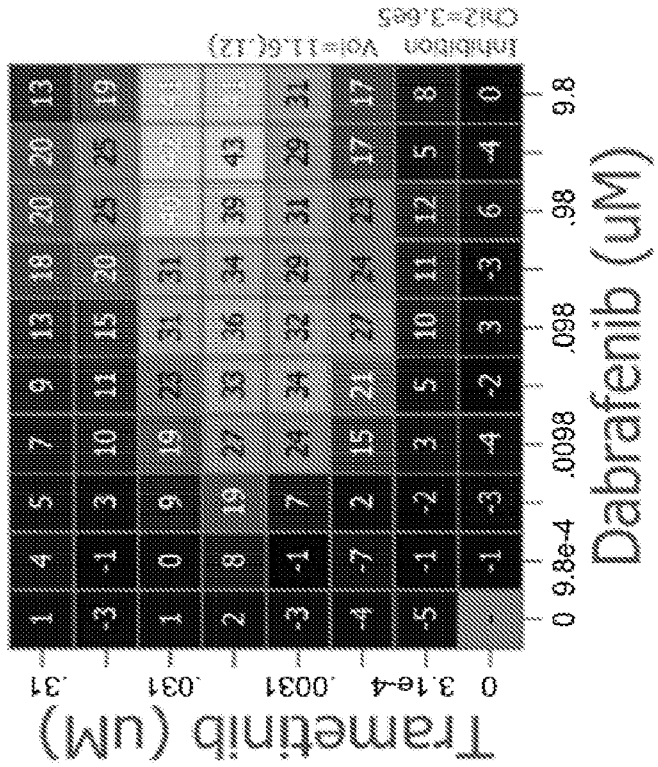
FIG. 25N shows Loewe excess for the combination in FIG. 25K
Figure 26A:
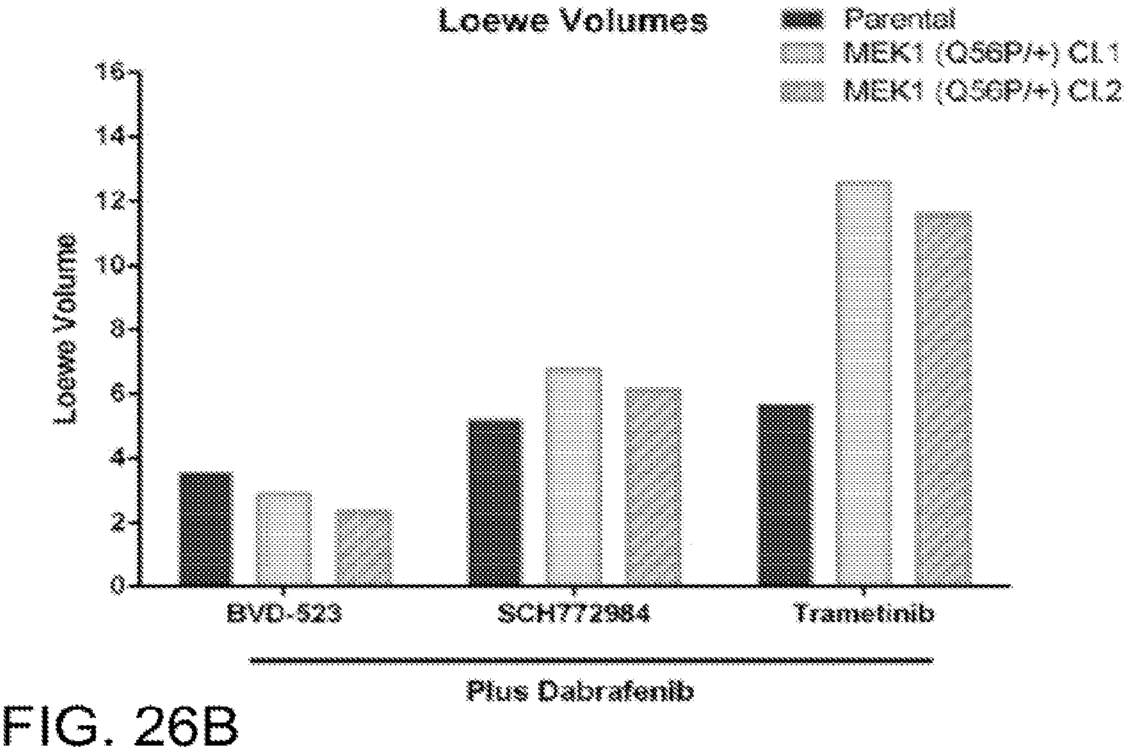
FIG. 26A shows Lowe Volumes for the combinations tested.
Figure 26B:
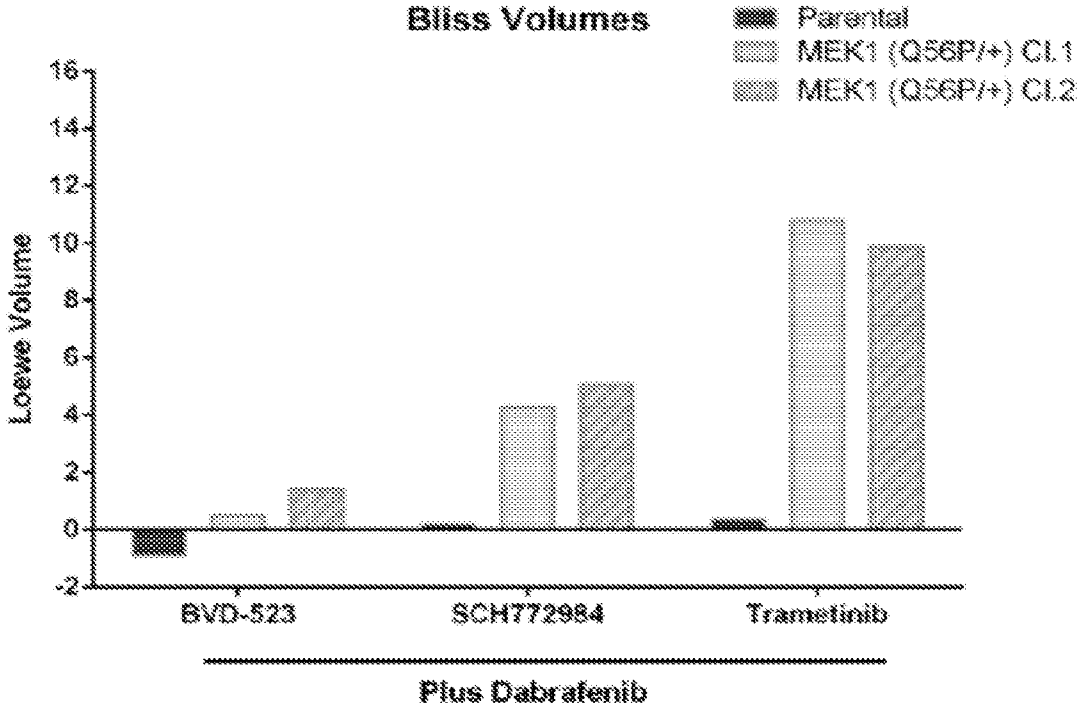
FIG. 26B shows Bliss Volumes for the combinations tested.
Figure 26C:
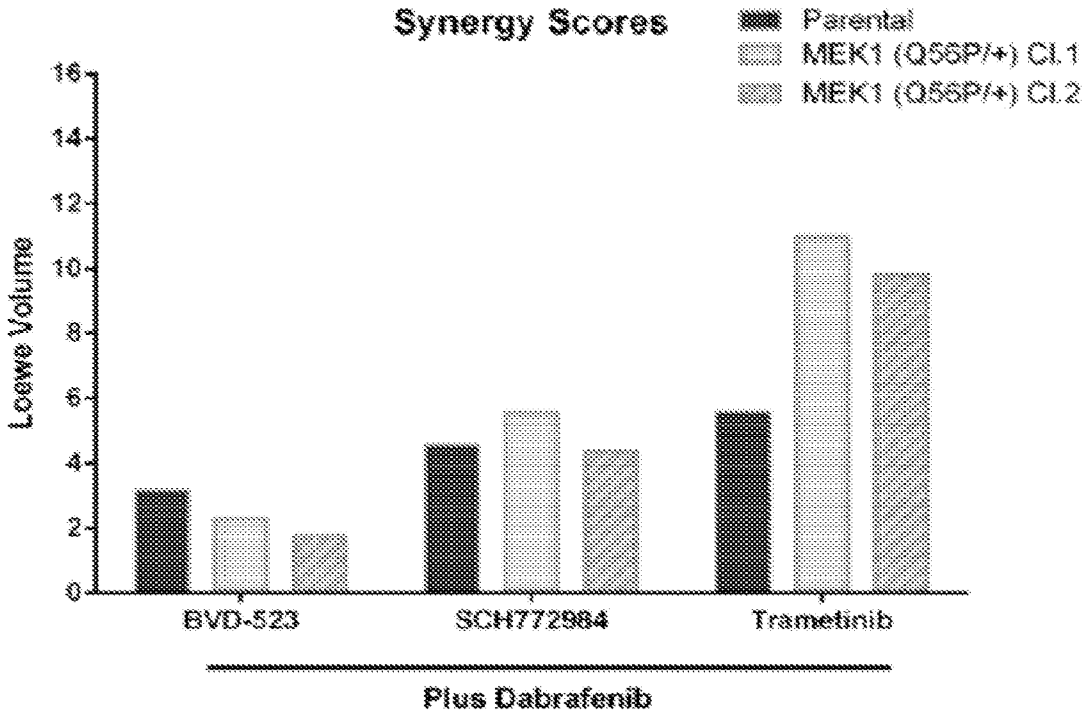
FIG. 26C shows Synergy Scores for the combinations tested.
Figure 27A:
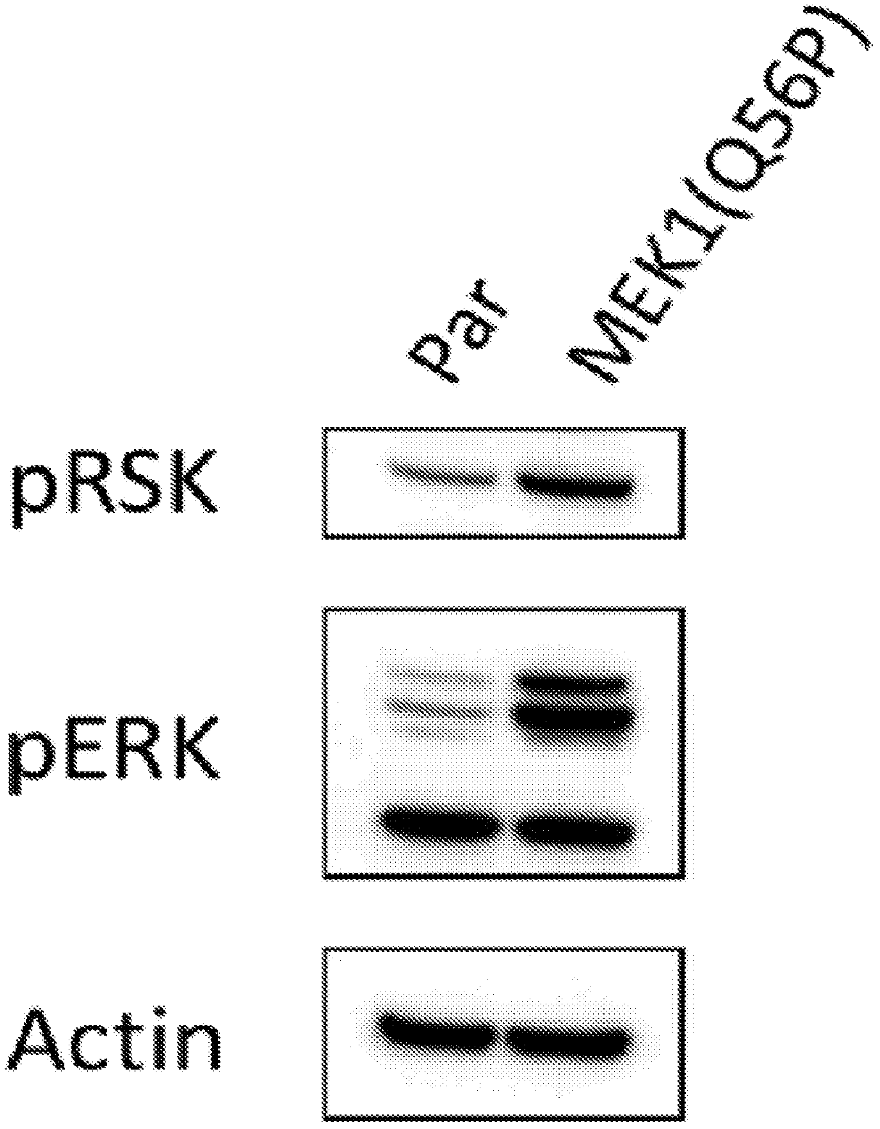
FIG. 27A-FIG. 27I show the changes in MAPK and Effector Pathway Signaling in MEK acquired resistance. Isogenic RKO parental and MEK1 (Q56P/+) cells were treated with compound for 4 or 24 h and then immunoblotted with the indicated antibodies. Dabrafenib was the BRAF inhibitor and trametinib was the MEK inhibitor.
Figure 27B:
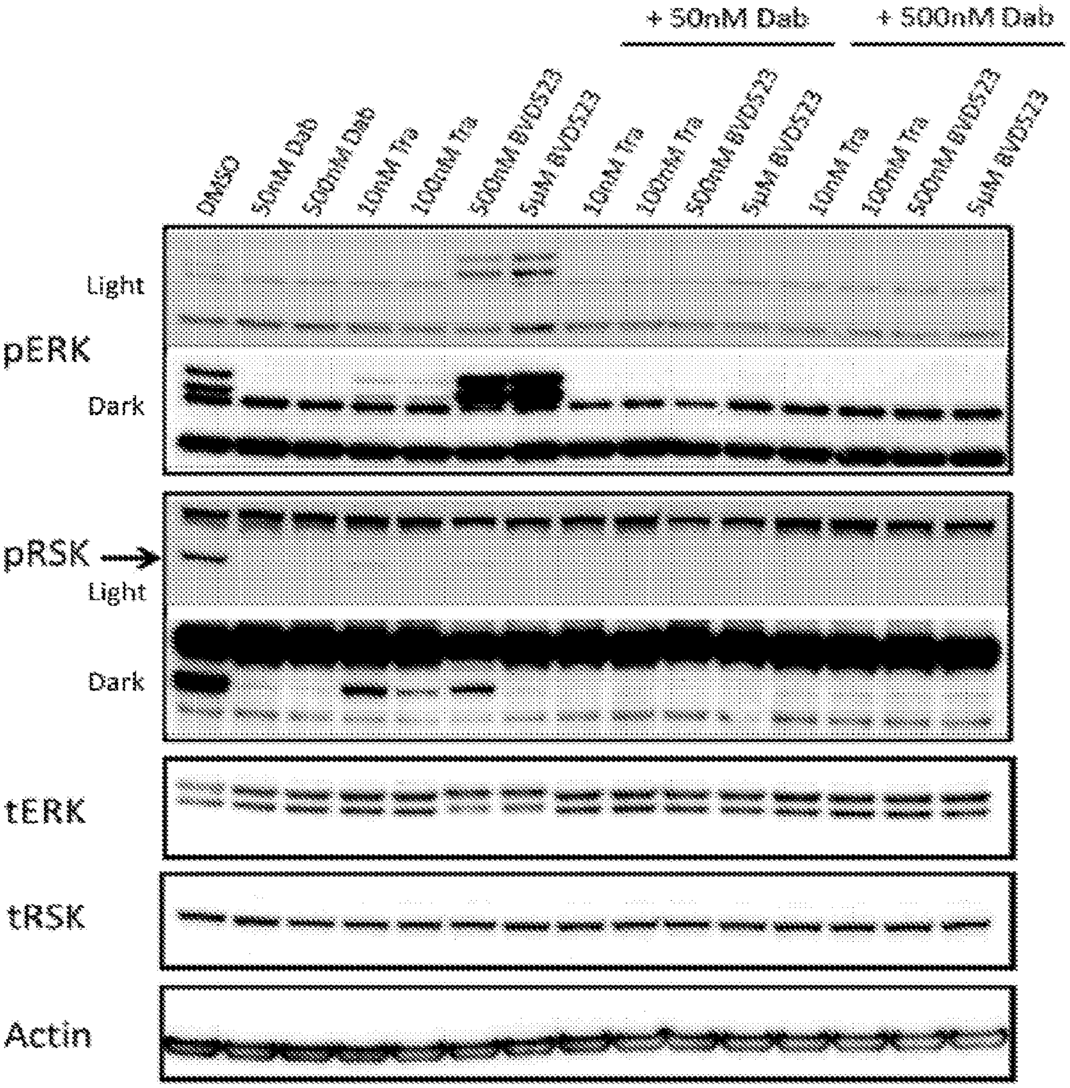
Figure 27C:
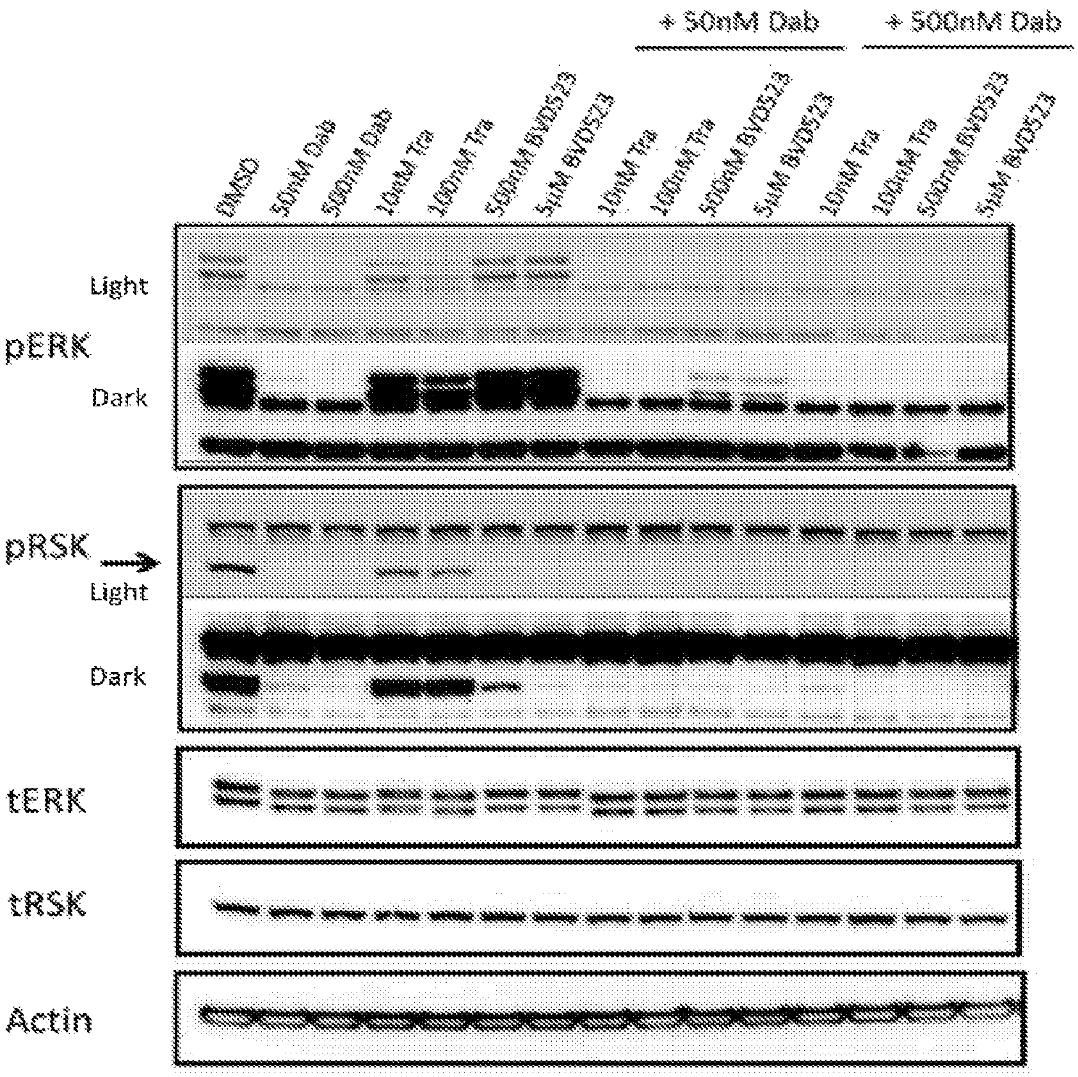
Figure 27D:
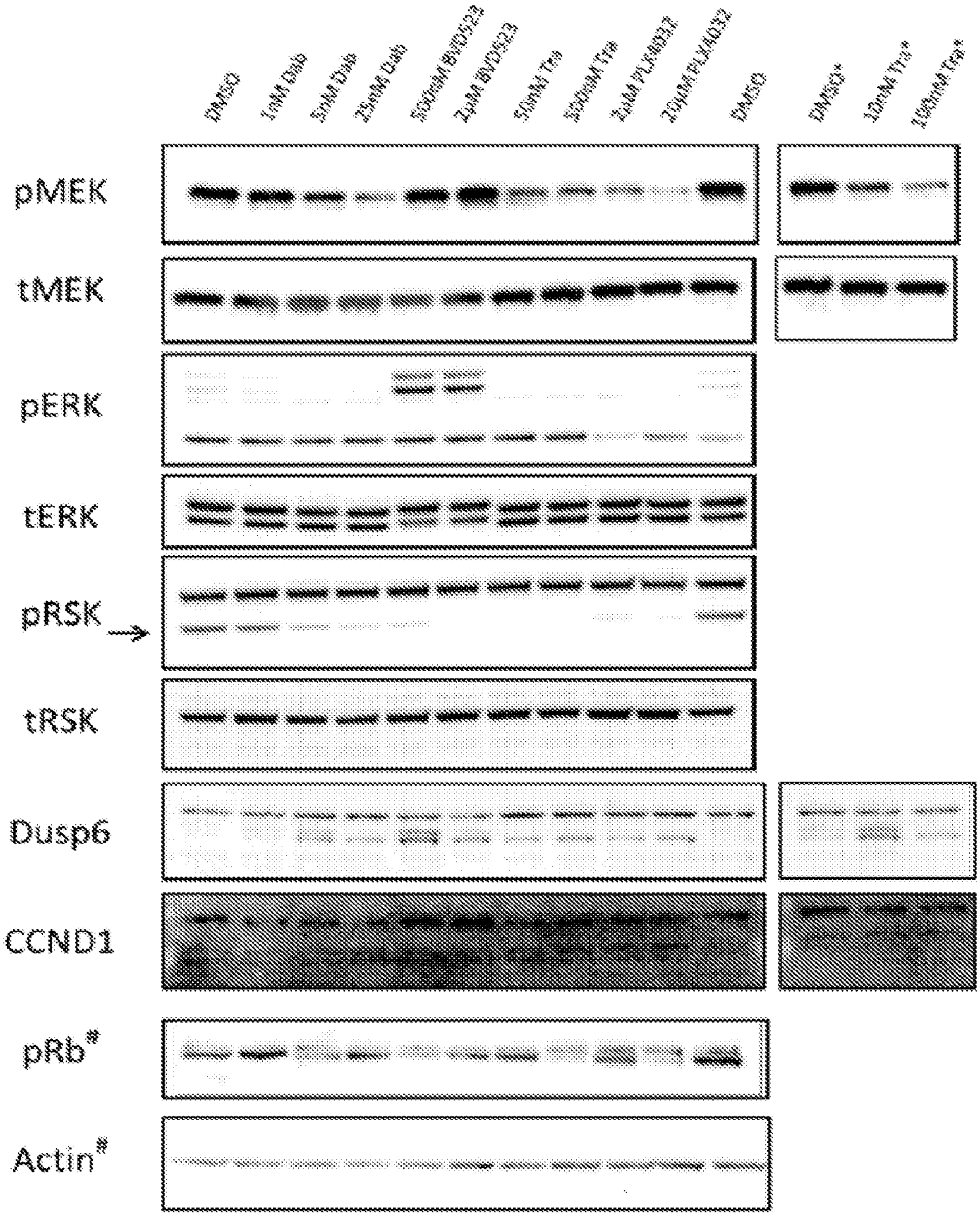
Figure 27E:
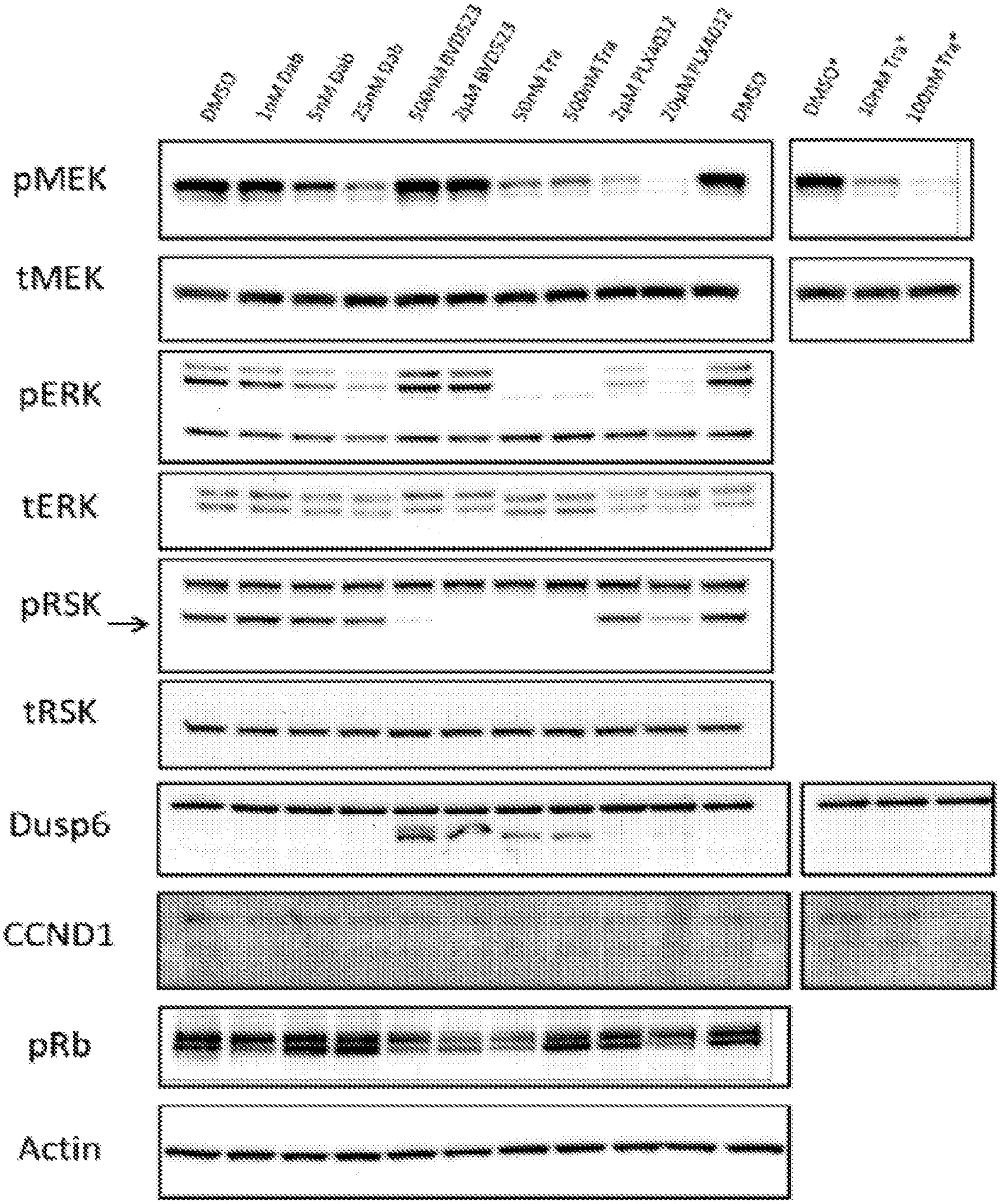
Figure 27F:
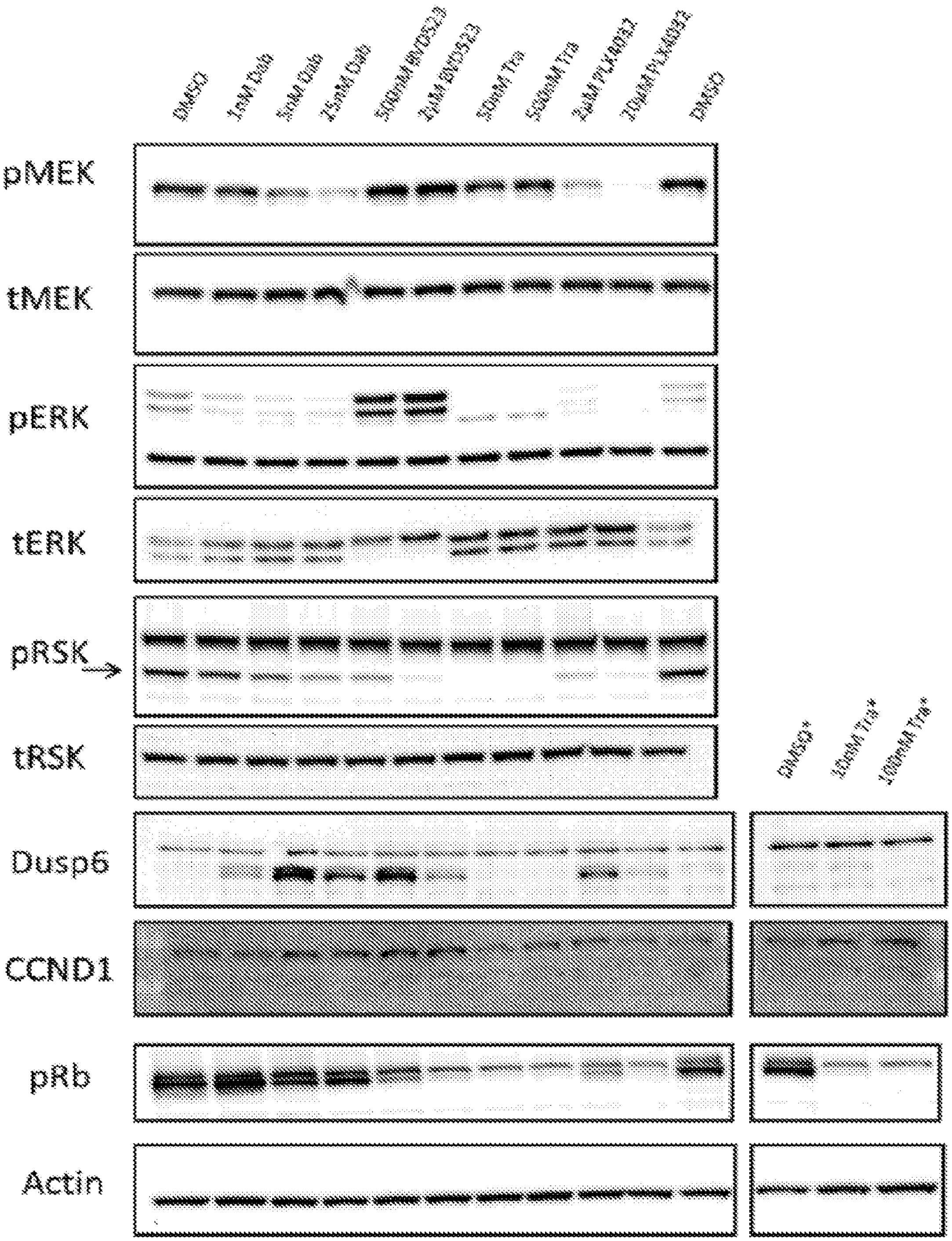
Figure 27G:
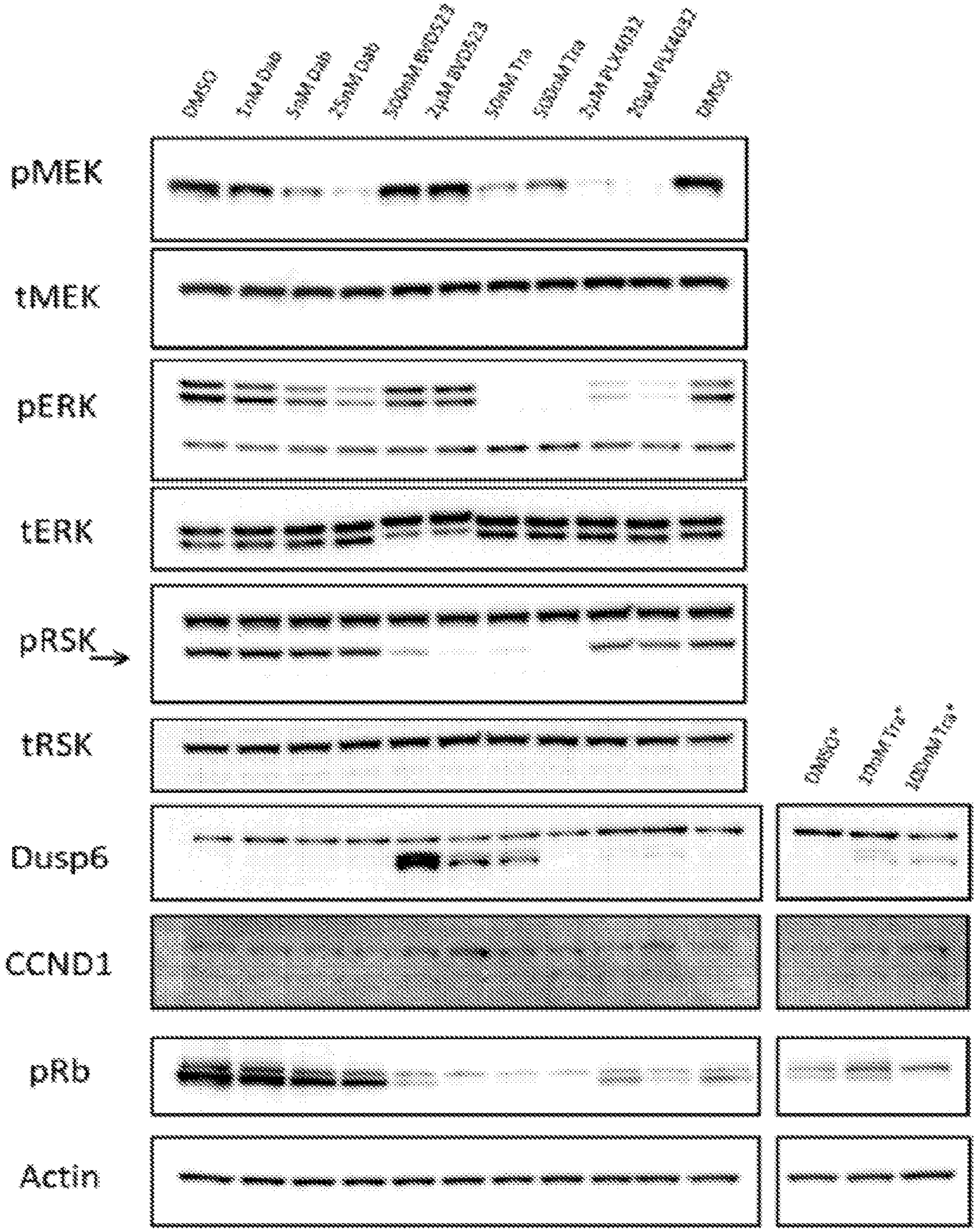
Figure 27H:
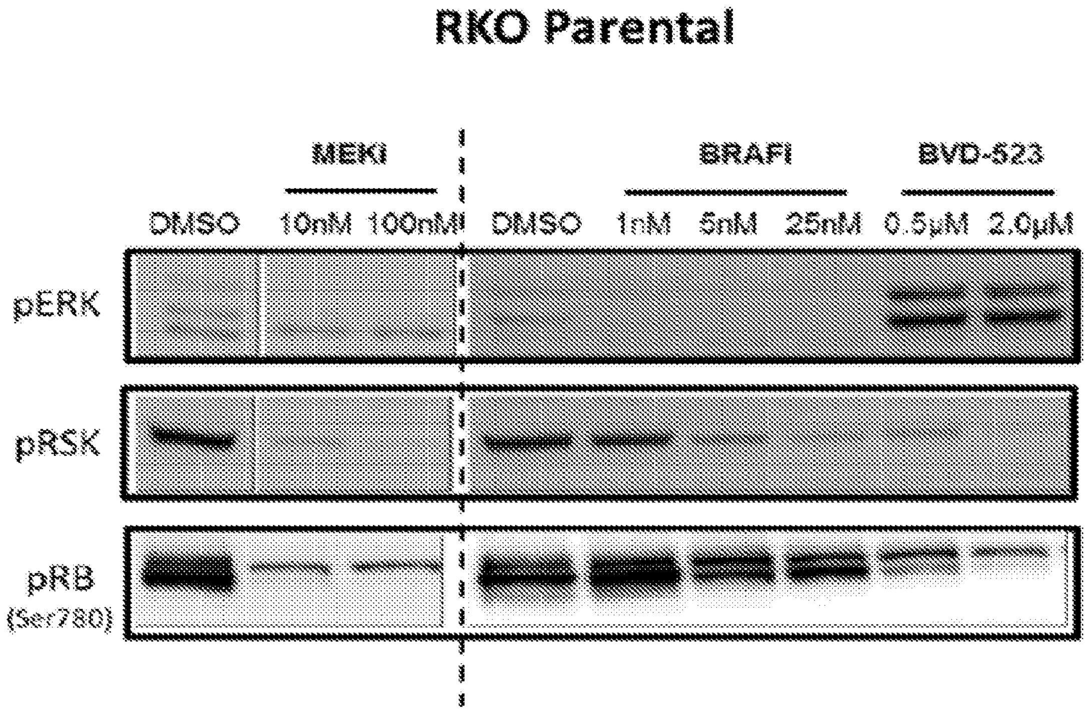
Figure 27I:
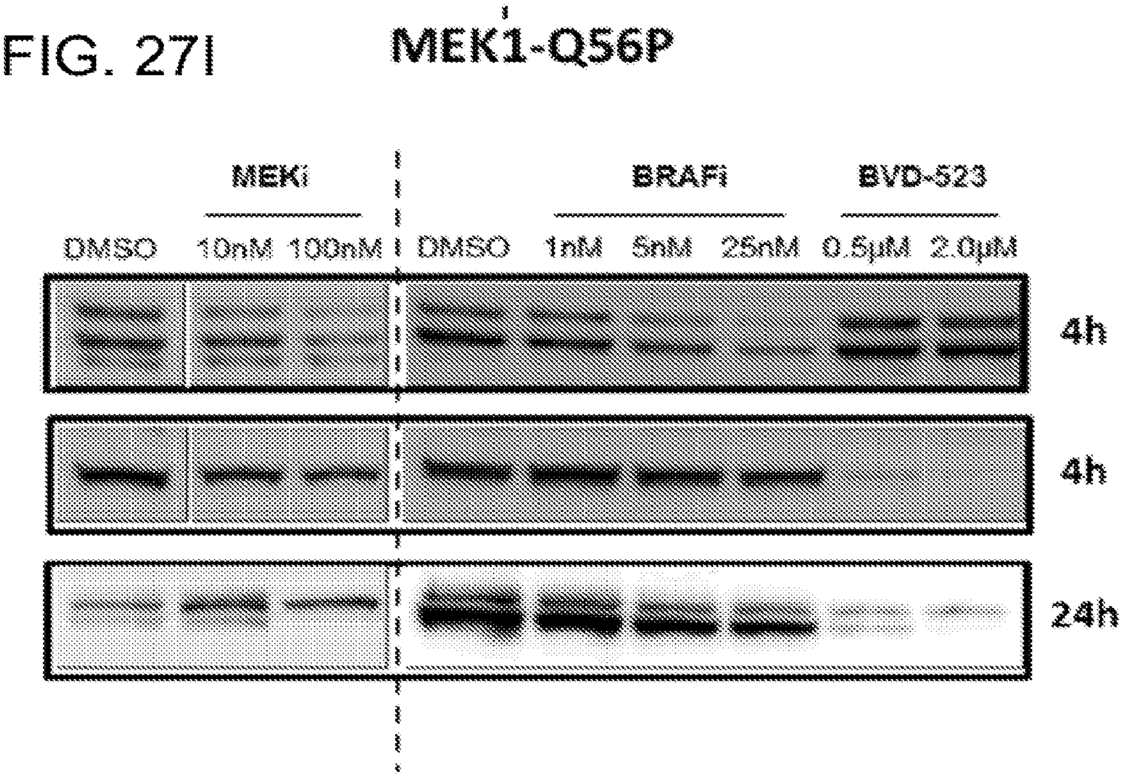
Figure 28A:
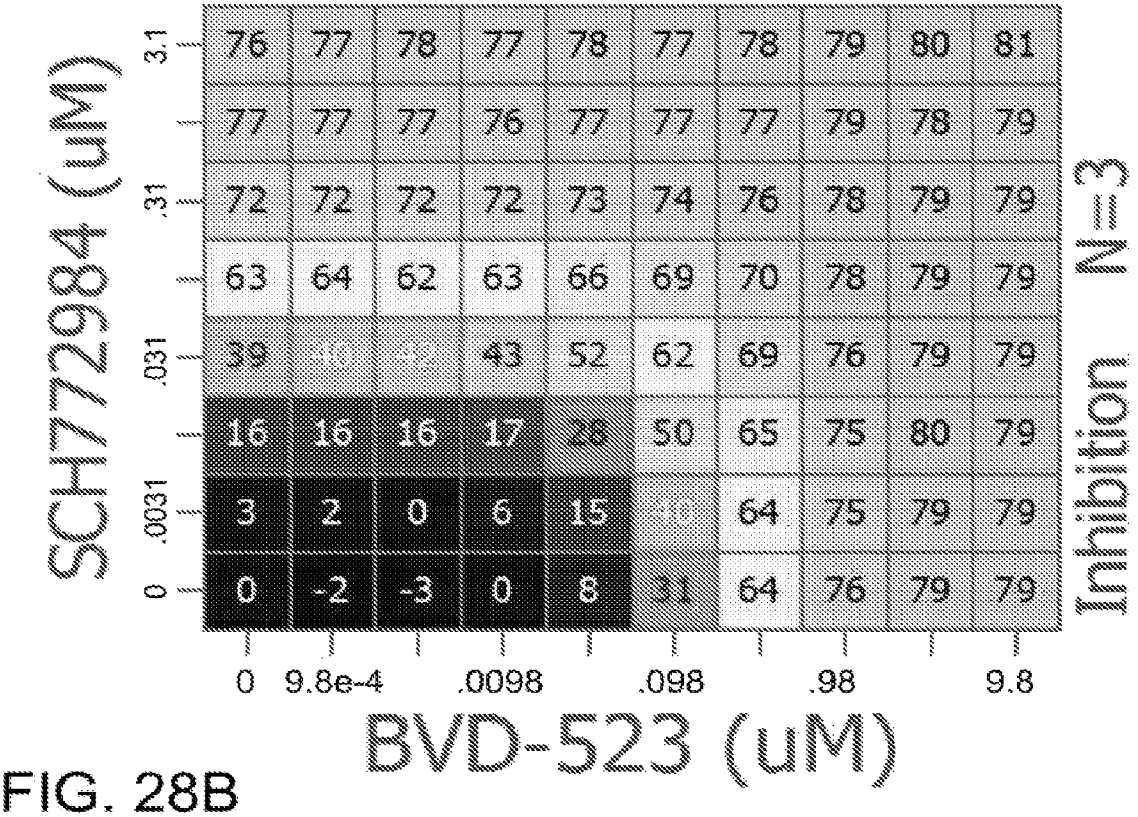
FIG. 28A-FIG. 28E show the results of the combination of BVD-523 and SCH772984.
Figure 28B:
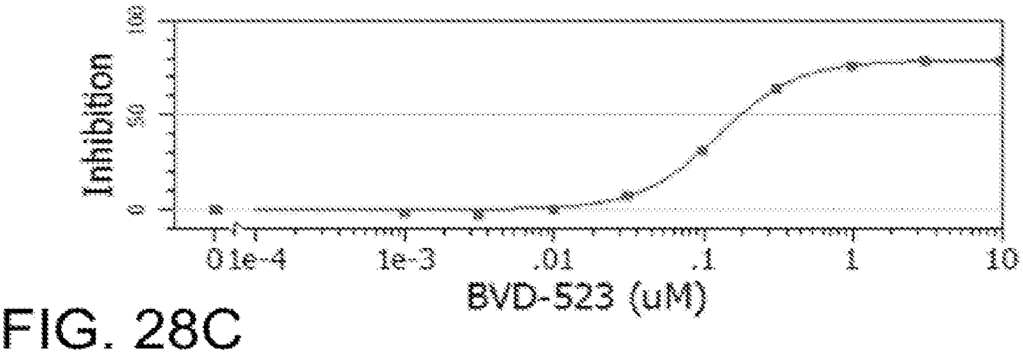
Figure 28C:
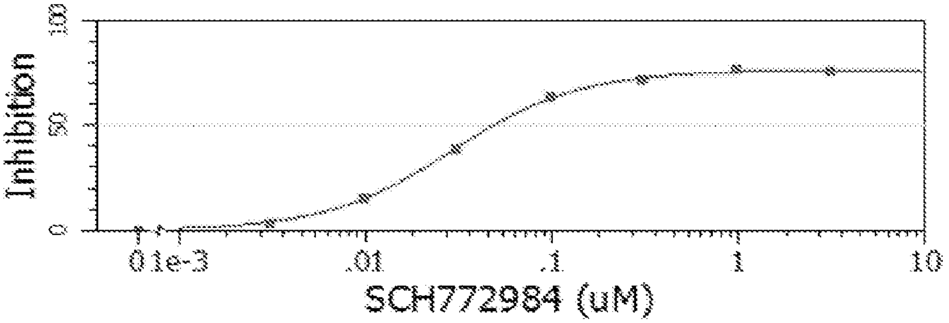
Figure 28D:
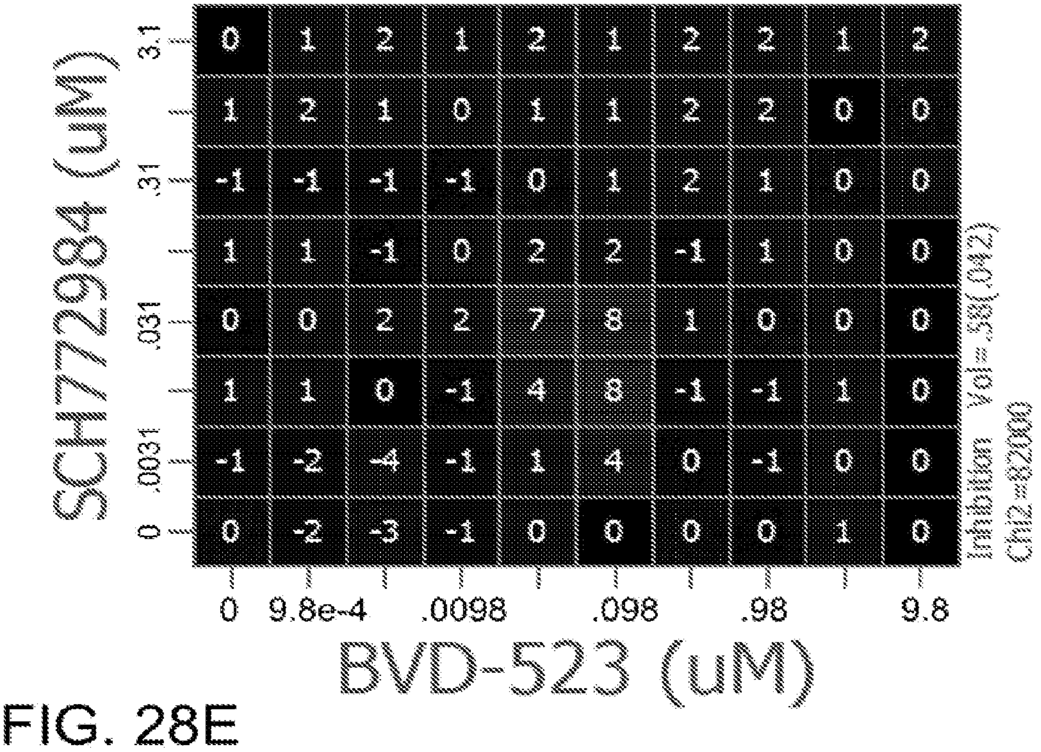
Figure 28E:
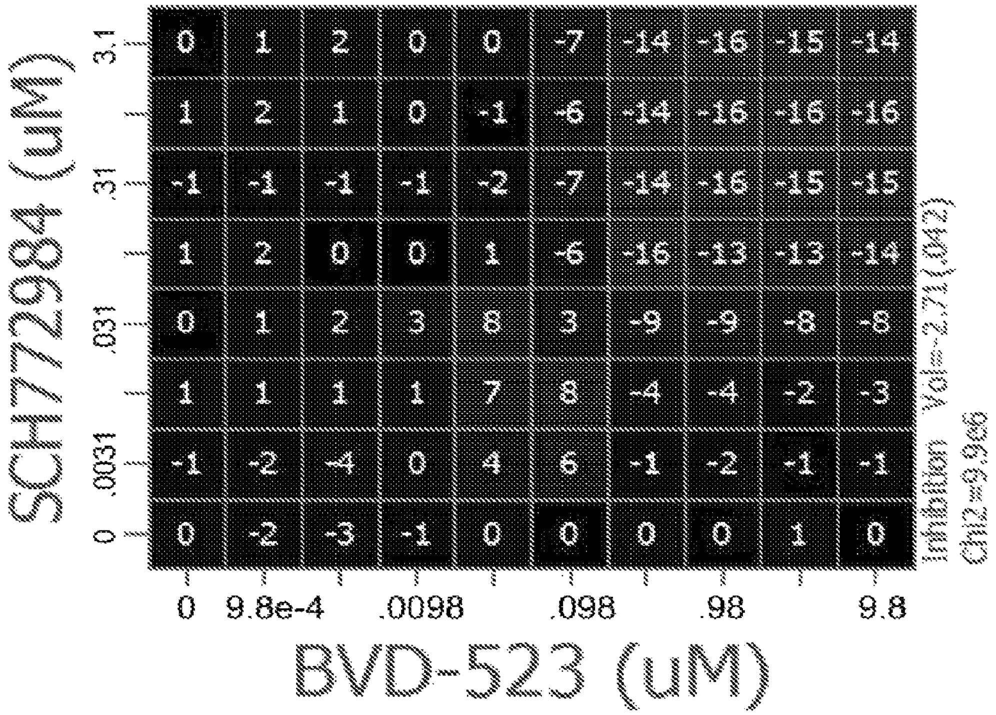

The results suggest that the BVD-523::Dabrafenib combination was mainly additive in the parental and mutant cell line. In contrast, the combination of a MEK inhibitor (trametinib) plus Dabrafenib, while being mostly additive in the parental cell line, showed strong synergy in the double mutant BRAF(V600E)::MEK1(Q56P) cell line (FIG. 25A-FIG. 25O). Loewe Volumes, Bliss Volumes and Synergy scores for the combinations tested are shown in Tables 18-20, respectively and are shown graphed in FIG. 26A-FIG. 26C.

TABLE 18

| Loewe Volumes | | | |
|---|---|---|---|
| | RKO Parental | RKO MEK1 (Q56P)—Clone 1 | RKO MEK1 (Q56P)—Clone 2 |
| BVD-523 × Dabrafenib | 3.54 | 2.88 | 2.35 |
| Dabrafenib × SCH772984 | 5.2 | 6.79 | 6.14 |
| Dabrafenib Trannetinib | 5.68 | 12.6 | 11.6 |

TABLE 19

| Bliss Volumes | | | |
|---|---|---|---|
| | RKO Parental | RKO MEK1 (Q56P)—Clone 1 | RKO MEK1 (Q56P)—Clone 2 |
| BVD-523 × Dabrafenib | −0.894 | 0.527 | 1.42 |
| Dabrafenib × SCH772984 | 0.209 | 4.3 | 5.07 |
| Dabrafenib × Trannetinib | 0.353 | 10.8 | 9.87 |

TABLE 20

| Synergy Scores | | | |
|---|---|---|---|
| | RKO Parental | RKO MEK1 (Q56P)—Clone 1 | RKO MEK1 (Q56P)—Clone 2 |
| BVD-523 × Dabrafenib | 3.18 | 2.31 | 1.77 |
| Dabrafenib × SCH772984 | 4.56 | 5.57 | 4.36 |
| Dabrafenib × Trannetinib | 5.58 | 11 | 9.83 |

Effects on MAPK pathway signally was assessed by Western blotting. The levels of basal ERK phosphorylation (DMSO samples) was markedly upregulated in the MEK1 (Q56P)-expressing line relative to parental further confirming that this isogenic model faithfully recapitulates the expected phenotype for the expression of MEK activating acquired resistance mutations.

In the parental BRAF(V600E) RKO cells, a reduced level of RSK1/2 phosphorylation is observed following acute treatment with RAF, MEK and ERK kinase inhibitors at pharmacologically active concentrations. In contrast, isogenic, double mutant BRAFV600E::MEK1Q56P cells do not exhibit reduced RSK phosphorylation following BRAF or MEK inhibitor treatment, while BVD-523 remains effective at similar concentrations (FIG. 27A-FIG. 27I). The dotted lines indicate that the trametinib-treated samples (plus matched DMSO control) and blots are derived from a separate experiment to the BRAFi and BVD-523 treated samples.

Changes in effector gene signaling consistent with cell growth inhibition patterns are observed following prolonged inhibitor treatment. In parental RKO lines, a reduced level of phosphorylated pRB is observed following prolonged MEK and ERK inhibitor treatment. At the level of pRB modulation, MEK1 mutant lines appear insensitive to low concentration MEK inhibitor treatment, while higher concentrations remain effective. Critically, BVD-523 potency against pRB activity does not appear to be strongly affected by MEK mutation. Surprisingly, RAF inhibitor treatment does not affect pRB status, despite potent inhibition of upstream signaling, in both parental and MEK mutant backgrounds.

In summary, these results show that BVD-523 is not susceptible to acquired resistance driven by MEK activating mutations such as MEK1 (Q56P). In addition they suggest that in combination the interactions between BVD-523 and BRAFi (exemplified by Dabrafenib) are additive irrespective of the presence of a MEK activating mutation.

Example 8

Combination Interactions Between ERK Inhibitors

RAF mutant melanoma cell line A375 cells were cultured in DMEM with 10% FBS and seeded into triplicate 96-well plates at an initial density of 2000 cells per well. Combination interactions between ERK inhibitors BVD-523 and SCH772984 were analyzed after 72 hours as described above in Example 4. Viability was determined using CellTiter-Glo® reagent (Promega, Madison, WI) according to manufacturer's instructions and luminescence was detected using the BMG FLUOstar plate reader (BMG Labtech, Ortenberg, Germany).

Visualization of the Loewe and Bliss 'excess inhibition' heat maps suggested that the combination of BVD-523 and SCH772984 was mainly additive with windows of potential synergy in mid-range doses (FIG. 28A-FIG. 28E).

In summary, these results suggest that interactions between BVD-523 and SCH772984 are at least additive, and in some cases synergistic.

Example 9

Targeting the MAPK Signaling Pathway in Cancer: Promising Activity with the Novel Selective ERK1/2 Inhibitor BVD-523 (Ulixertinib)

Treatment strategies for cancer have evolved from classic cytotoxic-based approaches to agents that counteract the effects of genetic lesions that drive aberrant signaling essential to tumor proliferation and survival. For example, the ERK module of the mitogen-activated protein kinase (MAPK) signaling cascade (RAS-RAF-MEK-ERK) (Cargnello and Rouxx 2011) can be engaged by several receptor tyrosine kinases (e.g., EGFR and ErbB-2) in addition to constitutively activated mutations of pathway components such as RAS and BRAF (Gollob et al. 2006). Through aberrant activation of ERK signaling, genetic alterations in RAS or BRAF result in rapid tumor growth, increased cell survival, and resistance to apoptosis (Poulikakos et al. 2011, Corcoran et al. 2010, Nazarian et al. 2010, Shi et al. 2014, Wagle et al. 2011). Activating mutations of RAS family members KRAS and NRAS are found in ~30% of all human cancers, with particularly high incidence in pancreatic (Kanda et al. 2012) and colorectal cancer (Arrington et al. 2014). Constitutively activating mutations in the BRAF gene that normally encodes for valine at amino acid 600 have been observed in melanoma, thyroid carcinoma, colorectal cancer, and non-small cell lung cancer (Hall et al. 2014). Cancers bearing genetic mutations that result in changes of the downstream components ERK and MEK have also been reported (Ojesina et al. 2014, Arcila et al. 2015). Alterations that activate the MAPK pathway are also common in the setting of resistance to targeted therapies (Groenendijk et al. 2014). Thus, targeting the MAPK pathway terminal master kinases (ERK1/2) is a promising strategy for tumors harboring such pathway activating alterations (e.g., BRAF, NRAS, and KRAS).

Three MAPK pathway-targeting drugs have been approved by the US Food and Drug Administration (FDA) for single-agent treatment of nonresectable or metastatic cutaneous melanoma with $BRAF^{V600}$ mutations: the BRAF inhibitors vemurafenib and dabrafenib and the MEK inhibitor trametinib. Furthermore, the combination of dabrafenib and trametinib is also approved in this indication (Queirolo et al. 2015 and Massey et al. 2015). An additional MEK inhibitor, cobimetinib, is approved in this indication as part of a combination regimen with BRAF inhibitors. Clinical experience with these drugs validates the MAPK pathway as a therapeutic target. In phase III trials of patients with $BRAF^{V600}$-mutant melanoma, the single agents vemurafenib and dabrafenib demonstrated superior response rates (approximately 50% vs. 5-19%) and median progression-free survival (PFS, 5.1-5.3 months vs. 1.6-2.7 months) over cytotoxic chemotherapy (dacarbazine) (Chapman et al. 2011 and Hauschild et al. 2012). Furthermore, clinical use of concomitant BRAF-plus MEK-targeted therapies has demonstrated that simultaneous targeting of different nodes in the MAPK pathway can enhance the magnitude and duration of response. First-line use of BRAF plus MEK-targeted agents (dabrafenib/trametinib or cobimetinib/vemurafenib) further improved median overall survival compared with single-agent BRAF inhibition (Robert et al. 2015, Long et al. 2015, Larkin et al. 2014). Thus, combined BRAF-/MEK-targeted therapy is a valuable treatment option for patients with metastatic melanoma with $BRAF^{V600}$ mutations.

Despite improvements in clinical outcomes seen with BRAF-/MEK-inhibitor combination therapies, durable benefit is limited by the eventual development of acquired resistance and subsequent disease progression, with median PFS ranging from approximately 9 to 11 months. (Robert et al. 2015, Long et al. 2015, Larkin et al. 2014, and Flaherty et al. 2012). Genetic mechanisms of acquired resistance to single-agent BRAF inhibition have been intensely studied, and identification of resistance mechanisms include splice variants of BRAF (Poulikakos et al. 2011), $BRAF^{V600E}$ amplification (Corcoran et al. 2010), MEK mutations (Wagle et al. 2014), NRAS mutations, and RTK activation (Nazarian et al. 2010 and Shi et al. 2014). Resistance mechanisms in the setting of BRAF-/MEK-inhibitor combination therapy are beginning to emerge and mirror that of BRAF single-agent resistance (Wagle et al. 2014 and Long et al. 2014). These genetic events all share in common the ability to reactivate ERK signaling. Indeed, reactivated MAPK pathway signaling as measured by ERK transcriptional targets is common in tumor biopsies from BRAF inhibitor-resistant patients (Rizos et al. 2014). Furthermore, ERK1/2 reactivation has been observed in the absence of a genetic mechanism of resistance (Carlino et al. 2015). Therefore, the quest to achieve durable clinical benefit has led researchers to focus on evaluating additional agents that target the downstream MAPK components ERK1/2. Inhibiting ERK may provide important clinical benefit to patients with acquired resistance to BRAF/MEK inhibition. ERK family kinases have shown promise as therapeutic targets in preclinical cancer models, including those cancers resistant to BRAF or MEK inhibitors (Morris et al. 2013 and Hatzivassiliou et al. 2012). However, the potential use of such ERK1/2 inhibitors expands beyond acquired-resistance in melanoma.

Targeting ERK1/2 is a rational strategy in any tumor type harboring known drivers of MAPK, not only BRAF/MEK therapy-relapsed patients. As ERK1 and ERK2 reside downstream in the pathway, they represent a particularly attractive treatment strategy within the MAPK cascade that may avoid upstream resistance mechanisms. Here, preclinical characterization of BVD-523 (ulixertinib) in models of MAPK pathway-dependent cancers is reported, including drug-naïve and BRAF/MEK therapy acquired-resistant models. Results of a phase I dose-finding study of BVD-523 are included as a companion publication in this journal. See, Examples 17-24.

In the present invention, BVD-523 was shown to be a potent, highly selective, reversible, small molecule ATP-competitive inhibitor of ERK1/2 with in vitro and in vivo anticancer activity.

BVD-523 (ulixertinib) was identified and characterized as a novel, reversible, ATP-competitive ERK1/2 inhibitor with high potency and ERK1/2 selectivity. BVD-523 caused reduced proliferation and enhanced caspase activity, most notably in cells harboring MAPK (RAS-RAF-MEK) pathway mutations. In in vivo $BRAF^{V600E}$ xenograft studies, BVD-523 showed dose-dependent growth inhibition and tumor regressions. Interestingly, BVD-523 inhibited phosphorylation of target substrates despite increased phosphorylation of ERK1/2. BVD-523 also demonstrated antitumor activity in models of acquired resistance to single-agent and combination BRAF/MEK targeted therapy. Synergistic antiproliferative effects in a $BRAF^{V600E}$-mutant melanoma cell line xenograph model were also demonstrated when BVD-523 was used in combination with BRAF inhibition. These studies suggest that BVD-523 holds promise as a treatment for ERK-dependent cancers, including those whose tumors have acquired resistance to other treatments targeting upstream nodes of the MAPK pathway.

Example 10

Discovery and Initial Characterization of a Novel ERK1/2 Inhibitor, BVD-523 (Ulixertinib)

Following extensive optimization of leads originally identified using a high-throughput, small-molecule screen (Aronov et al. 2009), a novel adenosine triphosphate (ATP)-competitive ERK1/2 inhibitor, BVD-523 (ulixertinib) was identified (FIG. 29 A). BVD-523 is a potent ERK inhibitor with a $K_i$ of 0.04±0.02 nM against ERK2. It was shown to be a reversible, competitive inhibitor of ATP, as the $IC_{50}$ values for ERK2 inhibition increased linearly with increasing ATP concentration (FIG. 29B and FIG. 29C). The $IC_{50}$ remained nearly constant for incubation times ≥10 minutes, suggesting rapid equilibrium and binding of BVD-523 with ERK2 (FIG. 29D). BVD-523 is also a tight-binding inhibitor of recombinant ERK1 (Rudolph et al. 2015), exhibiting a $K_i$ of <0.3 nM.

Figure 29A:
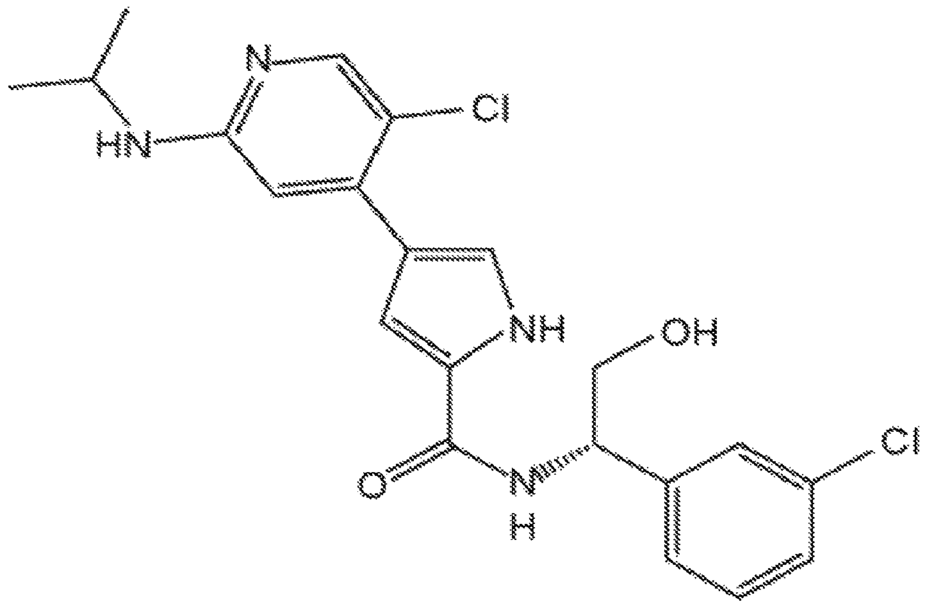
FIG. 29A-FIG. 29F show discovery and characterization of the novel ERK1/2 inhibitor BVD-523 (ulixertinib).
Figure 29B:
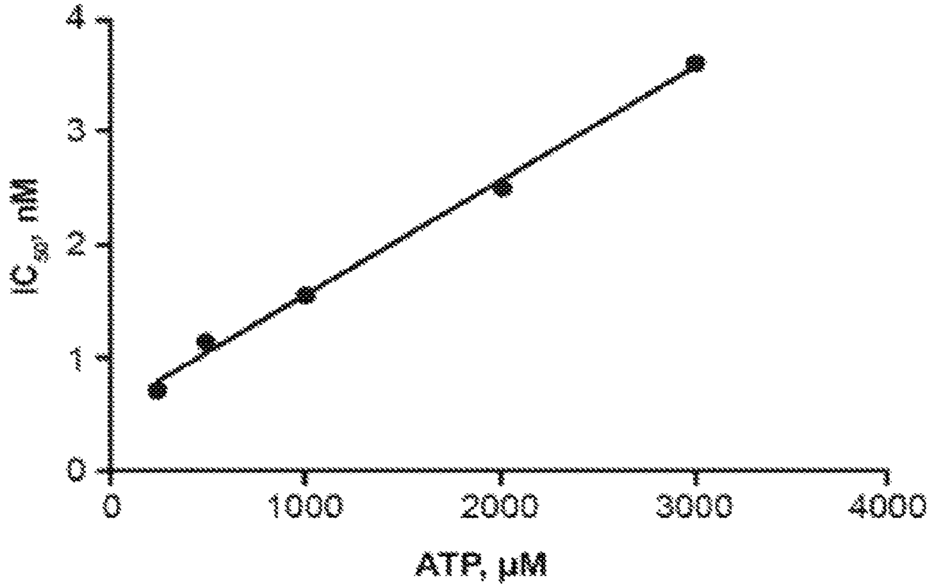
Figure 29C:
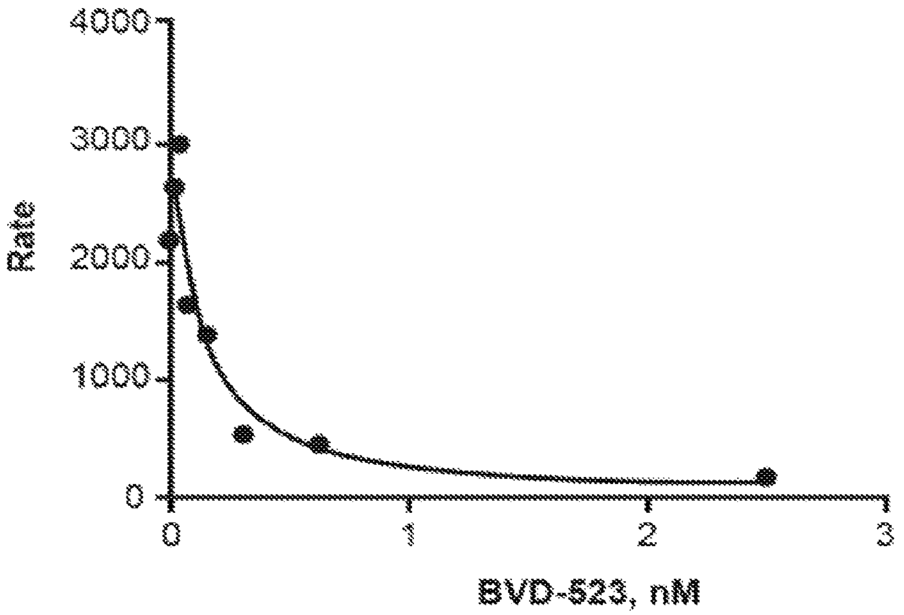
Figure 29D:
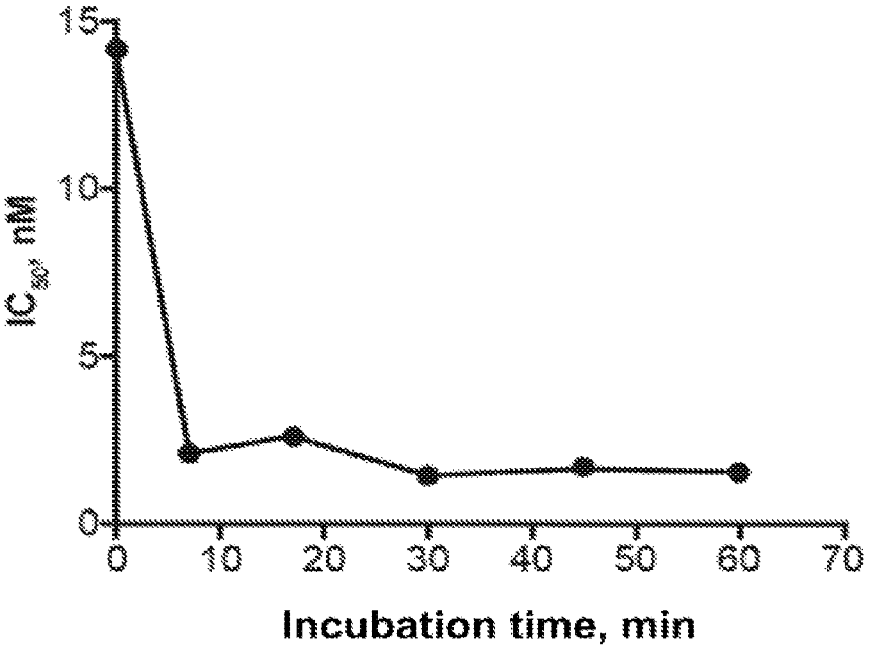
Figure 29E:
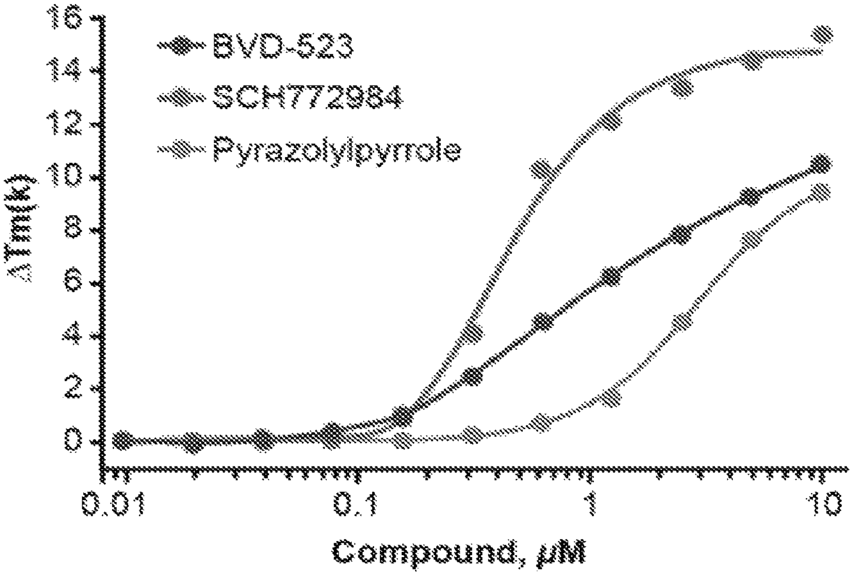
Figure 29F:
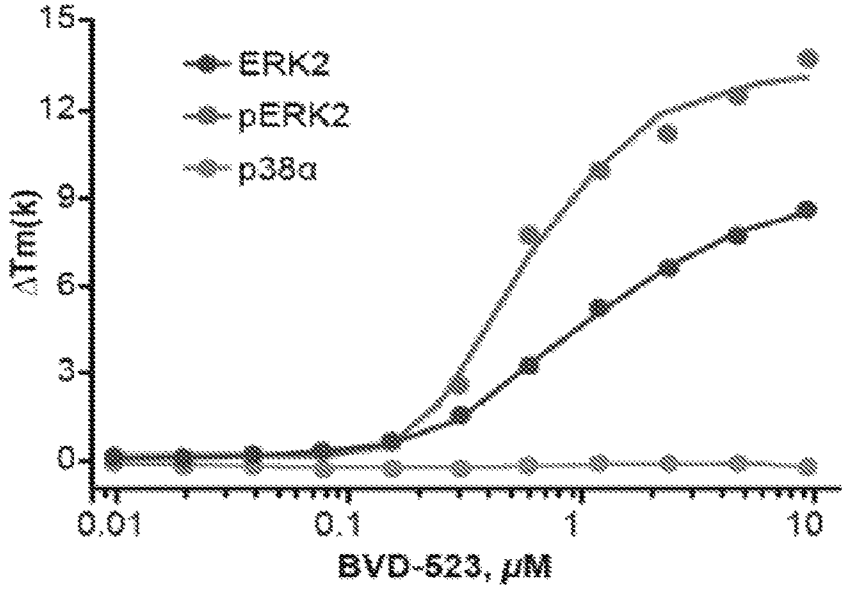

Binding of BVD-523 to ERK2 was demonstrated using calorimetric studies and compared to data generated using the ERK inhibitors SCH772984 and pyrazolylpyrrole (Arovov et al. 2007). All compounds bound and stabilized inactive ERK2 with increasing concentration, as indicated by positive ATm values (FIG. 29E). The 10- to 15-degree change in ΔTm observed with BVD-523 and SCH-772984 is consistent with compounds that have low-nanomolar binding affinities (Fedorov et al. 2012). BVD-523 demonstrated a strong binding affinity to both phosphorylated active ERK2 (pERK2) and inactive ERK2 (FIG. 29F). A stronger affinity to pERK2 compared with inactive ERK2 was observed. BVD-523 did not interact with the negative control protein p38α MAP kinase (FIG. 29F).

BVD-523 demonstrated excellent ERK1/2 kinase selectivity based on biochemical counter-screens against 75 kinases in addition to ERK1 and ERK2. The ATP concentrations were approximately equal to the $K_m$ in all assays. Kinases inhibited to greater than 50% by 2 μM BVD-523 were retested to generate $K_i$ values (or apparent Ki; Table 21). Twelve of the 14 kinases had a $K_i$ of <1 μM. The selectivity of BVD-523 for ERK2 was >7000-fold for all kinases tested except ERK1, which was inhibited with a Ki of <0.3 nM (10-fold). Therefore, BVD-523 is a highly potent and selective inhibitor of ERK1/2.

TABLE 21

BVD-523 displays selectivity for ERK1 and ERK2 kinases.

| Kinase | Ki (μM) |
|---|---|
| CDK1/cyclinB | 0.07[a] |
| CDK2/cyclinA | 0.36 |
| CDK5/p35 | 0.09[a] |
| CDK6/cycinD3 | 0.09 |
| ERK1 | 0.0003 |
| ERK2 | 0.00004 |
| GSK3b | 0.32 |
| JNK2α | 0.65[a] |
| JNIK3 | 1.3 |
| P38γ | 0.45[a] |
| P38δ | 0.24 |
| ROCKI | 11.1 |
| ROCKII | 0.27[a] |
| RSK3 | 0.45 |

[a]Apparent.

<50% inhibition at 2μM: ABL, AKT3, AMPK, AUR1, AUR2, AXL, BLX, CAMKII, CAMKIV, CHK1, CHK2, CK1, CK2, CSK, EGFR, EPHB4, FES, FGFR3, FLT3, FYN, IGF1R, IKKα, 1KKβ, IKKi, IRAK4, IRTK, 1TK, JAK3, JNKlα 1, KDR, LCK, LYN, cMET, MKK4, MKK6, MKK7β, MLK2, MSK1, MST2, NAK, NEK2, p38α, p38β, p70S6K, PAK2, PDGFRα, PDKI, PKA, PKQα, pKCβ II, PKCγ, PKCi, PKCθ, PRAK, PRK2, cRAF, SGK, SRC, SYK, TAM, TiE2, ZAP70

Example 11

BVD-523 Preferentially Inhibits Cellular Proliferation and Enhances Caspase-3/7 Activity In Vitro in Cancer Cell Lines with MAPK Pathway-Activating Mutations BVD-523 cellular activity was assessed in a panel of approximately 1,000 cancer cell lines of various lineages and genetic backgrounds (FIG. 30A and Table 22). Cell lines were classified as MAPK wild type (wt) or mutant depending on the absence or presence of mutations in RAS family members and BRAF. Although some MAPK-wt cell lines were sensitive to BVD-523, generally BVD-523 inhibited proliferation preferentially in cells with MAPK pathway alterations.

Figure 30B:
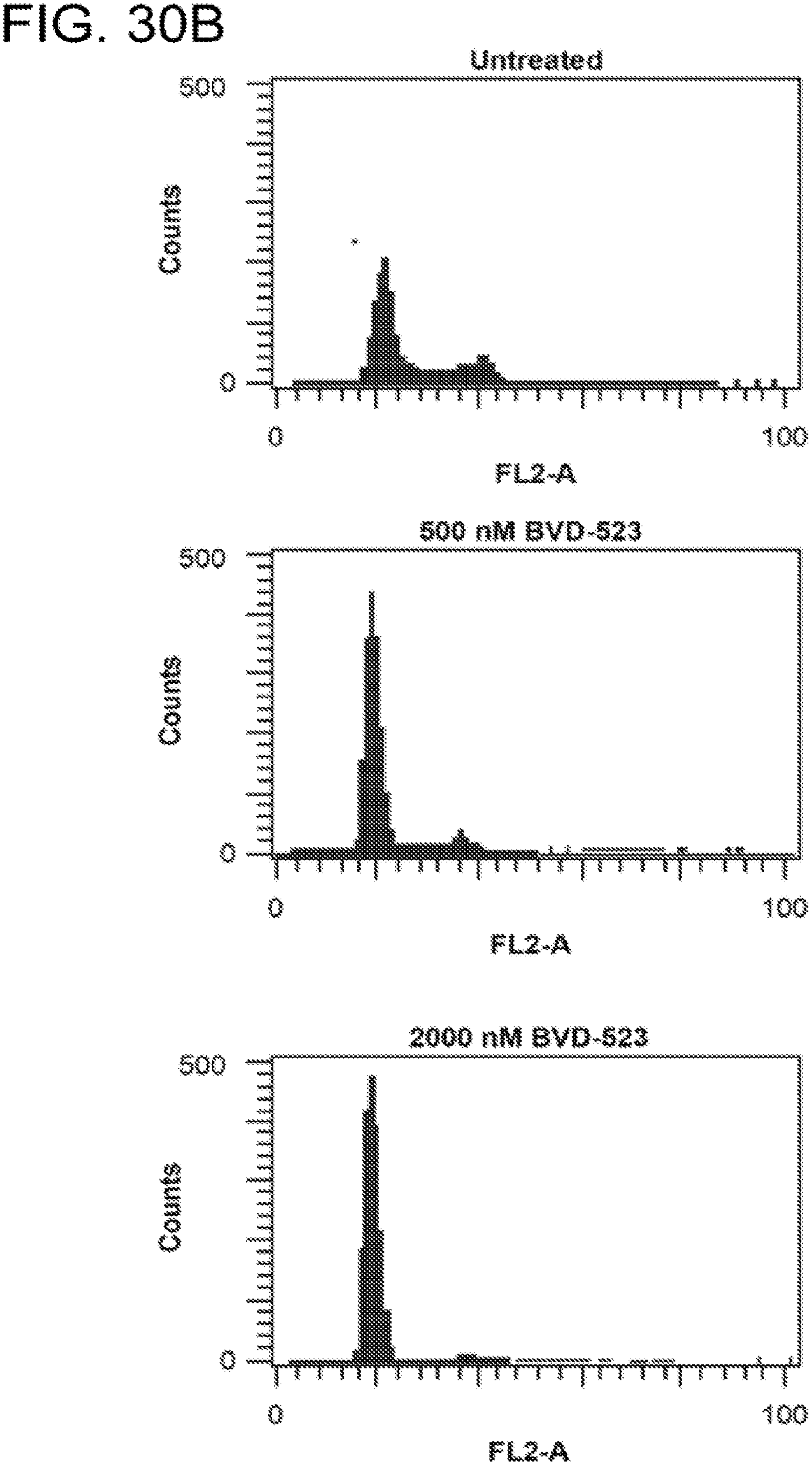

Next, the growth and survival impact of BVD-523 treatment on sensitive cells was characterized. Fluorescence activated cell sorting (FACS) analysis was performed on $BRAF^{V600E}$-mutant melanoma cell line UACC-62 following treatment with BVD-523 at 500 nM or 2000 nM for 24 hours. Treated cells were arrested in the G1 phase of the cell cycle in a concentration-dependent manner (FIG. 30B).

Figure 30C:
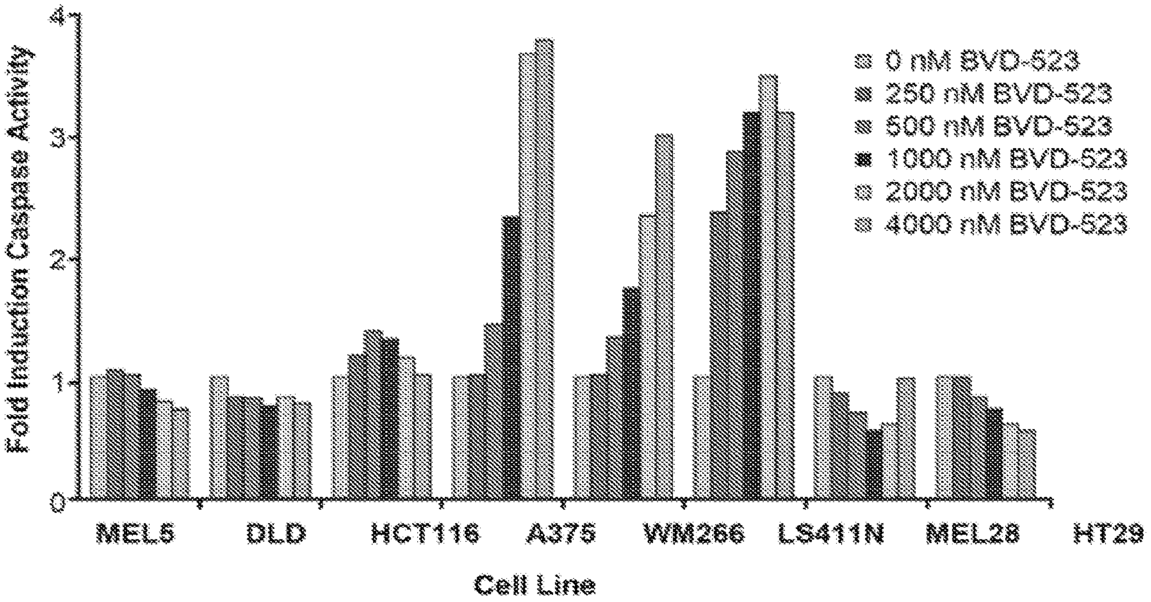

In addition, caspase-3/7 activity was analyzed as a measure of apoptosis in multiple human cancer cell lines. A concentration- and cell-line-dependent increase in caspase 3/7 was observed following treatment with BVD-523 for 72 hours (FIG. 30C). BVD-523 treatment resulted in pronounced caspase-3/7 induction in a subset of MAPK-activated cell lines harboring a $BRAF^{V600}$ mutation (A375, WM266, and LS411N). This is consistent with earlier observations for preferential inhibition of proliferation by BVD-523 in MAPK pathway-mutant cancer cell lines (FIG. 30A).

Figure 30D:
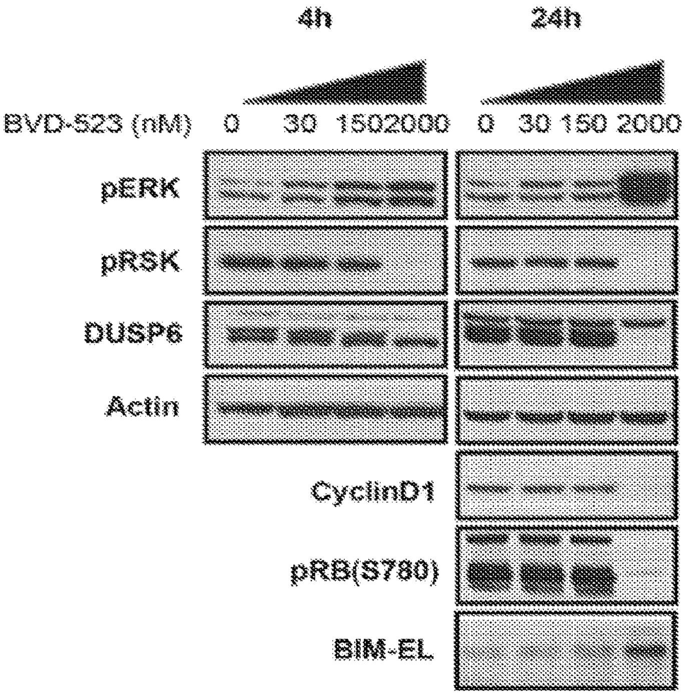

To further characterize the mechanism of action and effects on signaling elicited by BVD-523, the levels of various effector and MAPK-related proteins were assessed in BVD-523-treated $BRAF^{V600E}$-mutant A375 melanoma cells (FIG. 30D). Phospho-ERK1/2 levels increased in a concentration-dependent manner after 4 and 24 hours of BVD-523 treatment. Despite prominent concentration-dependent increases in pERK1/2 observed with 2 μM BVD-523 treatment, phosphorylation of the ERK1/2 target RSK1/2 was reduced at both 4 and 24 hours, which is consistent with sustained inhibition. Total protein levels of DUSP6, a distal marker of ERK1/2 activity, were also attenuated at 4 and 24 hours. Following 24 hours of treatment with BVD-523, the apoptotic marker BIM-EL increased in a dose-dependent manner, while cyclin D-1 and pRB was attenuated at 2 μM. All effects are consistent with on-target ERK1/2 inhibition.

TABLE_22

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_8049_00277140 | Biliary Tract | 8049 | ETK-1 | 456 | 3.525905 | 0.587 | 0.805 | 0.874 | 0.9304 | 0.8796 | 0.954 | 1.0285 | 1.094 | 0.9918 |
| 026_664_00277150 | Biliary Tract | 664 | HuCCT1 | 456 | 3.600435 | 0.663 | 0.734 | 0.847 | 0.9661 | 0.9652 | 1.029 | 0.9656 | 1.0172 | 0.9981 |
| 026_653_00278500 | Biliary Tract | 653 | EGI-1 | 456 | 4.229085 | 0.693 | 0.686 | 0.74 | 0.7843 | 0.8546 | 0.889 | 0.967 | 0.9286 | 0.9525 |
| 026_8204_00278540 | Biliary Tract | 8204 | TGBC24TKB | 456 | 5.609877 | 0.768 | 0.875 | 0.826 | 0.8122 | 0.8629 | 0.862 | 0.8909 | 0.9353 | 0.9353 |
| 026_8188_00293390 | Biliary Tract | 8188 | TGBCITKB | 456 | 6.179372 | 0.926 | 0.9299 | 0.913 | 0.9808 | 0.9201 | 1.144 | 1.0128 | 0.9048 | 0.9496 |
| 026_330_00278580 | Bone | 330 | H-EMC-SS | 456 | 0.038629 | 0.36 | 0.392 | 0.383 | 0.4615 | 0.437 | 0.566 | 0.7772 | 0.9442 | 0.9662 |
| 026_8047_00283120 | Bone | 8047 | ES7 | 456 | 1.846677 | 0.515 | 0.521 | 0.539 | 0.5362 | 0.7569 | 0.769 | 0.8353 | 0.9371 | 0.9503 |
| 026_8053_00287650 | Bone | 8053 | EW-13 | 456 | 2.197657 | 0.333 | 0.545 | 0.665 | 0.8165 | 0.9099 | 0.962 | 0.9571 | 0.9945 | 1.0406 |
| 026_8227_00288230 | Bone | 8227 | CADO-ES1 | 456 | 2.29467 | 0.359 | 0.554 | 0.585 | 1.0389 | 0.9034 | 0.952 | 1.1264 | 1.2671 | 1.0023 |
| 026_8050_00279380 | Bone | 8050 | EW-1 | 456 | 2.409222 | 0.487 | 0.555 | 0.593 | 0.6879 | 0.6908 | 0.788 | 0.8057 | 0.892 | 0.9331 |
| 026_306_00278530 | Bone | 306 | SK-ES-1 | 456 | 2.4607 | 0.527 | 0.556 | 0.577 | 0.682 | 0.673 | 0.855 | 0.8706 | 0.8641 | 0.8867 |
| 026_305_00277180 | Bone | 305 | U-2 OS | 456 | 2.847932 | 0.145 | 0.599 | 0.657 | 0.7441 | 0.8231 | 0.793 | 0.8449 | 0.9969 | 0.8925 |
| 026_337_00283440 | Bone | 337 | HuO9 | 456 | 2.916396 | 0.448 | 0.696 | 0.939 | 0.8026 | 0.8478 | 0.903 | 0.9796 | 0.8682 | 1.0954 |
| 26_8227_00304340 | Bone | 8227 | CADO-ES1 | 456 | 2.975471 | 0.542 | 0.666 | 0.884 | 0.8971 | 0.9918 | 0.974 | 1.0247 | 1.0031 | 1.0728 |
| 026_8043_00283110 | Bone | 8043 | ES1 | 456 | 2.981717 | 0.543 | 0.663 | 0.705 | 0.7865 | 0.811 | 0.835 | 0.7995 | 0.9278 | 0.8292 |
| 026_8142_00282550 | Bone | 8142 | NOS-1 | 456 | 3.203574 | 0.547 | 0.775 | 0.825 | 0.892 | 0.7556 | 0.894 | 0.8477 | 1.1038 | 0.9881 |
| 026_8055_00290580 | Bone | 8055 | EW-18 | 456 | 3.311765 | 0.638 | 0.688 | 0.718 | 1.1012 | 0.9293 | 0.993 | 1.0646 | 1.1078 | 1.0895 |
| 026_8058_00293350 | Bone | 8058 | EW-3 | 456 | 3.365484 | 0.715 | 0.595 | 0.72 | 0.7195 | 0.8774 | 0.8 | 0.8628 | 0.9101 | 1.2148 |
| 026_339_00277160 | Bone | 339 | NY | 456 | 3.400937 | 0.59 | 0.789 | 0.875 | 0.9222 | 0.9594 | 0.975 | 0.933 | 1.1433 | 0.9637 |
| 026_8165_00287690 | Bone | 8165 | SK-PN-DW | 456 | 3.476926 | 0.621 | 0.812 | 0.933 | 0.9706 | 0.9188 | 0.991 | 1.0026 | 1.0012 | 1.0432 |
| 026_326_00282540 | Bone | 326 | MHH-ES-1 | 456 | 3.524605 | 0.618 | 0.719 | 0.824 | 0.8235 | 0.8745 | 0.966 | 1.1187 | 1.0416 | 0.913 |
| 026_8048_00279370 | Bone | 8048 | ES8 | 456 | 3.530755 | 0.572 | 0.698 | 0.765 | 0.8053 | 0.8255 | 0.912 | 0.931 | 0.9069 | 0.9095 |
| 026_331_00278590 | Bone | 331 | HOS | 456 | 3.602447 | 0.53 | 0.798 | 0.748 | 0.7609 | 0.8727 | 0.839 | 0.8786 | 0.8236 | 0.972 |
| 026_8045_00282660 | Bone | 8045 | ES5 | 456 | 3.665641 | 0.704 | 0.653 | 0.874 | 0.8827 | 0.7407 | 0.913 | 0.8294 | 1.0585 | 1.162 |
| 026_8059_00283090 | Bone | 8059 | EW-7 | 456 | 3.82717 | 0.662 | 0.72 | 0.76 | 0.831 | 0.8857 | 0.95 | 0.9309 | 0.9266 | 0.9963 |
| 026_8201_00282520 | Bone | 8201 | ES3 | 456 | 3.982944 | 0.707 | 0.721 | 0.778 | 0.8414 | 0.8385 | 0.989 | 0.9588 | 1.024 | 1.0261 |
| 026_8056_00314310 | Bone | 8056 | EW-22 | 456 | 4.196343 | 0.701 | 0.827 | 0.819 | 0.8824 | 0.9413 | 0.894 | 0.9848 | 1.0221 | 1.1139 |
| 026_329_00282700 | Bone | 329 | G-292 Clone A141B1 | 456 | 4.264519 | 0.705 | 0.918 | 0.893 | 0.949 | 1.0435 | 1.016 | 0.9814 | 0.9215 | 1.1209 |
| 026_324_00278550 | Bone | 324 | CAL-72 | 456 | 4.286956 | 0.731 | 0.942 | 0.942 | 0.9262 | 0.9863 | 0.966 | 0.9797 | 0.9547 | 1.0113 |
| 026_304_00283460 | Bone | 304 | Saos-2 | 456 | 4.597501 | 0.742 | 0.784 | 0.9 | 0.8765 | 0.9306 | 0.926 | 0.9516 | 0.95 | 1.0352 |
| 026_325_00283060 | Bone | 325 | CAL-78 | 456 | 4.650689 | 0.727 | 0.913 | 0.918 | 0.9149 | 0.8999 | 0.897 | 0.9095 | 1.0242 | 1.0181 |
| 026_1138_00278560 | Bone | 1138 | CS1 | 456 | 4.765346 | 0.744 | 0.848 | 0.864 | 0.8601 | 0.8818 | 1.016 | 1.0005 | 0.9749 | 0.977 |
| 026_8162_00282560 | Bone | 8162 | SJSA-1 | 456 | 4.867747 | 0.802 | 0.803 | 0.805 | 0.7765 | 0.762 | 0.974 | 1.0651 | 1.0412 | 1.0623 |
| 026_336_00283430 | Bone | 336 | HuO-3N1 | 456 | 4.900372 | 0.724 | 0.86 | 0.806 | 0.8427 | 0.8308 | 0.87 | 0.8972 | 0.9772 | 1.0073 |
| 026_328_00278600 | Bone | 328 | TC-71 | 456 | 5.117725 | 0.844 | 0.939 | 0.97 | 1.0221 | 0.9857 | 1.072 | 1.023 | 1.0842 | 1.0771 |
| 026_8054_00282530 | Bone | 8054 | EW-16 | 456 | 5.180986 | 0.835 | 0.775 | 0.925 | 0.8021 | 0.8155 | 0.934 | 0.9339 | 1.058 | 1.1414 |
| 026_335_00308220 | Bone | 3355 | MG-63 | 456 | 5.257203 | 0.884 | 0.841 | 0.852 | 0.8745 | 1.0185 | 1.081 | 1.1007 | 1.0326 | 1.0709 |
| 026_1241_00283070 | Bone | 1241 | CHSA8926 | 456 | 5.394244 | 0.883 | 0.851 | 0.947 | 0.9788 | 0.9327 | 1.019 | 1.0879 | 1.0294 | 1.119 |
| 026_8044_00279340 | Bone | 8044 | ES4 | 456 | 6.158016 | 0.822 | 0.876 | 0.92 | 0.8612 | 0.8592 | 0.873 | 0.8969 | 0.9914 | 0.9632 |
| 026_8057_00283080 | Bone | 8057 | EW-24 | 456 | 6.273162 | 0.927 | 0.899 | 0.97 | 0.9817 | 0.9704 | 1.012 | 0.9822 | 0.9596 | 0.9793 |
| 026_8051_00285230 | Bone | 8051 | EW-11 | 456 | 6.340509 | 0.924 | 1.008 | 0.846 | 0.9309 | 1.047 | 0.868 | 0.9762 | 1.0834 | 1.048 |
| 026_8046_00279351 | Bone | 8046 | ES6 | 456 | 6.745328 | 0.882 | 1.065 | 1.046 | 1.0203 | 1.0617 | 0.85 | 0.8881 | 1.0547 | 0.9578 |
| 026_8146_00285140 | Brain | 8146 | ONS-76 | 456 | 1.017095 | 0.362 | 0.369 | 0.387 | 0.52 | 0.6146 | 0.733 | 0.8773 | 0.9176 | 1.1016 |
| 026_8009_00285111 | Brain | 8009 | AM-38 | 456 | 2.859683 | 0.545 | 0.617 | 0.664 | 0.5881 | 0.5592 | 0.692 | 0.826 | 0.9522 | 1.078 |
| 026_8091_00285281 | Brain | 8091 | KS-1 | 456 | 2.979142 | 0.617 | 0.59 | 0.62 | 0.7057 | 0.7844 | 0.875 | 0.9025 | 1.0584 | 1.1343 |
| 026_388_00285240 | Brain | 388 | MOG-G-CCM | 456 | 3.029922 | 0.505 | 0.754 | 0.852 | 0.977 | 0.9597 | 0.989 | 1.1211 | 1.0361 | 1.0747 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_352_00283150 | Brain | 352 | LN-229 | 456 | 3.053877 | 0.552 | 0.647 | 0.662 | 0.7206 | 0.8119 | 0.932 | 0.9285 | 1.0381 | 1.0748 |
| 026_8214_00290680 | Brain | 8214 | YH-13 | 456 | 3.068585 | 0.558 | 0.628 | 0.773 | 1.0443 | 0.9614 | 1.113 | 1.1139 | 1.093 | 1.2619 |
| 026_8214_00288290 | Brain | 8214 | YH-13 | 456 | 3.531592 | 0.627 | 0.651 | 0.866 | 0.8387 | 0.8073 | 0.922 | 1.077 | 1.0619 | 1.1182 |
| 026_358_00293700 | Brain | 358 | D283 Med | 456 | 3.551231 | 0.64 | 0.743 | 0.916 | 0.9078 | 0.9464 | 0.928 | 0.871 | 0.9767 | 1.4204 |
| 026_8061_00290830 | Brain | 8061 | GB-1 | 456 | 3.686496 | 0.613 | 0.692 | 0.809 | 0.8255 | 0.8977 | 0.877 | 0.9922 | 0.9416 | 0.8923 |
| 026_374_00283180 | Brain | 374 | U-251MG | 456 | 3.933399 | 0.654 | 0.733 | 0.861 | 0.881 | 0.8991 | 0.822 | 0.926 | 0.9972 | 1.134 |
| 026_343_00283160 | Brain | 343 | PFSK-1 | 456 | 3.963833 | 0.626 | 0.904 | 1.007 | 129.02 | 0.934 | 1.078 | 1.0411 | 1.0084 | 1.052 |
| 026_393_00283190 | Brain | 393 | YKG-1 | 456 | 3.987729 | 0.646 | 0.714 | 0.77 | 0.8178 | 0.8374 | 0.848 | 0.953 | 0.8805 | 1.0209 |
| 026_8028_00287630 | Brain | 8028 | D-263MG | 456 | 4.157483 | 0.662 | 0.709 | 0.734 | 0.7813 | 0.8341 | 0.839 | 0.9023 | 0.9333 | 1.0435 |
| 026_379_00283140 | Brain | 379 | GAMG | 456 | 4.214093 | 0.681 | 0.701 | 0.829 | 0.8043 | 0.8412 | 0.83 | 0.9322 | 0.8908 | 1.046 |
| 026_8019_00293320 | Brain | 8019 | CAS-1 | 456 | 4.309856 | 0.732 | 0.772 | 0.825 | 0.9222 | 0.9783 | 1.227 | 0.8865 | 0.8407 | 1.162 |
| 026_8001_00285100 | Brain | 8001 | 8-MG-BA | 456 | 4.345495 | 0.688 | 0.845 | 0.88 | 0.8958 | 0.9285 | 0.912 | 0.9148 | 0.9398 | 1.07 |
| 026_351_00283450 | Brain | 351 | LN-18 | 456 | 4.481815 | 0.685 | 0.822 | 0.862 | 0.8746 | 0.8966 | 0.902 | 0.9022 | 0.9311 | 0.932 |
| 026_357_00283410 | Brain | 357 | H4 | 456 | 4.481909 | 0.721 | 0.808 | 0.876 | 0.858 | 0.8822 | 0.94 | 1.0232 | 0.9287 | 1.061 |
| 026_8085_00293731 | Brain | 8085 | KINGS-1 | 456 | 4.48888 | 0.797 | 0.781 | 0.82 | 0.9645 | 0.9641 | 1.015 | 0.9981 | 1.0442 | 0.974 |
| 026_350_00284910 | Brain | 350 | M059J | 456 | 4.537622 | 0.723 | 0.834 | 0.869 | 0.8888 | 0.9473 | 0.909 | 0.9144 | 1.0191 | 1.081 |
| 026_8015_00308070 | Brain | 8015 | Becker | 456 | 4.548091 | 0.696 | 0.814 | 0.876 | 0.8121 | 0.825 | 0.889 | 0.917 | 0.9113 | 1.013 |
| 026_8160_00287680 | Brain | 8160 | SF539 | 456 | 4.738405 | 0.726 | 0.919 | 0.827 | 0.8875 | 0.9392 | 0.934 | 0.952 | 1.0525 | 0.928 |
| 026_8159_00287670 | Brain | 8159 | SF268 | 456 | 4.804304 | 0.786 | 0.825 | 0.923 | 0.9225 | 0.9772 | 0.99 | 0.978 | 0.9754 | 0.969 |
| 026_359_00283100 | Brain | 359 | Daoy | 456 | 4.81575 | 0.683 | 0.74 | 0.796 | 0.8102 | 0.876 | 0.896 | 0.9135 | 0.9254 | 0.925 |
| 026_8217_00290890 | Brain | 8217 | SK-MG-1 | 456 | 4.83361 | 0.725 | 0.784 | 0.83 | 0.844 | 0.8849 | 0.901 | 0.9119 | 0.9353 | 0.985 |
| 026_342_00285160 | Brain | 342 | SW 1783 | 456 | 4.84471 | 0.796 | 0.905 | 0.896 | 0.9349 | 1.0662 | 0.935 | 1.0347 | 1.0148 | 1.08 |
| 026_8029_00288240 | Brain | 8029 | D-336MG | 456 | 4.925588 | 0.792 | 0.892 | 0.997 | 0.8872 | 0.9556 | 0.944 | 1.105 | 1.0724 | 1.105 |
| 026_8030_00295500 | Brain | 8030 | D-392MG | 456 | 4.966575 | 0.791 | 0.866 | 0.824 | 0.9331 | 0.8638 | 1.022 | 0.9531 | 0.9688 | 1.053 |
| 026_8089_00287440 | Brain | 8089 | KNS-81-FD | 456 | 5.077406 | 0.804 | 0.89 | 0.869 | 0.8138 | 0.8421 | 1.049 | 1.0747 | 0.9317 | 1.122 |
| 026_8138_00285290 | Brain | 8138 | NMC-G1 | 456 | 5.086457 | 0.771 | 0.817 | 0.763 | 0.762 | 0.8138 | 0.887 | 0.968 | 1.0104 | 1.049 |
| 026_8139_00285130 | Brain | 8139 | no-10 | 456 | 5.147267 | 0.824 | 0.888 | 0.928 | 0.9069 | 0.9436 | 1.031 | 0.943 | 1.05 | 1.054 |
| 026_8083_00293720 | Brain | 8083 | KALS-1 | 456 | 5.203248 | 0.817 | 0.765 | 0.902 | 0.9843 | 0.9376 | 0.915 | 0.9382 | 1.0116 | 0.949 |
| 026_378_00284880 | Brain | 378 | DK-MG | 456 | 5.2953 | 0.789 | 0.757 | 0.713 | 0.7179 | 0.7297 | 0.849 | 0.8425 | 0.9101 | 1.011 |
| 026_383_00284900 | Brain | 383 | LN-405 | 456 | 5.313289 | 0.839 | 0.886 | 0.901 | 0.937 | 0.8868 | 1.041 | 0.949 | 1.0816 | 1.098 |
| 026_8032_00293340 | Brain | 8032 | D-542MG | 456 | 5.342096 | 0.822 | 0.856 | 0.927 | 0.9108 | 0.8977 | 0.934 | 0.9191 | 0.9743 | 0.989 |
| 026_344_00282720 | Brain | 344 | LNZTA3WT4 | 456 | 5.43481 | 0.777 | 1.136 | 0.931 | 0.9386 | 0.9371 | 1.018 | 1.0441 | 1.0001 | 0.994 |
| 026_8167_00290910 | Brain | 8167 | SNB75 | 456 | 5.474524 | 0.76 | 0.772 | 0.83 | 0.8023 | 0.8147 | 1.01 | 0.8801 | 1.0523 | 0.938 |
| 026_8087_00285270 | Brain | 8087 | KNS-42 | 456 | 5.484622 | 0.862 | 0.858 | 0.846 | 0.8777 | 0.9301 | 0.972 | 0.9923 | 1.0701 | 1.013 |
| 026_354_00287481 | Brain | 354 | U-87MG | 456 | 5.588679 | 0.851 | 0.949 | 0.942 | 0.9605 | 0.9939 | 1.004 | 1.0222 | 0.9964 | 1.085 |
| 026_8140_00285300 | Brain | 8140 | no-11 | 456 | 5.608459 | 0.844 | 0.885 | 0.896 | 0.959 | 0.9411 | 0.893 | 0.9627 | 1.0352 | 0.943 |
| 026_8221_00284860 | Brain | 8221 | D-423MG | 456 | 5.731372 | 0.807 | 0.783 | 0.798 | 0.8469 | 0.8833 | 0.945 | 0.9877 | 0.9131 | 0.921 |
| 026_348_00283400 | Brain | 348 | DBTRG-05MG | 456 | 5.749405 | 0.792 | 0.75 | 0.763 | 0.7919 | 0.7917 | 0.856 | 0.9393 | 0.9013 | 0.992 |
| 026_341_00285310 | Brain | 341 | SW 1088 | 456 | 5.805148 | 0.869 | 0.907 | 0.895 | 0.8893 | 0.9105 | 0.919 | 0.966 | 0.8961 | 1.095 |
| 026_356_00283420 | Brain | 356 | Hs 683 | 456 | 5.858982 | 0.841 | 0.993 | 0.888 | 0.8789 | 0.8908 | 1.04 | 0.8743 | 0.906 | 1.058 |
| 026_8031_00287640 | Brain | 8031 | D-502MG | 456 | 5.99897 | 0.825 | 0.819 | 0.771 | 0.7649 | 0.8658 | 0.834 | 0.9457 | 0.9922 | 0.9572 |
| 026_8224_00284870 | Brain | 8224 | D-566MG | 456 | 6.026403 | 0.839 | 0.84 | 0.858 | 0.8841 | 0.9252 | 0.941 | 0.968 | 0.9815 | 0.9816 |
| 026_389_00284920 | Brain | 389 | MOG-G-UVW | 456 | 6.074777 | 0.861 | 0.876 | 0.879 | 0.9129 | 0.9004 | 0.902 | 1.0597 | 0.9108 | 1.0304 |
| 026_341_00283470 | Brain | 341 | SW 1088 | 456 | 6.105387 | 0.913 | 0.89 | 0.897 | 0.897 | 0.9463 | 0.931 | 0.9486 | 0.9506 | 1.1024 |
| 026_375_00284850 | Brain | 375 | 42-MG-BA | 456 | 6.106423 | 0.896 | 0.892 | 0.932 | 0.944 | 0.9633 | 0.976 | 0.9735 | 0.9871 | 1.0285 |
| 026_1122_00283170 | Brain | 1122 | SF-295 | 456 | 6.112956 | 0.879 | 0.909 | 0.909 | 0.9301 | 0.9215 | 0.946 | 0.9199 | 0.9433 | 1.0329 |
| 026_8158_00290650 | Brain | 8158 | SF126 | 456 | 6.158755 | 0.86 | 0.97 | 1 | 1.0676 | 1.0025 | 1.187 | 0.9851 | 0.9627 | 1.1324 |
| 026_340_00285250 | Brain | 340 | CCF-STTG1 | 456 | 6.170298 | 0.851 | 0.911 | 0.916 | 0.9011 | 0.9748 | 0.919 | 0.9109 | 0.9323 | 0.9837 |
| 026_380_00284890 | Brain | 380 | GMS-10 | 456 | 6.23472 | 0.842 | 0.885 | 0.853 | 0.8466 | 0.8914 | 0.914 | 0.8882 | 1.0019 | 1.0545 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_354_00290361 | Brain | 354 | U-87 MG | 456 | 6.315816 | 0.93 | 0.874 | 0.977 | 0.9346 | 0.9336 | 1.084 | 0.9295 | 1.062 | 1.073 |
| 026_8063_00290841 | Brain | 8063 | GI-1 | 456 | 6.443002 | 0.809 | 0.877 | 0.913 | 0.9018 | 0.9184 | 0.86 | 0.9241 | 0.9072 | 0.9709 |
| 026_8027_00293330 | Brain | 8027 | D-247MG | 456 | 6.453915 | 0.928 | 0.905 | 0.908 | 0.8398 | 0.8592 | 0.911 | 0.9463 | 0.9529 | 0.9044 |
| 026_346_00283390 | Brain | 346 | A172 | 456 | 6.640511 | 0.941 | 0.953 | 0.995 | 1.0208 | 0.9242 | 1.026 | 1.0141 | 1.0236 | 1.0356 |
| 026_8089_00291170 | Brain | 8089 | KNS-81-FD | 456 | 7.067458 | 0.854 | 0.823 | 0.854 | 0.8437 | 0.8524 | 0.889 | 0.8917 | 0.9075 | 0.9111 |
| 026_355_00285180 | Brain | 355 | U-118MG | 456 | 7.408088 | 0.965 | 1.005 | 0.945 | 0.9352 | 0.9307 | 0.932 | 0.9407 | 0.945 | 0.9851 |
| 026_347_00282740 | Brain | 347 | T98G | 456 | 7.802123 | 0.986 | 1.098 | 0.951 | 1.0602 | 0.9957 | 1.038 | 1.0462 | 0.9753 | 0.982 |
| 026_417_00271110 | Breast | 417 | DU4475 | 456 | −3.0044 | 0.119 | 0.118 | 0.124 | 0.1202 | 0.1235 | 0.121 | 0.164 | 0.4789 | 0.6922 |
| 26_465_00271670 | Breast | 465 | MRK-nu-1 | 456 | 1.744742 | 0.115 | 0.398 | 0.572 | 0.6893 | 0.7807 | 0.868 | 0.921 | 0.9463 | 1.1175 |
| 026_438_00273540 | Breast | 438 | HCC1599 | 456 | 1.968855 | 0.352 | 0.459 | 0.617 | 0.7517 | 0.8021 | 0.899 | 0.9102 | 0.9757 | 1.0216 |
| 026_435_00271290 | Breast | 435 | HCC1187 | 456 | 2.132259 | 0.375 | 0.482 | 0.801 | 0.7466 | 0.7917 | 0.794 | 0.9164 | 0.9352 | 0.9707 |
| 026_403_00271400 | Breast | 403 | MCF7 | 456 | 2.857648 | 0.493 | 0.634 | 0.765 | 0.8761 | 0.9706 | 0.973 | 1.0249 | 1.0247 | 1.0456 |
| 026_401_00273450 | Breast | 401 | MDA-MB-468 | 456 | 3.05753 | 0.415 | 0.718 | 0.931 | 0.9526 | 0.909 | 0.954 | 0.9512 | 1.0282 | 0.9601 |
| 26_451_00271640 | Breast | 451 | CAL-85-1 | 456 | 3.06898 | 0.489 | 0.695 | 0.808 | 0.7646 | 0.8147 | 0.885 | 0.8459 | 1.0885 | 0.9906 |
| 026_404_00273430 | Breast | 404 | MDA-MB-231 | 456 | 3.086092 | 0.483 | 0.731 | 0.783 | 0.824 | 0.8358 | 0.874 | 0.9446 | 0.9609 | 1.0599 |
| 026_418_00271550 | Breast | 418 | Hs 578T | 456 | 3.125956 | 0.071 | 0.614 | 0.832 | 0.7916 | 0.8611 | 0.836 | 0.9569 | 0.9556 | 1.0186 |
| 026_402_00272120 | Breast | 402 | CAMA-1 | 456 | 3.166443 | 0.55 | 0.636 | 0.773 | 0.8152 | 0.9017 | 0.886 | 0.906 | 0.9417 | 0.9695 |
| 026_426_00274200 | Breast | 426 | HCC1569 | 456 | 3.228782 | 0.571 | 0.713 | 0.945 | 0.9056 | 0.9414 | 0.938 | 0.9814 | 1.028 | 1.0046 |
| 026_431_00271130 | Breast | 431 | HCC1806 | 456 | 3.337319 | 0.566 | 0.672 | 0.68 | 0.6852 | 0.6987 | 0.765 | 0.8378 | 1.0081 | 1.1468 |
| 026_414_00271900 | Breast | 414 | AU565 | 456 | 3.409308 | 0.533 | 0.816 | 0.949 | 0.9831 | 0.9841 | 0.924 | 0.9729 | 0.9876 | 1.1475 |
| 026_452_00272130 | Breast | 452 | COLO-824 | 456 | 3.645131 | 0.338 | 0.743 | 0.843 | 0.9519 | 0.9643 | 0.904 | 0.9021 | 1.0288 | 0.9665 |
| 026_416_00271360 | Breast | 416 | BT-549 | 456 | 3.723874 | 0.659 | 0.81 | 0.911 | 0.9492 | 0.9446 | 0.965 | 0.9707 | 0.9785 | 1.0314 |
| 026_8144_00274240 | Breast | 8144 | OCUB-M | 456 | 3.727884 | 0.44 | 0.801 | 0.89 | 0.9127 | 1.0139 | 1.046 | 0.9729 | 0.96 | 1.0167 |
| 026_432_00271960 | Breast | 432 | HCC70 | 456 | 3.73179 | 0.605 | 0.733 | 0.855 | 0.8647 | 0.8214 | 0.887 | 0.9582 | 0.9394 | 1.1987 |
| 026_457_00273420 | Breast | 457 | EVSA-T | 456 | 3.968951 | 0.686 | 0.879 | 0.927 | 0.9385 | 0.9505 | 0.975 | 0.9713 | 0.9606 | 1.0214 |
| 026_466_00274370 | Breast | 466 | YMB-1-E | 456 | 3.997753 | 0.654 | 0.836 | 0.87 | 0.9113 | 0.9082 | 0.908 | 0.9623 | 1.0457 | 0.9738 |
| 026_441_00285120 | Breast | 441 | HCC2157 | 456 | 3.997874 | 0.474 | 1.044 | 0.849 | 0.8244 | 0.6122 | 0.948 | 1.0739 | 0.6695 | 1.0405 |
| 026_443_00271990 | Breast | 443 | MDA-MB-330 | 456 | 4.004084 | 0.601 | 0.92 | 0.94 | 0.9085 | 0.9663 | 0.971 | 0.9817 | 0.9257 | 1.0607 |
| 026_436_00271300 | Breast | 436 | HCC1395 | 456 | 4.036641 | 0.703 | 0.897 | 0.946 | 0.9395 | 1.0136 | 1.033 | 1.0207 | 1.0407 | 1.1296 |
| 026_412_00277190 | Breast | 412 | UACC-893 | 456 | 4.234383 | 0.421 | 0.859 | 0.854 | 0.8448 | 0.9188 | 0.999 | 0.9512 | 1.0422 | 0.9971 |
| 026_450_00271390 | Breast | 450 | CAL-51 | 456 | 4.319545 | 0.678 | 0.725 | 0.783 | 0.8043 | 0.8395 | 0.899 | 0.9313 | 0.9642 | 1.0975 |
| 026_449_00271380 | Breast | 449 | CAL-148 | 456 | 4.389344 | 0.747 | 0.676 | 1.08 | 0.9571 | 0.7093 | 0.888 | 0.981 | 0.8213 | 1.2196 |
| 026_434_00271920 | Breast | 434 | HCC1143 | 456 | 4.464516 | 0.726 | 0.808 | 0.808 | 0.822 | 0.8993 | 0.923 | 0.919 | 0.949 | 1.1427 |
| 026_433_00276270 | Breast | 433 | HCC202 | 456 | 4.571252 | 0.686 | 0.9 | 0.944 | 0.8549 | 0.8115 | 0.943 | 0.972 | 0.9241 | 0.9618 |
| 026_422_00274230 | Breast | 422 | MDA-MB-175-VII | 456 | 4.594595 | 0.7 | 0.733 | 0.74 | 0.7666 | 0.8545 | 0.848 | 0.9155 | 0.9541 | 0.9487 |
| 026_461_00272170 | Breast | 461 | MFM-223 | 456 | 4.656681 | 0.787 | 0.875 | 0.908 | 0.9465 | 0.988 | 1.047 | 1.0015 | 1.1431 | 1.0159 |
| 026_427_00271330 | Breast | 427 | MDA-MB-453 | 456 | 4.669025 | 0.795 | 0.819 | 0.921 | 0.9998 | 0.9757 | 0.998 | 1.0349 | 1.0264 | 1.1651 |
| 026_448_00271370 | Breast | 448 | CAL-120 | 456 | 4.779687 | 0.744 | 0.746 | 0.796 | 0.8032 | 0.8728 | 0.85 | 0.9852 | 1.0071 | 1.0287 |
| 026_411_00271420 | Breast | 411 | UACC-812 | 456 | 5.072094 | 0.82 | 0.894 | 0.873 | 0.9564 | 0.9958 | 0.944 | 0.9931 | 1.0326 | 0.9659 |
| 026_442_00273480 | Breast | 442 | HCC2218 | 456 | 5.225292 | 0.614 | 0.923 | 0.963 | 1.0597 | 1.042 | 1.043 | 1.0714 | 1.0498 | 1.0318 |
| 026_398_00272150 | Breast | 398 | HCC1428 | 456 | 5.256241 | 0.85 | 0.899 | 1.013 | 0.8915 | 0.9851 | 0.983 | 0.9959 | 0.9937 | 1.0331 |
| 026_464_00308490 | Breast | 464 | T47D | 456 | 5.26439 | 0.825 | 0.853 | 0.869 | 0.8588 | 0.823 | 0.978 | 0.9397 | 0.9562 | 0.968 |
| 026_400_00273440 | Breast | 400 | MDA-MB-436 | 456 | 5.286367 | 0.725 | 0.844 | 0.848 | 0.8326 | 0.8721 | 0.851 | 0.8881 | 0.9805 | 0.933 |
| 026_437_00280161 | Breast | 437 | HCC1500 | 456 | 5.288806 | 0.796 | 0.982 | 0.913 | 0.8847 | 0.9397 | 1.088 | 0.8523 | 0.9109 | 0.9883 |
| 026_440_00271950 | Breast | 440 | HCC1954 | 456 | 5.303093 | 0.807 | 0.813 | 0.885 | 0.8155 | 0.8463 | 0.861 | 1.0199 | 1.0209 | 0.9481 |
| 026_413_00271930 | Breast | 413 | HCC1419 | 456 | 5.337084 | 0.839 | 0.926 | 0.932 | 0.9634 | 0.9633 | 0.941 | 0.9595 | 0.9516 | 1.1518 |
| 026_410_00272180 | Breast | 410 | ZR-75-30 | 456 | 5.373081 | 0.83 | 0.857 | 0.88 | 0.8529 | 0.9183 | 0.913 | 0.911 | 1.03 | 0.9685 |
| 026_439_00271940 | Breast | 439 | HCC1937 | 456 | 5.44243 | 0.841 | 0.952 | 0.975 | 1.0253 | 0.9632 | 0.953 | 1.0302 | 1.0262 | 1.0774 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_408_00271350 | Breast | 408 | BT-20 | 456 | 5.735872 | 0.871 | 0.955 | 0.93 | 0.9913 | 0.9764 | 0.972 | 1.0674 | 0.9818 | 1.1818 |
| 026_399_00272160 | Breast | 399 | MDA-MB-415 | 456 | 5.879088 | 0.884 | 0.875 | 0.885 | 0.8851 | 0.9175 | 0.914 | 0.9179 | 0.9049 | 0.9735 |
| 026_458_00274220 | Breast | 458 | HDQ-P1 | 456 | 6.259493 | 0.84 | 1.072 | 1.136 | 1.0763 | 1.0797 | 1.042 | 1.0437 | 1.0231 | 1.0073 |
| 026_397_00274350 | Breast | 397 | HCC38 | 456 | 6.744219 | 0.874 | 1.053 | 1.023 | 1.0222 | 0.9856 | 0.93 | 0.9274 | 0.9402 | 0.9941 |
| 026_405_00274360 | Breast | 405 | MDA-MB-361 | 456 | 6.792889 | 0.935 | 0.959 | 0.987 | 0.9819 | 0.9119 | 0.921 | 0.9597 | 0.998 | 0.9922 |
| 026_425_00280231 | Breast | 425 | MDA-MB-157 | 456 | 7.000504 | 0.906 | 1.069 | 1.05 | 0.9597 | 0.9229 | 0.966 | 0.9422 | 0.9712 | 0.9545 |
| 026_454_00272140 | Breast | 454 | EFM-192A | 456 | 7.097342 | 0.942 | 1.032 | 1.041 | 1.0545 | 0.9812 | 0.979 | 1.0186 | 1.0191 | 0.9742 |
| 026_420_00271541 | Breast | 420 | BT-474 | 456 | 7.458914 | 0.191 | 1.089 | 1.053 | 1.0824 | 1.0008 | 0.955 | 0.9764 | 0.9678 | 1.0149 |
| 026_453_00273410 | Breast | 453 | EFM-19 | 456 | 8.207256 | 1.096 | 1.286 | 1.208 | 1.1112 | 1.0544 | 1.042 | 1.0064 | 1.0474 | 1.0572 |
| 026_415_00316440 | Breast | 415 | BT-483 | 456 | 8.21654 | 1.148 | 1.275 | 1.181 | 1.1462 | 1.089 | 1.147 | 1.0671 | 1.0911 | 1.1123 |
| 026_8176_00316650 | Cervix | 8176 | TC-YIK | 456 | 0.842618 | 0.29 | 0.416 | 0.488 | 0.5211 | 0.5993 | 0.669 | 0.76 | 0.7877 | 1.0572 |
| 026_479_00264920 | Cervix | 479 | HT-3 | 456 | 1.420025 | 0.257 | 0.608 | 0.574 | 0.5844 | 0.5901 | 0.637 | 0.8649 | 0.8189 | 0.8617 |
| 026_478_00271910 | Cervix | 478 | C-33 A | 456 | 2.72591 | 0.472 | 0.615 | 0.658 | 0.6776 | 0.6753 | 0.734 | 0.7964 | 0.8383 | 0.9143 |
| 026_478_00269410 | Cervix | 478 | C-33 A | 456 | 2.976483 | 0.445 | 0.701 | 0.714 | 0.731 | 0.8172 | 0.771 | 0.9038 | 0.852 | 0.9634 |
| 026_493_00268830 | Cervix | 493 | ME-180 | 456 | 3.07379 | 0.509 | 0.667 | 0.695 | 0.7355 | 0.6828 | 0.732 | 0.7953 | 0.9097 | 1.0456 |
| 026_476_00269050 | Cervix | 476 | C-4 I | 456 | 3.232632 | 0.508 | 0.792 | 0.857 | 0.8645 | 0.8671 | 0.933 | 1.0078 | 1.0484 | 1.1636 |
| 026_8145_00271140 | Cervix | 8145 | OMC-1 | 456 | 3.295968 | 0.531 | 0.786 | 0.84 | 0.8546 | 0.9307 | 0.911 | 1.0261 | 1.0441 | 1.0392 |
| 026_484_00263710 | Cervix | 484 | Ca Ski | 456 | 3.639931 | 0.327 | 0.715 | 0.879 | 0.8811 | 0.8284 | 0.817 | 0.9599 | 1.0361 | 1.165 |
| 026_469_00264610 | Cervix | 469 | HeLa | 456 | 3.981495 | 0.311 | 0.783 | 0.933 | 0.9784 | 0.9807 | 0.982 | 0.9321 | 0.9429 | 0.9946 |
| 026_493_00262480 | Cervix | 493 | ME-180 | 456 | 4.007923 | 0.639 | 0.799 | 0.885 | 0.9474 | 0.9337 | 0.873 | 0.9457 | 0.8694 | 0.8949 |
| 026_474_00291006 | Cervix | 474 | SiHa | 456 | 4.596545 | 0.742 | 0.846 | 0.832 | 0.8807 | 0.9276 | 0.898 | 1.0004 | 0.9967 | 1.1646 |
| 026_482_00262520 | Cervix | 482 | SISO | 456 | 5.313141 | 0.851 | 0.946 | 0.96 | 0.9752 | 0.9888 | 0.276 | 0.975 | 0.947 | 0.966 |
| 026_482_00274250 | Cervix | 482 | SISO | 456 | 5.375837 | 0.842 | 0.881 | 0.887 | 0.9541 | 0.9605 | 0.96 | 0.9679 | 1.044 | 1.048 |
| 026_482_00269740 | Cervix | 482 | SISO | 456 | 5.709731 | 0.838 | 0.89 | 0.925 | 0.9202 | 0.9445 | 0.931 | 0.9609 | 0.9695 | 0.993 |
| 026_468_00264600 | Cervix | 468 | DoTc2 4510 | 456 | 5.749229 | 0.363 | 0.92 | 0.961 | 0.9796 | 0.9907 | 0.984 | 1.01 | 0.9525 | 0.985 |
| 026_473_00264650 | Cervix | 473 | SW756 | 456 | 5.953892 | 0.162 | 0.868 | 0.813 | 0.7938 | 0.8104 | 0.779 | 0.9163 | 0.8951 | 0.956 |
| 026_491_00264830 | Cervix | 491 | SKG-IIIa | 456 | 6.261878 | 0.721 | 1.002 | 1.008 | 1.007 | 1.0125 | 0.97 | 1.0049 | 0.9721 | 0.993 |
| 026_476_00264900 | Cervix | 476 | C-4 I | 456 | 6.792994 | 0.225 | 0.991 | 0.994 | 0.9093 | 0.8797 | 0.89 | 0.982 | 0.9123 | 0.914 |
| 026_474_00264930 | Cervix | 474 | SiHa | 456 | 7.505839 | 0.532 | 0.824 | 0.865 | 0.9092 | 0.9029 | 0.879 | 0.8904 | 0.8746 | 0.878 |
| 026_472_00264630 | Cervix | 472 | MS751 | 456 | 7.679336 | 1.023 | 0.945 | 0.949 | 0.9806 | 0.9744 | 0.979 | 0.9915 | 0.9775 | 0.982 |
| 026_8180_00276230 | Esophagus | 8180 | TE-15 | 456 | 0.823778 | 0.313 | 0.365 | 0.448 | 0.4963 | 0.618 | 0.64 | 0.8902 | 0.6859 | 1.036 |
| 026_502_00276550 | Esophagus | 502 | KYSE-450 | 456 | 1.219587 | 0.4222 | 0.41 | 0.448 | 0.5484 | 0.5334 | 0.703 | 0.7332 | 0.8892 | 0.853 |
| 026_497_00274050 | Esophagus | 497 | KYSE-150 | 456 | 1.304746 | 0.328 | 0.402 | 0.467 | 0.567 | 0.6585 | 0.801 | 0.8957 | 0.9976 | 0.971 |
| 026_8252_00276570 | Esophagus | 8252 | OACp4C | 456 | 1.678468 | 0.101 | 0.3 | 0.567 | 0.6503 | 0.7826 | 0.861 | 0.8531 | 0.9243 | 0.944 |
| 026_496_00276530 | Esophagus | 496 | KYSE-140 | 456 | 2.209734 | 0.522 | 0.516 | 0.476 | 0.5824 | 0.6741 | 0.815 | 0.8515 | 0.806 | 0.889 |
| 026_8233_00278570 | Esophagus | 8233 | ESO26 | 456 | 2.595405 | 0.493 | 0.568 | 0.679 | 0.7293 | 0.7791 | 0.852 | 0.8801 | 1.0449 | 0.825 |
| 026_8184_00282680 | Esophagus | 8184 | TE-6 | 456 | 2.946928 | 1.152 | 0.677 | 0.704 | 0.6755 | 0.7901 | 0.89 | 1.1989 | 1.0724 | 0.982 |
| 026_8277_00276670 | Esophagus | 8277 | TE-4 | 456 | 3.072573 | 0.518 | 0.605 | 0.768 | 0.8018 | 0.8549 | 0.883 | 0.9093 | 0.8952 | 0.957 |
| 026_506_00277170 | Esophagus | 506 | OE19 | 456 | 3.143883 | 0.544 | 0.752 | 0.743 | 0.8799 | 1.0437 | 0.937 | 1.0332 | 1.0004 | 1.070 |
| 026_8179_00276220 | Esophagus | 8179 | TE-12 | 456 | 3.163617 | 0.183 | 0.742 | 0.633 | 0.6476 | 0.7356 | 0.839 | 0.7964 | 0.8189 | 0.831 |
| 026_8185_00276250 | Esophagus | 8185 | TE-8 | 456 | 3.50176 | 0.201 | 0.606 | 0.658 | 0.7374 | 0.6587 | 0.744 | 0.775 | 0.681 | 0.925 |
| 026_8184_00293680 | Esophagus | 8184 | TE-6 | 456 | 3.545508 | 0.552 | 0.767 | 0.935 | 0.8745 | 0.8626 | 0.742 | 1.0239 | 0.863 | 0.923 |
| 026_8178_00280260 | Esophagus | 8178 | TE-10 | 456 | 3.804003 | 0.664 | 0.735 | 0.78 | 0.9124 | 0.8781 | 1.01 | 1.0331 | 0.9777 | 1.012 |
| 026_499_00276630 | Esophagus | 499 | KYSE-270 | 456 | 4.276810 | 0.678 | 0.727 | 0.767 | 0.7928 | 0.8774 | 0.984 | 0.9911 | 1.0386 | 1.0007 |
| 026 509 00276620 | Esophagus | 509 | KYSE-220 | 456 | 4.075564 | 0.637 | 0.656 | 0.682 | 0.7368 | 0.7969 | 0.844 | 0.873 | 0.9181 | 0.9229 |
| 026 8235 00276520 | Esophagus | 8235 | FLO-1 | 456 | 4.100409 | 0.604 | 0.732 | 0.778 | 0.7882 | 0.8071 | 0.864 | 0.8729 | 0.8842 | 0.9483 |
| 026 8251 00276640 | Esophagus | 8251 | OACM5-1 | 456 | 4.181038 | 0.673 | 0.784 | 0.878 | 0.8883 | 0.9366 | 0.926 | 0.9214 | 0.9309 | 0.9714 |
| 026 8186 00282690 | Esophagus | 8186 | TE-9 | 456 | 4.291684 | 0.689 | 0.795 | 0.742 | 0.8146 | 0.856 | 0.846 | 1.0123 | 0.8588 | 1.0654 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026 495 00274190 | Esophagus | 495 | COLO-680N | 456 | 4.332573 | 0.742 | 0.818 | 0.865 | 0.9122 | 0.97 | 0.96 | 1.1262 | 0.9684 | 1.0444 |
| 026 510 00273560 | Esophagus | 510 | KYSE-50 | 456 | 4.431288 | 0.658 | 0.743 | 0.781 | 0.8044 | 0.8395 | 0.815 | 0.8665 | 0.9009 | 1.0802 |
| 026_8186_00292740 | Esophagus | 8186 | TE-9 | 456 | 4.438695 | 0.739 | 0.769 | 0.893 | 0.8667 | 0.8573 | 0.944 | 1.0623 | 1.0025 | 1.1458 |
| 026_503_00274070 | Esophagus | 503 | KYSE-510 | 456 | 4.484808 | 0.731 | 0.796 | 0.816 | 0.8942 | 0.9487 | 0.912 | 0.9785 | 1.0104 | 1.0221 |
| 026 504 00276560 | Esophagus | 504 | KYSE-520 | 456 | 4.773857 | 0.716 | 0.731 | 0.748 | 0.7768 | 0.8124 | 0.867 | 0.9459 | 0.995 | 0.9576 |
| 026 8208 00276600 | Esophagus | 8208 | HCE-4 | 456 | 4.88732 | 0.748 | 0.785 | 0.808 | 0.8645 | 0.9033 | 0.954 | 0.9197 | 0.9231 | 0.9878 |
| 026_512 00274080 | Esophagus | 512 | T.T | 456 | 4.943912 | 0.781 | 0.839 | 0.89 | 0.9002 | 0.9769 | 0.929 | 0.9845 | 0.9744 | 1.0152 |
| 026 8268 00276650 | Esophagus | 8268 | SK-GT-4 | 456 | 5.079273 | 0.835 | 0.788 | 0.758 | 0.735 | 0.7503 | 0.833 | 0.9063 | 0.9163 | 0.972 |
| 026 505_00274210 | Esophagus | 505 | KYSE-70 | 456 | 5.137973 | 0.794 | 0.857 | 0.892 | 0.8943 | 0.9411 | 0.957 | 0.9493 | 0.9907 | 1.0431 |
| 026_508_00278520 | Esophagus | 508 | OE33 | 456 | 5.424479 | 0.701 | 0.81 | 0.783 | 0.7873 | 0.7763 | 0.833 | 0.8596 | 0.903 | 0.9287 |
| 026 498 00276540 | Esophagus | 498 | KYSE-180 | 456 | 5.533652 | 0.84 | 0.853 | 0.898 | 0.9109 | 0.9353 | 0.924 | 0.9336 | 0.9199 | 0.942 |
| 026 8202 00276660 | Esophagus | 8202 | TE-11 | 456 | 5.740526 | 0.822 | 0.845 | 0.848 | 0.8684 | 0.8821 | 0.913 | 0.9297 | 0.9627 | 1.0605 |
| 026_8039_00276580 | Esophagus | 8039 | EC-GI-10 | 456 | 5.844841 | 0.878 | 0.905 | 0.892 | 0.951 | 0.9277 | 0.926 | 0.9555 | 1.04 | 1.0068 |
| 026_501_00274060 | Esophagus | 501 | KYSE-410 | 456 | 6.135532 | 0.762 | 0.836 | 0.846 | 0.8398 | 0.8691 | 0.887 | 0.9278 | 0.9729 | 0.9854 |
| 026 8246 00276610 | Esophagus | 8246 | KYAE-1 | 456 | 6.1525 | 0.887 | 0.93 | 0.92 | 0.9326 | 0.9185 | 0.978 | 0.97 | 0.9663 | 0.9315 |
| 026_507 00278510 | Esophagus | 507 | OE21 | 456 | 6.23551 | 0.922 | 0.838 | 0.875 | 0.7771 | 0.8079 | 0.985 | 0.9753 | 0.9667 | 0.9919 |
| 026 8183 00276240 | Esophagus | 8183 | TE-5 | 456 | 6.777236 | 0.111 | 1.028 | 0.936 | 1.0341 | 1.0898 | 0.876 | 0.8843 | 0.9699 | 0.8561 |
| 026 8177 00282670 | Esophagus | 8177 | TE-1 | 456 | 7.848711 | 1.022 | 1.1 | 0.912 | 1.0973 | 1.0839 | 1.065 | 1.0874 | 1.0775 | 1.0749 |
| 026 545 00260020 | Head & Neck | 545 | DOK | 456 | −0.22061 | 0.308 | 0.451 | 0.33 | 0.4014 | 0.4436 | 0.534 | 0.6634 | 0.7589 | 0.8693 |
| 026_1217 00255750 | Head & Neck | 1217 | H3118 | 456 | 0.314816 | 0.254 | 0.413 | 0.453 | 0.4692 | 0.5199 | 0.565 | 0.691 | 0.6788 | 0.7738 |
| 026 526 00308740 | Head & Neck | 526 | PCI-4B | 456 | 1.887412 | 0.418 | 0.409 | 0.489 | 0.7595 | 0.7429 | 0.873 | 0.9067 | 0.918 | 1.0403 |
| 026 530 00260620 | Head & Neck | 530 | PCI-30 | 456 | 1.98819 | 0.142 | 0.356 | 0.628 | 0.7119 | 0.7851 | 0.825 | 0.9139 | 0.8747 | 0.8098 |
| 026 552 00252890 | Head & Neck | 552 | SAT | 456 | 2.534279 | 0.382 | 0.613 | 0.727 | 0.8554 | 0.7778 | 0.977 | 0.8474 | 0.7957 | 0.9605 |
| 026 550 00258980 | Head & Neck | 550 | SCC-4 | 456 | 2.544916 | 0.464 | 0.564 | 0.904 | 0.7519 | 0.7827 | 0.709 | 0.7715 | 0.8596 | 0.9574 |
| 026_1224 00256200 | Head & Neck | 1224 | SCC-9 | 456 | 2.68588 | 0.466 | 0.633 | 0.641 | 0.6635 | 0.6231 | 0.758 | 0.8287 | 0.8854 | 0.9263 |
| 026 1223 00259190 | Head & Neck | 1223 | SCC-25 | 456 | 2.934793 | 0.193 | 0.664 | 0.718 | 0.8957 | 0.937 | 0.932 | 1.0111 | 0.988 | 1.0055 |
| 026_548 00261030 | Head & Neck | 548 | RPMI 2650 | 456 | 3.095229 | 0.489 | 0.696 | 0.761 | 0.8664 | 0.8685 | 0.911 | 0.9177 | 0.9218 | 0.9624 |
| 026 517 00308680 | Head & Neck | 517 | JHU-011 | 456 | 3.112112 | 0.536 | 0.616 | 0.696 | 0.7845 | 0.8433 | 0.813 | 0.9157 | 0.9495 | 1.0827 |
| 026 8011 00257080 | Head & Neck | 8011 | BB30-HNC | 456 | 3.217966 | 0.541 | 0.677 | 0.734 | 0.7445 | 0.7909 | 0.917 | 0.9622 | 0.9832 | 1.0203 |
| 026 553 00259140 | Head & Neck | 553 | OSC-20 | 456 | 3.378306 | 0.587 | 0.751 | 0.792 | 0.8761 | 0.9722 | 0.983 | 1.0097 | 0.974 | 0.999 |
| 026 556 00257220 | Head & Neck | 556 | SKN-3 | 456 | 3.392608 | 0.207 | 0.626 | 0.805 | 0.7174 | 0.6353 | 0.718 | 0.757 | 0.8593 | 0.8383 |
| 026 536 00256080 | Head & Neck | 536 | BHY | 456 | 3.443799 | 0.593 | 0.821 | 0.877 | 0.8931 | 0.9405 | 1.049 | 1.0289 | 0.9991 | 1.0281 |
| 026 561 00257110 | Head & Neck | 561 | Ca9-22 | 456 | 3.710495 | 0.634 | 0.867 | 0.849 | 0.916 | 0.9493 | 0.99 | 1.0155 | 1.0225 | 1.0222 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026 532 00308750 | Head & Neck | 532 | PCI-6A | 456 | 3.742916 | 0.628 | 0.684 | 0.811 | 0.8452 | 0.8862 | 0.945 | 0.9298 | 0.9056 | 0.9974 |
| 026_8012_00266550 | Head & Neck | 8012 | BB49-HNC | 456 | 3.77782 | 0.46 | 0.775 | 0.9 | 0.8967 | 0.924 | 0.968 | 0.9717 | 1.0116 | 0.9946 |
| 026_8100 00256170 | Head & Neck | 8100 | LB771-HNC | 456 | 3.926882 | 0.701 | 0.899 | 0.929 | 0.9987 | 0.9867 | 0.989 | 1.0145 | 0.9621 | 0.9588 |
| 026 1222 00253030 | Head & Neck | 1222 | SCC-15 | 456 | 4.189701 | 0.411 | 0.772 | 0.855 | 0.8291 | 0.7747 | 1.02 | 0.8664 | | 0.9717 |
| 026_533_00260900 | Head & Neck | 533 | PCI-15A | 456 | 4.236361 | 1.325 | 1.15 | 0.832 | 0.8691 | 0.8188 | 0.863 | 0.9549 | 1.0427 | 1.0471 |
| 26 547 00314070 | Head & Neck | 547 | KOSC-2 c13-43 | 456 | 4.563275 | 0.708 | 0.872 | 0.897 | 0.9 | 0.8378 | 0.941 | 1.0131 | 0.9825 | 0.9292 |
| 026 544 00256140 | Head & Neck | 544 | Detroit 562 | 456 | 4.601961 | 0.746 | 0.964 | 0.951 | 0.9801 | 0.9656 | 0.967 | 0.9765 | 0.9793 | 0.9061 |
| 026 543 00256100 | Head & Neck | 543 | BICR 78 | 456 | 4.851894 | 0.728 | 0.818 | 0.868 | 0.8349 | 0.9283 | 0.925 | 0.9696 | 0.966 | 0.9649 |
| 026_537 00256120 | Head & Neck | 537 | CAL-33 | 456 | 5.580216 | 0.834 | 0.892 | 0.921 | 0.9097 | 0.9511 | 0.935 | 0.9977 | 1.0062 | 0.9837 |
| 026 549 00256220 | Head & Neck | 549 | HO-1-N-1 | 456 | 5.63511 | 0.866 | 0.873 | 0.883 | 0.8726 | 0.8907 | 0.97 | 0.987 | 0.9898 | 1.0714 |
| 026 557 00259180 | Head & Neck | 557 | SAS | 456 | 6.035072 | 0.913 | 0.97 | 0.967 | 0.9738 | 0.9866 | 1.043 | 1.0896 | 1.0407 | 1.0277 |
| 026 534 00256110 | Head & Neck | 534 | CAL 27 | 456 | 6.045151 | 0.85 | 0.904 | 0.912 | 0.9312 | 0.925 | 0.939 | 0.9758 | 0.9901 | 0.9927 |
| 026_542 00269190 | Head & Neck | 542 | BICR 31 | 456 | 6.045414 | 0.903 | 0.908 | 0.952 | 0.9408 | 0.977 | 0.97 | 0.9966 | 1.0002 | 1.0269 |
| 026 530 00262500 | Head & Neck | 530 | PCI-30 | 456 | 6.119674 | 0.884 | 0.955 | 1.145 | 0.9682 | 1.009 | 0.988 | 0.9261 | 1.0121 | 0.9861 |
| 026 540 00258490 | Head & Neck | 540 | BICR 10 | 456 | 6.128463 | 0.839 | 1.048 | 1.049 | 1.0556 | 1.0464 | 1.041 | 1.0301 | 0.974 | 0.9953 |
| 026 541 00256090 | Head & Neck | 541 | BICR 22 | 456 | 6.156446 | 0.828 | 1.076 | 1.058 | 0.9602 | 1.0898 | 1.064 | 1.0874 | 0.9689 | 1.0462 |
| 026 8003 00263440 | Head & Neck | 8003 | A253 | 456 | 6.291179 | 0.877 | 0.857 | 0.859 | 0.8594 | 0.9753 | 0.982 | 0.9985 | 0.9367 | 0.969 |
| 026 535 00256160 | Head & Neck | 535 | FaDu | 456 | 6.303565 | 0.841 | 1.063 | 1.091 | 1.0795 | 1.0793 | 1.034 | 1.0404 | 1.0191 | 1.0095 |
| 026 554 00257210 | Head & Neck | 554 | OSC-19 | 456 | 6.322489 | 0.938 | 0.942 | 0.914 | 0.9247 | 0.9682 | 1.004 | 1.0285 | 1.0504 | 1.0506 |
| 026_559 00256250 | Head & Neck | 559 | HSC-3 | 456 | 6.797258 | 0.909 | 1.024 | 1.057 | 1.0632 | 1.0572 | 1.029 | 1.0059 | 0.9701 | 0.9782 |
| 026 8071 00256760 | Head & Neck | 8071 | HCE-T | 456 | 6.917353 | 0.576 | 1.146 | 1.274 | 1.3514 | 1.1688 | 1.173 | 1.0336 | 1.1999 | 0.8849 |
| 026 521 00257180 | Head & Neck | 521 | JHU-022 | 456 | 7.049785 | 0.896 | 0.846 | 0.901 | 0.8757 | 0.9278 | 0.886 | 0.913 | 0.9436 | 0.9699 |
| 026_555_00256270 | Head & Neck | 555 | KON | 456 | 7.114386 | 0.946 | 0.982 | 0.977 | 0.9826 | 0.9957 | 0.96 | 0.9991 | 0.961 | 0.9207 |
| 026_538 00258510 | Head & Neck | 538 | HN | 456 | 7.118392 | 0.947 | 1.007 | 0.984 | 1.0014 | 1.0052 | 0.998 | 1.0105 | 0.9648 | 0.9952 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026 546 00259150 | Head & Neck | 546 | PE/CA-PJ15 | 456 | 7.26219 | 0.96 | 0.963 | 0.931 | 0.9179 | 0.9698 | 0.969 | 0.9884 | 1.006 | 0.9974 |
| 026_560_00256260 | Head & Neck | 560 | HSC-4 | 456 | 7.41962 | 1.005 | 0.994 | 1.003 | 0.9486 | 1.2114 | 0.897 | 0.9756 | 0.9433 | 0.9255 |
| 026 551 00259130 | Head & Neck | 551 | HO-1-u-1 | 456 | 7.903602 | 0.999 | 1.037 | 1.039 | 1.0722 | 1.0616 | 1.067 | 1.0655 | 1.0038 | 0.9405 |
| 026_558_00256240 | Head & Neck | 558 | HSC-2 | 456 | 8.185707 | 1.148 | 1.077 | 0.985 | 1.1269 | 1.0034 | 1.093 | 0.9608 | 0.9252 | 0.9888 |
| 026 531 00258970 | Head & Neck | 531 | PCI-38 | 456 | 8.493869 | 1.046 | 1.067 | 1.063 | 1.0751 | 1.0712 | 0.965 | 1.0236 | 1.0421 | 0.9848 |
| 026_570 00293670 | Intestine | 570 | SK-CO-1 | 456 | −0.30187 | 0.268 | 0.258 | 0.267 | 0.2555 | 0.3746 | 0.418 | 0.7306 | 0.9824 | 0.9276 |
| 026_8153_00295901 | Intestine | 8153 | RKO | 456 | 0.044041 | 0.222 | 0.197 | 0.246 | 0.3161 | 0.4612 | 0.693 | 0.7818 | 0.9061 | 1.1131 |
| 18 | Intestine | 586 | COLO205 | 456 | 0.350012 | 0.083 | 0.182 | 0.268 | 0.3978 | 0.5206 | 0.706 | 0.8518 | 0.9472 | 0.9745 |
| 026_582_00295550 | Intestine | 582 | LoVo | 456 | 0.399717 | 0.325 | 0.396 | 0.385 | 0.4168 | 0.4097 | 0.533 | 0.75 | 0.8239 | 0.9276 |
| 026_8108_00298530 | Intestine | 8108 | LS-513 | 456 | 0.423432 | 0.094 | 0.146 | 0.195 | 0.2527 | 0.5673 | 0.876 | 1.1755 | 1.0179 | 1.1926 |
| 026_8274_00258540 | Intestine | 8274 | SNU-61 | 456 | 0.467862 | 0.432 | 0.599 | 0.539 | 0.5369 | 0.5735 | 0.603 | 0.7283 | 0.7462 | 0.9243 |
| 026_8136_00260060 | Intestine | 8136 | NCI-H747 | 456 | 0.578701 | 0.356 | 0.465 | 0.488 | 0.5338 | 0.5471 | 0.613 | 0.7238 | 0.8107 | 0.9473 |
| 026_574_00298390 | Intestine | 574 | CL-11 | 456 | 0.894127 | 0.381 | 0.401 | 0.395 | 0.4593 | 0.6002 | 0.69 | 0.749 | 0.8474 | 0.9789 |
| 026_589_00295371 | Intestine | 589 | HCT 116 | 456 | 0.931657 | 0.336 | 0.381 | 0.435 | 0.4732 | 0.5791 | 0.862 | 1.1049 | 1.0627 | 1.1072 |
| 026_608_00293620 | Intestine | 608 | CCK-81 | 456 | 1.046144 | 0.242 | 0.394 | 0.399 | 0.4912 | 0.6325 | 0.738 | 0.9653 | 0.9069 | 0.9123 |
| 026_610_00293660 | Intestine | 610 | RCM-1 | 456 | 1.475794 | 0.45 | 0.416 | 0.414 | 0.6252 | 0.6775 | 0.804 | 0.981 | 1.0277 | 1.0565 |
| 026_569_00295390 | Intestine | 569 | HT-29 | 456 | 1.526342 | 0.48 | 0.464 | 0.5 | 0.5547 | 0.5893 | 0.74 | 0.9536 | 0.9048 | 0.9241 |
| 026_8271_00314300 | Intestine | 8271 | SNU-175 | 456 | 1.739925 | 0.382 | 0.522 | 0.535 | 0.5651 | 0.6481 | 0.701 | 0.7957 | 0.9458 | 0.9851 |
| 026_8108_00296610 | Intestine | 8108 | LS-513 | 456 | 1.815428 | 0.37 | 0.448 | 0.511 | 0.6156 | 0.8074 | 0.933 | 0.9905 | 0.9579 | 0.9991 |
| 026_592_00295380 | Intestine | 5959 | HT115 | 456 | 1.869689 | 0.377 | 0.436 | 0.5 | 0.6258 | 0.8213 | 1.101 | 1.0858 | 1.0169 | 1.1148 |
| 026_606_00293630 | Intestine | 606 | HCC-56 | 456 | 1.929923 | 0.646 | 0.514 | 0.536 | 0.5915 | 0.7207 | 0.867 | 0.8829 | 0.9131 | 0.9417 |
| 026_8107_00296450 | Intestine | 8107 | LS-411N | 456 | 2.297731 | 0.497 | 0.55 | 0.585 | 0.5585 | 0.6884 | 0.755 | 0.8626 | 0.8921 | 0.9253 |
| 026_595_00295420 | Intestine | 595 | LS180 | 456 | 2.32965 | 0.453 | 0.515 | 0.551 | 0.6999 | 0.8666 | 0.91 | 1.0102 | 0.9178 | 1.1155 |
| 026_8169_00295910 | Intestine | 8169 | SNU-C2B | 456 | 2.617884 | 0.503 | 0.566 | 0.598 | 0.7373 | 0.671 | 0.774 | 0.9066 | 0.8796 | 0.9886 |
| 026_564_00292860 | Intestine | 564 | NCI-H630 | 456 | 2.627492 | 0.496 | 0.556 | 0.55 | 0.7713 | 1.0007 | 0.964 | 0.9563 | 0.8783 | 0.9169 |
| 026_603_00292731 | Intestine | 603 | SW837 | 456 | 2.797981 | 0.525 | 0.597 | 0.586 | 0.7811 | 0.7763 | 1.002 | 1.023 | 1.0218 | 1.0696 |
| 026_588_00295360 | Intestine | 588 | GP5d | 456 | 2.925873 | 0.521 | 0.65 | 0.67 | 0.679 | 0.8325 | 0.964 | 1.0479 | 1.1013 | 1.0678 |
| 026_598_00302650 | Intestine | 598 | W 1417 | 456 | 3.077195 | 0.616 | 0.696 | 0.742 | 0.6531 | 1.034 | 1.029 | 1.0798 | 0.8321 | 1.2207 |
| 026_8276_00296000 | Intestine | 8276 | NU-C5 | 456 | 3.153347 | 0.603 | 0.592 | 0.612 | 0.6327 | 0.7283 | 0.812 | 0.8824 | 0.9411 | 0.9768 |
| 026_593_00295530 | Intestine | 593 | HT55 | 456 | 3.164186 | 0.589 | 0.646 | 0.61 | 0.7857 | 0.7974 | 1.03 | 1.1134 | 1.0941 | 1.1175 |
| 026_8106_00264670 | Intestine | 8106 | LS-123 | 456 | 3.191118 | 0.547 | 0.687 | 0.783 | 0.7554 | 0.8823 | 0.879 | 0.9202 | 0.965 | 0.9375 |
| 026_599_00296340 | Intestine | 599 | W 1463 | 456 | 3.237942 | 0.572 | 0.642 | 0.631 | 0.6255 | 0.6275 | 0.757 | 0.9237 | 0.9401 | 0.9681 |
| 026_8086_00296431 | Intestine | 8086 | KM12 | 456 | 3.240654 | 0.564 | 0.657 | 0.65 | 0.6739 | 0.8062 | 0.903 | 0.8858 | 0.9825 | 0.9793 |
| 026_587_00302320 | Intestine | 587 | COLO 741 | 456 | 3.269221 | 0.615 | 0.622 | 0.694 | 0.6624 | 0.7236 | 0.816 | 1.1058 | 1.0995 | 1.0783 |
| 026_8273_00295970 | Intestine | 8273 | NU-407 | 456 | 3.390403 | 0.577 | 0.622 | 0.663 | 0.7325 | 0.7399 | 0.745 | 0.8059 | 0.8644 | 1.0342 |
| 026_8270_00304630 | Intestine | 8270 | SNU-1040 | 456 | 3.643993 | 0.604 | 0.78 | 0.799 | 0.8256 | 0.8028 | 0.92 | 0.9246 | 0.9919 | 1.2066 |
| 026_8168_00295990 | Intestine | 8168 | NU-C1 | 456 | 3.717495 | 0.645 | 0.673 | 0.685 | 0.6875 | 0.8368 | 0.739 | 0.8513 | 1.1115 | 1.0883 |
| 026_8275_00256210 | Intestine | 8275 | NU-81 | 456 | 3.903109 | 0.338 | 0.659 | 0.68 | 0.6942 | 0.7065 | 0.761 | 0.7749 | 0.8653 | 0.9224 |
| 026_583_00295921 | Intestine | 583 | W-948 | 456 | 3.908038 | 0.735 | 0.672 | 0.851 | 0.9918 | 1.0392 | 0.979 | 0.9178 | 0.9736 | 0.9758 |
| 026_8274_00295980 | Intestine | 8274 | NU-61 | 456 | 4.14154 | 0.663 | 0.72 | 0.672 | 0.6639 | 0.7521 | 0.794 | 0.8775 | 0.8761 | 0.9371 |
| 026_8105_00296440 | Intestine | 8105 | S-1034 | 456 | 4.222062 | 0.732 | 0.754 | 0.781 | 0.8085 | 0.8857 | 1.006 | 1.1032 | 1.0973 | 1.0698 |
| 026_580_00295930 | Intestine | 580 | COLO-678 | 456 | 4.449849 | 0.891 | 0.793 | 0.767 | 0.8394 | 0.8741 | 0.917 | 1.0326 | 0.9344 | 1.0884 |
| 026_580_00266560 | Intestine | 580 | COLO-678 | 456 | 4.550688 | 0.724 | 0.686 | 0.785 | 0.8147 | 0.8701 | 0.885 | 0.9546 | 0.9558 | 0.9803 |
| 026_581_00295830 | Intestine | 581 | CT-15 | 456 | 4.608693 | 0.811 | 0.75 | 0.973 | 0.9405 | 1.0972 | 0.98 | 1.098 | 1.0722 | 1.1405 |

TABLE_22-continued

| Barcode | Organ | Cell ID | Cell Line | Compound No | Fitted | Viability ratio | | | | | | | | |
|---|---|---|---|---|---|---|---|---|---|---|---|---|---|---|
| | | | | | MGH.IC50 | 20 uM | 10 uM | 5 uM | 2.5 uM | 1.25 uM | 0.625 uM | 0.3125 uM | 0.15625 uM | 0.078125 uM |
| 026_573_00296370 | Intestine | 573 | SW620 | 456 | 4.816766 | 0.775 | 0.787 | 0.797 | 0.8519 | 0.8683 | 0.915 | 0.9626 | 1.0901 | 1.097 |
| 026_8021_00296390 | Intestine | 8021 | COLO-320-HSR | 456 | 4.87923 | 0.817 | 0.861 | 0.828 | 1.0219 | 0.8974 | 1.103 | 1.0927 | 0.9967 | 1.1145 |
| 026_8106_00298521 | Intestine | 8106 | LS-123 | 456 | 4.895207 | 0.706 | 0.749 | 0.852 | 0.7598 | 0.7605 | 0.923 | 0.8934 | 0.9319 | 1.0175 |
| 026_600_00296361 | Intestine | 600 | SW 48 | 456 | 4.951306 | 0.706 | 0.776 | 0.775 | 0.7937 | 0.8445 | 0.857 | 0.9382 | 0.915 | 0.9609 |
| 026_8070_00296411 | Intestine | 8070 | HCC2998 | 456 | 4.984157 | 0.701 | 0.788 | 0.743 | 0.7463 | 0.8151 | 0.891 | 0.9115 | 0.9572 | 0.9432 |
| 026_8135_00295950 | Intestine | 8135 | NCI-H716 | 456 | 4.988916 | 0.813 | 0.864 | 0.948 | 0.9832 | 0.9658 | 0.94 | 0.9372 | 0.9633 | 1.1237 |
| 026_8136_00295961 | Intestine | 8136 | NCI-H747 | 456 | 5.220086 | 0.699 | 0.693 | 0.763 | 0.7315 | 0.7863 | 0.815 | 0.8715 | 0.8842 | 1.1461 |
| 026_574_00263900 | Intestine | 574 | CL-11 | 456 | 5.294016 | 0.826 | 0.812 | 0.761 | 0.7543 | 0.8087 | 0.891 | 0.9784 | 0.9577 | 0.9649 |
| 026_8026_00300671 | Intestine | 8026 | CW-2 | 456 | 5.403672 | 0.827 | 0.955 | 0.974 | 0.9551 | 0.9288 | 0.954 | 0.9824 | 0.9866 | 1.0636 |
| 026_607_00293610 | Intestine | 607 | CaR-1 | 456 | 5.551737 | 0.834 | 0.873 | 0.912 | 0.8795 | 0.9318 | 0.939 | 0.9636 | 0.9483 | 0.9415 |
| 026_8074_00296420 | Intestine | 8074 | HUTU-80 | 456 | 5.701754 | 0.841 | 0.852 | 0.876 | 0.9027 | 0.8952 | 1.007 | 1.0026 | 0.966 | 0.9322 |
| 026_563_00316540 | Intestine | 563 | 2BBe1 | 456 | 5.783056 | 0.853 | 0.949 | 0.926 | 0.9333 | 0.9253 | 0.879 | 0.9164 | 1.0369 | 1.0733 |
| 026_596_00296280 | Intestine | 596 | DST8 | 456 | 6.402689 | 0.885 | 0.885 | 0.874 | 0.8768 | 0.9374 | 0.931 | 0.9758 | 0.9779 | 1.0734 |
| 026_597_00300651 | Intestine | 597 | W 1116 | 456 | 6.447765 | 0,647 | 1.058 | 0.925 | 1.031 | 0.9839 | 0.997 | 1.0631 | 1.0277 | 0.905 |
| 026_601_00296480 | Intestine | 601 | T84 | 456 | 7.233631 | 0.973 | 0.939 | 0.93 | 0.9736 | 0.9545 | 0.891 | 0.964 | 0.9372 | 1.0259 |
| 026_622_00288160 | Kidney | 622 | G-401 | 456 | 1.158385 | 0.353 | 0.358 | 0.433 | 0.5045 | 0.6202 | 0.865 | 0.8778 | 1.0261 | 1.0061 |
| 026_626_00298790 | Kidney | 626 | BFTC-909 | 456 | 1.589633 | 0.292 | 0.387 | 0.526 | 0.5522 | 0.8154 | 0.895 | 0.9347 | 1.005 | 1.054 |
| 026_623_00288201 | Kidney | 623 | SK-NEP-1 | 456 | 1.837955 | 0.412 | 0.444 | 0.507 | 0.7421 | 0.8141 | 0.813 | 0.9099 | 0.9209 | 0.981 |
| 026_8264_00290630 | Kidney | 8264 | CC-JF | 456 | 2.377362 | 0.452 | 0.535 | 0.585 | 0.6574 | 0.9675 | 0.851 | 0.9828 | 1.0591 | 1.0712 |
| 026_619_00290290 | Kidney | 619 | 769-P | 456 | 2.463867 | 0.439 | 0.58 | 0.576 | 0.7655 | 0.8898 | 0.994 | 1.0776 | 1.0508 | 1.1513 |
| 026_627_00291130 | Kidney | 627 | CAL-54 | 456 | 2.931844 | 0.586 | 0.588 | 0.649 | 0.6813 | 0.7826 | 0.858 | 0.9811 | 0.9726 | 1.0003 |
| 026_617_00290310 | Kidney | 617 | ACHN | 456 | 2.983353 | 0.545 | 0.592 | 0.627 | 0.7345 | 0.7447 | 0.733 | 0.7712 | 0.919 | 1.1152 |
| 026_8263_00290620 | Kidney | 8263 | RCC-FG2 | 456 | 3.111338 | 0.517 | 0.689 | 0.691 | 0.7857 | 0.7896 | 0.884 | 0.8746 | 0.9754 | 1.0284 |
| 026_8190_00290280 | Kidney | 8190 | TK10 | 456 | 3.318654 | 0.638 | 0.654 | 0.671 | 0.7606 | 0.892 | 0.932 | 1.0085 | 1.0009 | 0.9983 |
| 026_638_00288220 | Kidney | 638 | VMRC- RCZ | 456 | 3.36569 | 0.14 | 0.709 | 0.838 | 0.9211 | 0.92 | 0.981 | 0.9922 | 0.9588 | 0.989 |
| 026_8261_00308760 | Kidney | 8261 | RCC-AB | 456 | 3.394556 | 0.566 | 0.724 | 0.758 | 0.85 | 0.8258 | 0.948 | 0.9492 | 0.9471 | 0.9351 |
| 026_628_00288210 | Kidney | 628 | SW 13 | 456 | 3.41636 | 0.454 | 0.733 | 0.735 | 0.7572 | 0.8068 | 0.826 | 0.8584 | 0.9361 | 1.0195 |
| 026_8262_00290610 | Kidney | 8262 | RCC-ER | 456 | 3.745967 | 0.583 | 0.783 | 0.794 | 0.8415 | 0.9082 | 0.87 | 0.8861 | 0.9471 | 0.9855 |
| 026_8265_00302360 | Kidney | 8265 | RCC-JW | 456 | 3.749626 | 0.686 | 0.758 | 0.874 | 0.9595 | 1.0107 | 1.003 | 1.0135 | 1.0068 | 1.0345 |
| 026_8261_00311200 | Kidney | 8261 | RCC-AB | 456 | 3.919417 | 0.288 | 0.72 | 0.73 | 0.765 | 0.8515 | 0.878 | 0.9287 | 0.8965 | 0.94 |
| 026_618_00290300 | Kidney | 618 | 786-O | 456 | 3.967789 | 0.657 | 0.719 | 0.822 | 0.8016 | 0.8829 | 0.898 | 1.0239 | 0.917 | 1.0472 |
| 026_625_00290670 | Kidney | 625 | UO-31 | 456 | 3.998088 | 0.662 | 0.756 | 0.767 | 0.9002 | 0.8304 | 0.876 | 0.9012 | 1.0588 | 1.1507 |
| 026_8096_00290860 | Kidney | 8096 | LB2241-RCC | 456 | 3.99857 | 0.643 | 0.686 | 0.74 | 0.8137 | 0.8533 | 0.902 | 0.9235 | 0.9107 | 0.9322 |
| 026_614_00291210 | Kidney | 614 | SW 156 | 456 | 4.137243 | 0.651 | 0.665 | 0.71 | 0.7683 | 0.8365 | 0.896 | 0.903 | 0.9074 | 0.9013 |
| 026_8249_00295560 | Kidney | 8249 | NCC021 | 456 | 4.201277 | 0.701 | 0.897 | 0.903 | 0.9199 | 0.9735 | 0.942 | 0.9933 | 1.0276 | 1.0113 |
| 026_633_00290250 | Kidney | 633 | KMRC-20 | 456 | 4.24311 | 0.713 | 0.872 | 0.83 | 0.9644 | 0.8737 | 1.135 | 1.027 | 1.0923 | 1.0373 |
| 026_8068_00290231 | Kidney | 8068 | HA7-RCC | 456 | 4.403879 | 0.761 | 0.764 | 0.7 | 0.8322 | 0.7944 | 0.89 | 1.0474 | 1.1224 | 1.0563 |
| 026_8095_00290260 | Kidney | 8095 | LB1047-RCC | 456 | 4.460236 | 0.772 | 0.824 | 0.914 | 1.0356 | 1.0154 | 1.004 | 1.0739 | 1.1192 | 1.1745 |
| 026_626_00258890 | Kidney | 626 | BFTC-909 | 456 | 4.464205 | 0.741 | 0.932 | 1.057 | 1.0395 | 1.0888 | 1.03 | 1.0217 | 1.0625 | 1.0049 |
| 026_8147_00290270 | Kidney | 8147 | OS-RC-2 | 456 | 4.480976 | 0.767 | 0.794 | 0.799 | 0.8302 | 0.9419 | 1.023 | 1.0718 | 1.0847 | 1.1694 |
| 026_8013_00290220 | Kidney | 8013 | BB65-RCC | 456 | 4.50555 | 0.714 | 0.769 | 0.765 | 0.8909 | 0.8509 | 0.865 | 0.9509 | 1.0096 | 0.903 |
| 026_8006_00293300 | Kidney | 8006 | A704 | 456 | 4.630889 | 0.755 | 0.917 | 0.918 | 0.9328 | 0.9788 | 1.112 | 0.981 | 0.9813 | 1.0413 |
| 026_637_00290240 | Kidney | 637 | KMRC-1 | 456 | 4.786417 | 0.748 | 0.889 | 0.97 | 0.9322 | 0.836 | 1.012 | 1.0239 | 0.9503 | 1.088 |
| 026_624_00290320 | Kidney | 624 | Caki-1 | 456 | 4.808896 | 0.821 | 0.803 | 0.908 | 0.9738 | 0.9722 | 1.083 | 1.1676 | 1.1464 | 1.1228 |
| 026_8266_00290640 | Kidney | 8266 | RCC-MF | 456 | 4.811179 | 0.754 | 0.903 | 0.819 | 0.8455 | 0.8764 | 0.999 | 0.9885 | 0.935 | 1.1762 |
| 026_620_00288170 | Kidney | 620 | G-402 | 456 | 4.865533 | 0.694 | 0.721 | 0.686 | 0.7919 | 0.7766 | 0.804 | 0.8404 | 0.885 | 0.9093 |
| 026_8152_00293381 | Kidney | 8152 | RCC10 RGB | 456 | 5.110675 | 0.821 | 0.719 | 0.783 | 0.9032 | 0.8829 | 0.858 | 0.8991 | 0.9287 | 1.0343 |
| 026_640_00291220 | Kidney | 640 | VMRC-RCW | 456 | 5.287926 | 0.73 | 0.737 | 0.793 | 0.8088 | 0.8755 | 0.905 | 0.9003 | 0.9127 | 0.9163 |
| 026_8102_00293360 | Kidney | 8102 | LB996-RCC | 456 | 5.484542 | 0.855 | 0.901 | 0.954 | 0.9116 | 0.9765 | 0.98 | 0.958 | 0.9786 | 0.9921 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_1119_00290901 | Kidney | 1119 | SN-12C | 456 | 5.586587 | 0.818 | 0.749 | 0.747 | 0.783 | 0.8069 | 0.856 | 0.9038 | 0.9508 | 0.9573 |
| 026_626_00290810 | Kidney | 626 | BFTC-909 | 456 | 5.753321 | 0.799 | 0.854 | 0.903 | 0.9293 | 0.9289 | 0.92 | 0.9333 | 0.9322 | 0.9535 |
| 026_8005_00266530 | Kidney | 8005 | A498 | 456 | 5.843211 | 0.594 | 0.917 | 1.003 | 1.0079 | 0.9307 | 0.996 | 1.0002 | 1.0033 | 0.9941 |
| 026_8157_00296471 | Kidney | 8157 | RXF393 | 456 | 6.166218 | 0.853 | 0.878 | 0.91 | 0.8924 | 0.9071 | 0.932 | 0.9081 | 0.9505 | 0.9889 |
| 026_8102_00253000 | Kidney | 8102 | LB996-RCC | 456 | 6.306723 | 0.959 | 0.873 | 0.878 | 0.9741 | 0.9596 | 1.025 | 0.9525 | 0.9849 | 0.9931 |
| 026_8006_00263880 | Kidney | 8006 | A704 | 456 | 6.969306 | 1.351 | 0.929 | 1.157 | 0.9881 | 1.0206 | 0.957 | 1.0009 | 0.9583 | 0.9931 |
| 026_8152_00256190 | Kidney | 8152 | RCC10RGB | 456 | 7.15535 | 1.178 | 0.835 | 1.176 | 0.846 | 0.8683 | 1.123 | 1.1733 | 1.1056 | 1.0876 |
| 026_8005_00296380 | Kidney | 8005 | A498 | 456 | 8.190783 | 1.022 | 1.025 | 1.024 | 1.0158 | 1.03 | 1.032 | 1.0128 | 1.0239 | 1.0104 |
| 026_233_00277420 | Leukemia | 233 | SIG-M5 | 456 | 5.883853 | 0.228 | 0.243 | 0.233 | 0.2401 | 0.2362 | 0.247 | 0.2641 | 0.2732 | 0.4405 |
| 026_217_00277380 | Leukemia | 217 | OCI-AML2 | 456 | −1.42786 | 0.09 | 0.102 | 0.106 | 0.1256 | 0.1044 | 0.132 | 0.3277 | 0.8333 | 0.8618 |
| 026_179_00314500 | Leukemia | 179 | KMOE-2 | 456 | 0.249088 | 0.13 | 0.135 | 0.138 | 0.1591 | 0.3658 | 0.608 | 0.865 | 0.8967 | 1.0615 |
| 026_214_00285590 | Leukemia | 214 | NB-4 | 456 | 0.011745 | 0.18 | 0.323 | 0.315 | 0.3611 | 0.4215 | 0.592 | 0.8144 | 0.8865 | 0.9464 |
| 026_168_00280410 | Leukemia | 168 | JURL-MK1 | 456 | 0.181843 | 0.145 | 0.179 | 0.186 | 0.2526 | 0.4638 | 0.727 | 0.9379 | 0.904 | 0.9907 |
| 026_618_00290300 | Kidney | 618 | 786-O | 456 | 3.967789 | 0.657 | 0.719 | 0.822 | 0.8016 | 0.8829 | 0.898 | 1.0239 | 0.917 | 1.0472 |
| 026_625_00290670 | Kidney | 625 | UO-31 | 456 | 3.998088 | 0.662 | 0.756 | 0.767 | 0.9002 | 0.8304 | 0.876 | 0.9012 | 1.0588 | 1.1507 |
| 026_8096_00290860 | Kidney | 8096 | LB2241-RCC | 456 | 3.99857 | 0.643 | 0.686 | 0.74 | 0.8137 | 0.8533 | 0.902 | 0.9235 | 0.9107 | 0.9322 |
| 026_614_00291210 | Kidney | 614 | SW 156 | 456 | 4.137243 | 0.651 | 0.665 | 0.71 | 0.7683 | 0.8365 | 0.896 | 0.903 | 0.9074 | 0.9013 |
| 026_8249_00295560 | Kidney | 8249 | NCC021 | 456 | 4.201277 | 0.701 | 0.897 | 0.903 | 0.9199 | 0.9735 | 0.942 | 0.9933 | 1.0276 | 1.0113 |
| 026_633_00290250 | Kidney | 633 | KMRC-20 | 456 | 4.24311 | 0.713 | 0.872 | 0.83 | 0.9644 | 0.8737 | 1.135 | 1.027 | 1.0923 | 1.0373 |
| 026_8068_00290231 | Kidney | 8068 | HA7-RCC | 456 | 4.403879 | 0.761 | 0.764 | 0.7 | 0.8322 | 0.7944 | 0.89 | 1.0474 | 1.1224 | 1.0563 |
| 026_8095_00290260 | Kidney | 8095 | LB1047-RCC | 456 | 4.460236 | 0.772 | 0.824 | 0.914 | 1.0356 | 1.0154 | 1.004 | 1.0739 | 1.1192 | 1.1745 |
| 026_626_00258890 | Kidney | 626 | BFTC-909 | 456 | 4.464205 | 0.741 | 0.932 | 1.057 | 1.0395 | 1.0888 | 1.03 | 1.0217 | 1.0625 | 1.0049 |
| 026_8147_00290270 | Kidney | 8147 | OS-RC-2 | 456 | 4.480976 | 0.767 | 0.794 | 0.799 | 0.8302 | 0.9419 | 1.023 | 1.0718 | 1.0847 | 1.1694 |
| 026_8013_00290220 | Kidney | 8013 | BB65-RCC | 456 | 4.50555 | 0.714 | 0.769 | 0.765 | 0.8909 | 0.8509 | 0.865 | 0.9509 | 1.0096 | 0.903 |
| 026_8006_00293300 | Kidney | 8006 | A704 | 456 | 4.630889 | 0.755 | 0.917 | 0.918 | 0.9328 | 0.9788 | 1.112 | 0.981 | 0.9813 | 1.0413 |
| 026_637_00290240 | Kidney | 637 | KMRC-1 | 456 | 4.786417 | 0.748 | 0.889 | 0.97 | 0.9322 | 0.836 | 1.012 | 1.0239 | 0.9503 | 1.088 |
| 026_624_00290320 | Kidney | 624 | Caki-1 | 456 | 4.808896 | 0.821 | 0.803 | 0.908 | 0.9738 | 0.9722 | 1.083 | 1.1676 | 1.1464 | 1.1228 |
| 026_8266_00290640 | Kidney | 8266 | RCC-MF | 456 | 4.811179 | 0.754 | 0.903 | 0.819 | 0.8455 | 0.8764 | 0.999 | 0.9885 | 0.935 | 1.1762 |
| 026_620_00288170 | Kidney | 620 | G-402 | 456 | 4.865533 | 0.694 | 0.721 | 0.686 | 0.7919 | 0.7766 | 0.804 | 0.8404 | 0.885 | 0.9093 |
| 026_8152_00293381 | Kidney | 8152 | RCC10 RGB | 456 | 5.110675 | 0.821 | 0.719 | 0.783 | 0.9032 | 0.8829 | 0.858 | 0.8991 | 0.9287 | 1.0343 |
| 026_640_00291220 | Kidney | 640 | VMRC-RCW | 456 | 5.287926 | 0.73 | 0.737 | 0.793 | 0.8088 | 0.8755 | 0.905 | 0.9003 | 0.9127 | 0.9163 |
| 026_8102_00293360 | Kidney | 8102 | LB996-RCC | 456 | 5.484542 | 0.855 | 0.901 | 0.954 | 0.9116 | 0.9765 | 0.98 | 0.958 | 0.9786 | 0.9921 |
| 026_1119_00290901 | Kidney | 1119 | SN-12C | 456 | 5.586587 | 0.818 | 0.749 | 0.747 | 0.783 | 0.8069 | 0.856 | 0.9038 | 0.9508 | 0.9573 |
| 026_626_00290810 | Kidney | 626 | BFTC-909 | 456 | 5.753321 | 0.799 | 0.854 | 0.903 | 0.9293 | 0.9289 | 0.92 | 0.9333 | 0.9322 | 0.9535 |
| 026_8005_00266530 | Kidney | 8005 | A498 | 456 | 5.843211 | 0.594 | 0.917 | 1.003 | 1.0079 | 0.9307 | 0.996 | 1.0002 | 1.0033 | 0.9941 |
| 026_8157_00296471 | Kidney | 8157 | RXF393 | 456 | 6.166218 | 0.853 | 0.878 | 0.91 | 0.8924 | 0.9071 | 0.932 | 0.9081 | 0.9505 | 0.9889 |
| 026_8102_00253000 | Kidney | 8102 | LB996-RCC | 456 | 6.306723 | 0.959 | 0.873 | 0.878 | 0.9741 | 0.9596 | 1.025 | 0.9525 | 0.9849 | 0.9931 |
| 026_8006_00263880 | Kidney | 8006 | A704 | 456 | 6.969306 | 1.351 | 0.929 | 1.157 | 0.9881 | 1.0206 | 0.957 | 1.0009 | 0.9583 | 0.9931 |
| 026_8152_00256190 | Kidney | 8152 | RCC10RGB | 456 | 7.15535 | 1.178 | 0.835 | 1.176 | 0.846 | 0.8683 | 1.123 | 1.1733 | 1.1056 | 1.0876 |
| 026_8005_00296380 | Kidney | 8005 | A498 | 456 | 8.190783 | 1.022 | 1.025 | 1.024 | 1.0158 | 1.03 | 1.032 | 1.0128 | 1.0239 | 1.0104 |
| 026_233_00277420 | Leukemia | 233 | SIG-M5 | 456 | 5.883853 | 0.228 | 0.243 | 0.233 | 0.2401 | 0.2362 | 0.247 | 0.2641 | 0.2732 | 0.4405 |
| 026_217_00277380 | Leukemia | 217 | OCI-AML2 | 456 | −1.42786 | 0.09 | 0.102 | 0.106 | 0.1256 | 0.1044 | 0.132 | 0.3277 | 0.8333 | 0.8618 |
| 026_179_00314500 | Leukemia | 179 | KMOE-2 | 456 | 0.249088 | 0.13 | 0.135 | 0.138 | 0.1591 | 0.3658 | 0.608 | 0.865 | 0.8967 | 1.0615 |
| 026_214_00285590 | Leukemia | 214 | NB-4 | 456 | 0.011745 | 0.18 | 0.323 | 0.315 | 0.3611 | 0.4215 | 0.592 | 0.8144 | 0.8865 | 0.9464 |
| 026_168_00280410 | Leukemia | 168 | JURL-MK1 | 456 | 0.181843 | 0.145 | 0.179 | 0.186 | 0.2526 | 0.4638 | 0.727 | 0.9379 | 0.904 | 0.9907 |
| 026_194_00280680 | Leukemia | 194 | ML-2 | 456 | 0.294246 | 0.418 | 0.395 | 0.379 | 0.4439 | 0.4739 | 0.633 | 0.7874 | 0.8519 | 1.0223 |
| 026_186_00280670 | Leukemia | 186 | LAMA-84 | 456 | 0.295979 | 0.152 | 0.15 | 0.191 | 0.3623 | 0.6147 | 0.774 | 0.777 | 0.8716 | 0.8816 |
| 026_234_00314650 | Leukemia | 234 | SKM-1 | 456 | 0.349518 | 0.37 | 0.347 | 0.369 | 0.4439 | 0.4995 | 0.57 | 0.729 | 0.9566 | 1.2103 |
| 026_221_00280300 | Leukemia | 221 | OCI-M1 | 456 | 0.656393 | 0.183 | 0.235 | 0.344 | 0.5052 | 0.5942 | 0.759 | 0.8267 | 0.8418 | 1.1212 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_260_00280760 | Leukemia | 260 | KO52 | 456 | 0.674413 | 0.348 | 0.376 | 0.357 | 0.3446 | 0.4195 | 0.753 | 0.7217 | 0.7637 | 1.0996 |
| 026_45_00274530 | Leukemia | 45 | HL-60 | 456 | 0.756274 | 0.344 | 0.389 | 0.403 | 0.4669 | 0.6154 | 0.78 | 0.9211 | 0.9579 | 1.0107 |
| 026_218_00279140 | Leukemia | 218 | OCI-AML3 | 456 | 0.868641 | 0.368 | 0.38 | 0.401 | 0.4571 | 0.5459 | 0.76 | 0.8359 | 0.9311 | 0.9403 |
| 026_219_00280290 | Leukemia | 219 | OCI-AML5 | 456 | 0.879404 | 0.245 | 0.404 | 0.427 | 0.4943 | 0.686 | 0.712 | 0.8112 | 0.9498 | 0.9021 |
| 026_199_00314510 | Leukemia | 199 | MOLT-13 | 456 | 0.892109 | 0.227 | 0.339 | 0.454 | 0.5097 | 0.5774 | 0.766 | 0.8101 | 0.9633 | 1.1416 |
| 026_226_00280310 | Leukemia | 226 | PL-21 | 456 | 0.938066 | 0.406 | 0.425 | 0.463 | 0.4834 | 0.5377 | 0.657 | 0.7338 | 0.7978 | 0.8482 |
| 026_8141_00274380 | Leukemia | 8141 | NOMO-1 | 456 | 1.040856 | 0.375 | 0.445 | 0.435 | 0.4798 | 0.5465 | 0.636 | 0.9597 | 0.9214 | 0.9288 |
| 026_8069_00279180 | Leukemia | 8069 | HAL-01 | 456 | 1.147185 | 0.349 | 0.345 | 0.454 | 0.634 | 0.6764 | 1.103 | 0.7322 | 0.8261 | 1.0097 |
| 026_68_00273640 | Leukemia | 68 | MV-4-11 | 456 | 1.155322 | 0.061 | 0.367 | 0.445 | 0.5488 | 0.6586 | 0.777 | 0.8697 | 0.9167 | 1.045 |
| 026_175_00282940 | Leukemia | 175 | KARPAS-620 | 456 | 1.190853 | 0.562 | 0.517 | 0.444 | 0.6051 | 0.7411 | 0.916 | 0.9551 | 1.1003 | 1.0193 |
| 026_89_00278880 | Leukemia | 89 | MEG-01 | 456 | 1.211836 | 0.223 | 0.376 | 0.433 | 0.6062 | 0.6931 | 0.86 | 0.9075 | 0.9993 | 1.0376 |
| 026_8017_00279150 | Leukemia | 8017 | BV-173 | 456 | 1.464827 | 0.147 | 0.454 | 0.57 | 0.8503 | 0.5534 | 0.638 | 0.7679 | 0.8629 | 1.0089 |
| 026_225_00277400 | Leukemia | 225 | PF-382 | 456 | 1.646942 | 0.317 | 0.403 | 0.525 | 0.6985 | 0.7396 | 0.932 | 0.9611 | 0.9018 | 1.0833 |
| 026_285_00282960 | Leukemia | 285 | KY821A3 | 456 | 1.656661 | 0.422 | 0.426 | 0.445 | 0.6672 | 0.7837 | 0.935 | 1.0015 | 1.0293 | 1.0583 |
| 026_8008_00280620 | Leukemia | 8008 | ALL-PO | 456 | 1.659142 | 0.143 | 0.469 | 0.549 | 0.6225 | 0.6911 | 0.725 | 0.845 | 0.8482 | 1.019 |
| 026_177_00276860 | Leukemia | 177 | KE-37 | 456 | 1.711407 | 0.195 | 0.451 | 0.523 | 0.6745 | 0.9068 | 0.897 | 0.9087 | 0.9169 | 1.0477 |
| 026_126_00280270 | Leukemia | 126 | GDM-1 | 456 | 1.723253 | 0.297 | 0.444 | 0.595 | 0.682 | 0.7944 | 0.786 | 0.9053 | 0.9081 | 0.8666 |
| 026_261_00274440 | Leukemia | 261 | MY-M12 | 456 | 1.811821 | 0.395 | 0.471 | 0.59 | 0.6443 | 0.7461 | 0.832 | 0.8778 | 1.0023 | 1.0569 |
| 026_201_00277390 | Leukemia | 201 | MOLT-16 | 456 | 1.821177 | 0.276 | 0.43 | 0.578 | 0.7394 | 0.7801 | 0.857 | 0.9379 | 1.0322 | 0.9678 |
| 026_148_00277330 | Leukemia | 148 | CMK | 456 | 1.894859 | 0.275 | 0.484 | 0.637 | 0.6101 | 0.744 | 0.771 | 0.9002 | 0.8949 | 0.8668 |
| 026_28_00280320 | Leukemia | 28 | SUP-B15 | 456 | 1.921651 | 0.261 | 0.506 | 0.579 | 0.7214 | 0.7165 | 0.82 | 0.908 | 0.9679 | 0.9913 |
| 026_190_00287920 | Leukemia | 190 | ME-1 | 456 | 1.924633 | 0.611 | 0.596 | 0.587 | 0.5806 | 0.5987 | 0.684 | 0.7906 | 0.8581 | 0.9106 |
| 026_8150_00273700 | Leukemia | 8150 | QIMR-WIL | 456 | 1.928333 | 0.441 | 0.546 | 0.595 | 0.6574 | 0.7011 | 0.771 | 0.852 | 0.962 | 0.9148 |
| 026_8156_00273710 | Leukemia | 8156 | RPMI-8866 | 456 | 1.939976 | 0.339 | 0.474 | 0.598 | 0.694 | 0.7428 | 0.867 | 0.9518 | 0.9936 | 0.9682 |
| 026_161_00277350 | Leukemia | 161 | HC-1 | 456 | 1.948766 | 0.447 | 0.517 | 0.568 | 0.6165 | 0.6342 | 0.768 | 0.7642 | 0.9074 | 1.0155 |
| 026_195_00279120 | Leukemia | 195 | MOLM-13 | 456 | 1.961596 | 0.394 | 0.455 | 0.518 | 0.6868 | 0.817 | 0.872 | 0.9157 | 0.983 | 1.0345 |
| 026_209_00279130 | Leukemia | 209 | NALM-6 | 456 | 2.000316 | 0.14 | 0.471 | 0.592 | 0.6915 | 0.7587 | 0.808 | 0.8658 | 0.9205 | 0.9768 |
| 026_127_00278810 | Leukemia | 127 | CESS | 456 | 2.000616 | 0.342 | 0.505 | 0.625 | 0.6869 | 0.7679 | 0.843 | 0.9355 | 0.9565 | 0.9827 |
| 026_8196_00278790 | Leukemia | 8186 | 697 | 456 | 2.032634 | 0.337 | 0.476 | 0.61 | 0.7249 | 0.8167 | 0.885 | 1.0481 | 1.0695 | 1.0723 |
| 026_223_00276841 | Leukemia | 223 | P12-ICHIKAWA | 456 | 2.094412 | 0.266 | 0.472 | 0.62 | 1.0139 | 0.9551 | 0.864 | 0.9219 | 1.0283 | 0.907 |
| 026_157_00279291 | Leukemia | 157 | DND-41 | 456 | 2.109279 | 0.354 | 0.498 | 0.624 | 0.7174 | 0.8189 | 0.89 | 0.9495 | 0.9928 | 1.0144 |
| 026_174_00276850 | Leukemia | 174 | KARPAS-45 | 456 | 2.156973 | 0.368 | 0.541 | 0.63 | 0.778 | 0.8566 | 0.998 | 1.0142 | 0.9561 | 0.9985 |
| 026_223_00274461 | Leukemia | 223 | P12-ICHIKAWA | 456 | 2.170641 | 0.274 | 0.465 | 0.567 | 0.909 | 0.9914 | 1.041 | 1.0272 | 0.9908 | 1.0038 |
| 026_231_00277410 | Leukemia | 231 | RPMI-8402 | 456 | 2.171412 | 0.292 | 0.525 | 0.673 | 0.8379 | 0.894 | 0.956 | 1.0525 | 1.0069 | 1.0163 |
| 026_176_00278840 | Leukemia | 176 | KCL-22 | 456 | 2.178418 | 0.342 | 0.551 | 0.66 | 0.7185 | 0.7521 | 0.822 | 0.8942 | 1.034 | 0.9817 |
| 026_198_00279320 | Leukemia | 198 | MOLP-8 | 456 | 2.182175 | 0.422 | 0.613 | 0.604 | 0.6789 | 0.7123 | 0.753 | 0.8469 | 0.8678 | 0.9555 |
| 026_35_00274541 | Leukemia | 35 | MOLT-4 | 456 | 2.185513 | 0.368 | 0.518 | 0.657 | 0.7557 | 0.8266 | 0.893 | 0.9057 | 1.0649 | 1.0505 |
| 26_256_00273800 | Leukemia | 256 | U266B1 | 456 | 2.191112 | 0.423 | 0.53 | 0.596 | 0.6351 | 0.7316 | 0.782 | 0.8701 | 0.9616 | 0.9089 |
| 026_41_00278850 | Leukemia | 41 | KG-1 | 456 | 2.260524 | 0.445 | 0.507 | 0.569 | 0.7321 | 0.8443 | 0.89 | 0.9006 | 0.9237 | 0.9648 |
| 026_38_00278900 | Leukemia | 38 | THP-1 | 456 | 2.296961 | 0.389 | 0.568 | 0.692 | 0.7667 | 0.7899 | 0.895 | 0.9332 | 0.9649 | 0.9902 |
| 026_153_00277340 | Leukemia | 153 | CTV-1 | 456 | 2.301756 | 0.308 | 0.563 | 0.682 | 0.7882 | 0.8949 | 0.972 | 1.0362 | 1.0213 | 1.0568 |
| 26_284_00273770 | Leukemia | 284 | KY821 | 456 | 2.31293 | 0.459 | 0.524 | 0.599 | 0.642 | 0.7677 | 0.831 | 0.9119 | 0.9596 | 0.9938 |
| 026_256_00304780 | Leukemia | 256 | U266B1 | 456 | 2.374209 | 0.453 | 0.543 | 0.608 | 0.6629 | 0.7604 | 0.806 | 0.9117 | 0.9547 | 0.9487 |
| 026_8033_00279160 | Leukemia | 8033 | DEL | 456 | 2.390133 | 0.433 | 0.595 | 0.647 | 0.7617 | 0.7648 | 0.851 | 0.9096 | 0.9116 | 0.9641 |
| 026_227_00314640 | Leukemia | 227 | RCH-ACV | 456 | 2.405281 | 0.39 | 0.571 | 0.742 | 0.8517 | 0.9043 | 0.946 | 0.9917 | 1.0175 | 1.1197 |
| 026_33_00274521 | Leukemia | 33 | CCRF-CEM | 456 | 2.408403 | 0.354 | 0.606 | 0.685 | 0.7594 | 0.8191 | 0.904 | 0.9597 | 0.9629 | 1.0269 |
| 026_141_00276820 | Leukemia | 141 | K-562 | 456 | 2.457405 | 0.51 | 0.504 | 0.624 | 0.8081 | 0.8379 | 1.163 | 0.9404 | 1.0057 | 1.0193 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_8137_00273680 | Leukemia | 8137 | NKM-1 | 456 | 2.543263 | 0.464 | 0.601 | 0.622 | 0.6486 | 0.7425 | 0.801 | 0.8993 | 0.9038 | 0.9449 |
| 026_36_00274550 | Leukemia | 36 | Reh | 456 | 2.569808 | 0.418 | 0.628 | 0.742 | 0.8367 | 0.88 | 0.896 | 0.9262 | 0.8979 | 0.9849 |
| 026_8042_00285400 | Leukemia | 8042 | EoL-1-cell | 456 | 2.64235 | 0.232 | 0.569 | 0.651 | 0.7409 | 0.7743 | 0.894 | 0.8333 | 0.905 | 0.9094 |
| 026_281_00273690 | Leukemia | 281 | P30/OHK | 456 | 2.804566 | 0.473 | 0.654 | 0.769 | 0.9121 | 0.8865 | 1.022 | 1.0746 | 1.0233 | 1.0407 |
| 026_59_00278820 | Leukemia | 59 | J.RT3-T3.5 | 456 | 2.830428 | 0.457 | 0.659 | 0.795 | 0.8429 | 0.9259 | 1.002 | 1.0587 | 0.9873 | 1.1396 |
| 026_164_00277360 | Leukemia | 164 | HEL | 456 | 2.835925 | 0.426 | 0.745 | 0.939 | 0.9081 | 1.0194 | 0.987 | 1.0611 | 1.0159 | 0.9841 |
| 026_183_00277370 | Leukemia | 183 | L-363 | 456 | 2.864138 | 0.468 | 0.685 | 0.82 | 0.9025 | 0.9548 | 1.046 | 1.0249 | 0.9812 | 1.02 |
| 026_90_00282840 | Leukemia | 90 | KU812 | 456 | 2.874545 | 0.446 | 0.74 | 0.806 | 0.917 | 0.9589 | 0.978 | 0.9646 | 1.0111 | 1.0409 |
| 026_27_00278890 | Leukemia | 27 | RS4;11 | 456 | 2.914096 | 0.47 | 0.684 | 0.809 | 0.8895 | 0.9144 | 0.975 | 0.9547 | 0.9619 | 1.0194 |
| 026_167_00314490 | Leukemia | 167 | JURKAT | 456 | 2.954834 | 0.503 | 0.713 | 0.842 | 0.9399 | 0.9544 | 0.985 | 0.9987 | 1.034 | 1.0702 |
| 026_181_00278860 | Leukemia | 181 | KOPN-8 | 456 | 2.957727 | 0.484 | 0.669 | 0.731 | 0.7843 | 0.8662 | 0.92 | 0.9473 | 0.9339 | 0.9555 |
| 026_8155_00309110 | Leukemia | 277 | RPMI 8226 | 456 | 2.959542 | 0.648 | 0.63 | 0.689 | 0.8376 | 0.888 | 0.99 | 0.9938 | 1.0182 | 1.0157 |
| 026_8041_00280640 | Leukemia | 8041 | EM-2 | 456 | 3.022652 | 0.557 | 0.687 | 0.614 | 0.634 | 0.706 | 0.679 | 0.8613 | 0.8617 | 1.9538 |
| 026_142_00279280 | Leukemia | 142 | ALL-SIL | 456 | 3.085854 | 0.187 | 0.624 | 0.769 | 0.7092 | 0.7975 | 0.937 | 0.9525 | 0.9717 | 0.8276 |
| 026_277_00280420 | Leukemia | 277 | RPMI_8226 | 456 | 3.102844 | 0.659 | 0.636 | 0.566 | 0.6117 | 0.6594 | 0.722 | 0.8693 | 0.9508 | 0.9057 |
| 026_180_00279310 | Leukemia | 180 | KMS-12-BM | 456 | 3.125028 | 0.512 | 0.704 | 0.788 | 0.8503 | 0.8703 | 0.949 | 0.905 | 0.9806 | 0.9931 |
| 026_8066_00279170 | Leukemia | 8066 | GR-ST | 456 | 3.192114 | 0.532 | 0.681 | 0.762 | 0.8318 | 0.8448 | 0.865 | 1.0258 | 0.9609 | 0.9989 |
| 26_283_00273780 | Leukemia | 283 | LC4-1 | 456 | 3.243599 | 0.592 | 0.732 | 0.916 | 0.9522 | 1.0268 | 1.045 | 0.9517 | 1.0295 | 1.0135 |
| 026_114_00273650 | Leukemia | 114 | SUP-T1 | 456 | 3.397019 | 0.637 | 0.807 | 0.908 | 1.0154 | 0.984 | 1.031 | 0.99 | 0.9877 | 1.0134 |
| 026_138_00287901 | Leukemia | 138 | Loucy | 456 | 3.501279 | 0.289 | 0.749 | 0.772 | 0.942 | 0.9225 | 0.948 | 0.9678 | 0.9653 | 1.0654 |
| 026_8014_00282911 | Leukemia | 8014 | BE-13 | 456 | 3.615529 | 0.68 | 0.757 | 0.965 | 1.1246 | 1.0528 | 1.075 | 1.0884 | 1.0694 | 1.1037 |
| 26_274_00273860 | Leukemia | 274 | BALL-1 | 456 | 3.704228 | 0.65 | 0.709 | 0.777 | 0.8768 | 0.9725 | 0.983 | 0.9819 | 0.9839 | 0.9978 |
| 026_222_00280480 | Leukemia | 228 | OPM-2 | 456 | 3.757754 | 0.681 | 0.619 | 0.771 | 0.9443 | 0.8789 | 1.073 | 0.9014 | 0.9191 | 0.9051 |
| 026_8164_00283540 | Leukemia | 8164 | SK-MM-2 | 456 | 3.7 | 0.669 | 0.788 | 0.861 | 0.8903 | 0.938 | 0.941 | 1.0087 | 0.9277 | 0.9972 |
| 026_166_00278830 | Leukemia | 166 | JJN-3 | 456 | 3.901981 | 0.63636 | 0.791 | 0.85 | 0.8566 | 0.8711 | 0.916 | 0.9455 | 0.9892 | 1.057 |
| 026_230_00282970 | Leukemia | 230 | ROS-50 | 456 | 4.130585 | 0.741 | 0.775 | 0.805 | 0.9413 | 0.9813 | 1.11 | 1.1334 | 1.0559 | 0.999 |
| 026_159_00314480 | Leukemia | 159 | EJM | 456 | 4.251735 | 0.714 | 0.845 | 0.899 | 0.9099 | 1.0285 | 0.923 | 1.0677 | 1.0768 | 1.0543 |
| 026_278_00304730 | Leukemia | 278 | KMS-12-PE | 456 | 4.269602 | 0.765 | 0.814 | 0.84 | 1.0641 | 0.988 | 1.023 | 1.0045 | 1.0284 | 1.0665 |
| 026_8219_00282850 | Leukemia | 8219 | Mo-T | 456 | 4.313664 | 0.73 | 0.825 | 0.804 | 0.9425 | 0.9233 | 1.033 | 0.8454 | 1.1551 | 1.0561 |
| 026_279_00274450 | Leukemia | 279 | P31/FUJ | 456 | 4.386897 | 0.705 | 0.805 | 0.799 | 0.819 | 0.8632 | 1.043 | 1.0364 | 0.9822 | 1.0363 |
| 026_171_00285190 | Leukemia | 171 | KARPAS-231 | 456 | 4.404825 | 0.703 | 0.9 | 0.906 | 0.9339 | 0.9295 | 0.904 | 0.9725 | 0.9496 | 0.9164 |
| 026_244_00273660 | Leukemia | 244 | TALL-1 | 456 | 4.411016 | 0.698 | 0.758 | 0.785 | 0.8345 | 0.8593 | 0.861 | 1.0445 | 1.0026 | 1.0194 |
| 026_158_00291340 | Leukemia | 158 | EHEB | 456 | 4.509743 | 0.665 | 0.745 | 0.765 | 0.7841 | 0.8282 | 0.839 | 0.92 | 0.9348 | 1.0344 |
| 026_134_00278800 | Leukemia | 134 | ARH-77 | 456 | 4.545002 | 0.781 | 0.856 | 0.96 | 0.848 | 1.0568 | 1.029 | 1.0104 | 1.0156 | 1.0086 |
| 026_246_00273670 | Leukemia | 246 | U-698-M | 456 | 4.580953 | 0.754 | 0.891 | 0.936 | 0.9419 | 0.9607 | 0.937 | 1.032 | 0.9352 | 1.0229 |
| 026_8113_00280440 | Leukemia | 8113 | MHH-CALL-2 | 456 | 4.648418 | 0.771 | 0.883 | 0.929 | 0.9704 | 0.9337 | 0.987 | 1.0345 | 1.0223 | 1.0471 |
| 026_159_00311690 | Leukemia | 159 | EJM | 456 | 4.699945 | 0.746 | 0.894 | 0.921 | 0.9275 | 0.9393 | 0.941 | 0.9575 | 0.9338 | 0.9675 |
| 026_159_00282920 | Leukemia | 159 | EJM | 456 | 4.832393 | 0.746 | 0.976 | 1.016 | 0.9859 | 1.0015 | 1.002 | 1.1587 | 1.1041 | 1.0548 |
| 026_8115_00280450 | Leukemia | 8115 | MN-60 | 456 | 4.861437 | 0.826 | 0.804 | 0.822 | 1.0586 | 0.9555 | 0.947 | 1.0471 | 1.128 | 1.0314 |
| 026_204_00280460 | Leukemia | 204 | MONO-MAC-6 | 456 | 4.946039 | 0.736 | 0.802 | 0.771 | 0.8409 | 0.8712 | 0.833 | 0.8634 | 1.0677 | 0.855 |
| 026_8117_00280470 | Leukemia | 8117 | MUTZ-1 | 456 | 5.304526 | 0.823 | 0.984 | 1.063 | 1.051 | 1.0142 | 1.007 | 0.9986 | 0.9654 | 0.9525 |
| 026_188_00282930 | Leukemia | 188 | LP-1 | 456 | 5.373997 | 0.831 | 0.887 | 0.972 | 0.8808 | 0.9105 | 0.886 | 0.9533 | 0.9576 | 1.138 |
| 026_8081_00285580 | Leukemia | 8081 | JVM-3 | 456 | 5.581328 | 0.884 | 0.904 | 0.907 | 0.9131 | 1.01 | 1.097 | 1.0593 | 0.9629 | 1.0333 |
| 026_159_00309070 | Leukemia | 159 | EJM | 456 | 5.810283 | 0.882 | 0.986 | 0.998 | 1.0992 | 1.0048 | 1.045 | 1.0126 | 1.024 | 1.0649 |
| 026_8080_00280660 | Leukemia | 8080 | JVM-2 | 456 | 5.982881 | 0.867 | 0.876 | 0.901 | 0.8865 | 0.9235 | 0.909 | 0.9782 | 0.8964 | 0.9789 |
| 026_278_00306920 | Leukemia | 278 | KMS-12-PE | 456 | 6.629507 | 0.971 | 0.92 | 0.95 | 0.9554 | 0.9046 | 0.905 | 0.9657 | 1.0243 | 0.9236 |
| 026_8010_00280630 | Leukemia | 8010 | ATN-1 | 456 | 7.14863 | 1.03 | 0.958 | 0.835 | 0.8896 | 0.8651 | 0.907 | 0.9392 | 0.8582 | 0.9763 |
| 26_262_00273790 | Leukemia | 262 | MLMA | 456 | 7.68552 | 0.485 | 1.033 | 1.077 | 1.0216 | 1.0341 | 0.962 | 1.0378 | 0.9821 | 1.0245 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_278_00282950 | Leukemia | 278 | KMS-12-PE | 456 | 7.74945 | 0.958 | 1.101 | 1.04 | 1.1177 | 1.0046 | 1.029 | 1.0272 | 1.0311 | 1.0037 |
| 026_649_00264910 | Liver | 649 | Hep3B2.1-7 | 456 | 0.30042 | 0.134 | 0.098 | 0.087 | 0.1121 | 0.2203 | 0.601 | 0.8432 | 0.8926 | 0.9089 |
| 026_658_00262810 | Liver | 658 | JHH-1 | 456 | −0.185127 | 0.054 | 0.329 | 0.515 | 0.3993 | 0.5194 | 0.524 | 0.6608 | 0.6499 | 0.6863 |
| 026_649_00266180 | Liver | 649 | Hep3B2.1-7 | 456 | −0.037335 | 0.073 | 0.105 | 0.093 | 0.0908 | 0.1037 | 0.202 | 0.8123 | 0.9207 | 1.007 |
| 026_667_00273550 | Liver | 667 | HuH-7 | 456 | 1.289162 | 0.279 | 0.565 | 0.539 | 0.5535 | 0.7134 | 0.77 | 0.8626 | 0.9675 | 0.9662 |
| 026_659_00255780 | Liver | 659 | JHH-2 | 456 | 1.758427 | 0.283 | 0.473 | 0.657 | 0.7149 | 0.551 | 0.819 | 0.8858 | 0.8891 | 1.0202 |
| 026_643_00266460 | Liver | 643 | SNU-398 | 456 | 2.578054 | 0.415 | 0.687 | 0.643 | 0.6854 | 0.6879 | 0.717 | 0.7896 | 0.8076 | 0.9193 |
| 026_667_00269210 | Liver | 667 | HuH-7 | 456 | 2.760591 | 0.501 | 0.59 | 0.665 | 0.6852 | 0.6886 | 0.781 | 0.95 | 1.0287 | 1.0142 |
| 026_647_00269110 | Liver | 647 | SNU-387 | 456 | 2.930627 | 0.494 | 0.772 | 0.829 | 0.9402 | 0.9686 | 1.046 | 1.0372 | 1.0223 | 1.2144 |
| 026_661_00252500 | Liver | 661 | JHH-7 | 456 | 3.286573 | 0.539 | 0.889 | 0.794 | 0.8777 | 1.0776 | 0.953 | 0.9918 | 1.037 | 0.9476 |
| 026_643_00263980 | Liver | 643 | SNU-398 | 456 | 3.293137 | 0.487 | 0.768 | 0.854 | 0.8235 | 0.8763 | 0.883 | 0.9616 | 1.068 | 1.0718 |
| 026_642_00308440 | Liver | 642 | C3A | 456 | 3.554832 | 0.587 | 0.68 | 0.706 | 0.7687 | 0.817 | 0.878 | 0.9697 | 0.9574 | 0.9245 |
| 026_648_00258350 | Liver | 648 | SNU-423 | 456 | 3.576003 | 0.139 | 0.699 | 0.902 | 0.9157 | 0.9485 | 0.909 | 0.9218 | 0.9469 | 1.0028 |
| 026_656_00252510 | Liver | 656 | JHH-4 | 456 | 3.61979 | 0.701 | 0.653 | 0.631 | 0.8187 | 0.7968 | 0.977 | 0.9161 | 0.9897 | 0.9288 |
| 026_660_00252490 | Liver | 660 | JHH-6 | 456 | 3.831185 | 0.696 | 0.88 | 1.034 | 0.9294 | 0.9465 | 1.04 | 0.9417 | 1.0528 | 0.952 |
| 026_644_00252750 | Liver | 644 | SNU-449 | 456 | 4.40481 | 0.664 | 0.733 | 0.764 | 0.7954 | 0.8597 | 0.896 | 0.9485 | 0.9457 | 0.9162 |
| 026_644_00306170 | Liver | 644 | SNU-449 | 456 | 6.450644 | 0.96 | 0.961 | 0.745 | 1.0716 | 1.0197 | 1.08 | 0.991 | 0.9007 | 0.9369 |
| 26_646_00314060 | Liver | 646 | SNU-475 | 456 | 6.501654 | 0.181 | 0.97 | 0.971 | 0.9863 | 1.0061 | 1.007 | 1.0271 | 1.0202 | 0.057 |
| 026_654_00255800 | Liver | 654 | SK-HEP-1 | 456 | 6.515068 | 0.927 | 0.956 | 0.961 | 0.9827 | 0.9589 | 0.98 | 0.9783 | 0.9726 | 0.9998 |
| 026_668_00252690 | Liver | 668 | HLE | 456 | 7.25378 | 0.434 | 1.006 | 1.087 | 0.9897 | 1.1103 | 0.964 | 1.006 | 1.106 | 0.9541 |
| 026_662_00252460 | Liver | 662 | huH-1 | 456 | 7.722693 | 0.466 | 1.165 | 1.072 | 1.0401 | 1.0408 | 1.136 | 1.015 | 1.123 | 0.9778 |
| 026_645_00306160 | Liver | 645 | SNU-182 | 456 | 7.852049 | 1.105 | 1.061 | 1.063 | 1.0055 | 1.0268 | 1.053 | 1.0365 | 1.0318 | 1.0842 |
| 026_642_00252670 | Liver | 642 | C3A | 456 | 7.864415 | 0.386 | 1.1 | 1.007 | 1.108 | 0.9463 | 1.051 | 0.9803 | 1.029 | 0.9218 |
| 026_830_00304760 | Lung | 830 | NCI-H2135 | 456 | −0.374655 | 0.298 | 0.262 | 0.246 | 0.3049 | 0.3692 | 0.528 | 0.7269 | 0.8905 | 0.977 |
| 026_698_00300170 | Lung | 698 | NCI-H524 | 456 | 2.279246 | 0.443 | 0.506 | 0.63 | 0.8741 | 0.9302 | 1.005 | 1.0131 | 1.0304 | 1.0567 |
| 026_672_00314460 | Lung | 672 | NCI-H510A | 456 | 2.367223 | 0.323 | 0.585 | 0.763 | 0.783 | 0.8906 | 0.969 | 0.9972 | 1.1809 | 1.0131 |
| 026_761_00300410 | Lung | 761 | COR-L279 | 456 | 3.131703 | 0.559 | 0.745 | 0.868 | 0.9821 | 1.0079 | 1.06 | 1.0144 | 1.0182 | 1.0709 |
| 026_726_00304770 | Lung | 726 | NCI-H2171 | 456 | 3.185965 | 0.524 | 0.729 | 0.842 | 0.8655 | 0.9088 | 0.871 | 1.0252 | 0.9207 | 1.129 |
| 026_740_00302760 | Lung | 740 | NCI-H82 | 456 | 3.210581 | 0.542 | 0.755 | 0.865 | 0.9592 | 1.0522 | 0.888 | 0.9137 | 1.004 | 1.0151 |
| 026_787_00302910 | Lung | 787 | SBC-3 | 456 | 3.410219 | 0.582 | 0.655 | 0.694 | 0.802 | 0.8502 | 0.902 | 0.9485 | 0.9451 | 0.9885 |
| 026_695_00300150 | Lung | 695 | NCI-H211 | 456 | 3.515811 | 0.644 | 0.645 | 0.719 | 0.8327 | 0.8177 | 0.933 | 0.9519 | 0.9812 | 1.0305 |
| 026_721_00302860 | Lung | 721 | NCI-H2029 | 456 | 3.591515 | 0.606 | 0.8 | 0.891 | 0.9011 | 0.8579 | 0.931 | 0.9429 | 1.0032 | 1.0011 |
| 026_776_00303250 | Lung | 776 | MS-1-L | 456 | 3.614256 | 0.642 | 0.767 | 0.855 | 0.8458 | 1.1115 | 0.929 | 1.0414 | 1.0285 | 1.162 |
| 026_8197_00304741 | Lung | 8197 | LU-139 | 456 | 3.667637 | 0.66 | 0.84 | 0.901 | 1.0158 | 0.9097 | 0.912 | 1.0844 | 1.1048 | 1.0641 |
| 026_702_00302900 | Lung | 702 | NCI-H847 | 456 | 3.686524 | 0.818 | 0.707 | 0.668 | 0.6815 | 0.7184 | 0.743 | 0.7999 | 0.9145 | 0.9524 |
| 026_8203_00309050 | Lung | 8203 | IST-SL1 | 456 | 3.697133 | 0.635 | 0.801 | 0.87 | 0.931 | 0.9112 | 1 | 1.0127 | 0.9507 | 1.0704 |
| 026_724_00300140 | Lung | 724 | NCI-H2081 | 456 | 3.857634 | 0.623 | 0.866 | 0.895 | 0.9027 | 0.9349 | 0.948 | 0.969 | 0.9681 | 1.0072 |
| 026_765_00300050 | Lung | 765 | DMS 273 | 456 | 3.890251 | 0.702 | 0.844 | 0.904 | 0.9648 | 1.028 | 0.968 | 1.0795 | 1.0165 | 1.0825 |
| 026_829_00305160 | Lung | 829 | NCI-H2110 | 456 | 3.972695 | 0.67 | 0.694 | 0.776 | 0.8765 | 0.8765 | 0.946 | 1.0573 | 0.91 | 0.9398 |
| 026_742_00303230 | Lung | 742 | DMS 53 | 456 | 3.990104 | 0.711 | 0.802 | 0.867 | 0.9734 | 1.0075 | 1.037 | 1.0307 | 1.0204 | 1.0405 |
| 026_710_00316710 | Lung | 710 | NCI-H1341 | 456 | 4.024081 | 0.591 | 0.852 | 0.7 | 0.7407 | 0.8259 | 0.789 | 0.8069 | 0.8386 | 0.865 |
| 026_738_00302800 | Lung | 738 | NCI-H446 | 456 | 4.043153 | 0.692 | 0.871 | 0.917 | 1.0421 | 0.9341 | 0.915 | 1.0657 | 0.9649 | 1.0382 |
| 026_751_00308570 | Lung | 751 | NCI-H209 | 456 | 4.061511 | 0.657 | 0.848 | 0.89 | 0.9403 | 0.8939 | 0.91 | 0.9316 | 0.9524 | 0.9513 |
| 026_716_00298900 | Lung | 716 | NCI-H1876 | 456 | 4.083 | 0.744 | 0.866 | 0.936 | 0.9448 | 0.9881 | 0.979 | 0.9782 | 0.9994 | 1.0261 |
| 026_725_00303280 | Lung | 725 | NCI-H2141 | 456 | 4.09696 | 0.711 | 0.842 | 0.928 | 0.9702 | 0.9155 | 0.924 | 1.0044 | 1.0101 | 0.9559 |
| 026_688_00302810 | Lung | 688 | SW 1271 | 456 | 4.124557 | 0.602 | 0.761 | 0.79 | 0.8093 | 0.807 | 0.823 | 0.896 | 0.8782 | 0.9341 |
| 026_720_00302380 | Lung | 720 | NCI-H1994 | 456 | 4.130367 | 0.696 | 0.694 | 0.73 | 0.8114 | 0.9245 | 0.935 | 0.9484 | 0.9393 | 0.9738 |
| 026_811_00311720 | Lung | 811 | NCI-H1435 | 456 | 4.138326 | 0.635 | 0.803 | 0.855 | 0.8503 | 0.8571 | 0.89 | 0.8912 | 0.955 | 0.9956 |
| 026_704_00300250 | Lung | 704 | NCI-H1048 | 456 | 4.178908 | 0.166 | 0.762 | 0.867 | 0.8914 | 0.9318 | 0.923 | 0.9201 | 1.0122 | 0.9635 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_746_00302780 | Lung | 746 | SHP-77 | 456 | 4.20487 | 0.79 | 0.843 | 0.955 | 1.029 | 0.9896 | 1.021 | 1.0111 | 0.9931 | 1.0025 |
| 026_829_00311740 | Lung | 829 | NCI-H2110 | 456 | 4.22315 | 0.739 | 0.83 | 0.914 | 0.9675 | 0.9597 | 0.983 | 0.9791 | 1.032 | 0.9995 |
| 026_736_00300181 | Lung | 736 | NCI-H69 | 456 | 4.26966 | 0.798 | 0.87 | 0.945 | 1.0535 | 1.0472 | 1.143 | 1.0521 | 1.0846 | 1.1743 |
| 026_724_00303270 | Lung | 724 | NCI-H2081 | 456 | 4.274134 | 0.708 | 0.95 | 1.023 | 0.9666 | 1.0134 | 0.99 | 1.0037 | 1.0388 | 1.0531 |
| 026_714_00300260 | Lung | 714 | NCI-H1694 | 456 | 4.276996 | 0.701 | 0.831 | 0.843 | 0.8708 | 0.9426 | 0.93 | 0.9095 | 1.1071 | 1.0848 |
| 026_715_00298890 | Lung | 715 | NCI-H1836 | 456 | 4.291554 | 0.73 | 0.833 | 0.997 | 0.9315 | 0.9434 | 0.955 | 0.9291 | 0.9423 | 1 |
| 026_757_00302870 | Lung | 757 | CPC-N | 456 | 4.345126 | 0.718 | 0.819 | 0.887 | 0.8883 | 0.9167 | 0.938 | 0.9641 | 1.0154 | 1.0153 |
| 026_8229_00304990 | Lung | 8229 | COR-L303 | 456 | 4.468573 | 0.685 | 0.828 | 0.788 | 0.868 | 0.6881 | 0.855 | 0.9579 | 0.8466 | 0.9772 |
| 026_691_00308560 | Lung | 691 | NCI-H526 | 456 | 4.602758 | 0.748 | 0.932 | 0.944 | 0.9861 | 0.9744 | 0.954 | 1.0035 | 1.0955 | 1.0007 |
| 026_8099_00316740 | Lung | 8099 | LB647-SCLC | 456 | 4.613258 | 0.755 | 0.954 | 0.998 | 0.9372 | 0.957 | 1.041 | 1.0171 | 1.0259 | 0.9506 |
| 026_725_00302750 | Lung | 725 | NCI-H2141 | 456 | 4.618451 | 0.747 | 0.869 | 0.906 | 0.9009 | 0.9283 | 0.901 | 1.003 | 0.9238 | 1.1424 |
| 026_705_00314520 | Lung | 705 | NCI-H1092 | 456 | 4.678169 | 0.77 | 0.861 | 0.911 | 1.02 | 0.9158 | 1.082 | 0.9997 | 0.9139 | 0.961 |
| 026_684_00303260 | Lung | 684 | NCI-H1688 | 456 | 4.865947 | 0.832 | 0.831 | 0.988 | 1.0672 | 0.9906 | 1.099 | 1.0391 | 1.0378 | 1.0698 |
| 026_725_00300160 | Lung | 725 | NCI-H2141 | 456 | 4.894458 | 0.785 | 0.908 | 0.936 | 0.9468 | 0.9309 | 0.94 | 0.9635 | 1.0477 | 0.9963 |
| 026_8281_00300930 | Lung | 8281 | COR-L311 | 456 | 5.024667 | 0.792 | 0.892 | 0.947 | 0.9155 | 0.8604 | 0.871 | 1.0268 | 1.0989 | 1.045 |
| 026_757_00300940 | Lung | 757 | CPC-N | 456 | 5.046784 | 0.796 | 0.904 | 0.984 | 1.0041 | 1.0137 | 0.919 | 0.905 | 0.9063 | 1.0167 |
| 026_701_00309060 | Lung | 701 | NCI-H841 | 456 | 5.157768 | 0.826 | 0.808 | 0.939 | 0.891 | 0.8811 | 0.919 | 0.9514 | 1.0474 | 1.0933 |
| 026_814_00304750 | Lung | 814 | NCI-H1568 | 456 | 5.159278 | 0.784 | 0.726 | 0.739 | 0.745 | 0.7127 | 0.774 | 0.9411 | 0.9 | 0.9817 |
| 026_741_00305010 | Lung | 741 | NCI-H345 | 456 | 5.184481 | 0.801 | 0.818 | 0.835 | 0.9503 | 0.9116 | 0.894 | 0.8849 | 0.9853 | 1.083 |
| 026_705_00311700 | Lung | 705 | NCI-H1092 | 456 | 5.191642 | 0.849 | 0.892 | 0.945 | 1.0426 | 0.9184 | 0.981 | 1.0366 | 1.0158 | 1.0581 |
| 026_786_00300950 | Lung | 786 | SBC-5 | 456 | 5.281883 | 0.841 | 1.002 | 0.991 | 1.0148 | 0.9974 | 0.998 | 1.0298 | 1.0075 | 1.0015 |
| 026_723_00316720 | Lung | 723 | NCI-H2066 | 456 | 5.313778 | 0.793 | 0.815 | 0.866 | 0.86 | 0.9117 | 0.892 | 0.9084 | 0.923 | 0.9757 |
| 026_705_00309080 | Lung | 705 | NCI-H1092 | 456 | 5.329516 | 0.829 | 0.941 | 0.999 | 0.9672 | 0.8963 | 0.935 | 0.9991 | 0.9888 | 1.0506 |
| 026_709_00305000 | Lung | 709 | NCI-H1304 | 456 | 5.330039 | 0.838 | 0.882 | 0.906 | 0.8939 | 0.9384 | 0.978 | 1.0127 | 1.0322 | 1.0575 |
| 026_739_00314630 | Lung | 739 | NCI-H146 | 456 | 5.38813 | 0.858 | 0.893 | 0.978 | 1.0115 | 1.0583 | 0.937 | 0.9685 | 1.0018 | 1.0831 |
| 026_8110_00314450 | Lung | 8110 | LU-165 | 456 | 5.539798 | 0.87 | 0.909 | 0.986 | 0.9964 | 0.9809 | 1.094 | 0.9305 | 0.9513 | 1.1416 |
| 026_811_00305140 | Lung | 811 | NCI-H1435 | 456 | 5.586661 | 0.886 | 0.953 | 0.978 | 0.9914 | 1.0102 | 0.994 | 0.9871 | 0.9783 | 0.9731 |
| 026_711_00311710 | Lung | 711 | NCI-H1417 | 456 | 5.606717 | 0.875 | 0.91 | 0.911 | 0.9612 | 1.0374 | 0.917 | 1.267 | 1.0195 | 0.9447 |
| 026_712_00309090 | Lung | 712 | NCI-H1436 | 456 | 5.636542 | 0.85 | 0.918 | 0.976 | 0.9527 | 0.9331 | 0.932 | 0.9583 | 0.9477 | 1.0343 |
| 026_711_00305130 | Lung | 711 | NCI-H1417 | 456 | 5.804325 | 0.849 | 1.022 | 0.916 | 0.9247 | 0.9771 | 0.939 | 0.9326 | 1.0168 | 1.0143 |
| 026_728_00311760 | Lung | 728 | NCI-H2196 | 456 | 5.845371 | 0.89 | 0.908 | 0.918 | 0.9801 | 0.875 | 1.033 | 0.9519 | 0.931 | 1.0431 |
| 026_831_00311750 | Lung | 831 | NCI-H2172 | 456 | 5.851811 | 0.879 | 0.986 | 1.002 | 0.9709 | 0.9562 | 0.984 | 0.9781 | 1.0144 | 0.974 |
| 026_1216_00300060 | Lung | 1216 | H292 | 456 | 5.909493 | 0.869 | 0.823 | 0.808 | 0.8192 | 0.8429 | 0.864 | 0.9245 | 0.9789 | 1.0777 |
| 026_8109_00314440 | Lung | 8109 | LU-134-A | 456 | 5.930549 | 0.868 | 0.95 | 0.972 | 0.9375 | 0.9332 | 0.959 | 0.9516 | 1.1207 | 1.1025 |
| 026_831_00305170 | Lung | 831 | NCI-H2172 | 456 | 6.053261 | 0.837 | 0.856 | 0.908 | 0.8908 | 0.9397 | 0.905 | 0.9677 | 0.9512 | 0.9839 |
| 026_728_00305180 | Lung | 728 | NCI-H2196 | 456 | 6.171009 | 0.9 | 0.903 | 0.976 | 0.9979 | 0.9199 | 0.928 | 0.9453 | 0.9369 | 0.941 |
| 026_689_00300910 | Lung | 689 | NCI-H187 | 456 | 6.191556 | 0.887 | 1.009 | 0.976 | 0.9779 | 0.9535 | 1.047 | 1.021 | 1.0846 | 0.959 |
| 026_785_00302770 | Lung | 785 | SBC-1 | 456 | 6.234067 | 0.875 | 1.037 | 1.061 | 0.9376 | 1.0385 | 0.937 | 0.9403 | 1.0039 | 1.1602 |
| 026_8280_00306910 | Lung | 8280 | COR-L321 | 456 | 6.254083 | 0.965 | 0.937 | 1.019 | 0.8492 | 0.948 | 1.048 | 1.0366 | 1.0761 | 0.9586 |
| 026_706_00318720 | Lung | 706 | NCI-H1105 | 456 | 6.355 | 0.897 | 0.965 | 1.009 | 0.9821 | 0.9646 | 1.037 | 0.9974 | 0.9667 | 0.9589 |
| 026_712_00305150 | Lung | 712 | NCI-H1436 | 456 | 6.498513 | 0.959 | 0.818 | 0.938 | 1.1033 | 0.9924 | 0.922 | 1.0128 | 1.0035 | 0.9263 |
| 026_8079_00306720 | Lung | 8079 | IST-SL2 | 456 | 6.56418 | 0.947 | 0.972 | 0.935 | 0.9658 | 0.9445 | 0.966 | 0.9554 | 1.019 | 1.0006 |
| 026_743_00303220 | Lung | 743 | DMS 114 | 456 | 6.614771 | 0.862 | 0.853 | 0.785 | 0.7831 | 0.861 | 0.851 | 0.8815 | 0.9129 | 1.0374 |
| 026_8022_00306711 | Lung | 8022 | COLO-668 | 456 | 6.912523 | 0.97 | 0.968 | 0.956 | 1 | 0.9608 | 0.917 | 1.0093 | 0.9217 | 0.9308 |
| 026_8109_00308510 | Lung | 8109 | LU-134-A | 456 | 6.98132 | 0.924 | 1.012 | 1.105 | 0.9946 | 0.9684 | 1.081 | 0.9878 | 0.9397 | 0.9606 |
| 026_758_00303240 | Lung | 758 | HCC-33 | 456 | 7.022636 | 0.931 | 1.056 | 1.002 | 1.0822 | 1.0508 | 1.011 | 1.0081 | 1.1612 | 1.1932 |
| 026_771_00306940 | Lung | 771 | Lu-135 | 456 | 7.040802 | 0.988 | 0.969 | 0.972 | 1.0271 | 0.9989 | 1.006 | 0.993 | 1.0649 | 1.0235 |
| 026_694_00302790 | Lung | 694 | NCI-H196 | 456 | 7.041262 | 0.976 | 0.954 | 0.975 | 0.9548 | 0.9357 | 0.922 | 0.9564 | 0.9433 | 1.019 |
| 026_764_00308550 | Lung | 764 | COR-L95 | 456 | 7.251052 | 0.978 | 1.021 | 0.944 | 1.002 | 1.0708 | 0.947 | 0.9637 | 0.9383 | 0.903 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_763_00300900 | Lung | 763 | COR-L88 | 456 | 7.365052 | 0.96 | 1.168 | 0.891 | 1.1434 | 1.1503 | 0.976 | 1.0066 | 1.0636 | 1.052 |
| 026_8134_00306730 | Lung | 8134 | NCI-H64 | 456 | 7.782872 | 1.026 | 1.003 | 0.976 | 1.0025 | 0.951 | 1.047 | 0.9338 | 0.8997 | 1.0076 |
| 026_712_00311730 | Lung | 712 | NCI-H1436 | 456 | 7.804947 | 1.019 | 1.049 | 0.947 | 0.9403 | 0.9104 | 0.931 | 0.9349 | 0.9472 | 0.9659 |
| 026_8018_00304801 | Lung1NS CLC | 8018 | Calu-6 | 456 | −0.899538 | 0.106 | 0.165 | 0.183 | 0.2075 | 0.2699 | 0.394 | 0.8182 | 0.9121 | 1.0531 |
| 026_1246_00304570 | Lung1NS CLC | 1246 | NCI-H1770 | 456 | −0.072444 | 0.109 | 0.175 | 0.267 | 0.3543 | 0.4184 | 0.552 | 0.6475 | 1.0183 | 0.9838 |
| 026_847_00304580 | Lung1NS CLC | 847 | NCI-H2087 | 456 | 1.048994 | 0.368 | 0.402 | 0.458 | 0.4756 | 0.5065 | 0.683 | 0.7888 | 0.9774 | 0.9846 |
| 026_680_00298830 | Lung1NS CLC | 680 | NCI-H727 | 456 | 1.334143 | 0.329 | 0.434 | 0.475 | 0.4492 | 0.5064 | 0.604 | 0.8522 | 0.9134 | 0.98 |
| 026_748_00304590 | Lung1NS CLC | 748 | NCI-H226 | 456 | 1.690128 | 0.342 | 0.457 | 0.514 | 0.5901 | 0.7687 | 0.757 | 0.7854 | 1.0039 | 0.932 |
| 026_851_00298380 | Lung1NS CLC | 851 | CAL-12T | 456 | 1.708943 | 0.452 | 0.449 | 0.49 | 0.5839 | 0.7337 | 0.842 | 0.9205 | 0.938 | 0.9948 |
| 026_861_00300230 | Lung1NS CLC | 861 | LCLC-97TM1 | 456 | 2.249036 | 0.424 | 0.573 | 0.622 | 0.7209 | 0.7517 | 0.873 | 1.0412 | 0.9724 | 0.974 |
| 026_1245_00304550 | Lung1NS CLC | 1245 | NCI-H1648 | 456 | 2.511131 | 0.507 | 0.571 | 0.662 | 0.5623 | 0.7611 | 0.961 | 1.0696 | 1.0483 | 1.4204 |
| 026_1180_00308140 | Lung1NS CLC | 1180 | NCI-H3122 | 456 | 2.550953 | 0.534 | 0.517 | 0.616 | 0.6044 | 0.7162 | 0.883 | 0.9512 | 0.9659 | 0.9657 |
| 026_802_00298451 | Lung1NS CLC | 802 | NCI-H358 | 456 | 2.662533 | 0.509 | 0.53 | 0.626 | 0.7229 | 0.8072 | 0.806 | 0.8743 | 0.9218 | 0.9534 |
| 026_815_00311140 | Lung1NS CLC | 815 | NCI-H1623 | 456 | 2.802368 | 0.523 | 0.592 | 0.685 | 0.6168 | 0.6264 | 0.746 | 0.872 | 0.8493 | 1.0805 |
| 026_1180_00302350 | Lung1NS CLC | 1180 | NCI-H3122 | 456 | 2.945291 | 0.724 | 0.649 | 0.605 | 0.75 | 0.7455 | 0.913 | 0.9083 | 1.0538 | 1.1763 |
| 026_8040_00304501 | Lung1NS CLC | 8040 | EKVX | 456 | 3.134434 | 0.532 | 0.642 | 0.782 | 0.752 | 0.7074 | 0.804 | 0.9087 | 1.0521 | 1.0032 |
| 026_865_00308451 | Lung1NS CLC | 865 | COR-L23 | 456 | 3.225036 | 0.58 | 0.657 | 0.735 | 0.83 | 0.9489 | 0.935 | 1.0144 | 1.0355 | 1.0002 |
| 026_1243_00304541 | Lung1NS CLC | 1243 | NCI-H1395 | 456 | 3.23207 | 0.553 | 0.739 | 0.944 | 0.948 | 0.9289 | 0.926 | 0.9919 | 1.0441 | 1.1113 |
| 026_884_00308160 | Lung1NS CLC | 884 | RERF-LC-MS | 456 | 3.239905 | 0.585 | 0.663 | 0.662 | 0.6574 | 0.7423 | 0.886 | 0.9636 | 0.9621 | 0.9957 |
| 026_796_00295871 | Lung1NS CLC | 796 | NCI-H2009 | 456 | 3.244878 | 0.582 | 0.62 | 0.631 | 0.635 | 0.7036 | 0.747 | 0.8586 | 0.9443 | 0.9943 |
| 026_799_00295880 | Lung1NS CLC | 799 | NCI-H661 | 456 | 3.295179 | 0.667 | 0.587 | 0.685 | 0.6862 | 0.8151 | 0.782 | 1.0055 | 0.9053 | 0.9863 |
| 026_822_00311150 | Lung1NS CLC | 822 | NCI-H1869 | 456 | 3.570833 | 0.153 | 0.716 | 0.736 | 0.7399 | 0.8095 | 0.819 | 1.026 | 0.9674 | 1.0055 |
| 026_756_00302670 | Lung1NS CLC | 756 | BEN | 456 | 3.65632 | 0.639 | 0.833 | 0.942 | 0.9322 | 0.9128 | 0.965 | 0.9486 | 1.0116 | 1.0192 |
| 026_876_00299781 | Lung1NS CLC | 876 | LU65 | 456 | 3.69068 | 0.635 | 0.695 | 0.704 | 0.7208 | 0.8211 | 0.878 | 0.9851 | 1.0211 | 1.0551 |
| 026_805_00304531 | Lung1NS CLC | 805 | NCI-H1155 | 456 | 3.716538 | 0.61 | 0.788 | 0.787 | 0.8467 | 0.9573 | 0.91 | 0.953 | 1.0683 | 1.0508 |
| 026_834_00304610 | Lung1NS CLC | 834 | NCI-H2347 | 456 | 3.72347 | 0.653 | 0.736 | 0.756 | 0.8026 | 0.8524 | 0.984 | 0.9516 | 1.2251 | 1.0554 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_822_00304840 | Lung1NS CLC | 822 | NCI-H1869 | 456 | 3.749478 | 0.594 | 0.736 | 0.791 | 0.7802 | 0.8592 | 0.824 | 0.8872 | 0.9703 | 1.0592 |
| 026_835_00302390 | Lung1NS CLC | 835 | NCI-H2405 | 456 | 3.789193 | 0.693 | 0.659 | 0.651 | 0.6574 | 0.7337 | 0.768 | 0.8849 | 0.9046 | 1.0375 |
| 026_678_00304981 | Lung1NS CLC | 678 | UMC-11 | 456 | 3.815948 | 0.655 | 0.751 | 0.848 | 0.8851 | 0.9411 | 1.013 | 0.9806 | 1.0842 | 1.1132 |
| 026_807_00314280 | Lung1NS CLC | 807 | NCI-H650 | 456 | 3.884087 | 0.604 | 0.778 | 0.772 | 0.8577 | 0.8346 | 0.815 | 1.0068 | 0.831 | 0.9772 |
| 026_871_00299771 | Lung1NS CLC | 871 | LK-2 | 456 | 3.898613 | 0.684 | 0.806 | 0.903 | 0.9071 | 0.958 | 1.018 | 0.9981 | 1.0604 | 1.0786 |
| 026_1249_00308150 | Lung1NS CLC | 1249 | NCI-H720 | 456 | 3.907633 | 0.632 | 0.829 | 0.932 | 1.0847 | 1.526 | 0.799 | 0.8751 | 1.2042 | 1.1215 |
| 026_8231_00304510 | Lung1NS CLC | 8231 | EMC-BAC-1 | 456 | 3.943946 | 0.675 | 0.713 | 0.751 | 0.8781 | 0.831 | 0.931 | 0.976 | 1.0569 | 1.0459 |
| 026_820_00304560 | Lung1NS CLC | 8200 | NCI-H1755 | 456 | 3.964037 | 0.658 | 0.769 | 0.785 | 0.8744 | 0.8799 | 0.931 | 0.9563 | 1.1261 | 1.0206 |
| 026_815_00304830 | Lung1NS CLC | 8155 | NCI-H1623 | 456 | 3.981628 | 0.646 | 0.709 | 0.712 | 0.7108 | 0.8124 | 0.879 | 0.7844 | 1.0245 | 1.0786 |
| 026_839_00302410 | Lung1NS CLC | 8399 | SW 900 | 456 | 3.982367 | 0.65 | 0.725 | 0.782 | 0.8242 | 0.8576 | 0.897 | 0.9535 | 1.0086 | 0.9978 |
| 026_804_00308480 1333 | Lung1NS CLC | 804 | NCI-H810 | 456 | 4.03318 | 0.731 | 0.763 | 0.92 | 0.9442 | 0.9087 | 1.003 | 0.9482 | 0.9716 | 1.0139 |
| 026_678_00309011 | Lung1NS CLC | 678 | UMC-11 | 456 | 4.0744 | 0.514 | 0.846 | 0.86 | 0.931 | 0.9037 | 0.925 | 0.9312 | 0.9354 | 1.0786 |
| 026_842_00298540 | Lung1NS CLC | 842 | NCI-H520 | 456 | 4.082969 | 0.729 | 0.811 | 0.916 | 1.0516 | 1.0142 | 1.002 | 1.0457 | 1.0022 | 0.9761 |
| 026_824_00314260 | Lung1NS CLC | 824 | NCI-H1944 | 456 | 4.107799 | 0.695 | 0.731 | 0.691 | 0.7704 | 0.893 | 0.886 | 0.905 | 0.9791 | 1.0866 |
| 026_888_00298370 | Lung1NS CLC | 888 | ABC-1 | 456 | 4.123019 | 0.64 | 0.676 | 0.717 | 0.7343 | 0.8328 | 0.84 | 0.8774 | 0.9196 | 0.9448 |
| 026_823_00298430 | Lung1NS CLC | 823 | NCI-H1915 | 456 | 4.260241 | 0.691 | 0.707 | 0.702 | 0.7393 | 0.7957 | 0.834 | 0.9053 | 0.9613 | 0.9902 |
| 026_8232_00304520 | Lung1NS CLC | 8232 | EMC-BAC-2 | 456 | 4.327709 | 0.712 | 0.795 | 0.825 | 0.8558 | 0.8815 | 0.959 | 0.9014 | 1.1843 | 1.0135 |
| 026_755_00300611 | Lung1NS CLC | 755 | NCI-H1975 | 456 | 4.450033 | 0.666 | 0.968 | 0.963 | 0.9052 | 0.9346 | 0.928 | 0.9969 | 0.9681 | 0.973 |
| 026_868_00295440 | Lung1NS CLC | 868 | PC-14 | 456 | 4.458594 | 0.726 | 0.893 | 0.842 | 0.8971 | 0.9361 | 1.057 | 0.9146 | 1.1281 | 0.933 |
| 026_872_00299750 | Lung1NS CLC | 872 | HARA | 456 | 4.480998 | 0.731 | 0.742 | 0.798 | 0.8152 | 0.8972 | 0.941 | 0.9735 | 1.0074 | 1.0301 |
| 026_800_00298441 | Lung1NS CLC | 800 | NCI-H23 | 456 | 4.511394 | 0.702 | 0.698 | 0.786 | 0.7938 | 0.8549 | 0.889 | 0.9216 | 0.9447 | 1.013 |
| 026_836_00304620 | Lung1NS CLC | 836 | NCI-H2444 | 456 | 4.530511 | 0.684 | 0.798 | 0.819 | 0.8507 | 0.863 | 0.86 | 0.9116 | 1.0106 | 1.0518 |
| 026_865_00296401 | Lung1NS CLC | 865 | COR-L23 | 456 | 4.577187 | 0.791 | 0.78 | 0.815 | 0.8605 | 0.9148 | 0.924 | 1.1179 | 1.1287 | 1.1293 |
| 026_858_00300591 | Lung1NS CLC | 858 | HCC-78 | 456 | 4.583505 | 0.703 | 0.983 | 0.936 | 1.06 | 0.9813 | 0.96 | 1.0028 | 0.9854 | 1.0584 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_854_00300681 | Lung1NS CLC | 854 | EPLC-272H | 456 | 4.590654 | 0.736 | 0.914 | 0.943 | 1.0019 | 1.0017 | 0.864 | 0.8937 | 0.9686 | 1.0373 |
| 026_837_00311160 | Lung1NS CLC | 837 | NCI-H2122 | 456 | 4.595192 | 0.771 | 0.917 | 0.969 | 0.9878 | 0.9667 | 1.017 | 1.0165 | 1.0062 | 1.0324 |
| 026_8111_00308110 | Lung1NS CLC | 8111 | LXF-289 | 456 | 4.689278 | 0.711 | 0.796 | 0.884 | 0.8648 | 0.868 | 0.89 | 0.9108 | 0.8979 | 0.9642 |
| 026_1136_00308471 | Lung1NS CLC | 1136 | NCI-H1993 | 456 | 4.705234 | 0.725 | 0.768 | 0.682 | 0.7469 | 0.7866 | 0.883 | 0.9296 | 0.914 | 0.9652 |
| 026_827_00308860 | Lung1NS CLC | 827 | NCI-H2085 | 456 | 4.711775 | 0.79 | 0.823 | 0.87 | 0.9311 | 0.924 | 1.007 | 0.967 | 1.0124 | 1.1093 |
| 026_859_00311090 | Lung1NS CLC | 859 | HCC-827 | 456 | 4.735253 | 0.737 | 0.86 | 0.852 | 0.7863 | 0.8298 | 0.853 | 1.0366 | 1.1949 | 0.9783 |
| 026_886_00296261 | Lung1NS CLC | 886 | EBC-1 | 456 | 4.744821 | 0.761 | 0.848 | 0.884 | 0.9053 | 0.937 | 0.969 | 0.9903 | 0.9432 | 1.0947 |
| 026_8132_00308130 | Lung1NS CLC | 8132 | NCI-H2126 | 456 | 4.781635 | 0.749 | 0.796 | 0.839 | 0.8331 | 0.8916 | 0.939 | 0.9049 | 0.9661 | 0.9286 |
| 026_793_00299711 | Lung1NS CLC | 793 | NCI-H1781 | 456 | 4.904802 | 0.775 | 0.801 | 0.686 | 0.7429 | 0.7804 | 0.897 | 0.9136 | 0.9608 | 1.0112 |
| 026_1247_00314271 | Lung1NS CLC | 1247 | NCI-H2291 | 456 | 4.945975 | 0.773 | 0.893 | 0.836 | 0.831 | 0.851 | 1.029 | 1.0615 | 0.9828 | 1.0493 |
| 026_860_00298400 | Lung1NS CLC | 860 | LCLC-103H | 456 | 4.97209 | 0.751 | 0.819 | 0.803 | 0.8985 | 0.8725 | 0.898 | 0.9606 | 0.9519 | 1.061 |
| 026_806_00300270 | Lung1NS CLC | 806 | NCI-H647 | 456 | 5.044917 | 0.792 | 0.845 | 0.882 | 0.8698 | 0.8856 | 0.881 | 1.0769 | 0.9333 | 1.0648 |
| 026_877_00300630 | Lung1NS CLC | 877 | PC-3 [JPC-3] | 456 | 5.056812 | 0.847 | 0.832 | 0.968 | 0.9943 | 1.0985 | 1.01 | 1.0152 | 1.0063 | 1.1608 |
| 026_753_00298460 | Lung1NS CLC | 753 | NCI-H460 | 456 | 5.061076 | 0.839 | 0.888 | 0.945 | 0.9015 | 1.041 | 1.039 | 1.021 | 0.9905 | 1.0126 |
| 026_844_00295461 | Lung1NS CLC | 844 | SW 1573 | 456 | 5.077017 | 0.798 | 0.834 | 0.833 | 0.8824 | 0.8946 | 0.971 | 1.0223 | 0.9943 | 1.0074 |
| 026_8088_00314320 | Lung1NS CLC | 8088 | KNS-62 | 456 | 5.130485 | 0.86 | 0.847 | 0.879 | 0.9874 | 0.9738 | 1.047 | 1.0602 | 1.0303 | 0.9876 |
| 026_848_00300641 | Lung1NS CLC | 848 | SK-LU-1 | 456 | 5.2771 | 0.811 | 0.91 | 0.946 | 0.9174 | 0.9429 | 0.922 | 0.9544 | 1.0372 | 1.0115 |
| 026_864_00304961 | Lung1NS CLC | 864 | COR-L105 | 456 | 5.319498 | 0.718 | 0.78 | 0.762 | 0.8018 | 0.7683 | 0.837 | 0.9721 | 0.8644 | 0.9527 |
| 026_677_00298361 | Lung1NS CLC | 677 | A549 | 456 | 5.414187 | 0.763 | 0.799 | 0.843 | 0.8595 | 0.9001 | 0.919 | 0.9405 | 0.9783 | 0.996 |
| 026_8207_00304810 | Lung1NS CLC | 8207 | LC-1F | 456 | 5.423288 | 0.825 | 0.794 | 0.845 | 0.8457 | 0.8483 | 0.976 | 0.8421 | 0.8626 | 0.9602 |
| 026_833_00299790 | Lung1NS | 833 | NCI-H2342 | 456 | 5.548934 | 0.856 | 0.888 | 0.917 | 0.9241 | 0.9293 | 1.015 | 0.9449 | 1.0616 | 0.9624 |
| 026_870_00299801 | Lung1NS CLC | 870 | RERF-LC-KJ | 456 | 5.685511 | 0.892 | 0.96 | 0.999 | 0.9623 | 1.0469 | 1.054 | 1.0305 | 1.0128 | 1.0476 |
| 026_845_00311341 | Lung1NS CLC | 845 | NCI-H1838 | 456 | 5.711103 | 0.847 | 0.867 | 0.950 | 0.9088 | 0.9208 | 0.932 | 0.9775 | 0.9857 | 0.9755 |
| 026_8103_00306210 | Lung1NS CLC | 8103 | LC-2-ad | 456 | 5.718708 | 0.836 | 0.96 | 1.004 | 0.9427 | 1.0257 | 1.064 | 1.0682 | 0.9834 | 1.007 |
| 026_794_00300601 | Lung1NS CLC | 794 | NCI-H1792 | 456 | 5.721238 | 0.339 | 0.904 | 0.992 | 0.9248 | 0.9615 | 1.005 | 0.9405 | 0.9595 | 1.0225 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_890_00300220 | Lung1NS CLC | 890 | H3255 | 456 | 5.722728 | 0.903 | 0.862 | 0.844 | 0.9926 | 1.005 | 0.998 | 1.1503 | 1.1306 | 1.1501 |
| 026_862_00304820 | Lung1NS CLC | 862 | LOU-NH91 | 456 | 5.738178 | 0.886 | 0.864 | 0.837 | 0.9386 | 0.9258 | 0.887 | 0.948 | 1.0561 | 1.1752 |
| 026_812_00298410 | Lung1NS CLC | 812 | NCI-H1437 | 456 | 5.791603 | 0.894 | 0.945 | 0.993 | 0.9231 | 0.9704 | 1.003 | 1.0591 | 1.0305 | 1.0361 |
| 026_862_00316560 | Lung1NS CLC | 862 | LOU-NH91 | 456 | 5.867157 | 0.871 | 0.905 | 0.923 | 0.9415 | 0.9143 | 0.955 | 0.9491 | 0.9721 | 0.9923 |
| 026_857_00296270 | Lung1NS CLC | 857 | HCC-44 | 456 | 5.930045 | 0.904 | 0.868 | 0.893 | 0.9249 | 0.9348 | 0.956 | 1.0259 | 0.9727 | 1.0027 |
| 026_679_00296240 | Lung1NS CLC | 679 | ChaGo-K-1 | 456 | 5.965866 | 0.878 | 0.915 | 0.949 | 0.8968 | 0.942 | 0.953 | 0.9732 | 0.9711 | 1.0338 |
| 026_791_00298421 | Lung1NS CLC | 791 | NCI-H1650 | 456 | 5.971987 | 0.888 | 0.896 | 0.979 | 0.9429 | 0.9543 | 0.921 | 0.9516 | 0.9551 | 0.9966 |
| 026_864_00311551 | Lung1NS CLC | 864 | COR-L105 | 456 | 5.975297 | 0.765 | 0.838 | 0.843 | 0.8384 | 0.8225 | 0.848 | 0.8917 | 0.8749 | 0.9811 |
| 026_846_00300620 | Lung1NS CLC | 846 | NCI-H2030 | 456 | 6.014339 | 0.886 | 0.979 | 0.985 | 0.9316 | 1.0428 | 0.925 | 0.9778 | 1.056 | 0.9904 |
| 026_841_00296291 | Lung1NS CLC | 841 | NCI-H2170 | 456 | 6.01763 | 0.897 | 0.938 | 0.928 | 0.9356 | 0.9557 | 0.955 | 1.0968 | 1.0708 | 1.0963 |
| 026_813_00308231 | Lung1NS CLC | 813 | NCI-H1563 | 456 | 6.06364 | 0.856 | 0.979 | 0.977 | 0.9369 | 0.9242 | 0.912 | 0.8859 | 0.9059 | 0.8856 |
| 026_816_00295860 | Lung1NS CLC | 816 | NCI-H1651 | 456 | 6.160326 | 0.864 | 1.039 | 1.026 | 1.008 | 1.0776 | 0.871 | 1.0553 | 1.0199 | 0.9978 |
| 026_818_00308241 | Lung1NS CLC | 818 | NCI-H1703 | 456 | 6.172519 | 0.946 | 0.829 | 0.858 | 0.9042 | 0.9197 | 0.887 | 0.9097 | 0.9729 | 0.9634 |
| 026_808_00296300 | Lung1NS CLC | 808 | NCI-H838 | 456 | 6.172929 | 0.922 | 0.941 | 0.955 | 1.022 | 0.964 | 1.043 | 1.0358 | 1.0134 | 1.0658 |
| 026_855_00302330 | Lung1NS CLC | 855 | HCC-15 | 456 | 6.195295 | 0.868 | 0.911 | 0.901 | 0.8895 | 0.9071 | 0.95 | 0.9608 | 1.0091 | 1.0383 |
| 026_803_00298470 | Lung1NS CLC | 803 | NCI-H522 | 456 | 6.200929 | 0.878 | 0.933 | 0.953 | 0.8695 | 0.9015 | 0.833 | 0.8882 | 0.8789 | 1.1066 |
| 026_832_00303110 | Lung1NS CLC | 832 | NCI-H2228 | 456 | 6.240586 | 0.908 | 0.872 | 0.907 | 0.9005 | 0.9724 | 0.974 | 0.9776 | 0.9706 | 0.968 |
| 026_874_00308171 | Lung1NS CLC | 874 | RERF-LC-Sq1 | 456 | 6.282697 | 1.064 | 0.854 | 0.829 | 0.8009 | 0.8914 | 0.943 | 0.8612 | 0.9931 | 0.9393 |
| 026_879_00308101 | Lung1NS CLC | 879 | LU99A | 456 | 6.327465 | 0.881 | 0.987 | 0.995 | 1.0199 | 0.9725 | 0.948 | 0.9588 | 0.9756 | 0.9692 |
| 026_856_00299760 | Lung1NS CLC | 856 | HCC-366 | 456 | 6.328052 | 0.936 | 0.943 | 0.959 | 1.0286 | 0.9991 | 1.002 | 1.0072 | 1.0077 | 1.0015 |
| 026_798_00304790 | Lung1NS CLC | 798 | Calu-3 | 456 | 6.338698 | 0.926 | 0.986 | 0.869 | 0.9635 | 1.0683 | 1.166 | 1.1053 | 1.1123 | 1.1003 |
| 026_825_00308250 | Lung1NS CLC | 825 | NCI-H2023 | 456 | 6.435057 | 0.938 | 0.885 | 0.929 | 0.961 | 0.9166 | 0.959 | 0.9502 | 0.9835 | 0.9846 |
| 026_8072_00306200 | Lung1NS CLC | 8072 | HOP-62 | 456 | 6.481774 | 0.973 | 0.958 | 0.931 | 0.9405 | 0.9799 | 0.901 | 1.0374 | 0.9717 | 1.1512 |
| 026_843_00296331 | Lung1NS CLC | 843 | SK-MES-1 | 456 | 6.499026 | 0.91 | 0.99 | 0.934 | 0.9509 | 0.9694 | 1.003 | 0.9804 | 0.9674 | 1.0295 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_1251_00318710 | Lung1NS CLC | 1251 | NCI-H835 | 456 | 6.684349 | 0.964 | 1.054 | 0.854 | 0.9853 | 0.77 | 0.963 | 0.8714 | 0.9637 | 1.1416 |
| 026_816_00302370 | Lung1NS CLC | 816 | NCI-H1651 | 456 | 6.769433 | 0.903 | 1.072 | 1.021 | 1.002 | 1.0583 | 0.94 | 1.0664 | 1.0462 | 1.0774 |
| 026_801_00295941 | Lung1NS CLC | 801 | NCI-H1299 | 456 | 6.808075 | 1.036 | 0.898 | 0.912 | 0.9194 | 0.9832 | 0.955 | 1.0252 | 0.9946 | 1.085 |
| 026_850_00311050 | Lung1NS CLC | 850 | 201T | 456 | 6.874432 | 0.942 | 0.957 | 0.988 | 0.989 | 0.9596 | 0.985 | 0.9759 | 0.9839 | 0.9726 |
| 026_818_00309001 | Lung1NS CLC | 818 | NCI-H1703 | 456 | 7.192409 | 0.889 | 0.857 | 0.855 | 0.8355 | 0.8207 | 0.856 | 0.8191 | 0.9124 | 0.9468 |
| 026_1247_00304851 | Lung1NS CLC | 1247 | NCI-H2291 | 456 | 7.252153 | 1.162 | 1.047 | 0.877 | 1.034 | 0.8759 | 0.694 | 1.2149 | 1.0391 | 1.1021 |
| 026_819_00306250 | Lung1NS CLC | 819 | NCI-H1734 | 456 | 7.342705 | 1.046 | 1.007 | 1.012 | 1.018 | 0.9902 | 0.945 | 0.9742 | 0.9718 | 1.0221 |
| 026_821_00306261 | Lung1NS CLC | 821 | NCI-H1793 | 456 | 7.345651 | 1.015 | 1.1 | 1.058 | 1.0171 | 1.0121 | 1.065 | 1.0342 | 1.0776 | 1.0468 |
| 026_798_00308080 | Lung1NS CLC | 798 | Calu-3 | 456 | 7.389624 | 1.032 | 1 | 0.914 | 0.9927 | 1.0342 | 1.004 | 1.0095 | 0.9327 | 0.938 |
| 026_678_00306181 | Lung1NS CLC | 678 | UMC-11 | 456 | 7.458364 | 1.03 | 1.058 | 1.054 | 1.0958 | 1.0021 | 1.03 | 1.0784 | 1.0779 | 1.0688 |
| 026_797_00308730 | Lung1NS CLC | 797 | NCI-H596 | 456 | 7.556662 | 1.124 | 1.076 | 0.92 | 0.9992 | 0.9285 | 0.936 | 0.911 | 1.0276 | 0.8862 |
| 026_790_00306231 | Lung1NS CLC | 790 | NCI-H1573 | 456 | 7.606756 | 1.049 | 1 | 1.054 | 1.0146 | 1.0291 | 0.99 | 1.0304 | 1.0221 | 1.0512 |
| 026_752_00306191 | Lung1NS CLC | 752 | A-427 | 456 | 7.608444 | 1.109 | 0.988 | 1.054 | 1.0224 | 0.9429 | 1.084 | 1.0956 | 1.0273 | 1.0528 |
| 026_845_00306271 | Lung1NS CLC | 845 | NCI-H1838 | 456 | 7.666847 | 1.074 | 1.08 | 1.064 | 1.0779 | 1.0805 | 1.046 | 1.0674 | 0.9941 | 1.02 |
| 026_8133_00306280 | Lung1NS CLC | 8133 | NCI-H322M | 456 | 7.713112 | 1.158 | 1.06 | 1.135 | 1.1499 | 1.1305 | 1.103 | 1.1464 | 1.1475 | 1.0913 |
| 026_8130_00306220 | Lung1NS CLC | 8130 | NCI-H1355 | 456 | 7.765888 | 1.12 | 1.188 | 1.002 | 0.9001 | 0.8103 | 1.095 | 0.9608 | 0.9714 | 0.9997 |
| 026_683_00306241 | Lung1NS CLC | 683 | NCI-H1581 | 456 | 7.774034 | 1.163 | 1.024 | 0.949 | 1.0959 | 1.0605 | 1.114 | 1.0118 | 0.9537 | 0.9212 |
| 026_792_00306140 | Lung1NS CLC | 792 | NCI-H1666 | 456 | 7.825548 | 1.136 | 1.069 | 1.132 | 1.0901 | 1.0688 | 1.097 | 1.0684 | 1.0463 | 1.1115 |
| 026_840_00306151 | Lung1NS CLC | 840 | NCI-H441 | 456 | 7.946249 | 1.088 | 1.059 | 1.052 | 1.0622 | 1.0476 | 1.049 | 1.0439 | 1.045 | 1.0714 |
| 026_8075_00306131 | Lung1NS CLC | 8075 | IA-LM | 456 | 7.984543 | 1.046 | 1.042 | 1.043 | 1.0424 | 1.0323 | 1.048 | 1.0441 | 1.0279 | 1.0694 |
| 026_61_00285570 | Lymphoma | 61 | JSC-1 | 456 | 0.316646 | 0.313 | 0.329 | 0.341 | 0.3908 | 0.5654 | 0.63 | 0.724 | 0.8346 | 0.8527 |
| 026_8222_00291350 | Lymphoma | 8222 | H9 | 456 | 0.402947 | 0.102 | 0.284 | 0.272 | 0.3996 | 0.5762 | 0.732 | 0.8412 | 0.8346 | 0.8529 |
| 026_140_00291320 | Lymphoma | 140 | A3/KAW | 456 | 0.717935 | 0.185 | 0.296 | 0.408 | 0.4762 | 0.5561 | 0.736 | 0.8297 | 0.8761 | 0.8425 |
| 026_237_00291380 | Lymphoma | 237 | SU-DHL-16 | 456 | 0.982467 | 0.155 | 0.278 | 0.405 | 0.5737 | 0.6759 | 0.816 | 0.9129 | 0.9363 | 0.9318 |
| 026_220_00288720 | Lymphoma | 220 | OCI-LY-19 | 456 | 1.28484 | 0.324 | 0.393 | 0.455 | 0.5338 | 0.6443 | 0.826 | 0.9343 | 0.9969 | 1.073 |
| 026_257_00285640 | Lymphoma | 257 | WIL2 NS | 456 | 1.523653 | 0.32 | 0.456 | 0.509 | 0.6199 | 0.6926 | 0.771 | 0.8518 | 0.9524 | 0.934 |
| 026_239_00288750 | Lymphoma | 239 | SU-DHL-5 | 456 | 1.616577 | 0.174 | 0.577 | 0.461 | 0.7856 | 0.7368 | 0.845 | 0.9512 | 0.9535 | 1.2005 |
| 026_124_00287850 | Lymphoma | 124 | BC-1 | 456 | 1.816766 | 0.239 | 0.53 | 0.6 | 0.6778 | 0.8612 | 0.946 | 0.9754 | 0.9846 | 1.0038 |
| 026_104_00287960 | Lymphoma | 104 | TUR | 456 | 2.217781 | 0.396 | 0.51 | 0.597 | 0.7468 | 0.9062 | 0.94 | 0.9822 | 0.9761 | 1.0165 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_8199_00291330 | Lymphoma | 8199 | CTB-1 | 456 | 2.341488 | 0.445 | 0.509 | 0.654 | 0.6993 | 0.7792 | 0.767 | 0.8214 | 0.8543 | 0.9676 |
| 026_69_00283480 | Lymphoma | 69 | CA46 | 456 | 2.43077 | 0.358 | 0.6 | 0.775 | 0.78 | 0.8817 | 0.896 | 0.9912 | 0.9446 | 0.9358 |
| 026_112_00285620 | Lymphoma | 112 | SR | 456 | 2.466522 | 0.224 | 0.573 | 0.653 | 0.7668 | 0.8482 | 0.866 | 0.908 | 0.9409 | 0.9255 |
| 026_241_00288760 | Lymphoma | 241 | SU-DHL-8 | 456 | 2.509783 | 0.398 | 0.583 | 0.743 | 0.8249 | 0.935 | 0.956 | 1.0439 | 0.9903 | 1.0527 |
| 026_255_00285610 | Lymphoma | 255 | Sci-1 | 456 | 2.705483 | 0.445 | 0.61 | 0.788 | 0.9473 | 0.9153 | 1.003 | 0.9035 | 0.8642 | 0.8757 |
| 026_62_00293930 | Lymphoma | 62 | IM-9 | 456 | 2.809638 | 0.572 | 0.562 | 0.594 | 0.6839 | 0.7773 | 1.18 | 0.876 | 1.0089 | 1.0329 |
| 026_93_00287880 | Lymphoma | 93 | HH | 456 | 2.828886 | 0.523 | 0.575 | 0.731 | 0.804 | 0.9283 | 0.948 | 0.9965 | 0.999 | 1.0069 |
| 026_216_00290710 | Lymphoma | 216 | NU-DUL-1 | 456 | 2.880782 | 0.459 | 0.664 | 0.767 | 0.8093 | 0.7784 | 0.884 | 0.9338 | 0.9363 | 0.9519 |
| 026_123_00287860 | Lymphoma | 123 | BC-3 | 456 | 2.893681 | 0.495 | 0.678 | 0.776 | 0.9051 | 1.0108 | 1.003 | 1.0056 | 0.9841 | 0.9941 |
| 026_113_00288520 | Lymphoma | 113 | DB | 456 | 2.901204 | 0.478 | 0.705 | 0.868 | 0.9097 | 0.9559 | 0.984 | 1.0104 | 0.992 | 1.0313 |
| 026_8035_00303290 | Lymphoma | 8035 | DOHH-2 | 456 | 2.927461 | 0.508 | 0.78 | 0.831 | 0.8009 | 0.9998 | 0.997 | 1.0295 | 0.9393 | 1.0203 |
| 026_240_00300290 | Lymphoma | 240 | SU-DHL-6 | 456 | 2.933827 | 0.208 | 0.663 | 0.733 | 0.7473 | 0.7814 | 0.839 | 0.8554 | 0.9327 | 1.029 |
| 026_248_00285630 | Lymphoma | 248 | VAL | 456 | 2.964017 | 0.528 | 0.639 | 0.739 | 0.9112 | 0.9265 | 0.96 | 1.0023 | 0.9827 | 0.9859 |
| 026_162_00290790 | Lymphoma | 162 | HDLM-2 | 456 | 2.980685 | 0.56 | 0.811 | 0.678 | 0.7341 | 0.7627 | 0.782 | 0.7915 | 0.9638 | 0.7387 |
| 026_105_00287940 | Lymphoma | 105 | RPMI 6666 | 456 | 3.064381 | 0.516 | 0.701 | 0.691 | 0.7257 | 0.8234 | 0.904 | 0.9883 | 1.0013 | 1.033 |
| 026_240_00302920 | Lymphoma | 240 | SU-DHL-6 | 456 | 3.114948 | 0.326 | 0.629 | 0.741 | 0.7802 | 0.8119 | 0.831 | 0.9347 | 0.921 | 0.9838 |
| 026_163_00287730 | Lymphoma | 163 | HD-MY-Z | 456 | 3.123344 | 0.582 | 0.606 | 0.654 | 0.6825 | 0.785 | 0.896 | 0.9395 | 0.98 | 1.0207 |
| 026_139_00283530 | Lymphoma | 139 | MC116 | 456 | 3.12577 | 0.085 | 0.686 | 0.917 | 0.9565 | 0.9611 | 0.99 | 0.9875 | 0.9789 | 0.9559 |
| 026_133_00293941 | Lymphoma | 133 | NK-92MI | 456 | 3.297366 | 0.637 | 0.637 | 0.757 | 0.8911 | 0.8633 | 1.136 | 1.0548 | 0.89 | 0.9001 |
| 026_282_00287750 | Lymphoma | 282 | P32/ISH | 456 | 3.328203 | 0.416 | 0.744 | 0.875 | 0.8947 | 0.8754 | 0.907 | 0.9959 | 0.9144 | 0.9277 |
| 026_80_00287950 | Lymphoma | 80 | ST486 | 456 | 3.520498 | 0.263 | 0.688 | 0.699 | 0.7969 | 0.8071 | 0.904 | 0.8902 | 0.9142 | 1.017 |
| 026_73_00283500 | Lymphoma | 73 | EB-3 | 456 | 3.528971 | 0.566 | 0.739 | 0.806 | 0.8214 | 0.8547 | 1.09 | 0.8321 | 0.8619 | 0.8548 |
| 026_60_00287891 | Lymphoma | 60 | JM1 | 456 | 3.618767 | 0.577 | 0.678 | 0.734 | 0.7932 | 0.8209 | 0.833 | 0.8444 | 0.8567 | 0.902 |
| 026_185_00288820 | Lymphoma | 185 | L-540 | 456 | 3.666174 | 0.626 | 0.88 | 0.936 | 1.0302 | 1.0245 | 1.037 | 1.0524 | 1.0175 | 1.0525 |
| 026_70_00283490 | Lymphoma | 70 | Daudi | 456 | 3.687192 | 0.603 | 0.789 | 0.925 | 0.8867 | 0.9929 | 0.987 | 0.8586 | 0.9555 | 0.8243 |
| 026_228_00291370 | Lymphoma | 228 | RC-K8 | 456 | 3.710403 | 0.605 | 0.678 | 0.732 | 0.7776 | 0.8387 | 0.943 | 0.9437 | 0.9368 | 0.9149 |
| 026_74_00285600 | Lymphoma | 74 | Raji | 456 | 3.736373 | 0.639 | 0.768 | 0.89 | 0.8258 | 0.9671 | 0.97 | 0.9444 | 0.9665 | 1.046 |
| 026_173_00288920 | Lymphoma | 173 | KARPAS-422 | 456 | 3.812903 | 0.638 | 0.787 | 0.876 | 0.8937 | 0.8652 | 0.959 | 0.9976 | 0.9896 | 1.005 |
| 026_125_00287910 | Lymphoma | 125 | MC/CAR | 456 | 3.860302 | 0.687 | 0.792 | 0.873 | 0.8871 | 1.009 | 1.011 | 0.9976 | 0.987 | 1.0162 |
| 026_280_00285420 | Lymphoma | 280 | SCC-3 | 456 | 3.903427 | 0.648 | 0.86 | 0.895 | 0.9301 | 0.9335 | 0.934 | 1.0707 | 0.9 | 0.9445 |
| 026_242_00288770 | Lymphoma | 242 | SUP-HD1 | 456 | 4.023177 | 0.671 | 0.815 | 0.875 | 0.8573 | 0.8914 | 0.965 | 1.0137 | 0.9754 | 1.1043 |
| 026_160_00285410 | Lymphoma | 160 | GRANTA-519 | 456 | 4.112789 | 0.631 | 0.706 | 0.761 | 0.7798 | 0.7991 | 0.771 | 0.9167 | 0.9366 | 0.9971 |
| 026_144_00287710 | Lymphoma | 1444 | BL-41 | 456 | 4.441898 | 0.536 | 1.076 | 0.941 | 0.9045 | 0.8922 | 0.893 | 0.9542 | 0.9696 | 1.0289 |
| 026_184_00290800 | Lymphoma | 184 | L-428 | 456 | 4.489131 | 0.614 | 0.705 | 0.723 | 0.7315 | 0.7351 | 0.721 | 1.0011 | 0.7501 | 0.8687 |
| 026_128_00290690 | Lymphoma | 128 | Farage | 456 | 4.585156 | 0.766 | 0.834 | 0.861 | 0.8151 | 0.9324 | 0.908 | 1.3723 | 1.1697 | 1.2229 |
| 026_250_00285660 | Lymphoma | 250 | WSU-NHL | 456 | 4.693667 | 0.719 | 0.765 | 0.866 | 0.8242 | 0.9178 | 0.947 | 0.9725 | 0.9585 | 0.9714 |
| 026_182_00290700 | Lymphoma | 182 | L-1236 | 456 | 4.714251 | 0.76 | 0.859 | 0.875 | 0.8522 | 0.9702 | 0.962 | 1.0483 | 0.9432 | 1.3018 |
| 026_95_00283510 | Lymphoma | 95 | HT | 456 | 4.721481 | 0.719 | 0.842 | 0.88 | 0.8266 | 0.8534 | 0.902 | 1.0348 | 0.9564 | 0.966 |
| 026_264_00288840 | Lymphoma | 264 | TK | 456 | 4.750226 | 0.794 | 0.966 | 0.936 | 0.9709 | 1.0212 | 1.024 | 1.0348 | 1.0318 | 1.0681 |
| 026_266_00287760 | Lymphoma | 266 | SLVL | 456 | 4.90866 | 0.731 | 0.786 | 0.794 | 0.8012 | 0.8742 | 0.873 | 0.9435 | 0.9199 | 0.977 |
| 026_75_00282830 | Lymphoma | 75 | Jiyoye | 456 | 4.937844 | 0.801 | 0.99 | 0.974 | 1.0523 | 1.196 | 1.107 | 1.0641 | 1.1044 | 1.0749 |
| 026_111_00291360 | Lymphoma | 111 | Hs 445 | 456 | 5.022248 | 0.704 | 0.734 | 0.703 | 0.794 | 0.7451 | 0.779 | 0.8243 | 0.8675 | 0.946 |
| 026_8151_00288540 | Lymphoma | 8151 | Ramos-2G6-4C10 | 456 | 5.147746 | 0.243 | 0.868 | 0.954 | 0.9827 | 1.022 | 0.974 | 0.9967 | 0.9674 | 1.0529 |
| 026_156_00287720 | Lymphoma | 156 | DG-75 | 456 | 5.222394 | 0.834 | 1.001 | 1.03 | 1.0349 | 0.9848 | 0.996 | 1.012 | 0.9965 | 0.9857 |
| 026_243_00296620 | Lymphoma | 243 | SUP-M2 | 456 | 5.25553 | 0.648 | 0.888 | 0.96 | 0.9351 | 0.9518 | 0.968 | 0.9742 | 0.9627 | 0.9659 |
| 026_86_00287870 | Lymphoma | 86 | EB2 | 456 | 5.287284 | 0.86 | 1.017 | 1.01 | 1.0356 | 1.0217 | 1.05 | 1.0267 | 1.0118 | 1.0227 |
| 026_162_00288790 | Lymphoma | 162 | HDLM-2 | 456 | 5.425219 | 0.877 | 0.903 | 0.797 | 0.9228 | 1.0293 | 1.043 | 1.0157 | 1.0517 | 1.0837 |
| 026_172_00287740 | Lymphoma | 172 | KARPAS-299 | 456 | 5.433867 | 0.832 | 0.8911 | 0.95 | 0.9494 | 0.955 | 0.954 | 0.9499 | 0.9633 | 0.9487 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_235_00285430 | Lymphoma | 235 | SU-DHL-1 | 456 | 6.401484 | 0.835 | 0.997 | 0.987 | 0.9424 | 0.9387 | 0.884 | 0.8642 | 0.9464 | 0.9439 |
| 026_143_00288690 | Lymphoma | 143 | AMO-1 | 456 | 6.692908 | 0.924 | 1.025 | 1.129 | 1.034 | 1.1112 | 1.034 | 1.0278 | 1.0136 | 1.0255 |
| 026_193_00288830 | Lymphoma | 193 | MHH-PREB-1 | 456 | 6.799634 | 0.622 | 0.958 | 1.012 | 1.0149 | 1.0368 | 1.025 | 1.0064 | 0.9803 | 0.989 |
| 026_236_00288730 | Lymphoma | 236 | SU-DHL-10 | 456 | 6.99662 | 0.175 | 0.993 | 1.05 | 1.0763 | 1.0476 | 1.029 | 1.0509 | 1.0397 | 1.0494 |
| 026_81_00288530 | Lymphoma | 81 | GA-10 | 456 | 7.031749 | 0.602 | 1.003 | 1.009 | 1.1031 | 1.0252 | 1.021 | 1.0113 | 1.0077 | 1.0848 |
| 026_251_00287840 | Lymphoma | 251 | YT | 456 | 7.411746 | 0.64 | 0.986 | 1.008 | 1.0201 | 1.0204 | 1.022 | 1.0267 | 0.9848 | 1.0079 |
| 026_178_00288810 | Lymphoma | 178 | KM-H2 | 456 | 7.739504 | 1.008 | 1.009 | 0.976 | 1.0197 | 1.0404 | 1.036 | 1.0412 | 1.0156 | 1.0276 |
| 026_249_00285650 | Lymphoma | 249 | WSU-DLCL2 | 456 | 8.212885 | 1.047 | 1.226 | 1.172 | 1.1142 | 1.0869 | 1.071 | 0.9837 | 1.0247 | 1.0207 |
| 026_238_00288740 | Lymphoma | 238 | SU-DHL-4 | 456 | 8.647656 | 1.061 | 1.077 | 1.045 | 1.0257 | 1.0384 | 1.029 | 1.0236 | 1.018 | 1.0204 |
| 026_131_00287930 | Lymphoma | 131 | RL | 456 | 8.679308 | 1.124 | 1.094 | 1.048 | 1.024 | 1.0293 | 1.012 | 1.0293 | 0.9824 | 1.0061 |
| 026_915_00269070 | Miscellaneous | 915 | Hs 633T | 456 | 1.797943 | 0.344 | 0.532 | 0.607 | 0.6061 | 0.6357 | 0.736 | 0.8936 | 1.0346 | 1.1375 |
| 026_911_00269060 | Miscellaneous | 911 | GCT | 456 | 2.424125 | 0.433 | 0.617 | 0.642 | 0.6508 | 0.655 | 0.804 | 0.7763 | 0.9066 | 0.9967 |
| 026_8172_00269460 | Miscellaneous | 8172 | SW872 | 456 | 3.196748 | 0.511 | 0.716 | 0.719 | 0.7459 | 0.8264 | 0.881 | 0.9107 | 0.9313 | 1.0224 |
| 026_913_00271970 | Miscellaneous | 913 | JAR | 456 | 3.876744 | 0.685 | 0.695 | 0.794 | 0.851 | 0.9936 | 1.011 | 0.9013 | 1.0881 | 1.0491 |
| 026_8194_00271980 | Miscellaneous | 8194 | JEG-3 | 456 | 3.901223 | 0.623 | 0.880 | 0.876 | 0.9097 | 0.9037 | 0.874 | 0.9014 | 0.943 | 1.1354 |
| 026_8171_00269120 | Miscellaneous | 8171 | SW684 | 456 | 3.978538 | 0.693 | 0.91 | 0.98 | 1.1114 | 1.0275 | 1.032 | 0.9881 | 0.9218 | 1.0725 |
| 026_8112_00269450 | Miscellaneous | 8112 | MFH-ino | 456 | 4.013788 | 0.691 | 0.674 | 0.795 | 0.8068 | 0.8378 | 0.91 | 0.9824 | 1.0389 | 1.0625 |
| 026_916_00271320 | Miscellaneous | 916 | HT 1080 | 456 | 4.254215 | 0.695 | 0.804 | 0.766 | 0.7943 | 0.8276 | 0.873 | 1.1135 | 1.1006 | 1.1093 |
| 026_8004_00271280 | Miscellaneous | 8004 | A388 | 456 | 4.494172 | 0.743 | 0.793 | 0.841 | 0.8441 | 0.8899 | 0.888 | 1.1408 | 0.925 | 1.1327 |
| 026_8112_00271340 | Miscellaneous | 8112 | MFH-ino | 456 | 4.624376 | 0.721 | 0.732 | 0.741 | 0.7501 | 0.7753 | 0.799 | 1.017 | 0.9044 | 1.0866 |
| 026_8004_00269400 | Miscellaneous | 8004 | A388 | 456 | 4.778414 | 0.747 | 0.764 | 0.776 | 0.8164 | 0.8628 | 0.861 | 0.9217 | 0.8924 | 1.0697 |
| 026_8192_00269470 | Miscellaneous | 8192 | VA-ES-BJ | 456 | 4.956405 | 0.78 | 0.867 | 0.874 | 0.984 | 0.9192 | 0.889 | 0.9737 | 1.0227 | 1.0186 |
| 026_8194_00269440 | Miscellaneous | 8194 | JEG-3 | 456 | 5.058221 | 0.786 | 0.87 | 1.048 | 0.908 | 0.8876 | 0.984 | 0.8804 | 1.0294 | 1.0609 |
| 026_913_00269430 | Miscellaneous | 913 | JAR | 456 | 5.170211 | 0.816 | 0.841 | 0.849 | 0.8709 | 0.8661 | 0.88 | 1.0502 | 1.0585 | 1.0591 |
| 026_916_00269420 | Miscellaneous | 916 | HT 1080 | 456 | 5.302771 | 0.831 | 0.891 | 0.904 | 0.9053 | 0.9327 | 0.978 | 0.9465 | 1.1023 | 1.1108 |
| 026_8175_00269140 | Miscellaneous | 8175 | SW982 | 456 | 5.586364 | 0.832 | 0.968 | 0.988 | 1.1946 | 1.0638 | 1.017 | 1.0728 | 1.1006 | 1.2781 |
| 026_1225_00269660 | Muscle | 1255 | RD | 456 | 2.694207 | 0.612 | 0.595 | 0.602 | 0.575 | 0.6051 | 0.678 | 0.8404 | 0.9183 | 0.947 |
| 26_135_00271680 | Muscle | 135 | SJCRH30 | 456 | 2.740947 | 0.247 | 0.61 | 0.713 | 0.8654 | 0.8633 | 0.854 | 0.9433 | 0.9991 | 1.105 |
| 026_924_00269640 | Muscle | 924 | A673 | 456 | 2.779569 | 0.563 | 0.554 | 0.607 | 0.6884 | 0.7085 | 0.808 | 0.8122 | 0.8796 | 0.9437 |
| 26_562_00271660 | Muscle | 562 | KYM-1 | 456 | 2.818237 | 0.433 | 0.665 | 0.727 | 0.7663 | 0.7943 | 0.835 | 0.9132 | 0.9948 | 0.9596 |
| 026_135_00271410 | Muscle | 135 | SJCRH30 | 456 | 3.059385 | 0.345 | 0.672 | 0.79 | 0.8395 | 0.8741 | 0.957 | 0.9768 | 1.032 | 1.1796 |
| 026_923_00269680 | Muscle | 923 | RH-41 | 456 | 3.133389 | 0.309 | 0.65 | 0.731 | 0.7895 | 0.6971 | 0.795 | 0.7303 | 0.9458 | 0.9325 |
| 026_562_00270060 | Muscle | 562 | KYM-1 | 456 | 3.396905 | 0.586 | 0.748 | 0.78 | 0.8707 | 0.8698 | 0.955 | 1.0372 | 1.0323 | 1.0217 |
| 026_920_00269670 | Muscle | 920 | RH-1 | 456 | 3.433085 | 0.581 | 0.772 | 0.846 | 0.9032 | 0.9238 | 0.951 | 0.9496 | 0.9615 | 0.9852 |
| 026_135_00270070 | Muscle | 135 | SJCRH30 | 456 | 3.759361 | 0.326 | 0.727 | 0.825 | 0.8737 | 0.9084 | 0.931 | 0.9701 | 0.9946 | 0.9435 |
| 026_919_00269630 | Muscle | 919 | A-204 | 456 | 5.25605 | 0.778 | 0.798 | 0.868 | 0.8744 | 0.861 | 0.89 | 0.9735 | 0.9392 | 0.9765 |
| 026_921_00285151 | Muscle | 921 | RH-18 | 456 | 5.863422 | 0.84 | 0.987 | 0.961 | 0.9653 | 0.9811 | 0.903 | 0.8875 | 0.9228 | 0.9815 |
| 026_8182_00293791 | Muscle | 8182 | TE-441-T | 456 | 6.133177 | 0.848 | 1.001 | 1.103 | 1.0954 | 1.1007 | 0.855 | 0.8882 | 1.0698 | 0.8069 |
| 026_369_00258500 | Nervous System | 369 | CHP-212 | 456 | 4.151196 | 0.165 | 0.184 | 0.183 | 0.1873 | 0.1985 | 0.219 | 0.2948 | 0.3285 | 0.4946 |
| 026_390_00262920 | Nervous System | 390 | NB69 | 456 | −1.3827 | 0.056 | 0.074 | 0.068 | 0.0948 | 0.096 | 0.163 | 0.4343 | 0.6938 | 0.8833 |
| 026_629_00316570 | Nervous System | 629 | NB(TU)1-10 | 456 | −0.654294 | 0.322 | 0.361 | 0.388 | 0.398 | 0.4347 | 0.594 | 0.7533 | 0.6321 | 0.6782 |
| 026_366_00257090 | Nervous System | 366 | BE(2)-M17 | 456 | −0.258429 | 0.204 | 0.352 | 0.333 | 0.3872 | 0.4128 | 0.547 | 0.6415 | 0.7687 | 0.9298 |
| 026_384_00314240 | Nervous System | 384 | MHH-NB-11 | 456 | 1.316182 | 0.368 | 0.42 | 0.48 | 0.6318 | 0.5903 | 0.783 | 0.7802 | 0.9243 | 0.5317 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_385_00314290 | Nervous System | 385 | SIMA | 456 | 1.359572 | 0.402 | 0.496 | 0.488 | 0.5135 | 0.6006 | 0.629 | 0.8787 | 0.8808 | 1.0864 |
| 026_630_00264810 | Nervous System | 630 | NH-12 | 456 | 1.516245 | 0.143 | 0.443 | 0.537 | 0.5763 | 0.6816 | 0.684 | 0.7263 | 0.9504 | 0.791 |
| 026_8124_00308720 | Nervous System | 8124 | NB14 | 456 | 1.784337 | 0.802 | 0.401 | 0.6 | 0.6379 | 0.6871 | 0.943 | 0.8827 | 0.8247 | 0.9343 |
| 026_639_00271120 | Nervous System | 639 | GOTO | 456 | 1.784838 | 0.174 | 0.52 | 0.54 | 0.6353 | 0.6485 | 0.726 | 0.9341 | 0.8908 | 1.1295 |
| 026_8094_00314230 | Nervous System | 8094 | LAN-6 | 456 | 1.824343 | 0.55 | 0.565 | 0.476 | 0.5734 | 0.6862 | 0.656 | 0.7893 | 0.9264 | 0.7016 |
| 026_8076_00260401 | Nervous System | 8076 | IMR-5 | 456 | 1.864038 | 0.346 | 0.489 | 0.575 | 1.2246 | 0.8619 | 0.823 | 1.0781 | 0.7607 | 0.8894 |
| 026_8127_00258950 | Nervous System | 8127 | NB5 | 456 | 2.106125 | 0.202 | 0.628 | 0.611 | 0.6823 | 0.725 | 0.845 | 0.9541 | 0.9703 | 1.0012 |
| 026_8124_00311130 | Nervous System | 8124 | NB14 | 456 | 2.216808 | 0.544 | 0.563 | 0.516 | 0.5711 | 0.5857 | 0.776 | 0.9014 | 0.9091 | 1.0395 |
| 026_8126_00264800 | Nervous System | 8126 | NB17 | 456 | 2.289546 | 0.347 | 0.54 | 0.684 | 0.7567 | 0.8851 | 0.929 | 0.8729 | 0.9752 | 0.9196 |
| 026_641_00308180 | Nervous System | 641 | TGW | 456 | 2.326645 | 0.4556 | 0.502 | 0.593 | 0.7234 | 0.8006 | 0.88 | 0.9296 | 0.9651 | 0.9821 |
| 026_8121_00256290 | Nervous System | 8121 | NB10 | 456 | 2.356578 | 0.646 | 0.568 | 0.562 | 0.5835 | 0.6642 | 0.613 | 0.5487 | 0.6035 | 1.0005 |
| 026_8220_00308810 | Nervous System | 8200 | KP-N-YN | 456 | 2.470465 | 0.366 | 0.619 | 0.752 | 0.7815 | 0.7642 | 0.87 | 0.8457 | 0.8335 | 0.8942 |
| 026_8090_00263920 | Nervous System | 8090 | KP-N-YS | 456 | 2.547617 | 0.267 | 0.583 | 0.69 | 0.9135 | 0.905 | 0.924 | 0.9505 | 0.9232 | 1.012 |
| 026_363_00252730 | Nervous System | 363 | SK-N-FI | 456 | 2.667265 | 0.519 | 0.583 | 0.574 | 0.6332 | 0.5059 | 0.571 | 0.7766 | 0.6898 | 0.9188 |
| 026_382_00311110 | Nervous System | 382 | KELLY | 456 | 3.39659 | 0.518 | 0.757 | 0.767 | 0.7123 | 0.7538 | 0.883 | 0.8718 | 0.8733 | 0.9755 |
| 026_8064_00259120 | Nervous System | 8064 | GI-ME-N | 456 | 3.426922 | 0.582 | 0.763 | 0.78 | 0.8295 | 0.8371 | 0.955 | 1.0539 | 1.0652 | 1.104 |
| 026_8195_00318640 | Nervous System | 8195 | CHP-134 | 456 | 3.519288 | 0.6 | 0.8 | 0.86 | 0.90 | 0.9931 | 0.919 | 0.9533 | 0.941 | 1.0273 |
| 026_382_00308690 | Nervous System | 382 | KELLY | 456 | 3.678148 | 0.59 | 0.706 | 0.666 | 0.74 | 0.8277 | 0.814 | 0.8335 | 0.8742 | 0.9843 |
| 026_8129_00314250 | Nervous System | 8129 | NB7 | 456 | 3.824042 | 0.644 | 0.861 | 0.945 | 0.97 | 0.9655 | 0.998 | 1.0941 | 1.0771 | 1.0471 |
| 026_8126_00280241 | Nervous System | 8126 | NB17 | 456 | 3.845261 | 0.611 | 0.771 | 0.746 | 1.0569 | 0.8567 | 0.864 | 0.9408 | 0.9041 | 0.972 |
| 026_8007_00252850 | Nervous System | 8007 | ACN | 456 | 3.989797 | 0.411 | 0.72 | 0.821 | 0.7359 | 0.7717 | 0.797 | 0.8528 | 1.0702 | 0.9564 |
| 026_8122_00273460 | Nervous System | 8122 | NB12 | 456 | 4.358809 | 0.15 | 0.809 | 0.911 | 0.9912 | 0.9113 | 1.021 | 0.9055 | 0.8723 | 1.0083 |
| 026_8226_00252530 | Nervous System | 8226 | NBsus SR | 456 | 4.365592 | 1.14 | 0.81 | 0.878 | 0.6567 | 0.6737 | 0.94 | 0.7615 | 0.8399 | 1.1136 |
| 026_8064_00256670 | Nervous System | 8064 | GI-ME-N | 456 | 4.809816 | 0.398 | 0.871 | 0.839 | 0.9402 | 0.8757 | 0.96 | 0.9284 | 0.9838 | 1.0451 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_8128_00257200 | Nervous System | 8128 | NB6 | 456 | 4.886145 | 0.836 | 0.93 | 0.956 | 1.0121 | 0.9926 | 1.008 | 0.9893 | 0.9944 | 0.9472 |
| 026_8123_00256300 | Nervous System | 8123 | NB13 | 456 | 5.775254 | 0.837 | 1.028 | 1.034 | 0.9756 | 1.0272 | 0.974 | 0.9893 | 0.9781 | 0.9486 |
| 026_396_00261020 | Nervous System | 396 | NB-1 | 456 | 5.873385 | 0.813 | 1.039 | 0.892 | 0.8527 | 0.9085 | 0.934 | 0.9583 | 0.9709 | 1.0441 |
| 026_370_00252740 | Nervous System | 370 | SK-N-SH | 456 | 6.176056 | 0.926 | 0.811 | 0.891 | 1.0803 | 2.0427 | 1.01 | 0.892 | 0.9269 | 0.9864 |
| 026_364_00252720 | Nervous System | 364 | SK-N-DZ | 456 | 6.251974 | 0.895 | 1.012 | 0.958 | 1.0963 | 0.9642 | 0.976 | 1.0005 | 0.9787 | 0.9774 |
| 026_370_00258530 | Nervous System | 370 | SK-N-SH | 456 | 6.266144 | 0.36 | 0.933 | 1.052 | 1.0961 | 1.0754 | 0.948 | 0.9798 | 1.0134 | 0.9668 |
| 026_362_00252710 | Nervous System | 362 | SK-N-AS | 456 | 6.874316 | 0.911 | 1.075 | 0.916 | 1.0354 | 0.9179 | 0.939 | 1.178 | 0.9451 | 0.9362 |
| 026_368_00252700 | Nervous System | 368 | MC-IXC | 456 | 6.982443 | 0.084 | 0.616 | 1.087 | 1.1559 | 1.0678 | 1.11 | 1.0784 | 0.9917 | 0.9902 |
| 026_8122_00262490 | Nervous System | 8122 | NB12 | 456 | 7.149853 | 0.063 | 0.973 | 1.019 | 1.3067 | 1.0528 | 0.999 | 1.4063 | 0.9955 | 0.9632 |
| 026_934_00287430 | Ovary | 934 | A2780 | 456 | −0.227264 | 0.302 | 0.3 | 0.342 | 0.3503 | 0.3758 | 0.467 | 0.7239 | 0.7489 | 0.9268 |
| 026_1126_00293760 | Ovary | 1126 | OV-90 | 456 | 0.856076 | 0.323 | 0.361 | 0.384 | 0.4703 | 0.5785 | 0.701 | 0.8275 | 0.885 | 0.873 |
| 026_1129_00290660 | Ovary | 1129 | TOV-112D | 456 | 2.270257 | 0.47 | 0.481 | 0.592 | 0.7498 | 0.7692 | 0.925 | 0.9217 | 0.9942 | 1.1258 |
| 026_1220_00291150 | Ovary | 1220 | ES-2 | 456 | 2.397868 | 0.584 | 0.504 | 0.584 | 0.5655 | 0.9851 | 0.957 | 1.1602 | 1.1706 | 1.0966 |
| 026_949_00290350 | Ovary | 949 | TYK-nu | 456 | 2.489488 | 0.511 | 0.577 | 0.587 | 0.5768 | 0.6153 | 0.686 | 0.7718 | 1.0687 | 1.0378 |
| 026_925_00290850 | Ovary | 925 | IGROV-1 | 456 | 2.753994 | 0.494 | 0.608 | 0.578 | 0.7594 | 0.7462 | 0.857 | 0.9169 | 0.8966 | 0.8943 |
| 026_8244_00314220 | Ovary | 8244 | JHOS-4 | 456 | 2.779507 | 0.63 | 0.601 | 0.597 | 0.6381 | 0.7711 | 0.88 | 0.955 | 0.9128 | 0.9028 |
| 026_8279_00293400 | Ovary | 8279 | UWB1.289 | 456 | 2.893774 | 0.764 | 0.625 | 0.723 | 0.7182 | 0.783 | 1.079 | 0.9597 | 1.044 | 1.0467 |
| 026_940_00290340 | Ovary | 940 | RMG-I | 456 | 3.11591 | 0.587 | 0.604 | 0.66 | 0.6995 | 0.6871 | 0.846 | 0.8531 | 0.9424 | 1.0257 |
| 26_8238_00304370 | Ovary | 8238 | IOSE-364- | 456 | 3.149354 | 0.505 | 0.763 | 0.761 | 0.7451 | 0.8102 | 0.848 | 1.0558 | 1.0226 | 1.0295 |
| 026_8237_00295840 | Ovary | 8237 | Hey | 456 | 3.317969 | 0.551 | 0.783 | 0.688 | 0.776 | 0.8484 | 0.917 | 1.1038 | 1.0681 | 1.1892 |
| 026_8260_00292720 | Ovary | 8260 | PEO1 | 456 | 3.508406 | 0.648 | 0.61 | 0.642 | 0.7269 | 0.6891 | 0.74 | 1.0027 | 0.9408 | 0.9148 |
| 026_8230_00303100 | Ovary | 8230 | DOV13 | 456 | 3.68994 | 0.636 | 0.73 | 0.886 | 0.851 | 0.9406 | 0.961 | 0.9388 | 0.9681 | 1.0998 |
| 026_8230_00292650 | Ovary | 8230 | DOV13 | 456 | 3.809459 | 0.641 | 0.685 | 0.768 | 0.9488 | 0.8764 | 0.863 | 0.9076 | 0.9226 | 1.0565 |
| 026_8092_00295850 | Ovary | 8092 | KURAMOCHI | 456 | 3.819916 | 0.757 | 0.729 | 0.642 | 0.6589 | 0.7541 | 0.914 | 0.9211 | 1.0035 | 1.0531 |
| 026_8240_00291160 | Ovary | 8240 | IOSE-523- | 456 | 3.834885 | 0.676 | 0.747 | 0.827 | 0.9249 | 0.9868 | 1 | 0.9181 | 0.9742 | 1.0197 |
| 026_932_00291140 | Ovary | 932 | EFO-27 | 456 | 3.943589 | 0.65 | 0.668 | 0.65 | 0.7216 | 0.7753 | 0.887 | 0.9104 | 0.9136 | 0.9152 |
| 026_8084_00292670 | Ovary | 8084 | KGN | 456 | 4.00968 | 0.776 | 0.686 | 0.68 | 0.804 | 0.816 | 0.93 | 0.911 | 0.9826 | 0.9092 |
| 026_1125_00290571 | Ovary | 1125 | Caov-3 | 456 | 4.050855 | 0.676 | 0.787 | 0.855 | 0.951 | 0.9041 | 1.029 | 0.9092 | 0.8992 | 1.0107 |
| 026_8256_00292920 | Ovary | 8256 | OV-7 | 456 | 4.064163 | 0.666 | 0.844 | 0.821 | 0.9099 | 0.9293 | 0.961 | 1.0098 | 0.9638 | 0.9379 |
| 026_8241_00292900 | Ovary | 8241 | IOSE-75-16SV40 | 456 | 4.094216 | 0.698 | 0.804 | 0.834 | 0.8672 | 0.894 | 1.02 | 1.0443 | 1.0711 | 1.107 |
| 026_938_00287450 | Ovary | 938 | OAW42 | 456 | 4.158942 | 0.689 | 0.707 | 0.728 | 0.8613 | 0.7453 | 0.912 | 0.7815 | 1.0258 | 1.0515 |
| 026_1235_00298501 | Ovary | 1235 | Caov-4 | 456 | 4.19878 | 0.673 | 0.815 | 0.851 | 0.7794 | 0.8482 | 0.895 | 1.0046 | 1.0048 | 0.9449 |
| 026_1221_00293780 | Ovary | 1221 | SW 626 | 456 | 4.261643 | 0.636 | 0.704 | 0.69 | 0.6894 | 0.7014 | 0.755 | 0.8172 | 0.8859 | 1.0281 |
| 026_933_00295510 | Ovary | 933 | FU-OV-1 | 456 | 4.35795 | 0.921 | 0.786 | 0.66 | 0.785 | 0.7855 | 0.932 | 1.0797 | 1.0643 | 1.0563 |
| 026_8259_00292710 | Ovary | 8259 | OVK-18 | 456 | 4.419332 | 0.714 | 0.849 | 0.926 | 0.7816 | 0.8328 | 1.11 | 1.0158 | 0.9241 | 1.1619 |
| 026_8242_00295400 | Ovary | 8242 | JHOS-2 | 456 | 4.46038 | 0.744 | 0.845 | 0.843 | 0.8069 | 0.9687 | 1.09 | 0.9491 | 1.0683 | 1.0333 |
| 026_1128_00292620 | Ovary | 1128 | PA-1 | 456 | 4.524728 | 0.741 | 0.875 | 0.809 | 0.8925 | 0.9409 | 1.005 | 1.0033 | 1.0111 | 1.0682 |
| 026_938_00290330 | Ovary | 938 | OAW42 | 456 | 4.600882 | 0.772 | 0.772 | 0.843 | 0.9103 | 0.8456 | 1.001 | 1.0305 | 1.0314 | 1.0721 |
| 026_8148_00292700 | Ovary | 8148 | OVCAR-4 | 456 | 4.649732 | 0.715 | 0.824 | 0.723 | 0.6704 | 0.8391 | 0.855 | 0.9034 | 1.0922 | 1.0169 |
| 026_8243_00295410 | Ovary | 8243 | JHOS-3 | 456 | 4.699022 | 0.801 | 0.758 | 0.691 | 0.7427 | 0.8184 | 0.86 | 1.0104 | 0.9653 | 1.0478 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_1130_00308501 | Ovary | 1130 | TOV-21G | 456 | 4.743414 | 0.744 | 0.838 | 0.882 | 0.8952 | 0.9369 | 0.922 | 0.9212 | 0.9456 | 0.9683 |
| 026_931_00252940 | Ovary | 931 | EFO-21 | 456 | 4.786052 | 0.749 | 0.962 | 0.957 | 1.0202 | 1.0143 | 0.983 | 0.9976 | 0.9688 | 0.9523 |
| 026_931_00290820 | Ovary | 931 | EFO-21 | 456 | 4.852802 | 0.791 | 0.924 | 0.954 | 0.9827 | 1.0247 | 0.961 | 0.9353 | 0.9274 | 0.9237 |
| 026_932_00288450 | Ovary | 932 | EFO-27 | 456 | 4.890908 | 0.759 | 0.729 | 0.783 | 0.7813 | 0.828 | 0.851 | 0.9362 | 1.0032 | 1.0515 |
| 026_8258_00291180 | Ovary | 8258 | OVCA433 | 456 | 4.901177 | 0.703 | 0.713 | 0.753 | 0.7366 | 0.79 | 0.864 | 0.9468 | 0.9244 | 0.9669 |
| 026_928_00290870 | Ovary | 928 | OVCAR-5 | 456 | 4.903025 | 0.791 | 0.718 | 0.699 | 0.6913 | 0.7147 | 0.8 | 0.831 | 0.8925 | 0.9149 |
| 026_8257_00293650 | Ovary | 8257 | OVCA420 | 456 | 4.98883 | 0.716 | 0.738 | 0.79 | 0.8055 | 0.8238 | 0.819 | 0.8677 | 0.8812 | 1.0222 |
| 026_8257_00292690 | Ovary | 8257 | OVCA420 | 456 | 5.050268 | 0.789 | 0.822 | 0.798 | 0.9932 | 0.8382 | 0.876 | 0.928 | 0.9213 | 1.1024 |
| 026_8239_00292890 | Ovary | 8239 | IOSE-397 | 456 | 5.092878 | 0.842 | 0.8 | 0.866 | 0.8796 | 0.8926 | 0.921 | 1.2015 | 0.9976 | 1.2125 |
| 026_941_00288490 | Ovary | 941 | RKN | 456 | 5.095259 | 0.777 | 0.883 | 0.798 | 0.796 | 0.8682 | 1.049 | 1.195 | 1.0697 | 1.0119 |
| 026_929_00290880 | Ovary | 929 | OVCAR-8 | 456 | 5.147098 | 0.763 | 0.805 | 0.822 | 0.8457 | 0.8675 | 0.888 | 0.9211 | 0.9687 | 1.0047 |
| 026_8215_00287660 | Ovary | 8215 | OC-314 | 456 | 5.38803 | 0.869 | 0.99 | 0.986 | 1.0451 | 1.0092 | 1.01 | 1.0495 | 0.9963 | 1.0021 |
| 026_939_00287460 | Ovary | 939 | SK-OV-3 | 456 | 5.430154 | 0.806 | 0.848 | 0.834 | 0.8094 | 0.8719 | 0.891 | 0.9424 | 0.903 | 1.1026 |
| 026_945_00288480 | Ovary | 945 | OVMIU | 456 | 5.797932 | 0.75 | 0.737 | 0.748 | 0.7949 | 0.7921 | 0.844 | 0.8857 | 0.9368 | 0.9866 |
| 026_948_00291230 | Ovary | 948 | OVTOKO | 456 | 5.89738 | 0.829 | 0.912 | 0.942 | 0.9105 | 0.938 | 0.909 | 0.9025 | 0.9329 | 0.9575 |
| 026_8255_00293640 | Ovary | 8255 | OV-56 | 456 | 5.989644 | 0.874 | 0.894 | 0.904 | 0.9159 | 0.9189 | 0.911 | 0.9267 | 0.9453 | 0.9277 |
| 026_937_00288460 | Ovary | 937 | OAW28 | 456 | 6.027686 | 0.859 | 0.878 | 0.802 | 0.8512 | 0.7724 | 0.814 | 1.0447 | 0.8649 | 1.0363 |
| 026_1127_00296460 | Ovary | 1127 | NIH1OVCAR-3 | 456 | 6.109694 | 0.886 | 0.95 | 0.992 | 0.9785 | 0.8788 | 0.986 | 0.9619 | 1.0732 | 0.8745 |
| 026_947_00263500 | Ovary | 947 | OVKATE | 456 | 6.266319 | 0.819 | 0.823 | 0.875 | 0.8874 | 0.9093 | 0.906 | 0.9175 | 0.9563 | 0.9507 |
| 026_938_00292910 | Ovary | 938 | OAW42 | 456 | 6.299032 | 0.918 | 0.963 | 0.958 | 0.9614 | 0.9778 | 1.041 | 1.0213 | 0.9899 | 1.0087 |
| 026_945_00256180 | Ovary | 945 | OVMIU | 456 | 6.360298 | 0.891 | 0.987 | 1.001 | 0.9225 | 0.8452 | 0.776 | 0.8273 | 0.9233 | 1.0102 |
| 026_946_00291190 | Ovary | 946 | OVISE | 456 | 6.600815 | 0.805 | 0.739 | 0.737 | 0.7358 | 0.7593 | 0.759 | 0.8539 | 0.8664 | 0.8624 |
| 026_8254_00295890 | Ovary | 8254 | OV-17R | 456 | 6.877329 | 0.913 | 1.041 | 0.974 | 1.0282 | 1.0077 | 1.015 | 1.0376 | 0.9484 | 1.0604 |
| 026_973_00295540 | Pancreas | 973 | HUP-T4 | 456 | 0.866739 | 0.321 | 0.315 | 0.362 | 0.4721 | 0.5603 | 0.814 | 1.0984 | 0.8938 | 1.1407 |
| 026_983_00295450 | Pancreas | 983 | SUIT-2 | 456 | 1.197889 | 0.397 | 0.339 | 0.382 | 0.581 | 0.6565 | 0.942 | 0.9937 | 1.019 | 1.1926 |
| 026_982_00292940 | Pancreas | 982 | QGP-1 | 456 | 1.430625 | 0.538 | 0.437 | 0.492 | 0.5682 | 0.6307 | 0.8 | 0.8372 | 0.9601 | 1.0476 |
| 026_8118_00295430 | Pancreas | 8118 | MZ1-PC | 456 | 1.48113 | 0.363 | 0.489 | 0.495 | 0.5335 | 0.6471 | 0.671 | 0.9118 | 1.008 | 0.9838 |
| 026_8149_00293771 | Pancreas | 8149 | PSN1 | 456 | 1.829333 | 0.531 | 0.553 | 0.5 | 0.5231 | 0.6104 | 0.71 | 0.8375 | 0.909 | 0.9509 |
| 026_953_00295470 | Pancreas | 953 | AsPC-1 | 456 | 1.847893 | 0.476 | 0.515 | 0.508 | 0.4987 | 0.5741 | 0.746 | 0.8281 | 1.0377 | 1.0843 |
| 026_1256_00260300 | Pancreas | 1256 | 950-MP5 | 456 | 1.902786 | 0.332 | 0.473 | 0.515 | 0.7193 | 0.8035 | 0.916 | 0.9125 | 1.0441 | 0.9009 |
| 026_976_00298480 | Pancreas | 976 | Panc04.03 | 456 | 2.685969 | 0.592 | 0.594 | 0.57 | 0.562 | 0.6645 | 0.706 | 0.8319 | 0.9296 | 1.0176 |
| 026_954_00292870 | Pancreas | 954 | BxPC-3 | 456 | 2.90077 | 0.574 | 0.607 | 0.558 | 0.6572 | 0.7404 | 0.813 | 1.0541 | 1.0916 | 0.9092 |
| 026_967_00292570 | Pancreas | 967 | Capan-1 | 456 | 3.140577 | 0.522 | 0.69 | 0.758 | 0.8527 | 0.6713 | 0.874 | 0.9506 | 0.894 | 0.958 |
| 026_975_00295591 | Pancreas | 975 | YAPC | 456 | 3.507979 | 0.613 | 0.705 | 0.797 | 0.9196 | 0.8833 | 0.921 | 1.0616 | 1.0323 | 1.0675 |
| 026_1135_00292930 | Pancreas | 1135 | PL18 | 456 | 3.513426 | 0.636 | 0.623 | 0.694 | 0.6978 | 0.7917 | 0.832 | 0.9096 | 0.9334 | 0.9721 |
| 026_977_00308210 | Pancreas | 977 | KP-1N | 456 | 3.657778 | 0.607 | 0.764 | 0.684 | 0.7525 | 0.7655 | 0.980 | 0.9944 | 0.9837 | 0.9553 |
| 026_969_00295580 | Pancreas | 969 | PA-TU-8988T | 456 | 3.657963 | 0.604 | 0.653 | 0.725 | 0.7145 | 0.7879 | 0.992 | 1.0299 | 1.0048 | 1.0863 |
| 026_1491_00273490 | Pancreas | 1491 | SNU-324 | 456 | 3.732679 | 0.387 | 0.683 | 0.791 | 0.7879 | 0.8486 | 0.832 | 0.9455 | 0.9813 | 0.9695 |
| 026_961_00295570 | Pancreas | 961 | Panc02.03 | 456 | 4.088522 | 0.702 | 0.699 | 0.633 | 0.701 | 0.7003 | 0.795 | 0.8748 | 0.9019 | 1.1113 |
| 026_974_00292601 | Pancreas | 974 | HUP-T3 | 456 | 4.280085 | 0.684 | 0.754 | 0.793 | 0.909 | 0.7596 | 0.88 | 0.9895 | 0.9696 | 1.0099 |
| 026_963_00293710 | Pancreas | 963 | Hs 766T | 456 | 4.34359 | 0.709 | 0.746 | 0.833 | 0.7623 | 0.8169 | 1.052 | 0.9605 | 0.9551 | 1.0544 |
| 026_959_00292630 | Pancreas | 959 | Panc03.27 | 456 | 4.482408 | 0.701 | 0.682 | 0.805 | 0.8272 | 0.7565 | 0.838 | 0.9087 | 0.9434 | 1.0258 |
| 026_981_00293750 | Pancreas | 981 | KP-4 | 456 | 4.755774 | 0.733 | 0.9 | 0.784 | 0.9218 | 0.8875 | 1.007 | 0.9325 | 1.0003 | 0.8788 |
| 026_968_00292580 | Pancreas | 968 | CFPAC-1 | 456 | 4.814885 | 0.772 | 0.822 | 0.87 | 0.9195 | 0.9082 | 0.935 | 0.8889 | 1.0106 | 1.1286 |
| 026_1134_00300280 | Pancreas | 1134 | PL4 | 456 | 4.8 | 0.738 | 0.739 | 0.727 | 0.7443 | 0.7816 | 0.797 | 0.9521 | 0.9663 | 1.0376 |
| 026_979_00293740 | Pancreas | 979 | KP-3 | 456 | 4.900084 | 0.956 | 0.777 | 0.839 | 0.8825 | 0.8836 | 0.909 | 0.9593 | 0.9092 | 0.9686 |
| 026_956_00292591 | Pancreas | 956 | HPAF-II | 456 | 5.005523 | 0.734 | 0.786 | 0.762 | 0.6523 | 0.7269 | 0.755 | 0.9185 | 0.979 | 1.0195 |
| 026_953_00257150 | Pancreas | 953 | AsPC-1 | 456 | 5.141432 | 0.761 | 0.708 | 0.731 | 0.7295 | 0.7369 | 0.79 | 0.8534 | 0.891 | 0.957 |
| 26_968_00304350 | Pancreas | 968 | CFPAC-1 | 456 | 5.151366 | 0.817 | 0.828 | 0.864 | 0.8724 | 0.8715 | 1.008 | 1.007 | 0.9779 | 1.001 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_957_00296350 | Pancreas | 957 | SW 1990 | 456 | 5.575766 | 0.849 | 0.911 | 0.906 | 0.8954 | 0.9494 | 0.957 | 0.977 | 0.9769 | 1.1173 |
| 026_960_00296311 | Pancreas | 960 | Panc08.13 | 456 | 5.65459 | 0.875 | 0.894 | 0.924 | 0.9669 | 0.9243 | 0.93 | 1.1005 | 1.065 | 1.0309 |
| 026_951_00256230 | Pancreas | 951 | HPAC | 456 | 5.736336 | 0.862 | 1.024 | 0.931 | 0.8532 | 0.9386 | 1.035 | 1.0328 | 1.0507 | 1.0612 |
| 026_964_00295480 | Pancreas | 964 | Capan-2 | 456 | 5.74256 | 0.877 | 0.928 | 0.759 | 0.8346 | 0.9905 | 0.925 | 1.0364 | 1.027 | 0.9499 |
| 026_1134_00298560 | Pancreas | 1134 | PL4 | 456 | 5.771259 | 0.844 | 0.812 | 0.91 | 0.8479 | 0.7738 | 0.977 | 0.9068 | 1.059 | 0.9774 |
| 026_970_00293370 | Pancreas | 970 | PA-TU-8902 | 456 | 5.772043 | 0.841 | 0.97 | 0.919 | 0.8896 | 0.9177 | 0.966 | 0.9181 | 1.322 | 0.9871 |
| 026_952_00292610 | Pancreas | 952 | MIA PaCa-2 | 456 | 5.946631 | 0.923 | 0.885 | 0.718 | 0.8919 | 0.8505 | 1.058 | 1.0586 | 0.8995 | 1.1403 |
| 026_972_00296250 | Pancreas | 972 | DAN-G | 456 | 5.955955 | 0.897 | 0.924 | 0.945 | 0.9646 | 0.9703 | 0.978 | 1.0074 | 1.032 | 1.0585 |
| 026_951_00295520 | Pancreas | 951 | HPAC | 456 | 5.962773 | 0.923 | 0.889 | 0.787 | 0.9719 | 0.9562 | 1.118 | 0.986 | 0.9708 | 1.1145 |
| 026_975_00252910 | Pancreas | 975 | YAPC | 456 | 5.989883 | 1.015 | 0.914 | 0.897 | 0.8713 | 0.8903 | 1.037 | 0.977 | 1.1409 | 0.981 |
| 026_963_00252950 | Pancreas | 963 | Hs 766T | 456 | 6.264463 | 0.496 | 0.974 | 0.953 | 1.0445 | 0.9118 | 1.028 | 0.9324 | 1.0245 | 1.0186 |
| 026_958_00296320 | Pancreas | 958 | Panc10.05 | 456 | 6.318194 | 0.851 | 0.835 | 0.851 | 0.824 | 0.8929 | 0.879 | 0.9003 | 1.0065 | 1.0291 |
| 026_955_00292640 | Pancreas | 955 | SU.86.86 | 456 | 6.593699 | 1.017 | 0.82 | 0.986 | 0.9378 | 1.1258 | 1.072 | 1.0873 | 1.0381 | 0.9789 |
| 026_759_00300240 | Pleura | 759 | MSTO-211H | 456 | 3.066599 | 0.666 | 0.637 | 0.664 | 0.6954 | 0.8026 | 0.901 | 1.0485 | 1.0165 | 1.0436 |
| 026_1213_00303050 | Pleura | 1213 | H2818 | 456 | 3.157415 | 0.577 | 0.674 | 0.728 | 0.8558 | 0.9032 | 0.962 | 0.9285 | 1.0744 | 1.1008 |
| 026_8116_00303080 | Pleura | 8116 | MPP-89 | 456 | 3.723631 | 0.416 | 0.808 | 0.823 | 0.9733 | 0.9887 | 0.968 | 1.0012 | 0.9912 | 1.0294 |
| 026_1206_00302600 | Pleura | 1206 | H2722 | 456 | 3.764667 | 0.604 | 0.768 | 0.801 | 0.8049 | 0.8692 | 0.937 | 0.9073 | 0.9842 | 0.9698 |
| 026_1210_00302610 | Pleura | 1210 | H2803 | 456 | 4.117283 | 0.686 | 0.723 | 0.669 | 0.7081 | 0.719 | 0.892 | 0.9533 | 1.0129 | 0.9547 |
| 026_1215_00311260 | Pleura | 12 | H290 | 456 | 4.122 | 0.6 | 0.7 | 0.6 | 0.76 | 0.77 | 0.7 | 0.81 | 0.985 | 0.981 |
| 026_1206_00308200 | Pleura | 1206 | H2722 | 456 | 4.184817 | 0.699 | 0.769 | 0.85 | 0.8838 | 0.889 | 0.906 | 1.0135 | 0.9948 | 1.0129 |
| 026_1212_00300580 | Pleura | 1212 | H2810 | 456 | 4.445211 | 0.69 | 0.929 | 0.942 | 0.9243 | 0.9927 | 0.884 | 0.9289 | 0.9051 | 0.9626 |
| 026_682_00304600 | Pleura | 682 | NCI-H2452 | 456 | 4.452468 | 0.722 | 0.847 | 0.891 | 0.906 | 0.9407 | 0.899 | 0.9567 | 1.0786 | 1.1287 |
| 026_1200_00300690 | Pleura | 1200 | H2373 | 456 | 4.612295 | 0.695 | 0.911 | 0.887 | 0.9257 | 0.9258 | 0.849 | 0.9218 | 0.9772 | 0.9399 |
| 026_1214_00308460 | Pleura | 1214 | H2869 | 456 | 4.934927 | 0.775 | 0.881 | 0.878 | 0.926 | 0.9241 | 0.914 | 0.9475 | 0.9536 | 1.0138 |
| 026_1214_00308790 | Pleura | 1214 | H2869 | 456 | 4.961713 | 0.802 | 0.879 | 0.908 | 0.9132 | 0.9528 | 0.991 | 0.9959 | 1.0132 | 1.0202 |
| 026_1202_00303040 | Pleura | 1202 | H2591 | 456 | 5.067997 | 0.82 | 0.918 | 0.945 | 1.0327 | 0.9338 | 0.983 | 0.9541 | 1.0755 | 1.1707 |
| 026_1209_00300210 | Pleura | 1209 | H28 | 456 | 5.341766 | 0.817 | 0.821 | 0.827 | 0.8331 | 0.8999 | 0.927 | 0.9491 | 1.0072 | 0.9857 |
| 026_8078_00303060 | Pleura | 8078 | IST-MES1 | 456 | 5.358253 | 0.782 | 0.897 | 0.859 | 0.8822 | 0.8445 | 0.907 | 0.9752 | 0.926 | 1.0513 |
| 026_1199_00300560 | Pleura | 1199 | H2369 | 456 | 5.439636 | 0.82 | 0.91 | 0.99 | 0.8596 | 0.9184 | 0.984 | 0.9172 | 0.9896 | 1.1394 |
| 026_8078_00304970 | Pleura | 8078 | IST-MES1 | 456 | 5.505825 | 0.847 | 0.88 | 0.853 | 0.8587 | 0.8938 | 0.89 | 0.9416 | 0.9423 | 1.0968 |
| 026_1207_00298510 | Pleura | 1207 | H2731 | 456 | 5.56988 | 0.819 | 1.018 | 1.003 | 0.8986 | 0.9778 | 0.921 | 0.9543 | 0.9856 | 0.9695 |
| 026_1198_00302580 | Pleura | 1198 | H2052 | 456 | 5.579483 | 0.859 | 0.966 | 0.995 | 0.9551 | 0.9651 | 1.01 | 1.0265 | 1.0233 | 1.0095 |
| 026_1201_00302590 | Pleura | 1201 | H2461 | 456 | 5.654117 | 0.856 | 0.868 | 0.914 | 0.904 | 0.8852 | 0.908 | 0.9343 | 1.0239 | 1.1079 |
| 026_1213_00300720 | Pleura | 1213 | H2818 | 456 | 5.828097 | 0.843 | 0.946 | 0.86 | 0.9682 | 0.9236 | 0.942 | 0.9493 | 0.9688 | 0.9576 |
| 026_1211_00300570 | Pleura | 1211 | H2804 | 456 | 5.890027 | 0.881 | 0.886 | 0.907 | 0.8753 | 0.9153 | 0.955 | 0.969 | 0.9857 | 1.0448 |
| 026_1218_00300730 | Pleura | 1218 | H513 | 456 | 5.953268 | 0.9 | 0.905 | 0.905 | 1.0722 | 1.0284 | 0.976 | 0.9507 | 1.0341 | 1.2023 |
| 026_1208_00300710 | Pleura | 1208 | H2795 | 456 | 6.063798 | 0.3 | 0.943 | 0.961 | 0.8752 | 0.9823 | 0.905 | 0.9466 | 0.9643 | 0.975 |
| 026_1203_00300850 | Pleura | 1203 | H2595 | 456 | 6.184806 | 0.92 | 0.909 | 0.899 | 1.0357 | 1.0632 | 0.905 | 0.974 | 1.018 | 0.9037 |
| 026_8245_00282710 | pleural effusion | 8245 | KMS-11 | 456 | 0.702427 | 0.356 | 0.384 | 0.404 | 0.4804 | 0.491 | 0.652 | 0.7128 | 1.0645 | 1.1048 |
| 026_996_00298490 | Prostate | 996 | 22RV1 | 456 | 2.346887 | 0.542 | 0.521 | 0.592 | 0.6234 | 0.6635 | 0.707 | 0.7764 | 0.8517 | 0.9168 |
| 026_985_00303070 | Prostate | 985 | LNCaP clone FGC | 456 | 4.018762 | 0.727 | 0.863 | 0.923 | 1.1164 | 1.0922 | 0.984 | 1.0179 | 1.1749 | 1.0533 |
| 026_987_00298550 | Prostate | 987 | PC-3 | 456 | 4.097696 | 0.698 | 0.761 | 0.871 | 0.9338 | 0.9109 | 0.914 | 0.9938 | 1.2109 | 0.991 |
| 026_1001_00002003 | Prostate | 1001 | DU 145 | 456 | 5.044916 | 0.768 | 0.832 | 0.867 | 0.8699 | 0.8879 | 0.906 | 0.9933 | 0.9168 | 1.1136 |
| 026_988_00308270 | Prostate | 988 | PWR-1E | 456 | 5.228199 | 0.804 | 0.854 | 0.877 | 0.8566 | 0.8621 | 0.923 | 0.9727 | 0.9516 | 0.9806 |
| 026_997_00300660 | Prostate | 997 | BPH-1 | 456 | 5.448713 | 0.479 | 0.868 | 1.201 | 1.1209 | 1.1016 | 0.674 | 0.9562 | 1.1603 | 0.8983 |
| 026_1000_00300740 | Prostate | 1000 | VCaP | 456 | 5.968581 | 0.692 | 1.071 | 1.005 | 1.0988 | 0.9203 | 0.91 | 0.9225 | 0.9154 | 1.1301 |
| 026_1009_00264700 | Skin | 1009 | WM35 | 456 | 2.372512 | 0.112 | 0.201 | 0.203 | 0.2168 | 0.2138 | 0.242 | 0.3676 | 0.463 | 0.7025 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_8212_00264590 | Skin | 8212 | CP50-MEL-B | 456 | −1.651586 | 0.151 | 0.398 | 0.392 | 0.3817 | 0.3556 | 0.35 | 0.4631 | 0.5633 | 0.8209 |
| 026_1039_00265170 | Skin | 1039 | SK-MEL-30 | 456 | 1.476493 | 0.263 | 0.352 | 0.317 | 0.3236 | 0.3515 | 0.424 | 0.5534 | 0.8565 | 0.8549 |
| 026_1023_00269690 | Skin | 1023 | SK-MEL-2 | 456 | −1.357658 | 0.147 | 0.207 | 0.235 | 0.2621 | 0.2935 | 0.343 | 0.5053 | 0.6866 | 0.8936 |
| 026_1034_00264680 | Skin | 1034 | MEL-HO | 456 | −0.964561 | 0.144 | 0.372 | 0.375 | 0.3139 | 0.3537 | 0.327 | 0.4189 | 0.6188 | 0.8613 |
| 026_8073_00263480 | Skin | 8073 | HT-144 | 456 | 0.641233 | 0.154 | 0.241 | 0.236 | 0.3036 | 0.3695 | 0.397 | 0.6432 | 0.7444 | 0.9033 |
| 026_8114_00259970 | Skin | 8114 | MMAC-SF | 456 | 0.613008 | 0.211 | 0.399 | 0.492 | 0.3813 | 0.4238 | 0.662 | 0.5683 | 0.6942 | 1.0563 |
| 026_8209_00266540 | Skin | 8209 | A4-Fuk | 456 | 0.557176 | 0.179 | 0.476 | 0.467 | 0.4234 | 0.4176 | 0.498 | 0.6644 | 0.7338 | 0.7609 |
| 026_1046_00263470 | Skin | 1045 | HMVII | 456 | 0.454742 | 0.389 | 0.419 | 0.403 | 0.3903 | 0.4097 | 0.503 | 0.6117 | 0.8285 | 1.0625 |
| 026_8120_00262840 | Skin | 8120 | MZ7-mel | 456 | 0.254795 | 0.073 | 0.323 | 0.41 | 0.4001 | 0.4106 | 0.468 | 0.6687 | 0.6311 | 0.8761 |
| 026_8191_00260580 | Skin | 8191 | UACC-257 | 456 | 0.10266 | 0.456 | 0.468 | 0.426 | 0.404 | 0.4006 | 0.534 | 0.6654 | 0.7954 | 0.894 |
| 026_1176_00266430 | Skin | 1176 | 451Lu | 456 | 0.00066 | 0.26 | 0.428 | 0.38 | 0.386 | 0.4254 | 0.499 | 0.6795 | 0.8423 | 0.9729 |
| 026_1149_00263460 | Skin | 1149 | G-MEL | 456 | 0.018696 | 0.065 | 0.23 | 0.181 | 0.1928 | 0.2465 | 0.404 | 0.7707 | 0.8991 | 0.9576 |
| 026_1147_00263750 | Skin | 1147 | SK-MEL-28 | 456 | 0.142676 | 0.187 | 0.48 | 0.376 | 0.4566 | 0.4611 | 0.565 | 0.6083 | 0.8116 | 0.9418 |
| 026_1037_00260080 | Skin | 1037 | SK-MEL-1 | 456 | 0.168848 | 0.176 | 0.417 | 0.368 | 0.3716 | 0.3919 | 0.613 | 0.6978 | 0.9091 | 0.966 |
| 026_1190_00266570 | Skin | 1190 | Hs 939.T | 456 | 0.185332 | 0.283 | 0.631 | 0.615 | 0.5802 | 0.5603 | 0.559 | 0.5576 | 0.7187 | 0.8082 |
| 026_1024_00265150 | Skin | 1024 | M-14 | 456 | 0.192152 | 0.418 | 0.433 | 0.383 | 0.391 | 0.4651 | 0.618 | 0.742 | 0.7678 | 0.9177 |
| 026_1025_00269710 | Skin | 1025 | COLO-679 | 456 | 0.228168 | 0.267 | 0.288 | 0.296 | 0.3664 | 0.4611 | 0.681 | 0.8141 | 0.9334 | 1.1196 |
| 026_8161_00263740 | Skin | 8161 | SH-4 | 456 | 0.433257 | 0.203 | 0.383 | 0.33 | 0.3147 | 0.3323 | 0.488 | 0.7539 | 0.8959 | 0.983 |
| 026_8097_00262820 | Skin | 8097 | LB2518-MEL | 456 | 0.437866 | 0.076 | 0.501 | 0.37 | 0.3843 | 0.4237 | 0.706 | 0.7414 | 0.8914 | 0.9396 |
| 026_8120_00260550 | Skin | 8120 | MZ7-mel | 456 | 0.447706 | 0.299 | 0.428 | 0.435 | 0.4782 | 0.4839 | 0.498 | 0.6521 | 0.7326 | 0.8788 |
| 026_1033_00262470 | Skin | 1033 | IPC-298 | 456 | 0.460127 | 0.363 | 0.36 | 0.404 | 0.4297 | 0.5245 | 0.562 | 0.7868 | 0.9191 | 0.8529 |
| 026_1031_00264030 | Skin | 1031 | IGR-37 | 456 | 0.57267 | 0.159 | 0.498 | 0.512 | 0.4794 | 0.5367 | 0.602 | 0.8381 | 0.9754 | 1.0032 |
| 026_1006_00260110 | Skin | 1006 | WM-115 | 456 | 0.616077 | 0.079 | 0.437 | 0.583 | 0.4912 | 0.4928 | 0.627 | 0.6176 | 0.6485 | 0.9586 |
| 026_8023_00265291 | Skin | 8023 | COLO-829 | 456 | 0.740747 | 0.164 | 0.659 | 0.533 | 0.5534 | 0.5976 | 0.709 | 0.8699 | 0.9148 | 0.9877 |
| 026_1036_00264690 | Skin | 1036 | RVH-421 | 456 | 0.784255 | 0.099 | 0.511 | 0.489 | 0.5329 | 0.5785 | 0.531 | 0.5954 | 0.5867 | 0.7408 |
| 026_1011_00269770 | Skin | 1011 | WM278 | 456 | 0.944573 | 0.289 | 0.463 | 0.457 | 0.4545 | 0.4605 | 0.568 | 0.7513 | 0.8836 | 0.9597 |
| 026_1003_00269650 | Skin | 1003 | G-361 | 456 | 0.948854 | 0.099 | 0.326 | 0.434 | 0.5233 | 0.6155 | 0.705 | 0.83 | 0.8998 | 1.0756 |
| 026_8002_00263700 | Skin | 8002 | A101D | 456 | 0.960267 | 0.088 | 0.468 | 0.524 | 0.5105 | 0.5276 | 0.55 | 0.5835 | 0.7643 | 0.8791 |
| 026_8104_00260540 | Skin | 8104 | LOXIMVI | 456 | 1.072404 | 0.278 | 0.403 | 0.39 | 0.4769 | 0.6158 | 0.839 | 0.877 | 0.864 | 0.9209 |
| 026_1005_00268780 | Skin | 1005 | A-375 | 456 | 1.191442 | 0.45 | 0.499 | 0.485 | 0.4604 | 0.5149 | 0.506 | 0.6624 | 0.892 | 0.928 |
| 026_1004_00260870 | Skin | 1004 | C32 | 456 | 1.195832 | 0.288 | 0.331 | 0.256 | 0.265 | 0.3055 | 0.504 | 0.8497 | 0.9278 | 0.9753 |
| 026_1030_00264020 | Skin | 1030 | IGR-1 | 456 | 1.307792 | 0.075 | 0.388 | 0.556 | 0.5173 | 0.6922 | 0.688 | 0.8911 | 0.7819 | 0.8658 |
| 026_1035_00265160 | Skin | 1035 | MEL-JUSO | 456 | 1.414781 | 0.305 | 0.481 | 0.494 | 0.5153 | 0.7013 | 0.739 | 0.9127 | 0.9597 | 1.0093 |
| 026_8119_00259980 | Skin | 8119 | MZ2-MEL. | 456 | 1.446447 | 0.402 | 0.467 | 0.438 | 0.4246 | 0.4152 | 0.679 | 0.7345 | 0.8985 | 0.9484 |
| 026_8097_00260530 | Skin | 8097 | LB2518-MEL | 456 | 1.447504 | 0.439 | 0.438 | 0.44 | 0.3578 | 0.3688 | 0.635 | 0.8111 | 0.8622 | 0.8731 |
| 026_8225_00264640 | Skin | 8225 | SK-MEL-5 | 456 | 1.574212 | 0.07 | 0.432 | 0.581 | 0.5597 | 0.6534 | 0.603 | 0.7648 | 0.9285 | 1.0194 |
| 026_8104_00262830 | Skin | 8104 | LOXIMVI | 456 | 1.676415 | 0.172 | 0.565 | 0.594 | 0.5546 | 0.7085 | 0.865 | 1.2098 | 1.0454 | 1.1061 |
| 026_1042_00274340 | Skin | 1042 | COLO792 | 456 | 1.75025 | 0.329 | 0.514 | 0.573 | 0.6166 | 0.6518 | 0.787 | 0.8993 | 0.9066 | 0.9485 |
| 026_1026_00269720 | Skin | 1026 | COLO-783 | 456 | 1.791757 | 0.479 | 0.599 | 0.603 | 0.6144 | 0.5728 | 0.634 | 0.6979 | 0.8575 | 0.9077 |
| 026_1010_00262530 | Skin | 1010 | WM1552C | 456 | 2.109919 | 0.3664 | 0.794 | 0.685 | 0.6806 | 0.6737 | 0.881 | 0.8586 | 0.9992 | 0.9359 |
| 026_1041_00263450 | Skin | 1041 | A431 | 456 | 2.481335 | 0.436 | 0.563 | 0.633 | 0.821 | 0.8517 | 0.858 | 1.0792 | 0.8962 | 0.9346 |
| 026_8098_00269090 | Skin | 8098 | LB373- | 456 | 2.623655 | 0.496 | 0.615 | 0.627 | 0.6225 | 0.6708 | 0.815 | 0.8109 | 0.9711 | 1.0201 |
| 026_1022_00262940 | Skin | 1022 | RPMI-7951 | 456 | 2.647594 | 0.249 | 0.552 | 0.678 | 0.6664 | 0.7181 | 0.824 | 0.8966 | 0.8605 | 0.908 |
| 026_1181_00269080 | Skin | 1181 | Hs 944.T | 456 | 2.824283 | 0.206 | 0.612 | 0.779 | 0.8499 | 0.8608 | 0.892 | 0.9924 | 1.1546 | 1.1214 |
| 026_1008_00262540 | Skin | 1008 | WM793B | 456 | 2.933974 | 0.371 | 0.744 | 0.693 | 0.6962 | 0.7393 | 0.731 | 0.8508 | 0.9586 | 0.8942 |
| 026_1027_00265280 | Skin | 1027 | COLO-800 | 456 | 3.132083 | 0.537 | 0.717 | 0.804 | 0.8959 | 0.9417 | 0.926 | 0.9678 | 0.954 | 1.0136 |
| 026_8034_00265300 | Skin | 8034 | DJM-1 | 456 | 3.234358 | 0.554 | 0.778 | 0.806 | 0.9452 | 0.9331 | 1.005 | 0.9966 | 1.0061 | 1.0084 |
| 026_1181_00264620 | Skin | 1181 | Hs 944.T | 456 | 3.491747 | 0.094 | 0.698 | 0.822 | 0.9152 | 0.8448 | 0.9 | 0.9921 | 0.9743 | 0.9841 |
| 026_8225_00263510 | Skin | 8225 | SK-MEL-5 | 456 | 3.505326 | 0.234 | 0.653 | 0.694 | 0.7331 | 0.7681 | 0.79 | 0.9216 | 0.9437 | 0.9528 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_1145_00263720 | Skin | 1145 | CHL-1 | 456 | 3.811805 | 0.609 | 0.895 | 0.833 | 0.8778 | 0.9025 | 0.855 | 0.9286 | 0.9316 | 1.0458 |
| 026_8060_00265311 | Skin | 8060 | GAK | 456 | 4.2621 | 0.37 | 0.758 | 0.827 | 0.7891 | 0.8733 | 0.894 | 0.9899 | 0.9692 | 0.9911 |
| 026_1047_00265320 | Skin | 1047 | MEWO | 456 | 4.342961 | 0.779 | 0.931 | 0.98 | 0.9757 | 0.9449 | 0.991 | 1.0008 | 0.9996 | 1 |
| 026_1022_00260910 | Skin | 10 | RPMI-7951 | 456 | 4.58823 | 0.257 | 0.748 | 0.801 | 0.8703 | 0.8751 | 0.884 | 0.9495 | 0.9173 | 0.9542 |
| 026_1038_00260090 | Skin | 1038 | SK-MEL-3 | 456 | 4.834702 | 0.151 | 0.731 | 0.777 | 0.7955 | 0.7955 | 0.827 | 0.8793 | 0.913 | 0.9361 |
| 026_1002_00260861 | Skin | 1002 | A2058 | 456 | 5.928358 | 0.795 | 0.897 | 0.85 | 0.894 | 0.8474 | 0.885 | 1.0053 | 0.8902 | 0.984 |
| 026_8025_00306491 | Skin | 8025 | CP66-MEL | 456 | 6.278644 | 0.914 | 0.888 | 1.059 | 0.9053 | 1.0334 | 0.961 | 0.8798 | 1.0258 | 0.9475 |
| 026_1120_00264061 | Skin | 1120 | UACC-62 | 456 | 6.317961 | 0.417 | 0.99 | 0.941 | 0.9531 | 0.9635 | 1.005 | 1.0535 | 1.0033 | 0.9903 |
| 026_1049_00269761 | Skin | 1049 | VMRC-MELG | 456 | 6.363031 | 0.904 | 0.991 | 0.949 | 0.974 | 0.9849 | 1.004 | 1.032 | 1.0282 | 1.0264 |
| 026_8077_00311281 | Skin | 8077 | IST-MEL1 | 456 | 6.486215 | 0.817 | 0.849 | 0.783 | 0.8212 | 0.8361 | 0.894 | 0.8285 | 0.9342 | 0.9134 |
| 026_1002_00262871 | Skin | 1002 | A2058 | 456 | 6.768535 | 0.494 | 1.023 | 0.918 | 0.9957 | 0.9334 | 0.899 | 0.9223 | 0.931 | 0.9502 |
| 026_1191_00266580 | Skin | 1191 | Hs 940.T | 456 | 7.017835 | 0.562 | 0.98 | 1.123 | 1.1931 | 0.9727 | 1.159 | 1.1334 | 1.0446 | 1.0643 |
| 026_8211_00306531 | Skin | 8211 | SK-MEL-24 | 456 | 7.240348 | 0.995 | 1.062 | 1.047 | 0.9379 | 1.0364 | 1.075 | 1.0521 | 1.0504 | 1.0137 |
| 026_1004_00262880 | Skin | 1004 | C32 | 456 | 7.407136 | 1.327 | 0.196 | 1.169 | 0.1356 | 1.1547 | 0.213 | 1.1935 | 0.7281 | 1.1468 |
| 026_8077_00263490 | Skin | 8077 | IST-MEL1 | 456 | 8.189893 | 1.25 | 1.21 | 1.184 | 1.1565 | 0.9453 | 0.931 | 1.1642 | 1.0861 | 1.0387 |
| 026_1076_00260350 | Stomach | 1076 | OCUM-1 | 456 | −1.975727 | 0.138 | 0.299 | 0.203 | 0.1441 | 0.1472 | 0.137 | 0.1598 | 0.2644 | 0.5747 |
| 026_1050_00262790 | Stomach | 1050 | AGS | 456 | 0.402284 | 0.198 | 0.304 | 0.337 | 0.4411 | 0.6201 | 0.452 | 0.6355 | 0.7729 | 1.0239 |
| 026_1070_00258920 | Stomach | 1070 | HSC-39 | 456 | 1.218484 | 0.163 | 0.38 | 0.469 | 0.5806 | 0.7048 | 0.892 | 1.16 | 0.922 | 1.1787 |
| 026_8193_00311240 | Stomach | 8193 | ECC10 | 456 | 1.328742 | 0.306 | 0.42 | 0.445 | 0.5445 | 0.7218 | 0.758 | 0.8813 | 0.9883 | 0.9993 |
| 026_1052_00255810 | Stomach | 1052 | SNU-1 | 456 | 1.425654 | 0.369 | 0.469 | 0.497 | 0.5342 | 0.5814 | 0.77 | 0.7984 | 0.8285 | 0.947 |
| 026_1056_00316590 | Stomach | 1056 | KATO III | 456 | 1.949149 | 0.309 | 0.531 | 0.622 | 0.6777 | 0.7504 | 0.912 | 0.9052 | 1.0407 | 1.0158 |
| 026_1060_00256830 | Stomach | 1060 | MKN45 | 456 | 2.285447 | 0.504 | 0.586 | 0.532 | 0.5224 | 0.5043 | 0.577 | 0.7757 | 0.8156 | 0.9028 |
| 026_1072_00258880 | Stomach | 1072 | 23132/87 | 456 | 2.907608 | 0.473 | 0.717 | 0.911 | 0.8748 | 1.0846 | 1.055 | 1.07 | 0.981 | 1.001 |
| 026_1060_00262910 | Stomach | 1060 | MKN45 | 456 | 2.913103 | 0.498 | 0.498 | 0.474 | 0.9422 | 0.5296 | 0.623 | 1.0575 | 0.9958 | 0.8867 |
| 026_1078_00263960 | Stomach | 1078 | IM-95 | 456 | 3.209661 | 0.345 | 0.625 | 0.723 | 1.042 | 0.7453 | 0.866 | 0.8746 | 0.9835 | 0.9734 |
| 026_1054_00308870 | Stomach | 1054 | SNU-16 | 456 | 3.34225 | 0.574 | 0.78 | 0.883 | 0.9578 | 0.9599 | 0.973 | 0.9861 | 1.0293 | 1.027 |
| 026_1064_00258960 | Stomach | 1064 | NUGC-3 | 456 | 3.516892 | 0.253 | 0.754 | 0.947 | 0.9636 | 0.9596 | 1.019 | 1.0426 | 1.0278 | 1.0027 |
| 026_1075_00308260 | Stomach | 1075 | NUGC-4 | 456 | 3.652276 | 0.617 | 0.827 | 0.703 | 0.9984 | 1.0102 | 1.068 | 1.1379 | 0.9929 | 1.1512 |
| 026_1065_00273570 | Stomach | 1065 | MKN7 | 456 | 3.792655 | 0.621 | 0.777 | 0.872 | 0.891 | 0.9122 | 0.904 | 0.9197 | 0.9359 | 0.9547 |
| 026_1067_00311560 | Stomach | 1067 | RERF-GC-1B | 456 | 4.166168 | 0.732 | 0.677 | 0.761 | 0.8438 | 0.781 | 0.877 | 0.8716 | 0.958 | 1.0772 |
| 26_1067_00314080 | Stomach | 1067 | RERF-GC-1B | 456 | 4.402339 | 0.708 | 0.833 | 0.831 | 0.8383 | 0.8843 | 0.854 | 0.9212 | 0.9276 | 1.1227 |
| 026_1068_00258930 | Stomach | 1068 | MKN28 | 456 | 4.480011 | 0.554 | 0.885 | 0.897 | 0.9579 | 0.9774 | 1.009 | 1.0156 | 1.0042 | 1.0326 |
| 026_1057_00271310 | Stomach | 1057 | Hs 746T | 456 | 4.481195 | 0.745 | 0.743 | 0.677 | 0.6977 | 0.6882 | 0.86 | 0.875 | 0.9503 | 1.0984 |
| 026_1060_00260890 | Stomach | 1060 | MKN45 | 456 | 4.604315 | 0.753 | 0.738 | 0.731 | 0.6895 | 0.6891 | 0.836 | 1.0727 | 1.0008 | 0.9928 |
| 026_1051_00269200 | Stomach | 1051 | FU97 | 456 | 4.755599 | 0.738 | 0.851 | 0.914 | 0.8985 | 0.8947 | 0.955 | 0.9241 | 0.9866 | 1.0457 |
| 026_8187_00316461 | Stomach | 8187 | TGBC11TKB | 456 | 4.931222 | 0.775 | 0.953 | 0.925 | 0.9227 | 0.9488 | 0.988 | 0.9649 | 0.9982 | 0.9763 |
| 026_1058_00263730 | Stomach | 1058 | NCI-N87 | 456 | 5.400356 | 0.754 | 0.824 | 0.808 | 0.8382 | 0.8486 | 0.868 | 0.9105 | 0.9132 | 0.9828 |
| 026_1064_00264040 | Stomach | 1064 | NUGC-3 | 456 | 6.53754 | 0.915 | 1.021 | 1.007 | 1.0316 | 0.9966 | 1.014 | 1.0431 | 0.9819 | 1.0068 |
| 026_1077_00264820 | Stomach | 1077 | SCH | 456 | 6.77844 | 0.466 | 1.271 | 1.195 | 1.2103 | 1.1255 | 0.977 | 0.9179 | 1.1315 | 1.1153 |
| 026_1051_00265140 | Stomach | 1051 | FU97 | 456 | 6.812551 | 0.149 | 0.752 | 0.783 | 0.8562 | 0.833 | 0.758 | 0.8748 | 0.8287 | 0.8438 |
| 026_8067_00258320 | Stomach | 8067 | GT3TKB | 456 | 7.007727 | 0.623 | 0.977 | 1.004 | 1.0575 | 1.0443 | 1.026 | 1.0598 | 1.0143 | 1.0267 |
| 026_1053_00258360 | Stomach | 1053 | SNU-5 | 456 | 7.265878 | 1 | 0.967 | 0.868 | 0.95 | 0.958 | 1.018 | 1.0763 | 1.0284 | 1.0105 |
| 026_1073_00258910 | Stomach | 1073 | HGC-27 | 456 | 7.474785 | 0.055 | 1.003 | 1.012 | 1.0288 | 1.0225 | 1.013 | 1.0331 | 0.9845 | 0.9972 |
| 026_8062_00266170 | Stomach | 8062 | GCIY | 456 | 7.70033 | 1.076 | 1.218 | 0.962 | 1.0422 | 0.9155 | 1.202 | 0.9466 | 0.9302 | 1.1001 |
| 026_1059_00256820 | Stomach | 1059 | MKN1 | 456 | 7.84127 | 1.023 | 1.223 | 1.097 | 1.1806 | 1.0334 | 0.924 | 1.0209 | 0.9691 | 0.9885 |
| 026_8216_00258330 | Stomach | 8216 | RF-48 | 456 | 8.041101 | 0.627 | 1.056 | 1.075 | 1.0873 | 1.0084 | 1.031 | 1.0144 | 1.008 | 0.9914 |
| 026_8143_00302630 | Testes | 8143 | NTERA- | 456 | 4.238289 | 0.709 | 0.74 | 0.781 | 0.8439 | 0.8942 | 0.971 | 0.9553 | 0.9264 | 1.0878 |
| 026_1081_00299690 | Testes | 1081 | NCC-IT-A3 | 456 | 4.69755 | 0.834 | 0.925 | 0.99 | 1.0022 | 1.0753 | 0.959 | 1.0664 | 0.9907 | 0.9674 |
| 026_1082_00300430 | Testes | 1082 | NEC8 | 456 | 5.794775 | 0.518 | 0.919 | 1.026 | 1.1263 | 1.0267 | 0.882 | 1.2293 | 0.8205 | 0.9481 |

TABLE_22-continued

| | | | | | Fitted | Viability ratio | | | | | | | | |
|---|---|---|---|---|---|---|---|---|---|---|---|---|---|---|
| Barcode | Organ | Cell ID | Cell Line | Compound No | MGH.IC50 | 20 uM | 10 uM | 5 uM | 2.5 uM | 1.25 uM | 0.625 uM | 0.3125 uM | 0.15625 uM | 0.078125 uM |
| 026_1087_00311210 | Thyroid | 1087 | BHT-101 | 456 | 0.094631 | 0.409 | 0.402 | 0.405 | 0.4025 | 0.4677 | 0.606 | 0.749 | 0.9156 | 0.9734 |
| 026_1098_00252970 | Thyroid | 1098 | IHH-4 | 456 | 0.734299 | 0.193 | 0.418 | 0.365 | 0.5027 | 0.4309 | 0.680 | 0.6796 | 0.9903 | 0.9333 |
| 026_1093_00253040 | Thyroid | 1093 | TT2609-C02 | 456 | 1.438563 | 0.33 | 0.462 | 0.489 | 0.4674 | 0.6027 | 0.719 | 0.8623 | 0.9552 | 1.0031 |
| 026_1100_00252990 | Thyroid | 1100 | KMH-2 | 456 | 1.898194 | 0.142 | 0.5 | 0.577 | 0.6566 | 0.6074 | 0.682 | 0.7694 | 0.8888 | 0.9822 |
| 026_1085_00252920 | Thyroid | 1085 | 8505C | 456 | 2.3348 | 0.536 | 0.498 | 0.605 | 0.5369 | 0.584 | 0.788 | 0.7985 | 1.0523 | 0.937 |
| 026_1088_00252930 | Thyroid | 1088 | CAL-62 | 456 | 2.495611 | 0.451 | 0.785 | 0.606 | 0.8114 | 0.6653 | 0.836 | 1.0285 | 1.0053 | 0.944 |
| 026_1089_00261010 | Thyroid | 1089 | HTC-C3 | 456 | 2.538171 | 0.577 | 0.55 | 0.623 | 0.7757 | 0.5886 | 0.616 | 0.7161 | 0.7476 | 0.9625 |
| 026_1090_00311330 | Thyroid | 1090 | ML-1 | 456 | 2.64388 | 0.368 | 0.64 | 0.793 | 0.8005 | 0.8127 | 0.931 | 0.9783 | 0.9389 | 1.0355 |
| 026_1090_00253010 | Thyroid | 1090 | ML-1 | 456 | 3.121258 | 0.165 | 0.778 | 0.787 | 0.6376 | 0.6432 | 0.975 | 1.0524 | 0.7737 | 1.0765 |
| 026_1090_00308850 | Thyroid | 1090 | ML-1 | 456 | 3.18393 | 0.308 | 0.673 | 0.724 | 0.8112 | 0.8338 | 0.925 | 0.9016 | 0.8988 | 1.0407 |
| 026_1086_00255730 | Thyroid | 1086 | B-CPAP | 456 | 3.682081 | 0.171 | 0.695 | 0.763 | 0.7585 | 0.7239 | 0.856 | 0.9452 | 0.9473 | 1.0079 |
| 026_8020_00314210 | Thyroid | 8020 | CGTH-W-1 | 456 | 4.407018 | 0.694 | 0.874 | 0.871 | 0.8186 | 0.9478 | 0.965 | 0.9497 | 1.0206 | 1.0176 |
| 026_1084_00266520 | Thyroid | 1084 | 8305C | 456 | 4.442179 | 0.592 | 0.739 | 0.746 | 0.7517 | 0.73 | 0.793 | 0.8273 | 0.8894 | 0.8901 |
| 026_8213_00259200 | Thyroid | 8213 | TT | 456 | 4.648028 | 0.769 | 0.966 | 0.965 | 0.9831 | 0.9968 | 0.984 | 0.9765 | 0.9632 | 0.942 |
| 026_8082_00252980 | Thyroid | 8082 | K5 | 456 | 6.244906 | 0.27 | 0.935 | 0.007 | 0.9319 | 0.951 | 0.93 | 0.997 | 0.9506 | 0.9691 |
| 026_1099_00306470 | Thyroid | 1099 | ASH-3 | 456 | 6.262224 | 0.912 | 0.905 | 0.964 | 0.9293 | 0.932 | 0.965 | 0.9777 | 0.9947 | 1.0629 |
| 026_1094_00259110 | Thyroid | 1094 | FTC-133 | 456 | 6.573461 | 0.084 | 0.958 | 0.978 | 1.0951 | 1.0879 | 1.057 | 1.063 | 1.0254 | 0.8654 |
| 026_1092_00259170 | Thyroid | 1092 | S-117 | 456 | 6.767861 | 0.271 | 0.973 | 0.988 | 1.0669 | 1.039 | 1.047 | 1.018 | 1.0563 | 1.0542 |
| 026_1097_00259160 | Thyroid | 1097 | RO82-W-1 | 456 | 7.698514 | 0.685 | 1.079 | 1.053 | 1.0554 | 1.0411 | 1.049 | 1.0682 | 1.0349 | 1.0563 |
| 26_8036_00304360 | Urinary Track | 8036 | DSH1 | 456 | 1.200178 | 0.377 | 0.348 | 0.397 | 0.5545 | 0.7402 | 0.871 | 0.9778 | 0.9884 | 1.0288 |
| 026_24_00298840 | Urinary Track | 24 | RT4 | 456 | 2.281802 | 0.504 | 0.543 | 0.577 | 0.6272 | 0.7473 | 0.889 | 1.0564 | 1.0628 | 1.0768 |
| 026_18_00299720 | Urinary Track | 18 | RT-112 | 456 | 2.448355 | 0.479 | 0.581 | 0.587 | 0.6728 | 0.7768 | 0.797 | 0.8705 | 1.106 | 1.03 |
| 026_24_00252540 | Urinary Track | 24 | RT4 | 456 | 2.668527 | 0.216 | 0.59 | 0.634 | 0.6994 | 0.7144 | 0.855 | 0.9368 | 0.9696 | 1.0194 |
| 026_8036_00257170 | Urinary Track | 8036 | DSH1 | 456 | 2.728478 | 0.679 | 0.605 | 0.639 | 0.6941 | 0.7355 | 0.829 | 0.9411 | 1.0033 | 1.0113 |
| 026_9_00298850 | Urinary Track | 9 | SW 780 | 456 | 2.896276 | 0.523 | 0.587 | 0.676 | 0.7538 | 0.7859 | 0.866 | 0.9594 | 0.9717 | 1.0348 |
| 026_15_00316530 | Urinary Track | 15 | BFTC-905 | 456 | 3.218144 | 0.607 | 0.59 | 0.688 | 0.6971 | 0.8338 | 0.848 | 0.8978 | 1.0448 | 1.0799 |
| 026_8_00298880 | Urinary Track | 8 | UM-UC-3 | 456 | 3.221517 | 0.557 | 0.72 | 0.789 | 0.8471 | 0.8599 | 0.995 | 1.0484 | 1.045 | 1.0264 |
| 026_6_00303090 | Urinary Track | 6 | 5637 | 456 | 3.348554 | 0.553 | 0.725 | 0.744 | 0.7649 | 0.9313 | 0.918 | 0.9221 | 0.9563 | 1.0354 |
| 026_6_00256650 | Urinary Track | 6 | 5637 | 456 | 3.837233 | 0.726 | 0.703 | 0.715 | 0.7187 | 0.7189 | 0.755 | 0.9193 | 0.965 | 1.0004 |
| 026_8101_00256280 | Urinary Track | 8101 | LB831-BLC | 456 | 3.939929 | 0.504 | 0.835 | 0.952 | 1.0143 | 1.0014 | 1.01 | 0.9848 | 0.9739 | 0.9713 |
| 026_11_00298870 | Urinary Track | 11 | T24 | 456 | 4.120815 | 0.697 | 0.744 | 0.763 | 0.8533 | 0.8788 | 0.941 | 0.9969 | 1.0222 | 1.1105 |
| 026_19_00298860 | Urinary Track | 19 | SW-1710 | 456 | 4.713264 | 0.758 | 0.847 | 0.828 | 0.8254 | 0.8943 | 0.979 | 0.9968 | 1.0264 | 1.0955 |
| 026_7_00302400 | Urinary Track | 7 | SCaBER | 456 | 4.780909 | 0.779 | 0.775 | 0.708 | 0.7824 | 0.8163 | 0.882 | 1.0463 | 0.9494 | 1.0621 |
| 026_8101_00302620 | Urinary Track | 8101 | LB831-BLC | 456 | 4.856105 | 0.76 | 0.882 | 0.929 | 0.9235 | 0.9393 | 0.926 | 0.9386 | 0.9281 | 1.0507 |

TABLE_22-continued

| Barcode | Organ | Cell ID | Cell Line | Compound No | Fitted MGH.IC50 | Viability ratio 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_22_00298810 | Urinary Track | 22 | HT 1376 | 456 | 4.888331 | 0.823 | 0.879 | 1.047 | 0.8692 | 1.0283 | 0.988 | 1.0731 | 1.1432 | 1.097 |
| 026_20_00299740 | Urinary Track | 20 | VM-CUB1 | 456 | 4.987745 | 0.751 | 0.753 | 0.758 | 0.8989 | 0.8726 | 0.877 | 0.9581 | 0.9471 | 0.9762 |
| 026_14_00298780 | Urinary Track | 14 | 647-V | 456 | 5.049696 | 0.854 | 0.851 | 0.873 | 0.8859 | 0.9584 | 1.097 | 1.1389 | 1.2074 | 1.0083 |
| 026_12_00299730 | Urinary Track | 12 | TCCSUP | 456 | 5.306108 | 0.821 | 0.876 | 0.897 | 0.9178 | 0.9315 | 0.962 | 0.9176 | 1.0469 | 1.0217 |
| 026_13_00298770 | Urinary Track | 13 | 639-V | 456 | 5.658711 | 0.867 | 0.933 | 0.849 | 0.9317 | 0.8466 | 1.046 | 1.0223 | 1.1266 | 1.2765 |
| 026_16_00298800 | Urinary Track | 16 | CAL-29 | 456 | 5.956916 | 0.811 | 0.834 | 0.909 | 0.8884 | 0.9073 | 0.924 | 0.956 | 0.9709 | 0.9841 |
| 026_3_00308800 | Urinary Track | 3 | HT-1197 | 456 | 6.060787 | 0.877 | 0.935 | 0.984 | 0.8762 | 0.9541 | 0.87 | 1.0393 | 1.0266 | 1.0429 |
| 026_17_00300420 | Urinary Track | 17 | KU-19-19 | 456 | 6.388593 | 0.216 | 0.953 | 0.975 | 0.9996 | 0.9834 | 0.744 | 0.9959 | 0.9777 | 1.0473 |
| 026_10_00298820 | Urinary Track | 10 | J82 | 456 | 6.755266 | 0.951 | 0.965 | 0.925 | 0.9536 | 1.0393 | 1.06 | 1.0882 | 1.0657 | 1.037 |
| 026_8154_00262510 | Uterus | 8154 | RL95-2 | 456 | 0.033885 | 0.116 | 0.241 | 0.307 | 0.315 | 0.5516 | 0.413 | 0.6863 | 0.814 | 0.8778 |
| 026_1116_00268860 | Uterus | 1116 | SNG-M | 456 | 2.236003 | 0.377 | 0.605 | 0.635 | 0.4653 | 0.7155 | 0.805 | 0.9708 | 1.0702 | 1.1724 |
| 026_8154_00280250 | Uterus | 8154 | RL95-2 | 456 | 2.655708 | 0.475 | 0.611 | 0.69 | 0.592 | 0.6865 | 0.677 | 0.826 | 0.8426 | 0.9723 |
| 026_8166_00269750 | Uterus | 8166 | SK-UT-1 | 456 | 2.769805 | 0.399 | 0.642 | 0.861 | 0.9305 | 0.8691 | 0.946 | 0.8217 | 0.867 | 0.9308 |
| 026_1115_00268850 | Uterus | 1115 | SKN | 456 | 3.232484 | 0.402 | 0.724 | 0.819 | 0.8345 | 0.9291 | 0.941 | 1.0001 | 0.9878 | 0.9814 |
| 026_1112_00268820 | Uterus | 1112 | Ishikawa (Heraklio) 02 ER- | 456 | 3.572844 | 0.62 | 0.659 | 0.62 | 0.6814 | 0.702 | 0.72 | 0.9036 | 0.8807 | 1.0744 |
| 026_1107_00311310 | Uterus | 1107 | MFE-296 | 456 | 3.590101 | 0.601 | 0.697 | 0.647 | 0.7074 | 0.7773 | 0.802 | 0.8186 | 0.9166 | 1.0105 |
| 026_1108_00308840 | Uterus | 1108 | MFE-319 | 456 | 3.953038 | 0.7 | 0.723 | 0.698 | 0.8033 | 0.8993 | 0.819 | 0.9773 | 1.1189 | 1.0369 |
| 026_1109_00269701 | Uterus | 1109 | COLO684 | 456 | 4.059524 | 0.645 | 0.818 | 0.925 | 0.873 | 0.8541 | 0.934 | 0.9505 | 0.9782 | 1.0023 |
| 026_1102_00268790 | Uterus | 1102 | AN3CA | 456 | 4.238238 | 0.395 | 0.808 | 0.815 | 0.8203 | 0.9291 | 0.817 | 0.9786 | 0.9815 | 0.9877 |
| 026_1108_00314330 | Uterus | 1108 | MFE-319 | 456 | 4.375739 | 0.745 | 0.784 | 0.794 | 0.8526 | 0.9259 | 0.907 | 1.0498 | 1.0643 | 1.1339 |
| 026_1113_00268840 | Uterus | 1113 | MES-SA | 456 | 4.83984 | 0.832 | 0.962 | 1.003 | 0.9833 | 0.9906 | 0.984 | 0.9981 | 1.0121 | 0.9684 |
| 026_1117_00268810 | Uterus | 1117 | HEC-1 | 456 | 5.215029 | 0.824 | 0.904 | 0.885 | 0.8856 | 0.9834 | 0.972 | 0.9217 | 1.0697 | 1.0963 |
| 026_1113_00318661 | Uterus | 1113 | MES-SA | 456 | 5.307659 | 0.807 | 0.995 | 0.947 | 0.9632 | 1.0122 | 1.033 | 1.0384 | 1.0103 | 0.9636 |
| 026_8206_00264270 | Uterus | 8206 | KLE | 456 | 5.888467 | 0.885 | 1 | 1.029 | 1.0338 | 1.0454 | 1.029 | 0.9964 | 1.0291 | 0.9684 |
| 026_1105_00308190 | Uterus | 1105 | ESS-1 | 456 | 6.082924 | 0.887 | 0.915 | 0.911 | 0.9349 | 0.8927 | 0.94 | 0.9007 | 0.9407 | 0.9198 |
| 026_1104_00306500 | Uterus | 1104 | EN | 456 | 7.302741 | 1.047 | 0.983 | 0.999 | 0.9204 | 1.0053 | 1.011 | 1.0162 | 1.0749 | 1.0308 |
| 026_1106_00306510 | Uterus | 1106 | MFE-280 | 456 | 7.686964 | 1.124 | 0.983 | 1 | 0.9683 | 1.0601 | 1.156 | 1.0799 | 1.0206 | 0.9018 |
| 026_8163_00302640 | Vulva | 8163 | SK-LMS-1 | 456 | 2.432701 | 0.479 | 0.526 | 0.621 | 0.7198 | 0.8786 | 0.991 | 1.0278 | 1.0369 | 1.1613 |
| 026_8173_00302660 | Vulva | 8173 | SW954 | 456 | 2.875791 | 0.539 | 0.622 | 0.644 | 0.6956 | 0.8294 | 0.806 | 1.072 | 1.0089 | 1.087 |
| 26_8174_00304380 | Vulva | 8174 | SW962 | 456 | 4.641057 | 0.756 | 0.704 | 0.824 | 0.7868 | 0.8056 | 0.875 | 0.851 | 0.96 | 1.0607 |
| 026_481_00302570 | Vulva | 481 | CAL-39 | 456 | 5.164144 | 0.803 | 0.856 | 0.841 | 0.8864 | 0.9389 | 0.924 | 0.983 | 0.9909 | 1.1127 |
| 026_8174_00306540 | Vulva | 8174 | SW962 | 456 | 6.896884 | 0.97 | 0.963 | 1.002 | 0.9267 | 1.0771 | 0.973 | 1.0027 | 1.0435 | 1.0588 |

Example 12

BVD-523 Demonstrates In Vivo Antitumor Activity in $BRAF^{V600E}$-Mutant Cancer Cell Line Xenograft Models Based on our in vitro findings that BVD-523 reduced proliferation and induced apoptosis in a concentration-dependent manner, BVD-523 was administered by oral gavage to demonstrate its in vivo anti-tumor activity in models with MAPK/ERK-pathway dependency. Xenograft models of melanoma (cell line A375), and colorectal cancer (cell line Colo205), were utilized, both of which harbor a $BRAF^{V600E}$ mutation.

Figure 31A:
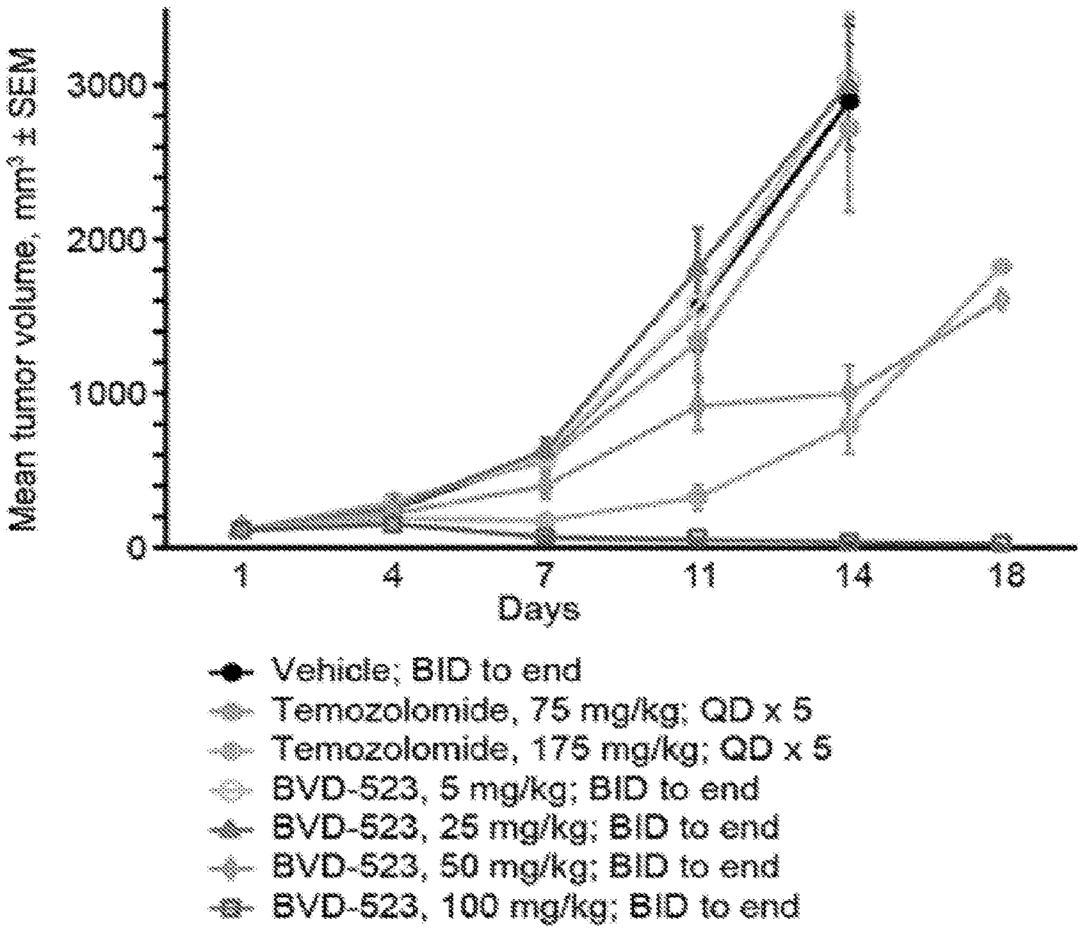
FIG. 31A-FIG. 31C show in vivo BVD-523 anti-tumor activity. BVD-523 monotherapy inhibits tumor growth in (FIG. 31A) A375 and (FIG. 31B) Colo205 cell line xenograft models ($^{a}$P<0.0001, compared with vehicle control; CPT-11 dosed on Day 14 and Day 18 only). Abbreviations: BID, twice daily; CMC, carboxymethylcellulose; QD, every day; Q4D, every 4 days.

In A375 cell line xenografts, BVD-523 efficacy was compared with the control cytotoxic alkylating agent temozolomide following 14 days of treatment. BVD-523 demonstrated significant dose-dependent antitumor activity starting at 50 mg/kg twice daily (BID) (FIG. 31A). Doses of 50 and 100 mg/kg BID significantly attenuated tumor growth, with tumor growth inhibition (TGI) of 71% (P=0.004) and 99% (P<0.001), respectively. Seven partial regressions (PRs) were noted in the 100 mg/kg BID group, no regression responses were noted in any other group. The efficacy observed compared favorably with that of temozolomide, which when administered at 75 and 175 mg/kg resulted in modest dose-dependent TGI of 34% (P>0.05) and 78% (P=0.005), respectively.

Figure 31B:
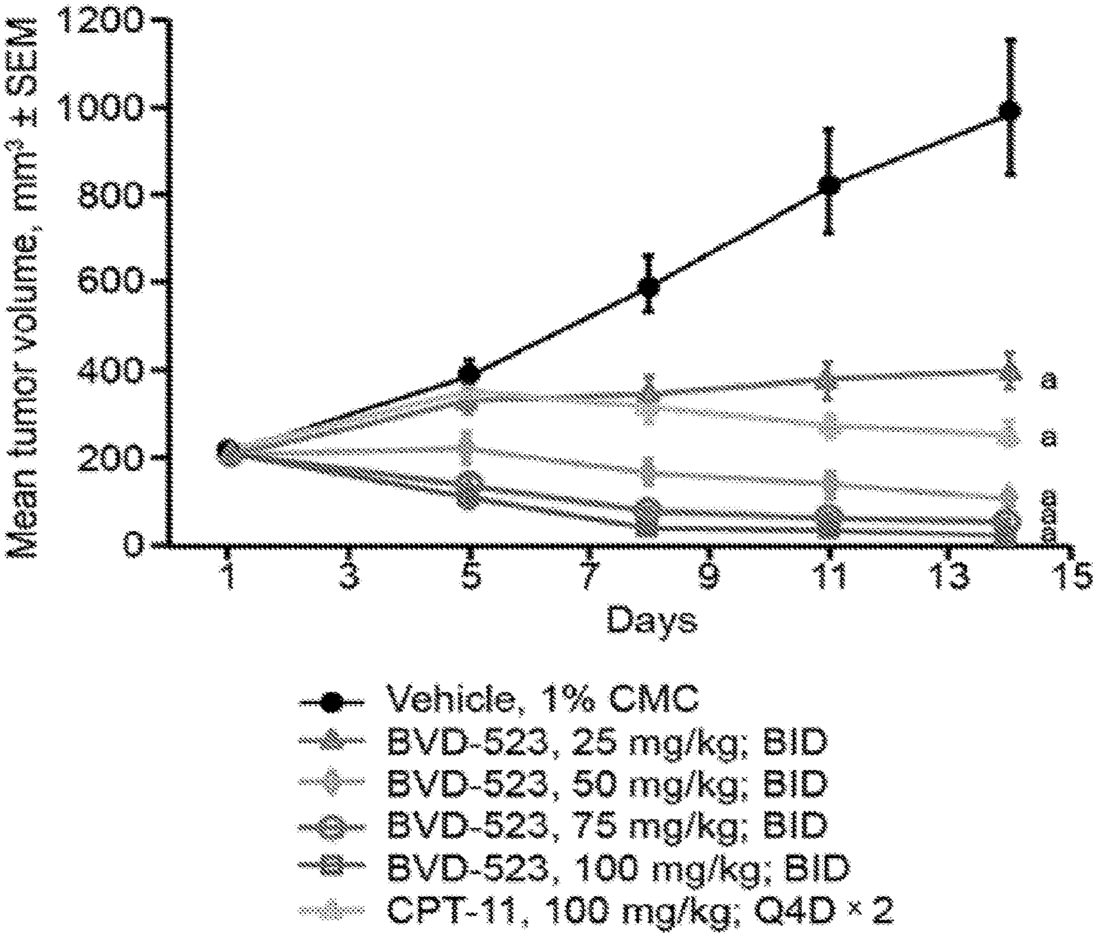

Additionally, BVD-523 demonstrated antitumor efficacy in a Colo205 human colorectal cancer cell line xenograft model (FIG. 31B). BVD-523 again showed significant dose-dependent tumor regressions at doses of 50, 75, and 100 mg/kg BID, yielding mean tumor regressions $T/T_i$ (T=End of treatment, $T_i$=Treatment initiation) of −48.2%, −77.2%, and −92.3%, respectively (all P<0.0001). Regression was not observed at the lowest dose of BVD-523 (25 mg/kg BID); however, significant tumor growth inhibition, with a T/C (T=Treatment, C=Control) of 25.2% (P<0.0001), was observed. Although not well tolerated, the positive control chemotherapeutic agent irinotecan (CPT-11) showed significant antitumor activity, inhibiting Colo205 tumor growth with a T/C of 6.4% (P<0.0001). However, even at its maximum tolerated dose in mice, CPT-11 was not as effective as BVD-523 at doses of 50, 75, or 100 mg/kg BID.

Figure 31C:
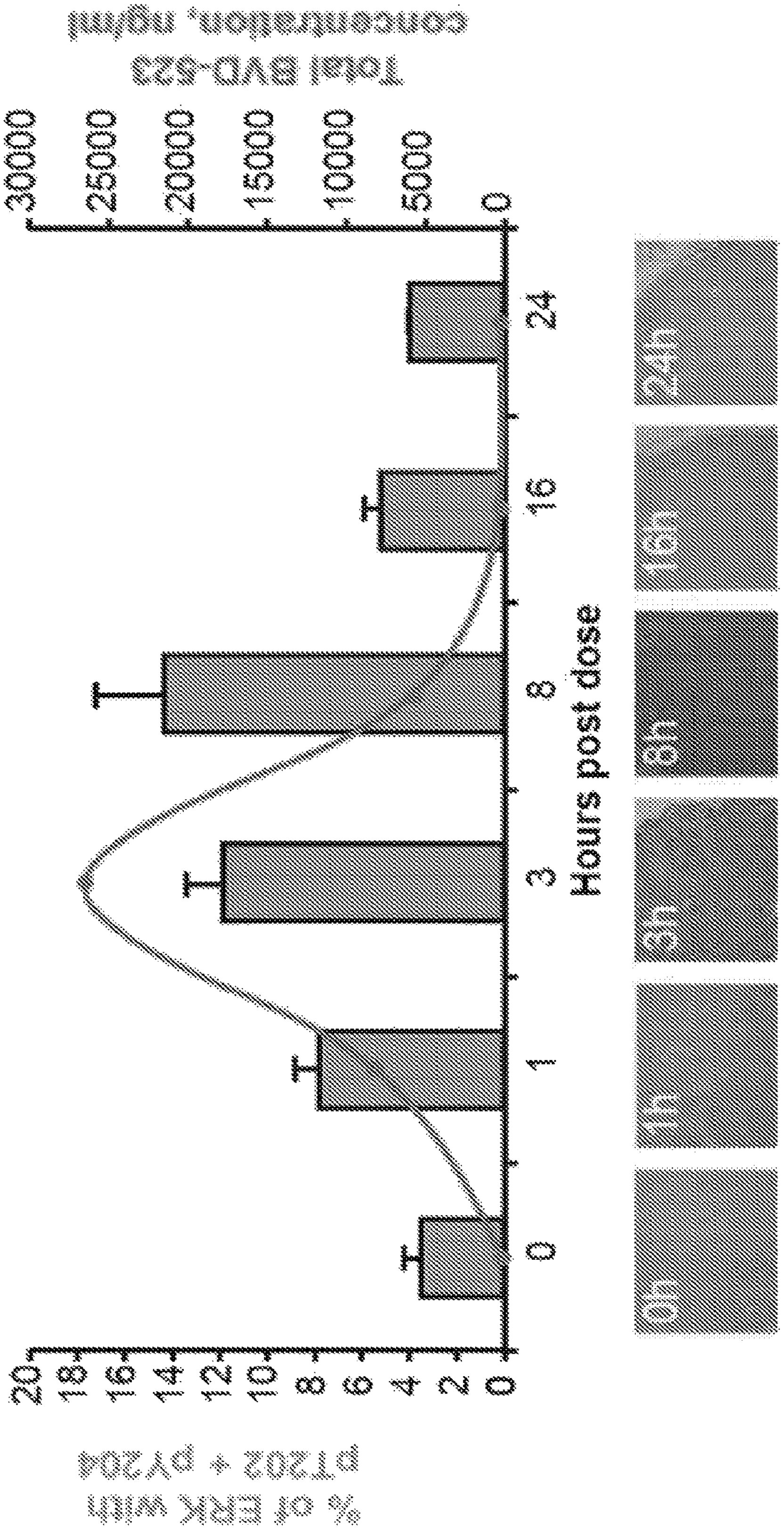

To establish the relationship between pharmacokinetics and pharmacodynamics, BVD-523 plasma concentrations were compared with pERK1/2 levels measured in the tumor by immunohistochemistry and isotope-tagged internal standard mass spectrometry over a 24-hour period following a single 100 mg/kg oral dose of BVD-523 (FIG. 31C). Phosphorylation of ERK1/2 was low in untreated tumors (0 hours). Following treatment with BVD-523, ERK1/2 phosphorylation steadily increased from 1 hour post-dose to maximal levels at 8 hours post-dose, then returned to pre-dose levels by 24 hours. This increase in pERK1/2 correlated with BVD-523 drug plasma concentrations. The in vivo observation of increased pERK1/2 with BVD-523 treatment is consistent with earlier in vitro findings (FIG. 30D).

Example 13

Figure 32A:
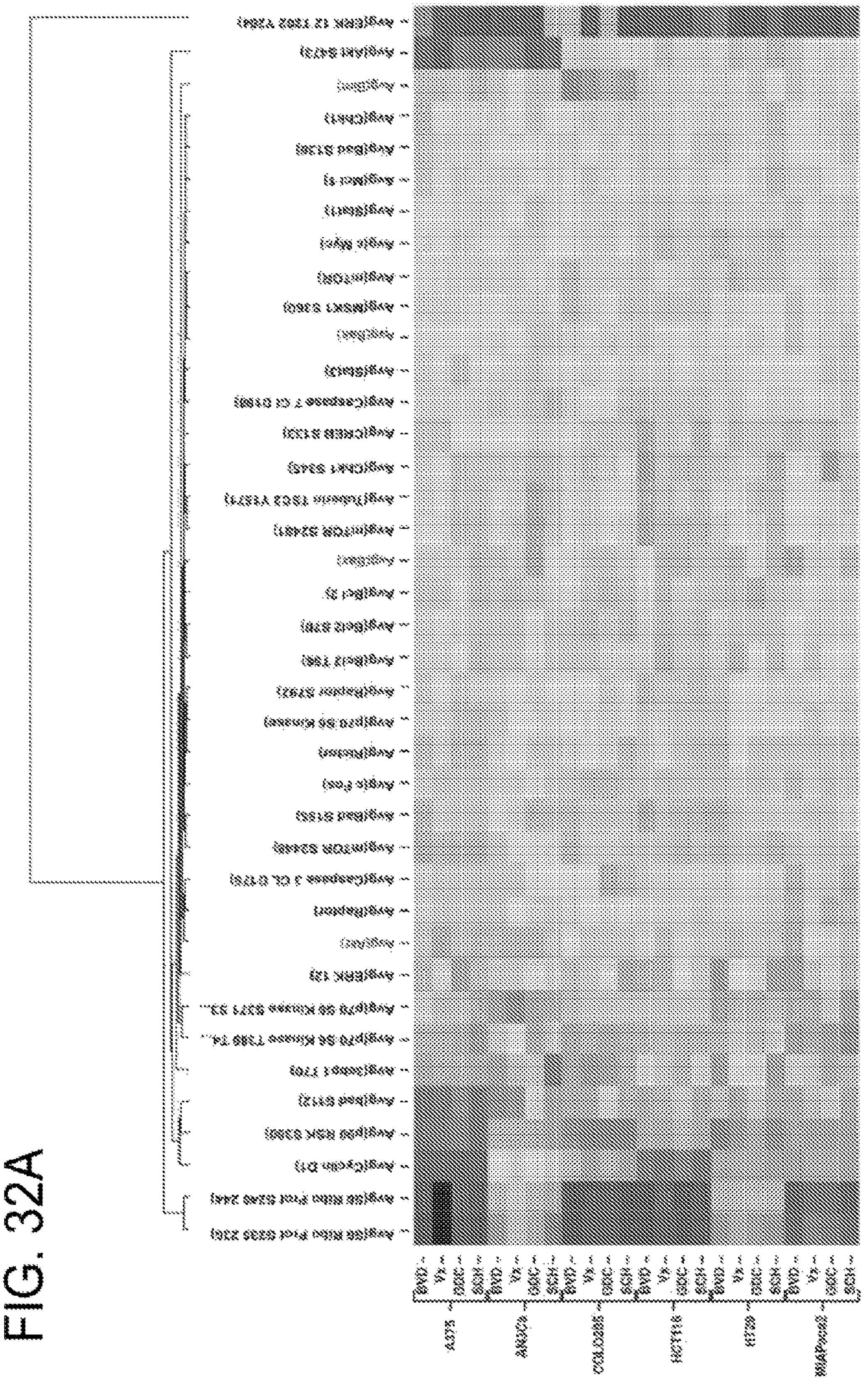
FIG. 32A shows signaling effects of ERK1/2 inhibitors. Using RPPA, effects on proteins are measured in cell lines (A375, AN3Ca, Colo205, HCT116, HT29 and MIAPaca2) following treatment with ERK1/2 inhibitors BVD-523 (BVD), Vx11e (Vx), GDC-0994 (GDC), or SCH722984 (SCH).
Figure 32B:
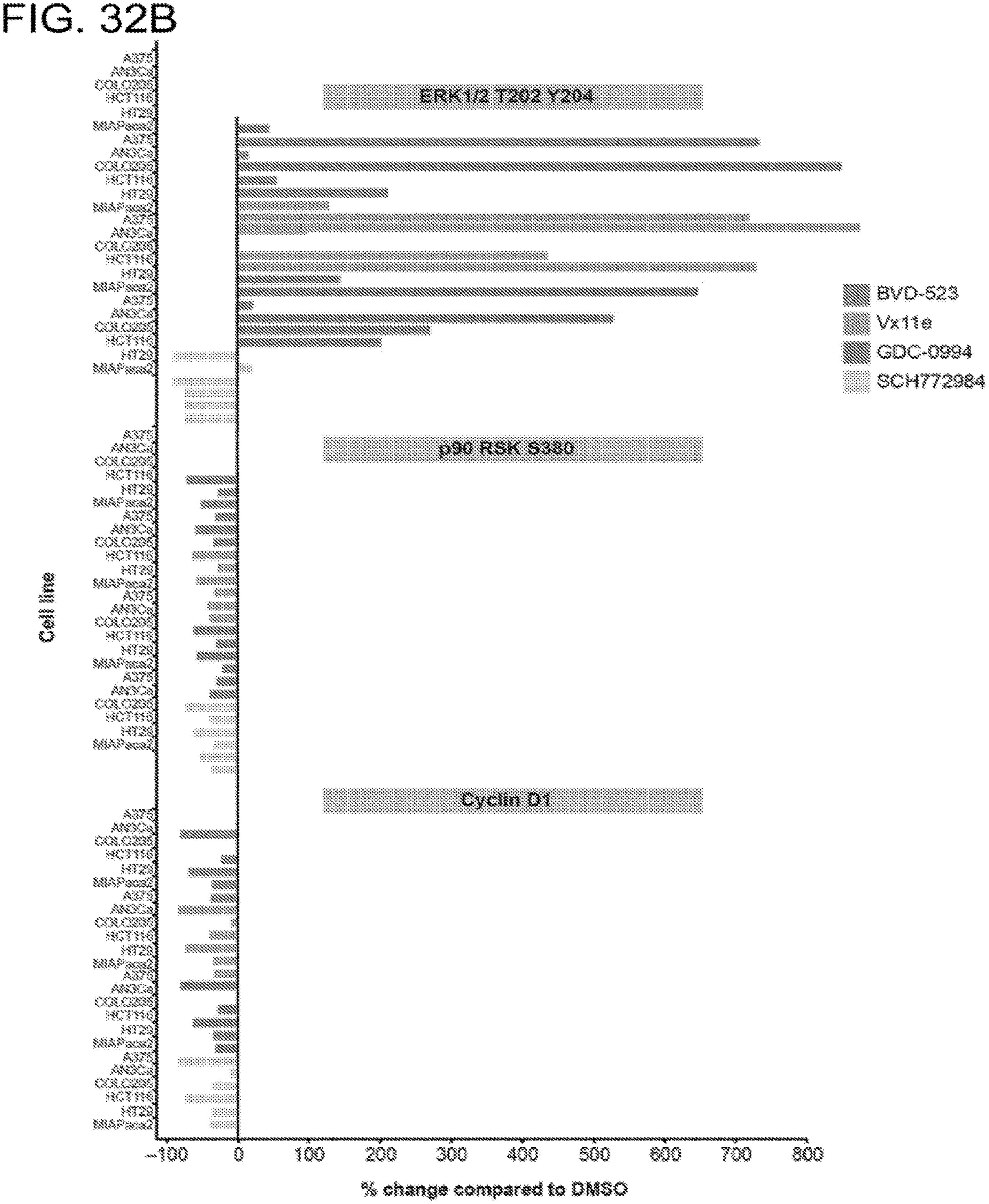
FIG. 32B shows that the ERK inhibitors BVD-523, GDC-0994, and Vx11e have differential effects on phospho-ERK (ERK 1/2 T202 Y204) compared with SCH722984; phospho-RSK (p90 RSK 380) and Cyclin D1 are inhibited by the ERK inhibitors tested. Abbreviations: BRAFi, BRAF inhibitors; MEKi, MEK inhibitors.

BVD-523 Results in ERK1/2 Substrate Inhibition Despite Increased ERK1/2 Phosphorylation To examine the effects of BVD-523 on signaling relative to other known ERK1/2 inhibitors (SCH772984, GDC-0994, and Vx-11e) (Morris et al. 2013 and Liu et al. 2015), a large-scale reverse phase protein array (RPPA) of approximately 40 proteins was employed in a variety of cell lines with sensitivity to ERK inhibition. Cell lines with common alterations in BRAF and RAS were assayed: $BRAF^{V600E}$ mutant lines A375, Colo205, and HT29; $KRAS^{G12C}$-mutant cell line MIAPACa-2; $KRAS^{G13D}$-mutant cell line HCT116; and AN3Ca with atypical $HRAS^{F82L}$ mutation. Changes in protein levels are shown as a percentage change from dimethyl sulfoxide (DMSO)-treated parental control (FIG. 32A and Table 23). All ERK inhibitors elicited qualitatively similar protein effects, with the exception of phosphorylation of ERK1/2 (pERK1/2 [ERK1/2-T202, -Y204]); SCH7722984 inhibited pERK1/2 in all cell lines, while BVD-523, GDC-0994, and Vx-11e markedly increased pERK1/2. Phospho-p90 RSK (pRSK1) and cyclin D1, which are proximal and distal targets of pERK1/2, respectively, were similarly inhibited by all inhibitors tested regardless of the degree of ERK1/2 phosphorylation (FIG. 32B). These independent findings for BVD-523 are consistent with studies showing that phosphorylation of ERK1/2 substrates RSK1/2 remained inhibited despite dramatically elevated pERK1/2 by Western blots in A375 cells (FIG. 32D), in addition to protein-binding studies demonstrating BVD-523 binding and stabilization of pERK1/2 and inactive ERK1/2 (FIG. 29E and FIG. 29F). Therefore, measuring increased pERK1/2 levels could be considered as a clinical pharmacodynamic biomarker for BVD-523, while quantifying inhibition of ERK1/2 targets such as pRSK1 and DUSP6 as well could serve a similar purpose.

Figure 33:
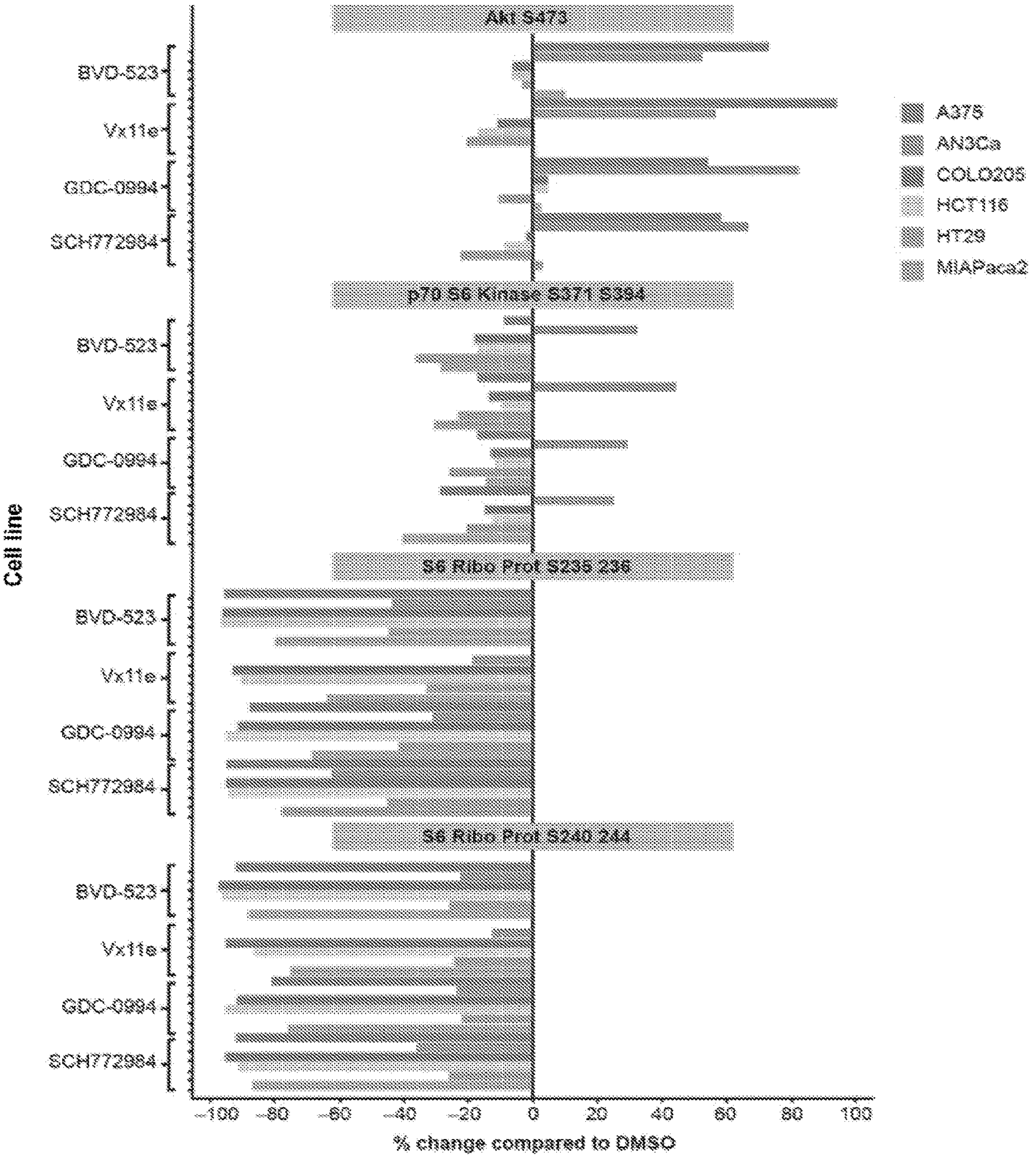
FIG. 33 shows that the ERK inhibitors BVD-523, Vx11, GDC-0994, and SCH772984 (SCH) demonstrate cell line-dependent changes in phospho-ATK levels. Abbreviation: DMSO, dimethyl sulfoxide.

Additional protein changes are of note in this RPPA dataset (FIG. 32A). Decreased pS6-ribosomal protein appears to be another pharmacodynamic marker of ERK1/2 inhibition, as evidenced in all cell lines with all compounds (FIG. 32B). Furthermore, prominent induction of pAKT appears to be a cell line-dependent observation, where each ERK1/2 inhibitor induced pAKT in cell lines A375 and AN3CA cells (FIG. 33). Interestingly, the degree of inhibition of survival marker pBAD appears to differ between compounds, with only modest inhibition of pBAD by GDC-0994 compared with the other ERK1/2 inhibitors tested (FIG. 32A).

Figure 32C:
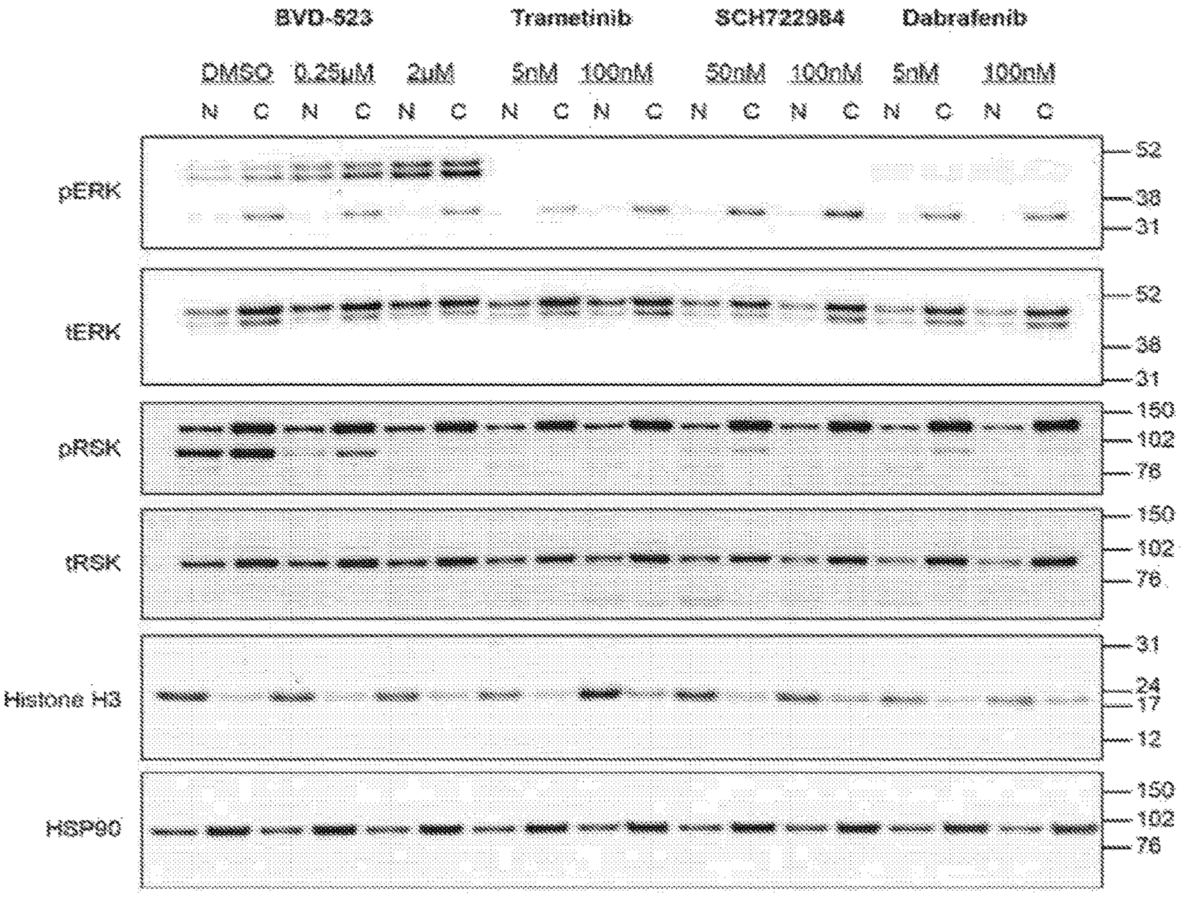
FIG. 32C shows a western blot assay of cellular and nuclear fractions from a RKO cell line following treatment with BVD-523, trametinib, SCH722984, or dabrafenib. Histone H3 (nuclear localized protein) and HSP90 (cytoplasmically localized protein) were included as positive controls to confirm that the nuclear and cytoplasmic fractions were properly enriched; nuclear fractions have high H3 and cytoplasmic fractions have higher HSP90.

Next, how BVD-523 affects cellular localization of ERK1/2 and downstream target pRSK in a $BRAF^{V600E}$-mutant RKO colorectal cell line (FIG. 32C) was investigated. In resting cells, ERK1/2 localizes to the cytoplasm, and once stimulated pERK1/2 migrates to target organelles, particularly the nucleus where transcriptional targets are activated (Wainstein et al. 2016). In DMSO-treated control cells, pERK1/2 is evident in both nuclear and cytoplasmic fractions, which is likely reflective of MAPK pathway activity due to the presence of $BRAF^{V600E}$ in this cell line. Treatment with BVD-523 resulted in elevated pERK1/2 in the nucleus and cytoplasm as well as a modest increase in nuclear total ERK1/2 compared with DMSO-treated cells, suggesting that compound-induced stabilization of pERK1/2 stimulates some nuclear translocation. Despite increased pERK1/2 in both compartments, pRSK levels are lower in the cytoplasmic and nuclear compartments compared with DMSO control. Comparator MAPK signaling inhibitors (i.e., trametinib, SCH7722984, dabrafenib) inhibited phosphorylation of ERK1/2 and RSK, as reflected by lower levels in the nuclear and cytoplasmic compartments. These data again suggest that BVD-523-associated increases in pERK1/2 are evident in both the cytoplasm and nucleus; however, this does not translate to activation of target substrates. This is consistent with data presented in FIG. 30D and FIG. 32A.

TABLE 23

| | | % change from DMSO (matched cell line) | | | | | |
|---|---|---|---|---|---|---|---|
| Cell Line | Treatment | Avg (S6 Ribo Prot S235 236) | Avg (S6 Ribo Prot S240 244) | Avg (Oyclin D1) | Avg (p90 RSK S380) | Avg (bad S112) | Avg (4ebp1 T70) |
| A375 | BVD | −95.3 | −91.98 | −81.45 | −71 | −72.37 | −31.82 |
| A375 | Vx | (Empty) | (Empty) | −85.46 | −65.25 | −69.29 | 23.33 |
| A375 | GDC | −87.61 | −80.3 | −81.65 | −60.74 | −55.32 | −29.47 |
| A375 | SCH | −94.71 | −91.78 | −84.05 | −72.44 | −71.44 | −31.75 |
| AN3Ca | BVD | −43.41 | −22.2 | −0.69 | −28.11 | −54.1 | 32.17 |
| AN3Ca | Vx | −18.54 | −12.55 | −9.59 | −28.41 | −45.63 | 16.67 |
| AN3Ca | GDC | −30.74 | −23.47 | 0.34 | −29.44 | 2.53 | 11.28 |
| AN3Ca | SCH | −61.99 | −35.88 | −11.33 | −40.26 | −39.14 | 61.57 |
| COLO205 | BVD | −96.15 | −97.33 | −23.65 | −50.84 | −31.51 | −36.35 |
| COLO205 | Vx | −93.04 | −94.89 | −39.79 | −58.6 | −30.28 | −43.71 |
| COLO205 | GDC | −91.19 | −91.59 | −28.02 | −57.5 | −6.12 | −36.69 |
| COLO205 | SCH | −94.67 | −95.09 | −36.7 | −62.31 | −29.4 | −27.51 |
| HCT116 | BVD | −96.31 | −96.26 | −69.62 | −31.81 | −34.27 | 4.03 |
| HCT116 | Vx | −90.03 | −86.06 | −72.72 | −33.05 | −23.88 | 10.35 |
| HCT116 | GDC | −94.82 | −95.1 | −63.59 | −22.25 | −12.36 | 20.5 |
| HCT116 | SCH | −93.86 | −91.07 | −73.21 | −33.7 | −31.29 | 5.6 |
| HT29 | BVD | −44.68 | −25.67 | −37.21 | −60.5 | −20.66 | −41.47 |
| HT29 | Vx | −32.8 | −24.35 | −35.2 | −43.41 | −35.62 | −2.89 |
| HT29 | GDC | −41.45 | −21.74 | −35.69 | −30.59 | −12.98 | 1.95 |
| HT29 | SCH | −44.9 | −25.73 | −36.66 | −53.88 | −33.9 | −40.58 |
| MIAPaca2 | BVD | −79.46 | −88.03 | −37.9 | −35 | −30.29 | −9.42 |
| MIAPaca2 | Vx | −63.36 | −74.82 | −33.96 | −39.91 | −20.85 | −15.72 |
| MIAPaca2 | GDC | −67.9 | −75.59 | −31.92 | −39.09 | −10.08 | −34.01 |
| MIAPaca2 | SCH | −77.57 | −86.61 | −39.88 | −38.58 | −33.07 | 19.27 |

| | | % change from DMSO (matched cell line) | | | | | |
|---|---|---|---|---|---|---|---|
| Cell Line | Treatment | Avg (p70 S6 Kinase T389 T412) | Avg (p70 S6 Kinase S371 S394) | Avg (ERK 12) | Avg (Akt) | Avg (Raptor) | Avg (Caspase 3 CL D175) |
| A375 | BVD | −23.79 | −8.58 | −22.91 | −14.03 | −7.77 | −8.06 |
| A375 | Vx | −25.54 | −17.32 | −5.39 | −30.34 | −12.7 | −9.27 |
| A375 | GDC | −31.9 | −17.34 | 31.55 | −20.7 | −14.32 | −16.74 |
| A375 | SCH | −42.73 | −28.72 | −21.65 | −23.26 | −11.66 | −9.87 |
| AN3Ca | BVD | −14.78 | 32.26 | −9.05 | −22.43 | −13.82 | −10.8 |
| AN3Ca | Vx | 0.56 | 44.04 | −11.27 | −24.62 | −2.47 | −12.7 |
| AN3Ca | GDC | 26.01 | 29.09 | −2.87 | −26.04 | −8.05 | 1.55 |
| AN3Ca | SCH | −16.63 | 24.56 | −9.27 | −16.35 | −11.09 | 1.25 |
| COLO205 | BVD | −36.4 | −18.11 | −18.83 | −3.85 | −7.14 | −3.18 |
| COLO205 | Vx | −28 | −13.64 | −12.32 | −12.51 | −0.05 | −2.67 |
| COLO205 | GDC | −32.2 | −13.02 | −3.33 | −11.83 | −5.48 | 23.06 |
| COLO205 | SCH | −30.4 | −14.59 | −31.87 | −10.31 | −2.2 | 14.08 |
| HCT116 | BVD | −28.11 | −16.9 | −29.42 | 4.41 | −7.06 | −10.11 |
| HCT116 | Vx | −20.99 | −9.89 | −24.01 | −18.15 | −4.32 | −5.19 |
| HCT116 | GDC | −24.73 | −11.47 | −1.9 | −6.13 | −6.2 | −8.36 |
| HCT116 | SCH | −24.63 | −12.3 | −10.22 | −9.86 | −9.66 | −4.63 |
| HT29 | BVD | −24.58 | −35.94 | −44.3 | −13.41 | −8.53 | −7.03 |
| HT29 | Vx | −12.31 | −22.86 | 0.24 | −17.84 | −6.53 | −2.86 |
| HT29 | GDC | −20.86 | −25.73 | 4.66 | −10.01 | −6.85 | −3.44 |
| HT29 | SCH | −9.55 | −20.52 | −37 | −16.93 | −12.18 | −7.9 |
| MIAPaca2 | BVD | −39.23 | −28.27 | −40.33 | 23.63 | 21.15 | 22.35 |
| MIAPaca2 | Vx | −30.66 | −30.35 | −14.85 | −0.15 | 5.4 | 6.17 |
| MIAPaca2 | GDC | −40.99 | −14.4 | −6.88 | 4.33 | 22.43 | 10.47 |
| MIAPaca2 | SCH | −50.97 | −40.47 | −23.09 | 13.47 | 17.66 | 21.05 |

| | | % change from DMSO (matched cell line) | | | | | | |
|---|---|---|---|---|---|---|---|---|
| Cell Line | Treatment | Avg (mTOR S2448) | Avg (Bad S155) | Avg (cFos) | Avg (Rictor) | Avg (p70 S6 Kinase) | Avg (Raptor S792) | Avg (Bcl 2 T56) |
| A375 | BVD | −27.87 | −21.9 | 4.39 | −20.11 | −7.6 | −10.33 | −8.54 |
| A375 | Vx | −21.66 | −6.3 | −13.65 | −8.16 | −6.42 | −0.86 | −7.53 |
| A375 | GDC | −23.61 | −13.31 | −12.46 | −23.29 | −18.11 | −15.93 | −4.1 |
| A375 | SCH | −26.17 | −13.86 | −12.51 | −22.13 | −17.66 | −6.89 | −19.55 |
| AN3Ca | BVD | −10.79 | 0.66 | −5.15 | −4.52 | −10.27 | −8.47 | −12.85 |
| AN3Ca | Vx | −2.37 | 4.59 | −5.52 | 0.02 | −2.33 | 0.37 | −11.73 |
| AN3Ca | GDC | −2.96 | 17.31 | −0.63 | −9.21 | −3.67 | 4.85 | 1.23 |

TABLE 23-continued

| | | | | | | | | |
|---|---|---|---|---|---|---|---|---|
| AN3Ca | SCH | −4.84 | 12.92 | −9.18 | −10.89 | −7.71 | −4.03 | −10.73 |
| COLO205 | BVD | −23.51 | −18.18 | −12.25 | −5.21 | 0.14 | 0.41 | −11.84 |
| COLO205 | Vx | −8.52 | −9.72 | −19.34 | 1.65 | −3.42 | 0.2 | −12.02 |
| COLO205 | GDC | −7.36 | −9.11 | −21.33 | −5.04 | 5.83 | −9.04 | −4.6 |
| COLO205 | SCH | −9.44 | −10.96 | −15.17 | −19.07 | −2.85 | −4.17 | −6.73 |
| HCT116 | BVD | −12.78 | −30.72 | −14.08 | −13.05 | −12.86 | −22.04 | −8.36 |
| HCT116 | Vx | −10.12 | −15.59 | −13.89 | 1.78 | −4.45 | −11.21 | −25 |
| HCT116 | GDC | −19.33 | −19.71 | −10.36 | −10.98 | −9.9 | −15.77 | −11.96 |
| HCT116 | SCH | −16.05 | −22.96 | −15.27 | −18.5 | −14.12 | −18.18 | −15.89 |
| HT29 | BVD | −20.68 | −25.9 | −13.48 | −18.76 | −10.64 | −10.48 | −8.18 |
| HT29 | Vx | −13.94 | −11.26 | −8.23 | −2.6 | −1.72 | −2.13 | −25.01 |
| HT29 | GDC | −11.44 | −6.7 | −12.92 | −10.62 | −2.83 | −1.75 | 1.61 |
| HT29 | SCH | −22.65 | −7.98 | −9.26 | −13.03 | −2.36 | −6.38 | −17.9 |
| MIAPaca2 | BVD | −11.73 | −5.65 | −18.44 | −11.11 | −3.59 | 5.95 | −1.78 |
| MIAPaca2 | Vx | −5.38 | 7.38 | −4.43 | −13.24 | −9.27 | −3.74 | −9.86 |
| MIAPaca2 | GDC | 11.84 | 8.18 | −16.12 | −11.25 | −3.25 | 2.18 | −2.12 |
| MIAPaca2 | SCH | −11.48 | −1.71 | −8.99 | −15.15 | −7.51 | 4.43 | −1.98 |

| | | % change from DMSO (matched cell line) | | | | | | |
|---|---|---|---|---|---|---|---|---|
| Cell Line | Treatment | Avg (Bcl 2 S70) | Avg (Bcl2) | Avg (Bax) | Avg (mTOR S2481) | Avg (Tuberin TS02 Y1571) | (Chk1 S345) | Avg (CREB S133) |
| A375 | BVD | −7.91 | −12.55 | −6.98 | −3.36 | −6.32 | −7.43 | −12.65 |
| A375 | Vx | −4.02 | −9.93 | −5.05 | −2.9 | −3.55 | 0.56 | −15.8 |
| A375 | GDC | 6.3 | −3.13 | 3.97 | −19.37 | −16.74 | −18.35 | −1.18 |
| A375 | SCH | −12.91 | −18.53 | −17.32 | −15.82 | −13.7 | −10.59 | −1.55 |
| AN3Ca | BVD | −14.81 | −16.83 | −10.47 | 2.75 | 2.86 | −13.34 | 1.03 |
| AN3Ca | Vx | −14.39 | −18.77 | −7.89 | 7.22 | 3.8 | −9.54 | 0.16 |
| AN3Ca | GDC | −0.65 | 7.8 | 23.83 | 25.42 | 25.18 | 15.46 | 5.03 |
| AN3Ca | SCH | −12.42 | −5.14 | 0.15 | 11.24 | 13.44 | 14.56 | 3.64 |
| COLO205 | BVD | −10.2 | −0.13 | 0.28 | −1.33 | −3.48 | −4.63 | −2.67 |
| COLO205 | Vx | −20.82 | −14.09 | −9.16 | −9.43 | −9.45 | 13.12 | −10.64 |
| COLO205 | GDC | −9 | 17.95 | 8.2 | 0.96 | 0.66 | 6.08 | −11.85 |
| COLO205 | SCH | −18.52 | −14.56 | −6.44 | −6.68 | −1.38 | 1 | −14.56 |
| HCT116 | BVD | −8.23 | −3.59 | −0.8 | −34.09 | −29.89 | −39.65 | −30.64 |
| HCT116 | Vx | −17.79 | −17.3 | −20.46 | −17.82 | −16.51 | −16.49 | −9.17 |
| HCT116 | GDC | −12.53 | −4.56 | −20.11 | −18.34 | −9.4 | −18.77 | −8.56 |
| HCT116 | SCH | −18.34 | −10.58 | −13.86 | −22.53 | −16.17 | −18.51 | −24.18 |
| HT29 | BVD | 2.83 | 10.68 | 8.39 | −8.64 | 0.66 | −13.48 | −3.46 |
| HT29 | Vx | −12.55 | −16.73 | −18.47 | 0.52 | 2.85 | 6.44 | 14.16 |
| HT29 | GDC | 10.59 | 18.16 | 1.1 | 3.23 | 11.86 | 6.88 | 9.54 |
| HT29 | SCH | −11.45 | −10.01 | −20.59 | 13.93 | 13.25 | 19.05 | 9.87 |
| MIAPaca2 | BVD | 0.89 | 5.86 | 23.44 | −0.24 | 1.7 | 1.2 | −19.26 |
| MIAPaca2 | Vx | −7.83 | −2.3 | 4.33 | −3.12 | −0.01 | 2.09 | −13.28 |
| MIAPaca2 | GDC | −6.78 | −7.8 | 3.48 | 3.65 | 5.71 | 32.96 | −21.37 |
| MIAPaca2 | SCH | −4.23 | 4.96 | 15.67 | 2.43 | 8.86 | 13.39 | −6.63 |

| | | % change from DMSO (matched cell line) | | | | | | | |
|---|---|---|---|---|---|---|---|---|---|
| Cell Line | Treatment | Avg (Caspase 7 CI D198) | Avg (Stat3) | Avg (Bak) | Avg (MSK1 S360) | Avg (mTOR) | Avg (cMyc) | Avg (Stat1) | Avg (Mcl1) |
| A375 | BVD | 3.18 | 6.02 | −3.26 | 3.35 | 0.2 | 2.56 | 1.32 | 10.67 |
| A375 | Vx | −7.62 | 1.71 | 0.65 | −7.63 | −3.31 | −0.97 | 0.23 | 1.6 |
| A375 | GDC | −5.53 | 14.24 | 2.76 | −5.21 | −6.2 | −9.11 | −5.67 | −9.09 |
| A375 | SCH | −6 | −1.42 | −2.37 | 0.97 | −5.18 | 1.86 | −6.01 | 2.11 |
| AN3Ca | BVD | −12.35 | −4.97 | 3.38 | 0.49 | 5.58 | −0.58 | −5.65 | −4.9 |
| AN3Ca | Vx | −8.09 | −7.67 | −1.6 | 6.83 | −6.27 | −5.47 | −0.83 | −4.24 |
| AN3Ca | GDC | −15.56 | −13.05 | 7.33 | 6.84 | −2.85 | 3.99 | 9.15 | −4.16 |
| AN3Ca | SCH | −24.17 | −6.01 | 9.73 | −5.02 | −5.33 | 0.88 | 5.52 | −7.15 |
| COLO205 | BVD | 6.76 | −2.58 | 3.79 | 14.69 | 12.77 | −1.11 | 0.53 | −2.7 |
| COLO205 | Vx | 0.03 | −7.96 | −2.79 | 6.22 | 3.62 | −7.42 | −6.1 | −10.64 |
| COLO205 | GDC | 1.37 | −0.86 | 6.58 | 0.82 | 3.39 | −6.22 | 7.26 | 2.5 |
| COLO205 | SCH | 12.36 | −6.1 | 4.59 | 7.54 | −5.62 | −0.64 | −4.31 | −0.14 |
| HCT116 | BVD | −21.09 | −5.52 | −13.16 | −13.45 | −11.96 | −11.15 | −13.76 | −8.72 |
| HCT116 | Vx | −11.41 | −7.76 | −3.07 | −13.73 | −0.59 | 18.56 | −14.06 | −7.79 |
| HCT116 | GDC | −13.99 | −0.25 | −1.74 | −12.93 | −4.85 | 12.03 | −6.32 | −4.77 |
| HCT116 | SCH | −16.35 | −7.67 | −4.66 | −15.32 | −12.56 | 12.86 | −10.74 | −6.55 |
| HT29 | BVD | −6.93 | −6.46 | −1.42 | 1.49 | 5.02 | 17.85 | 4.74 | −2.83 |
| HT29 | Vx | 8.28 | −4.28 | 2.69 | 5.64 | 16.94 | 10.71 | 4.29 | 1.36 |
| HT29 | GDC | −0.88 | −3.69 | 3.56 | −0.04 | 10.45 | 7.56 | 2.58 | 3.71 |
| HT29 | SCH | 7.02 | −2.15 | 2.78 | 1.25 | 9.31 | 13.55 | 5.79 | 14.05 |
| MIAPaca2 | BVD | −6.44 | −1.23 | −15.15 | −10.72 | −3.27 | −8.77 | 8.62 | −7.27 |
| MIAPaca2 | Vx | −0.32 | 0.61 | −1.93 | −0.87 | −1.58 | −5.94 | −1.64 | −6.58 |
| MIAPaca2 | GDC | −4.92 | −9.44 | −8.11 | −5.25 | −9.8 | −7.84 | 7.4 | −1.79 |
| MIAPaca2 | SCH | 8.35 | −9.19 | −10.88 | 2.74 | 1.64 | 2.11 | 7.17 | −1.88 |

TABLE 23-continued

| | | % change from DMSO (matched cell line) | | | | |
|---|---|---|---|---|---|---|
| Cell Line | Treatment | Avg (Bad S136) | Avg (Chk1) | Avg (Bim) | Avg (Akt S473) | Avg (ERK 1 2 T202 Y204) |
| A375 | BVD | 12.31 | 16.94 | 14.57 | 73.07 | 43.34 |
| A375 | Vx | 5.06 | −0.86 | 12.32 | 93.85 | 128.93 |
| A375 | GDC | −6.21 | −7.72 | 9.8 | 53.66 | 142.37 |
| A375 | SCH | 5.32 | 2.83 | 17.52 | 58.13 | −90.63 |
| AN3Ca | BVD | −1.02 | −8.45 | −12.57 | 52.11 | 733.27 |
| AN3Ca | Vx | −3.81 | −0.46 | −1.46 | 56.17 | 718.94 |
| AN3Ca | GDC | 0.71 | 9.43 | −11.63 | 82.37 | 645.5 |
| AN3Ca | SCH | 5.26 | 1.35 | −14.09 | 66.17 | 19.75 |
| COLO205 | BVD | 5.05 | −2.86 | 41.73 | −5.78 | 14.39 |
| COLO205 | Vx | −1.01 | −9.16 | 34.1 | −10.96 | 98.48 |
| COLO205 | GDC | 4 | 5.06 | 20.59 | 4.45 | 20.01 |
| COLO205 | SCH | 1.88 | 7.49 | 29.22 | −1.74 | −91.43 |
| HCT116 | BVD | −11.49 | −11.26 | 12.44 | −6.14 | 849.12 |
| HCT116 | Vx | −5.39 | −8.63 | 4.82 | −16.94 | 873.33 |
| HCT116 | GDC | −1.24 | 2.28 | 6.2 | 4.69 | 526.64 |
| HCT116 | SCH | −10.55 | −5.58 | 1.95 | −8.76 | −75.21 |
| HT29 | BVD | 10.73 | 7.4 | 2.81 | −3.06 | 54.82 |
| HT29 | Vx | 5.53 | 4.68 | 3.12 | −20.5 | 435.68 |
| HT29 | GDC | 2 | 5.68 | 7.74 | −10.5 | 268.99 |
| HT29 | SCH | 9.67 | 14.64 | 0.69 | −22.14 | −74.84 |
| MIAPaca2 | BVD | −4.12 | −3.51 | −12.51 | 9.9 | 209.14 |
| MIAPaca2 | Vx | 0.36 | −1.8 | 2.1 | 0.48 | 729.27 |
| MIAPaca2 | GDC | 2.25 | 6.56 | 5.07 | 2.24 | 199.59 |
| MIAPaca2 | SCH | 8.62 | 12.07 | 2.08 | 2.84 | −76.71 |

Example 14

Figure 34A:
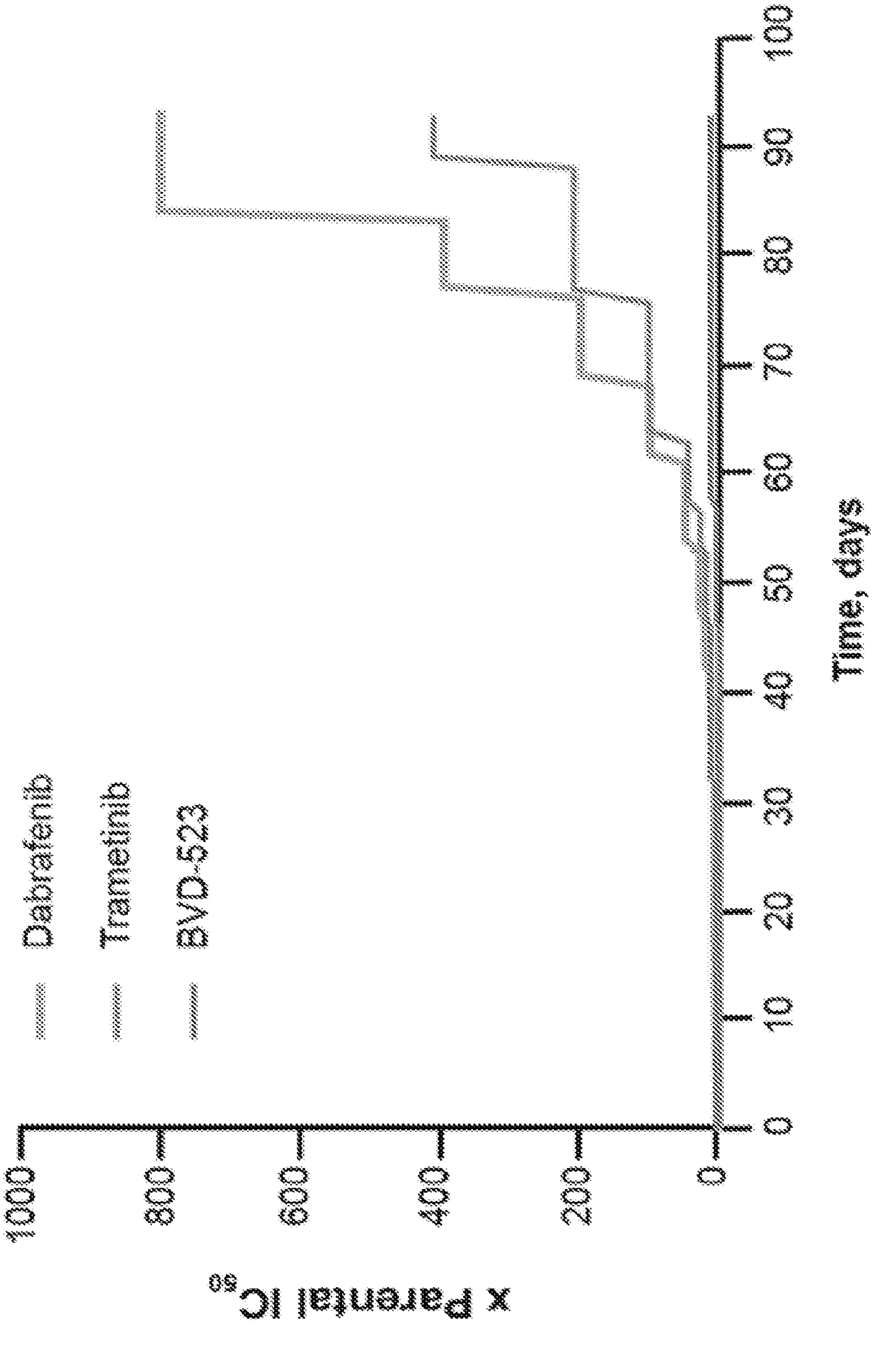

BVD-523 Exhibited Activity in In Vitro Models of BRAF and MEK Inhibitor Resistance Emergence of resistance to BRAF and MEK inhibitors limits their clinical efficacy. Here, the experiments sought to model and compare the development of resistance to BRAF (dabrafenib), MEK (trametinib), and ERK1/2 (BVD-523) inhibition in vitro. Over several months, $BRAF^{V600E}$-mutant A375 cells were cultured in progressively increasing concentrations of each inhibitor. Drug-resistant A375 cell lines were readily obtained following growth in high concentrations of trametinib or dabrafenib, while developing cell lines with resistance to BVD-523 proved challenging (FIG. 34A). Overall, these in vitro data suggest that at concentrations yielding similar target inhibition, resistance to BVD-523 is delayed compared with dabrafenib or trametinib, and may translate to durable responses in the clinic.

Reactivation and dependence on ERK1/2 signaling is a common feature of acquired resistance to BRAF/MEK inhibition (Morris et al. 2013 and Hatzivassiliou et al. 2012); therefore, the activity of BVD-523 in in vitro models of acquired resistance was evaluated. First, a dabrafenib and trametinib combination-resistant A375 population was obtained using the increased concentration method described. The $IC_{50}$ and $IC_{50}$-fold change from parental A375 for dabrafenib, trametinib, and BVD-523 in the BRAF/MEK combination-resistant population is shown in Table 24. BVD-523 $IC_{50}$ was modestly shifted (2.5-fold), while dabrafenib and trametinib were more significantly shifted (8.5-fold and 13.5-fold, respectively) (Table 24). The cytotoxic agent paclitaxel was tested as a control with only a modest shift in potency observed. These data support the investigation of BVD-523 in the setting of BRAF/MEK therapy resistance, although the mechanism of resistance in this cell population remains to be characterized.

TABLE 24

BVD-523 activity in models of BRAF/MEK inhibition

| Cell Line | Dabrafenib | Trametinib | BVD-523 | Paclitaxel |
|---|---|---|---|---|
| Parental ($IC_{50}$nM) | 2.1 | 0.2 | 129 | 1.9 |
| BRAFi- + MEKi-resistant ($IC_{50}$nM) | 17.9 | 2.7 | 323 | 3.5 |
| Fold Change | +8.5 | +13.5 | +2.5 | +1.8 |

Figure 34B:
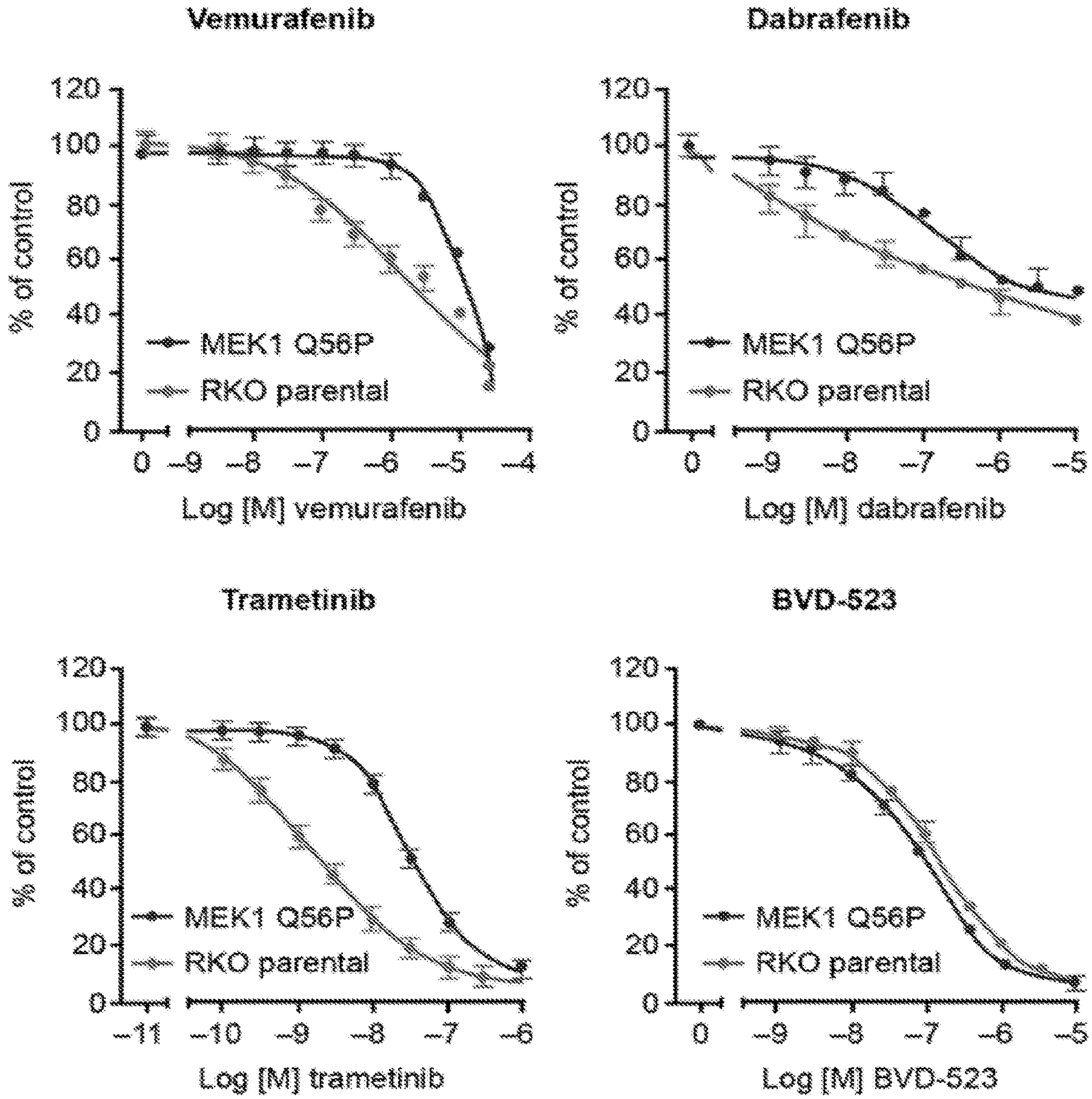

To further investigate the tractability of ERK1/2 inhibition in a model with a known mechanism of BRAF inhibitor resistance, AAV-mediated gene targeting was used to generate a pair of RKO $BRAF^{V600E}$-mutant cell lines isogenic for the presence or absence of an engineered heterozygous knock-in of $MEK1^{Q56P}$-activating mutation (Trunzer et al. 2013 and Emery et al. 2009). MEK1/2 mutations, including $MEK1^{Q56P}$, have been implicated in both single-agent BRAF and combination BRAF/MEK therapy-acquired resistance in patients (Wagle et al. 2011, Wagle et al. 2014, Emery et al. 2009 and Johnson et al. 2015). Single-agent assays demonstrated that relative to the parental $BRAF^{V600E}$::$MEK1^{wt}$ cells, the double-mutant $BRAF^{V600E}$::$MEK1^{Q56P}$ cells displayed a markedly reduced sensitivity to the BRAF inhibitors vemurafenib and dabrafenib and the MEK inhibitor trametinib (FIG. 34B). In contrast, response to BVD-523 was essentially identical in both the parental and $MEK^{Q56P}$-mutant cells, indicating that BVD-523 is not susceptible to this mechanism of acquired resistance. These results were confirmed in 2 independently derived double-mutant $BRAF^{V600E}$::$MEK1^{Q56P}$ cell line clones, thus validating that results were specifically related to the presence of the $MEK1^{Q56P}$ mutation rather than an unrelated clonal artifact (data not shown). Similar results were also observed with a second mechanistically distinct ERK1/2 inhibitor (SCH772984), supporting the expectation that these observations are specifically related to mechanistic inhibition of ERK1/2 and not due to an off-target compound effect.

To further characterize the mechanistic effects of BVD-523 on MAPK pathway signaling in $BRAF^{V600E}$::$MEK1^{Q56P}$ cell lines, protein levels were assessed by Western blot (FIG. 34C). In the parental $BRAF^{V600E}$ RKO cells, a reduced level of pRSK1/2 was observed following 4-hour treatment with BRAF (vemurafenib), MEK (trametinib), or ERK1/2 (BVD-523) inhibitors at pharmacologically active concentrations. In contrast, isogenic double-mutant $BRAF^{V600E}$::$MEK1^{Q56P}$ cells did not exhibit reduced RSK phosphorylation following BRAF or MEK inhibitor treatment, while BVD-523 remained effective in inhibiting pRSK1/2 to a level comparable to parental RKO. Similarly, pRB is reduced, indicating G0/G1 arrest, by 24 hours of BVD-523 treatment in both parental RKO and $BRAF^{V600E}$::$MEK1^{Q56P}$.

Figure 34D:
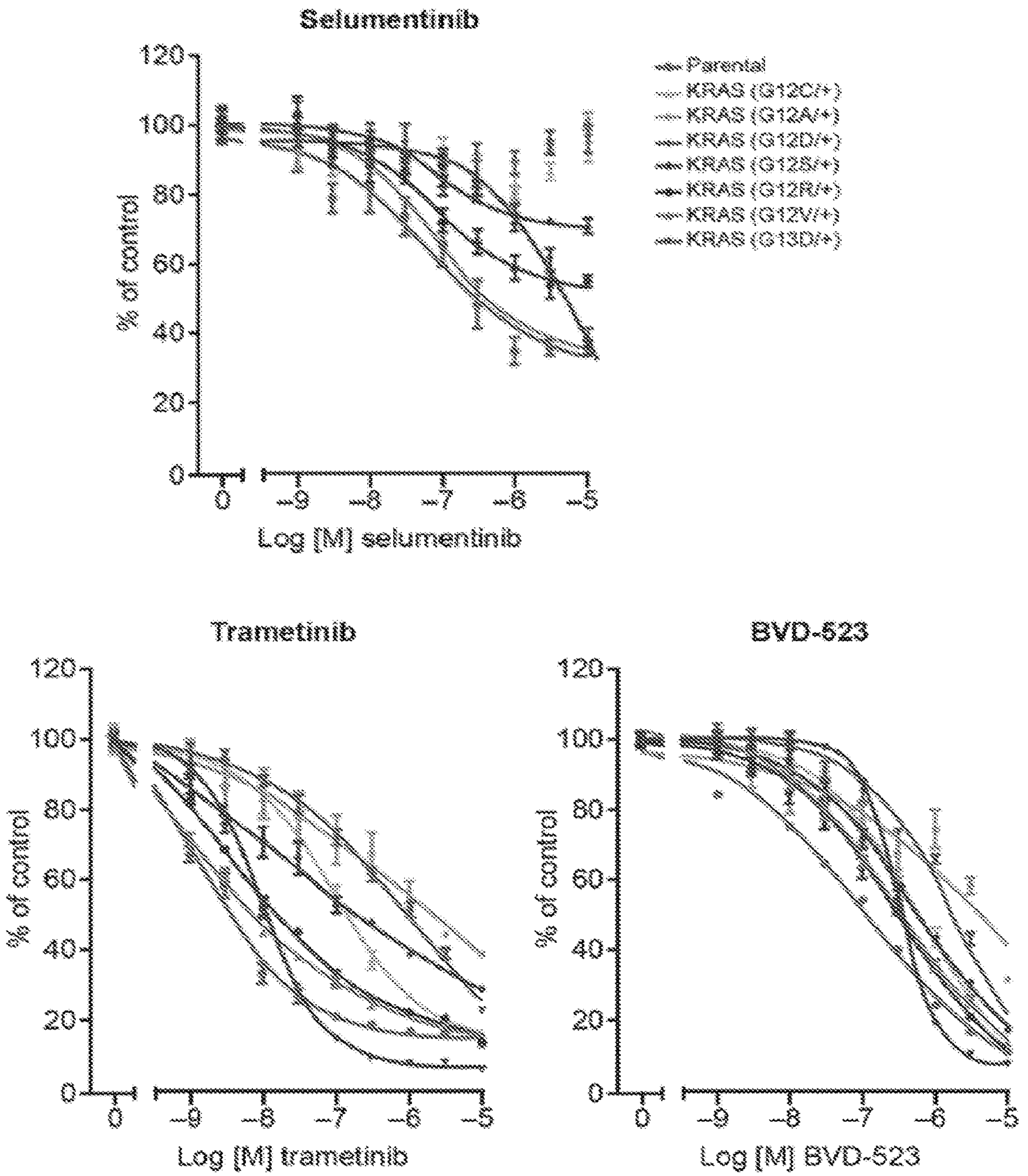
Figure 37A:
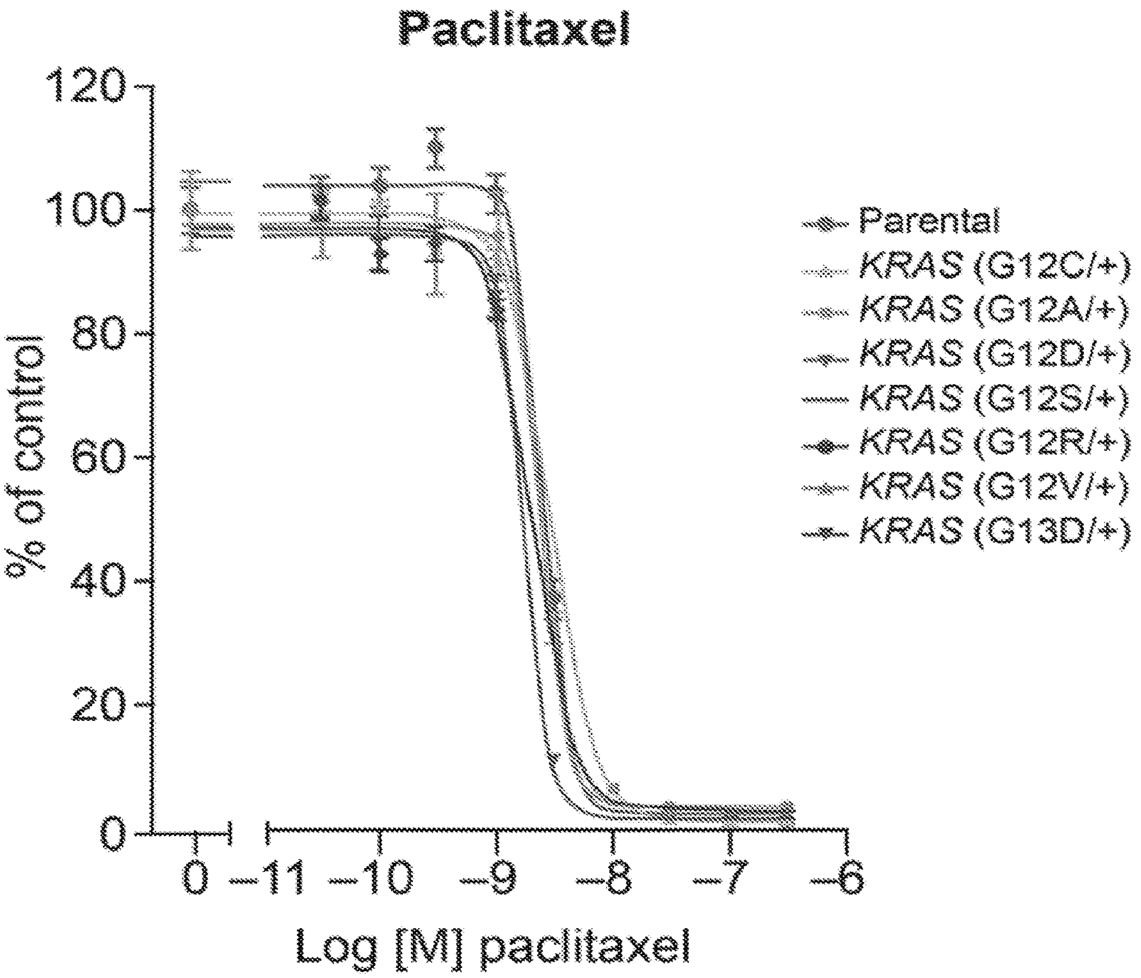
FIG. 37A shows that, in SW48 colorectal cells engineered with KRAS alleles, response to paclitaxel was unaltered compared to control.

Acquired KRAS mutations are also known drivers of resistance to MAPK pathway inhibitors. To understand the susceptibility of BVD-523 to this mechanism of resistance, an isogenic panel of clinically relevant KRAS mutations in colorectal cell line SW48 was used. Sensitivity to BVD-523 was compared with MEK inhibitors selumetinib and trametinib (FIG. 34D). Sensitivity to paclitaxel was unaltered (FIG. 37A). While several mutant KRAS alleles conferred robust to intermediate levels of resistance to MEK inhibition, sensitivity to BVD-523 was unaltered by the majority of alleles, and where a shift in sensitivity was observed, it was not to the extent observed with trametinib or selumetinib. Overall, these data suggest that BVD-523 is more efficacious in this context than MEK inhibitors.

Example 15

Figure 35A:
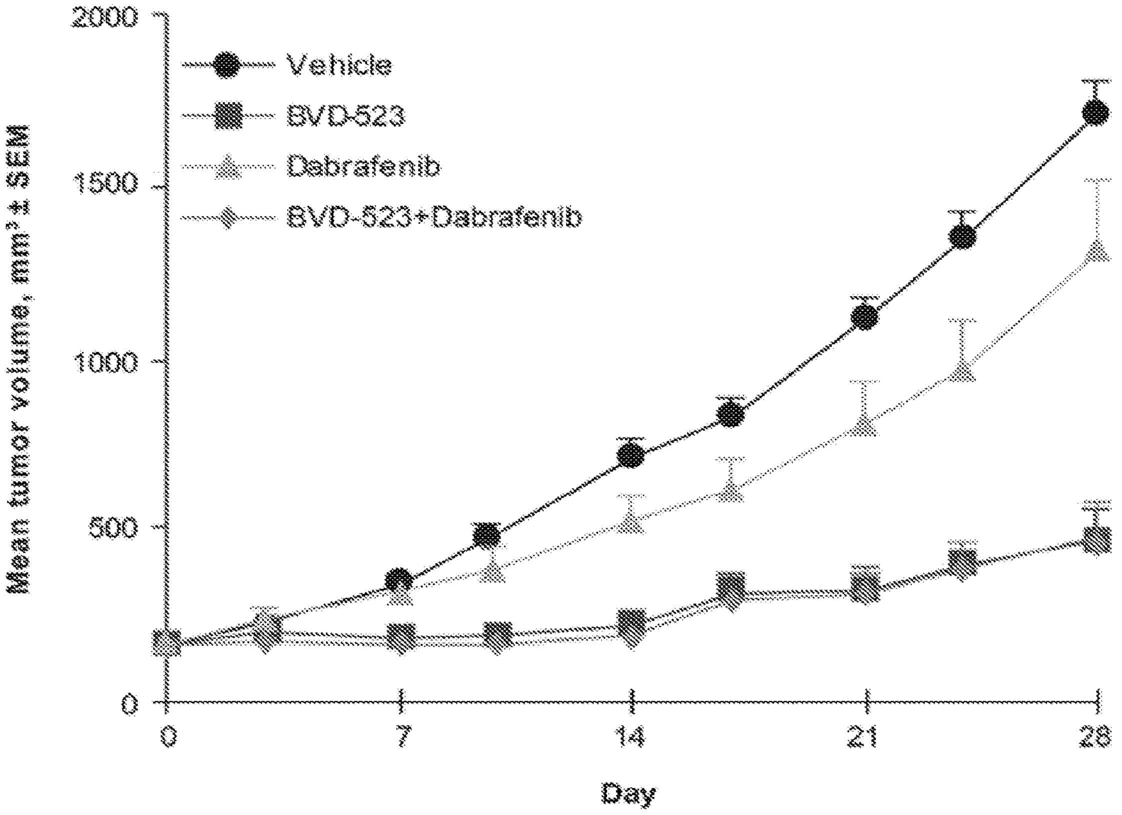
FIG. 35A shows BVD-523 in vivo activity in xenografts derived from a vemurafenib-relapsed patient. Mean tumor volume (±SEM) is shown for BVD-523 100 mg/kg BID alone, dabrafenib 50 mg/kg BID alone, and BVD-523 100 mg/kg BID plus dabrafenib 50 mg/kg BID. Abbreviations: BID, twice daily; SEM, standard error of mean.

BVD-523 Demonstrates In Vivo Activity in a BRAF Inhibitor-Resistant Patient-Derived Melanoma Xenograft Model To confirm and extend the antitumor effects of BVD-523 observed in in vitro models of BRAF-/MEK-acquired resistance, a BRAF-resistant xenograft model derived from a patient with resistance to vemurafenib was utilized. BVD-523 was dosed by oral gavage at 100 mg/kg BID for 28 days, both alone and in combination with dabrafenib at 50 mg/kg BID (FIG. 35). As expected, minimal antitumor activity was demonstrated for single-agent dabrafenib (22% TGI). BVD-523 activity was significant compared with vehicle control ($P \leq 0.05$), with a TGI of 78%. In this model, combining BVD-523 with dabrafenib resulted in a TGI of 76% ($P \leq 0.05$); therefore, further benefit was not gained for the combination compared with single-agent BVD-523 in this model of BRAF-acquired resistance.

Example 16

Figure 37B:
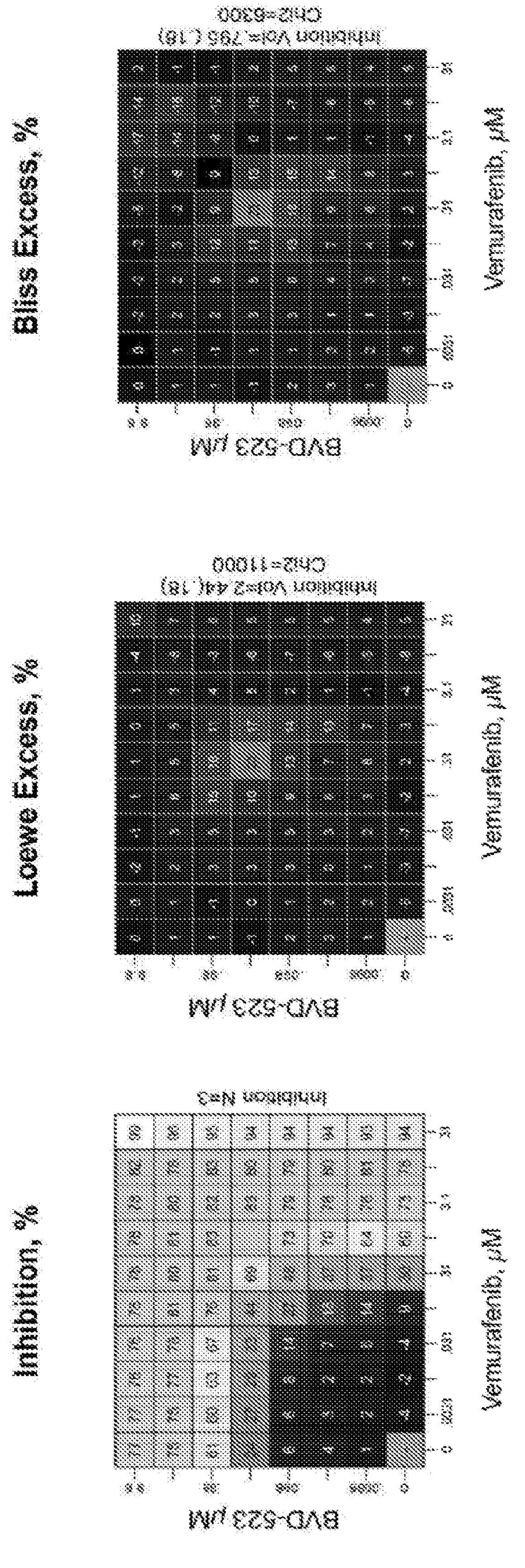
FIG. 37B shows combination interactions between BVD-523 and vemurafenib, which were assessed using an 8×10 matrix of concentrations using the Loewe Additivity and Bliss Independence Models, and analyzed with Horizon's Chalice, Bioinformatics Software. Chalice enables potential synergistic interactions to be identified by displaying the calculated excess inhibition over that predicted as being additive across the dose matrix as a heat map, and by reporting a quantitative "Synergy Score" based on the Loewe model. The results suggest that interactions between BVD-523 and vemurafenib are at least additive, and in some cases synergistic in melanoma cell lines carrying a $BRAF^{V600E}$ mutation.
Figure 37C:
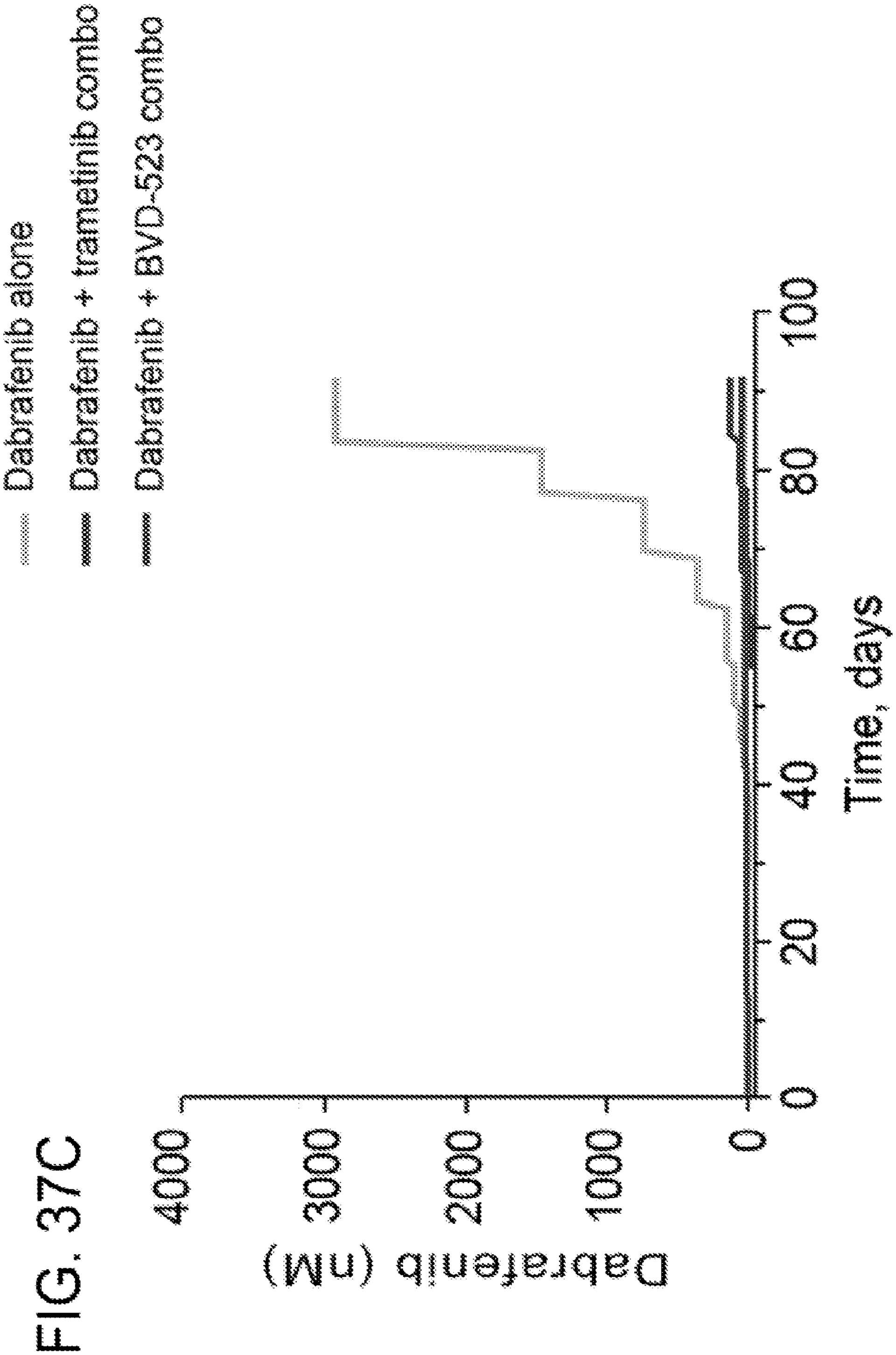
FIG. 37C shows that BVD-523 in combination with dabrafenib markedly delays the onset of acquired resistance in A375 $BRAF^{V600E}$ melanoma cells. The temporal acquisition of resistance in response to escalating concentrations of dabrafenib alone or in combination with BVD-523 or trametinib was assessed. Strict criteria were applied as to when the dose could be increased to ensure that the kinetics of adaptation was comparable between treatments. See, Example 1.

Combination Therapy with BVD-523 and a BRAF Inhibitor Provides Promising Antitumor Activity Patients with BRAF-mutant cancer may acquire resistance to combined BRAF/MEK therapy (Wagle et al. 2014), warranting consideration of other combination approaches within the MAPK pathway. The anti-proliferative effects of combining BVD-523 with the BRAF inhibitor vemurafenib was assessed in the $BRAF^{V600E}$-mutant melanoma cell line G-361. As anticipated, single agents BVD-523 and vemurafenib were both active, and modest synergy was observed when combined (FIG. 37B). This indicates that BVD-523 combined with BRAF inhibitors are at least additive and potentially synergistic in melanoma cell lines carrying a $BRAF^{V600E}$ mutation. Furthermore, generating acquired resistance in vitro following continuous culturing of $BRAF^{V600E}$ mutant cell line (A375) in BRAF inhibitor plus BVD-523 was challenging. In contrast generating resistance to dabrafenib alone occurred relatively rapidly (FIG. 37C). Even resistance to combined dabrafenib and trametinib emerged before dabrafenib plus trametinib.

Figure 36A:
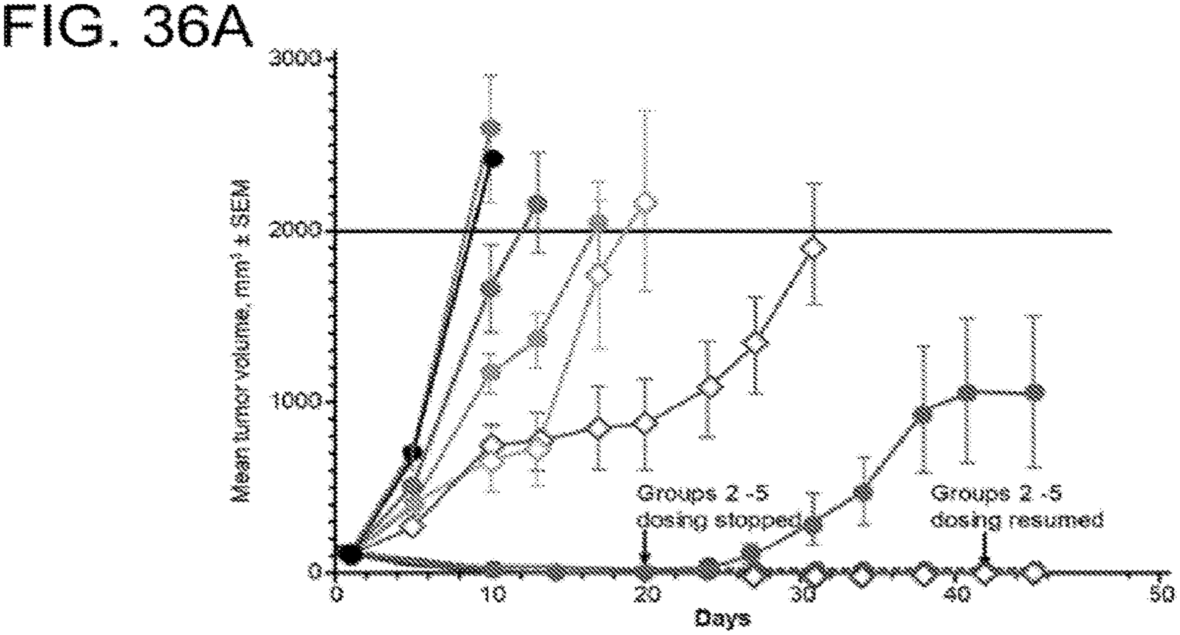
FIG. 36A-FIG. 36D show the benefit of combined BVD-523 and BRAF inhibition.
Figure 36B:
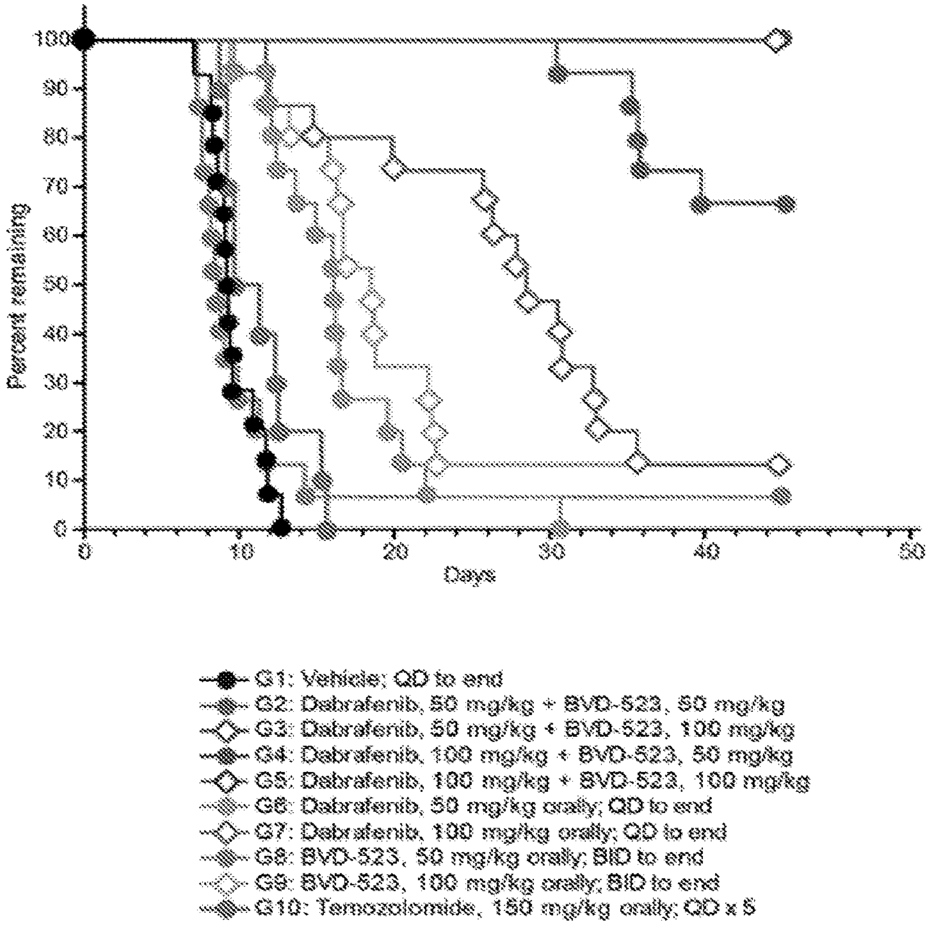

The benefit of combined BRAF and ERK inhibition may not be fully realized in in vitro combination studies where concentrations are not limited by tolerability. To understand the benefit of the combination, efficacy was assessed in vivo utilizing xenografts of the $BRAF^{V600E}$-mutant human melanoma cell line A375. Due to the noteworthy response to combination treatment, dosing in the combination groups was stopped on Day 20 to monitor for tumor regrowth, and was reinitiated on Day 42 (FIG. 36A). Tumors were measured twice weekly until the study was terminated on Day 45. The median time to endpoint (TTE) for controls was 9.2 days, and the maximum possible tumor growth delay (TGD) of 35.8 days was defined as 100%. Temozolomide treatment resulted in a TGD of 1.3 days (4%) and no regressions. The 50- and 100-mg/kg dabrafenib monotherapies produced TGDs of 6.9 days (19%) and 19.3 days (54%), respectively, a significant survival benefit ($P<0.001$), and 1 PR in the 100-mg/kg group. The 100-mg/kg BVD-523 monotherapy resulted in a TGD of 9.3 days (26%), a significant survival benefit ($P<0.001$), and 2 durable complete responses. The combinations of dabrafenib with BVD-523 each produced the maximum possible 100% TGD with noteworthy regression responses, and statistically superior overall survival compared with their corresponding monotherapies ($P<0.001$). The lowest dose combination produced a noteworthy 7/15 tumor-free survivors (TFS), and the 3 higher-dosage combinations produced a total of 43/44 TFS, consistent with curative or near-curative activity (FIG. 36B). In summary, the combination of dabrafenib with BVD-523 produced a greater number of TFS and superior efficacy to either single agent.

Figure 36C:
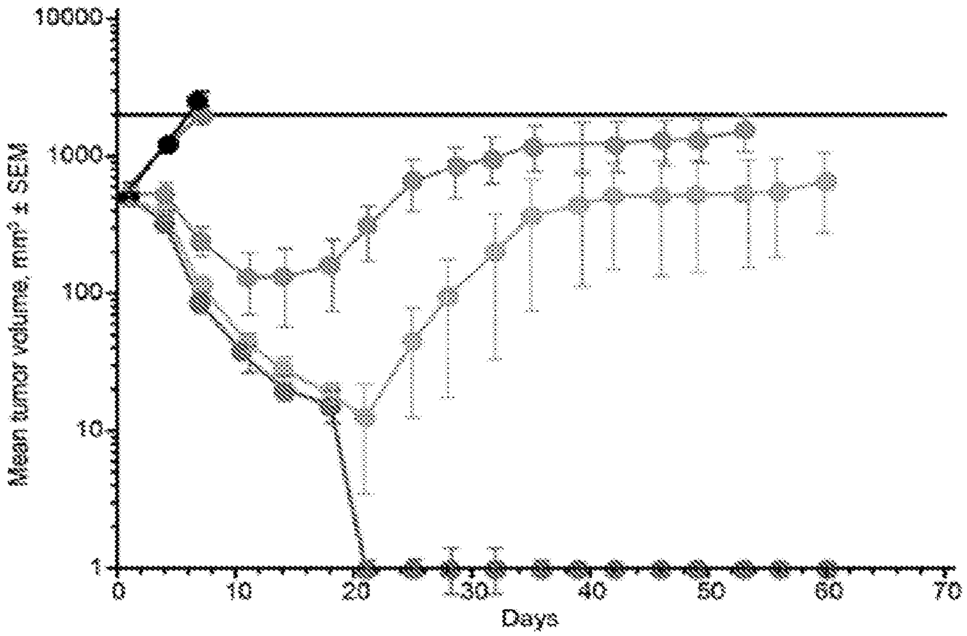
Figure 36D:
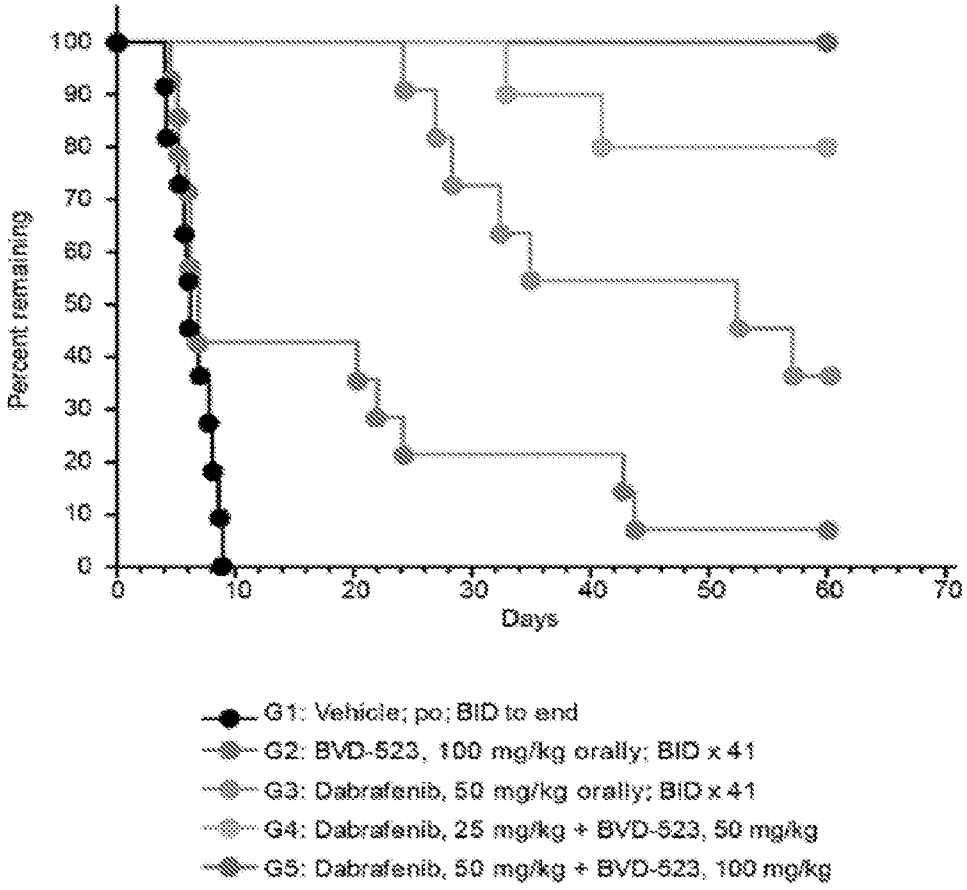

Based on the activity of BVD-523 plus dabrafenib in A375 xenograft models with a starting tumor volume of approximately 75-144 $mm^3$, a follow-up experiment was conducted to determine the efficacy of combination therapy in "upstaged" A375 xenografts (average tumor start volume, 700-800 $mm^3$) (FIG. 36C). The median TTE for controls was 6.2 days, establishing a maximum possible TGD of 53.8 days, which was defined as 100% TGD for the 60-day study. BVD-523 100-mg/kg monotherapy produced a negligible TGD (0.7 day, 1%) and no significant survival difference from controls ($P>0.05$). The distribution of TTEs and 2 PRs suggested there may have been a subset of responders to treatment with BVD-523 alone. Dabrafenib 50-mg/kg monotherapy was efficacious, yielding a TGD of 46.2 days (86%) and a significant survival benefit compared with controls ($P<0.001$). This group had 5 PRs and 5 CRs, including 3 TFS, among the 11 evaluable mice (FIG. 36D). Both combinations of dabrafenib with BVD-523 produced the maximum 100% TGD and a significant survival benefit compared with controls ($P<0.001$). Each combination produced 100% regression responses among evaluable mice, though there were distinctions in regression activity. The 25-mg/kg dabrafenib and 50-mg/kg BVD-523 combination had 2 PRs and 8 CRs, with 6/10 TFS, whereas the 50-mg/kg dabrafenib and 100-mg/kg BVD-523 combination had 11/11

TFS on Day 60 (FIG. 36D). Overall, these data support the rationale for frontline combination of BVD-523 with BRAF-targeted therapy in $BRAF^{V600}$-mutant melanoma, and this is likely to extend to other tumor types harboring this alteration.

Discussion

BVD-523 is a potent, highly selective, reversible, small molecule ATP-competitive inhibitor of ERK1/2 with activity in in vivo and in vitro cancer models. In vitro, BVD-523 demonstrated potent inhibition against several human tumor cell lines, particularly those harboring activating mutations in the MAPK signaling pathway, consistent with its mechanism of action. BVD-523 elicited changes in downstream target and effector proteins, including inhibition of direct substrate of ERK1/2, pRSK, and total DUSP6 protein levels. These findings are in line with those of previous studies of other ERK1/2 inhibitors, which demonstrated effective suppression of pRSK with ERK1/2 inhibition (Morris et al. 2013 and Hatzivassiliou et al. 2012). Interestingly, BVD-523 treatment resulted in a marked increase in ERK1/2 phosphorylation in vitro and in vivo. Similar to our findings, an increase in pERK1/2 has been reported with the ERK1/2 inhibitor Vx11e; conversely, pERK1/2 inhibition occurs with SCH772984 (Morris et al. 2013). Although differences in pERK1/2 levels were observed among the various ERK1/2 inhibitors tested, downstream effectors (i.e., pRSK1 and total DUSP6) were similarly inhibited. These findings suggest quantifying ERK1/2 target substrates, such as pRSK1, may serve as reliable pharmacodynamic biomarkers for BVD-523-mediated inhibition of ERK1/2 activity.

While BRAF (dabrafenib, vemurafenib) and MEK (trametinib, cobimetinib) inhibitors validate the MAPK pathway as a therapeutic target, particularly in patients with $BRAF^{V600}$ mutations, the antitumor response is limited by the emergence of acquired resistance and subsequent disease progression. Resistance has been attributed to the upregulation and activation of compensatory signaling molecules (Nazarian et al. 2010, Villanueva et al. 2010, Johannessen et al. 2010 and Wang et al. 2011), amplification of the target genes (Corcoran et al. 2010), and activating mutations of pathway components (e.g., RAS, MEK) (Wagle et al. 2011, Emery et al. 2009 and Wang et al. 2011). Reactivation of the ERK1/2 pathway is one common consequence of acquired resistance mechanism. When introduced into the $BRAF^{V600E}$-mutant melanoma cell line A375, $MEK^{Q56P}$ conferred resistance to MEK and BRAF inhibition (Wagle et al. 2011). By contrast, BVD-523 retained its potent inhibitory activity in the engineered $MEK^{Q56P}$ cell line, indicating that ERK1/2 inhibition is effective in the setting of upstream activating alterations which can arise in response to BRAF/MEK treatment. As further evidence of a role for BVD-523 in the context of acquired resistance, efficacy of BVD-523 was evident in a xenograft model derived from a tumor sample from a patient whose disease progressed on vemurafenib; the BRAF inhibitor dabrafenib was not effective in this model. These data support a role for targeting ERK1/2 in the setting of BRAF/MEK resistance, and complement previously published findings (Morris et al. 2013 and Hatzivassiliou et al. 2012). To further characterize resistance to inhibitors of the MAPK pathway, the emergence of resistance to BVD-523 itself was investigated. It was found that single-agent treatment of cancer cells with BVD-523 was durable and more challenging to develop resistance compared with other agents targeting upstream MAPK signaling components (i.e., dabrafenib, trametinib). This may suggest that acquiring resistance to ERK1/2-targeting agents is harder to achieve than acquiring resistance to BRAF or MEK therapy, potentially due to the fact that BVD-523 preferentially targets the more conserved active confirmation of the ATP binding site. However, in vitro studies with other ERK1/2 inhibitors have identified specific mutants in ERK1/2 that drive resistance (Jha et al. 2016 and Goetz et al. 2014); these specific mutations have yet to be identified in clinical samples from ERK1/2 inhibitor-relapsed patients.

The potential clinical benefit of ERK1/2 inhibition with BVD-523 extends beyond the setting of BRAF/MEK therapy-resistant patients. As ERK1/2 is a downstream master node within this MAPK pathway, its inhibition is attractive in numerous cancer settings where tumor growth depends on MAPK signaling. Approximately 30% of all cancers harbor RAS mutations; therefore, targeting downstream ERK1/2 with BVD-523 is a rational treatment approach for these cancers. Furthermore, results from a study by Hayes et al. indicate that prolonged ERK1/2 inhibition in KRAS-mutant pancreatic cancer is associated with senescent-like growth suppression (Hayes et al. 2016). However, a combination approach may be required for maximal and durable attenuation of MAPK signaling in the setting of RAS mutations. For example, MEK inhibition in KRAS-mutant colorectal cancer cell results in an adaptive response of ErbB family activation, which dampens the response to MEK inhibition (Sun et al. 2014). Similar context-specific adaptive responses may occur following ERK1/2 inhibition with BVD-523. The optimal treatment combinations for various genetic profiles and cancer histologies are the subject of ongoing research. In addition to $BRAF^{V600}$ and RAS mutations, other alterations which drive MAPK are emerging. For example, novel RAF fusions and atypical non-V600 BRAF mutations which promote RAF dimerization activate the MAPK pathway (Yao et al. 2015). BRAF inhibitors such as vemurafenib and dabrafenib which inhibit $BRAF^{V600}$-mutant monomer proteins have been shown to be inactive in atypical RAF alterations which drive MAPK signaling in a dimerization-dependent manner (Yao et al. 2015). However, treatment with BVD-523 to target downstream ERK1/2 in these tumors may be a novel approach to addressing this unmet medical need.

In the setting of $BRAF^{V600}$-mutant melanoma tumors, combined BRAF and MEK inhibition exemplifies how agents targeting different nodes of the same pathway can improve treatment response and duration. Our combination studies in $BRAF^{V600E}$-mutant xenografts of human melanoma cell line A375 provides support for combination therapy with BVD-523 and BRAF inhibitors. The combination demonstrated superior benefit relative to single-agent treatments, including results consistent with curative responses. The clinical efficacy and tolerability of combined BRAF/BVD-523 therapy remains to be determined. It would not be unreasonable to expect that a BRAF/ERK1/2 combination will at least be comparable in efficacy to a targeted BRAF/MEK combination. Furthermore, the in vitro observation that acquired resistance to BVD-523 is more challenging to achieve compared with other MAPK pathway inhibitors suggests that the BRAF/BVD-523 inhibitor combination has the potential to provide a more durable response.

Significant progress has also been made using immunotherapy for melanoma. The US FDA has approved various immune checkpoint inhibitors for the treatment of advanced melanoma, including the cytotoxic T-lymphocyte antigen-4 targeted agent ipilimumab and the programmed death-1 inhibitors pembrolizumab and nivolumab. Combining BVD-523 with such immunotherapies is an attractive therapeutic option, further investigation is warranted to explore dosing schedules and to assess whether synergistic response can be achieved.

Based on the preclinical data, BVD-523 may hold promise for treatment of patients with malignancies dependent on MAPK signaling, including those whose tumors have acquired resistance to other treatments. The clinical development of BVD-523 is described below. See, Examples 17-24

Example 17

Phase I Dose-Escalation Study of the First-In-Class Novel Oral ERK1/2 Kinase Inhibitor BVD-523 (ulixertinib) in Patients with Advanced Solid Tumors The present invention describes the first-in-human dose escalation study of an ERK1/2 inhibitor for the treatment of patients with advanced solid tumors. BVD-523 has an acceptable safety profile with favorable pharmacokinetics and early evidence of clinical activity.

Mitogen-activated protein kinase (MAPK) signaling via the RAS-RAF-MEK-ERK cascade plays a critical role in oncogenesis; thus attracting significant interest as a therapeutic target. This ubiquitous pathway is composed of RAS upstream of a cascade of the protein kinases RAF, MEK1/2, and ERK1/2. RAS is activated by GTP binding, which in turn results in activation of each protein kinase sequentially. Although they appear to be the only physiologic substrates for MEK1/2, ERK1/2 have many targets in the cytoplasm and nucleus, including the transcription factors Elk1, c-Fos, p53, Ets1/2, and c-Jun (Shaul et al. 2007). ERK1/2 activation and kinase activity influences cellular proliferation, differentiation, and survival through a variety of mechanisms (Rasola et al. 2010), including activation of the ribosomal S6 kinase (RSK) family members (Romeo et al. 2012).

Constitutive, aberrant activation of the RAS-RAF-MEK1/2-ERK1/2 signaling pathway has been identified and implicated in the development or maintenance of many cancers (Schubbert et al. 2007 and Gollob et al. 2006). Mutations in RAS family genes, such as KRAS, NRAS, and HRAS are the most common, with activating RAS mutations occurring in ~30% of human cancers (Schubbert et al. 2007). KRAS mutations are prevalent in pancreatic (>90%) (Kanda et al. 2012), biliary tract (3%-50%) (Hezel et al. 2014), colorectal (30%-50%) (Arrington et al. 2012), lung (27%) (Pennycuick et al. 2012), ovarian (15%-39%) (Dobrzycka et al. 2009), and endometrioid endometrial (18%) (O'Hara and Bell 2012) cancers; NRAS mutations are prevalent in melanoma (20%) (Khattak et al. 2013) and myeloid leukemia (8%-13%) (Yohe 2015); and HRAS mutations are prevalent in bladder (12%) cancer (Fernández-Medarde and Santos 2011). Mutations in RAF family genes, most notably BRAF, are frequent, particularly in melanoma. BRAF mutations have been identified in 66% of malignant melanomas and in ~7% of a wide range of other cancers (Davies et al. 2002), while MEK mutations are rarer, occurring at an overall frequency of 8% in melanomas (Nikolaev et al. 2012). In contrast, ERK mutations resulting in tumorigenesis have been reported only rarely to date (Deschenes-Simard et al. 2014).

The US Food and Drug Administration (FDA) has approved two selective BRAF inhibitors, vemurafenib and dabrafenib, as monotherapies for patients with $BRAF^{V600}$-mutant metastatic melanoma (Taflinar [package insert] and Zelboraf [package insert]). Though response rates for these targeted therapies can be as high as 50% in in patients with $BRAF^{V600}$ mutations, duration of response is often measured in months, not years (Hauschild et al. 2012 and McArthur et al. 2014). The MEK1/2 inhibitor trametinib is also approved as a monotherapy in this setting (Mekinist [package insert]), but is more commonly used in combination with the BRAF inhibitor dabrafenib. First-line use of trametinib administered in combination with dabrafenib offers an even greater improvement in overall survival compared with vemurafenib monotherapy without increased overall toxicity (Robert et al. 2015), highlighting the potential utility of simultaneously targeting multiple proteins of this MAPK signaling pathway. This therapeutic combination was also associated with a lower incidence of MEK inhibitor-associated rash and BRAF inhibitor-induced hyperproliferative skin lesions compared with each single agent alone (Flaherty et al. 2012). Recently, a phase III trial also demonstrated significant improvements in overall survival (25.1 vs. 18.7 months, hazard ratio [HR] 0.71, P=0.0107), progression-free survival (PFS) (11.0 vs. 8.8 months, HR 0.67, P=0.0004), and overall response (69% vs. 53%; P=0.0014) with dabrafenib plus trametinib versus dabrafenib alone in patients with $BRAF^{V600E/K}$ mutation-positive melanoma (Long et al. 2015). Similarly, significant improvements in PFS (9.9 vs. 6.2 months, HR 0.51, P<0.001) and the rate of complete response (CR) or partial response (PR) (68% vs. 45%; P<0.001) have been demonstrated with the combination of cobimetinib plus vemurafenib compared with vemurafenib alone (Larkin et al. 2014). To this end, FDA approval was recently granted for the combination of vemurafenib and cobimetinib for $BRAF^{V600E/K}$-mutated melanoma. Based on these and related findings, the combination of a BRAF inhibitor plus a MEK inhibitor has become a standard targeted treatment option for patients with metastatic melanoma containing $BRAF^{V600E/K}$ mutations.

Though BRAF/MEK-targeted combination therapy has been demonstrated to provide significant additional benefit beyond single-agent options, most patients eventually develop resistance and disease progression after ~12 months (Robert et al. 2015, Flaherty et al. 2012 and Long et al. 2015). Several mechanisms of acquired resistance following either single-agent or combination therapies have been identified, including the generation of BRAF splicing variants, BRAF amplification, development of NRAS or MEK mutations, and upregulation of bypass pathways (Poulikakos et al. 2011, Corcoran et al. 2010, Nazarian et al. 2010, Shi et al. 2014, Johannessen et al. 2010, Wagle et al. 2011, Wagle et al. 2014 and Ahronian et al. 2015). Central to many of these mechanisms of resistance is the reactivation of ERK signaling, which enables the rapid recovery of MAPK pathway signaling and escape of tumor cells from single-agent BRAF or combination BRAF/MEK inhibitor therapies (Paraiso et al. 2010). ERK inhibition may provide the opportunity to avoid or overcome resistance from upstream mechanisms, as it is the most distal master kinase of this MAPK signaling pathway. This is supported by preclinical evidence that inhibition of ERK by small molecule inhibitors acted to both inhibit the emergence of resistance and overcome acquired resistance to BRAF and MEK inhibitors (Morris et al. 2013 and Hatzivassiliou et al. 2012).

BVD-523 is a highly potent, selective, reversible, ATP-competitive ERK1/2 inhibitor which has been shown to reduce tumor growth and induce tumor regression in BRAF and RAS mutant xenograft models. Furthermore, single-agent BVD-523 inhibited human xenograft models that were cross-resistant to both BRAF and MEK inhibitors. See, Examples 9-16. Therefore, an open-label, first-in-human study (Clinicaltrials.gov identifier, NCT01781429) of oral BVD-523 to identify both the maximum tolerated dose and the recommended dose for further study was undertaken. The present study also aimed to assess pharmacokinetic and pharmacodynamic properties as well as preliminary efficacy in patients with advanced cancers.

Example 18

Patient Characteristics

A total of 27 patients were enrolled and received at least one dose of study drug from Apr. 4, 2013 to Dec. 1, 2015. Baseline demographics and disease characteristics are shown in Table 25. The median patient age was 61 years (range, 33-86 years). Fifty-two percent (14/27) of patients were male and 63% (17/27) had an Eastern Cooperative Oncology Group (ECOG) performance status of 1. Melanoma was the most common cancer (30%; BRAF mutation present in 7/8 of these patients). The remaining patients had colorectal (19%; 5/27), papillary thyroid (15%; 4/27), or non-small cell lung cancer (NSCLC) (7%; 2/27), and 8 (30%) were classified as having other cancers (2 pancreatic, 1 appendiceal, 1 nonseminomatous germ cell, 1 ovarian and 3 with unknown primary). The majority of patients had received 2 or more prior lines of systemic therapy, with 41% (11/27) receiving 2 to 3 and 48% (13/27) receiving >3 prior lines of systemic therapy.

TABLE 25

Baseline demographics and clinical characteristics of patients

| Parameter | N = 27 |
|---|---|
| Median age, years (range) | 61 (33-86) |
| Sex, n (%) | |
| Female | 13 (48) |
| Male | 14 (52) |
| Ethnicity, n (%) | |
| Not Hispanic/Latino | 27 (100) |
| ECOG performance status | |
| 0 | 10 (37) |
| 1 | 17 (63) |
| Cancer type, n (%) | |
| Melanoma[a] | 8 (30) |
| Colorectal | 5 (19) |
| Papillary thyroid | 4 (15) |
| Non-small cell lung | 2 (7) |
| Other[b] | 8 (30) |
| Molecular abnormalities, n (%)[c] | |
| BRAF mutant | 13 (48) |
| KRAS mutant | 6 (22) |
| NRAS mutant | 2 (7) |
| Other[d] | 7 (26) |
| Unknown | 4 (15) |
| Number of prior systemic anticancer regimens, | |
| n(%) | 1 (4) |
| 0 | 2 (7) |
| 1 | 11 (41) |
| 2-3 | 13 (48) |
| >3 | |
| Prior BRAF/MEK-targeted | 11 (41) |
| therapy[e], n (%) | |
| BRAF | 5 (19) |
| MEK | 6 (22) |
| BRAF/MEK | 2 (7) |

[a]Seven were BRAF mutant and 1 was unknown.

[b]Two pancreatic, 1 appendiceal, 1 non-seminomatous germ cell, 1 ovarian, 3 unknown primary.

[c]Patients may have more than 1 molecular abnormality.

[d]Other molecular abnormalities included ERCC1, RRM1, thymidylate synthetase, GNAS, MEK1, TP53, CREBBP, ROS1, PTEN, AKT3, and PIK3CA.

[e]Some patients were treated with more than one BRAF inhibitor.

Abbreviation: ECOG, Eastern Cooperative Oncology Group.

Example 19

Ex Vivo Effects of BVD-523 on RSK1/2 Phosphorylation

Figure 38:
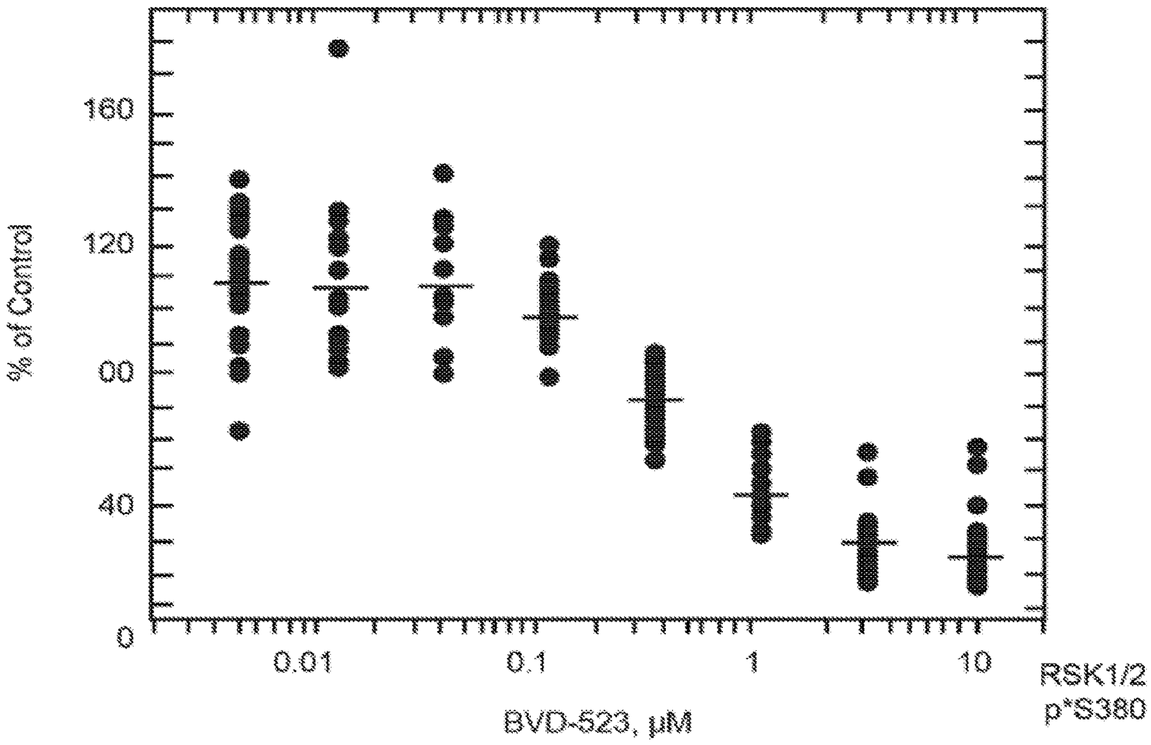
FIG. 38 shows that BVD-523 inhibits ex vivo PMA-stimulated RSK1/2 phosphorylation in human whole blood. Averages of BVD-523 concentration data set are indicated by (–). n=20 for each concentration of BVD-523. Abbreviations: PBMC, peripheral blood mononuclear cells; RSK, ribosomal S6 kinase.

An ex vivo biomarker assay that could be used to support clinical studies was developed to demonstrate the inhibitory effects of BVD-523 on ERK activity. The assay extends preclinical cellular data where inhibitors of MAPK signaling, such as BVD-523, dabrafenib, trametinib, and vemurafenib, have been shown to inhibit RSK phosphorylation as a function of inhibitor concentration in BRAF mutant cancer cell lines. See, Examples 9-16. Specifically, ERK inhibitor-dependent inhibition of phorbol 12-myristate 13-acetate (PMA)-stimulated phosphorylation of the ERK substrate RSK1 in whole blood was used as a target marker. When BVD-523 was added directly to whole blood from healthy volunteers, PMA-stimulated RSK phosphorylation decreased with increasing concentrations of BVD-523 (FIG. 38). The mean $IC_{50}$ for the cumulative data was 461±20 nM for BVD-523, with a maximum inhibition of 75.8±2.7% at 10 μM BVD-523. Maximum inhibition was defined as the RSK phosphorylation measured in the presence of 10 μM BVD-523. Patient-derived whole blood samples, collected just prior to dosing or at defined timepoints following dosing with BVD-523, were similarly treated and RSK phosphorylation levels quantitated.

Example 20

Dose Escalation, Dose-Limiting Toxicities (DLTs), Maximum Tolerated Dose (MTD), and Recommended Phase II Dose (RP2D)

As per protocol, 5 single-patient cohorts (from 10 to 150 mg twice-daily [BID]) proceeded without evidence of a DLT. The 300-mg BID cohort was expanded to more fully characterize BVD-523 exposures. One of 6 patients given 600 mg BID experienced a DLT of Grade 3 rash. The 900-mg BID dose exceeded the MTD, with one patient experiencing Grade 3 pruritus and elevated aspartate aminotransferase (AST) and another patient experiencing Grade 3 diarrhea, vomiting, dehydration, and elevated creatinine (Table 26). The subsequent intermediate dose of 750 mg BID also exceeded the MTD, with DLTs of Grade 3 rash and Grade 2 diarrhea in 1 patient and Grade 2 hypotension, elevated creatinine, and anemia in another patient. Therefore, the MTD and RP2D were determined to be 600 mg BID.

TABLE 26

| Dose, mg (BID) | DLT Frequency | DLT Description |
|---|---|---|
| Dose-limiting toxicities in Cycle 1 (21 days) | | |
| 10 | 0/1 | N/A |
| 20 | 0/1 | N/A |
| 40 | 0/1 | N/A |
| 75 | 0/1 | N/A |
| 150 | 0/1 | N/A |
| 300 | 0/4 | N/A |
| 600 | 1/8 | Rash (Grade 3) |
| 750[a] | 2/4 | Rash (Grade 3), diarrhea (Grade 2)<br>Hypotension (Grade 2), elevated creatinine (Grade 2), anemia (Grade 2), delay to cycle 2 dosing |
| 900 | 2/7 | Pruritus (Grade 3), elevated AST (Grade 3)<br>Diarrhea (Grade 3), vomiting (Grade 3), dehydration (Grade 3), elevated creatinine (Grade 3) |

[a]Intermediate dose.
Abbreviations: AST, aspartate transaminase, BID, twice daily; DLT, dose-limiting toxicity; N/A, not applicable.

Example 21

Adverse Events (AEs)

Investigator-assessed treatment-related AEs of any grade were noted in 26 of 27 patients (96%). The most common treatment-related AEs (>30%) were rash (predominately acneiform) (70%), fatigue (59%), diarrhea (52%), and nausea (52%) (Table 27). No patients experienced a Grade 4 or 5 treatment-related AE or discontinued treatment due to a treatment-related AE. Most events were Grade 1 to 2, with treatment-related Grade 3 events noted in 13 of 27 patients (48%). The only Grade 3 treatment-related events present in ≥10% of patients were diarrhea (15%) and increased liver function tests (11%), all of which occurred above the 600-mg BID dose.

TABLE 27

Adverse events possibly/definitely related to BVD-523 in ≥10% of patients

| Event | N = 27 Any grade, n (%) | Grade 1 or 2, n (%) | Grade 3[a], n n (%) |
|---|---|---|---|
| Rash | 20 (74) | 18 (67) | 2[b] (7) |
| Fatigue | 17 (63) | 16 (59) | 1 (4) |
| Diarrhea | 16 (59) | 12 (44) | 4 (15) |
| Nausea | 14 (52) | 14 (52) | 0 |
| Vomiting | 8 (30) | 7 (26) | 1 (4) |
| Anorexia | 6 (22) | 6 (22) | 0 |
| Pruritus | 6 (22) | 6 (22) | 0 |
| Anemia | 5 (19) | 3 (11) | 2 (7) |
| Increased creatinine | 5 (19) | 4 (15) | 1 (4) |
| Dehydration | 5 (19) | 3 (11) | 2 (7) |
| Peripheral edema | 4 (15) | 4 (15) | 0 |
| Increased LFTs (ALT and AST) | 4 (14) | 1 (4) | 3 (11) |
| Blurry/dimmed visionb | 3 (11) | 3 (11) | 0 |
| Constipation | 3 (11) | 3 (11) | 0 |
| Fever | 3 (11) | 3 (11) | 0 |

[a]No patients experienced Grade 4 or 5 AEs that were possibly or definitely related toBVD-523 treatment.
[b]Acneiform and maculo-papular rash.
[c]One Grade 1 event of related central serous retinopathy.
Analysis cut-off date: Dec. 1, 2015.
Abbreviations: AEs, adverse events; ALT, alanine transaminase, AST, aspartate transaminase, LFTs, liver function tests.

Fourteen patients experienced a total of 28 serious AEs (SAEs). Nine of these were considered to be related or possibly related to BVD-523 by the investigator, which included dehydration, diarrhea, or elevated creatinine (2 patients each), vomiting, nausea, and fever (1 patient each). All other SAEs were considered to be unrelated to treatment with BVD-523. Dose reductions resulting from AEs occurred in 3 patients during the study: 1 patient reduced from 600 mg BID to 300 mg BID and 2 patients reduced from 900 mg BID to 600 mg BID.

Example 22

Pharmacokinetics

Figure 39A:
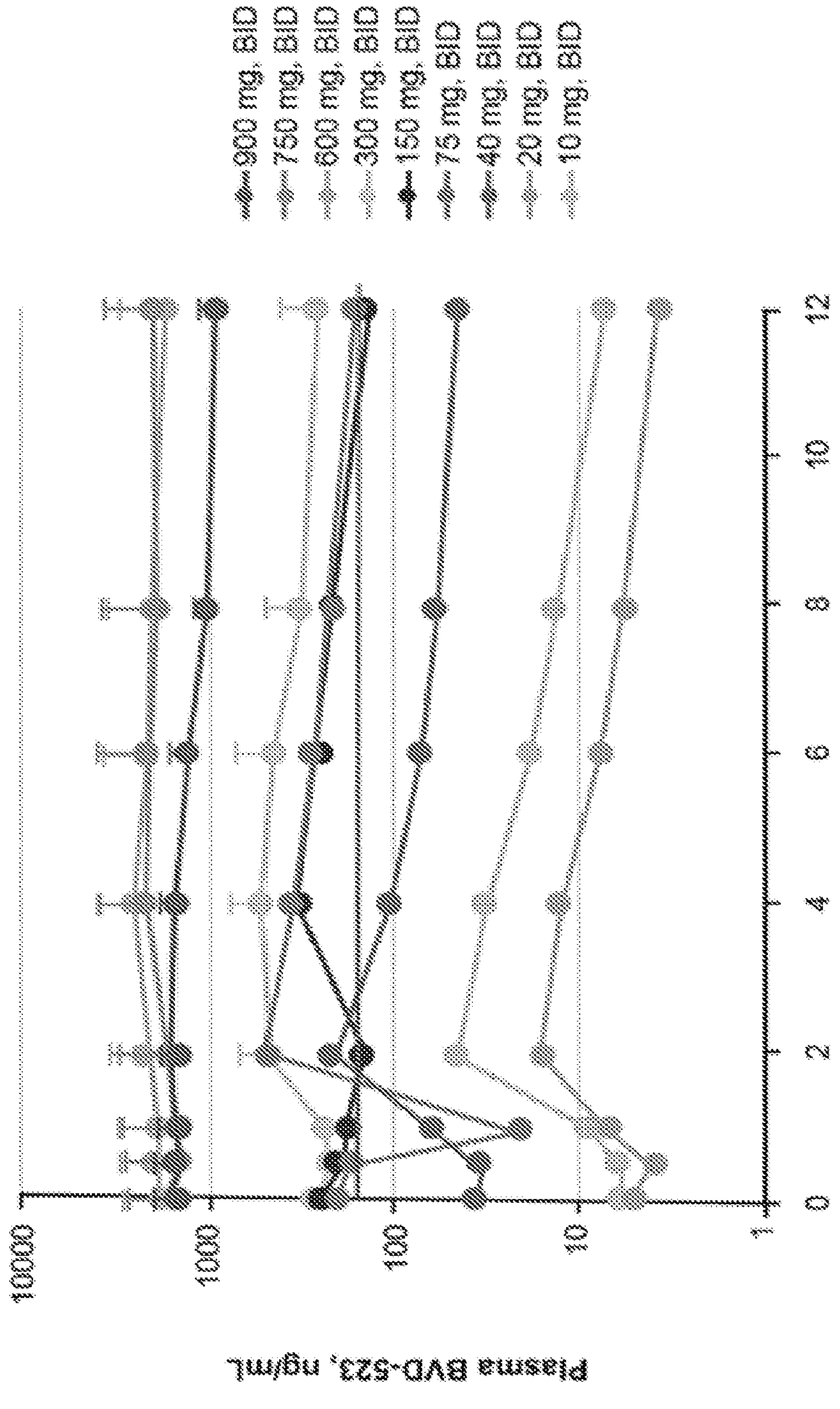
FIG. 39A shows steady-state BVD-523 pharmacokinetics (Cycle 1, Day 15). The dashed red line indicates an $EC_{50}$ 200 ng/mL HWB. Abbreviations: AUC, area under the curve; BID, twice daily; $C_{max}$, maximum concentration; $EC_{50}$, 50% maximum effective concentration; HWB, human whole blood; SD, standard deviation.

Single-dose and steady-state pharmacokinetics of BVD-523 are summarized in FIG. 39A and Table 28. Generally, orally administered BVD-523 was slowly absorbed in patients with advanced malignancies. After reaching the maximum concentration ($C_{max}$), plasma BVD-523 levels remained sustained for approximately 2 to 4 hours. Subsequently, plasma drug concentrations slowly declined. Since plasma drug concentrations were measured only up to 12 hours after the morning dose, it was not possible to calculate an effective or terminal phase elimination rate. BVD-523 pharmacokinetics were linear and dose proportional in terms of both $C_{max}$ and area under the curve (AUC) when administered up to 600 mg BID. A further increase in exposure was not observed as the dose increased from 600 to 900 mg BID. The $C_{max}$ reached the level of the $EC_{50}$ based on the ex vivo whole blood assay (≈200 ng/mL) for all doses above 20 mg BID. Additionally, steady-state exposures remained at or above the target $EC_{50}$ for dose levels of ≥150 mg BID throughout the dosing period. Minimal plasma accumulation of BVD-523 and its metabolites were observed on Day 15 at the lower (<75 mg BID) dose levels, whereas accumulation ranged from approximately 1.3- to 4.0-fold for the higher dose levels. Predose concentrations on Day 22 were generally similar to those on Day 15, indicating that steady state had already been attained by Day 15 (data not shown). The degree of interpatient variability in plasma exposure to BVD-523 and its metabolites was considered moderate and not problematic.

TABLE 28

| Steady-state BVD-523 pharmacokinetics (Cycle 1, Day 15) | | | | | |
|---|---|---|---|---|---|
| | | $C_{max}$,ng/mL ± SD | | $AUC_{0-12}$,ng·hr/mL ± SD | |
| Dose, mg[a] | n = | Day 1 | Day 15 | Day 1 | Day 15 |
| 10 | 1 | 48.2 | 45.7 | 220 | 234 |
| 20 | 1 | 14.9 | 15.8 | 91.7 | 98.7 |
| 40 | 1 | 100 | 191 | 614 | 999 |
| 150 | 1 | 133 | 326 | 817 | 2770 |
| 300 | 4[b] | 765 ± 234 | 586 ± 257 | 4110 ± 1140 | 4460 ± 2460 |
| 600[c] | 7[d] | 1110 ± 589 | 2750 ± 1740 | 2750 ± 1740 | 24400 ± 16200 |
| 750 | 4[h] | 1450 ± 539 | 2290 ± 1790[f] | 10700 ± 1120[g] | 23300 ± 19800[f] |
| 950 | 7[e] | 1430 ± 1010 | 1720 ± 328 | 10800 ± 6320[h] | 15900 ± 1300[e] |

[a]Dose level administered twice daily;

[b]n = 3 on Day 15;

[c]Number of subjects for Day 15 at the 600 mg dose level includes two subjects who started Day 1 dosing at 900 mg and were later reduced to 600 mg;

[d]n = 8 on Day 15;

[e]n = 4 on Day 15;

[f]One subject started on Day 1 dosing at 750 mg and was later reduced to 450 mg, Day 15 parameters for this subject reflect at least 10 consecutive doses at 450 mg/dose. Individual Day 15 parameters were 1300 ng/mL for $C_{max}$ and 10700 ng·hr/mL for $AU_{C0-12}$;

[g]n = 3;

[h]n =5.

The urinary excretion after first dose and at steady state of BVD-523 was negligible (<0.2% of the dose) at all dose levels within 12 hours postdose, and not dose-related within this very low percentage range. Renal clearance appeared to be dose-independent. Individual renal clearance values ranged from 0.128 to 0.0895 L/hr (where n=1 per dose level) and mean values ranged from 0.0149 to 0.0300 L/hr (where n≥3).

Example 23

Pharmacodynamic Confirmation of Target Inhibition by BVD-523

Figure 39B:
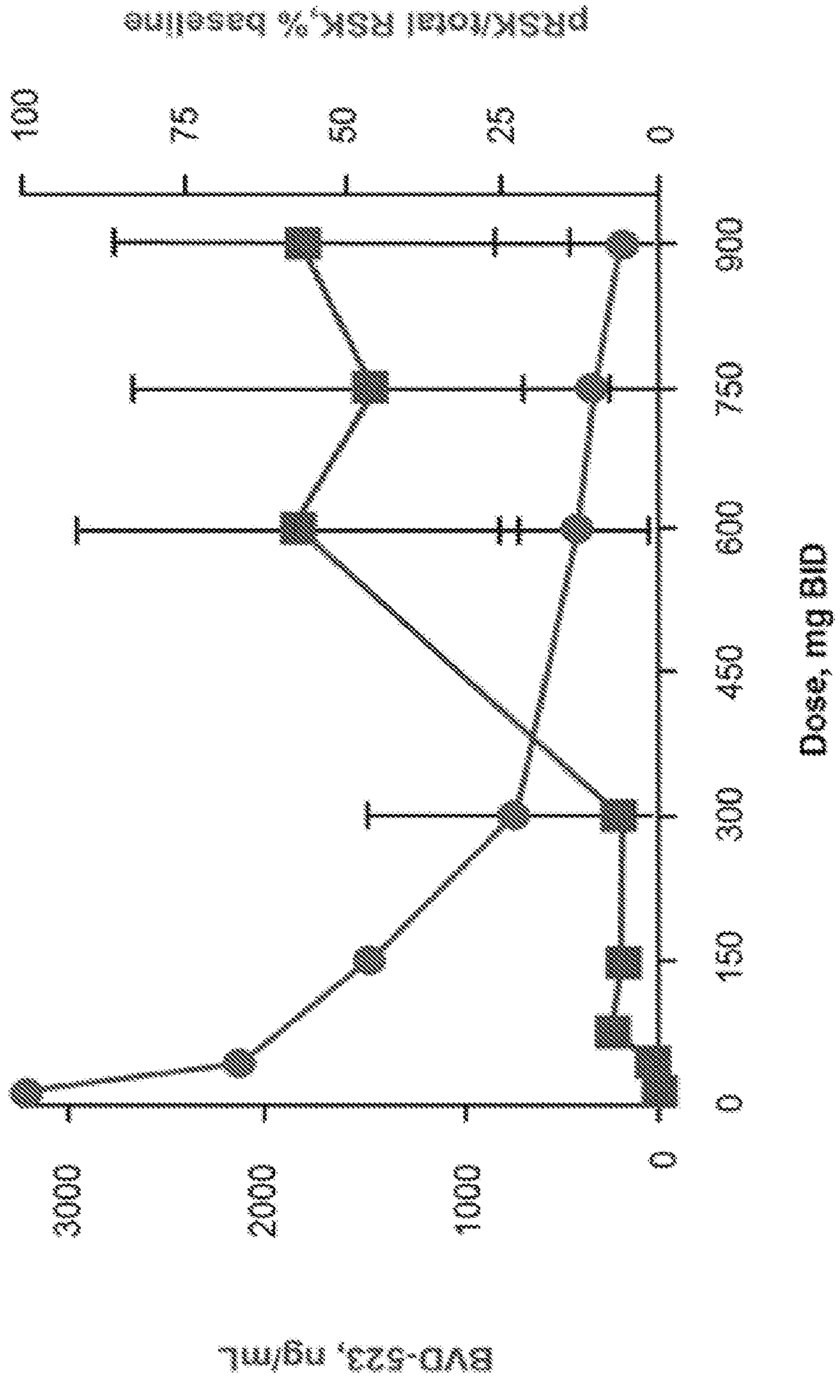
FIG. 39B shows pharmacodynamic inhibition of RSK phosphorylation by BVD-523 in human whole blood. Abbreviations: BID, twice daily; pRSK, phospho-RSK; RSK, ribosomal S6 kinase.

To confirm on-target and pathway inhibition by BVD-523, RSK-1 phosphorylation was examined as a target biomarker in human whole blood samples from patients with solid tumors who received BVD-523. Steady state whole blood samples collected just prior to Day 15 dosing from BVD-523-treated patients displayed concentration-dependent inhibition of PMA stimulated ERK activity (FIG. 39B), ranging from 0% ERK inhibition with BVD-523 dosing at 10 mg BID to 93±8% ERK inhibition with dosing at 900 mg BID. The plasma concentrations of BVD-523 that yielded 50% inhibition of RSK phosphorylation were similar whether BVD-523 was spiked directly into healthy volunteer plasma or was present following oral dosing of patients.

Example 24

Antitumor Effects

Figure 40A:
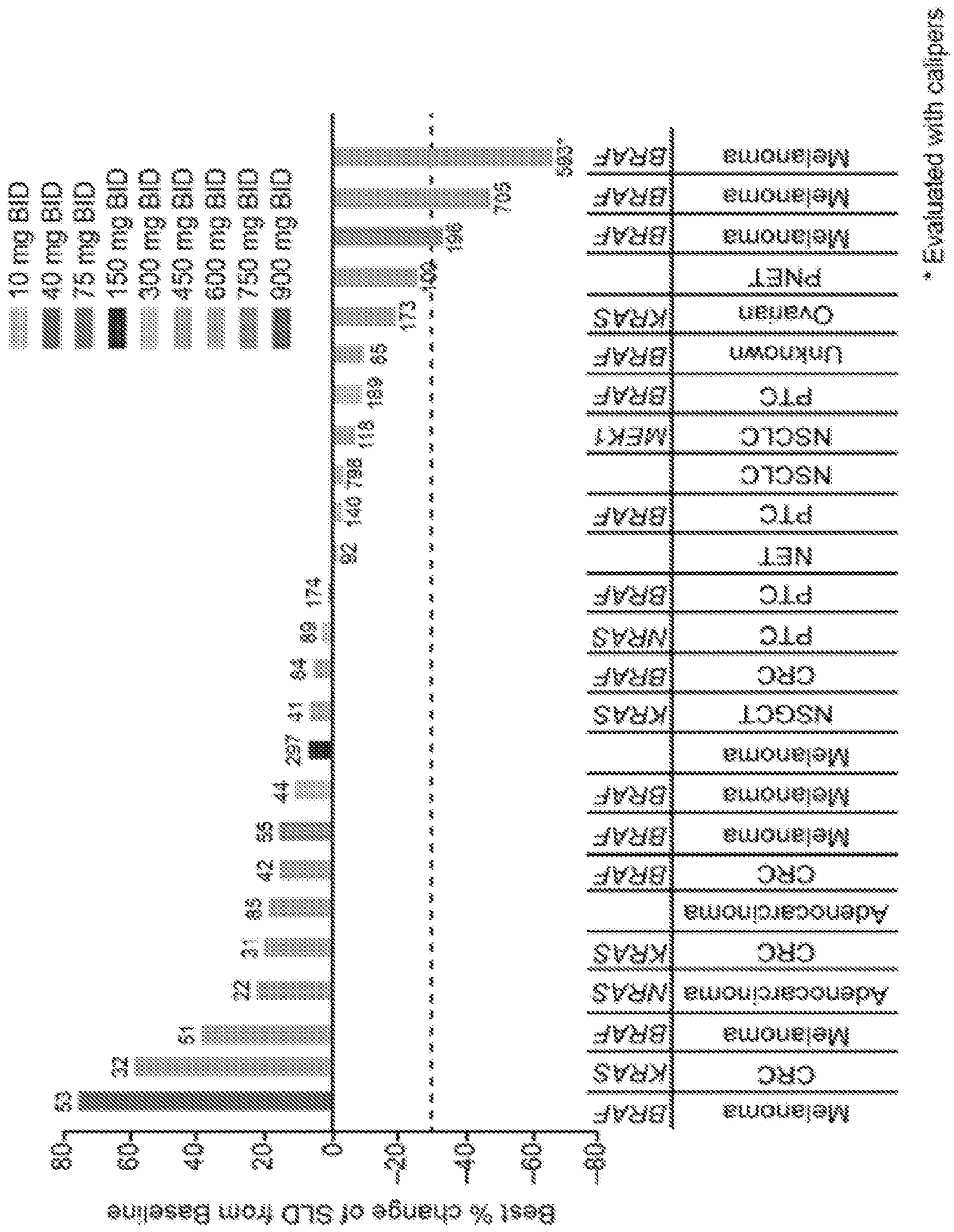
FIG. 40A shows the best radiographic response in patients treated with BVD-523. Included are all patients with disease measured by RECIST v1.1 who received 1 dose of study treatment and had >1 on-treatment tumor assessment (25/27; 2 did not receive both scans of target lesions). Response was measured as the change from baseline in the sum of the longest diameter of each target lesion. Dose shown is that which the patient was receiving at the time of response. The dashed line indicates the threshold for a partial response according to RECIST v1.1. Abbreviations: CRC, colorectal cancer; NET, neuroendocrine tumors; NSCLC, non-small cell lung cancer; NSGCT, nonseminomatous germ cell tumors; PNET, pancreatic NET; PTC, papillary thyroid cancer; RECIST v1.1, Response Evaluation Criteria in Solid Tumors version 1.1; SLD, sum of the largest diameter.

Tumor response to BVD-523 was assessed in 25 evaluable patients using Response Evaluation Criteria in Solid Tumors version 1.1 (RECIST v1.1); 2 patients did not receive both scans of target lesions and were thus not evaluated using RECIST v1.1. No patients achieved a complete response, but 3 patients (all patients with melanoma with $BRAF^{V600}$ mutations) achieved a partial response (129 days [BRAF/MEK-inhibitor naïve], 294 days ongoing at [refractory to prior BRAF/MEK inhibitors], 313 days ongoing by the data cutoff date [intolerant to other BRAF/MEK inhibitors]) (FIG. 40A). Interestingly, all 3 partial responders had BRAF-mutant melanoma. One partial responder, who was receiving BVD-523 at a dose of 450 mg BID, had an approximate 70% reduction in the sum of target lesions from baseline, while the other partial responders showed reductions of 47.0% and 33.6%. Stable disease was demonstrated in 18 patients, with 6 having stable disease for more than 6 months, and 6 additional patients having stable disease for more than 3 months. In this study, 4 patients displayed progressive disease at first evaluation.

Figure 40B:
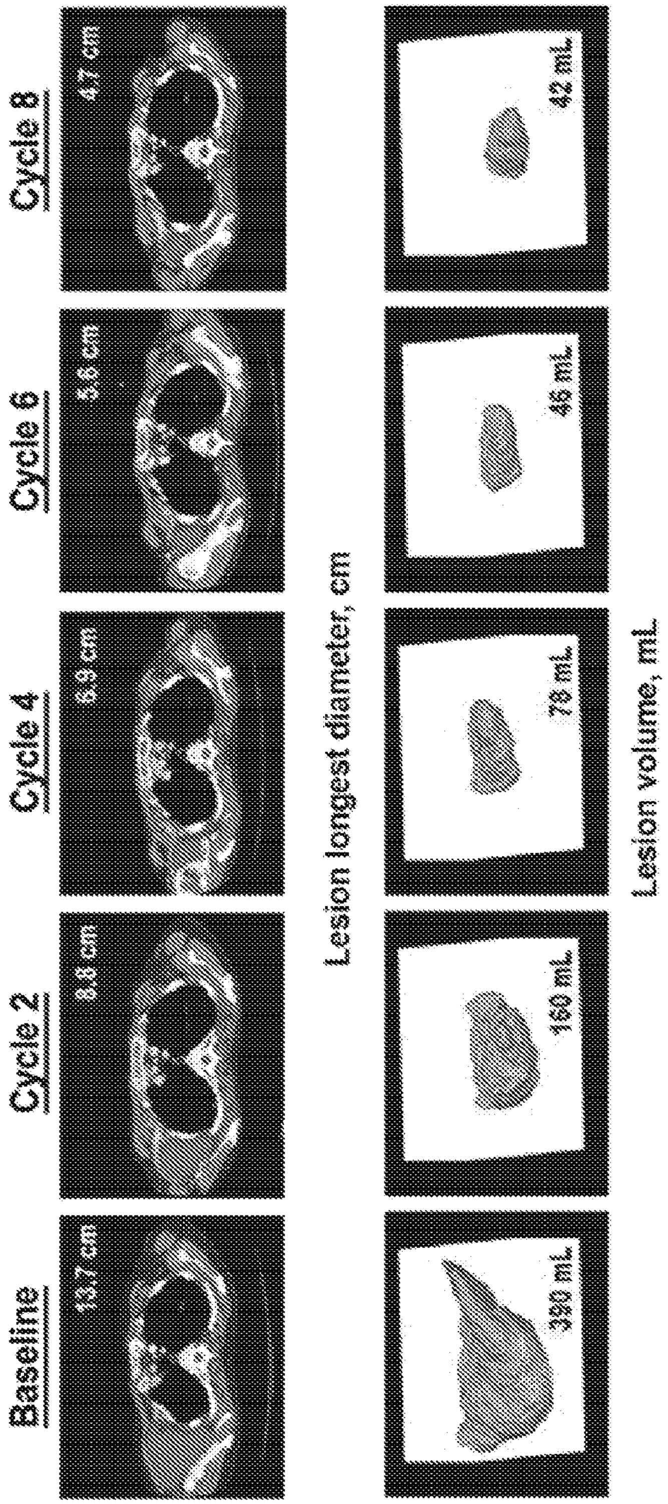
FIG. 40B shows a computerized tomography scan of a confirmed partial response in a 61-year-old patient with a BRAF-mutant melanoma treated with BVD-523.

FIG. 40B shows computed tomography (CT) scans of 1 of the 3 partial responders (RECIST v1.1) who had progressed on prior vemurafenib and subsequent dabrafenib/trametinib treatment; a durable partial response was observed following dosing of BVD-523 600 mg BID for >300 days. BVD-523 was associated with a metabolic response using fluorodeoxyglucose-positive emission tomography ($^{18}$F-FDG-PET) in 5 of 16 evaluable patients.

Figure 41:
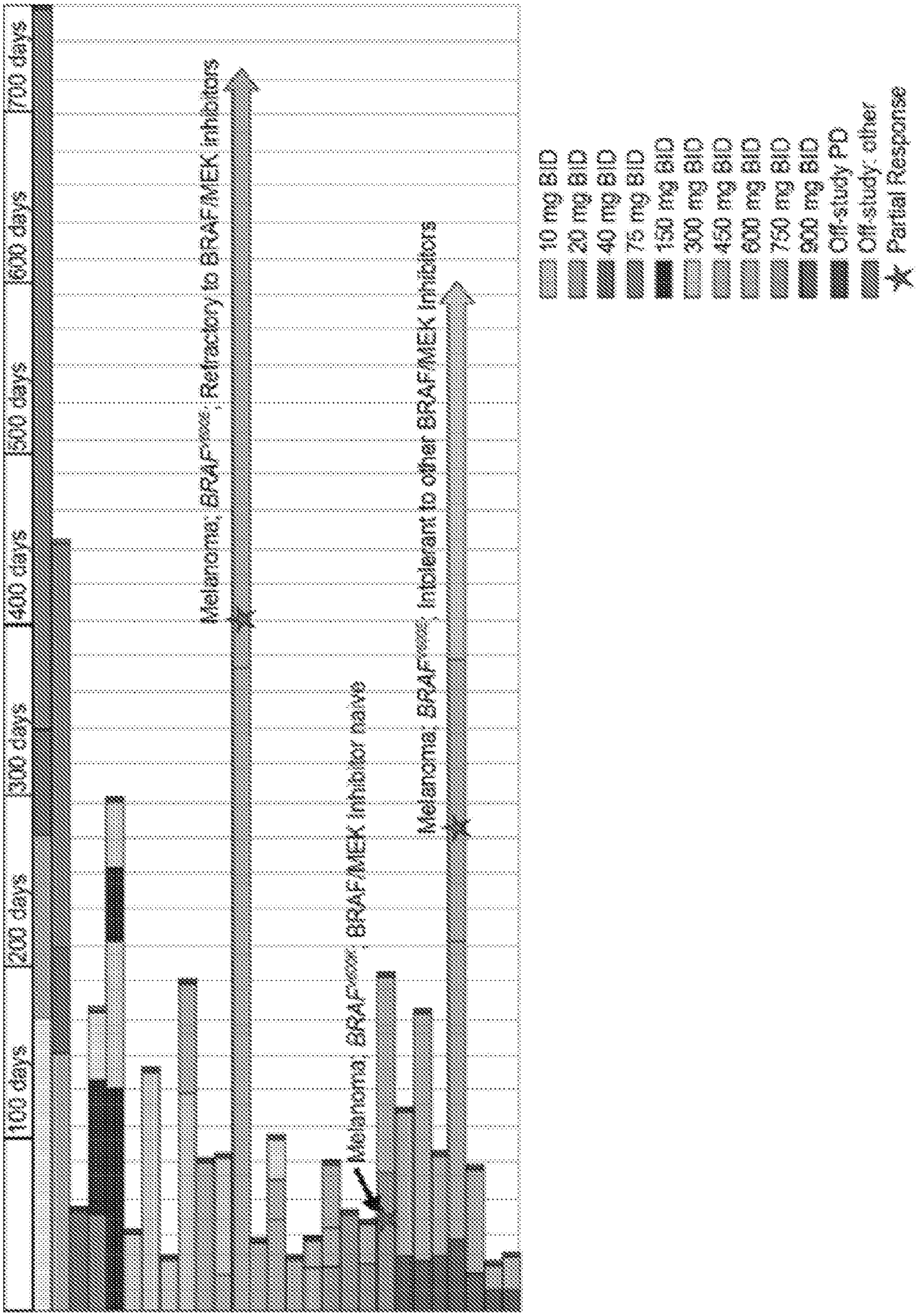
FIG. 41 shows tumor response and tumor progression. Shown is a swimmer plot of tumor response, tumor progression, and duration of treatment in response-evaluable patients treated with BVD-523. Origin of the vertical axis corresponds to randomization date or reference start date. Analysis cut-off date: Dec. 1, 2015. Abbreviation: BID, twice daily.

FIG. 41 depicts the time to response and the duration of response in the study population. The two patients who demonstrated responses to BVD-523 remained on study and continued with BVD-523 treatment as of the study cutoff date (>500 days); additionally, one patient with bronchoalveolar NSCLC (not enough tissue for molecular profiling) had been on treatment for >700 days with stable disease. Twenty-four of 27 patients (90%) discontinued treatment due to progressive disease (22/27, 82%) or other reasons (2/27, 7%). The mean duration of BVD-523 treatment before discontinuation was 4.7 months.

Discussion

The present invention presents results from a first-in-human study evaluating the safety, pharmacokinetics, pharmacodynamics, and preliminary efficacy of BVD-523 in 27 patients with advanced solid tumors. In this dose-escalation study, oral treatment with BVD-523 resulted in both radiographic responses by RECIST v1.1 (3 partial responses) and prolonged disease stabilization in some patients, the majority of whom had been treated with ≥2 prior systemic therapies. Evidence of BVD-523-dependent inhibition of metabolic response in tumors was established in a subset of patients by imaging tumor uptake of $^{18}$F-glucose. Drug exposures increased linearly with increasing doses up to 600 mg BID, with exposures at 600 mg BID providing near complete 24/7 inhibition of ERK-dependent substrate (RSK- 1) phosphorylation in an ex vivo whole blood assay. Furthermore, tolerability to BVD-523 was manageable when administered up to its MTD and RP2D, determined to be 600 mg BID.

BVD-523 was generally well tolerated, with manageable and reversible toxicity. The most common AEs were rash (usually acneiform), fatigue, and gastrointestinal side effects, including nausea, vomiting, and diarrhea. The safety profile of BVD-523 is consistent with its selective inhibition of the MAPK pathway; the AE profile shows considerable overlap with MEK inhibitor experience. However, toxicities associated with any targeted therapy may include dependence on both the specific mechanism and the degree of target inhibition as well as any off-target effects (Zelboraf [package insert] and Hauschild et al. 2012). Ongoing and future investigations will extend both the efficacy and safety profile demonstrated in this dose-escalation study, and will guide how the unique profile of the ERK inhibitor BVD-523 might be used as a single agent or in combination with other agents.

Durable responses by RAF and MEK inhibitors are often limited by intrinsic and eventual acquired resistance, with a common feature often involving reactivation of the ERK pathway (Poulikakos et al. 2011, Corcoran et al. 2010, Nazarian et al. 2010, Shi et al. 2014, Johannessen et al. 2010, Wagle et al. 2011, Wagle et al. 2014, Ahronian et al. 2015 and Paraiso et al. 2010). Thus, ERK inhibition with BVD-523 alone or in combination with other MAPK signaling pathway inhibitors may have the potential to delay the development of resistance to existing therapies and to benefit a broader patient population. That ERK inhibitors, including BVD-523, retain their potency in BRAF- and MEK-resistant cell lines provide preclinical evidence for the use of ERK inhibitors in patients with acquired resistance to standard of care (BRAF/MEK combination therapy) See, e.g., Examples 9-16. Importantly, in this study, a patient whose cancer had progressed after experiencing stable disease when treated initially with a BRAF inhibitor (vemurafenib) and subsequently with a combination of BRAF and MEK inhibitors (dabrafenib/trametinib) had a partial response when receiving single-agent BVD-523. This patient has remained on-study for a total of 708 days, as of the cutoff date of the study reported herein. Based in part on the antitumor effects observed in this patient, the FDA has designated as a Fast Track development program the investigation of BVD-523 for the treatment of patients with unresectable or metastatic $BRAF^{V600}$ mutation-positive melanoma that is refractory to or has progressed following treatment with a BRAF and/or MEK inhibitor(s). Precise definition of exactly how BVD-523 might best support patient care (eg, as a single agent or in various combinations) requires additional clinical studies.

In summary, the present examples present data from an initial data from the dose escalation portion of a phase I study evaluating BVD-523, a novel first-in-class ERK inhibitor, as a treatment for patients with advanced cancers. Continuous, twice-daily oral treatment with BVD-523 resulted in antitumor effects in several patients, including patients either naïve to or having progressed on available MAPK pathway-targeted therapies. BVD-523 was generally well tolerated in this advanced cancer patient population and toxicities were manageable, the MTD and RP2D were 600 mg BID. BVD-523 exposures increased linearly up to the RP2D and robust pharmacodynamics effects were evident at this dose level. An expansion of this phase I clinical study is currently underway to confirm and extend the observations made in the dose-escalation phase. Specifically, patients are being enrolled into molecularly classified expansion cohorts (e.g., NRAS, BRAF, MEK or ERK alterations) across various tumor histologies. Furthermore, expansion cohorts are evaluating the use of BVD-523 in patients with cancer who are either naïve to available MAPK pathway therapies or those whose disease has progressed on such treatments.

Documents

ABSALAN, Farnaz, Mostafa Ronaghi (2008). Molecular Inversion Probe Assay. Methods in Molecular Biology 396. Humana Press. pp. 315-330.

AHRONIAN L G, Sennott E M, Van Allen E M, Wagle N, Kwak E L, Faris J E, et al. Clinical acquired resistance to RAF inhibitor combinations in BRAF-mutant colorectal cancer through MAPK pathway alterations. Cancer Discov 2015; 5:358-67.

ARCILA M E, Drilon A, Sylvester B E, Lovly C M, Borsu L, Reva B, et al. MAP2K1 (MEK1) mutations define a distinct subset of lung adenocarcinoma associated with smoking. Clin Cancer Res 2015; 21:1935-43.

ARONOV A M, Baker C, Bemis G W, Cao J, Chen G, Ford P J, et al. Flipped out: structure-guided design of selective pyrazolylpyrrole ERK inhibitors. J Med Chem 2007; 50:1280-7.

ARONOV A M, Tang Q, Martinez-Botella G, Bemis G W, Cao J, Chen G, et al. Structure-guided design of potent and selective pyrimidylpyrrole inhibitors of extracellular signal-regulated kinase (ERK) using conformational control. J Med Chem 2009; 52:6362-8.

ARRINGTON A K, Heinrich E L, Lee W, Duldulao M, Patel S, Sanchez J, et al. Prognostic and predictive roles of KRAS mutation in colorectal cancer. Int J Mol Sci 2012; 13:12153-68.

CARGNELLO M, Roux P P. Activation and function of the MAPKs and their substrates, the MAPK-activated protein kinases. Microbiol Mol Biol Rev 2011; 75:50-83.

CARLINO M S, Fung C, Shahheydari H, Todd J R, Boyd S C, Irvine M, et al. Preexisting MEK1P124 mutations diminish response to BRAF inhibitors in metastatic melanoma patients. Clin Cancer Res 2015; 21:98-105.

CHAPMAN P B, Hauschild A, Robert C, Haanen J B, Ascierto P, Larkin J, et al. Improved survival with vemurafenib in melanoma with BRAF V600E mutation. N Engl J Med 2011; 364:2507-16.

CORCORAN, R. B., et al. BRAF gene amplification can promote acquired resistance to MEK inhibitors in cancer cells harboring the BRAF V600E mutation. Sci Signal (2010); 3(149): ra84.

DAI, B., et al. STAT3 mediates resistance to MEK inhibitor through microRNA miR-17. Cancer Res (2011); 71:3658-3668.

DAVIES H, Bignell G R, Cox C, Stephens P, Edkins S, Clegg S, et al. Mutations of the BRAF gene in human cancer. Nature 2002; 417:949-54.

DESCHENES-SIMARD X, Kottakis F, Meloche S, Ferbeyre G. ERKs in cancer: friends or foes? Cancer Res 2014; 74:412-9.

DOBRZYCKA B, Terlikowski S J, Kowalczuk O, Niklinska W, Chyczewski L, Kulikowski M. Mutations in the KRAS gene in ovarian tumors. Folia Histochem Cytobiol 2009; 47:221-4.

EMERY, C. M., et al. MEK1 mutations confer resistance to MEK and B-RAF inhibition. PNAS (2009); 106(48): 20411-6.

FEDOROV O, Niesen F H, Knapp S. Kinase inhibitor selectivity profiling using differential scanning fluorimetry. Methods Mol Biol 2012; 795:109-18.

FERNÁNDEZ-MEDARDE A, Santos E. Ras in cancer and developmental diseases. Genes Cancer 2011; 2:344-58.

FLAHERTY K T, Infante J R, Daud A, Gonzalez R, Kefford R F, Sosman J, et al. Combined BRAF and MEK inhibition in melanoma with BRAF V600 mutations. N Engl J Med 2012; 367:1694-703.

GOETZ E M, Ghandi M, Treacy D J, Wagle N, Garraway L A. ERK mutations confer resistance to mitogen-activated protein kinase pathway inhibitors. Cancer Res 2014; 74:7079-89.

GOLLOB J A, Wilhelm S, Carter C, Kelley S L. Role of Raf kinase in cancer: therapeutic potential of targeting the Raf/MEK/ERK signal transduction pathway. Semin Oncol 2006; 33:392-406.

GREGER, James G., et al. "Combinations of BRAF, MEK, and PI3K/mTOR inhibitors overcome acquired resistance to the BRAF inhibitor GSK2118436 dabrafenib, mediated by NRAS or MEK mutations." Molecular cancer therapeutics 11.4 (2012): 909-920.

GROENENDIJK F H, Bernards R. Drug resistance to targeted therapies: deja vu all over again. Mol Oncol 2014; 8:1067-83.

HALL R D, Kudchadkar R R. BRAF mutations: signaling, epidemiology, and clinical experience in multiple malignancies. Cancer Control 2014; 21:221-30.

HARDENBOL, P., et al. Multiplexed genotyping with sequence-tagged molecular inversion probes. Nat. Biotechnol. 2003, no. 21, p. 673-678.

HATZIVASSILIOU, Georgia, et al. "RAF inhibitors prime wild-type RAF to activate the MAPK pathway and enhance growth." Nature 464.7287 (2010): 431-435.

HATZIVASSILIOU G, Liu B, O'Brien C, Spoerke J M, Hoeflich K P, Haverty P M, et al. ERK inhibition overcomes acquired resistance to MEK inhibitors. Mol Cancer Ther 2012; 11:1143-54.

HAUSCHILD A, Grob J-J, Demidov L V, Jouary T, Gutzmer R, Millward M, et al. Dabrafenib in BRAF-mutated metastatic melanoma: a multicentre, open-label, phase 3 randomised controlled trial. Lancet 2012; 380:358-65.

HAYES T K, Neel N F, Hu C, Gautam P, Chenard M, Long B, et al. Long-Term ERK Inhibition in KRAS-Mutant Pancreatic Cancer Is Associated with MYC Degradation and Senescence-like Growth Suppression. Cancer Cell 2016; 29:75-89.

HEZEL A F, Noel M S, Allen J N, Abrams T A, Yurgelun M, Faris J E, et al. Phase II study of gemcitabine, oxaliplatin in combination with panitumumab in KRAS wild-type unresectable or metastatic biliary tract and gallbladder cancer. Br J Cancer 2014; 111:430-6.

JHA S, Morris E J, Hruza A, Mansueto M S, Schroeder G, Arbanas J, et al. Dissecting therapeutic resistance to ERK inhibition. Mol Cancer Ther 2016; 15:548-59.

JOHANNESSEN, C. M., et al. COT/MAP3K8 drives resistance to RAF inhibition through MAP kinase pathway reactivation. Nature (2010); 468(7326):968-972.

JOHNSON D B, Menzies A M, Zimmer L, Eroglu Z, Ye F, Zhao S, et al. Acquired BRAF inhibitor resistance: A multicenter meta-analysis of the spectrum and frequencies, clinical behaviour, and phenotypic associations of resistance mechanisms. Eur J Cancer 2015; 51:2792-9.

KANDA M, Matthaei H, Wu J, Hong S M, Yu J, Borges M, et al. Presence of somatic Mutations in most early-stage pancreatic intraepithelial neoplasia. Gastroenterology 2012; 142:730-733.

KHATTAK M, Fisher R, Turajlic S, Larkin J. Targeted therapy and immunotherapy in advanced melanoma: an evolving paradigm. Ther Adv Med Oncol 2013; 5:105-18.

KING, Alastair J., et al. "Dabrafenib; preclinical characterization, increased efficacy when combined with trametinib, while BRAF/MEK tool combination reduced skin lesions." PloS one 8.7 (2013): e67583.

LARKIN J, Ascierto P A, Dréno B, Atkinson V, Liszkay G, Maio M, et al. Combined vemurafenib and cobimetinib in BRAF-mutated melanoma. N Engl J Med 2014; 371: 1867-76.

LITTLE, A. S., et al., Amplification of the Driving Oncogene, KRAS or BRAF, Underpins Acquired Resistance to MEK1/2 Inhibitors in Colorectal Cancer Cells. Sci. Signal. 4, ra17 (2011).

LIU, Dingxie, et al. "BRAF V600E maintains proliferation, transformation, and tumorigenicity of BRAF-mutant papillary thyroid cancer cells." Journal of Clinical Endocrinology & Metabolism 92.6 (2007): 2264-2271.

LIU B, Fu L, Zhang C, Zhang L, Zhang Y, Ouyang L, et al. Computational design, chemical synthesis, and biological evaluation of a novel ERK inhibitor (BL-EI001) with apoptosis-inducing mechanisms in breast cancer. Oncotarget 2015; 6:6762-75.

LONG G V, Fung C, Menzies A M, Pupo G M, Carlino M S, Hyman J, et al. Increased MAPK reactivation in early resistance to dabrafenib/trametinib combination therapy of BRAF-mutant metastatic melanoma. Nat Commun 2014; 5:5694.

LONG G V, Stroyakovskiy D, Gogas H, Levchenko E, de Braud F, Larkin J, et al. Dabrafenib and trametinib versus dabrafenib and placebo for Val600 BRAF-mutant melanoma: a multicentre, double-blind, phase 3 randomised controlled trial. Lancet 2015; 386:444-51.

MANANDHAR S P, Hildebrandt E R, Schmidt W K. Small-molecule inhibitors of the Rce1p CaaX protease. J Biomol Screen. 2007; 12(7):983-993.

MASSEY P R, Prasad V, Figg W D, Fojo T. Multiplying therapies and reducing toxicity in metastatic melanoma. Cancer Biol Ther 2015; 16:1014-8.

MAURER, T, Garrenton, L S, Oh, A, Pitts, K, Anderson, D J, Skelton, N J, Fauber, B P, Pan, B, Malek, S, Stokoe, D, Ludlam, M J C, Bowman, K K, Wu, J, Giannetti, A M, Starovasnik, M A, Mellman, I, Jackson, P K, Rudolph, J, Wang, W, Fang, G. Small-molecule ligands bind to a distinct pocket in Ras and inhibit SOS-mediated nucleotide exchange activity. PNAS. 2012; 109(14):5299-304.

MCARTHUR G A, Chapman P B, Robert C, Larkin J, Haanen J B, Dummer R, et al. Safety and efficacy of vemurafenib in $BRAF^{v600E}$ and $BRAF^{v600K}$ mutation-positive melanoma (BRIM-3): extended follow-up of a phase 3, randomised, open-label study. Lancet Oncol 2014; 15:323-32.

MEKINIST [package insert]. Research Triangle Park, N C: GlaxoSmithKline; 2014.

METZKER, Emerging technologies in DNA sequencing Genome Res. 2005. 15: 1767-1776.

MITTAL, Rohit et al. "The acetyltransferase activity of the bacterial toxin YopJ of Yersinia is activated by eukaryotic host cell inositol hexakisphosphate." Journal of Biological Chemistry 285.26 (2010): 19927-19934.

MORRIS E J, Jha S, Restaino C R, Dayananth P, Zhu H, Cooper A, et al. Discovery of a novel ERK inhibitor with activity in models of acquired resistance to BRAF and MEK inhibitors. Cancer Discov 2013; 3:742-50.

NAZARIAN, R., et al. Melanomas acquire resistance to B-RAF (V600E) inhibition by RTK or N-RAS upregulation. Nature. 2010; 468(7326):973-977.

NIKOLAEV S I, Rimoldi D, Iseli C, Valsesia A, Robyr D, Gehrig C, et al. Exome sequencing identifies recurrent somatic MAP2K1 and MAP2K2 mutations in melanoma. Nat Genet 2012; 44:133-9.

NILSSON, M., et al. Padlock probes: circularizing oligonucleotides for localized DNA detection. Science. 1994, no. 265, p. 2085-2088.

O'HARA A J, Bell D W. The genomics and genetics of endometrial cancer. Adv Genomics Genet 2012; 2012:33-47.

OJESINA A I, Lichtenstein L, Freeman S S, Pedamallu C S, Imaz-Rosshandler I, Pugh T J, et al. Landscape of genomic alterations in cervical carcinomas. Nature 2014; 506:371-5.

OTA et al., Single nucleotide polymorphism detection by polymerase chain reaction-restriction fragment length polymorphism. Nat Protoc. 2007; 2(11):2857-64.

PARAISO K H T, Fedorenko I V, Cantini L P, Munko A C, Hall M, Sondak V K, et al. Recovery of phospho-ERK activity allows melanoma cells to escape from BRAF inhibitor therapy. Br J Cancer 2010; 102:1724-30.

PATGIRI A, Yadav, K K, Arora, P S, Bar-Sagi, D. An orthosteric inhibitor of the Ras-Sos interaction. Nat Chem Biol. 2011; 7:585-587.

PENNYCUICK A, Simpson T, Crawley D, Lal R, Santis G, Cane P, et al. Routine EGFR and KRAS mutation analysis using COLD-PCR in non-small cell lung cancer. Int J Clin Pract 2012; 66:748-52.

PORTER S B, Hildebrandt E R, Breevoort S R, Mokry D Z, Dore™, Schmidt W K. Inhibition of the CaaX proteases Rce1p and Ste24p by peptidyl (acyloxy)methyl ketones. Biochim Biophys Acta. 2007; 1773(6):853-862.

POULIKAKOS P I, Persaud Y, Janakiraman M, Kong X, Ng C, Moriceau G, et al. RAF inhibitor resistance is mediated by dimerization of aberrantly spliced BRAF(V600E). Nature 2011; 480:387-90.

QUEIROLO P, Picasso V, Spagnolo F. Combined BRAF and MEK inhibition for the treatment of BRAF-mutated metastatic melanoma. Cancer Treat Rev 2015; 41:519-26.

RASOLA A, Sciacovelli M, Chiara F, Pantic B, Brusilow W S, Bernardi P. Activation of mitochondrial ERK protects cancer cells from death through inhibition of the permeability transition. Proc Natl Acad Sci USA 2010; 107: 726-31.

RIZOS H, Menzies A M, Pupo G M, Carlino M S, Fung C, Hyman J, et al. BRAF inhibitor resistance mechanisms in metastatic melanoma: spectrum and clinical impact. Clin Cancer Res 2014; 20:1965-77.

ROBERT C, Karaszewska B, Schachter J, Rutkowski P, Mackiewicz A, Stroiakovski D, et al. Improved overall survival in melanoma with combined dabrafenib and trametinib. N Engl J Med 2015; 372:30-9.

ROMEO Y, Zhang X, Roux P P. Regulation and function of the RSK family of protein kinases. Biochem J 2012; 441:553-69.

RUDOLPH J, Xiao Y, Pardi A, Ahn N G. Slow inhibition and conformation selective properties of extracellular signal-regulated kinase 1 and 2 inhibitors. Biochemistry 2015; 54:22-31.

SHAUL Y D, Seger R. The MEK/ERK cascade: from signaling specificity to diverse functions. Biochim Biophys Acta 2007; 1773:1213-26.

SHI H, Hugo W, Kong X, Hong A, Koya R C, Moriceau G, et al. Acquired resistance and clonal evolution in melanoma during BRAF inhibitor therapy. Cancer Discov 2014; 4:80-93.

SHIMA, F, Yoshikawa, Y, Ye, M, Araki, M, Matsumoto, S, Liao, J, Hu, L, Sugimoto, T, Ijiri, Y, Takeda, A, Nishiyama, Y, Sato, C, Muraoka, S, Tamura, A, Osoda, T, Tsuda, K-I, Miyakawa, T, Fukunishi, H, Shimada, J, Kumasaka, Yamamoto, M, Kataoka, T. In silico discovery of small-molecule Ras inhibitors that display antitumor activity by blocking the Ras-effector interaction. PNAS. 2013; 110(20):8182-7.

SCHUBBERT S, Shannon K, Bollag G. Hyperactive Ras in developmental disorders and cancer. Nat Rev Cancer 2007; 7:295-308.

SUN C, Hobor S, Bertotti A, Zecchin D, Huang S, Galimi F, et al. Intrinsic resistance to MEK inhibition in KRAS mutant lung and colon cancer through transcriptional induction of ERBB3. Cell Rep 2014; 7:86-93.

TAFLINAR [package insert]. Research Triangle Park, N C: GlaxoSmithKline; 2015.

TRUNZER K, Pavlick A C, Schuchter L, Gonzalez R, McArthur G A, Hutson T E, et al. Pharmacodynamic effects and mechanisms of resistance to vemurafenib in patients with metastatic melanoma. J Clin Oncol 2013; 31:1767-74.

VILLANUEVA, J., et al. Acquired resistance to BRAF inhibitors mediated by a RAF kinase switch in melanoma can be overcome by cotargeting MEK and IGF-1R/PI3K. Cancer Cell. 2010; 18:683-695.

WAGLE, N., et al. Dissecting therapeutic resistance to RAF inhibition in melanoma by tumor genomic profiling. Journal of Clinical Oncology 2011; 29(22):3085-3096.

WAGLE N, Van Allen E M, Treacy D J, Frederick D T, Cooper Z A, Taylor-Weiner A, et al. MAP kinase pathway alterations in BRAF-mutant melanoma patients with acquired resistance to combined RAF/MEK inhibition. Cancer Discov 2014; 4:61-8.

Wainstein E, Seger R. The dynamic subcellular localization of ERK: mechanisms of translocation and role in various organelles. Curr Opin Cell Biol 2016; 39:15-20.

WANG, H., et al. Identification of the MEK1(F129L) activating mutation as a potential mechanism of acquired resistance to MEK inhibition in human cancers carrying the B-RAF V600E mutation. Cancer Res (2011); 71(16): 5535-45.

YANG W, Soares J, Greninger P, Edelman E J, Lightfoot H, Forbes S, et al. Genomics of Drug Sensitivity in Cancer (GDSC): a resource for therapeutic biomarker discovery in cancer cells. Nucleic Acids Res 2013; 41:D955-D961.

YAO Z, Torres N M, Tao A, Gao Y, Luo L, Li Q, et al. BRAF Mutants Evade ERK-Dependent Feedback by Different Mechanisms that Determine Their Sensitivity to Pharmacologic Inhibition. Cancer Cell 2015; 28:370-83.

YOHE S. Molecular genetic markers in acute myeloid leukemia. J Clin Med 2015; 4:460-78.

ZELBORAF [package insert]. South San Francisco, CA: Genentech USA, Inc.; 2015.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for treating or ameliorating effects of a cancer selected from pancreatic cancer, papillary thyroid cancer, colorectal cancer, non-small cell lung cancer, ovarian cancer, endometrioid endometrial cancer or melanoma in a subject, comprising administering to the subject an effective amount of (i) BVD-523 (ulixertinib) that has a structure of

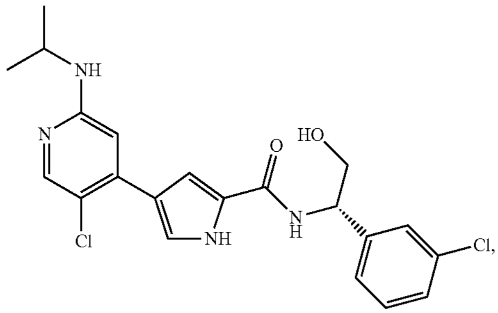 [SMILES: CC(C)Nc1cc(-c2c[nH]c(C(=O)N[C@H](CO)c3cccc(Cl)c3)c2)c(Cl)cn1], or a pharmaceutically acceptable salt thereof, and (ii) SCH772984.

2. The method of claim 1, wherein the cancer is melanoma.

3. The method of claim 1, wherein the cancer is pancreatic cancer.

4. The method of claim 1, wherein the subject is selected from the group consisting of humans, primates, farm animals, and domestic animals.

5. The method of claim 1, wherein the subject is a human.

6. The method of claim 1, wherein the subject has previously received an anti-cancer agent selected from a RAS inhibitor, a RAF inhibitor, a MEK inhibitor, and combinations thereof.

7. The method of claim 1, comprising administering to the subject at least 100 mg/kg body weight BID of BVD-523 or a pharmaceutically acceptable salt thereof.

8. The method of claim 7, comprising administering to the subject 600 mg/kg body weight BID of BVD-523 or a pharmaceutically acceptable salt thereof.

* * * * *

SEQUENCE LISTING

<160> NUMBER OF SEQ ID NOS: 82

<210> SEQ ID NO 1
<211> LENGTH: 2949
<212> TYPE: DNA
<213> ORGANISM: Homo sapiens

<400> SEQUENCE: 1

```
cgcctccctt ccccctcccc gcccgacagc ggccgctcgg gccccggctc tcggttataa     60

gatggcggcg ctgagcggtg gcggtggtgg cggcgcggag ccgggccagg ctctgttcaa    120

cggggacatg gagcccgagg ccggcgccgg cgccggcgcc gcggcctctt cggctgcgga    180

ccctgccatt ccggaggagg tgtggaatat caaacaaatg attaagttga cacaggaaca    240

tatagaggcc ctattggaca aatttggtgg ggagcataat ccaccatcaa tatatctgga    300

ggcctatgaa gaatacacca gcaagctaga tgcactccaa caaagagaac aacagttatt    360

ggaatctctg gggaacggaa ctgatttttc tgtttctagc tctgcatcaa tggataccgt    420

tacatcttct tcctcttcta gcctttcagt gctaccttca tctctttcag tttttcaaaa    480

tcccacagat gtggcacgga gcaaccccaa gtcaccacaa aaacctatcg ttagagtctt    540

cctgcccaac aaacagagga cagtggtacc tgcaaggtgt ggagttacag tccgagacag    600

tctaaagaaa gcactgatga tgagaggtct aatcccagag tgctgtgctg tttacagaat    660

tcaggatgga gagaagaaac caattggttg ggacactgat atttcctggc ttactggaga    720

agaattgcat gtggaagtgt tggagaatgt tccacttaca acacacaact ttgtacgaaa    780

aacgtttttc accttagcat tttgtgactt ttgtcgaaag ctgcttttcc agggtttccg    840

ctgtcaaaca tgtggttata aatttcacca gcgttgtagt acagaagttc cactgatgtg    900

tgttaattat gaccaacttg atttgctgtt tgtctccaag ttctttgaac accacccaat    960

accacaggaa gaggcgtcct tagcagagac tgccctaaca tctggatcat ccccttccgc   1020

acccgcctcg gactctattg ggccccaaat tctcaccagt ccgtctcctt caaaatccat   1080

tccaattcca cagcccttcc gaccagcaga tgaagatcat cgaaatcaat ttgggcaacg   1140

agaccgatcc tcatcagctc ccaatgtgca tataaacaca atagaacctg tcaatattga   1200

tgacttgatt agagaccaag gatttcgtgg tgatggagga tcaaccacag gtttgtctgc   1260

taccccccct gcctcattac ctggctcact aactaacgtg aaagccttac agaaatctcc   1320

aggacctcag cgagaaagga agtcatcttc atcctcagaa gacaggaatc gaatgaaaac   1380

acttggtaga cgggactcga gtgatgattg ggagattcct gatgggcaga ttacagtggg   1440

acaaagaatt ggatctggat catttggaac agtctacaag ggaaagtggc atggtgatgt   1500

ggcagtgaaa atgttgaatg tgacagcacc tacacctcag cagttacaag ccttcaaaaa   1560

tgaagtagga gtactcagga aaacacgaca tgtgaatatc ctactcttca tgggctattc   1620

cacaaagcca caactggcta ttgttaccca gtggtgtgag ggctccagct tgtatcacca   1680

tctccatatc attgagacca aatttgagat gatcaaactt atagatattg cacgacagac   1740

tgcacagggc atggattact tacacgccaa gtcaatcatc cacagagacc tcaagagtaa   1800

taatatattt cttcatgaag acctcacagt aaaaataggt gattttggtc tagctacagt   1860

gaaatctcga tggagtgggt cccatcagtt tgaacagttg tctggatcca ttttgtggat   1920

ggcaccagaa gtcatcagaa tgcaagataa aaatccatac agctttcagt cagatgtata   1980

tgcatttgga attgttctgt atgaattgat gactggacag ttaccttatt caaacatcaa   2040

caacagggac cagataattt ttatggtggg acgaggatac ctgtctccag atctcagtaa   2100
```

```
ggtacggagt aactgtccaa aagccatgaa gagattaatg gcagagtgcc tcaaaaagaa   2160

aagagatgag agaccactct ttccccaaat tctcgcctct attgagctgc tggcccgctc   2220

attgccaaaa attcaccgca gtgcatcaga accctccttg aatcgggctg gtttccaaac   2280

agaggatttt agtctatatg cttgtgcttc tccaaaaaca cccatccagg caggggggata  2340

tggtgcgttt cctgtccact gaaacaaatg agtgagagag ttcaggagag tagcaacaaa   2400

aggaaaataa atgaacatat gtttgcttat atgttaaatt gaataaaata ctctcttttt   2460

ttttaaggtg aaccaaagaa cacttgtgtg gttaaagact agatataatt tttccccaaa   2520

ctaaaattta tacttaacat tggattttta acatccaagg gttaaaatac atagacattg   2580

ctaaaaattg gcagagcctc ttctagaggc tttactttct gttccgggtt tgtatcattc   2640

acttggttat tttaagtagt aaacttcagt ttctcatgca acttttgttg ccagctatca   2700

catgtccact agggactcca gaagaagacc ctacctatgc ctgtgtttgc aggtgagaag   2760

ttggcagtcg gttagcctgg gttagataag gcaaactgaa cagatctaat ttaggaagtc   2820

agtagaattt aataattcta ttattattct taataatttt tctataacta tttcttttta   2880

taacaatttg gaaaatgtgg atgtctttta tttccttgaa gcaataaact aagtttcttt   2940

ttataaaaa                                                           2949
```

<210> SEQ ID NO 2
<211> LENGTH: 765
<212> TYPE: PRT
<213> ORGANISM: Homo sapiens

<400> SEQUENCE: 2

```
Ala Ala Leu Ser Gly Gly Gly Gly Gly Gly Ala Glu Pro Gly Gln Ala
1               5                   10                  15

Leu Phe Asn Gly Asp Met Glu Pro Glu Ala Gly Ala Gly Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Met Asp Thr Val Thr Ser Ser Ser Ser Ser Ser Leu Ser
        115                 120                 125

Val Leu Pro Ser Ser Leu Ser Val Phe Gln Asn Pro Thr Asp Val Ala
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
```

-continued

```
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Ala Leu Thr Ser Gly Ser Ser Pro Ser Ala Pro
305                 310                 315                 320

Ala Ser Asp Ser Ile Gly Pro Gln Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Gly Asp Gly Gly Ser Thr Thr Gly Leu Ser Ala Thr
385                 390                 395                 400

Pro Pro Ala Ser Leu Pro Gly Ser Leu Thr Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640
```

Phe Gly Ile Val Leu Tyr Glu Leu Met Thr Gly Gln Leu Pro Tyr Ser
645 650 655

Asn Ile Asn Asn Arg Asp Gln Ile Ile Phe Met Val Gly Arg Gly Tyr
660 665 670

Leu Ser Pro Asp Leu Ser Lys Val Arg Ser Asn Cys Pro Lys Ala Met
675 680 685

Lys Arg Leu Met Ala Glu Cys Leu Lys Lys Lys Arg Asp Glu Arg Pro
690 695 700

Leu Phe Pro Gln Ile Leu Ala Ser Ile Glu Leu Leu Ala Arg Ser Leu
705 710 715 720

Pro Lys Ile His Arg Ser Ala Ser Glu Pro Ser Leu Asn Arg Ala Gly
725 730 735

Phe Gln Thr Glu Asp Phe Ser Leu Tyr Ala Cys Ala Ser Pro Lys Thr
740 745 750

Pro Ile Gln Ala Gly Gly Tyr Gly Ala Phe Pro Val His
755 760 765

<210> SEQ ID NO 3
<211> LENGTH: 3906
<212> TYPE: DNA
<213> ORGANISM: Rattus norvegicus

<400> SEQUENCE: 3
atggcggcgc tgagtggcgg cggtggcagc agcagcggtg gcggtggcgg cggcggcggc 60
ggcggtggtg gcggcggcgg cggcggcgcc gaacagggac aggctctgtt caatggcgac 120
atggagccgg aggccggcgc tggcgccgcg gcctcttcgg ccgcggaccc ggccattcct 180
gaagaggtgt ggaatatcaa gcaaatgatt aagttgacac aggaacatat agaggcccta 240
ttggacaagt ttggtgggga gcataaccca ccgtcaatat acctggaggc ctatgaagag 300
tacaccagca agctagatgc ccttcagcag agagagcagc agctgttgga atccctggtt 360
tttcaaactc ccacagatgt atcacggaac aaccccaagt caccacagaa acctatcgtt 420
cgtgtcttcc tgcccaacaa acagaggaca gtggtgcccg caagatgtgg tgtaacggtc 480
cgagacagtc taaagaaagc actaatgatg aggggtctca tcccagagtg ctgtgctgtt 540
tacagaattc aggacggaga gaagaaacca attggctggg acactgacat ttcctggctt 600
actggagagg agctacatgt tgaagtacta gagaatgttc ctctgacaac ccacaacttc 660
gtacggaaaa cttttttcac cttagcattt tgtgactttt gccgaaagct gcttttccag 720
ggtttccgct gtcaaacatg tggttataag tttcaccagc gttgtagtac agaggttcca 780
ctgatgtgtg ttaattatga ccaacttgat ttgctgtttg tctccaagtt ctttgagcat 840
cacccagtac cacaggagga ggccttctca gcagagacta cccttccatc tggatgctct 900
tccgcacccc cctcagactc tattgggccc caaatcctca ccagtccatc tccttcaaaa 960
tccattccaa ttccacagcc cttccggcca gcagatgaag atcatcgcaa tcagtttggg 1020
caacgagacc gctcctcctc cgctcccaat gttcatataa acacaatcga acctgtcaat 1080
attgatgaaa aattcccaga agtggaatta caggatcaaa gggatttgat tagagaccag 1140
gggtttcgtg gggatggagc ccctttgaac cagctgatgc gctgtcttcg gaaataccaa 1200
tcccggactc ccagcccccct cctccattct gtccccagtg aaatagtgtt tgattttgag 1260
cctggcccag tgttcagagg gtcaaccaca ggcttgtcgg ccaccccacc tgcctcatta 1320
cctggctcac tcactaacgt gaaagcctta cagaaatctc caggacctca gcgggaaagg 1380

-continued

```
aagtcctcct cctcctcctc ctccacggaa gacagaagtc ggatgaaaac acttggtaga   1440
agagattcaa gtgatgattg ggagattcct gatggacaga ttacagtggg acagagaatt   1500
ggatctgggt cctttggaac tgtctacaag ggaaagtggc atggcgacgt ggcagtgaaa   1560
atgctgaatg tgacagcacc cacacctcag cagttacagg ccttcaaaaa cgaagtcgga   1620
gtactcagga aaactcgaca tgtgaacatc ctccttttca tgggctattc tacaaagcca   1680
cagctggcta ttgttacaca gtggtgtgaa ggctccagct tatatcacca tctccacatc   1740
attgagacca aatttgagat gatcaaactt atagatattg cacggcagac tgcacagggc   1800
atggattact tacacgccaa gtcaatcatc cacagagacc tcaagagtaa taatatattt   1860
cttcatgaag acctcacggt aaaaataggt gactttggtt tagccacagt gaagtcccga   1920
tggagtgggt cccatcagtt tgaacagttg tctggatcta ttttgtggat ggcacccgaa   1980
gtaatcagaa tgcaagataa aaacccatat agctttcagt cagacgtgta tgcatttggg   2040
attgttctgt atgaactgat gactggtcag ctaccttatt caaacatcaa caacagggat   2100
cagataattt ttatggtggg acgaggatac ctatctccag atctcagtaa ggtacggagt   2160
aactgtccaa aagccatgaa gagattaatg gcagagtgcc tcaaaaagaa aagagacgag   2220
agaccactct ttccccaaat tctcgcctct attgagctgc tggcccgctc attgccaaaa   2280
attcaccgca gtgcatcaga accctccttg aatcgggctg gtttccaaac agaagatttt   2340
agtctgtatg cttgtgcttc tccaaaaaca cccatccaag caggggggata tggagaattt   2400
gcagccttca agtagccact ccatcatggc agcatctact ctttatttct taagtcttgt   2460
gttcatacaa tttgttaaca tcaaaacaca gttctgttcc tcaaattttt tttaaagata   2520
caaaattttc aatgcataag ctcgtgtgga acagaatgga atttcctatt caacaaaaga   2580
gggaagaatg ttttaggaac cagaattctc tgctgcccgt gtttcttctt caacacaaat   2640
atcatgtgca tacaactctg cccattccca agaagaaaga ggagagaccc cgaattctgc   2700
ccttttggtg gtcaggcatg atggaaagaa tttgctgctg cagcttggga aaaattgcta   2760
tggaaagtct gccagtcaac tttgcccttc taaccaccag atccatttgt ggctggtcat   2820
ctgatggggc gatttcaatc accaagcatc gttcttgcct gttgtgggat tatgtcgtgg   2880
agcactttcc ctatccacca ccgttaattt ccgagggatg gagtaaatgc agcataccct   2940
ttgtgtagca cctgtccagt cctcaaccaa tgctatcaca gtgaagctct ttaaatttaa   3000
gtggtgggtg agtgttgagg agagactgcc ttgggggcag agaaaagggg atgctgcatc   3060
ttcttcctca cctccagctc tctcacctcg ggttgccttg cacactgggc tccgcctaac   3120
cactcgggct gggcagtgct ggcacacatt gccgcctttt ctcattgggt ccagcaattg   3180
agcagagggt tgggggattg tttcctccac aatgtagcaa attctcagga aaatacagtc   3240
catatcttcc tctcagctct tccagtcacc aaatacttac gtggctcctt tgtccaggac   3300
ataaaacacc gtggacaaca cctaattaaa agcctacaaa actgcttact gacagttttg   3360
aatgtgagac atttgtgtaa tttaaatgta aggtacaggt cttaatttct tctattaagt   3420
ttcttctatt tttatttaaa cgaagaaaat aattttcagg tttaattgga ataaacgaat   3480
acttcccaaa agactatata ccctgaaaat tatatttttg ttaattgtaa acaactttta   3540
aaaaatggtt attatccttt tctctaccta aaattatggg aaatcttagc ataatgacaa   3600
ttatttatac tttttaaata aatggtactt gctggatcca cactaacatc tttgctaaca   3660
ttcccattgt ttcttccaac ttcactccta cactacatcc tccatcctct ttctagtctt   3720
ttatctataa tatgcaacct aaaataaaag tggtggtgtc tccattcatt cttcttcttc   3780
```

-continued

_____ cttttttccc caagcctggt cttcaaaagg ttgggtaatt tagtagctga gttccctagg    3840
tagaaataga actattaggg acattggggt tgtaggaaag cgtgaggcct gtcaccagtt    3900
gttctt                                                               3906

<210> SEQ ID NO 4
<211> LENGTH: 804
<212> TYPE: PRT
<213> ORGANISM: Rattus norvegicus

<400> SEQUENCE: 4

Met Ala Ala Leu Ser Gly Gly Gly Gly Ser Ser Ser Gly Gly Gly Gly
1               5                   10                  15

Gly Gly Gly Gly Gly Gly Gly Gly Gly Gly Gly Gly Gly Ala Glu Gln
                20                  25                  30

Gly Gln Ala Leu Phe Asn Gly Asp Met Glu Pro Glu Ala Gly Ala Gly
            35                  40                  45

Ala Ala Ala Ser Ser Ala Ala Asp Pro Ala Ile Pro Glu Glu Val Trp
        50                  55                  60

Asn Ile Lys Gln Met Ile Lys Leu Thr Gln Glu His Ile Glu Ala Leu
65                  70                  75                  80

Leu Asp Lys Phe Gly Gly Glu His Asn Pro Pro Ser Ile Tyr Leu Glu
                85                  90                  95

Ala Tyr Glu Glu Tyr Thr Ser Lys Leu Asp Ala Leu Gln Gln Arg Glu
                100                 105                 110

Gln Gln Leu Leu Glu Ser Leu Val Phe Gln Thr Pro Thr Asp Val Ser
            115                 120                 125

Arg Asn Asn Pro Lys Ser Pro Gln Lys Pro Ile Val Arg Val Phe Leu
            130                 135                 140

Pro Asn Lys Gln Arg Thr Val Val Pro Ala Arg Cys Gly Val Thr Val
145                 150                 155                 160

Arg Asp Ser Leu Lys Lys Ala Leu Met Met Arg Gly Leu Ile Pro Glu
                165                 170                 175

Cys Cys Ala Val Tyr Arg Ile Gln Asp Gly Glu Lys Lys Pro Ile Gly
            180                 185                 190

Trp Asp Thr Asp Ile Ser Trp Leu Thr Gly Glu Glu Leu His Val Glu
            195                 200                 205

Val Leu Glu Asn Val Pro Leu Thr Thr His Asn Phe Val Arg Lys Thr
        210                 215                 220

Phe Phe Thr Leu Ala Phe Cys Asp Phe Cys Arg Lys Leu Leu Phe Gln
225                 230                 235                 240

Gly Phe Arg Cys Gln Thr Cys Gly Tyr Lys Phe His Gln Arg Cys Ser
            245                 250                 255

Thr Glu Val Pro Leu Met Cys Val Asn Tyr Asp Gln Leu Asp Leu Leu
            260                 265                 270

Phe Val Ser Lys Phe Phe Glu His His Pro Val Pro Gln Glu Glu Ala
        275                 280                 285

Phe Ser Ala Glu Thr Thr Leu Pro Ser Gly Cys Ser Ser Ala Pro Pro
        290                 295                 300

Ser Asp Ser Ile Gly Pro Gln Ile Leu Thr Ser Pro Ser Pro Ser Lys
305                 310                 315                 320

Ser Ile Pro Ile Pro Gln Pro Phe Arg Pro Ala Asp Glu Asp His Arg
                325                 330                 335

Asn Gln Phe Gly Gln Arg Asp Arg Ser Ser Ser Ala Pro Asn Val His

-continued

```
            340                 345                 350

Ile Asn Thr Ile Glu Pro Val Asn Ile Asp Glu Lys Phe Pro Glu Val
        355                 360                 365

Glu Leu Gln Asp Gln Arg Asp Leu Ile Arg Asp Gln Gly Phe Arg Gly
    370                 375                 380

Asp Gly Ala Pro Leu Asn Gln Leu Met Arg Cys Leu Arg Lys Tyr Gln
385                 390                 395                 400

Ser Arg Thr Pro Ser Pro Leu Leu His Ser Val Pro Ser Glu Ile Val
                405                 410                 415

Phe Asp Phe Glu Pro Gly Pro Val Phe Arg Gly Ser Thr Thr Gly Leu
            420                 425                 430

Ser Ala Thr Pro Pro Ala Ser Leu Pro Gly Ser Leu Thr Asn Val Lys
        435                 440                 445

Ala Leu Gln Lys Ser Pro Gly Pro Gln Arg Glu Arg Lys Ser Ser Ser
    450                 455                 460

Ser Ser Ser Ser Thr Glu Asp Arg Ser Arg Met Lys Thr Leu Gly Arg
465                 470                 475                 480

Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765
```

Ser Leu Asn Arg Ala Gly Phe Gln Thr Glu Asp Phe Ser Leu Tyr Ala
770 775 780

Cys Ala Ser Pro Lys Thr Pro Ile Gln Ala Gly Gly Tyr Gly Glu Phe
785 790 795 800

Ala Ala Phe Lys

<210> SEQ ID NO 5
<211> LENGTH: 9728
<212> TYPE: DNA
<213> ORGANISM: Mus musculus

<400> SEQUENCE: 5
ccctcaggct cggctgcgcc ggggccgccg gcgggttcca gaggtggcct ccgccccggc 60
cgctccgccc acgccccccg cgcctccgcg cccgcctccg cccgccctgc gcctcccttc 120
cccctccccg ccccgcggcg gccgctcggc ccggctcgcg cttcgaagat ggcggcgctg 180
agtggcggcg gtggcagcag cagcggtggc ggcggcggcg gtggcggcgg cggtggcggt 240
ggcgacggcg gcggcggcgc cgagcagggc caggctctgt tcaatggcga catggagccg 300
gaggccggcg ctggcgccgc ggcctcttcg gctgcggacc cggccattcc tgaagaggta 360
tggaatatca agcaaatgat taagttgaca caggaacata tagaggccct attggacaaa 420
tttggtggag agcataaccc accatcaata tacctggagg cctatgaaga gtacaccagc 480
aagctagatg cccttcagca aagagaacag cagcttttgg aatccctggt tttcaaact 540 cccacagatg catcacggaa caaccccaag tcaccacaga aacctatcgt tagagtcttc 600
ctgcccaaca aacagaggac agtggtaccc gcaagatgtg gtgttacagt tcgagacagt 660
ctaaagaaag cactgatgat gagaggtctc atcccagaat gctgtgctgt ttacagaatt 720
caggatggag agaagaaacc aattggctgg gacacggaca tttcctggct tactggagag 780
gagttacatg ttgaagtact ggagaatgtc ccacttacaa cacacaactt tgtacggaaa 840 actttttca ccttagcatt ttgtgacttt tgccgaaagc tgcttttcca gggtttccgt 900
tgtcaaacat gtggttataa atttcaccag cgttgtagta cagaggttcc actgatgtgt 960
gtaaattatg accaacttga tttgctgttt gtctccaagt tctttgagca tcacccagta 1020
ccacaggagg aggcctcctt cccagagact gcccttccat ctggatcctc ttccgcaccc 1080
ccctcagact ctactgggcc ccaaatcctc accagtccat ctccttcaaa atccattcca 1140
attccacagc ccttccgacc agcagatgaa gatcatcgca atcagtttgg gcaacgagac 1200
cggtcctcct cagctcccaa tgttcatata aacacaattg agcctgtgaa tatcgatgaa 1260
aaattcccag aagtggaatt acaggatcaa agggatttga ttagagacca ggggtttcgt 1320
ggtgatggag ccccccttgaa ccaactgatg cgctgtcttc ggaaatacca atcccggact 1380
cccagccccc tcctccattc tgtccccagt gaaatagtgt ttgattttga gcctggccca 1440
gtgttcagag ggtcaaccac aggcttgtcc gccaccccgc ctgcctcatt acctggctca 1500
ctcactaacg tgaaagcctt acagaaatct ccaggtcctc agcgggaaag gaagtcatct 1560
tcttcctcat cctcggagga cagaagtcgg atgaaaacac ttggtagaag agattcaagt 1620
gatgactggg agattcctga tggacagatt acagtgggac agagaattgg atctgggtca 1680
tttggaactg tctacaaggg aaagtggcat ggtgatgtgg cagtgaaaat gttgaatgtg 1740
acagcaccca cacctcaaca gctacaggcc ttcaaaaatg aagtaggagt gctcaggaaa 1800
actcgacatg tgaatatcct ccttttcatg ggctattcta caaagccaca actggcaatt 1860

-continued

```
gttacacagt ggtgtgaggg ctccagctta tatcaccatc tccacatcat tgagaccaaa   1920
tttgagatga tcaaacttat agatattgct cggcagactg cacagggcat ggattactta   1980
cacgccaagt caatcatcca cagagacctc aagagtaata atatatttct tcatgaagac   2040
ctcacggtaa aaataggtga ctttggtcta gccacagtga aatctcggtg gagtgggtcc   2100
catcagtttg aacagttgtc tggatctatt ttgtggatgg caccagaagt aatcagaatg   2160
caagataaaa acccgtatag ctttcagtca gacgtgtatg cgtttgggat tgttctgtac   2220
gaactgatga ccggccagct accttattca aacatcaaca acagggatca gataattttt   2280
atggtgggac gaggatacct atctccagat ctcagtaagg tacggagtaa ctgtccaaaa   2340
gccatgaaga gattaatggc agagtgcctc aaaaagaaaa gagacgagag accactcttt   2400
ccccaaattc tcgcctccat tgagctgctg gcccgctcat tgccaaaaat tcaccgcagt   2460
gcatcagaac cttccttgaa tcgggctggt ttccaaacag aagattttag tctgtatgct   2520
tgtgcttctc cgaaaacacc catccaagca gggggatatg gagaatttgc agccttcaag   2580
tagccagtcc atcatggcag catctactct ttatttctta agtcttgtgt tcatacagtt   2640
tgttaacatc aaaacacagt tctgttcctc aaaaaatttt ttaaagatac aaaattttca   2700
atgcataagt tcatgtggaa cagaatggaa tttcctattc aacaaaagag ggaagaatgt   2760
tttaggaacc agaattctct gctgcccgtg tttcttcttc aacataacta tcacgtgcat   2820
acaagtctgc ccattcccaa gaagaaagag gagagaccct gaattctgcc cttttggtgg   2880
tcaggcatga tggaaagaat ttgctgctgc agcttgggaa aattgctatg gaaagtctgc   2940
cagtcgactt tgcccttcta accaccagat cagcctgtgg ctggtcatct gatggggcga   3000
tttccatcac caagcatcgt tcttgcctat tctgggatta tgttgtggag cactttccct   3060
gtccagcacc gttcatttct gagggatgga gtaaatgcag cattcccttg tgtagcgcct   3120
gttcagtcct cagcagctgc tgtcacagcg aagcttttta cagttaagtg gtgggggaga   3180
gttgaggaga gcctgcctcg gggcagagaa aaggggggtgc tgcatcttct tcctcacctc   3240
cagctctctc acctcgggtt gccttgctca ctgggctccg cctaaccact caggctgctc   3300
agtgctggca cacattgcct tcttttctca ttgggtccag caattgagga gagggttggg   3360
ggattgtttc ctcctcaatg tagcaaattc tcaggaaaat acagtccata tcttcctctc   3420
agctcttcca gtcaccaaat acttacgtgg ctcctttgtc caggacataa aacaccgtgg   3480
acaacaccta attaaaagcc tacaaaactg cttactgaca gttttgaatg tgagacactt   3540
gtgtaattta aatgtaaggt acaggtttta atttctgagt ttcttctatt tttatttaaa   3600
agaagaaaat aattttcagt tttaattgga ataaatgagt acttcccaca agactatata   3660
ccctgaaaat tatattttg ttaattgtaa acaactttta aagaataatt attatccttt   3720
tctctaccta aaaattatgg ggaatcttag cataatgaca attatttata ctttttaaat   3780
aaatggtact tgctggatcc acactaacat ctttgctaac aatcccattg tttcttccaa   3840
cttaactcct acactacatc ctacatcctc tttctagtct tttatctata atatgcaacc   3900
taaaataaac gtggtggcgt ctccattcat tctccctctt cctgttttcc ccaagcctgg   3960
tcttcaaaag gttgggtaat cggtccctga gctccctagc tggcaatgca actattaggg   4020
acattggagt tgcaggagag caggaagcct gtccccagct gttcttctag aaccctaaat   4080
cttatctttg cacagatcaa aagtatcacc tcgtcacagt tctccttagc ctttacttac   4140
aggtaatata aataaaaatc accatagtag taaagaaaac aactggatgg attgatgacc   4200
agtacctctc agagccagga atcttgaatc tccaggattt atacgtgcaa atttaaggag   4260
```

```
atgtacttag caacttcaag ccaagaactt ccaaaatact agcgaatcta aaataaaatg   4320
gaattttgag ttatttttaa agttcaaatt ataattgata ccactatgta tttaagccta   4380
ctcacagcaa gttagatgga ttttgctaaa ctcattgcca gactgtggtg gtggtggtgg   4440
tagtgtgcac ctttaatcca agcaactcag caatcagaat gaggtaaatc tctgtgaata   4500
caaggcctgc ctagtctgca gcgctagttc caggatagcc agggctacac acacaaaaac   4560
cctctctcaa aaaaaacaaa attaattagt tgataataaa aaataactaa agtatcatca   4620
aaggaaggcc tactggaagt tttatatatt cccagtaaat tgaaaaatat tctgaagtta   4680
ttaaccagtt agcaacaatg tgtttttaag tcttacataa acagagcaaa gtcttcaaat   4740
gtttcagagc tgagaagata attgtgcttg atatgaaaaa tagcctctcc atatgatgtg   4800
ccacattgaa aggcgtcatt accctttttaa atacttctta atgtggcttt gttcccttta   4860
cccaggatta gctagaaaga gctaggtagg cttcggccac agttgcacat ttcgggcctg   4920
ctgaagaatg ggagctttga aggctggcct tggtggagga gcccctcagt gctggagggt   4980
ggggcgtgta cgcagcatgg aagtggtcta gacagagtgc aaagggacag acttctttct   5040
cattttagta tagggtgatg tctcacttga aatgagaaag tagagttgat attaaacgaa   5100
gctgtgccca gaaaccaggc tcagggtatt gtgagatttt ctttttaaat agagaatata   5160
aaagatagaa ataaatattt aaaccttcct tcttattttc tatcaaatag atttttttta   5220
tcatttgcaa acaacataaa aaaaggtttc ttttgtgggg ttttctttcc ttcttttttt   5280
tttttttttt tttttaagac tgcagataat cttgttgagc tcctcggaaa atacaaggaa   5340
gtccgtgttt gtgcagagcg ctttatgagt aactgtatag acagtgtggc tgcttcactc   5400
atcccagagg gctgcagctg tcggcccatg aagtggctgc agtgcctcgt gagatctgct   5460
ttgttttgtt tggagtgaag tctttgaaag gtttgagtgc aactatatag gactgttttt   5520
aaataagtag tattcctcat gaactttctc attgttaagc tacaggaccc aaactctacc   5580
actaagatat tattaacctc aaaatgtagt ttatagaagg aatttgcaaa tagaatatcc   5640
agttcgtact tatatgcatc ttcaacaaag attctctgtg acttgttgga tttggttcct   5700
gaacagccca tttctgtatt tgaggttagg agggcataat gaggcatcct aaaagacaat   5760
ctgatataaa ctgtatgcta gatgtatgct ggtaggggag aaagcattct gtaaagacat   5820
gatttaagac ttcagctctg tcaaccagaa accttgtaaa tacttcctgt cttggtgcag   5880
ccccgcccct ttgatcacac gatgttgtct tgtgcttgtc agacactgtc agagctgctg   5940
ttcgtccctc tgcagatctc acctgtcccc actgcacacc cacctcctgc ctcttgcaga   6000
cctcagcatc tagctttagt tggaaacagt tcagggttca ggtgacttct taaaaaaaaa   6060
aaaaaaccct acctcctcag aatgaggtaa tgaatagtta tttatttaaa gtatgaagag   6120
tcaggagcgc tcgaacatga aggtgattta agatggttcc tttcgtgtgt attgtagctg   6180
agcacttgtt tttgtcctaa agggcattat acatttaagc agtgattctg tttaaagatg   6240
tttttcttta aaggtgtagc tcagagtatc tgttgttgga attggtgcca gagtctgctt   6300
aatagatttc agaatcctaa gcttaagtca gtcgcatgaa gttaagtagt tatggtaaca   6360
ctttgctagc catgatataa ttctactttt taggagtagg tttggcaaaa ctgtatgcct   6420
tcaaagtgag ttggccacag ctttgtcaca tgcacagata ctcatctgaa gagactgccc   6480
agctaagagg gcggaaggat acccttttttt cctacgattc gcttctttgt ccacgttggc   6540
attgttagta ctagtttatc agcaccttga ccagcagatg tcaaccaata agctattttt   6600
```

-continued

```
aaaaccatag ccagagatgg agaggtcact gtgagtagaa acagcaggac gcttacagga   6660
gtgaaatggt gtagggaggc tctagaaaaa tatcttgaca atttgccaaa tgatcttact   6720
gtgccttcat gatgcaataa aaaagctaac attttagcag aaatcagtga tttacgaaga   6780
gagtggccag tctggtttaa ctcagctggg ataatatttt tagagtgcaa tttagactgc   6840
gaagataaat gcactaaaga gtttatagcc aattcacatt tgaaaaataa gaaaatggta   6900
aattttcagt gaaatatttt tttaaagcac ataatcccta gtgtagccag aaatatttac   6960
cacatagagc agctaggctg agatacagtc cagtgacatt tctagagaaa ccttttctac   7020
tcccacgggc tcctcaaagc atggaaattt tatacaaaat gtttgacatt ttaagatact   7080
gctgtagttt agttttgaaa tagtatgtgc tgagcagcaa tcatgtacta actcagagag   7140
agaaaacaac aacaaattgt gcatctgatt tgttttcaga gaaatgctgc caacttagat   7200
actgagttct cagagcttca agtgtaaact tgcctcccaa gtcctgtttg caaatgaagt   7260
tggctagtgc tactgactgc tccagcacat gatggaaggc agggggctgt ctctgaagtg   7320
tcttctataa agggacaata gaatagtgag agacctggtc agtgtgtgtc agctggacac   7380
tccatgctat gggacttgca tcttctgtcc tcaccatccc caagacattg tgctttcctc   7440
agttgtcctc tagctgtttc actcagacac caagatgaat tactgatgcc agaaggggcc   7500
aaaatggcca gtgtgttttg gggttgtat cagttgactg gacaataact ttaatagttt   7560
cagatcattt atttttactt ccattttgac agacatttaa atggaaattt agtcctaact   7620
tttgtcattt gaaaggaaaa attaacagtt cctataagat acttttgagg tggaatctga   7680
catcctaatt ttttttcttt tcagtgggtt tgcagcgagg gtcttgtatg cactaggcaa   7740
gggttctacc actaagccac atttcccagg aaataaaatg ttaacagtta aaacatacac   7800
acaaatacac aaacacctta ttaccacttt agtaaagtga gagatgtgcg tcctttgtct   7860
cagtctccac gatttcagct gccccttgta tgaataactc agtctcgcta aactgtttac   7920
ttttatttac ctggtttgac tagttgcagc tatataacca gttgtgcatg aggacaacag   7980
ccagtgtgtt tgttttgttt ttggtttttt gtggtacatt ttttgtaaag aattctgtag   8040
attgaagtgc tctttgaaaa cagaactgag atatatttat tcttgttagc atcaaaaaac   8100
attttgtgca aatgatttgc ttttcctggc aggctgagta ccatatccag cgcccacaat   8160
tgcgggttcc catctaccat gtccacaggg gagacagacg ggaagcacat gaggggtgtg   8220
tttacagagt tgtaggagtt atgtagttct cttgttgcct tggaaatcac tgttgtttta   8280
agactgttga acccgtgtgt ttggctgggc tgtgagttac atgaagaaac tgcaaactag   8340
catatgcaga caaagctcac agactaggcg taaatggagg aaaatggacc aaaataaggc   8400
agggtgacac ataaaccttg ggcttcggag aaaactaagg gtggagatga actataatca   8460
cctgaataca atgtaagagt gcaataagtg tgcttattct aagctgtgaa cttcttttaa   8520
atcattcctt tctaatacat ttatgtatgt tccattgctg actaaaacca gctatgagaa   8580
catatgcctt tttattcatg ttaactacca gtttaagtgg ctaaccttaa tgtcttattt   8640
atcttcattt tgtattagtt tacataccag gtatgtgtgt gtgctgtact cttcttccct   8700
ttatttgaaa acacttttca ctgggtcatc tccttggcca ttccacaaca caactttggt   8760
ttggctttca atgtcacctt atttgatggc ctgtgtccca gtagcagaat ttatggtatt   8820
cccattgctg gctgctcttc cgaccctttg cttctacagc acttgtctct cctaagatag   8880
tcagaaacta actgatcagg ggatggactt caccattcat cgtgtctctt caattctatt   8940
aaatagacca ctcttgggct ttagaccagg aaaaaggaga cagctctagc catctaccaa   9000
```

```
gcctcaccct aaaaggtcac ccgtacttct tggtctgagg acaagtctcc actccagtaa   9060

gggagagggg aggaaatgct tcctgtttga aatgcagtga attcctatgg ctcctgtttc   9120

accacccgca cctatggcaa cccatataca ttcctcttgt ctgtaactgc caaaggttgg   9180

gtttatgtca cttcagttcc actcaagcat tgaaaaggtt ctcatggagt ctggggtgtg   9240

cccagtgaaa agatggggac tttttcatta tccacagacc tctctatacc tgctttgcaa   9300

aaattataat ggagtaacta tttttaaagc ttatttttca attcataaga aaaagacatt   9360

tattttcaat caaatggatg atgtctctta tcccttatcc ctcaatgttt gcttgaattt   9420

tgtttgttcc ctatacctac tccctaattc tttagttcct tcctgctcag gtcccttcat   9480

ttgtactttg gagtttttct catgtaaatt tgtataatgg aaaatattgt tcagtttgga   9540

tagaaaagcat ggagaaataa ataaaaaaag atagctgaaa atcaaattga agaaatttat   9600

ttctgtgtaa agttatttaa aaactctgta ttatatttaa agaaaaaagc ccaacccccc   9660

aaaaagtgct atgtaattga tgtgaatatg cgaatactgc tataataaag attgactgca   9720

tggagaaa                                                            9728
```

<210> SEQ ID NO 6
<211> LENGTH: 804
<212> TYPE: PRT
<213> ORGANISM: Mus musculus

<400> SEQUENCE: 6

```
Met Ala Ala Leu Ser Gly Gly Gly Gly Ser Ser Ser Gly Gly Gly Gly
1               5                   10                  15

Gly Gly Gly Gly Gly Gly Gly Gly Gly Asp Gly Gly Gly Gly Ala Glu
            20                  25                  30

Gln Gly Gln Ala Leu Phe Asn Gly Asp Met Glu Pro Glu Ala Gly Ala
        35                  40                  45

Gly Ala Ala Ala Ser Ser Ala Ala Asp Pro Ala Ile Pro Glu Glu Val
    50                  55                  60

Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu
                85                  90                  95

Glu Ala Tyr Glu Glu Tyr Thr Ser Lys Leu Asp Ala Leu Gln Gln Arg
            100                 105                 110

Glu Gln Gln Leu Leu Glu Ser Leu Val Phe Gln Thr Pro Thr Asp Ala
        115                 120                 125

Ser Arg Asn Asn Pro Lys Ser Pro Gln Lys Pro Ile Val Arg Val Phe
    130                 135                 140

Leu Pro Asn Lys Gln Arg Thr Val Val Pro Ala Arg Cys Gly Val Thr
145                 150                 155                 160

Val Arg Asp Ser Leu Lys Lys Ala Leu Met Met Arg Gly Leu Ile Pro
                165                 170                 175

Glu Cys Cys Ala Val Tyr Arg Ile Gln Asp Gly Glu Lys Lys Pro Ile
            180                 185                 190

Gly Trp Asp Thr Asp Ile Ser Trp Leu Thr Gly Glu Glu Leu His Val
        195                 200                 205

Glu Val Leu Glu Asn Val Pro Leu Thr Thr His Asn Phe Val Arg Lys
    210                 215                 220

Thr Phe Phe Thr Leu Ala Phe Cys Asp Phe Cys Arg Lys Leu Leu Phe
225                 230                 235                 240
```

-continued

```
Gln Gly Phe Arg Cys Gln Thr Cys Gly Tyr Lys Phe His Gln Arg Cys
                245                 250                 255

Ser Thr Glu Val Pro Leu Met Cys Val Asn Tyr Asp Gln Leu Asp Leu
            260                 265                 270

Leu Phe Val Ser Lys Phe Phe Glu His His Pro Val Pro Gln Glu Glu
        275                 280                 285

Ala Ser Phe Pro Glu Thr Ala Leu Pro Ser Gly Ser Ser Ser Ala Pro
    290                 295                 300

Pro Ser Asp Ser Thr Gly Pro Gln Ile Leu Thr Ser Pro Ser Pro Ser
305                 310                 315                 320

Lys Ser Ile Pro Ile Pro Gln Pro Phe Arg Pro Ala Asp Glu Asp His
                325                 330                 335

Arg Asn Gln Phe Gly Gln Arg Asp Arg Ser Ser Ser Ala Pro Asn Val
            340                 345                 350

His Ile Asn Thr Ile Glu Pro Val Asn Ile Asp Glu Lys Phe Pro Glu
        355                 360                 365

Val Glu Leu Gln Asp Gln Arg Asp Leu Ile Arg Asp Gln Gly Phe Arg
    370                 375                 380

Gly Asp Gly Ala Pro Leu Asn Gln Leu Met Arg Cys Leu Arg Lys Tyr
385                 390                 395                 400

Gln Ser Arg Thr Pro Ser Pro Leu Leu His Ser Val Pro Ser Glu Ile
                405                 410                 415

Val Phe Asp Phe Glu Pro Gly Pro Val Phe Arg Gly Ser Thr Thr Gly
            420                 425                 430

Leu Ser Ala Thr Pro Pro Ala Ser Leu Pro Gly Ser Leu Thr Asn Val
        435                 440                 445

Lys Ala Leu Gln Lys Ser Pro Gly Pro Gln Arg Glu Arg Lys Ser Ser
    450                 455                 460

Ser Ser Ser Ser Ser Glu Asp Arg Ser Arg Met Lys Thr Leu Gly Arg
465                 470                 475                 480

Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655
```

-continued

```
Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys


<210> SEQ ID NO 7
<211> LENGTH: 2232
<212> TYPE: DNA
<213> ORGANISM: Oryctolagus cuniculus

<400> SEQUENCE: 7

atggggaatg tgtggaatat caaacaaatg attaagttga cacaggagca tatagaggcc      60

ctattggaca aatttggtgg ggagcataat ccaccatcaa tatatctgga ggcctacgaa     120

gaatacacca gcaagctaga tgccctccaa caaagagaac agcagttatt ggaatcccta     180

gtttttcaaa atcccacaga tgtgtcacgg agcaacccca agtcaccaca aaaacctatt     240

gttagagtct tcctgcccaa caaacagagg acagtggtac ctgcaagatg tggagttacg     300

gttcgagaca gtctaaagaa agcgctgatg atgagaggtc tgatcccaga atgctgtgct     360

gtttacagaa ttcaggatgg agagaagaag ccaattggct gggacactga tatttcctgg     420

ctcactggag aagagctgca tgtggaagtg ttagagaatg tcccactcac cacacataac     480

tttgtacgga aacttttttt caccttagca ttttgtgact tctgtagaaa gctgcttttc     540

cagggtttcc gctgtcaaac atgtggctac aaatttcacc agcgttgtag tacggaagtt     600

ccactgatgt gtgttaatta tgaccaactt gatttgctgt ttgtctccaa gttctttgaa     660

caccacccag taccacagga ggaggcctcc ttagcagaga ctgccctcac atctgggtca     720

tcgccttccg cacctccctc agactctatt gggcaccaaa ttctcaccag tccgtcccct     780

tcaaaatcca ttccgattcc acagtccttc cgaccagcag atgaagatca tcgaaatcag     840

tttgggcaac gagaccggtc ttcatcagcg cctaatgttc acattaacac aatagaacct     900

gtcaatattg atgaaaaatt cccagaagtg gaattacagg atcaaaggga cttgattaga     960

gaccaagggt ttcgtggtga tggagcccct ttgaaccagc tgatgcgctg tcttcggaaa    1020

taccaatccc ggactcccag tcccctccta ccttctgtcc ccagtgacat agtgtttgat    1080

tttgagcctg gcccagtgtt cagaggatcg accacgggtt tgtctgccac tccccctgcc    1140

tcattacctg gctcactcac tagtgtgaaa gctgtacaga gatccccagg acctcagcga    1200

gagaggaagt cgtcttcctc ctcagaagac aggaatcgaa tgaaaactct tggtagacgg    1260
```

-continued

```
gattcaagtg atgattggga gattcctgat gggcagatca ccgtgggaca gagaattgga   1320

tctggatcat ttggaaccgt ctacaaggga aaatggcacg gtgatgtggc agtaaaaatg   1380

ttgaatgtga cagcacctac acctcagcag ttacaggcct tcaaaaatga agtaggagta   1440

ctcaggaaaa cacgacatgt gaatatccta cttttcatgg gctattccac aaagccacag   1500

ctggctattg ttacccagtg gtgtgagggc tccagtttat atcaccatct ccacatcatt   1560

gagaccaaat tcgagatgat caaacttata gatattgcac ggcagactgc acagggcatg   1620

gattacttac acgccaagtc aatcatccac agagacctca agagtaataa tatatttctt   1680

catgaagacc tcacagtaaa aataggtgat tttggtctag ccacagtgaa atctcgatgg   1740

agtgggtccc atcagtttga acaattgtct ggatccattt tgtggatggc accagaagta   1800

atcagaatgc aagacaaaaa cccatatagc tttcagtcag atgtatatgc atttgggatt   1860

gttctgtatg aattgatgac tgggcagtta ccttactcaa acatcaacaa cagggaccag   1920

atcattttta tggtgggacg tggctacctg tctccagacc tcagtaaggt acggagtaac   1980

tgtccgaaag ccatgaagag attaatggca gagtgcctca aaaagaaaag agatgagaga   2040

ccactctttc cccaaattct cgcctccatt gagctgctgg cccgctcatt gccaaaaatc   2100

caccgcagtg catcagaacc ctccttgaat cgggctggtt tccagacaga ggattttagt   2160

ctatatgctt gtgcttctcc aaaaacaccc atccaggcag ggggatatgg agaatttgca   2220

gccttcaagt ag                                                       2232
```

```
<210> SEQ ID NO 8
<211> LENGTH: 743
<212> TYPE: PRT
<213> ORGANISM: Oryctolagus cuniculus

<400> SEQUENCE: 8

Met Gly Asn Val Trp Asn Ile Lys Gln Met Ile Lys Leu Thr Gln Glu
1               5                   10                  15

His Ile Glu Ala Leu Leu Asp Lys Phe Gly Gly Glu His Asn Pro Pro
            20                  25                  30

Ser Ile Tyr Leu Glu Ala Tyr Glu Glu Tyr Thr Ser Lys Leu Asp Ala
        35                  40                  45

Leu Gln Gln Arg Glu Gln Gln Leu Leu Glu Ser Leu Val Phe Gln Asn
    50                  55                  60

Pro Thr Asp Val Ser Arg Ser Asn Pro Lys Ser Pro Gln Lys Pro Ile
65                  70                  75                  80

Val Arg Val Phe Leu Pro Asn Lys Gln Arg Thr Val Val Pro Ala Arg
                85                  90                  95

Cys Gly Val Thr Val Arg Asp Ser Leu Lys Lys Ala Leu Met Met Arg
            100                 105                 110

Gly Leu Ile Pro Glu Cys Cys Ala Val Tyr Arg Ile Gln Asp Gly Glu
        115                 120                 125

Lys Lys Pro Ile Gly Trp Asp Thr Asp Ile Ser Trp Leu Thr Gly Glu
    130                 135                 140

Glu Leu His Val Glu Val Leu Glu Asn Val Pro Leu Thr Thr His Asn
145                 150                 155                 160

Phe Val Arg Lys Thr Phe Phe Thr Leu Ala Phe Cys Asp Phe Cys Arg
                165                 170                 175

Lys Leu Leu Phe Gln Gly Phe Arg Cys Gln Thr Cys Gly Tyr Lys Phe
            180                 185                 190

His Gln Arg Cys Ser Thr Glu Val Pro Leu Met Cys Val Asn Tyr Asp
```

-continued

```
        195                 200                 205

Gln Leu Asp Leu Leu Phe Val Ser Lys Phe Phe Glu His His Pro Val
    210                 215                 220

Pro Gln Glu Glu Ala Ser Leu Ala Glu Thr Ala Leu Thr Ser Gly Ser
225                 230                 235                 240

Ser Pro Ser Ala Pro Pro Ser Asp Ser Ile Gly His Gln Ile Leu Thr
                245                 250                 255

Ser Pro Ser Pro Ser Lys Ser Ile Pro Ile Pro Gln Ser Phe Arg Pro
            260                 265                 270

Ala Asp Glu Asp His Arg Asn Gln Phe Gly Gln Arg Asp Arg Ser Ser
        275                 280                 285

Ser Ala Pro Asn Val His Ile Asn Thr Ile Glu Pro Val Asn Ile Asp
    290                 295                 300

Glu Lys Phe Pro Glu Val Glu Leu Gln Asp Gln Arg Asp Leu Ile Arg
305                 310                 315                 320

Asp Gln Gly Phe Arg Gly Asp Gly Ala Pro Leu Asn Gln Leu Met Arg
                325                 330                 335

Cys Leu Arg Lys Tyr Gln Ser Arg Thr Pro Ser Pro Leu Leu Pro Ser
            340                 345                 350

Val Pro Ser Asp Ile Val Phe Asp Phe Glu Pro Gly Pro Val Phe Arg
        355                 360                 365

Gly Ser Thr Thr Gly Leu Ser Ala Thr Pro Pro Ala Ser Leu Pro Gly
    370                 375                 380

Ser Leu Thr Ser Val Lys Ala Val Gln Arg Ser Pro Gly Pro Gln Arg
385                 390                 395                 400

Glu Arg Lys Ser Ser Ser Ser Ser Glu Asp Arg Asn Arg Met Lys Thr
                405                 410                 415

Leu Gly Arg Arg Asp Ser Ser Asp Asp Trp Glu Ile Pro Asp Gly Gln
            420                 425                 430

Ile Thr Val Gly Gln Arg Ile Gly Ser Gly Ser Phe Gly Thr Val Tyr
        435                 440                 445

Lys Gly Lys Trp His Gly Asp Val Ala Val Lys Met Leu Asn Val Thr
    450                 455                 460

Ala Pro Thr Pro Gln Gln Leu Gln Ala Phe Lys Asn Glu Val Gly Val
465                 470                 475                 480

Leu Arg Lys Thr Arg His Val Asn Ile Leu Leu Phe Met Gly Tyr Ser
                485                 490                 495

Thr Lys Pro Gln Leu Ala Ile Val Thr Gln Trp Cys Glu Gly Ser Ser
            500                 505                 510

Leu Tyr His His Leu His Ile Ile Glu Thr Lys Phe Glu Met Ile Lys
        515                 520                 525

Leu Ile Asp Ile Ala Arg Gln Thr Ala Gln Gly Met Asp Tyr Leu His
    530                 535                 540

Ala Lys Ser Ile Ile His Arg Asp Leu Lys Ser Asn Asn Ile Phe Leu
545                 550                 555                 560

His Glu Asp Leu Thr Val Lys Ile Gly Asp Phe Gly Leu Ala Thr Val
                565                 570                 575

Lys Ser Arg Trp Ser Gly Ser His Gln Phe Glu Gln Leu Ser Gly Ser
            580                 585                 590

Ile Leu Trp Met Ala Pro Glu Val Ile Arg Met Gln Asp Lys Asn Pro
        595                 600                 605

Tyr Ser Phe Gln Ser Asp Val Tyr Ala Phe Gly Ile Val Leu Tyr Glu
    610                 615                 620
```

```
Leu Met Thr Gly Gln Leu Pro Tyr Ser Asn Ile Asn Asn Arg Asp Gln
625                 630                 635                 640

Ile Ile Phe Met Val Gly Arg Gly Tyr Leu Ser Pro Asp Leu Ser Lys
                645                 650                 655

Val Arg Ser Asn Cys Pro Lys Ala Met Lys Arg Leu Met Ala Glu Cys
            660                 665                 670

Leu Lys Lys Lys Arg Asp Glu Arg Pro Leu Phe Pro Gln Ile Leu Ala
        675                 680                 685

Ser Ile Glu Leu Leu Ala Arg Ser Leu Pro Lys Ile His Arg Ser Ala
    690                 695                 700

Ser Glu Pro Ser Leu Asn Arg Ala Gly Phe Gln Thr Glu Asp Phe Ser
705                 710                 715                 720

Leu Tyr Ala Cys Ala Ser Pro Lys Thr Pro Ile Gln Ala Gly Gly Tyr
                725                 730                 735

Gly Glu Phe Ala Ala Phe Lys
            740


<210> SEQ ID NO 9
<211> LENGTH: 2186
<212> TYPE: DNA
<213> ORGANISM: Cavia porcellus

<400> SEQUENCE: 9

atggcggcgc tcagcggcgg cggtggcgcg gagcagggcc aggctctgtt caacggggac     60

atggagctcg aggccggcgc cggcgccgca gcctcttcgg ctgcagaccc tgccattccc    120

gaggaggtat ggaatatcaa acaaatgatt aagttgacgc aggaacacat agaggcccta    180

ttggacaaat ttggtggaga gcataatcca ccatcaatat acctggaggc ctatgaagaa    240

tacaccagca aactagatgc cctccaacaa agagaacagc agttactgga atccctcggg    300

aatggaactg atttttctgt ttctagctct gcatcactgg acaccgttac atcttcttct    360

tcttctagcc tttcagtact accttcatct ctttcagttt ttcaaaatcc tacagatgtg    420

tcacggagca accccaaatc accacaaaaa cctattgtta gagtcttcct gcccaacaaa    480

cagaggacag tggtacctgc aaggtgtgga gttacagtcc gagacagtct gaagaaagca    540

ctcatgatga gaggtcttat cccagagtgc tgtgctgtgt acagaattca ggatggagaa    600

aagaaaccaa ttggctggga cactgacatt tcctggctta ctggggaaga attacatgta    660

gaagtattgg agaatgttcc acttacaaca cacaattttg tatgtatctt tatatttttt    720

ttgctgtttg tctccaagtt ctttgaacac cacccaatac cacaggagga ggcttcctta    780

gcagagacca cccttacatc tggatcatcc ccttctgcac ccccctcaga gtccattggg    840

cccccaattc tcaccagccc atctccttca aaatccattc caattccaca gcctttccgg    900

ccaggagagg aagatcatcg aaatcaattt gggcagcgag accggtcctc atctgctccc    960

aatgtgcata taaacacaat agaacctgtc aatattgatg atttgattag agaccaaggg   1020

tttcgtagtg atggaggatc aactacaggt ttgtctgcca ccccacctgc ctcattacct   1080

ggctcactca ctaatgtgaa agccttacag aaatctccag gacctcagcg agaaaggaag   1140

tcatcttcat cctcagaaga cagaaatcga atgaaaacgc ttggtagacg ggactcaagt   1200

gatgattggg agattcctga tgggcagatt acagtgggac aaagaattgg atctgggtca   1260

tttggaacag tctacaaggg gaagtggcat ggtgacgtgg cagtgaaaat gttgaatgtg   1320

acagcaccca cacctcaaca gttacaggcc ttcaaaaatg aagtaggagt actcaggaaa   1380
```

```
acacgacatg tgaatatcct actcttcatg ggctattcca caaagccaca gctagctatt   1440

gttacccagt ggtgtgaggg ctccagctta taccaccatc tccacatcat cgagaccaaa   1500

tttgagatga tcaaacttat agatattgca cgacagactg cccagggcat ggattactta   1560

cacgccaagt caatcatcca cagagacctc aagagtaata atatatttct tcacgaagac   1620

ctcacggtta aaataggtga ttttggtcta gccacagtga aatctcgatg gagtgggtcc   1680

catcagtttg aacagttgtc tggatccatt ttgtggatgg caccagaagt aatcagaatg   1740

cgagataaaa acccatacag ttttcagtcc gatgtatatg catttgggat tgttctatat   1800

gaattgatga ctgggcagtt accctattca aatatcaaca acagggacca gataattttt   1860

atggtgggac gaggatatct atctccagat ctcagcaagg tacggagtaa ctgtccaaaa   1920

gccatgaaga ggttaatggc ggagtgcctc aaaaagaaaa gagatgagag accactcttt   1980

ccccaaattc tcgcctctat tgagctgctg gcccgctcat tgccaaaaat tcaccgcagt   2040

gcatcagaac cctccttgaa tcgggctggt ttccaaacag aggattttag tctctatgct   2100

tgtgcttctc caaaaacacc catccaggca gggggatatg gtgcgtttcc tgtccactga   2160

tgcaaattaa atgagtgaga aataaa                                        2186
```

<210> SEQ ID NO 10
<211> LENGTH: 719
<212> TYPE: PRT
<213> ORGANISM: Cavia porcellus

<400> SEQUENCE: 10

```
Met Ala Ala Leu Ser Gly Gly Gly Gly Ala Glu Gln Gly Gln Ala Leu
1               5                   10                  15

Phe Asn Gly Asp Met Glu Leu Glu Ala Gly Ala Gly Ala Ala Ala Ser
            20                  25                  30

Ser Ala Ala Asp Pro Ala Ile Pro Glu Glu Val Trp Asn Ile Lys Gln
        35                  40                  45

Met Ile Lys Leu Thr Gln Glu His Ile Glu Ala Leu Leu Asp Lys Phe
    50                  55                  60

Gly Gly Glu His Asn Pro Pro Ser Ile Tyr Leu Glu Ala Tyr Glu Glu
65                  70                  75                  80

Tyr Thr Ser Lys Leu Asp Ala Leu Gln Gln Arg Glu Gln Gln Leu Leu
                85                  90                  95

Glu Ser Leu Gly Asn Gly Thr Asp Phe Ser Val Ser Ser Ser Ala Ser
            100                 105                 110

Leu Asp Thr Val Thr Ser Ser Ser Ser Ser Ser Leu Ser Val Leu Pro
        115                 120                 125

Ser Ser Leu Ser Val Phe Gln Asn Pro Thr Asp Val Ser Arg Ser Asn
    130                 135                 140

Pro Lys Ser Pro Gln Lys Pro Ile Val Arg Val Phe Leu Pro Asn Lys
145                 150                 155                 160

Gln Arg Thr Val Val Pro Ala Arg Cys Gly Val Thr Val Arg Asp Ser
                165                 170                 175

Leu Lys Lys Ala Leu Met Met Arg Gly Leu Ile Pro Glu Cys Cys Ala
            180                 185                 190

Val Tyr Arg Ile Gln Asp Gly Glu Lys Lys Pro Ile Gly Trp Asp Thr
        195                 200                 205

Asp Ile Ser Trp Leu Thr Gly Glu Glu Leu His Val Glu Val Leu Glu
    210                 215                 220

Asn Val Pro Leu Thr Thr His Asn Phe Val Cys Ile Phe Ile Phe Phe
```

-continued

```
225                 230                 235                 240

Leu Leu Phe Val Ser Lys Phe Phe Glu His His Pro Ile Pro Gln Glu
                245                 250                 255

Glu Ala Ser Leu Ala Glu Thr Thr Leu Thr Ser Gly Ser Ser Pro Ser
            260                 265                 270

Ala Pro Pro Ser Glu Ser Ile Gly Pro Pro Ile Leu Thr Ser Pro Ser
        275                 280                 285

Pro Ser Lys Ser Ile Pro Ile Pro Gln Pro Phe Arg Pro Gly Glu Glu
    290                 295                 300

Asp His Arg Asn Gln Phe Gly Gln Arg Asp Arg Ser Ser Ser Ala Pro
305                 310                 315                 320

Asn Val His Ile Asn Thr Ile Glu Pro Val Asn Ile Asp Asp Leu Ile
                325                 330                 335

Arg Asp Gln Gly Phe Arg Ser Asp Gly Gly Ser Thr Thr Gly Leu Ser
            340                 345                 350

Ala Thr Pro Pro Ala Ser Leu Pro Gly Ser Leu Thr Asn Val Lys Ala
        355                 360                 365

Leu Gln Lys Ser Pro Gly Pro Gln Arg Glu Arg Lys Ser Ser Ser Ser
    370                 375                 380

Ser Glu Asp Arg Asn Arg Met Lys Thr Leu Gly Arg Arg Asp Ser Ser
385                 390                 395                 400

Asp Asp Trp Glu Ile Pro Asp Gly Gln Ile Thr Val Gly Gln Arg Ile
                405                 410                 415

Gly Ser Gly Ser Phe Gly Thr Val Tyr Lys Gly Lys Trp His Gly Asp
            420                 425                 430

Val Ala Val Lys Met Leu Asn Val Thr Ala Pro Thr Pro Gln Gln Leu
        435                 440                 445

Gln Ala Phe Lys Asn Glu Val Gly Val Leu Arg Lys Thr Arg His Val
    450                 455                 460

Asn Ile Leu Leu Phe Met Gly Tyr Ser Thr Lys Pro Gln Leu Ala Ile
465                 470                 475                 480

Val Thr Gln Trp Cys Glu Gly Ser Ser Leu Tyr His His Leu His Ile
                485                 490                 495

Ile Glu Thr Lys Phe Glu Met Ile Lys Leu Ile Asp Ile Ala Arg Gln
            500                 505                 510

Thr Ala Gln Gly Met Asp Tyr Leu His Ala Lys Ser Ile Ile His Arg
        515                 520                 525

Asp Leu Lys Ser Asn Asn Ile Phe Leu His Glu Asp Leu Thr Val Lys
    530                 535                 540

Ile Gly Asp Phe Gly Leu Ala Thr Val Lys Ser Arg Trp Ser Gly Ser
545                 550                 555                 560

His Gln Phe Glu Gln Leu Ser Gly Ser Ile Leu Trp Met Ala Pro Glu
                565                 570                 575

Val Ile Arg Met Arg Asp Lys Asn Pro Tyr Ser Phe Gln Ser Asp Val
            580                 585                 590

Tyr Ala Phe Gly Ile Val Leu Tyr Glu Leu Met Thr Gly Gln Leu Pro
        595                 600                 605

Tyr Ser Asn Ile Asn Asn Arg Asp Gln Ile Ile Phe Met Val Gly Arg
    610                 615                 620

Gly Tyr Leu Ser Pro Asp Leu Ser Lys Val Arg Ser Asn Cys Pro Lys
625                 630                 635                 640

Ala Met Lys Arg Leu Met Ala Glu Cys Leu Lys Lys Lys Arg Asp Glu
                645                 650                 655
```

```
Arg Pro Leu Phe Pro Gln Ile Leu Ala Ser Ile Glu Leu Leu Ala Arg
            660                 665                 670

Ser Leu Pro Lys Ile His Arg Ser Ala Ser Glu Pro Ser Leu Asn Arg
        675                 680                 685

Ala Gly Phe Gln Thr Glu Asp Phe Ser Leu Tyr Ala Cys Ala Ser Pro
    690                 695                 700

Lys Thr Pro Ile Gln Ala Gly Gly Tyr Gly Ala Phe Pro Val His
705                 710                 715


<210> SEQ ID NO 11
<211> LENGTH: 3229
<212> TYPE: DNA
<213> ORGANISM: Canis familiaris

<400> SEQUENCE: 11

gtaatgctgg attttcatgg aataagtttg acctgtgctg cagtggcctc cagcaaggta     60

cccgcaagat gtggagttac agtccgggac agtctaaaga aagctctgat gatgagaggt    120

ctaatcccag agtgctgtgc tgtttacaga attcaggatg gagagaagaa accgattggc    180

tgggacactg atatttcctg gctcactgga gaggaattgc atgtagaagt gttggaaaat    240

gttccgctta ccacacacaa ctttgtacgg aaaacttttt tcaccttagc attttgtgac    300

ttttgtcgaa agctgctttt ccagggtttt cgctgtcaaa catgtggtta taaatttcac    360

cagcgttgta gtacagaggt tccactgatg tgtgttaatt atgaccaact tgatttgctg    420

tttgtctcca agttctttga acaccaccca ataccacagg aggaggcctc catagcagag    480

actgccctta cgtctggatc atccccttct gctcccccct ccgattctcc tgggccccca    540

attctgacca gtccgtctcc ttcaaaatcc attccaattc cacagccttt ccgaccagca    600

gatgaagatc atcgaaatca gtttggacaa cgagaccggt cctcatcagc tccaaatgtg    660

catataaaca caatagaacc cgtcaacatt gatgacttga ttagagacca agggtttcgt    720

agtgatggag gatcaaccac aggtttgtct gccacccccc ctgcctcatt gcctggctca    780

ctcactaatg taaaagcatt acagaaatct ccaggacctc agcgggaaag aaaatcatct    840

tcatcctcag aagataggaa tcgaatgaaa acacttggta gacgggattc aagtgatgat    900

tgggagatac ctgatgggca gatcacagtg ggacagagaa ttggatccgg gtcatttggg    960

acagtctaca agggaaagtg gcatggtgac gtggcagtga aaatgttgaa tgtgacagca   1020

cccacacctc agcagttaca ggccttcaaa aatgaagtag gagtactcag gaaaactcga   1080

catgtgaata tcctactctt tatgggctat tcaacaaagc cccaactggc tattgttacc   1140

cagtggtgtg agggctccag cttatatcac catctccaca tcattgagac caaatttgag   1200

atgataaagc ttatagatat tgcacggcag actgcacagg gcatggatta cttacacgcc   1260

aagtcaatca tccacagaga cctcaagagt aataatattt ttcttcatga agacctcaca   1320

gtaaaaatag gtgattttgg tctagccaca gtgaaatctc gatggagtgg gtcccatcag   1380

tttgaacagt tgtctggatc cattttgtgg atggcaccag aagtgatccg aatgcaagac   1440

aaaaacccat atagcttcca gtcagatgta tacgcatttg ggattgttct atatgaattg   1500

atgacagggc agttacctta ttcaaacatc aacaacaggg accagataat ttttatggtg   1560

ggacgaggat atctttctcc agatctcagt aaggtacgga gtaactgtcc aaaagccatg   1620

aagagattga tggcagagtg cctaaaaaag aaaagagatg agaggccact ctttccccaa   1680

attctcgcct ctattgagct gctggcccgc tcattgccaa aaattcaccg cagtgcatca   1740
```

```
gaaccctcct tgaatcgggc tggcttccaa acagaggatt ttagtctcta tgcttgcgct   1800

tctccaaaaa cacccatcca ggcaggggga tacggagaat ttgcagcctt caagtagcca   1860

caccatcatg gcaacaacta ctcttatttc ttaagtcttg tgttcgtaca atttgttaac   1920

atcaaaacac agttctgttc ctcaaatctt tttttaaaga tacagaattt tcaatgcata   1980

agctggtgtg gaacagaatg gaatttccca tccaacaaaa gagggaagaa tgttttagga   2040

accagaattc tctgctgcca gtgtttcttc ttcaacacaa ataccacgtg catacaagtc   2100

tgcccactcc caggaaggaa gaggagagcc tgagttctga ccttttgatg gtcaggcatg   2160

atggaaagaa actgctgcta cagcttggga gattggctgt ggagagcctg cccgtcagct   2220

ctgcccttct aaccgccaga tgagtgtgtg gctggtcacc tgacagggca gctgcaatcg   2280

ccaagcatcg ttctctttcc tgtcctggga ttttgtcgtg gagctctttc cccctagtca   2340

ccaccggttc atttctgagg gatggaacaa aaatgcagca tggcctttct gtgtggtgca   2400

tgtccggtct ttgacaaatt tttatcaagt gaagctcttg tatttaaatg gagaatgaga   2460

ggcgaggggg ggggatcacg ttttggtgta ggggcaaagg gaatgctgca tctttttcct   2520

gacccactgg gtttctggcc tttgtttcct tgctcactga gggtgtctgc ctataaccac   2580

gcaggctgga aagtgctggc acacattgcc ttctcttctc actgggtcca gcaatgaaga   2640

caagtgttgg ggattttttt ttttgccctc cacaatgtag caagttctca ggaaaataca   2700

gttaatatct tcctcctaag ctcttccagt catcaagtac ttatgtggct actttgtcca   2760

gggcacaaaa tgccatggcg gtatccaatt aaaagcctac aaaactgctt gataacagtt   2820

ttgaatgtgt gagacattta tgtaatttaa atgtaaggta caagttttaa tttctgagtt   2880

tctctattat atttttatta aaaagaaaat aattttcaga tttaattgaa ttggaataaa   2940

ataatacttc ccaccagaat tatatatcct ggaaaattgt atttttgtta tataaacaac   3000

ttttaaagaa agatcattat ccttttctct acctaaatat ggggagtctt agcataatga   3060

cagatattta taatttttaa attaatggta cttgctggat ccacactaac atctttgcta   3120

atatctcatg ttttcctcca acttactcct acactacatc ctccatcctc tttccagtct   3180

tttatctaga atatgcaacc taaaataaaa atggtggtgt ctccattca               3229
```

<210> SEQ ID NO 12
<211> LENGTH: 617
<212> TYPE: PRT
<213> ORGANISM: Canis familiaris

<400> SEQUENCE: 12

```
Met Leu Asp Phe His Gly Ile Ser Leu Thr Cys Ala Ala Val Ala Ser
1               5                   10                  15

Ser Lys Val Pro Ala Arg Cys Gly Val Thr Val Arg Asp Ser Leu Lys
            20                  25                  30

Lys Ala Leu Met Met Arg Gly Leu Ile Pro Glu Cys Cys Ala Val Tyr
        35                  40                  45

Arg Ile Gln Asp Gly Glu Lys Lys Pro Ile Gly Trp Asp Thr Asp Ile
    50                  55                  60

Ser Trp Leu Thr Gly Glu Glu Leu His Val Glu Val Leu Glu Asn Val
65                  70                  75                  80

Pro Leu Thr Thr His Asn Phe Val Arg Lys Thr Phe Phe Thr Leu Ala
                85                  90                  95

Phe Cys Asp Phe Cys Arg Lys Leu Leu Phe Gln Gly Phe Arg Cys Gln
            100                 105                 110
```

-continued

```
Thr Cys Gly Tyr Lys Phe His Gln Arg Cys Ser Thr Glu Val Pro Leu
        115                 120                 125

Met Cys Val Asn Tyr Asp Gln Leu Asp Leu Leu Phe Val Ser Lys Phe
    130                 135                 140

Phe Glu His His Pro Ile Pro Gln Glu Glu Ala Ser Ile Ala Glu Thr
145                 150                 155                 160

Ala Leu Thr Ser Gly Ser Ser Pro Ser Ala Pro Pro Ser Asp Ser Pro
                165                 170                 175

Gly Pro Pro Ile Leu Thr Ser Pro Ser Pro Ser Lys Ser Ile Pro Ile
            180                 185                 190

Pro Gln Pro Phe Arg Pro Ala Asp Glu Asp His Arg Asn Gln Phe Gly
        195                 200                 205

Gln Arg Asp Arg Ser Ser Ser Ala Pro Asn Val His Ile Asn Thr Ile
    210                 215                 220

Glu Pro Val Asn Ile Asp Asp Leu Ile Arg Asp Gln Gly Phe Arg Ser
225                 230                 235                 240

Asp Gly Gly Ser Thr Thr Gly Leu Ser Ala Thr Pro Pro Ala Ser Leu
                245                 250                 255

Pro Gly Ser Leu Thr Asn Val Lys Ala Leu Gln Lys Ser Pro Gly Pro
            260                 265                 270

Gln Arg Glu Arg Lys Ser Ser Ser Ser Ser Glu Asp Arg Asn Arg Met
        275                 280                 285

Lys Thr Leu Gly Arg Arg Asp Ser Ser Asp Asp Trp Glu Ile Pro Asp
    290                 295                 300

Gly Gln Ile Thr Val Gly Gln Arg Ile Gly Ser Gly Ser Phe Gly Thr
305                 310                 315                 320

Val Tyr Lys Gly Lys Trp His Gly Asp Val Ala Val Lys Met Leu Asn
                325                 330                 335

Val Thr Ala Pro Thr Pro Gln Gln Leu Gln Ala Phe Lys Asn Glu Val
            340                 345                 350

Gly Val Leu Arg Lys Thr Arg His Val Asn Ile Leu Leu Phe Met Gly
        355                 360                 365

Tyr Ser Thr Lys Pro Gln Leu Ala Ile Val Thr Gln Trp Cys Glu Gly
    370                 375                 380

Ser Ser Leu Tyr His His Leu His Ile Ile Glu Thr Lys Phe Glu Met
385                 390                 395                 400

Ile Lys Leu Ile Asp Ile Ala Arg Gln Thr Ala Gln Gly Met Asp Tyr
                405                 410                 415

Leu His Ala Lys Ser Ile Ile His Arg Asp Leu Lys Ser Asn Asn Ile
            420                 425                 430

Phe Leu His Glu Asp Leu Thr Val Lys Ile Gly Asp Phe Gly Leu Ala
        435                 440                 445

Thr Val Lys Ser Arg Trp Ser Gly Ser His Gln Phe Glu Gln Leu Ser
    450                 455                 460

Gly Ser Ile Leu Trp Met Ala Pro Glu Val Ile Arg Met Gln Asp Lys
465                 470                 475                 480

Asn Pro Tyr Ser Phe Gln Ser Asp Val Tyr Ala Phe Gly Ile Val Leu
                485                 490                 495

Tyr Glu Leu Met Thr Gly Gln Leu Pro Tyr Ser Asn Ile Asn Asn Arg
            500                 505                 510

Asp Gln Ile Ile Phe Met Val Gly Arg Gly Tyr Leu Ser Pro Asp Leu
        515                 520                 525

Ser Lys Val Arg Ser Asn Cys Pro Lys Ala Met Lys Arg Leu Met Ala
```

```
    530                 535                 540

Glu Cys Leu Lys Lys Lys Arg Asp Glu Arg Pro Leu Phe Pro Gln Ile
545                 550                 555                 560

Leu Ala Ser Ile Glu Leu Leu Ala Arg Ser Leu Pro Lys Ile His Arg
                565                 570                 575

Ser Ala Ser Glu Pro Ser Leu Asn Arg Ala Gly Phe Gln Thr Glu Asp
            580                 585                 590

Phe Ser Leu Tyr Ala Cys Ala Ser Pro Lys Thr Pro Ile Gln Ala Gly
        595                 600                 605

Gly Tyr Gly Glu Phe Ala Ala Phe Lys
    610                 615


<210> SEQ ID NO 13
<211> LENGTH: 1889
<212> TYPE: DNA
<213> ORGANISM: Canis familiaris

<400> SEQUENCE: 13

ggaatatcaa acaaatgatt aagttgacac aggaacatat agaagcccta ttggacaagt     60

ttggtgggga gcataatcca ccatcaatat atctggaggc ctatgaagaa tacaccagca    120

aactagatgc cctccaacag cgagaacaac agttattgga atccctgggg aatggaactg    180

atttttctgt ttctagctct gcatcaacgg acaccgttac atcttcttcc tcttctagcc    240

tttcagtgct accttcatct ctttcagttt ttcaaaatcc cacagatata tcacggagca    300

atcccaagtc accacaaaaa cctatcgtta gagtcttcct gcccaataaa cagaggacgg    360

tggtacccgc aagatgtgga gttacagtcc gggacagtct aaagaaagct ctgatgatga    420

gaggtctaat cccagagtgc tgtgctgttt acagaattca ggatggagag aagaaaccga    480

ttggctggga cactgatatt tcctggctca ctggagagga attgcatgta gaagtgttgg    540

aaaatgttcc gcttaccaca cacaactttg tacggaaaac ttttttcacc ttagcatttt    600

gtgacttttg tcgaaagctg cttttccagg gttttcgctg tcaaacatgt ggttataaat    660

ttcaccagcg ttgtagtaca gaggttccac tgatgtgtgt taattatgac caacttgatt    720

tgctgtttgt ctccaagttc tttgaacacc acccaatacc acaggaggag gcctccatag    780

cagagactgc ccttacgtct ggatcatccc cttctgctcc cccctccgat tctcctgggc    840

ccccaattct gaccagtccg tctccttcaa aatccattcc aattccacag cctttccgac    900

cagcagatga agatcatcga aatcagtttg gacaacgaga ccggtcctca tcagctccaa    960

atgtgcatat aaacacaata gaacccgtca acattgatga cttgattaga gaccaagggt   1020

ttcgtagtga tggaggatca accacaggtt tgtctgccac ccccccctgcc tcattgcctg   1080

gctcactcac taatgtaaaa gcattacaga aatctccagg acctcagcgg gaaagaaaat   1140

catcttcatc ctcagaagat aggaatcgaa tgaaaacact tggtagacgg gattcaagtg   1200

atgattggga gatacctgat gggcagatca cagtgggaca gagaattgga tccgggtcat   1260

ttgggacagt ctacaaggga aagtggcatg gtgacgtggc agtgaaaatg ttgaatgtga   1320

cagcacccac acctcagcag ttacaggcct tcaaaaatga agtaggagta ctcaggaaaa   1380

ctcgacatgt gaatatccta ctctttatgg gctattcaac aaagccccaa ctggctattg   1440

ttacccagtg gtgtgagggc tccagcttat atcaccatct ccacatcatt gagaccaaat   1500

ttgagatgat aaagcttata gatattgcac ggcagactgc acagggcatg gattacttac   1560

acgccaagtc aatcatccac agagacctca agagtaataa tatttttctt catgaagacc   1620
```

-continued

```
tcacagtaaa aataggtgat tttggtctag ccacagtgaa atctcgatgg agtgggtccc   1680

atcagtttga acagttgtct ggatccattt tgtggatggc accagaagtg atccgaatgc   1740

aagacaaaaa cccatatagc ttccagtcag atgtatacgc atttgggatt gttctatatg   1800

aattgatgac agggcagtta ccttattcaa acatcaacaa cagggaccag ctcagatcat   1860

gatcacggtg tcatgagatc aagccccac                                     1889


<210> SEQ ID NO 14
<211> LENGTH: 615
<212> TYPE: PRT
<213> ORGANISM: Canis familiaris

<400> SEQUENCE: 14

Met Ile Lys Leu Thr Gln Glu His Ile Glu Ala Leu Leu Asp Lys Phe
1               5                   10                  15

Gly Gly Glu His Asn Pro Pro Ser Ile Tyr Leu Glu Ala Tyr Glu Glu
            20                  25                  30

Tyr Thr Ser Lys Leu Asp Ala Leu Gln Gln Arg Glu Gln Gln Leu Leu
        35                  40                  45

Glu Ser Leu Gly Asn Gly Thr Asp Phe Ser Val Ser Ser Ser Ala Ser
    50                  55                  60

Thr Asp Thr Val Thr Ser Ser Ser Ser Ser Ser Leu Ser Val Leu Pro
65                  70                  75                  80

Ser Ser Leu Ser Val Phe Gln Asn Pro Thr Asp Ile Ser Arg Ser Asn
                85                  90                  95

Pro Lys Ser Pro Gln Lys Pro Ile Val Arg Val Phe Leu Pro Asn Lys
            100                 105                 110

Gln Arg Thr Val Val Pro Ala Arg Cys Gly Val Thr Val Arg Asp Ser
        115                 120                 125

Leu Lys Lys Ala Leu Met Met Arg Gly Leu Ile Pro Glu Cys Cys Ala
    130                 135                 140

Val Tyr Arg Ile Gln Asp Gly Glu Lys Lys Pro Ile Gly Trp Asp Thr
145                 150                 155                 160

Asp Ile Ser Trp Leu Thr Gly Glu Glu Leu His Val Glu Val Leu Glu
                165                 170                 175

Asn Val Pro Leu Thr Thr His Asn Phe Val Arg Lys Thr Phe Phe Thr
            180                 185                 190

Leu Ala Phe Cys Asp Phe Cys Arg Lys Leu Leu Phe Gln Gly Phe Arg
        195                 200                 205

Cys Gln Thr Cys Gly Tyr Lys Phe His Gln Arg Cys Ser Thr Glu Val
    210                 215                 220

Pro Leu Met Cys Val Asn Tyr Asp Gln Leu Asp Leu Leu Phe Val Ser
225                 230                 235                 240

Lys Phe Phe Glu His His Pro Ile Pro Gln Glu Glu Ala Ser Ile Ala
                245                 250                 255

Glu Thr Ala Leu Thr Ser Gly Ser Ser Pro Ser Ala Pro Pro Ser Asp
            260                 265                 270

Ser Pro Gly Pro Pro Ile Leu Thr Ser Pro Ser Pro Ser Lys Ser Ile
        275                 280                 285

Pro Ile Pro Gln Pro Phe Arg Pro Ala Asp Glu Asp His Arg Asn Gln
    290                 295                 300

Phe Gly Gln Arg Asp Arg Ser Ser Ser Ala Pro Asn Val His Ile Asn
305                 310                 315                 320

Thr Ile Glu Pro Val Asn Ile Asp Asp Leu Ile Arg Asp Gln Gly Phe
```

```
                325                 330                 335

Arg Ser Asp Gly Gly Ser Thr Thr Gly Leu Ser Ala Thr Pro Pro Ala
            340                 345                 350

Ser Leu Pro Gly Ser Leu Thr Asn Val Lys Ala Leu Gln Lys Ser Pro
        355                 360                 365

Gly Pro Gln Arg Glu Arg Lys Ser Ser Ser Ser Ser Glu Asp Arg Asn
    370                 375                 380

Arg Met Lys Thr Leu Gly Arg Arg Asp Ser Ser Asp Asp Trp Glu Ile
385                 390                 395                 400

Pro Asp Gly Gln Ile Thr Val Gly Gln Arg Ile Gly Ser Gly Ser Phe
            405                 410                 415

Gly Thr Val Tyr Lys Gly Lys Trp His Gly Asp Val Ala Val Lys Met
            420                 425                 430

Leu Asn Val Thr Ala Pro Thr Pro Gln Gln Leu Gln Ala Phe Lys Asn
        435                 440                 445

Glu Val Gly Val Leu Arg Lys Thr Arg His Val Asn Ile Leu Leu Phe
    450                 455                 460

Met Gly Tyr Ser Thr Lys Pro Gln Leu Ala Ile Val Thr Gln Trp Cys
465                 470                 475                 480

Glu Gly Ser Ser Leu Tyr His His Leu His Ile Ile Glu Thr Lys Phe
            485                 490                 495

Glu Met Ile Lys Leu Ile Asp Ile Ala Arg Gln Thr Ala Gln Gly Met
            500                 505                 510

Asp Tyr Leu His Ala Lys Ser Ile Ile His Arg Asp Leu Lys Ser Asn
        515                 520                 525

Asn Ile Phe Leu His Glu Asp Leu Thr Val Lys Ile Gly Asp Phe Gly
    530                 535                 540

Leu Ala Thr Val Lys Ser Arg Trp Ser Gly Ser His Gln Phe Glu Gln
545                 550                 555                 560

Leu Ser Gly Ser Ile Leu Trp Met Ala Pro Glu Val Ile Arg Met Gln
            565                 570                 575

Asp Lys Asn Pro Tyr Ser Phe Gln Ser Asp Val Tyr Ala Phe Gly Ile
            580                 585                 590

Val Leu Tyr Glu Leu Met Thr Gly Gln Leu Pro Tyr Ser Asn Ile Asn
        595                 600                 605

Asn Arg Asp Gln Leu Arg Ser
    610                 615


<210> SEQ ID NO 15
<211> LENGTH: 3521
<212> TYPE: DNA
<213> ORGANISM: Felis catus
<220> FEATURE:
<221> NAME/KEY: misc_feature
<222> LOCATION: (630)..(649)
<223> OTHER INFORMATION: n is a, c, g, or t

<400> SEQUENCE: 15

atgcctaacc tcagtctctg ccaccacggc caatttgctc atgtgcccac tgtgtcggca      60

ctgggatatt ttgtgatttg ccttggccat tgtccactgt ccttgacatt gcctgaagga     120

gaaccactga tgctaatgtt gaaggtgacc tttgcaggct ctccactact cataccaaag     180

atgcggcccc ctgataatcc cagagccact gtctgcacat gggcaaaaca ggctacattc     240

tgtgcagact ggggagaaag gttccaagaa cacagtgcca tagttttggg cagagagttt     300

caacacagca tagtgtctat ggcagtatct ggatttggcc gggggaagtg cccaagagga     360
```

```
gacagtcagg ctgtgtccta cggccaagga cctgcactta tttttgcatg cagtggttta    420
gcacagggaa gagaacgaag taggaaatcg gagccatgga aacggcagag cggaggaaac    480
gtgcacgcgc gagggtgggc acgaaaggaa agaaccctcc ccagaagact gcgcgagggc    540
gctcctagga ttacgtcacg caccccgcga aaactgaaat gtactgtgtg tggtctttta    600
attgaactat cttccttatg tgcacttaan nnnnnnnnnn nnnnnnnnng cggcggcggc    660
ggtggcgcgg agcagggcca ggctctgttc aacggggaca tggagcccga agccggcgcc    720
gcggcctctt cggctgcgga ccctgccatt cccgaggagg tgtggaatat caaacaaatg    780
attaagttga cacaggaaca tatagaggcc ctattggaca aatttggtgg ggagcataat    840
ccaccatcaa tatatctaga ggcctatgaa gaatacacca gcaagctaga tgccctccaa    900
cagagagaac aacagttatt ggaatccctg gggaatggaa ctgatttttc tgtttctagc    960
tctgcatcaa cagacaccgt tacatcttcc tcctcttcta gcctttcagt gctaccttca   1020
tctctttcag tttttcaaaa ccccacagat gtgtcacgga gcaatcccaa gtcaccacag   1080
aaacctatcg ttagagtctt cctgcctaat aaacagagga cagtggtacc tgcaagatgt   1140
ggagttacag tccgggacag tctaaagaaa gctctgatga tgagaggtct aatccctgag   1200
tgctgtgctg tttacagaat tcaggatgga gagaagaaac caattggctg ggacactgat   1260
atctcctggc tcaccggaga ggaattgcat gtagaagtgt tggaaaatgt tccacttaca   1320
actcacaact ttgtatgtac ggaaaacgtt ttcaccttag cattttgtga cttttgtcga   1380
aagctgcttt tccaaggttt tcgctgtcaa acgtgtggtt ataaatttca ccagcgttgt   1440
agtacagagg ttccactgat gtgtgttaat tatgaccaac ttgatttgct gtttgtctcc   1500
aagttctttg aacaccaccc aataccacag gaggaggcct ccatagcaga gactgcccta   1560
acgtctggat cgtccccttc tgcccccccc tccgattcta ctgggcccca aattctcacc   1620
agtccgtctc cttcaaaatc cattccaatt ccacagcctt tccgaccagc agatgaagat   1680
catcgaaatc aatttggaca gcgagaccgg tcctcatcag ctccaaatgt gcatataaat   1740
acaatagaac ctgtcaatat tgatgacttg attagagacc aggggtttcg tagtgatgga   1800
ggatcaacca caggcttgtc tgccaccccc cctgcctcat tgccgggctc tctcactaat   1860
gtaaaagcat tacagaaatc tccagggcct cagcgggaaa ggaaatcttc ttcatcctca   1920
gaagatagga atcgaatgaa aacacttggt agaagggatt caagtgatga ttgggagatt   1980
cctgatgggc agatcacagt gggacagaga attggatccg ggtcatttgg gacagtctac   2040
aagggaaagt ggcatggtga tgtggcagtg aaaatgttga atgtgacagc acccacacct   2100
cagcagttac aggccttcaa aaatgaagta ggagtactca ggaaaactcg gcatgtgaac   2160
atcctgctct tcatgggcta ttcaacaaag ccccagctgg ctattgtcac ccagtggtgt   2220
gagggctcca gcttatacca ccatctccac atcatcgaga ccaaattcga gatgatcaag   2280
ctgatagata ttgctcggca gactgcgcag ggcatggatt acttacacgc caagtcaatc   2340
atccacagag acctcaagag taataatatt tttcttcacg aagacctcac agtaaaaata   2400
ggtgattttg gtctagccac agtgaaatct cgatggagtg ggtcccatca gtttgaacag   2460
ttgtctggat ccattttgtg gatggcacca gaagtaattc gaatgcaaga taaaaaccca   2520
tatagctttc agtcagatgt atatgcattt gggattgttc tatatgaatt gatgactgga   2580
cagttacctt attcaaacat caacaacagg gaccagataa tttttatggt gggacgagga   2640
tatctttctc cagatctcag taaggtacga agtaactgtc caaaagccat gaagagattg   2700
```

-continued

```
atggcagagt gcctaaaaaa gaaaagagat gagaggccac tgtttcccca aattcttgcc   2760

tctattgagc tgctggcccg ctcattgcca aaaattcacc gcagtgcatc agaaccctcc   2820

ttgaatcggg ctggcttcca gacagaggat tttagtctct atgcttgtgc ttctccaaaa   2880

acacccatcc aggcaggggg atatggtgcg tttcccgtcc actgagataa gttagatgag   2940

tgcgcgagtg cagggggccg gggccaagga ggtggaaatg tgcgtgcttc tgtactaagt   3000

tggatagcat cttctttttt aaaaaaagat gaaccaaaga atgtgtatgt ttttaaagac   3060

tagatataat tatttcctga tctaaaatgt atacttagct ttggattttc aatatccaag   3120

ggttttcaaa atgcacagac attgctgaac atttgcagta cctcttctgg aggctttact   3180

tcctgttaca aattggtttt gtttactggc ttatcctaat tattaaactt caattaaact   3240

tttctcctgc accttttgtt atgagctatc acatgtccct tagggactcg caagagcagt   3300

actgcccccg tgtacgggct tgcaggtaga aaggggatga cgggttttaa cacctgtgtg   3360

aggcaaggca gtccgaacag atctcattta ggaagccacg agagttgaat aagttatttt   3420

tattcttagt atttttctg taactacttt ttattataac ttggaaaata tggatgtcct   3480

ttatacacct tagcaataga ctgaatttct ttttataaat t                       3521
```

```
<210> SEQ ID NO 16
<211> LENGTH: 974
<212> TYPE: PRT
<213> ORGANISM: Felis catus
<220> FEATURE:
<221> NAME/KEY: misc_feature
<222> LOCATION: (210)..(217)
<223> OTHER INFORMATION: Xaa can be any naturally occurring amino acid

<400> SEQUENCE: 16

Met Pro Asn Leu Ser Leu Cys His His Gly Gln Phe Ala His Val Pro
1               5                   10                  15

Thr Val Ser Ala Leu Gly Tyr Phe Val Ile Cys Leu Gly His Cys Pro
            20                  25                  30

Leu Ser Leu Thr Leu Pro Glu Gly Glu Pro Leu Met Leu Met Leu Lys
        35                  40                  45

Val Thr Phe Ala Gly Ser Pro Leu Leu Ile Pro Lys Met Arg Pro Pro
    50                  55                  60

Asp Asn Pro Arg Ala Thr Val Cys Thr Trp Ala Lys Gln Ala Thr Phe
65                  70                  75                  80

Cys Ala Asp Trp Gly Glu Arg Phe Gln Glu His Ser Ala Ile Val Leu
                85                  90                  95

Gly Arg Glu Phe Gln His Ser Ile Val Ser Met Ala Val Ser Gly Phe
            100                 105                 110

Gly Arg Gly Lys Cys Pro Arg Gly Asp Ser Gln Ala Val Ser Tyr Gly
        115                 120                 125

Gln Gly Pro Ala Leu Ile Phe Ala Cys Ser Gly Leu Ala Gln Gly Arg
    130                 135                 140

Glu Arg Ser Arg Lys Ser Glu Pro Trp Lys Arg Gln Ser Gly Gly Asn
145                 150                 155                 160

Val His Ala Arg Gly Trp Ala Arg Lys Glu Arg Thr Leu Pro Arg Arg
                165                 170                 175

Leu Arg Glu Gly Ala Pro Arg Ile Thr Ser Arg Thr Pro Arg Lys Leu
            180                 185                 190

Lys Cys Thr Val Cys Gly Leu Leu Ile Glu Leu Ser Ser Leu Cys Ala
        195                 200                 205
```

-continued

```
Leu Xaa Xaa Xaa Xaa Xaa Xaa Xaa Xaa Gly Gly Gly Gly Gly Ala Glu
    210                 215                 220

Gln Gly Gln Ala Leu Phe Asn Gly Asp Met Glu Pro Glu Ala Gly Ala
225                 230                 235                 240

Ala Ala Ser Ser Ala Ala Asp Pro Ala Ile Pro Glu Glu Val Trp Asn
                245                 250                 255

Ile Lys Gln Met Ile Lys Leu Thr Gln Glu His Ile Glu Ala Leu Leu
            260                 265                 270

Asp Lys Phe Gly Gly Glu His Asn Pro Pro Ser Ile Tyr Leu Glu Ala
        275                 280                 285

Tyr Glu Glu Tyr Thr Ser Lys Leu Asp Ala Leu Gln Gln Arg Glu Gln
    290                 295                 300

Gln Leu Leu Glu Ser Leu Gly Asn Gly Thr Asp Phe Ser Val Ser Ser
305                 310                 315                 320

Ser Ala Ser Thr Asp Thr Val Thr Ser Ser Ser Ser Ser Ser Leu Ser
                325                 330                 335

Val Leu Pro Ser Ser Leu Ser Val Phe Gln Asn Pro Thr Asp Val Ser
            340                 345                 350

Arg Ser Asn Pro Lys Ser Pro Gln Lys Pro Ile Val Arg Val Phe Leu
        355                 360                 365

Pro Asn Lys Gln Arg Thr Val Val Pro Ala Arg Cys Gly Val Thr Val
    370                 375                 380

Arg Asp Ser Leu Lys Lys Ala Leu Met Met Arg Gly Leu Ile Pro Glu
385                 390                 395                 400

Cys Cys Ala Val Tyr Arg Ile Gln Asp Gly Glu Lys Lys Pro Ile Gly
                405                 410                 415

Trp Asp Thr Asp Ile Ser Trp Leu Thr Gly Glu Glu Leu His Val Glu
            420                 425                 430

Val Leu Glu Asn Val Pro Leu Thr Thr His Asn Phe Val Cys Thr Glu
        435                 440                 445

Asn Val Phe Thr Leu Ala Phe Cys Asp Phe Cys Arg Lys Leu Leu Phe
    450                 455                 460

Gln Gly Phe Arg Cys Gln Thr Cys Gly Tyr Lys Phe His Gln Arg Cys
465                 470                 475                 480

Ser Thr Glu Val Pro Leu Met Cys Val Asn Tyr Asp Gln Leu Asp Leu
                485                 490                 495

Leu Phe Val Ser Lys Phe Phe Glu His His Pro Ile Pro Gln Glu Glu
            500                 505                 510

Ala Ser Ile Ala Glu Thr Ala Leu Thr Ser Gly Ser Ser Pro Ser Ala
        515                 520                 525

Pro Pro Ser Asp Ser Thr Gly Pro Gln Ile Leu Thr Ser Pro Ser Pro
    530                 535                 540

Ser Lys Ser Ile Pro Ile Pro Gln Pro Phe Arg Pro Ala Asp Glu Asp
545                 550                 555                 560

His Arg Asn Gln Phe Gly Gln Arg Asp Arg Ser Ser Ser Ala Pro Asn
                565                 570                 575

Val His Ile Asn Thr Ile Glu Pro Val Asn Ile Asp Asp Leu Ile Arg
            580                 585                 590

Asp Gln Gly Phe Arg Ser Asp Gly Gly Ser Thr Thr Gly Leu Ser Ala
        595                 600                 605

Thr Pro Pro Ala Ser Leu Pro Gly Ser Leu Thr Asn Val Lys Ala Leu
    610                 615                 620

Gln Lys Ser Pro Gly Pro Gln Arg Glu Arg Lys Ser Ser Ser Ser Ser
```

```
625                 630                 635                 640

Glu Asp Arg Asn Arg Met Lys Thr Leu Gly Arg Arg Asp Ser Ser Asp
                645                 650                 655

Asp Trp Glu Ile Pro Asp Gly Gln Ile Thr Val Gly Gln Arg Ile Gly
            660                 665                 670

Ser Gly Ser Phe Gly Thr Val Tyr Lys Gly Lys Trp His Gly Asp Val
        675                 680                 685

Ala Val Lys Met Leu Asn Val Thr Ala Pro Thr Pro Gln Gln Leu Gln
    690                 695                 700

Ala Phe Lys Asn Glu Val Gly Val Leu Arg Lys Thr Arg His Val Asn
705                 710                 715                 720

Ile Leu Leu Phe Met Gly Tyr Ser Thr Lys Pro Gln Leu Ala Ile Val
                725                 730                 735

Thr Gln Trp Cys Glu Gly Ser Ser Leu Tyr His His Leu His Ile Ile
            740                 745                 750

Glu Thr Lys Phe Glu Met Ile Lys Leu Ile Asp Ile Ala Arg Gln Thr
        755                 760                 765

Ala Gln Gly Met Asp Tyr Leu His Ala Lys Ser Ile Ile His Arg Asp
    770                 775                 780

Leu Lys Ser Asn Asn Ile Phe Leu His Glu Asp Leu Thr Val Lys Ile
785                 790                 795                 800

Gly Asp Phe Gly Leu Ala Thr Val Lys Ser Arg Trp Ser Gly Ser His
                805                 810                 815

Gln Phe Glu Gln Leu Ser Gly Ser Ile Leu Trp Met Ala Pro Glu Val
            820                 825                 830

Ile Arg Met Gln Asp Lys Asn Pro Tyr Ser Phe Gln Ser Asp Val Tyr
        835                 840                 845

Ala Phe Gly Ile Val Leu Tyr Glu Leu Met Thr Gly Gln Leu Pro Tyr
    850                 855                 860

Ser Asn Ile Asn Asn Arg Asp Gln Ile Ile Phe Met Val Gly Arg Gly
865                 870                 875                 880

Tyr Leu Ser Pro Asp Leu Ser Lys Val Arg Ser Asn Cys Pro Lys Ala
                885                 890                 895

Met Lys Arg Leu Met Ala Glu Cys Leu Lys Lys Lys Arg Asp Glu Arg
            900                 905                 910

Pro Leu Phe Pro Gln Ile Leu Ala Ser Ile Glu Leu Leu Ala Arg Ser
        915                 920                 925

Leu Pro Lys Ile His Arg Ser Ala Ser Glu Pro Ser Leu Asn Arg Ala
    930                 935                 940

Gly Phe Gln Thr Glu Asp Phe Ser Leu Tyr Ala Cys Ala Ser Pro Lys
945                 950                 955                 960

Thr Pro Ile Gln Ala Gly Gly Tyr Gly Ala Phe Pro Val His
                965                 970
```

<210> SEQ ID NO 17
<211> LENGTH: 3853
<212> TYPE: DNA
<213> ORGANISM: Bos taurus

<400> SEQUENCE: 17

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttccccct ccccgcccag cagcggtcgc tcgggcccgg     180
```

-continued ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc accccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaaat tctcgcctct attgagctgc 2340
tggcccgctc attgccaaaa attcaccgca gtgcatcaga accctccttg aatcgggctg 2400
gcttccaaac agaggatttt agtctatatg cttgtgcttc tccaaaaaca cccattcagg 2460
caggggggata tggtacgttt cctgttcact gaaacaaacc gagtgagtga cagcatgtag 2520
gagggtaggg acaaaagaaa gtgaacaaat gtttgcttat atatttgtta aattgaatag 2580

-continued

```
gattttcttt ttctttaaag gtgaacaaga gaacatgtgt gtttttaaag tttggatata   2640
gttttcttcc cagtctaaaa cccatagtta gcattacatt ttcaacatcg aatttttttt   2700
taattcatag acattgctga aaatttataa tacctttttcc agaggcttta cttcccattc   2760
caagtttgtt ttgtttactt ggttagtcta atcattaaac tttaaacttt ccccacctac   2820
cttttgctgt tagctatccc gcatccatta ggggctccaa gaacagcact gtctgcgtgt   2880
gtgtgttggc aggtgggaag ctgatggtaa gttaggctgt gttagtgaag gtaaactgac   2940
caggtctaat taggagtcac tagaattgaa taagcttatt tttattaata ttttttctta   3000
taactatttc tttttgtaat aatttagaaa atataattgt tctttattcc cttacagcag   3060
tataaattat tggtgcaggt aaccaaagat attactgagg agtggcatgt ttgacatgag   3120
tgacatggtt taactttgga tttttagtta atatttcttt atatattaag gatgtcttac   3180
acattataga agtcaaattt actgacaaag gtattgcctc ctcttcctcc ccaaaaacac   3240
agcaaaattc tctgggaact cgtagcattg ttggtttttct tttggatgac tatggttgcc   3300
aaacaaccaa gtaattgatt ttttttaaat tattattgct ttagattata ctcacctctc   3360
atgatgcctg ttagcaatca cctttatcca tgtgtcttgt aaaatatctt tcctccttat   3420
attctttgcc caacaagagt ctacttgtta tgaatgagta ctattttctt tttttgattc   3480
cccagtataa ttagtatgtt tagtgctttc taggacttcc actttcttat gttaaaaaaa   3540
aaaacaaact aatgtggcag tcagtatatt cttactgtga atcagagtct ttactgggaa   3600
tcaaagtgaa agaagcagct gttctgactt cagagtcagc ctagggacca aaaccagcct   3660
cttaaataca ccttcattta ttcagtttgg atttgtgatg attttcatta tagctgacag   3720
ttcaaggtta ttcagtggca cacagatagc atctgcataa atgcctttct tcttgaaaat   3780
aaaggagaaa attgggaaga ctttacacca atagtttagt ctttaagtac cacagataac   3840
acacaccata aat                                                      3853
```

<210> SEQ ID NO 18
<211> LENGTH: 764
<212> TYPE: PRT
<213> ORGANISM: Bos taurus

<400> SEQUENCE: 18

```
Ala Ala Leu Ser Gly Gly Gly Gly Gly Gly Gly Gly Gly Ala Glu Gln
1               5                   10                  15

Gly Gln Ala Leu Phe Asn Gly Asp Met Glu Pro Glu Ala Gly Ala Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Leu Ser Val
        115                 120                 125

Leu Pro Ser Ser Leu Ser Val Phe Gln Asn Pro Thr Asp Val Ser Arg
    130                 135                 140
```

-continued

```
Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
        275                 280                 285

Val Ser Lys Phe Phe Glu His His Pro Ile Pro Gln Glu Glu Ala Ser
    290                 295                 300

Leu Ala Glu Thr Thr Leu Pro Cys Gly Ser Ser Pro Ser Ala Pro Pro
305                 310                 315                 320

Ser Asp Ser Ile Gly Pro Pro Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ser Ala Pro Asn Val His
        355                 360                 365

Ile Asn Thr Ile Glu Pro Val Asn Ile Asp Asp Leu Ile Arg Asp Gln
    370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Ser Asn Val Lys Ala Leu Gln Lys
                405                 410                 415

Ser Pro Gly Pro Gln Arg Glu Arg Lys Ser Ser Ser Ser Ser Glu Asp
            420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
    450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525

Trp Cys Glu Gly Ser Ser Leu Tyr His His Leu His Ile Ile Glu Thr
    530                 535                 540

Lys Phe Glu Met Ile Lys Leu Ile Asp Ile Ala Arg Gln Thr Ala Gln
545                 550                 555                 560
```

```
Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Thr Phe Pro Val His
        755                 760
```

<210> SEQ ID NO 19
<211> LENGTH: 4936
<212> TYPE: DNA
<213> ORGANISM: Bos taurus

<400> SEQUENCE: 19

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttcccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg gggaatggaa ctgatttttc tgtttctagc tctgcatcaa     540

cggacaccgt tacatcttct tcctcttcta gcctttcagt gctgccttca tctctttcag     600

tttttcaaaa tcccacagat gtgtcacgga gcaaccccaa gtcaccacaa aaacctatcg     660

ttagagtctt cctgcccaat aaacagagga cagtggtacc tgcacggtgt ggagtcacag     720

tccgggacag cctgaagaag gcactgatga tgagaggtct aatcccagag tgctgtgctg     780

tttacagaat tcaggatggg gagaagaaac caattggctg ggacactgat atttcctggc     840

ttactggaga ggagttgcat gtagaagtgt tggagaatgt tccacttaca acacacaact     900

ttgtacggaa aacttttttc accttagcat tttgtgactt ctgtagaaag ctgcttttcc     960
```

agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc accccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaagt aggaaagact ctcctaagca 2340
agagacaaaa ttcagaagtt atcagggaaa aagataagca gattctcgcc tctattgagc 2400
tgctggcccg ctcattgcca aaaattcacc gcagtgcatc agaaccctcc ttgaatcggg 2460
ctggcttcca aacagaggat tttagtctat atgcttgtgc ttctccaaaa acacccattc 2520
aggcaggggg atatgaagca gatttggctc ttacatcaaa taaaaataga gtagaagttg 2580
ggatttagag atttcctgac atgcaagaag gaataagcaa gaaaaaaagg tttgttttcc 2640
ccaaatcata tctattgtct tttacttcta ttttttctta aatttttgt gatttcagag 2700
acatgtagag ttttattgat acctaaacta tgagttcttt tttttttttt tttttcatta 2760
ttttgatttt tttggccaag aggcatatgg gatcttagct tgagaaagca acaattttct 2820
tgatgtcatt ttgggtgagg gcacatattg ctgtgaacag tgtggtgata gccaccaggg 2880
accaaactca cacccgctgc attgaaaggt gaagtcttaa acactggacc agcagagaaa 2940
ttcctactct atgagttctt tttgtcatcc cctccccgca ccctccaccc ccaacctaaa 3000
gtctgatgat gaaatcaaca actattccat tagaagcagt agattctggt agcatgatct 3060
ttagtttgtt agtaagattt tgtgctttgt ggggttgtgt cgttttaagg ctaatattta 3120
agtttgtcaa atagaatgct gttcagattg taaaaatgag taataaacat ctgaagtttt 3180
ttttaagtta tttttaacat ggtatataca gttgagctta gagtttatca ttttctgata 3240
ttctcttact tagtagatga attctagcca ttttttataa agatttctgt taagcaaatc 3300
ctgttttcac atgggcttcc tttaagggat tttagattct gctggatatg gtgactgctc 3360
ataagactgt tgaaaattac ttttaagatg tattagaata cttctgaaaa aaaatagcaa 3420
ccttaaaacc ataagcaaaa gtagtaaggg tgtttataca tttctagagt ccctgtttag 3480
gtaatagcct cctatgattg tactttaaat gttttgctct ccaaggtttt agtaacttgg 3540 cttttttct aatcagtgcc aaactccccc agttttttta actttaaata tgaggtaata 3600
aatcttttac ccttccttga tcttttgact tataatacct tggtcagttg tttcttaaaa 3660
ggaatcctta aatggaaaga gacaatatca ctgtctgcag ttctgattag tagttttatt 3720
cagaatggaa aaacagatta ttcatttttg aaaattgttc aggggtatgt tcattgttag 3780
gaccttggac tttggagtca gtgcctagct atgcattcca ggtctgccat tttctggctg 3840
tgaaattttg gacaagttac ttaaccactt taaaccccag ctttaagaag taaattaacc 3900
ccagtaaatt aagaagtaat agcagccact tcgtagagtt gttatgaggc tcagatgcag 3960
tgcaaatgtg tataaagtat tcagggagtc acctggtata ctataataga cactagaata 4020
gttgccaata ttatcagcat acaatctgag gattctgtca gccaatcatt agcaatctgt 4080
tgtttgttgg gacatgccag tgttctccag ttgaaatcag tagcaatcta aaaatggata 4140
gattattcct catttaaata gtgtgttcat ataagtgatt gcttggatcc ttatcagaag 4200
ttgctgttac tgaaaaatga taaggctgac taaattgtga tagttgtcag ttactaacca 4260
actcccagaa atgaataaga ggaacctatc tctagttcct agtagaaggt atggacaaaa 4320
tagtaggtga aaaataatgt cttgaacccc caaattaagt aagctttaaa gagtacaata 4380
cctcaaaggg tctttgcggt ttaaaatttg tatgctgaga atgatgttca ttgacatgtg 4440
cctatatgta atttttgat agtttaaaag gtgaaatgaa ctacagatgg gagaggtctg 4500
aattttcttg ccttcagtca aatgtgtaat gtggacatat tatttgacct gtgaatttta 4560
tcttttaaaa aagattaatt cctgcttctt ccttcctaat agttgcatta taataatgaa 4620
aatgagttga taatttgggg ggaaagtatt ctacaaatca accttattat tttaccattg 4680
gtttctgaga aattttgttc atttgaaccg tttatagctt gattagaatc atagcatgta 4740
aaacccaact gagggattat ctgcagactt aatgtagtat tatgtaagtt gtcttctttc 4800
atttcgacct tttttgcttt tgttgttgct agatctgtag tatgtagcta gtcacctttc 4860
agcgaggttt cagcgaggct tttctgtgtc tctaggttat ttgagataac ttttttaaaa 4920
ttagctcttg tcctcc 4936

<210> SEQ ID NO 20
<211> LENGTH: 797
<212> TYPE: PRT
<213> ORGANISM: Bos taurus

<400> SEQUENCE: 20

Met Ala Ala Leu Ser Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln

-continued

```
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510
```

```
Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750

Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Glu Ala Asp Leu
    770                 775                 780

Ala Leu Thr Ser Asn Lys Asn Arg Val Glu Val Gly Ile
785                 790                 795
```

<210> SEQ ID NO 21
<211> LENGTH: 4154
<212> TYPE: DNA
<213> ORGANISM: Bos taurus

<400> SEQUENCE: 21

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480
```

aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc accccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaagt aggaaagact ctcctaagca 2340
agagacaaaa ttcagaagtt atcagggaaa aagataagca gattctcgcc tctattgagc 2400
tgctggcccg ctcattgcca aaaattcacc gcagtgcatc agaaccctcc ttgaatcggg 2460
ctggcttcca aacagaggat tttagtctat atgcttgtgc ttctccaaaa acacccattc 2520
aggcaggggg atatggctga gcacattgtc catcacccac aagtggctgg ttctcatcgc 2580
agaatctacg tagggaatcg ggcgtgaaat tcacttaaga gatagagcag aggaagtgtt 2640
ctgtttacag gaatggagat gagagttatg agtaagttgc ttagtcagtt ggctttgttt 2700
tgaaaattat tgtgttatat ttgtgttaac ctacttgtgt tttgacagta tatgtcacat 2760
aggaagaaac ctcagactag cataataaca aagctcagac taggcacaga tgtacacaga 2820
atggaccaaa atgggatggg ggaaggtatg ggaataagtc taggggtagg gaaaaattga 2880

-continued

```
tgtgagggtg ggaaataaac tgtaattacc tgaaataaaa tgtaagagtg caataagtgt   2940

gctttttatt ctaagctgtg aatgggtttt ttaaaaaaag cattccttcc caatgcattt   3000

gcctatgttc catagctgat taaaaccagc tatataaaca tatgcctttt tattcatgtt   3060

aattaccaat ataaatggct aacctttacg tcttatttat cttcatgtta tgttagttta   3120

catacaggga tgtgtgtgtg tgtgtatgct ataaattttc cctccttcgt ttaaaaacgc   3180

gtttgttgga tcctctctgt ttccttaggc catgccacag ctcatagtct cagcttggcc   3240

ttcctgtcac ctgatctgaa ggactatcac agtgacgtag ctcgttcatt ggttgtacac   3300

actctaaccc ttttccttgc tcagcaatta ctgtgtcttc taaaacagga gtgtacaacc   3360

atgagattgc aattaattgt ttgacatatg tccctttgaa ttctatttat tagttatgat   3420

tgattgctct ttggtttgga ccaagaaaaa cgaaatccca cctccccacc ttttcactta   3480

tttcttactt tgaggacaat tctgtaagag agaggaaagg gaactccttc atgttttaac   3540

tgcagcaagt taatggccct ggtttacacc aaacattatg gtgattcaca ttcacattcc   3600

tctcctctct tgctgccaga ggtttgggtt ttgttcagtt ctgctcaagc actgaaaaag   3660

ttttcatgga gtctggagag tgcccagtga aaagatggtt tttaattgtc cacagacctt   3720

tctgttcctg ctttgcaaaa attacaaagg agtaactatt tttaaagctt atttttcaat   3780

tcataaaaaa gacatttatt ttcagtcaga tgatgtctcc ttgtccctta atcctcaatg   3840

tttgcttgaa tctttttttt ttttctgatt ttctcccatc cccacttctt gatacttctt   3900

gagttctctt tcctgctcag gtcctttcat ttgtactttg gagtttttttc tcatgtaaat   3960

ttgtacaatg gaaaatattg ttcagtttgg atagaacgca tggagaatta aataaaaaag   4020

atagctgaaa ttcagattga aatttatttg tgtaaagtta tttaaaaact ctgtactata   4080

taaaaggcaa aaaaagttct atgtacttga tgtgaatatg cgaatactgc tataataaag   4140

attgactgca tgga                                                     4154
```

```
<210> SEQ ID NO 22
<211> LENGTH: 781
<212> TYPE: PRT
<213> ORGANISM: Bos taurus

<400> SEQUENCE: 22

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
    130                 135                 140
```

```
Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560
```

```
Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750

Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Gly
    770                 775                 780
```

<210> SEQ ID NO 23
<211> LENGTH: 7914
<212> TYPE: DNA
<213> ORGANISM: Bos taurus

<400> SEQUENCE: 23

```
ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900
```

```
ttgtacggaa aactttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
ccccttctgc accccctcc gattctattg ggcccccaat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaaat tctcgcctct attgagctgc   2340
tggcccgctc attgccaaaa attcaccgca gtgcatcaga accctccttg aatcgggctg   2400
gcttccaaac agaggatttt agtctatatg cttgtgcttc tccaaaaaca cccattcagg   2460
caggggata tggagaattt gcagccttca agtagccaca ccatcatgac agcatctact   2520
cttatttctt aagtcttgtg ttcgtacaat ttgttaacat caaaacacag ttctgttcct   2580
caactctttt taaagttaaa atttttcagt gcataagctg gtgtggaaca gaaggaaatt   2640
tcccatccaa caaaagaggg aagaatgttt taggaaccag aattctctgc tgccagtgtt   2700
tcttcttcaa cacaaatatc acaagtctgc ccactcccag gaagaaagag gagagaccct   2760
gagttctgac cttttgatgg tcaggcatga tggaaagaaa ctgctgctac agcttgggag   2820
atttgctctg ggaagtctgc cagtcaactt tgcccttcta accaccagat caatatgtgg   2880
ctgatcatct gatggggcag ttgcaatcac caagccttgt tctctttcct gttctgggat   2940
tgtgttgtgg aaccctttc cctagccacc accagttcat ttctgaggga tggaacaaaa   3000
atgcagcatg cccttcctgt gtggtgcatg ttcagtcctt gacaaatttt taccaaaatg   3060
aagctacttt atttaaaagg agggtgagag gtgaggaggt cactttgggt gtggcggaaa   3120
gggaatgctg catcttttc ctgggctgct ggggctctgg ccttggcttg ccagccggaa    3180
gcgctggcac gcatcgcctt cttttcccat tgggtccagc aatgaagacg agtgtttggg   3240
```

-continued

```
gttttttttt tctccaccat gtagcaagtt ctcaggaaaa tacaattgat atcttcctcc   3300
taagctcttc caatcagtca ccaagtactt atgtggttac tttgtccagg gcacaaaatg   3360
cctgtatcta attaaaagcc tacaaaactg cttgataaca gttttgaatg tgagacattt   3420
atgtaattta aatgtaaggt acaagtttta atttctgagt ttcttctatt atatttttat   3480
taaaaaaaga aaataatttt cagattgaat tggagtaaaa taatattact tcccactaga   3540
attatatatc ctggaaaatt gtatttttgt tacataagca gcttttaaag aaagatcatt   3600
acccttttct ctacataaat atatggggag tcttagccta atgacaaata tttataattt   3660
ttaaattaat ggtacttgct ggatccatac taacatcttt actaatacct cattgtttct   3720
tccaacttac tcctacacta catcctacat cttcttccta gtcttttatc tagaatatgc   3780
aacctcaaat aaaaatggtg gtgtcctcat tcattctcct ccttcctttt ttcccaagcc   3840
tgatcttcaa aggttggtt aatttggcag ctgagttcct ccccaggcag agaatagacc   3900
aattttaggt gtattgggac tgagggagga tgtgtaaaga ttaacatcag taaagaaccg   3960
ctgtggagta attaagaact ttgttcttta taactggaga atataaccta accctaacat   4020
ccctcagcct ttactaaagt gtggcgtaaa tcacagtagt agcaaagaaa gtgactctgg   4080
atgtgttcct ggccagtacc tcccttatca tgaatgtaga ctctctcatc aagatttagg   4140
aatataaatc aaatcaaatg tgcccagcca agctatgtag taagggactt gaacaatatt   4200
aggcagaacc tataaaataa atcagggaat tagaaattat ttaaagtttt caaattgtaa   4260
attgccccgg tgtctttcag cctactgcca ttatttttgc tacaatacct acatttcaga   4320
ggagggccta ctgaaaattc catgcaagtg gaaaataatc ctcaagttat taatgagttt   4380
gaaaagcaat gagttcttaa gtctttgtga gtagagcaag atcctacaaa attcagaaat   4440
agtaaaaatg gattcatgct gatttgaaga gcatctgtgt gcataatata atgctgcatc   4500
tcttttaaaa gcagtctatt tttcttttta aatttgtccc catagatgct tttgaacatg   4560
aacatgctta tgttaccttt tccgaggttg ggaagagcca ggagctctca ggcagggccc   4620
cctccctcag ctgggcagga gctgctcagg aggagctagt tatagaggaa gcttagcgtt   4680
ggcattttca aaattcaagg tgataacgct ttcttcttcc tttctgtttt agaatagatt   4740
gctgtctgat ttgaaaaagg gaaatagatt tgatctcaaa tgaatctgtg cccagaagcc   4800
aggctcaggg tattcagaga tttgtatagt gccctcaaaa aataacaaaa ttttagcttt   4860
cctttttttct tcttttctcc atcaaattct tttttctcta gtttacaaat gacatggaaa   4920
aggaatttcc cctgagtttt gtatgccttt ttttttttgg cttagactat agataggcgt   4980
gttgagctcc taagaaaata caaggaggaa ctctttgttg tgcagagcac tttatgagta   5040
gtttgtgtgg ataatatgtg actgcttccc tgacgagctt gtgaggctgt acttatgtct   5100
ttcctgtaag gcagcttcag tgccttctgt agtgtatata aggaaagatt acgccttctg   5160
aaaaatctca gagcaaccat aagattattt taaaatatgt agtatgactg atggactttt   5220
tcatcattaa attagtctag catctaaact tttaccactg aaataatatt gaccaaaaag   5280
caatttataa aaggtatttg tgaatagaaa atacaatgtg atcatttgta cttatgtgca   5340
ccttaaaaga ggaattctgt ctagctgtca aattctggtt ccttaacatc cagtccttga   5400
ttgtgattga gatctggtag gacgtgctgg ggcacgctag cagataaaat cccgtatact   5460
ttaggataga tgttacattt atgtcagtgt tggcaaagag cattgtgtag taataaagaa   5520
ttcaagactt cagcaatgtc aacctgaaac tttgtaaata tttcctagat tgttatttga   5580
tgcagtcaca gctctttatc acacaatgtt gtctttccct catcaggcaa ttttagaact   5640
```

```
gctgcacacc cctcctcaga tctcacctgc ccctcctgta cattcacctc tccagccttg   5700
tgcacacctc atttagcttt agtttgaaac acattgcagg gttcaggtga cctcttcaaa   5760
aactacctcc tcagaatgag gtaatgaata gttatttatt ttaaaatatg aaaagtcagg   5820
agctctagaa tatgaagatg atctaagatt ttaactttta tgtatacttg ttgagcactc   5880
tccttttgtc ctaaagggca ttatacattt aagcagtaat actgaaaaat gtagctcaga   5940
gtaactgaat gttgttgaaa gtggtgccag aatctgtttt aggggtacgt atcagaatct   6000
taatcttaaa tcggttacat gaaattaaat agttaatggt aacacttgac taacagatat   6060
aattttaatt ttcggtaggc ttttagcaag acagtaagta catcttcata atgagttagc   6120
cacagcttca tcacatgcac agattttcct gttgagagac tgcccagtta agagggtaga   6180
atgatgaacc atttttcagg attctcttct ttgtccaaac tggcattgtg agtgctagaa   6240
tatcagcact ttcaaactag tgattccaac tattaggcta ttaaaaagca aaacaaacca   6300
aacaaaccat agccagacat gggaagttta ctatgagtat aaacagcaaa tagcttacag   6360
gtcatacatt gaaatggtgt aggtaaggcg ttagaaaaat accttgacaa tttgccaaat   6420
gatcttactg tgccttcatg atgcaataaa aaaaaaaaaa atttagcata aatcagtgat   6480
ttgtgaagag agcagccacc ctggtctaac tcagctgtgt taatattttt tagcgtgcaa   6540
tttagactgc aaagataaat gcactaaaga gtttatagcc aaaatcacat ttaaaaaatg   6600
agagaaaaca caggtaaatt ttcagtgaac aaaattattt ttttaaagta cataatccct   6660
agtatagtca gatatattta tcacatagag caaataggtt gaaatcacaa ttcagtgaca   6720
tttctagaga aactttttct actcccatag gttcttcaaa gcatggaact tttatataac   6780
agaaatgtgt gacggtcatt ttaaattgct gtagtttggg gctgaagtac tgtgtgctgg   6840
gcagcaatca catgtattaa ctagtgagaa aggagaaatt aagatatagg acagaatttg   6900
attttcttgt tcccagatta ctgctgccaa cctagacact gagtttccag aggctgaaac   6960
gtaaacttgc agctcagcaa ctgttttgca aagttagtgg gactgtcctg cttatgctgt   7020
tcaaaaatgc tctgagggcc aggtggggcc tccaggggct cctctctgag gggacatcag   7080
actagctaac gacctggcgg gcggatgtga accggacaca ctccatggtg tgcttcttgt   7140
atcggtccct cgccaccctc aagaaaggct tcagcgggtt ctctagacgt ctccactaag   7200
gtgtgttact aacagccatg ggttgttgag cacccgagga gtgcaatagc atctctgcat   7260
gattgtatat tggcccgaag agaatgaagt ggccagtgta ctcatgttcc atgttgctag   7320
ctctggtaaa ctgaaaatac tggtaagatt tttgttttat cagtacacta gagagtaagc   7380
tttgttttgt tgtttttaga taatgttttc acttccattt ggaaagacat ttaaattgag   7440
tttcagtcct aaattttgcc agtcatggta attagcagtt tctatcaggt atttttaagg   7500
tagaagagga tagaaacata agttctaaaa gcttaaggta accgtggttt attttaaaat   7560
gtttaggggt ggttagtctc tacctcaaaa aaagtgagtg aatcttttat ttcagcattc   7620
acaagttcgg ctgttgtttt tgtaatacat ttttttttta accttttgac ccccctttac   7680
ctaagtgtca atgtagtttt attaattact aagtcagttt cattaaaatg tttatttagc   7740
agttttgact aattgcaatg attaatatag ccagttgtgc atgaggacac agccagtgag   7800
tatatctggg tttttttgt gatgcttttt ttcttaagac ttctgtagat ttatgaagta    7860
ctcattgaaa acaactaaaa tacgtttatt cgtgttaata tggaaaaaaa aaaa         7914
```

<210> SEQ ID NO 24

<211> LENGTH: 766
<212> TYPE: PRT
<213> ORGANISM: Bos taurus

<400> SEQUENCE: 24

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
```

-continued

```
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Glu Phe Ala Ala Phe Lys
        755                 760                 765
```

<210> SEQ ID NO 25
<211> LENGTH: 4670
<212> TYPE: DNA
<213> ORGANISM: Bos taurus

<400> SEQUENCE: 25

-continued

```
ggtgtgtcat agtgcagcag attgaatgca gaagatatga aaattcagat gtcttctgtt     60
aaggtgtgga atatcaaaca aatgattaag ttgacacagg agcatataga ggccctattg    120
gacaaatttg gtggggagca taatccacca tcaatatatc tggaggccta tgaagaatac    180
accagcaagc tagatgccct ccaacaaaga gaacaacagt tattggaatc cctggggaat    240
ggaactgatt tttctgtttc tagctctgca tcaacggaca ccgttacatc ttcttcctct    300
tctagccttt cagtgctgcc ttcatctctt tcagtttttc aaaatcccac agatgtgtca    360
cggagcaacc ccaagtcacc acaaaaacct atcgttagag tcttcctgcc caataaacag    420
aggacagtgg tacctgcacg gtgtggagtc acagtccggg acagcctgaa gaaggcactg    480
atgatgagag gtctaatccc agagtgctgt gctgtttaca gaattcagga tggggagaag    540
aaaccaattg gctgggacac tgatatttcc tggcttactg gagaggagtt gcatgtagaa    600
gtgttggaga atgttccact tacaacacac aactttgtac ggaaaacttt tttcacctta    660
gcattttgtg acttctgtag aaagctgctt ttccagggat tccgctgtca aacatgtggt    720
tataaatttc accagcgttg tagtacagag gttccactga tgtgtgttaa ttatgaccaa    780
ctagatttgc tgtttgtctc caagttcttt gaacaccacc caataccaca ggaggaggcc    840
tccttagcag agactaccct tccatgtggc tcatcccctt ctgcaccccc ctccgattct    900
attgggcccc caattctcac cagtccatct ccttcaaaat ccattccaat tccacagcct    960
ttccgaccag cagatgaaga tcatcgaaat cagtttggac aacgagaccg gtcctcatca   1020
gctccaaatg tgcatataaa cacaatagaa cccgtcaata ttgatgactt gattagagac   1080
caagggtttc gtagtgatgg aggatcaacc acaggtttat ccgccacacc ccctgcctca   1140
ttacctggct cactctctaa tgtgaaagca ttgcagaaat ctccaggacc tcagcgagaa   1200
agaaagtcct cttcatcctc agaagacagg aatcgaatga aaacgcttgg tagacgggat   1260
tcaagtgacg attgggagat tcctgatgga cagatcacag tgggacaaag aattggatca   1320
gggtcatttg ggacagtcta caagggaaag tggcatggtg atgtggcagt gaaaatgttg   1380
aatgtgacag cacccacacc tcagcagtta caggccttca aaaatgaagt aggagtactc   1440
aggaaaacgc gacatgtgaa tatcctcctc ttcatgggtt attcaacaaa gccacaactg   1500
gctattgtta cccagtggtg tgagggctcc agtttatatc atcatctcca catcattgag   1560
accaaattcg agatgatcaa acttatagat attgcacggc agactgcaca gggcatggat   1620
tacttacacg ccaagtcaat catccacaga gacctcaaga gtaataatat ttttcttcat   1680
gaagacctca cagtaaaaat aggtgatttt ggtctagcca cagtgaaatc tcgatggagt   1740
gggtcccatc agtttgaaca gttgtctgga tccattttgt ggatggcacc agaagtaatc   1800
agaatgcaag ataaaaaccc atatagcttt cagtcagatg tatatgcatt tgggattgtt   1860
ctgtatgaat tgatgaccgg acagttacct tattcaaata tcaacaacag ggaccagata   1920
atttttatgg tgggacgagg atatctgtct ccagatctca gtaaggtacg gagtaactgt   1980
ccaaaagcca tgaagagatt aatggcagag tgcctaaaaa agaaaagaga tgaaagacca   2040
ctctttcccc aagtaggaaa gactctccta agcaagagac aaaattcaga agttatcagg   2100
gaaaaagata agcagattct cgcctctatt gagctgctgg cccgctcatt gccaaaaatt   2160
caccgcagtg catcagaacc ctccttgaat cgggctggct tccaaacaga ggattttagt   2220
ctatatgctt gtgcttctcc aaaaacaccc attcaggcag ggggatatga agcagatttg   2280
gctcttacat caaataaaaa tagagtagaa gttgggattt agagatttcc tgacatgcaa   2340
gaaggaataa gcaagaaaaa aaggtttgtt ttccccaaat catatctatt gtcttttact   2400
```

```
tctatttttt cttaaatttt ttgtgatttc agagacatgt agagttttat tgatacctaa   2460
actatgagtt cttttttttt ttttttttc attattttga tttttttggc caagaggcat   2520
atgggatctt agcttgagaa agcaacaatt ttcttgatgt cattttgggt gagggcacat   2580
attgctgtga acagtgtggt gatagccacc agggaccaaa ctcacacccg ctgcattgaa   2640
aggtgaagtc ttaaacactg gaccagcaga gaaattccta ctctatgagt tctttttgtc   2700
atcccctccc cgcaccctcc acccccaacc taaagtctga tgatgaaatc aacaactatt   2760
ccattagaag cagtagattc tggtagcatg atctttagtt tgttagtaag attttgtgct   2820
ttgtggggtt gtgtcgtttt aaggctaata tttaagtttg tcaaatagaa tgctgttcag   2880
attgtaaaaa tgagtaataa acatctgaag ttttttttaa gttattttta acatggtata   2940
tacagttgag cttagagttt atcattttct gatattctct tacttagtag atgaattcta   3000
gccatttttt ataaagattt ctgttaagca aatcctgttt tcacatgggc ttcctttaag   3060
ggattttaga ttctgctgga tatggtgact gctcataaga ctgttgaaaa ttacttttaa   3120
gatgtattag aatacttctg aaaaaaaata gcaaccttaa aaccataagc aaaagtagta   3180
agggtgttta tacatttcta gagtccctgt ttaggtaata gcctcctatg attgtacttt   3240
aaatgttttg ctctccaagg ttttagtaac ttggcttttt ttctaatcag tgccaaactc   3300
ccccagtttt tttaacttta aatatgaggt aataaatctt ttacccttcc ttgatctttt   3360
gacttataat accttggtca gttgtttctt aaaaggaatc cttaaatgga aagagacaat   3420
atcactgtct gcagttctga ttagtagttt tattcagaat ggaaaaacag attattcatt   3480
tttgaaaatt gttcaggggt atgttcattg ttaggacctt ggactttgga gtcagtgcct   3540
agctatgcat tccaggtctg ccattttctg gctgtgaaat tttggacaag ttacttaacc   3600
actttaaacc ccagctttaa gaagtaaatt aaccccagta aattaagaag taatagcagc   3660
cacttcgtag agttgttatg aggctcagat gcagtgcaaa tgtgtataaa gtattcaggg   3720
agtcacctgg tatactataa tagacactag aatagttgcc aatattatca gcatacaatc   3780
tgaggattct gtcagccaat cattagcaat ctgttgtttg ttgggacatg ccagtgttct   3840
ccagttgaaa tcagtagcaa tctaaaaatg gatagattat tcctcattta aatagtgtgt   3900
tcatataagt gattgcttgg atccttatca gaagttgctg ttactgaaaa atgataaggc   3960
tgactaaatt gtgatagttg tcagttacta accaactccc agaaatgaat aagaggaacc   4020
tatctctagt tcctagtaga aggtatggac aaaatagtag gtgaaaaata atgtcttgaa   4080
cccccaaatt aagtaagctt taaagagtac aatacctcaa agggtctttg cggtttaaaa   4140
tttgtatgct gagaatgatg ttcattgaca tgtgcctata tgtaattttt tgatagttta   4200
aaaggtgaaa tgaactacag atgggagagg tctgaatttt cttgccttca gtcaaatgtg   4260
taatgtggac atattatttg acctgtgaat tttatctttt aaaaaagatt aattcctgct   4320
tcttccttcc taatagttgc attataataa tgaaaatgag ttgataattt ggggggaaag   4380
tattctacaa atcaacctta ttattttacc attggtttct gagaaatttt gttcatttga   4440
accgtttata gcttgattag aatcatagca tgtaaaaccc aactgaggga ttatctgcag   4500
acttaatgta gtattatgta agttgtcttc tttcatttcg accttttttg cttttgttgt   4560
tgctagatct gtagtatgta gctagtcacc tttcagcgag gtttcagcga ggcttttctg   4620
tgtctctagg ttatttgaga taactttttt aaaattagct cttgtcctcc              4670
```

<210> SEQ ID NO 26

<211> LENGTH: 761
<212> TYPE: PRT
<213> ORGANISM: Bos taurus

<400> SEQUENCE: 26

```
Met Lys Ile Gln Met Ser Ser Val Lys Val Trp Asn Ile Lys Gln Met
1               5                   10                  15

Ile Lys Leu Thr Gln Glu His Ile Glu Ala Leu Leu Asp Lys Phe Gly
            20                  25                  30

Gly Glu His Asn Pro Pro Ser Ile Tyr Leu Glu Ala Tyr Glu Glu Tyr
        35                  40                  45

Thr Ser Lys Leu Asp Ala Leu Gln Gln Arg Glu Gln Gln Leu Leu Glu
    50                  55                  60

Ser Leu Gly Asn Gly Thr Asp Phe Ser Val Ser Ser Ser Ala Ser Thr
65                  70                  75                  80

Asp Thr Val Thr Ser Ser Ser Ser Ser Ser Leu Ser Val Leu Pro Ser
                85                  90                  95

Ser Leu Ser Val Phe Gln Asn Pro Thr Asp Val Ser Arg Ser Asn Pro
            100                 105                 110

Lys Ser Pro Gln Lys Pro Ile Val Arg Val Phe Leu Pro Asn Lys Gln
        115                 120                 125

Arg Thr Val Val Pro Ala Arg Cys Gly Val Thr Val Arg Asp Ser Leu
    130                 135                 140

Lys Lys Ala Leu Met Met Arg Gly Leu Ile Pro Glu Cys Cys Ala Val
145                 150                 155                 160

Tyr Arg Ile Gln Asp Gly Glu Lys Lys Pro Ile Gly Trp Asp Thr Asp
                165                 170                 175

Ile Ser Trp Leu Thr Gly Glu Glu Leu His Val Glu Val Leu Glu Asn
            180                 185                 190

Val Pro Leu Thr Thr His Asn Phe Val Arg Lys Thr Phe Phe Thr Leu
        195                 200                 205

Ala Phe Cys Asp Phe Cys Arg Lys Leu Leu Phe Gln Gly Phe Arg Cys
    210                 215                 220

Gln Thr Cys Gly Tyr Lys Phe His Gln Arg Cys Ser Thr Glu Val Pro
225                 230                 235                 240

Leu Met Cys Val Asn Tyr Asp Gln Leu Asp Leu Leu Phe Val Ser Lys
                245                 250                 255

Phe Phe Glu His His Pro Ile Pro Gln Glu Glu Ala Ser Leu Ala Glu
            260                 265                 270

Thr Thr Leu Pro Cys Gly Ser Ser Pro Ser Ala Pro Pro Ser Asp Ser
        275                 280                 285

Ile Gly Pro Pro Ile Leu Thr Ser Pro Ser Pro Ser Lys Ser Ile Pro
    290                 295                 300

Ile Pro Gln Pro Phe Arg Pro Ala Asp Glu Asp His Arg Asn Gln Phe
305                 310                 315                 320

Gly Gln Arg Asp Arg Ser Ser Ser Ala Pro Asn Val His Ile Asn Thr
                325                 330                 335

Ile Glu Pro Val Asn Ile Asp Asp Leu Ile Arg Asp Gln Gly Phe Arg
            340                 345                 350

Ser Asp Gly Gly Ser Thr Thr Gly Leu Ser Ala Thr Pro Pro Ala Ser
        355                 360                 365

Leu Pro Gly Ser Leu Ser Asn Val Lys Ala Leu Gln Lys Ser Pro Gly
    370                 375                 380

Pro Gln Arg Glu Arg Lys Ser Ser Ser Ser Ser Glu Asp Arg Asn Arg
```

-continued

```
385                 390                 395                 400

Met Lys Thr Leu Gly Arg Arg Asp Ser Ser Asp Asp Trp Glu Ile Pro
                405                 410                 415

Asp Gly Gln Ile Thr Val Gly Gln Arg Ile Gly Ser Gly Ser Phe Gly
            420                 425                 430

Thr Val Tyr Lys Gly Lys Trp His Gly Asp Val Ala Val Lys Met Leu
        435                 440                 445

Asn Val Thr Ala Pro Thr Pro Gln Gln Leu Gln Ala Phe Lys Asn Glu
    450                 455                 460

Val Gly Val Leu Arg Lys Thr Arg His Val Asn Ile Leu Leu Phe Met
465                 470                 475                 480

Gly Tyr Ser Thr Lys Pro Gln Leu Ala Ile Val Thr Gln Trp Cys Glu
                485                 490                 495

Gly Ser Ser Leu Tyr His His Leu His Ile Ile Glu Thr Lys Phe Glu
            500                 505                 510

Met Ile Lys Leu Ile Asp Ile Ala Arg Gln Thr Ala Gln Gly Met Asp
        515                 520                 525

Tyr Leu His Ala Lys Ser Ile Ile His Arg Asp Leu Lys Ser Asn Asn
    530                 535                 540

Ile Phe Leu His Glu Asp Leu Thr Val Lys Ile Gly Asp Phe Gly Leu
545                 550                 555                 560

Ala Thr Val Lys Ser Arg Trp Ser Gly Ser His Gln Phe Glu Gln Leu
                565                 570                 575

Ser Gly Ser Ile Leu Trp Met Ala Pro Glu Val Ile Arg Met Gln Asp
            580                 585                 590

Lys Asn Pro Tyr Ser Phe Gln Ser Asp Val Tyr Ala Phe Gly Ile Val
        595                 600                 605

Leu Tyr Glu Leu Met Thr Gly Gln Leu Pro Tyr Ser Asn Ile Asn Asn
    610                 615                 620

Arg Asp Gln Ile Ile Phe Met Val Gly Arg Gly Tyr Leu Ser Pro Asp
625                 630                 635                 640

Leu Ser Lys Val Arg Ser Asn Cys Pro Lys Ala Met Lys Arg Leu Met
                645                 650                 655

Ala Glu Cys Leu Lys Lys Lys Arg Asp Glu Arg Pro Leu Phe Pro Gln
            660                 665                 670

Val Gly Lys Thr Leu Leu Ser Lys Arg Gln Asn Ser Glu Val Ile Arg
        675                 680                 685

Glu Lys Asp Lys Gln Ile Leu Ala Ser Ile Glu Leu Leu Ala Arg Ser
    690                 695                 700

Leu Pro Lys Ile His Arg Ser Ala Ser Glu Pro Ser Leu Asn Arg Ala
705                 710                 715                 720

Gly Phe Gln Thr Glu Asp Phe Ser Leu Tyr Ala Cys Ala Ser Pro Lys
                725                 730                 735

Thr Pro Ile Gln Ala Gly Gly Tyr Glu Ala Asp Leu Ala Leu Thr Ser
            740                 745                 750

Asn Lys Asn Arg Val Glu Val Gly Ile
        755                 760
```

<210> SEQ ID NO 27
<211> LENGTH: 4816
<212> TYPE: DNA
<213> ORGANISM: Bos taurus

<400> SEQUENCE: 27

-continued

```
ctcagctgcg ccgggtctca caagacggtt cccgaggtgg cccaggcgcc gtcccaccgc     60
cgacgccgcc cgggccgccc gggccgtccc tccccgctgc cccccgtcct ccgcctccgc    120
ctccccccgc cctcagcctc ccttcccccct ccccgcccag cagcggtcgc tcgggcccgg    180
ctctcggtta taagatggcg gcgctgagtg gcggcggcgg cggcggcggc ggtggcgcgg    240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg ggaatggaa ctgatttttc tgtttctagc tctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag agcccccaat tctcaccagt ccatctcctt   1080
caaaatccat tccaattcca cagcctttcc gaccagcaga tgaagatcat cgaaatcagt   1140
ttggacaacg agaccggtcc tcatcagctc caaatgtgca tataaacaca atagaacccg   1200
tcaatattga tgacttgatt agagaccaag ggtttcgtag tgatggagga tcaaccacag   1260
gtttatccgc cacacccccct gcctcattac ctggctcact ctctaatgtg aaagcattgc   1320
agaaatctcc aggacctcag cgagaaagaa agtcctcttc atcctcagaa gacaggaatc   1380
gaatgaaaac gcttggtaga cgggattcaa gtgacgattg ggagattcct gatggacaga   1440
tcacagtggg acaaagaatt ggatcagggt catttgggac agtctacaag ggaaagtggc   1500
atggtgatgt ggcagtgaaa atgttgaatg tgacagcacc cacacctcag cagttacagg   1560
ccttcaaaaa tgaagtagga gtactcagga aaacgcgaca tgtgaatatc ctcctcttca   1620
tgggttattc aacaaagcca caactggcta ttgttaccca gtggtgtgag ggctccagtt   1680
tatatcatca tctccacatc attgagacca aattcgagat gatcaaactt atagatattg   1740
cacggcagac tgcacagggc atggattact tacacgccaa gtcaatcatc cacagagacc   1800
tcaagagtaa taatattttt cttcatgaag acctcacagt aaaaataggt gattttggtc   1860
tagccacagt gaaatctcga tggagtgggt cccatcagtt tgaacagttg tctggatcca   1920
ttttgtggat ggcaccagaa gtaatcagaa tgcaagataa aaacccatat agctttcagt   1980
cagatgtata tgcatttggg attgttctgt atgaattgat gaccggacag ttaccttatt   2040
caaatatcaa caacagggac cagataattt ttatggtggg acgaggatat ctgtctccag   2100
atctcagtaa ggtacggagt aactgtccaa aagccatgaa gagattaatg gcagagtgcc   2160
taaaaaagaa aagagatgaa agaccactct ttccccaagt aggaaagact ctcctaagca   2220
agagacaaaa ttcagaagtt atcagggaaa aagataagca gattctcgcc tctattgagc   2280
tgctggcccg ctcattgcca aaaattcacc gcagtgcatc agaaccctcc ttgaatcggg   2340
ctggcttcca aacagaggat tttagtctat atgcttgtgc ttctccaaaa acacccattc   2400
```

```
aggcaggggg atatgaagca gatttggctc ttacatcaaa taaaaataga gtagaagttg   2460
ggatttagag atttcctgac atgcaagaag gaataagcaa gaaaaaaagg tttgttttcc   2520
ccaaatcata tctattgtct tttacttcta ttttttctta aattttttgt gatttcagag   2580
acatgtagag ttttattgat acctaaacta tgagttcttt tttttttttt tttttcatta   2640
ttttgatttt tttggccaag aggcatatgg gatcttagct tgagaaagca acaattttct   2700
tgatgtcatt ttgggtgagg gcacatattg ctgtgaacag tgtggtgata gccaccaggg   2760
accaaactca cacccgctgc attgaaaggt gaagtcttaa acactggacc agcagagaaa   2820
ttcctactct atgagttctt tttgtcatcc cctccccgca ccctccaccc ccaacctaaa   2880
gtctgatgat gaaatcaaca actattccat tagaagcagt agattctggt agcatgatct   2940
ttagtttgtt agtaagattt tgtgctttgt ggggttgtgt cgttttaagg ctaatattta   3000
agtttgtcaa atagaatgct gttcagattg taaaaatgag taataaacat ctgaagtttt   3060
ttttaagtta tttttaacat ggtatataca gttgagctta gagtttatca ttttctgata   3120
ttctcttact tagtagatga attctagcca ttttttataa agatttctgt taagcaaatc   3180
ctgttttcac atgggcttcc tttaagggat tttagattct gctggatatg gtgactgctc   3240
ataagactgt tgaaaattac ttttaagatg tattagaata cttctgaaaa aaaatagcaa   3300
ccttaaaacc ataagcaaaa gtagtaaggg tgtttataca tttctagagt ccctgtttag   3360
gtaatagcct cctatgattg tactttaaat gttttgctct ccaaggtttt agtaacttgg   3420
cttttttttct aatcagtgcc aaactccccc agttttttta actttaaata tgaggtaata   3480
aatcttttac ccttccttga tcttttgact tataatacct tggtcagttg tttcttaaaa   3540
ggaatcctta aatggaaaga gacaatatca ctgtctgcag ttctgattag tagttttatt   3600
cagaatggaa aaacagatta ttcatttttg aaaattgttc aggggtatgt tcattgttag   3660
gaccttggac tttggagtca gtgcctagct atgcattcca ggtctgccat tttctggctg   3720
tgaaattttg gacaagttac ttaaccactt taaaccccag ctttaagaag taaattaacc   3780
ccagtaaatt aagaagtaat agcagccact tcgtagagtt gttatgaggc tcagatgcag   3840
tgcaaatgtg tataaagtat tcagggagtc acctggtata ctataataga cactagaata   3900
gttgccaata ttatcagcat acaatctgag gattctgtca gccaatcatt agcaatctgt   3960
tgtttgttgg gacatgccag tgttctccag ttgaaatcag tagcaatcta aaaatggata   4020
gattattcct catttaaata gtgtgttcat ataagtgatt gcttggatcc ttatcagaag   4080
ttgctgttac tgaaaaatga taaggctgac taaattgtga tagttgtcag ttactaacca   4140
actcccagaa atgaataaga ggaacctatc tctagttcct agtagaaggt atggacaaaa   4200
tagtaggtga aaaataatgt cttgaacccc caaattaagt aagctttaaa gagtacaata   4260
cctcaaaggg tctttgcggt ttaaaatttg tatgctgaga atgatgttca ttgacatgtg   4320
cctatatgta atttttttgat agtttaaaag gtgaaatgaa ctacagatgg gagaggtctg   4380
aattttcttg ccttcagtca aatgtgtaat gtggacatat tatttgacct gtgaatttta   4440
tcttttaaaa aagattaatt cctgcttctt ccttcctaat agttgcatta taataatgaa   4500
aatgagttga taatttgggg ggaaagtatt ctacaaatca accttattat tttaccattg   4560
gtttctgaga aattttgttc atttgaaccg tttatagctt gattagaatc atagcatgta   4620
aaacccaact gagggattat ctgcagactt aatgtagtat tatgtaagtt gtcttctttc   4680
atttcgacct tttttgcttt tgttgttgct agatctgtag tatgtagcta gtcacctttc   4740
```

-continued

```
agcgaggttt cagcgaggct tttctgtgtc tctaggttat ttgagataac tttttaaaa   4800

ttagctcttg tcctcc                                                  4816


<210> SEQ ID NO 28
<211> LENGTH: 757
<212> TYPE: PRT
<213> ORGANISM: Bos taurus

<400> SEQUENCE: 28

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Glu Pro Pro
        275                 280                 285

Ile Leu Thr Ser Pro Ser Pro Ser Lys Ser Ile Pro Ile Pro Gln Pro
    290                 295                 300

Phe Arg Pro Ala Asp Glu Asp His Arg Asn Gln Phe Gly Gln Arg Asp
305                 310                 315                 320

Arg Ser Ser Ser Ala Pro Asn Val His Ile Asn Thr Ile Glu Pro Val
                325                 330                 335

Asn Ile Asp Asp Leu Ile Arg Asp Gln Gly Phe Arg Ser Asp Gly Gly
            340                 345                 350

Ser Thr Thr Gly Leu Ser Ala Thr Pro Pro Ala Ser Leu Pro Gly Ser
```

```
        355                 360                 365

Leu Ser Asn Val Lys Ala Leu Gln Lys Ser Pro Gly Pro Gln Arg Glu
    370                 375                 380

Arg Lys Ser Ser Ser Ser Ser Glu Asp Arg Asn Arg Met Lys Thr Leu
385                 390                 395                 400

Gly Arg Arg Asp Ser Ser Asp Asp Trp Glu Ile Pro Asp Gly Gln Ile
                405                 410                 415

Thr Val Gly Gln Arg Ile Gly Ser Gly Ser Phe Gly Thr Val Tyr Lys
            420                 425                 430

Gly Lys Trp His Gly Asp Val Ala Val Lys Met Leu Asn Val Thr Ala
        435                 440                 445

Pro Thr Pro Gln Gln Leu Gln Ala Phe Lys Asn Glu Val Gly Val Leu
    450                 455                 460

Arg Lys Thr Arg His Val Asn Ile Leu Leu Phe Met Gly Tyr Ser Thr
465                 470                 475                 480

Lys Pro Gln Leu Ala Ile Val Thr Gln Trp Cys Glu Gly Ser Ser Leu
                485                 490                 495

Tyr His His Leu His Ile Ile Glu Thr Lys Phe Glu Met Ile Lys Leu
            500                 505                 510

Ile Asp Ile Ala Arg Gln Thr Ala Gln Gly Met Asp Tyr Leu His Ala
        515                 520                 525

Lys Ser Ile Ile His Arg Asp Leu Lys Ser Asn Asn Ile Phe Leu His
    530                 535                 540

Glu Asp Leu Thr Val Lys Ile Gly Asp Phe Gly Leu Ala Thr Val Lys
545                 550                 555                 560

Ser Arg Trp Ser Gly Ser His Gln Phe Glu Gln Leu Ser Gly Ser Ile
                565                 570                 575

Leu Trp Met Ala Pro Glu Val Ile Arg Met Gln Asp Lys Asn Pro Tyr
            580                 585                 590

Ser Phe Gln Ser Asp Val Tyr Ala Phe Gly Ile Val Leu Tyr Glu Leu
        595                 600                 605

Met Thr Gly Gln Leu Pro Tyr Ser Asn Ile Asn Asn Arg Asp Gln Ile
    610                 615                 620

Ile Phe Met Val Gly Arg Gly Tyr Leu Ser Pro Asp Leu Ser Lys Val
625                 630                 635                 640

Arg Ser Asn Cys Pro Lys Ala Met Lys Arg Leu Met Ala Glu Cys Leu
                645                 650                 655

Lys Lys Lys Arg Asp Glu Arg Pro Leu Phe Pro Gln Val Gly Lys Thr
            660                 665                 670

Leu Leu Ser Lys Arg Gln Asn Ser Glu Val Ile Arg Glu Lys Asp Lys
        675                 680                 685

Gln Ile Leu Ala Ser Ile Glu Leu Leu Ala Arg Ser Leu Pro Lys Ile
    690                 695                 700

His Arg Ser Ala Ser Glu Pro Ser Leu Asn Arg Ala Gly Phe Gln Thr
705                 710                 715                 720

Glu Asp Phe Ser Leu Tyr Ala Cys Ala Ser Pro Lys Thr Pro Ile Gln
                725                 730                 735

Ala Gly Gly Tyr Glu Ala Asp Leu Ala Leu Thr Ser Asn Lys Asn Arg
            740                 745                 750

Val Glu Val Gly Ile
        755

<210> SEQ ID NO 29
```

<211> LENGTH: 2499
<212> TYPE: DNA
<213> ORGANISM: Bos taurus

<400> SEQUENCE: 29
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttcccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg ggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc accccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacaccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220

```
atctcagtaa ggtacggagt aactgtccaa aagccatgaa gagattaatg gcagagtgcc   2280

taaaaaagaa aagagatgaa agaccactct ttccccaagt aggaaagact ctcctaagca   2340

agagacaaaa ttcagaagtt atcagggaaa aagataagca ggaaaagtat gtttctttag   2400

tacattccag gcatttggga ttacagtaaa aacaatattc tcgcctctat tgagctgctg   2460

gcccgctcat tgccaaaaat tcaccgcagt gcatcagaa                          2499


<210> SEQ ID NO 30
<211> LENGTH: 744
<212> TYPE: PRT
<213> ORGANISM: Bos taurus

<400> SEQUENCE: 30

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320
```

```
Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Glu Lys Tyr Val Ser Leu Val
                725                 730                 735

His Ser Arg His Leu Gly Leu Gln
```

740

<210> SEQ ID NO 31
<211> LENGTH: 2404
<212> TYPE: DNA
<213> ORGANISM: Bos taurus

<400> SEQUENCE: 31
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttcccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac taccettcca tgtggctcat 1140
ccccttctgc accccctcc gattctattg ggccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatatttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaaga tctctcttcc caccatagac 2340
acaaaaattt cagatggcta caggtttaca tgtaaaaaac agaattataa caaatgattt 2400
ttat 2404

<210> SEQ ID NO 32
<211> LENGTH: 726
<212> TYPE: PRT
<213> ORGANISM: Bos taurus

<400> SEQUENCE: 32

Met Ala Ala Leu Ser Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

Val Leu Pro Ser Ser Leu Ser Val Phe Gln Asn Pro Thr Asp Val Ser
130 135 140

Arg Ser Asn Pro Lys Ser Pro Gln Lys Pro Ile Val Arg Val Phe Leu
145 150 155 160

Pro Asn Lys Gln Arg Thr Val Val Pro Ala Arg Cys Gly Val Thr Val
165 170 175

Arg Asp Ser Leu Lys Lys Ala Leu Met Met Arg Gly Leu Ile Pro Glu
180 185 190

Cys Cys Ala Val Tyr Arg Ile Gln Asp Gly Glu Lys Lys Pro Ile Gly
195 200 205

Trp Asp Thr Asp Ile Ser Trp Leu Thr Gly Glu Glu Leu His Val Glu
210 215 220

Val Leu Glu Asn Val Pro Leu Thr Thr His Asn Phe Val Arg Lys Thr
225 230 235 240

Phe Phe Thr Leu Ala Phe Cys Asp Phe Cys Arg Lys Leu Leu Phe Gln
245 250 255

Gly Phe Arg Cys Gln Thr Cys Gly Tyr Lys Phe His Gln Arg Cys Ser
260 265 270

Thr Glu Val Pro Leu Met Cys Val Asn Tyr Asp Gln Leu Asp Leu Leu
275 280 285

Phe Val Ser Lys Phe Phe Glu His His Pro Ile Pro Gln Glu Glu Ala
290 295 300

Ser Leu Ala Glu Thr Thr Leu Pro Cys Gly Ser Ser Pro Ser Ala Pro

```
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Asp Leu Ser Ser His His Arg His Lys Asn Phe Arg
705                 710                 715                 720

Trp Leu Gln Val Tyr Met
                725
```

<210> SEQ ID NO 33
<211> LENGTH: 2331
<212> TYPE: DNA
<213> ORGANISM: Bos taurus

<400> SEQUENCE: 33
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac taccctcca tgtggctcat 1140 ccccttctgc acccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100

```
cagatgtata tgcatttggg attgttctgt atgaattgat gaccggacag ttaccttatt   2160

caaatatcaa caacagggac caggtgcttt gtcctccatg ggagtgtaat aaatgctgtg   2220

caagggctta cttcccatga gagaagtgag tgaccaacag aaggataatt tttatggtgg   2280

gacgaggata tctgtctcca gatctcagta aggtacggag taactgtcca a            2331


<210> SEQ ID NO 34
<211> LENGTH: 681
<212> TYPE: PRT
<213> ORGANISM: Bos taurus

<400> SEQUENCE: 34

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335
```

-continued

```
Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680


<210> SEQ ID NO 35
<211> LENGTH: 2319
<212> TYPE: DNA
<213> ORGANISM: Bos taurus

<400> SEQUENCE: 35

ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttccccct ccccgcccag cagcggtcgc tcgggcccgg     180
```

```
ctctcggtta taagatggcg gcgctgagtg gcggcggcgg cggcggcggc ggtggcgcgg    240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg gggaatggaa ctgatttttc tgtttctagc tctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aacttttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
ccccttctgc acccccctcc gattctattg ggcccccaat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacaccccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac caggtgcttt gtcctccatg ggagtgtaat aaatgctgtg   2220
caagggctta cttcccatga gagaagtgag tgaccaacag aaggtctgtg caaggaaaag   2280
agacaaagcc acggatcaga agcacatggc cataactga                          2319
```

<210> SEQ ID NO 36
<211> LENGTH: 681
<212> TYPE: PRT
<213> ORGANISM: Bos taurus

<400> SEQUENCE: 36

Met Ala Ala Leu Ser Gly Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

Val Leu Pro Ser Ser Leu Ser Val Phe Gln Asn Pro Thr Asp Val Ser
130 135 140

Arg Ser Asn Pro Lys Ser Pro Gln Lys Pro Ile Val Arg Val Phe Leu
145 150 155 160

Pro Asn Lys Gln Arg Thr Val Val Pro Ala Arg Cys Gly Val Thr Val
165 170 175

Arg Asp Ser Leu Lys Lys Ala Leu Met Met Arg Gly Leu Ile Pro Glu
180 185 190

Cys Cys Ala Val Tyr Arg Ile Gln Asp Gly Glu Lys Lys Pro Ile Gly
195 200 205

Trp Asp Thr Asp Ile Ser Trp Leu Thr Gly Glu Glu Leu His Val Glu
210 215 220

Val Leu Glu Asn Val Pro Leu Thr Thr His Asn Phe Val Arg Lys Thr
225 230 235 240

Phe Phe Thr Leu Ala Phe Cys Asp Phe Cys Arg Lys Leu Leu Phe Gln
245 250 255

Gly Phe Arg Cys Gln Thr Cys Gly Tyr Lys Phe His Gln Arg Cys Ser
260 265 270

Thr Glu Val Pro Leu Met Cys Val Asn Tyr Asp Gln Leu Asp Leu Leu
275 280 285

Phe Val Ser Lys Phe Phe Glu His His Pro Ile Pro Gln Glu Glu Ala
290 295 300

Ser Leu Ala Glu Thr Thr Leu Pro Cys Gly Ser Ser Pro Ser Ala Pro
305 310 315 320

Pro Ser Asp Ser Ile Gly Pro Pro Ile Leu Thr Ser Pro Ser Pro Ser
325 330 335

Lys Ser Ile Pro Ile Pro Gln Pro Phe Arg Pro Ala Asp Glu Asp His
340 345 350

Arg Asn Gln Phe Gly Gln Arg Asp Arg Ser Ser Ser Ala Pro Asn Val
355 360 365

His Ile Asn Thr Ile Glu Pro Val Asn Ile Asp Asp Leu Ile Arg Asp
370 375 380

Gln Gly Phe Arg Ser Asp Gly Gly Ser Thr Thr Gly Leu Ser Ala Thr
385 390 395 400

Pro Pro Ala Ser Leu Pro Gly Ser Leu Ser Asn Val Lys Ala Leu Gln
405 410 415

```
Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680
```

<210> SEQ ID NO 37
<211> LENGTH: 2661
<212> TYPE: DNA
<213> ORGANISM: Bos taurus

<400> SEQUENCE: 37

```
tcagctgcgc cgggtctcac aagacggttc ccgaggtggc ccaggcgccg tcccaccgcc      60

gacgccgccc gggccgcccg ggccgtccct ccccgctgcc ccccgtcctc cgcctccgcc     120

tccccccgcc ctcagcctcc cttccccctc cccgcccagc agcggtcgct cgggcccggc     180

tctcggttat aagatggcgg cgctgagtgg cggcggcggc ggcggcggcg gtggcgcgga     240

gcagggccag gctctgttca acggggacat ggagcccgag gccggcgccg cggcctcttc     300

ggctgcggac cccgccattc ccgaggaggt gtggaatatc aaacaaatga ttaagttgac     360

acaggagcat atagaggccc tattggacaa atttggtggg gagcataatc caccatcaat     420

atatctggag gcctatgaag aatacaccag caagctagat gccctccaac aaagagaaca     480

acagttattg gaatccctgg ggaatggaac tgatttttct gtttctagct ctgcatcaac     540

ggacaccgtt acatcttctt cctcttctag cctttcagtg ctgccttcat ctctttcagt     600
```

```
ttttcaaaat cccacagatg tgtcacggag caaccccaag tcaccacaaa aacctatcgt    660
tagagtcttc ctgcccaata aacagaggac agtggtacct gcacggtgtg gagtcacagt    720
ccgggacagc ctgaagaagg cactgatgat gagaggtcta atcccagagt gctgtgctgt    780
ttacagaatt caggatgggg agaagaaacc aattggctgg gacactgata tttcctggct    840
tactggagag gagttgcatg tagaagtgtt ggagaatgtt ccacttacaa cacacaactt    900
tgtacggaaa actttttca ccttagcatt ttgtgacttc tgtagaaagc tgcttttcca    960
gggattccgc tgtcaaacat gtggttataa atttcaccag cgttgtagta cagaggttcc   1020
actgatgtgt gttaattatg accaactaga tttgctgttt gtctccaagt tctttgaaca   1080
ccacccaata ccacaggagg aggcctcctt agcagagact acccttccat gtggctcatc   1140
cccttctgca cccccctccg attctattgg gcccccaatt ctcaccagtc catctccttc   1200
aaaatccatt ccaattccac agcctttccg accagcagat gaagatcatc gaaatcagtt   1260
tggacaacga gaccggtcct catcagctcc aaatgtgcat ataaacacaa tagaacccgt   1320
caatattgat gacttgatta gagaccaagg gtttcgtagt gatggaggat caaccacagg   1380
tttatccgcc acaccccctg cctcattacc tggctcactc tctaatgtga aagcattgca   1440
gaaatctcca ggacctcagc gagaaagaaa gtcctcttca tcctcagaag acaggaatcg   1500
aatgaaaacg cttggtagac gggattcaag tgacgattgg gagattcctg atggacagat   1560
cacagtggga caaagaattg gatcagggtc atttgggaca gtctacaagg gaaagtggca   1620
tggtgatgtg gcagtgaaaa tgttgaatgt gacagcaccc acacctcagc agttacaggc   1680
cttcaaaaat gaagtaggag tactcaggaa aacgcgacat gtgaatatcc tcctcttcat   1740
gggttattca acaaagccac aactggctat tgttacccag tggtgtgagg gctccagttt   1800
atatcatcat ctccacatca ttgagaccaa attcgagatg atcaaactta tagatattgc   1860
acggcagact gcacagggca tggattactt acacgccaag tcaatcatcc acagagacct   1920
caagagtaat aatatttttc ttcatgaaga cctcacagta aaaataggtg attttggtct   1980
agccacagtg aaatctcgat ggagtgggtc ccatcagttt gaacagttgt ctggatccat   2040
tttgtggatg gcaccagaag taatcagaat gcaagataaa aacccatata gctttcagtc   2100
agatgtatat gcatttggga ttgttctgta tgaattgatg accggacagt taccttattc   2160
aaatatcaac aacagggacc agtctgtgca aggaaaagag acaaagccac ggatcagaag   2220
cacatggcca taactgaaga ttttgtgaac tctcacaagg aaaaaatttg ctctttgaac   2280
aataagaagg aactcactaa aatgtaactg agaactgttc aacaggttga aagctgaaag   2340
atgccattgg aactgacaaa atgtttctta aacataaatg atgaaacagt gaaactacat   2400
aatatctcct ctggctgaaa cattcaagaa gtttaaaatg cttaagttaa aaataaaatc   2460
ctagtaaaca atggacttac tgtgcaacat agagaatatc ttacgataac ctgtaatgga   2520
aaagaatctg aaaaagaatg tatataactg aatcactttg ctgtaaacta gaatctgaca   2580
caacactgta aatcactaca cttttctgtt gcatgccaaa gattatttaa taacgtcatt   2640
aaaaaattat tttaataatt a                                              2661
```

<210> SEQ ID NO 38
<211> LENGTH: 679
<212> TYPE: PRT
<213> ORGANISM: Bos taurus

<400> SEQUENCE: 38

-continued

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
```

```
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ser Val Gln Gly Lys Glu Thr Lys Pro
            660                 665                 670

Arg Ile Arg Ser Thr Trp Pro
        675
```

<210> SEQ ID NO 39
<211> LENGTH: 7434
<212> TYPE: DNA
<213> ORGANISM: Bos taurus

<400> SEQUENCE: 39

```
acaccgttac atcttcttcc tcttctagcc tttcagtgct gccttcatct ctttcagttt     60

ttcaaaatcc cacagatgtg tcacggagca accccaagtc accacaaaaa cctatcgtta    120

gagtcttcct gcccaataaa cagaggacag tggtacctgc acggtgtgga gtcacagtcc    180

gggacagcct gaagaaggca ctgatgatga gaggtctaat cccagagtgc tgtgctgttt    240

acagaattca ggatggggag aagaaaccaa ttggctggga cactgatatt tcctggctta    300

ctggagagga gttgcatgta gaagtgttgg agaatgttcc acttacaaca cacaactttg    360

tacggaaaac ttttttcacc ttagcatttt gtgacttctg tagaaagctg cttttccagg    420

gattccgctg tcaaacatgt ggttataaat ttcaccagcg ttgtagtaca gaggttccac    480

tgatgtgtgt taattatgac caactagatt tgctgtttgt ctccaagttc tttgaacacc    540

acccaatacc acaggaggag gcctccttag cagagactac ccttccatgt ggctcatccc    600

cttctgcacc cccctccgat tctattgggc ccccaattct caccagtcca tctccttcaa    660
```

```
aatccattcc aattccacag cctttccgac cagcagatga agatcatcga aatcagtttg    720
gacaacgaga ccggtcctca tcagctccaa atgtgcatat aaacacaata gaacccgtca    780
atattgatga cttgattaga gaccaagggt ttcgtagtga tggaggatca accacaggtt    840
tatccgccac accccctgcc tcattacctg gctcactctc taatgtgaaa gcattgcaga    900
aatctccagg acctcagcga gaaagaaagt cctcttcatc ctcagaagac aggaatcgaa    960
tgaaaacgct tggtagacgg gattcaagtg acgattggga gattcctgat ggacagatca   1020
cagtgggaca aagaattgga tcagggtcat ttgggacagt ctacaaggga aagtggcatg   1080
gtgatgtggc agtgaaaatg ttgaatgtga cagcacccac acctcagcag ttacaggcct   1140
tcaaaaatga agtaggagta ctcaggaaaa cgcgacatgt gaatatcctc ctcttcatgg   1200
gttattcaac aaagccacaa ctggctattg ttacccagtg gtgtgagggc tccagtttat   1260
atcatcatct ccacatcatt gagaccaaat tcgagatgat caaacttata gatattgcac   1320
ggcagactgc acagggcatg gattacttac acgccaagtc aatcatccac agagacctca   1380
agagtaataa tatttttctt catgaagacc tcacagtaaa aataggtgat tttggtctag   1440
ccacagtgaa atctcgatgg agtgggtccc atcagtttga acagttgtct ggatccattt   1500
tgtggatggc accagaagta atcagaatgc aagataaaaa cccatatagc tttcagtcag   1560
atgtatatgc atttgggatt gttctgtatg aattgatgac cggacagtta ccttattcaa   1620
atatcaacaa cagggaccag ataattttta tggtgggacg aggatatctg tctccagatc   1680
tcagtaaggt acggagtaac tgtccaaaag ccatgaagag attaatggca gagtgcctaa   1740
aaaagaaaag agatgaaaga ccactctttc cccaagtagg aaagactctc ctaagcaaga   1800
gacaaaattc agaagttatc agggaaaaag ataagcagat tctcgcctct attgagctgc   1860
tggcccgctc attgccaaaa attcaccgca gtgcatcaga accctccttg aatcgggctg   1920
gcttccaaac agaggatttt agtctatatg cttgtgcttc tccaaaaaca cccattcagg   1980
caggggggata tggagaattt gcagccttca agtagccaca ccatcatgac agcatctact   2040
cttatttctt aagtcttgtg ttcgtacaat ttgttaacat caaaacacag ttctgttcct   2100
caactctttt taaagttaaa atttttcagt gcataagctg gtgtggaaca gaaggaaatt   2160
tcccatccaa caaaagaggg aagaatgttt taggaaccag aattctctgc tgccagtgtt   2220
tcttcttcaa cacaaatatc acaagtctgc ccactcccag gaagaaagag gagagaccct   2280
gagttctgac cttttgatgg tcaggcatga tggaaagaaa ctgctgctac agcttgggag   2340
atttgctctg ggaagtctgc cagtcaactt tgcccttcta accaccagat caatatgtgg   2400
ctgatcatct gatggggcag ttgcaatcac caagccttgt tctctttcct gttctgggat   2460
tgtgttgtgg aacccttttc cctagccacc accagttcat ttctgaggga tggaacaaaa   2520
atgcagcatg ccccttcctgt gtggtgcatg ttcagtcctt gacaaatttt taccaaaatg   2580
aagctacttt atttaaaagg agggtgagag gtgaggaggt cactttgggt gtggcggaaa   2640
gggaatgctg catctttttc ctgggctgct ggggctctgg ccttggcttg ccagccggaa   2700
gcgctggcac gcatcgcctt cttttcccat tgggtccagc aatgaagacg agtgtttggg   2760
gtttttttttt tctccaccat gtagcaagtt ctcaggaaaa tacaattgat atcttcctcc   2820
taagctcttc caatcagtca ccaagtactt atgtggttac tttgtccagg gcacaaaatg   2880
cctgtatcta attaaaagcc tacaaaactg cttgataaca gttttgaatg tgagacattt   2940
atgtaattta aatgtaaggt acaagtttta atttctgagt ttcttctatt atatttttat   3000
```

taaaaaaaga aaataatttt cagattgaat tggagtaaaa taatattact tcccactaga 3060
attatatatc ctggaaaatt gtatttttgt tacataagca gcttttaaag aaagatcatt 3120
acccttttct ctacataaat atatggggag tcttagccta atgacaaata tttataattt 3180
ttaaattaat ggtacttgct ggatccatac taacatcttt actaatacct cattgtttct 3240
tccaacttac tcctacacta catcctacat cttcttccta gtcttttatc tagaatatgc 3300
aacctcaaat aaaaatggtg gtgtcctcat tcattctcct ccttcctttt ttcccaagcc 3360
tgatcttcaa aaggttggtt aatttggcag ctgagttcct ccccaggcag agaatagacc 3420
aattttaggt gtattgggac tgagggagga tgtgtaaaga ttaacatcag taaagaaccg 3480
ctgtggagta attaagaact ttgttcttta taactggaga atataaccta accctaacat 3540
ccctcagcct ttactaaagt gtggcgtaaa tcacagtagt agcaaagaaa gtgactctgg 3600
atgtgttcct ggccagtacc tcccttatca tgaatgtaga ctctctcatc aagatttagg 3660
aatataaatc aaatcaaatg tgcccagcca agctatgtag taagggactt gaacaatatt 3720
aggcagaacc tataaaataa atcagggaat tagaaattat ttaaagtttt caaattgtaa 3780
attgccccgg tgtctttcag cctactgcca ttatttttgc tacaatacct acatttcaga 3840
ggagggccta ctgaaaattc catgcaagtg gaaaataatc ctcaagttat taatgagttt 3900
gaaaagcaat gagttcttaa gtctttgtga gtagagcaag atcctacaaa attcagaaat 3960
agtaaaaatg gattcatgct gatttgaaga gcatctgtgt gcataatata atgctgcatc 4020
tcttttaaaa gcagtctatt tttcttttta aatttgtccc catagatgct tttgaacatg 4080
aacatgctta tgttaccttt tccgaggttg ggaagagcca ggagctctca ggcagggccc 4140
cctccctcag ctgggcagga gctgctcagg aggagctagt tatagaggaa gcttagcgtt 4200
ggcattttca aaattcaagg tgataacgct ttcttcttcc tttctgtttt agaatagatt 4260
gctgtctgat ttgaaaaagg gaaatagatt tgatctcaaa tgaatctgtg cccagaagcc 4320
aggctcaggg tattcagaga tttgtatagt gccctcaaaa aataacaaaa ttttagcttt 4380
ccttttttct tcttttctcc atcaaattct tttttctcta gtttacaaat gacatggaaa 4440
aggaatttcc cctgagtttt gtatgccttt tttttttttgg cttagactat agataggcgt 4500
gttgagctcc taagaaaata caaggaggaa ctctttgttg tgcagagcac tttatgagta 4560
gtttgtgtgg ataatatgtg actgcttccc tgacgagctt gtgaggctgt acttatgtct 4620
ttcctgtaag gcagcttcag tgccttctgt agtgtatata aggaaagatt acgccttctg 4680
aaaaatctca gagcaaccat aagattattt taaaatatgt agtatgactg atggactttt 4740
tcatcattaa attagtctag catctaaact tttaccactg aaataatatt gaccaaaaag 4800
caatttataa aaggtatttg tgaatagaaa atacaatgtg atcatttgta cttatgtgca 4860
ccttaaaaga ggaattctgt ctagctgtca aattctggtt ccttaacatc cagtccttga 4920
ttgtgattga gatctggtag gacgtgctgg ggcacgctag cagataaaat cccgtatact 4980
ttaggataga tgttacattt atgtcagtgt tggcaaagag cattgtgtag taataaagaa 5040
ttcaagactt cagcaatgtc aacctgaaac tttgtaaata tttcctagat tgttatttga 5100
tgcagtcaca gctctttatc acacaatgtt gtctttccct catcaggcaa ttttagaact 5160
gctgcacacc cctcctcaga tctcacctgc ccctcctgta cattcacctc tccagccttg 5220
tgcacacctc atttagcttt agtttgaaac acattgcagg gttcaggtga cctcttcaaa 5280
aactacctcc tcagaatgag gtaatgaata gttatttatt ttaaaatatg aaaagtcagg 5340
agctctagaa tatgaagatg atctaagatt ttaactttta tgtatacttg ttgagcactc 5400

```
tccttttgtc ctaaagggca ttatacattt aagcagtaat actgaaaaat gtagctcaga   5460
gtaactgaat gttgttgaaa gtggtgccag aatctgtttt aggggtacgt atcagaatct   5520
taatcttaaa tcggttacat gaaattaaat agttaatggt aacacttgac taacagatat   5580
aattttaatt ttcggtaggc ttttagcaag acagtaagta catcttcata atgagttagc   5640
cacagcttca tcacatgcac agattttcct gttgagagac tgcccagtta agagggtaga   5700
atgatgaacc atttttcagg attctcttct ttgtccaaac tggcattgtg agtgctagaa   5760
tatcagcact ttcaaactag tgattccaac tattaggcta ttaaaaagca aaacaaacca   5820
aacaaaccat agccagacat gggaagttta ctatgagtat aaacagcaaa tagcttacag   5880
gtcatacatt gaaatggtgt aggtaaggcg ttagaaaaat accttgacaa tttgccaaat   5940
gatcttactg tgccttcatg atgcaataaa aaaaaaaaaa atttagcata aatcagtgat   6000
ttgtgaagag agcagccacc ctggtctaac tcagctgtgt taatattttt tagcgtgcaa   6060
tttagactgc aaagataaat gcactaaaga gtttatagcc aaaatcacat ttaaaaaatg   6120
agagaaaaca caggtaaatt ttcagtgaac aaaattattt ttttaaagta cataatccct   6180
agtatagtca gatatattta tcacatagag caaataggtt gaaatcacaa ttcagtgaca   6240
tttctagaga aactttttct actcccatag gttcttcaaa gcatggaact tttatataac   6300
agaaatgtgt gacggtcatt ttaaattgct gtagtttggg gctgaagtac tgtgtgctgg   6360
gcagcaatca catgtattaa ctagtgagaa aggagaaatt aagatatagg acagaatttg   6420
attttcttgt tcccagatta ctgctgccaa cctagacact gagtttccag aggctgaaac   6480
gtaaacttgc agctcagcaa ctgttttgca aagttagtgg gactgtcctg cttatgctgt   6540
tcaaaaatgc tctgagggcc aggtggggcc tccaggggct cctctctgag gggacatcag   6600
actagctaac gacctggcgg gcggatgtga accggacaca ctccatggtg tgcttcttgt   6660
atcggtccct cgccaccctc aagaaaggct tcagcgggtt ctctagacgt ctccactaag   6720
gtgtgttact aacagccatg ggttgttgag cacccgagga gtgcaatagc atctctgcat   6780
gattgtatat tggcccgaag agaatgaagt ggccagtgta ctcatgttcc atgttgctag   6840
ctctggtaaa ctgaaaatac tggtaagatt tttgttttat cagtacacta gagagtaagc   6900
tttgttttgt tgtttttaga taatgttttc acttccattt ggaaagacat ttaaattgag   6960
tttcagtcct aaattttgcc agtcatggta attagcagtt tctatcaggt atttttaagg   7020
tagaagagga tagaaacata agttctaaaa gcttaaggta accgtggttt attttaaaat   7080
gtttaggggt ggttagtctc tacctcaaaa aaagtgagtg aatcttttat ttcagcattc   7140
acaagttcgg ctgttgtttt tgtaatacat ttttttttta accttttgac ccccctttac   7200
ctaagtgtca atgtagtttt attaattact aagtcagttt cattaaaatg tttatttagc   7260
agttttgact aattgcaatg attaatatag ccagttgtgc atgaggacac agccagtgag   7320
tatatctggg ttttttttgt gatgcttttt ttcttaagac ttctgtagat ttatgaagta   7380
ctcattgaaa acaactaaaa tacgtttatt cgtgttaata tggaaaaaaa aaaa         7434
```

<210> SEQ ID NO 40
<211> LENGTH: 603
<212> TYPE: PRT
<213> ORGANISM: Bos taurus

<400> SEQUENCE: 40

```
Met Met Arg Gly Leu Ile Pro Glu Cys Cys Ala Val Tyr Arg Ile Gln
1               5                   10                  15
```

-continued

```
Asp Gly Glu Lys Lys Pro Ile Gly Trp Asp Thr Asp Ile Ser Trp Leu
            20                  25                  30

Thr Gly Glu Glu Leu His Val Glu Val Leu Glu Asn Val Pro Leu Thr
        35                  40                  45

Thr His Asn Phe Val Arg Lys Thr Phe Phe Thr Leu Ala Phe Cys Asp
    50                  55                  60

Phe Cys Arg Lys Leu Leu Phe Gln Gly Phe Arg Cys Gln Thr Cys Gly
65                  70                  75                  80

Tyr Lys Phe His Gln Arg Cys Ser Thr Glu Val Pro Leu Met Cys Val
                85                  90                  95

Asn Tyr Asp Gln Leu Asp Leu Leu Phe Val Ser Lys Phe Phe Glu His
            100                 105                 110

His Pro Ile Pro Gln Glu Glu Ala Ser Leu Ala Glu Thr Thr Leu Pro
        115                 120                 125

Cys Gly Ser Ser Pro Ser Ala Pro Pro Ser Asp Ser Ile Gly Pro Pro
    130                 135                 140

Ile Leu Thr Ser Pro Ser Pro Ser Lys Ser Ile Pro Ile Pro Gln Pro
145                 150                 155                 160

Phe Arg Pro Ala Asp Glu Asp His Arg Asn Gln Phe Gly Gln Arg Asp
                165                 170                 175

Arg Ser Ser Ser Ala Pro Asn Val His Ile Asn Thr Ile Glu Pro Val
            180                 185                 190

Asn Ile Asp Asp Leu Ile Arg Asp Gln Gly Phe Arg Ser Asp Gly Gly
        195                 200                 205

Ser Thr Thr Gly Leu Ser Ala Thr Pro Pro Ala Ser Leu Pro Gly Ser
    210                 215                 220

Leu Ser Asn Val Lys Ala Leu Gln Lys Ser Pro Gly Pro Gln Arg Glu
225                 230                 235                 240

Arg Lys Ser Ser Ser Ser Ser Glu Asp Arg Asn Arg Met Lys Thr Leu
                245                 250                 255

Gly Arg Arg Asp Ser Ser Asp Asp Trp Glu Ile Pro Asp Gly Gln Ile
            260                 265                 270

Thr Val Gly Gln Arg Ile Gly Ser Gly Ser Phe Gly Thr Val Tyr Lys
        275                 280                 285

Gly Lys Trp His Gly Asp Val Ala Val Lys Met Leu Asn Val Thr Ala
    290                 295                 300

Pro Thr Pro Gln Gln Leu Gln Ala Phe Lys Asn Glu Val Gly Val Leu
305                 310                 315                 320

Arg Lys Thr Arg His Val Asn Ile Leu Leu Phe Met Gly Tyr Ser Thr
                325                 330                 335

Lys Pro Gln Leu Ala Ile Val Thr Gln Trp Cys Glu Gly Ser Ser Leu
            340                 345                 350

Tyr His His Leu His Ile Ile Glu Thr Lys Phe Glu Met Ile Lys Leu
        355                 360                 365

Ile Asp Ile Ala Arg Gln Thr Ala Gln Gly Met Asp Tyr Leu His Ala
    370                 375                 380

Lys Ser Ile Ile His Arg Asp Leu Lys Ser Asn Asn Ile Phe Leu His
385                 390                 395                 400

Glu Asp Leu Thr Val Lys Ile Gly Asp Phe Gly Leu Ala Thr Val Lys
                405                 410                 415

Ser Arg Trp Ser Gly Ser His Gln Phe Glu Gln Leu Ser Gly Ser Ile
            420                 425                 430
```

-continued

```
Leu Trp Met Ala Pro Glu Val Ile Arg Met Gln Asp Lys Asn Pro Tyr
        435                 440                 445

Ser Phe Gln Ser Asp Val Tyr Ala Phe Gly Ile Val Leu Tyr Glu Leu
    450                 455                 460

Met Thr Gly Gln Leu Pro Tyr Ser Asn Ile Asn Asn Arg Asp Gln Ile
465                 470                 475                 480

Ile Phe Met Val Gly Arg Gly Tyr Leu Ser Pro Asp Leu Ser Lys Val
                485                 490                 495

Arg Ser Asn Cys Pro Lys Ala Met Lys Arg Leu Met Ala Glu Cys Leu
            500                 505                 510

Lys Lys Lys Arg Asp Glu Arg Pro Leu Phe Pro Gln Val Gly Lys Thr
        515                 520                 525

Leu Leu Ser Lys Arg Gln Asn Ser Glu Val Ile Arg Glu Lys Asp Lys
    530                 535                 540

Gln Ile Leu Ala Ser Ile Glu Leu Leu Ala Arg Ser Leu Pro Lys Ile
545                 550                 555                 560

His Arg Ser Ala Ser Glu Pro Ser Leu Asn Arg Ala Gly Phe Gln Thr
                565                 570                 575

Glu Asp Phe Ser Leu Tyr Ala Cys Ala Ser Pro Lys Thr Pro Ile Gln
            580                 585                 590

Ala Gly Gly Tyr Gly Glu Phe Ala Ala Phe Lys
        595                 600
```

<210> SEQ ID NO 41
<211> LENGTH: 2295
<212> TYPE: DNA
<213> ORGANISM: Equus caballus
<220> FEATURE:
<221> NAME/KEY: misc_feature
<222> LOCATION: (79)..(79)
<223> OTHER INFORMATION: n is a, c, g, or t

<400> SEQUENCE: 41

```
atgaagacgc tgagcggcgg cggcggcggc gcggagcagg gccaggctct gttcaacggg      60

gacatggaac ccggaggcnc cgcgccggcg cccgcggcct cgtcggccgc ggaccctgcc     120

attcccgagg aggtatggaa tatcaaacaa atgattaaat tgacacagga acatatagag     180

gccctattgg acaaatttgg tggggagcat aatccaccat caatatatct ggaggcctat     240

gaagaataca ccagcaagct agatgccctc caacaaagag aacaacagtt attggaatcc     300

ctggggaatg gaactgattt ttctgtttct agttctgcat caacggacac cgttacatct     360

tcttcctctt ctagcctttc agtgctacct tcatctcttt cagtttttca aaatcccaca     420

gatgtgtcac ggagcaaccc taagtcacca caaaaaccta tcgttagagt cttcctgccc     480

aacaaacaga ggacagtggt acctgcaagg tgtggcgtta cagtccggga cagtctaaag     540

aaagcactga tgatgagagg tctaatccca gagtgctgtg ctgtttacag aattcaggat     600

ggagagaaga aaccaattgg ctgggacact gatatttcct ggctcactgg agaggaattg     660

catgtagaag tgttggagaa tgttccactt acaacacaca actttgtacg gaaaactttt     720

ttcaccttag cattttgtga cttttgtcga aagctgcttt tccagggttt ccgctgtcaa     780

acatgtggtt ataaatttca ccagcgttgt agtacagagg ttccactgat gtgtgttaat     840

tatgaccaac ttgatttgct gtttgtctcc aagttctttg aacaccaccc agtatcacag     900

gaggaggcct ccttagcaga gactgccctt acatctggat catccccttc tgcaccccccc    960

tccgattcca ttgggcccca aattctcacc agtccatctc cttcaaaatc cattccaatt    1020
```

```
ccacagcctt tccgaccagc agatgaagat catcgaaatc agtttggaca acgagaccgg   1080

tcctcatcag ctccaaatgt acatataaac acaatagaac ctgtcaatat tgatgacttg   1140

attagagacc aagggtttcg tagtgatgga ggatcaacca caggtttatc tgccaccccc   1200

cctgcctcat tacctggctc actcactaat gtgaaggcat tacagaaatc tccaggacct   1260

caacgggaaa ggaaatcatc ttcatcctca gaagacagga atcgaatgaa aactcttggt   1320

agacgggatt caagtgacga ttgggagatt cctgatgggc agatcacagt gggacaaaga   1380

attggatctg ggtcatttgg gacagtctac aagggaaagt ggcatggtga tgtggcagtg   1440

aaaatgttga atgtgacagc acccacacct cagcagttac aggccttcaa aaatgaagta   1500

ggagtactca ggaaaactcg acatgtgaat atcctactct tcatgggcta ttcaacaaag   1560

ccacaactgg ctattgttac ccagtggtgt gagggctcca gcttatatca ccatctccac   1620

atcattgaga ccaaatttga gatgatcaaa cttatagata ttgctcggca aactgcacag   1680

ggcatggatt acttacacgc caagtcaatc atccacagag acctcaagag taataatatt   1740

tttcttcatg aagacctcac agtaaaaata ggtgattttg gtctagccac agtgaaatct   1800

cgatggagtg ggtcccatca gtttgaacag ttgtctggat ccattttgtg gatggcacca   1860

gaagtaatca gaatgcaaga taaaaacccg tatagctttc aatcagatgt atatgccttt   1920

gggattgttc tgtatgaatt gatgactgga cagttacctt attcaaacat caacaacagg   1980

gaccagataa tttttatggt gggaagagga tatctatctc cagatctcag taaggtacgg   2040

agtaactgtc caaaagccat gaagagatta atggcagagt gcctaaaaaa gaaaagagac   2100

gagagaccac tcttccccca aattctcgcc tctattgagc tgctggcccg ctcattgcca   2160

aaaattcacc gcagtgcatc agagccctcc ttgaatcggg ctggcttcca gacagaggat   2220

tttagtctat atgcttgtgc ttctccgaaa acacccatcc aggcaggggg atatggtgcg   2280

tttcctgtcc actga                                                    2295
```

```
<210> SEQ ID NO 42
<211> LENGTH: 764
<212> TYPE: PRT
<213> ORGANISM: Equus caballus
<220> FEATURE:
<221> NAME/KEY: misc_feature
<222> LOCATION: (27)..(27)
<223> OTHER INFORMATION: Xaa can be any naturally occurring amino acid

<400> SEQUENCE: 42

Met Lys Thr Leu Ser Gly Gly Gly Gly Gly Ala Glu Gln Gly Gln Ala
1               5                   10                  15

Leu Phe Asn Gly Asp Met Glu Pro Gly Gly Xaa Ala Pro Ala Pro Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Ser Leu Ser Val
        115                 120                 125
```

-continued

```
Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
        275                 280                 285

Val Ser Lys Phe Phe Glu His His Pro Val Ser Gln Glu Glu Ala Ser
    290                 295                 300

Leu Ala Glu Thr Ala Leu Thr Ser Gly Ser Ser Pro Ser Ala Pro Pro
305                 310                 315                 320

Ser Asp Ser Ile Gly Pro Gln Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ser Ala Pro Asn Val His
        355                 360                 365

Ile Asn Thr Ile Glu Pro Val Asn Ile Asp Asp Leu Ile Arg Asp Gln
    370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Thr Asn Val Lys Ala Leu Gln Lys
                405                 410                 415

Ser Pro Gly Pro Gln Arg Glu Arg Lys Ser Ser Ser Ser Ser Glu Asp
            420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
    450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525

Trp Cys Glu Gly Ser Ser Leu Tyr His His Leu His Ile Ile Glu Thr
    530                 535                 540
```

```
Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Ala Phe Pro Val His
        755                 760
```

<210> SEQ ID NO 43
<211> LENGTH: 2678
<212> TYPE: DNA
<213> ORGANISM: Gallus gallus

<400> SEQUENCE: 43

```
tccccctccc tcgccccagc gcttcgatcc aagatggcgg cgctgagcag cggcagcagc     60

gccgaggggg cctcgctctt caacggggac atggagcccg agccgccgcc gcccgtgctg    120

ggcgcctgct acgccgggag cggcggcggc gacccggcca tcccggagga ggtgtggaat    180

atcaaacaga tgattaaatt aacacaagaa catatagaag cgctgttaga caagtttgga    240

ggagagcata acccaccatc aatatattta gaggcctatg aggagtacac cagcaaacta    300

gatgctctac agcagagaga acagcagtta ttggaatcca tgggaaatgg aactgatttc    360

tctgtttcca gttcagcttc aacggacaca gttgcatcat cttcctcctc tagcctctct    420

gtagcacctt catccctttc agtttatcaa aatcctactg atatgtcgcg gaataaccct    480

aagtctccac agaagcctat tgttagagtc ttcctgccca acaagcaaag gactgtggtt    540

ccggcaagat gtggggtgac agtccgagac agcctgaaga aagctctgat gatgagaggt    600

cttattccag aatgctgtgc tgtttacaga atacaggatg gagagaagaa gccaattggc    660

tgggacactg acatttcctg gctaaccgga gaggagttac acgtggaggt cttggagaat    720

gtgccactca caacacacaa ttttgtacga aaaacattct tcacgttagc gttctgcgac    780

ttctgtcgaa agctgctttt ccagggattc cgatgccaga catgtggcta caaatttcac    840

cagcgctgta gcacagaagt gccactgatg tgtgttaact acgaccaact cgatttgctg    900
```

```
tttgtctcca agttctttga acatcacccc atatcgcagg aggagaccac cttaggagag    960
accaccccgg catcgggatc gtacccctca gtgcccccat cagattctgt tggaccacca   1020
attctcccta gtccttctcc ttcaaaatcc attccaatcc cacagccctt ccgaccagca   1080
gatgaagacc atcggaatca gtttgggcaa cgcgaccgat cctcttcagc tcccaatgtt   1140
cacatcaata caattgagcc agtcaatatt gatgacttga ttagagacca gggtgtacga   1200
ggagagggag ccccctttgaa ccagctgatg cgctgtcttc ggaaatacca atcccggact   1260
cccagtcccc tccttcattc tgtccccagt gaaatagtgt ttgattttga gcctggccca   1320
gtgttcagag gttcaactgc aggtttgtct gcaacacctc ctgcatcttt gcctgggtca   1380
cttaccaatg tgaaagcatt acagaaatca ccaggccccc aacgggaaag gaaatcatcc   1440
tcatcctcag aagacagaaa taggatgaaa acccttggtc gacgagattc aagtgatgat   1500
tgggaaatac cagatgggca gatcacagtt ggacaaagga taggatctgg atcatttgga   1560
acagtctaca aaggaaagtg gcatggtgac gtggcagtga aaatgttgaa tgttacagca   1620
cccacacctc aacagttaca ggctttcaaa aatgaagtag gagtgctcag gaaaacacgg   1680
catgtgaata tcctactttt tatgggttat tcaacaaaac ctcagttggc tattgttaca   1740
cagtggtgtg aggggtccag cttatatcac catctgcaca taattgagac caagtttgaa   1800
atgatcaaac taattgatat tgcacgacag actgcacaag gcatggatta tttgcatgcc   1860
aagtcaatca tccacagaga cctcaagagt aataatattt ttcttcatga agacctcaca   1920
gtaaaaatag gtgacttcgg tctggctaca gtgaaatcac gatggagtgg atctcatcaa   1980
tttgaacagt tatctggatc aattctatgg atggcaccgg aagtgatcag gatgcaagac   2040
aaaaacccat atagctttca gtcagatgtg tatgcattcg ggattgtgct ttatgaactg   2100
atgactggac agttaccata ctcaaacatc aacaacaggg accagataat ttttatggtg   2160
ggacgaggat atctatctcc agacctcagt aaagtaagaa gtaactgtcc aaaagctatg   2220
aagagactaa tggcagaatg cttgaaaaag aaaagagatg agagacctct tttccacag   2280
attcttgcct ccattgagct tctggcccgg tcgttgccaa aaattcaccg cagtgcatct   2340
gagccgtcac taaaccgggc tggcttccag accgaggatt tcagtctgta tgcttgtgct   2400
tctccaaaaa cgcccatcca agcaggggga tacggtgggt ttccagtaca ctgaaaagaa   2460
atgtgaaagc gtgtgcctgt ttgctcatgt gctggtgtgt tcctgtgtgt gcaacgcata   2520
cgtacgttct cagttcctac cagcgacttt ttaaggttta ctgagggaat gaagactcat   2580
ttcctaacat ggggcattga acgtcctgag cacaagtcag tgctggtaag gaatgtcttg   2640
ggaacagctg gcaagaagaa ttagaaggta cttaaagg                            2678
```

<210> SEQ ID NO 44
<211> LENGTH: 806
<212> TYPE: PRT
<213> ORGANISM: Gallus gallus

<400> SEQUENCE: 44

```
Met Ala Ala Leu Ser Ser Gly Ser Ser Ala Glu Gly Ala Ser Leu Phe
1               5                   10                  15

Asn Gly Asp Met Glu Pro Glu Pro Pro Pro Pro Val Leu Gly Ala Cys
            20                  25                  30

Tyr Ala Gly Ser Gly Gly Gly Asp Pro Ala Ile Pro Glu Glu Val Trp
        35                  40                  45

Asn Ile Lys Gln Met Ile Lys Leu Thr Gln Glu His Ile Glu Ala Leu
```

```
            50              55              60

Leu Asp Lys Phe Gly Gly Glu His Asn Pro Pro Ser Ile Tyr Leu Glu
65              70              75              80

Ala Tyr Glu Glu Tyr Thr Ser Lys Leu Asp Ala Leu Gln Gln Arg Glu
                85              90              95

Gln Gln Leu Leu Glu Ser Met Gly Asn Gly Thr Asp Phe Ser Val Ser
                100             105             110

Ser Ser Ala Ser Thr Asp Thr Val Ala Ser Ser Ser Ser Ser Ser Leu
                115             120             125

Ser Val Ala Pro Ser Ser Leu Ser Val Tyr Gln Asn Pro Thr Asp Met
                130             135             140

Ser Arg Asn Asn Pro Lys Ser Pro Gln Lys Pro Ile Val Arg Val Phe
145             150             155             160

Leu Pro Asn Lys Gln Arg Thr Val Val Pro Ala Arg Cys Gly Val Thr
                165             170             175

Val Arg Asp Ser Leu Lys Lys Ala Leu Met Met Arg Gly Leu Ile Pro
                180             185             190

Glu Cys Cys Ala Val Tyr Arg Ile Gln Asp Gly Glu Lys Lys Pro Ile
                195             200             205

Gly Trp Asp Thr Asp Ile Ser Trp Leu Thr Gly Glu Glu Leu His Val
                210             215             220

Glu Val Leu Glu Asn Val Pro Leu Thr Thr His Asn Phe Val Arg Lys
225             230             235             240

Thr Phe Phe Thr Leu Ala Phe Cys Asp Phe Cys Arg Lys Leu Leu Phe
                245             250             255

Gln Gly Phe Arg Cys Gln Thr Cys Gly Tyr Lys Phe His Gln Arg Cys
                260             265             270

Ser Thr Glu Val Pro Leu Met Cys Val Asn Tyr Asp Gln Leu Asp Leu
                275             280             285

Leu Phe Val Ser Lys Phe Phe Glu His His Pro Ile Ser Gln Glu Glu
                290             295             300

Thr Thr Leu Gly Glu Thr Thr Pro Ala Ser Gly Ser Tyr Pro Ser Val
305             310             315             320

Pro Pro Ser Asp Ser Val Gly Pro Pro Ile Leu Pro Ser Pro Ser Pro
                325             330             335

Ser Lys Ser Ile Pro Ile Pro Gln Pro Phe Arg Pro Ala Asp Glu Asp
                340             345             350

His Arg Asn Gln Phe Gly Gln Arg Asp Arg Ser Ser Ser Ala Pro Asn
                355             360             365

Val His Ile Asn Thr Ile Glu Pro Val Asn Ile Asp Asp Leu Ile Arg
                370             375             380

Asp Gln Gly Val Arg Gly Glu Gly Ala Pro Leu Asn Gln Leu Met Arg
385             390             395             400

Cys Leu Arg Lys Tyr Gln Ser Arg Thr Pro Ser Pro Leu Leu His Ser
                405             410             415

Val Pro Ser Glu Ile Val Phe Asp Phe Glu Pro Gly Pro Val Phe Arg
                420             425             430

Gly Ser Thr Ala Gly Leu Ser Ala Thr Pro Pro Ala Ser Leu Pro Gly
                435             440             445

Ser Leu Thr Asn Val Lys Ala Leu Gln Lys Ser Pro Gly Pro Gln Arg
                450             455             460

Glu Arg Lys Ser Ser Ser Ser Ser Glu Asp Arg Asn Arg Met Lys Thr
465             470             475             480
```

```
Leu Gly Arg Arg Asp Ser Ser Asp Asp Trp Glu Ile Pro Asp Gly Gln
                485                 490                 495

Ile Thr Val Gly Gln Arg Ile Gly Ser Gly Ser Phe Gly Thr Val Tyr
            500                 505                 510

Lys Gly Lys Trp His Gly Asp Val Ala Val Lys Met Leu Asn Val Thr
        515                 520                 525

Ala Pro Thr Pro Gln Gln Leu Gln Ala Phe Lys Asn Glu Val Gly Val
    530                 535                 540

Leu Arg Lys Thr Arg His Val Asn Ile Leu Leu Phe Met Gly Tyr Ser
545                 550                 555                 560

Thr Lys Pro Gln Leu Ala Ile Val Thr Gln Trp Cys Glu Gly Ser Ser
                565                 570                 575

Leu Tyr His His Leu His Ile Ile Glu Thr Lys Phe Glu Met Ile Lys
            580                 585                 590

Leu Ile Asp Ile Ala Arg Gln Thr Ala Gln Gly Met Asp Tyr Leu His
        595                 600                 605

Ala Lys Ser Ile Ile His Arg Asp Leu Lys Ser Asn Asn Ile Phe Leu
    610                 615                 620

His Glu Asp Leu Thr Val Lys Ile Gly Asp Phe Gly Leu Ala Thr Val
625                 630                 635                 640

Lys Ser Arg Trp Ser Gly Ser His Gln Phe Glu Gln Leu Ser Gly Ser
                645                 650                 655

Ile Leu Trp Met Ala Pro Glu Val Ile Arg Met Gln Asp Lys Asn Pro
            660                 665                 670

Tyr Ser Phe Gln Ser Asp Val Tyr Ala Phe Gly Ile Val Leu Tyr Glu
        675                 680                 685

Leu Met Thr Gly Gln Leu Pro Tyr Ser Asn Ile Asn Asn Arg Asp Gln
    690                 695                 700

Ile Ile Phe Met Val Gly Arg Gly Tyr Leu Ser Pro Asp Leu Ser Lys
705                 710                 715                 720

Val Arg Ser Asn Cys Pro Lys Ala Met Lys Arg Leu Met Ala Glu Cys
                725                 730                 735

Leu Lys Lys Lys Arg Asp Glu Arg Pro Leu Phe Pro Gln Ile Leu Ala
            740                 745                 750

Ser Ile Glu Leu Leu Ala Arg Ser Leu Pro Lys Ile His Arg Ser Ala
        755                 760                 765

Ser Glu Pro Ser Leu Asn Arg Ala Gly Phe Gln Thr Glu Asp Phe Ser
    770                 775                 780

Leu Tyr Ala Cys Ala Ser Pro Lys Thr Pro Ile Gln Ala Gly Gly Tyr
785                 790                 795                 800

Gly Gly Phe Pro Val His
                805
```

<210> SEQ ID NO 45
<211> LENGTH: 4454
<212> TYPE: DNA
<213> ORGANISM: Homo sapiens

<400> SEQUENCE: 45

```
gaaacgtccc gtgtgggagg ggcgggtctg ggtgcggcct gccgcatgac tcgtggttcg      60

gaggcccacg tggccggggc ggggactcag gcgcctgggg cgccgactga ttacgtagcg     120

ggcggggccg gaagtgccgc tccttggtgg gggctgttca tggcggttcc ggggtctcca     180

acatttttcc cggctgtggt cctaaatctg tccaaagcag aggcagtgga gcttgaggtt     240
```

-continued

```
cttgctggtg tgaaatgact gagtacaaac tggtggtggt tggagcaggt ggtgttggga    300
aaagcgcact gacaatccag ctaatccaga accactttgt agatgaatat gatcccacca    360
tagaggattc ttacagaaaa caagtggtta tagatggtga aacctgtttg ttggacatac    420
tggatacagc tggacaagaa gagtacagtg ccatgagaga ccaatacatg aggacaggcg    480
aaggcttcct ctgtgtattt gccatcaata atagcaagtc atttgcggat attaacctct    540
acagggagca gattaagcga gtaaaagact cggatgatgt acctatggtg ctagtgggaa    600
acaagtgtga tttgccaaca aggacagttg atacaaaaca agcccacgaa ctggccaaga    660
gttacgggat tccattcatt gaaacctcag ccaagaccag acagggtgtt gaagatgctt    720
tttacacact ggtaagagaa atacgccagt accgaatgaa aaaactcaac agcagtgatg    780
atgggactca gggttgtatg ggattgccat gtgtggtgat gtaacaagat acttttaaag    840
ttttgtcaga aaagagccac tttcaagctg cactgacacc ctggtcctga cttccctgga    900
ggagaagtat tcctgttgct gtcttcagtc tcacagagaa gctcctgcta cttccccagc    960
tctcagtagt ttagtacaat aatctctatt tgagaagttc tcagaataac tacctcctca   1020
cttggctgtc tgaccagaga atgcacctct tgttactccc tgttattttt ctgccctggg   1080
ttcttccaca gcacaaacac acctctgcca ccccaggttt ttcatctgaa aagcagttca   1140
tgtctgaaac agagaaccaa accgcaaacg tgaaattcta ttgaaaacag tgtcttgagc   1200
tctaaagtag caactgctgg tgattttttt tttcttttta ctgttgaact tagaactatg   1260
ctaatttttg gagaaatgtc ataaattact gttttgccaa gaatatagtt attattgctg   1320
tttggtttgt ttataatgtt atcggctcta ttctctaaac tggcatctgc tctagattca   1380
taaatacaaa aatgaatact gaattttgag tctatcctag tcttcacaac tttgacgtaa   1440
ttaaatccaa ctttcacagt gaagtgcctt tttcctagaa gtggtttgta gacttccttt   1500
ataatatttc agtggaatag atgtctcaaa aatccttatg catgaaatga atgtctgaga   1560
tacgtctgtg acttatctac cattgaagga aagctatatc tatttgagag cagatgccat   1620
tttgtacatg tatgaaattg gttttccaga ggcctgtttt ggggctttcc caggagaaag   1680
atgaaactga aagcacatga ataatttcac ttaataattt ttacctaatc tccacttttt   1740
tcataggtta ctacctatac aatgtatgta atttgtttcc cctagcttac tgataaacct   1800
aatattcaat gaacttccat ttgtattcaa atttgtgtca taccagaaag ctctacattt   1860
gcagatgttc aaatattgta aaactttggt gcattgttat ttaatagctg tgatcagtga   1920
ttttcaaacc tcaaatatag tatattaaca aattacattt tcactgtata tcatggtatc   1980
ttaatgatgt atataattgc cttcaatccc cttctcaccc caccctctac agcttccccc   2040
acagcaatag gggcttgatt atttcagttg agtaaagcat ggtgctaatg gaccagggtc   2100
acagtttcaa aacttgaaca atccagttag catcacagag aaagaaattc ttctgcattt   2160
gctcattgca ccagtaactc cagctagtaa ttttgctagg tagctgcagt tagccctgca   2220
aggaaagaag aggtcagtta gcacaaaccc tttaccatga ctggaaaact cagtatcacg   2280
tatttaaaca tttttttttc ttttagccat gtagaaactc taaattaagc caatattctc   2340
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
gaagttgaaa ttgttgagac aggaatggaa aatataatta attgatacct atgaggattt   2520
ggaggcttgg cattttaatt tgcagataat accctggtaa ttctcatgaa aaatagactt   2580
```

-continued ggataacttt tgataaaaga ctaattccaa aatggccact ttgttcctgt ctttaatatc 2640
taaatactta ctgaggtcct ccatcttcta tattatgaat tttcatttat taagcaaatg 2700
tcatattacc ttgaaattca gaagagaaga aacatatact gtgtccagag tataatgaac 2760
ctgcagagtt gtgcttctta ctgctaattc tgggagcttt cacagtactg tcatcatttg 2820
taaatggaaa ttctgctttt ctgtttctgc tccttctgga gcagtgctac tctgtaattt 2880
tcctgaggct tatcacctca gtcatttctt ttttaaatgt ctgtgactgg cagtgattct 2940
ttttcttaaa aatctattaa atttgatgtc aaattaggga gaaagatagt tactcatctt 3000
gggctcttgt gccaatagcc cttgtatgta tgtacttaga gttttccaag tatgttctaa 3060
gcacagaagt ttctaaatgg ggccaaaatt cagacttgag tatgttcttt gaataccttा 3120 agaagttaca attagccggg catggtggcc cgtgcctgta gtcccagcta cttgagaggc 3180
tgaggcagga gaatcacttc aacccaggag gtggaggtta cagtgagcag agatcgtgcc 3240
actgcactcc agcctgggtg acaagagaga cttgtctcca aaaaaaaagt tacacctagg 3300
tgtgaatttt ggcacaaagg agtgacaaac ttatagttaa aagctgaata acttcagtgt 3360
ggtataaaac gtggttttta ggctatgttt gtgattgctg aaaagaattc tagtttacct 3420
caaaatcctt ctctttcccc aaattaagtg cctggccagc tgtcataaat tacatattcc 3480
ttttggtttt tttaaaggtt acatgttcaa gagtgaaaat aagatgttct gtctgaaggc 3540
taccatgccg gatctgtaaa tgaacctgtt aaatgctgta tttgctccaa cggcttacta 3600
tagaatgtta cttaatacaa tatcatactt attacaattt ttactatagg agtgtaatag 3660
gtaaaattaa tctctatttt agtgggccca tgtttagtct ttcaccatcc tttaaactgc 3720
tgtgaatttt tttgtcatga cttgaaagca aggatagaga aacactttag agatatgtgg 3780
ggttttttta ccattccaga gcttgtgagc ataatcatat ttgctttata tttatagtca 3840
tgaactccta agttggcagc tacaaccaag aaccaaaaaa tggtgcgttc tgcttcttgt 3900
aattcatctc tgctaataaa ttataagaag caaggaaaat tagggaaaat attttatttg 3960
gatggtttct ataaacaagg gactataatt cttgtacatt atttttcatc tttgctgttt 4020
ctttgagcag tctaatgtgc cacacaatta tctaaggtat ttgttttcta taagaattgt 4080
tttaaaagta ttcttgttac cagagtagtt gtattatatt tcaaaacgta agatgatttt 4140
taaaagcctg agtactgacc taagatggaa ttgtatgaac tctgctctgg agggagggga 4200
ggatgtccgt ggaagttgta agacttttat ttttttgtgc catcaaatat aggtaaaaat 4260
aattgtgcaa ttctgctgtt taaacaggaa ctattggcct ccttggccct aaatggaagg 4320
gccgatattt taagttgatt attttattgt aaattaatcc aacctagttc tttttaattt 4380
ggttgaatgt tttttcttgt taaatgatgt ttaaaaaata aaaactggaa gttcttggct 4440
tagtcataat tctt 4454

<210> SEQ ID NO 46
<211> LENGTH: 189
<212> TYPE: PRT
<213> ORGANISM: Homo sapiens

<400> SEQUENCE: 46

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly

-continued

```
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 47
<211> LENGTH: 1326
<212> TYPE: DNA
<213> ORGANISM: Rattus norvegicus

<400> SEQUENCE: 47

```
gccgttcatg gcggtttcgg ggtctccaac agcttctcag gttgaaatcc aaaagcctcc     60

cgaggcgggg tctgcggagt ttgagatttt tgcaggtgtg aaatgactga gtacaaactg    120

gtggtggttg gagcaggtgg cgttgggaaa agtgctttga caatccagct aatccagaac    180

cactttgtgg atgaatatga tcccaccata gaggattctt accgaaaaca agtggtgatt    240

gacggtgaga cctgtctact ggacatactg gacacagctg gacaagagga gtacagtgcc    300

atgagagacc aatacatgag gacaggcgaa gggttcctct gtgtgtttgc catcaataat    360

agcaaatcct ttgcagatat taacctctac agggagcaaa ttaagcgcgt gaaagactct    420

gatgatgtac ccatggtgct ggtagggaac aagtgtgact tgccaacaag gacagttgac    480

acaaagcaag cccacgagct ggccaagagt tatggaattc cattcattga aacctcagcc    540

aagacccgac agggtgtgga ggatgccttt tacacgcttg taagggagat acgccagtac    600

cggatgaaga agctcaacag cagtgaggat ggcactcaag gctgtatggg gctgccctgt    660

gtggtgatgt agtaagaccc tttaaaagtt ctgtcatcag aaacgagcca ctttcaagcc    720

tcactgatgc cctggttctg acatccctgg aggagacgtg tttctgctgc tctctgcatc    780

tcagagaagc tcctgcttcc tgcttcccca acttagttac tgagcacagc catctaacct    840

gagacctctt cagaataact acctcctcac tcggctgtcc gaccagagaa atgaacctgt    900

ttctccccag tagttctctg ccctgggttt cccctagaaa caaacacacc tgccagctgg    960

ctttgtcctc cgaaaagcag tttacattga tgcagagaac caaactatag acaagcaatt   1020

ctgttgtcaa cagtttctta agctctaagg taacaattgc tggtgatttc cccctttgcc   1080

cccaactgtt gaacttggcc ttgttagttt tgggggaaat gtcaaaaatt aatctcttcc   1140

cgagaataga attagtgttg ctgattgcct gatttgcaat gtgatcagct atattctata   1200

agctggcgtc tgctctgtat tcataaatgc aaacatgagt actgacgtaa gtgcatccct   1260
```

agtcttctca gctgcatgca attaaatcca acgttcacaa caaaaaaaaa aaaaaaaaaa 1320
aaaaaa 1326

<210> SEQ ID NO 48
<211> LENGTH: 189
<212> TYPE: PRT
<213> ORGANISM: Rattus norvegicus

<400> SEQUENCE: 48

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Glu Asp
                165                 170                 175

Gly Thr Gln Gly Cys Met Gly Leu Pro Cys Val Val Met
            180                 185

<210> SEQ ID NO 49
<211> LENGTH: 4470
<212> TYPE: DNA
<213> ORGANISM: Mus musculus

<400> SEQUENCE: 49
gggactgggg cgccttgggc gcctagtgat tacgtagcgg gtggggccgg aagtgccgct 60
ccctggcggg ggctgttcat ggcggtttcg gggtctccaa cagcttctca ggttgaagtc 120
caaaagcctc ccgaggcggg gtctgcggag tttgaggttt ttgctggtgt gaaatgactg 180
agtacaaact ggtggtggtt ggagcaggtg gtgttgggaa aagcgccttg acgatccagc 240
taatccagaa ccactttgtg gatgaatatg atcccaccat agaggattct taccgaaagc 300
aagtggtgat tgatggtgag acctgcctgc tggacatact ggacacagct ggacaagagg 360
agtacagtgc catgagagac cagtacatga ggacaggcga agggttcctc tgtgtatttg 420
ccatcaataa tagcaaatca tttgcagata ttaacctcta cagggagcaa attaagcgtg 480
tgaaagattc tgatgatgtc cccatggtgc tggtaggcaa caagtgtgac ttgccaacaa 540
ggacagttga cacaaagcaa gcccacgaac tggccaagag ttacggaatt ccattcattg 600
agacctcagc caagacccga cagggtgtgg aggatgcctt ttacacactg gtaagggaga 660
tacgccagta ccgaatgaaa aagctcaaca gcagtgacga tggcactcaa ggttgtatgg 720

-continued

```
ggctgccctg tgtgctgatg tagtaagaca ctttgaaagt tctgtcatca gaaaagagcc     780

actttgaagc tgcactgatg ccctggttct gacatccctg gaggagacct gttcctgctg     840

ctctctgcat ctcagagaag ctcctgcttc ctgcttcccc gactcagtta ctgagcacag     900

ccatctaacc tgagacctct tcagaataac tacctcctca ctcggctgtc tgaccagaga     960

aatagacctg tctctcccgg tcgttctctg ccctgggttc ccctagaaac agacacagcc    1020

tccagctggc tttgtcctct gaaaagcagt ttacattgat gcagagaacc aaactagaca    1080

tgccattctg ttgacaacag tttcttatac tctaaggtaa caactgctgg tgattttccc    1140

ctgcccccaa ctgttgaact tggccttgtt ggtttggggg gaaaatgtca taaattactt    1200

tcttcccaaa atataattag tgttgctgat tgatttgtaa tgtgatcagc tatattccat    1260

aaactggcat ctgctctgta ttcataaatg caaacacgaa tactctcaac tgcatgcaat    1320

taaatccaac attcacaaca aagtgccttt ttcctaaaag tgctctgtag gctccattac    1380

agtttgtaat tggaatagat gtgtcaagaa ccattgtata ggaaagtgac tctgagccat    1440

ctacctttga gggaaaggtg tatgtacctg atggcagatg ctttgtgtat gcacatgaag    1500

atagtttccc tgtctgggat tctcccagga gaaagatgga actgaaacaa ttacaagtaa    1560

tttcatttaa ttctagctaa tctttttttt tttttttttt tttttggta gactatcacc    1620

tataaatatt tggaatatct tctagcttac tgataatcta ataattaatg agcttccatt    1680

ataatgaatt ggttcatacc aggaagccct ccatttatag tatagatact gtaaaaattg    1740

gcatgttgtt actttatagc tgtgattaat gattcctcag accttgctga gatatagtta    1800

ttagcagaca ggttatatct ttgctgcata gtttcttcat ggaatatata tctatctgta    1860

tgtggagaga acgtggccct cagttccctt ctcagcatcc ctcatctctc agcctagaga    1920

agttcgagca tcctagaggg gcttgaacag ttatctcggt taaaccatgg tgctaatgga    1980

ccgggtcatg gtttcaaaac ttgaacaagc cagttagcat cacagagaaa cagtccatcc    2040

atatttgctc cctgcctatt attcctgctt acagactttt gcctgatgcc tgctgttagt    2100

gctacaagga taaagcttgt gtggttctca ccaggactgg aagtacctgg tgagctctgg    2160

ggtaagccta gatatcttta cattttcaga cccttattct tagccacgtg gaaactgaag    2220

ccagagtcca tacctccatc tccttccccc cccaaaaaaa ttagattaat gttctttata    2280

tagctttttt aaagtattta aaacatgtct ataagttagg ctgccaacta acaaaagctg    2340

atgtgtttgt tcaaataaag aggtatcctt cgctactcga gagaagaatg taaaatgcca    2400

ttgattgttg tcacttggag gcttgatgtt tgccctgata attcattagt gggttttgtt    2460

tgtcacatga tacctaagat gtaactcagc tcagtaattc taatgaaaac ataaattgga    2520

taccttaatt gaaaaaagca aacctaattc caaaatggcc attttctctt ctgatcttgt    2580

aatacctaaa attctgaggt ccttgggatt cttttgttta taacaggatc ttgctgtgta    2640

gtcctagctg gcctcaaact cacaatactc ttcctggatc aatctcccaa gtgctgggat    2700

tacaggcaca ttccaccaca cacacctgac tgagctcgtt cctaatgagt tttcattaag    2760

caaattcccc atcaccttga aactaatcag aaggggggaag aaacatttgc tatgctcctg    2820

agtgctaaca ctgggatcat tcacatgggg tttgcattcc taggcaaact aaactgctgc    2880

cttttacaac aaggctcagt catcttcctg aagctgctga gaccagcact tggtcttgtt    2940

ttgtttttaat atgtctatat gactggtggt ggatccctaa atagtttatt aattaaactc    3000

cagttaagga gaaagttact caccttgacc cgtttgacca tatcccgtgt gtgtgtgtgt    3060
```

-continued

```
gtgtgtgtgt gtgtgtgtgt gtgtgtgtgt gtgcacgcgt atgtacgtac gtatgtatgt   3120

aggtatgtag gtggtttcca gtataaacac agaaacaaat ggagccaatt caggtttcag   3180

atgcccttac taacatatat tcccacgggg tgtgggtttt ggcacaacag tgacaaactt   3240

aaaagccaag taagagccgg gcgtggtggc gcacgccttt aatcccagca cttgggaggc   3300

agaggcaggc ggatttctga gttctaggcc atcctggtct acagtgagtt ccaggacagc   3360

cagtgctaca cagagaaacc ctgtctcgaa aagccaaaaa aaaaaaaaaa aaaaaaaaaa   3420

aaaagccaag taggtccagt tggtatagta tcaaagtgtt tttagagtaa ttagtgaagg   3480

tctgctttac ctcaaagttg cagagcctct cttcctgagt ttaagtgcct ggccggcagt   3540

cacaaattaa catgttgctg taaggcagtt agttgaagct ttgttcacac attggagagt   3600

atgaaaataa agtgttctaa gagcgctgat actggatctg tgtaaacctg gtaaatgccg   3660

tttgtccagg acttagcgtg tgtgagttgg tagctcagta cgagtttact agttccgcag   3720

tgtgtacaat ggaggcgggt ttgttttagc tggccacctg tagaatcagc ctttaaactg   3780

ctgtgaactt tgtcatgact tgaatatgaa gatagacaaa aactctgtaa agacaaatgt   3840

ttgttttccc ccttacagaa cgtgtgagct tggttttatc ttcctttgta tttagtcata   3900

acctctcaag ctggcagctc cgaccaagga tcagaagctg tgtgcgttcc acctggtgga   3960

attagctcag ctctatatga gaagtggagt taatggaaaa cgtgttgact gggtggtttc   4020

tatttaaaag agtgatgata attcttgaac agtagttttt attttgctat ttctttaagc   4080

tgactgatgt gccacaaaat tattttaagg tatttgtgtt ttaagagtgt tctcatgaga   4140

ttagttgtag atatttttta aaatacaact ggtttttaaa atctgagtat tgctctaagc   4200

aagtgtttag actcttacgg gaaggtgggt ggaagttgtt tggcttccgt atttccatgc   4260

gtgccgtcag acataggtca gaacgccaac tgtgcatcct gctgtttaaa gacctcttgg   4320

cctctgtgac cctcatgaag ggctgatat  tttaagttga ctgtttgatt gtaaattaat   4380

cctttctaat ttttaaagac ttgcttgact gttttccttg ttaaataatt ttaaaaaaat   4440

aaaaaactgg aagttctttg cttaactgta                                    4470
```

```
<210> SEQ ID NO 50
<211> LENGTH: 189
<212> TYPE: PRT
<213> ORGANISM: Mus musculus

<400> SEQUENCE: 50

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125
```

```
Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Leu Met
            180                 185


<210> SEQ ID NO 51
<211> LENGTH: 570
<212> TYPE: DNA
<213> ORGANISM: Cavia porcellus

<400> SEQUENCE: 51

atgactgagt ataaactggt ggtggttgga gcaggtggtg tcgggaaaag tgcactgacc      60

atccagctaa ttcagaacca ctttgtcgat gaatatgatc ccaccataga ggattcttac     120

cgaaaacagg tggttataga tggtgaaact tgtctgttgg atattctgga tacagctgga     180

caagaggagt acagtgccat gagagaccaa tacatgagga caggcgaagg cttcctctgt     240

gtgtttgcca tcaataatag caaatcattt gcagatatta acctctacag ggagcagatt     300

aaacgagtaa aagactcaga tgatgtacct atggtgctgg tagggaacaa gtgtgatttg     360

ccaacaagga ctgttgacac aaaaacaagcc catgaactgg ccaagagtta cgggattcca     420

ttcattgaaa cctcagccaa gaccagacag ggtgttgaag atgcatttta cacactcgta     480

agagaaatac gccagtacag aatgaaaaaa ctcaacagca atgatgatgg gactcaaggt     540

tgtatggggt tgccatgtgt ggtgatgtaa                                      570


<210> SEQ ID NO 52
<211> LENGTH: 189
<212> TYPE: PRT
<213> ORGANISM: Cavia porcellus

<400> SEQUENCE: 52

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160
```

```
Arg Glu Ile Arg Gln Tyr Arg Met Lys Lys Leu Asn Ser Asn Asp Asp
                165                 170                 175

Gly Thr Gln Gly Cys Met Gly Leu Pro Cys Val Val Met
            180                 185


<210> SEQ ID NO 53
<211> LENGTH: 1220
<212> TYPE: DNA
<213> ORGANISM: Cavia porcellus

<400> SEQUENCE: 53

gttccggggt cctcaacgtt tctcagggtt gagattctat atccttttga agctggggcg     60

gcagagcttg aggttcttgc tggtgtgaaa tgactgagta taaactggtg gtggttggag    120

caggtggtgt cgggaaaagt gcactgacca tccagctaat tcagaaccac tttgtcgatg    180

aatatgatcc caccatagag gattcttacc gaaaacaggt ggttatagat ggtgaaactt    240

gtctgttgga tattctggat acagctggac aagaggagta cagtgccatg agagaccaat    300

acatgaggac aggcgaaggc ttcctctgtg tgtttgccat caataatagc aaatcatttg    360

cagatattaa cctctacagg gagcagatta aacgagtaaa agactcagat gatgtaccta    420

tggtgctggt agggaacaag tgtgatttgc caacaaggac tgttgacaca aaacaagccc    480

atgaactggc caagagttac gggattccat tcattgaaac ctcagccaag accagacagg    540

gtgttgaaga tgcattttac acactcgtaa gagaaatacg ccagtacaga atgaaaaaac    600

tcaacagcaa tgatgatggg actcaaggtt gtatggggtt gccatgtgtg gtgatgtaac    660

aagatattta acaaagttct atcagaaaag agccactttc aagctgcact gataccctgg    720

tcctgacttc cctggaggag aagtatccct gttgctctct tcatctcaga gaagctcctg    780

ctgtttgtcc acctctcagt gtatgagcac agtctctgct tgagaacttc tcagaataac    840

tacctcctca cttggttgtc tgaccagaga aatgcacctc ttgttaattc cccaataatt    900

ttctgccctg ggctctcccc aacaaaaaac aaacacttct gccatccaaa aagcaacttg    960

gtctgaaaca gaaccaaact gtagattgaa attctcttaa aaagtcttga gctctaaagt   1020

tagcaaccgc tggtgatttt tattttcctt tttatttttg aacttggaac tgacctatgt   1080

tagattttgg agaaatgtca taaagtactg ttgtgccaag aagataatta tgttgctgaa   1140

tggttgattt atagtgttat cagctatatt ttacaaactg gcatctgctc tgtattcata   1200

aatacaaaaa tgaagccagg                                                1220


<210> SEQ ID NO 54
<211> LENGTH: 189
<212> TYPE: PRT
<213> ORGANISM: Cavia porcellus

<400> SEQUENCE: 54

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80
```

-continued

```
Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Asn Asp Asp
                165                 170                 175

Gly Thr Gln Gly Cys Met Gly Leu Pro Cys Val Val Met
            180                 185


<210> SEQ ID NO 55
<211> LENGTH: 1307
<212> TYPE: DNA
<213> ORGANISM: Canis familiaris

<400> SEQUENCE: 55

tgattacgta gcgggcgggg ccggaagtgc cgctccctag tgggggctgt tcatggcggt      60

tccggggtct ccaacctttc tcctagttgt ggtcctaaat acgtcggaag cggaggcggc     120

gaagcttgag gttcttgctg gtgtgaaatg actgagtaca aactggtggt ggttggagca     180

ggtggtgttg ggaaaagcgc actgacaatc cagctaatcc agaaccactt tgtagatgaa     240

tatgatccca ccatagagga ttcttaccga aaacaggtgg ttatagacgg tgaaacctgt     300

ctgttggata tactggatac agctggtcaa gaagagtaca gtgccatgag agaccaatac     360

atgaggacag gcgaaggctt cctctgtgta tttgccatca ataatagcaa atcatttgca     420

gacattaacc tctacaggga acagattaag cgagtaaaag attcagatga tgtacctatg     480

gtgctagtag gaaacaagtg tgatttgcca acaaggacag ttgacacaaa acaagcccat     540

gaactggcca agagttatgg gattccattc attgaaacct cagccaagac cagacagggt     600

gtcgaggatg ccttttacac actggtaaga gaaatacgtc agtaccgaat gaagaaactc     660

aacagcagtg atgatgggac tcaaggttgt atggggttac catgtgtggt gatgtaacaa     720

gacactttta aagttctagc atcagaaaag agccactgtc aagctgcact gacaccctgg     780

tcctgacttc cctggaggag aagtattcct gttgctatct tcagtctcac aaagaagctc     840

ctgctacttc cccaactctc agtagatcag tacaatgttc tctatttgag aagttctccg     900

aacaactacc tcctcacttg gttgtctgac cagagaaatg aacctcttgt tccttcccgc     960

tgtttttcca ccctgaattc tcccccaaca cacataaaca aacctctgcc atcccaggtt    1020

tttcatctga aaaataattc atgctctgaa acagagaaca aaactgtaga catgaaattc    1080

tgtaggaaac aaggtcttga gctcaaaagt agcaactgct ggtgaccttt ttttcccccc    1140

tttttactgt tgaacttgga actatgttgg tttttggaga aatgtcataa gttactgttt    1200

tgctgagaat atagttaagt tgacatttgg tttgtttgta atatcattag ctattttcta    1260

taaattggca tctgctctgc attcataaat acacgagtga attctga                  1307


<210> SEQ ID NO 56
<211> LENGTH: 189
<212> TYPE: PRT
<213> ORGANISM: Canis familiaris
```

<400> SEQUENCE: 56

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 57
<211> LENGTH: 3104
<212> TYPE: DNA
<213> ORGANISM: Felis catus

<400> SEQUENCE: 57
aaaaaataaa taaatttaag aaaccatttt aaaattatgc acagttgcag cctggaaaac 60
ttaaggtggc gccttatagt atcaatctta ggagctttat ttggtgcatt taacgcaact 120
ggtaattgca aaatccactt cgcctgtgta agtgaaaaat atagactgtt atcttgttgg 180
ccctatgaaa ttctgcactt ggtatttagc atatactcta ccttcattac tatctggcaa 240
gatgttctgc cttagcactc agttgcattc ttttcctttt ctttcctgtt cattatgctt 300
taattctgag gaccatatga gggtagaata tattaaaaat tacaaaaatt ataaaaattt 360
gtataggcaa accatttcct taagttgatg gccaaatgtt aaaatgttat ttttcatatc 420
atttataatc ttgtcacagt ccacttaacg aagtttggtt agatttcagt gaaaattatc 480
ttccagagta gttttttttt ttttttcctg ggattaggga ggggggtaac tttactgcaa 540
ttagtatgta tggtgcagaa tttcatgcaa atgaggtgtg ccagcagtgt ggtaatttaa 600
tcgtatttaa acaaaaacaa acaaaaaaaa aacgaatgca caaacttgct gctgcttaga 660
tcactgcagc ttctaggacc cagtttcttt tactgatttc aaaacaaaac aaaacaaaaa 720
aataaaaaaa gttgtgcctg aaatgaatct tgtttttttt ataagtagcc gcctggttcc 780
tgtgtcctgt gaaatacagg cacttgaccc ttggtgtagc ttctgttcga ctttatatca 840
cgggaatgga ttggtctgat ttcttggccc tcatcttgaa ttggccacat ccagggtccc 900
tggccagtgg actgaaggct ttgtctaaga ggacaagggc agctcagggg atgtggggga 960
gggcgctttt atcttccccg ttgtcgtttg aggttttgat cttctctggg taaagaggcc 1020

```
gtttatcttt gtaaacacaa aacatttttg ctttctccag ttttctgtta atggcgaaag   1080
aatggaagcg aataaagttt tactgatttt tgagactcta gcacctagcg ctttcatttt   1140
tgaaacgtcc tgtgtgggag gggcgggtct gggtgcggcc cgccgcgtga ctcctgagtc   1200
gggggcccac gtggctgggg cggggactcg gacgccccgg gcgccgactg attacgtagc   1260
gggcggggcc ggaagtgccg ctccctagtg ggggctgttc atggcggttc cggggtctcc   1320
atcctttttc ccagttgttc taaatcagtc ggaagcggag gcagcgaagt ttgaggttct   1380
cgctggtgtg aaatgactga gtacaaactg gtggtggttg gagcaggtgg tgttgggaaa   1440
agcgcactga caatccagct aatccagaac cactttgtag atgaatatga tcccaccata   1500
gaggattctt accgaaaaca ggtggttata gacggtgaaa cctgtctgtt ggacatactg   1560
gatacagctg gtcaagaaga gtacagtgcc atgagagacc aatacatgag gacaggcgaa   1620
ggcttcctct gtgtatttgc catcaacaat agcaaatcat ttgcagatat taacctttac   1680
agggaacaga ttaagcgagt aaaagactcc gatgatgtac ctatggtgct agtaggaaac   1740
aagtgtgatt tgccaacaag gaccgtcgac acaaaacaag cccacgaact ggccaagagt   1800
tatgggattc cattcattga aacctcagcc aagaccagac agggtgttga agatgccttt   1860
tacacactgg taagagaaat acgtcagtac cgaatgaaga aactcaacag cagtgatgac   1920
gggactcaag gttgtatggg gttaccgtgt gtggtgatgt aacaagatac ttttaaagtt   1980
ctagcatcag aaaagagcca ctgtcaagct gcactgacac cctggtcctg acttccctgg   2040
aggagaagcg ttcctgttgc tattttcagt ttcacaaaga agctcctgct atttccccaa   2100
ctctccgtag atcagtacat tattctctgt ttgagaagtt ctccgaataa ctacctcctc   2160
acttggttgt ctgaccagag aaatgaacct cttgttactc cccactgttt ttccaccctg   2220
gttctccccc agcacatata aacaaacctc ccaggttttt catctgaaaa gtaattcatg   2280
ctctgaaaca gagaaccaaa ctgtagacat gaaattctgt aggaaacaat gtcttgagct   2340
ctaaagtagc aactgctggt gacttttttt tttttttttt ccttttttact gttgaacttg   2400
gaactatgtt ggtttttgga gaaatgtcgt aagttactgt tttgctgagt atatagttaa   2460
gtttaccatt cggtttgttt gtaatgtcat tggctatact ctgtacctgg catctgctct   2520
gcattcataa atacaaaagt gaattctgac ttttgagtct atcctagtgt tctcaacttc   2580
cacataatta aatctaactt ttgcagcaaa gtgccttttt cctagaagtg gtttgtagat   2640
ttgctttata atactttggt ggaatagatg tctcaaaaac cattatacat gaaaatgaat   2700
gtctgagata cgtctatgat ctgtctacct ttgagggaaa aatataccga cataatagca   2760
gatgccatgt cttacgtgta tgaagttgga tttccagaga cctgatttgg gtctcttcca   2820
agagaaagat gaaactggaa acaattatga ataacttcac ttaattttta cctaatctct   2880
acttcggggt gggagggcag ggagtaggtt accacttaca aaatatatgc aatttgtttc   2940
ttctagctta ctgataatga acttccattc ttatttaaat ttaggtcata tcctaaagct   3000
ttacatttgc aggtgttcga aattgtaagt ttaatgcagt tttatttaat agctatgatc   3060
aatgattttc aagcctcaga tgtattaacg gacacatttt cact                      3104
```

<210> SEQ ID NO 58
<211> LENGTH: 189
<212> TYPE: PRT
<213> ORGANISM: Felis catus

<400> SEQUENCE: 58

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 59
<211> LENGTH: 4283
<212> TYPE: DNA
<213> ORGANISM: Bos taurus

<400> SEQUENCE: 59
ggccgctccc tagtgggggc tgttcatggc ggttccgggg tctcccaaca attttcccgg 60
ttgtggtcgt aatctatccg aagtggaggc agtggagcta gaggttcttg ctggtgtgaa 120
atgactgagt acaaactggt ggtggttgga gcaggtggtg ttgggaaaag tgcactgaca 180
atccagctaa tccagaacca ctttgtagat gaatatgatc ccaccataga ggattcctac 240
cgaaaacagg tggttataga tggtgaaacc tgtctgttgg acatactgga tacagctgga 300
caagaggagt acagtgccat gagagaccaa tacatgagga caggcgaagg cttcctttgt 360
gtgtttgcca tcaataatag caaatcattt gcagatatta acctctacag ggaacagata 420
aagcgtgtaa aggactcgga tgatgtacct atggtgctag taggaaacaa gtgtgatttg 480
ccaacaagga cagttgacac aaaacaagcc catgaactgg ccaaaagtta tgggattcca 540
ttcattgaaa cctcagccaa gaccagacag ggtgttgaag atgcctttta cacactggta 600
agagaaatac gtcagtaccg aatgaaaaag ctcaacagca gtgatgatgg cactcaaggc 660
tgtatggggt tgccgtgtgt ggtgatgtaa caagatactt ttaaagttct cacatcagaa 720
aagagccact gtcaagctgc actgacaccc tggtcctgac ttccctggag gagaagtatt 780
cctgttgcta tcttcagttt caaaaagaag ctcctgctat ttccccaact ctcagtagat 840
caatataata ttctctattt gagaagttct caagaataac tacctcctca cttggttgtc 900
tgaccagaga attgaacctc ttgttactcc cagtattttt ccaccctggg ttctccccca 960
gcacacacaa acgcacctct gccacccagg tttttcatct gaaaagcaat taatactctg 1020
aaacagagaa ccaaactgta gaaacatgaa attctgtaga aaacaatgtc ttgagctcta 1080
aagtagcaac tgctggtgat tttttttttt tttttttcct ttttattgtt gaacttggaa 1140
ctatgttggt ttgtggagaa atgtcataaa ttactgtttt gctgagaata tagttaatgt 1200
tgctctctgg tttgtttgta atgttatcag ctatattcta taaactggca tctactctgt 1260
atttagaaat acaaaaatga atactgacct tttgagtcta ccctcatctt ctcgactttc 1320
ttgtaattaa atgtaacttt cacgatgaag tgccttttgc ctgggagtga ctcgtagact 1380
tcctttaaaa tacttcagtg gaatagatgt ctcagaaact gttatacata agaataaatg 1440
tctgagatat gtctatgacc catctagctt tgagggaaag atataccaat atgatagcag 1500
atgccatttc ttacatctat aacgttgatt ttctggagac ctattttggg gctctccgag 1560
agaaagatga gactataaat gattaggaat aatttcactt aatttttaca taacctccac 1620
tttttgtttt gtagtttact acctgcaaaa catataattt gattcctttt agcttacaga 1680
taatctaatg ttaaatgaac ttccattcat attttaattt ggatcatatc aggaagtcta 1740
catttgcagg tgttcaaaaa ttgtaaaagt gtgatgcagt tttatttaat agctgtgatc 1800
aatgattttc aagcctcaaa tatgttaata gacacatttt cactgtatat catggtatta 1860
ataattattg atgtatataa ttgtccttgg tccccttctc tgttcatcac ctcatggcaa 1920
tggcttgatt aattatttca gctgagtaaa gcatggtgct aatagaccag ggtcacagtg 1980
tcaaaacttc agtgagccag taagcatcac agagaaagaa attctttcac atttgctcac 2040
cattaactcc agctaatagt tttgccagat gtgtgtggtt agtcctgcaa ggaaaggaga 2100
agtcagttaa tacaaattct taaccaggac tggaaaaact tgttttcctg agaagggtca 2160
gcttagaagt ctttatctgg actctatttt tagccacatg gaaatcaaat taagctgatc 2220
tttttctca agtttttgag agtgaggatg cctcagatca acatttttaa aatattcttt 2280
attcttacgt tcttttaagg gtttaaaaca acgttgagta attagtctgg gcataccagg 2340
taacaagctg ataagtttgt gctgaacaag aagtagcctt tggattgaaa ttgctgtttt 2400
gagaagggat agaaaatata attaataatt atgagacttg acttttctat ttgcagataa 2460
tatcctgata attctgatga aaatagactt ggataatttt tgataaaaga atcgttccaa 2520
aatggccact tgctgttctt gtcttctaat gtgtaaatac ttactgaggt cctcttctaa 2580
tatgagttgt catttattaa gcaaattcca cattgccttg aaatgaattc ggaagagaag 2640
aaaaagtcat agtataccca gagaatgaaa aatccagaga attgtgctcc ttagtgttaa 2700
ttctgaagcc ttcgtagtcc acacccatag acagaaactc tctgccactt tgcttctgct 2760
cctcttggag cattgcgctg tcatttcctt gaggatagat tgaggcttgt caactcagtt 2820
gtattgtctt cctcctcttc ctcttgtctg tgtgactgac agtgtgactc ttactaatgt 2880
cagatgcggg gatgcgggga ggtggggggg agtagctcat tttaggctct tgcacccttt 2940
accgttgtat gtgtgtgtct tttagttttc tcaagaatgt tctaagcaca gaagtatcta 3000
aatggggcca aaattcagac ttgaaaatgt tcttttaata gcttcttaaa aagttacact 3060
ttggtgtgaa ttttggcagg atagagtgac aaactcttaa acgctgaata acttcagtta 3120
gtgtgttata gtttttagaa tatgtttgtg attgctgaaa acaattatag tttacctcaa 3180
aatctgaaag tctctttccc caagttaagt gcctggccag ctgtcaaaga ttacatatta 3240
ctttatgttt gtttgttttt taaaggttgc acattcaaga ttgtgaaaat aaggtgttct 3300
gtctgaaagc taccatgcct gtctgtaaat gaatccactg agtgctgtac ttgttccaac 3360
agcttactac agaatgctac ttggtaatat catactcgtt acagttttca cttcaggagt 3420

```
gtactaggta gaatgatcct gtgtgtattg tagtgggctc catgtttagt cttttcagca   3480

tcctttaaac tgctgtgaat ttttgtcttg acttgaaagc aaggatagag aaacacttta   3540

aagagatact ttgggttttt ttccattcca gaattggtga gcatagttag attttgcttt   3600

acatttacag tcatgaactc ttaagctggc agctacaacc aagaaccaaa agagggtgca   3660

ttctgcttct tgtaattcat ctttgctaat aaattatgag aagcaaagat aattaattag   3720

agaaactatt ttatttgggt ggtttctata aacaagggac tataattctt aaacattatt   3780

tttcattttt gctgtttctt taagaaacct aatgtgccac aacattattt taaggtgttt   3840

cttaaaagaa ttgtttttaa aagtgttctc attttcagag taattgtaga tatatttcaa   3900

aatataactg ataattttta aaggcctgag tactgaccta agaagcagtt gtatgaattc   3960

tctgggggga agggaggagc tcagtgaaag ttgtatgact tttatatttc tgtgccatca   4020

aataaaggta aaaatgtctt ttgtgcagtt ttgctgttca aacagaaact attggcctcc   4080

ttggccctaa atgaaagggc tggtatttta agttgactat tttattgtaa attaatccat   4140

cttaattttt ttaaatttgg ttgaatgttc tcttgttaaa tgtttaaaaa ataaaaaactg   4200

gaagttcttt gcttagtcat aaaaaaaaaa aaaaaaaaaa aaaaaaaaaa aaaaaaaaaa   4260

aaaaaaataa aaaaaaaaaa aaa                                           4283
```

<210> SEQ ID NO 60
<211> LENGTH: 189
<212> TYPE: PRT
<213> ORGANISM: Bos taurus

<400> SEQUENCE: 60

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 61
<211> LENGTH: 4825
<212> TYPE: DNA
<213> ORGANISM: Gallus gallus

<400> SEQUENCE: 61

```
gcgccgggac cggaagccgg aagctttgca gaagggtgtt ccgcgttcgc ggtgcgggag     60
cggtcagccg gggtggcggg gctggggccg gccggggcag gcggctccgc gctccgcact    120
gggccgctgg gagggcgatg actgaataca agctggtggt ggtgggagct ggcggcgtcg    180
ggaagagcgc gttgaccatc cagctcatcc agaaccactt cgtggacgag tacgacccca    240
ccatcgagga ttcgtacaga aagcaggttg tcatcgatgg agagacgtgc ttgttggaca    300
ttctggacac tgcaggacag gaagaataca gtgctatgcg tgatcagtac atgagaactg    360
gggaaggatt cctttgtgtg tttgccatta acaacagtaa atcattcgct gatattaacc    420
tttacagaga gcaaatcaag agagtgaaag attcagacga tgtgccaatg gtgctggtgg    480
ggaataagtg cgatttgcca acaaggacag tagacaccaa acaggctcaa gagttagcaa    540
aaagctacgg cattcccttc atagagacat cagccaaaac gagacagggt gtggaagatg    600
cgttttacac actggtgagg gagattcggc agtaccggat gaaaaagctc aacagcaacg    660
aagatgggaa tcagggctgt atggggttgt cctgcattgt gatgtgataa gatgccaggt    720
tcagatgtag ctgctggaca agtctcgatg ctactgtatt gtgtctcatg ctgatgccct    780
gcagtatttt ggtgccagcg accagactct tggtaccagt taattagctc aggatccttt    840
cctgtgctcc atctgaagaa aacatctctg gtatctacct ccttgctcag ctcacagagc    900
agtcatatct cttggtgtac tgggattctt ttctagctgt gttgtctggg tttgttcaag    960
aagaaaacca gtcacaagaa aagtgaatta cagagactaa atgctgtgaa aaagatcaca   1020
ctttacctcc agagtaaaag ctagaagtgg cgtttgaccc ctttgcattg gattcagatt   1080
tgcggtgttg tcagaggagt ggcagaagta attttgccat tacaaaggtt tctgtcacca   1140
gtcggattgg tatctgctgt ctgtgcaccc acacagtgta tctgcaacat ctgcattgtg   1200
ccagaagtat cacttaactg atgaactgat cctttatttt tctgtaataa aaaggagata   1260
tctttgctaa cttaagtgcc tgtttgctca gaaggttgga ggttgtatgc tgttcccttg   1320
ggctgaggag aaccccaagg atgaatttct tgggtgctca ttgtcttgag caggcaagtt   1380
ttgtgtgggt gatctctttt catggcagga tattaaaatg ggaatttgta gtctggaaga   1440
tggagcagct gtttgtgaga ctcttgagtt agggagagaa atgtatacca cgtctgttct   1500
cgatccatca gaatggatcc atccacctct ttgtgtgtgg aactgtgtat agtctgtatt   1560
ggttttctac agcacttgga tctctttgga ccaaattagc gagctgttca ttttaacata   1620
actgccagta tttatagaca atttcttacg gacagataat gaatttagaa actggaggtt   1680
actttgggca gctgttcctc agctctgtct gtaacttgca aattattctg agttattttc   1740
tgcagaacct ccttccttat cacgggagga gcctgggagt tgaggttgac tgtaattggg   1800
tcaatggttg tcacagactt aaggtgtcca ggctgattgg aggaggcact gagccctaac   1860
agagcactga gctgacttct aattgcagca tccttgcaaa atgaggaagg gagttcagtg   1920
atgtctgcac tgaagatgta tgatacactg atagcagttc tgggtatgtt gtaacagctt   1980
caaagtagaa ccgcagtact gcgtgagctg tgtgacttct tcctagaaca cagcactgtc   2040
accccatatg gttgggacgt gcaggtgaga ccaacaccta ccaggttccc tggcgtaccg   2100
tggccttctc agttcttgtg ccagtgatac tgggttctgt tctgtggtgt cagacagcgt   2160
cctgtagcaa agctgaattc ccacttagtc tggtgagaga ataaagagcc atcagccaac   2220
agagggagcg ttcattctgc tggagcagtg cgagctgtaa gcattacgag aggcgtagtt   2280
```

-continued

```
tcagtttgtt gcagtcaggt tcctatattt tcaaagctga aatcagaaat aagtaaatac   2340
ggagaaaata agctgttgct tttaatgctc tttcctccac taattgtact cttaattttc   2400
ttcttgggag gccgaggatc catctgcata actttagctg tgatgctcca gataagtgtt   2460
tagaattcat tttatctttg actgatggga ctgataagaa gttaacgcac aatattttta   2520
catacaacat cgttttccag tgacctcctg agcggtggga agcattatgg gatagcaccg   2580
gctgtgactc gagttcattt gaaggcgatc tcttgcctgc aggttaaatg ggacggagtc   2640
agaatcactg tgagccgtct gtaatcagca aacagtctgt gggcttttct tactgtgttc   2700
tctctgtttg ccttagtttg gtgcaggaag agttccttgt gacagcgtcc tttgaggtgt   2760
gttgcaggag ctgaccattt gctccttgag ctgtgtgatg aactgttgtc cacttaatgg   2820
agttacagaa gcagcttctg ggagtcgcat ctggtcgcat acattcagtg ttttgggaag   2880
ctgtcagtgt ggtgtttgca ctgtgtttga atggtgttca tggtgggtct gttatgctcc   2940
tggatgattt ggggagatgt ggggctgctt ccgtggcaga caggatcagc tcagggcgct   3000
gctgcctatg gctgtgggaa acctcacagt tggtgtttga atagtggcca agtatgtcaa   3060
ttaaaaatac attttgaagg gaggtttgtc atagctctgt actttggcat gctctgctta   3120
ctgaaaacat actagctgta gctcaaaaaa agttgtgaat cctcagaata atacaggagc   3180
tggcaattgt ggctgctttc tctttgtgtt ccttttctct tgggttggat gaagctttaa   3240
aaaggaagga gccctggtga gggttggtca gtgtgcattt cattcttgga accagagagg   3300
aagttgcatc aactttcagg acgctgcaga gctcacttgc acaggtggtg ctccagtcta   3360
tgtgattttt ggggtcaaat cttgagatga tcttacaaaa tcagattttg tacccatcat   3420
gagcatgagg tgagtggttg tgctcggttt ctagctgcat gtatgtatac agacacgtgt   3480
atgcagacat gtctatgtgt gagtagttcg agtcagtcaa ggttactggc agcacctaaa   3540
gcgtatgcac cacataatgc atgcaggcaa aagtcctatc ttaggagcca tctcttcatg   3600
ggtttgggtt tatataggca gtatttttaa acagaatatc cgaagcactt tctggagttc   3660
tgtggtaatg cagtgacacc tatttggatg aaggaagatg tgtctgagga gcacgtaagc   3720
agatttgctg ccctaacaga gaggttttgg taaccgtgga aaaggttttc tcctggatct   3780
gtgtgtgctc ttggtgagct gcaatccatg acagggcaca accagatgag aaggaaaccc   3840
ggccatccca tgcttgagca cagctctgac tcagtagttc caccagatgt gccctttcag   3900
tcaaagtgtt ctgatctctt agagctttct gtagttcaag ttaccactca ctctccagct   3960
tgctcggtta atgtctgttg gcggcgttga gttggacttg ggaaaggtgt gtgtggtagg   4020
aacaagcaga gtgtgatgtg cttctgttat caggacttaa gctagagtgg ttggcagata   4080
ggaaatgcag ctattccttg aaagcaagca gatcatggat ggtcagccaa actgccctgg   4140
ctttggtggg agctgcactg cagaaggacc aaaccccaac aagatttggc acatttgttt   4200
agaagataag cacagatggt tttgcacaag gcagctcctc ataatggtgg ctttgtagat   4260
ttagtccaaa tgttcttatt tagatctagc agcacatcac tgtgtccgtg cccatctaac   4320
ctcgctatcc taagtagagc agaccccaaa caaccttgtt caaaaactac cagtgcaaat   4380
aactgaacta aatatttgtt actgctgact gagaacagct gttcgagtgt agcattgtgg   4440
cttgttaatg tgagtgcccc aactctatgg tcttattaaa gaaacccaaa cattgctcag   4500
attttgttct tattgtcatc ataagacttg aatagtgatg gtaatgctta cgtagacgtg   4560
tcttgtgagt gcacttcagt gatttagaaa gaactggatt tcaagcaact ttggacctgt   4620
ggggggaggg agattaatga aggtttgaat cacattctaa ttctatgtac agtccttcat   4680
```

tactccacaa gcctaaatcc tatacagcct ccaggatagc tggaaactgt tgagatctgg 4740 acttttttttt tttaatccaa gggctaactt gttgtaactt ggtataatta tctgctttcg 4800
gaaatgcatc tctgttggtt tgaaa 4825

<210> SEQ ID NO 62
<211> LENGTH: 189
<212> TYPE: PRT
<213> ORGANISM: Gallus gallus

<400> SEQUENCE: 62

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Ser Lys Ser Phe Ala Asp Ile Asn Leu Tyr
85 90 95

Arg Glu Gln Ile Lys Arg Val Lys Asp Ser Asp Asp Val Pro Met Val
100 105 110

Leu Val Gly Asn Lys Cys Asp Leu Pro Thr Arg Thr Val Asp Thr Lys
115 120 125

Gln Ala Gln Glu Leu Ala Lys Ser Tyr Gly Ile Pro Phe Ile Glu Thr
130 135 140

Ser Ala Lys Thr Arg Gln Gly Val Glu Asp Ala Phe Tyr Thr Leu Val
145 150 155 160

Arg Glu Ile Arg Gln Tyr Arg Met Lys Lys Leu Asn Ser Asn Glu Asp
165 170 175

Gly Asn Gln Gly Cys Met Gly Leu Ser Cys Ile Val Met
180 185

<210> SEQ ID NO 63
<211> LENGTH: 2603
<212> TYPE: DNA
<213> ORGANISM: Homo sapiens

<400> SEQUENCE: 63
aggcgaggct tccccttccc cgcccctccc ccggcctcca gtccctccca gggccgcttc 60
gcagagcggc taggagcacg gcggcggcgg cactttcccc ggcaggagct ggagctgggc 120
tctggtgcgc gcgcggctgt gccgcccgag ccggagggac tggttggttg agagagagag 180
aggaagggaa tcccgggctg ccgaaccgca cgttcagccc gctccgctcc tgcagggcag 240
cctttcggct ctctgcgcgc gaagccgagt cccgggcggg tggggcgggg gtccactgag 300
accgctaccg gcccctcggc gctgacggga ccgcgcgggg cgcacccgct gaaggcagcc 360
ccggggcccg cggcccggac ttggtcctgc gcagcgggcg cggggcagcg cagcgggagg 420
aagcgagagg tgctgccctc cccccggagt tggaagcgcg ttacccgggt ccaaaatgcc 480
caagaagaag ccgacgccca tccagctgaa cccggccccc gacggctctg cagttaacgg 540
gaccagctct gcggagacca acttggaggc cttgcagaag aagctggagg agctagagct 600

-continued

```
tgatgagcag cagcgaaagc gccttgaggc ctttcttacc cagaagcaga aggtgggaga    660

actgaaggat gacgactttg agaagatcag tgagctgggg gctggcaatg gcggtgtggt    720

gttcaaggtc tcccacaagc cttctggcct ggtcatggcc agaaagctaa ttcatctgga    780

gatcaaaccc gcaatccgga accagatcat aagggagctg caggttctgc atgagtgcaa    840

ctctccgtac atcgtgggct tctatggtgc gttctacagc gatggcgaga tcagtatctg    900

catggagcac atggatggag gttctctgga tcaagtcctg aagaaagctg gaagaattcc    960

tgaacaaatt ttaggaaaag ttagcattgc tgtaataaaa ggcctgacat atctgaggga   1020

gaagcacaag atcatgcaca gagatgtcaa gccctccaac atcctagtca actcccgtgg   1080

ggagatcaag ctctgtgact ttggggtcag cgggcagctc atcgactcca tggccaactc   1140

cttcgtgggc acaaggtcct acatgtcgcc agaaagactc caggggactc attactctgt   1200

gcagtcagac atctggagca tgggactgtc tctggtagag atggcggttg ggaggtatcc   1260

catccctcct ccagatgcca aggagctgga gctgatgttt gggtgccagg tggaaggaga   1320

tgcggctgag accccaccca ggccaaggac ccccgggagg ccccttagct catacggaat   1380

ggacagccga cctcccatgg caatttttga gttgttggat tacatagtca acgagcctcc   1440

tccaaaactg cccagtggag tgttcagtct ggaatttcaa gattttgtga ataaatgctt   1500

aataaaaaac cccgcagaga gagcagattt gaagcaactc atggttcatg cttttatcaa   1560

gagatctgat gctgaggaag tggattttgc aggttggctc tgctccacca tcggccttaa   1620

ccagcccagc acaccaaccc atgctgctgg cgtctaagtg tttgggaagc aacaaagagc   1680

gagtcccctg cccggtggtt tgccatgtcg cttttgggcc tccttcccat gcctgtctct   1740

gttcagatgt gcatttcacc tgtgacaaag gatgaagaac acagcatgtg ccaagattct   1800

actcttgtca tttttaatat tactgtcttt attcttatta ctattattgt tcccctaagt   1860

ggattggctt tgtgcttggg gctatttgtg tgtatgctga tgatcaaaac ctgtgccagg   1920

ctgaattaca gtgaaatttt ggtgaatgtg ggtagtcatt cttacaattg cactgctgtt   1980

cctgctccat gactggctgt ctgcctgtat tttcgggatt ctttgacatt tggtggtact   2040

ttattcttgc tgggcatact ttctctctag gagggagcct tgtgagatcc ttcacaggca   2100

gtgcatgtga agcatgcttt gctgctatga aaatgagcat cagagagtgt acatcatgtt   2160

attttattat tattatttgc ttttcatgta gaactcagca gttgacatcc aaatctagcc   2220

agagcccttc actgccatga tagctggggc ttcaccagtc tgtctactgt ggtgatctgt   2280

agacttctgg ttgtatttct atatttattt tcagtatact gtgtgggata cttagtggta   2340

tgtctcttta agttttgatt aatgtttctt aaatggaatt attttgaatg tcacaaattg   2400

atcaagatat taaaatgtcg gatttatctt tccccatatc caagtaccaa tgctgttgta   2460

aacaacgtgt atagtgccta aaattgtatg aaaatccttt taaccatttt aacctagatg   2520

tttaacaaat ctaatctctt attctaataa atatactatg aaataaaaaa aaaaggatga   2580

aagctaaaaa aaaaaaaaaa aaa                                           2603
```

<210> SEQ ID NO 64
<211> LENGTH: 393
<212> TYPE: PRT
<213> ORGANISM: Homo sapiens

<400> SEQUENCE: 64

```
Met Pro Lys Lys Lys Pro Thr Pro Ile Gln Leu Asn Pro Ala Pro Asp
1               5                   10                  15
```

-continued

```
Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390
```

<210> SEQ ID NO 65
<211> LENGTH: 2151
<212> TYPE: DNA
<213> ORGANISM: Rattus norvegicus

<400> SEQUENCE: 65

```
cggccgcgcg ctccctgctg agttgcaggc tgtttcccgg ctgcaagatg cccaagaaga     60
agccgacgcc catccagctg aacccggccc ccgatggctc cgcggttaac gggaccagct    120
cggccgagac caacctggag gccttgcaga agaagctgga ggagctggag ctggacgagc    180
agcagcggaa gcgccttgag gcctttctga cgcagaagca gaaggtggga gagttgaagg    240
atgatgactt tgagaagatc agtgaactgg gggctggcaa tggtggagtg gtgttcaagg    300
tctcccacaa gccatctggc ctggttatgg ctaggaagct aattcacctg gagatcaaac    360
ccgcaatccg gaaccagatc atccgggagc tgcaggtgct gcatgagtgc aactccccgt    420
acatagtggg cttctacggg gccttctaca gtgacggcga gatcagcatc tgcatggagc    480
acatggatgg tgggtccttg gatcaagtgc tgaagaaagc tggaagaatt cctgagcaaa    540
ttttaggaaa agtcagcatc gctgtgataa aaggcctgac atatctacga gagaagcaca    600
agattatgca cagagatgtc aagccttcca acattctagt gaactcacgt ggggagatca    660
aactctgcga ttttggggtc agcgggcagc taattgactc catggccaac tccttcgtgg    720
gaacaaggtc ctacatgtcg cctgagagac tccaggggac tcactactct gtgcagtcgg    780
acatctggag catggggctc tctctggtgg agatggcagt tggaagatac cccattcctc    840
ctcctgatgc caaggagctg gagctgctgt ttggatgcca ggtggaagga gacgcggccg    900
aaacgccacc caggccaagg accccctggga ggcccctcag ctcatatgga atggatagcc    960
gacctcccat ggcaattttt gagttgttgg attacatcgt caatgagcct cctccaaaac   1020
tgcccagtgg agtattcagt ctggaatttc aggattttgt gaataagtgc ttaataaaga   1080
accctgcaga gagagcagat ctgaagcagc tcatggtaca tgctttcatc aagagatctg   1140
atgccgagga ggtagacttc gcaggctggc tctgctccac cattgggctt aaccagccca   1200
gcacaccaac ccacgctgcc agcatctgag cctttgggaa gcagcagaga ggaatcctct   1260
gcccagtggc atgccatgtt gctttcaggc ctctcccatg cttgtctatg ttcagatgtg   1320
catctcatct gtgacaaagg atgaagaaca cagcatgtgc caaatcgtac ttgtgtcatt   1380
tttaatattg tctttatcgc tatggttact cccctaagtg gattggcttt gtgcttgggg   1440
ctatttgtct gttcatcaaa tacatgccag gttgaactac agtgaaaccc tggtgacctg   1500
ggtggtcttc ttactgatgt ttgcgctgct gttcatcgtg actcactagc tggctgcctg   1560
tattgtcagg attctcggac ccttggtact tcactcttgc tggtgacctc tcagtctgag   1620
gagaggggc cttctgagac ccttcacagg cagtgcatgc atgaaaagca tgctttgctg   1680
ctactgaaat gagcaccaga acgtgtacat catggtattt tatttttgct tttggtatag   1740
aactcagcag ttcccattta aaaaaaaaat ctaaccagag cccatcactg ccatgatagc   1800
tggggcttca gtctgtctac tgtggtgatt tttagacttc tggttgtatt tctatattta   1860
tttttaaata tactgtgtgg gatacttagt ggtatatgtc tctgagtttg gattagtgtt   1920
tctaaattgg tagttatttt gaatgtcaca aatggattaa ggaatcaacg tatcaagagt   1980
tctatctttc ttccagtcta agtaccaatg ctattgtaaa cgtgtatagt gcctacaaat   2040
tgtatgaaaa cccttttaac cactttactc aagatgttta tcaaatctaa tctcttattc   2100
taataaaaat actatcaagt taaagtaaaa aaaaaaaaaa aaaaaaaaaa a            2151
```

<210> SEQ ID NO 66
<211> LENGTH: 393
<212> TYPE: PRT
<213> ORGANISM: Rattus norvegicus -continued

<400> SEQUENCE: 66

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Leu Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Ser Ile
385                 390
```

<210> SEQ ID NO 67

<211> LENGTH: 2387
<212> TYPE: DNA
<213> ORGANISM: Mus musculus

<400> SEQUENCE: 67
agtccctcac tgggacgtct gtgcgcggcg tctcggagcg ccggagcagc ggtggccgca 60
ctttctccaa gctggggctg tagctgagct gtgggtagtg cgcagggagc cgtccgagcc 120
cgaggaaccg gtgtgctgag gcgagagttc ccggccggcg agcgcgcgca gctggttctc 180
cgcgtgggtt gggcggaggg tcccaggagc gcggcgttga tcgagccgcc ccgactctgg 240
gcagagccga gggaggaagc gagaagcggc cgcgcgctcc ctgctgagtt gcaggctctt 300
tcccggctgc aagatgccca agaagaagcc gacgcccatc cagctgaacc cggcccccga 360
tggctcggcg gttaacggga ccagctcggc cgagaccaac ctggaggcct tgcagaagaa 420
gctggaggag ctggagcttg acgagcagca gcggaagcgg ctcgaggcct ttctgacgca 480
gaagcagaag gtgggggaac tgaaggatga tgactttgag aagatcagcg aactgggagc 540
tggcaacggt ggagtggtct tcaaggtctc ccacaagcca tctggcctgg ttatggctag 600
aaagctgatc cacctggaga tcaaacccgc aatccggaac cagatcatcc gggagctgca 660
ggtactgcac gagtgcaact ccccgtacat cgtgggcttc tacggggcct tctacagcga 720
cggcgagatc agcatctgca tggagcacat ggatggtggg tccttggatc aagttctgaa 780
gaaagctgga agaattcctg agcaaatttt aggaaaagtt agcattgctg tgataaaagg 840
cctgacctat cttcgggaga agcacaagat tatgcacaga gatgtcaagc catccaacat 900
tctagtgaac tcacgtgggg agatcaaact ctgtgatttt ggggtcagcg ggcagctaat 960
tgactctatg gccaactcct tcgtgggcac gagatcctac atgtcgcctg agagactcca 1020
ggggactcac tactctgtgc agtcggacat ctggagcatg ggctctctc tggtggagat 1080
ggcagttggg agatacccca ttcctcctcc tgatgccaag gagctggagc tactgtttgg 1140
atgccatgtg gaaggagacg cagccgaaac accacccagg ccaaggaccc ctgggaggcc 1200
tctcagctca tatggaatgg acagccgacc tcccatggca atttttgagt tgttggatta 1260
cattgtcaat gagcctcctc caaaactgcc cagtggagta ttcagtctgg agtttcagga 1320
ttttgtgaat aaatgcttaa taaagaaccc tgcagagaga gcagatctga agcagctcat 1380
ggtacatgct ttcatcaaaa gatctgacgc cgaggaggta gacttcgcag gctggctctg 1440
ctccaccatt gggcttaacc agcccagcac accaacccac gctgccagca tctgagcctt 1500
taggaagcag caaagaggaa ttctctgccc agtggcatgc catgttgctt tcaggcctct 1560
cccatgcttg tctatgttca gacgtgcatc tcatctgtga caaaggatga agaacacagc 1620
atgtgccaaa ttgtacttgt gtcattttta atatcattgt ctttatcact atggttactc 1680
ccctaagtgg attggctttg tgcttggggc tatttgtctg ttcatcaaac acatgccagg 1740
ctgaactaca gtgaaaccct agtgacctgg gtggtcgttc ttactgatgt ttgcactgct 1800
gttcatcgtg actcactagc tggctgcctg tattgtcagg attctcggac cttggtactt 1860
cactcttgct ggtgacctct cagtctgaga gggagccttg tgagaccctt cacaggcagt 1920
gcatgcatgg aaagcatgct ttgctgctac tgaaatgagc atcagaacgt gtacgtcatg 1980
gtatttttat tttttgcttt tggtatagaa ctcagcaatt cccatcaaaa aaacctaagc 2040
agagcccatc actgccatga tagctgggct tcagtctgtc tactgtggtg atttttagac 2100
ttctggttgt atttctatat ttatttttaa atatacagtg tgggatactt agtggtgtgt 2160
gtctctaagt ttggattagt gtttctaaat tggtggttat tttgaatgtc acaaatggat 2220
taaagcatca atgtatcaag agttctatct ttcttccagt ctaagtacca atgctattgt 2280
aaacaacgtg tatagtgcct acaaattgta tgaaacccct tttaaccact ttaatcaaga 2340
tgtttatcaa atctaatctc ttattctaat aaaaatacta tcaagtt 2387

<210> SEQ ID NO 68
<211> LENGTH: 393
<212> TYPE: PRT
<213> ORGANISM: Mus musculus

<400> SEQUENCE: 68

Met Pro Lys Lys Lys Pro Thr Pro Ile Gln Leu Asn Pro Ala Pro Asp
1 5 10 15

Gly Ser Ala Val Asn Gly Thr Ser Ser Ala Glu Thr Asn Leu Glu Ala
20 25 30

Leu Gln Lys Lys Leu Glu Glu Leu Glu Leu Asp Glu Gln Gln Arg Lys
35 40 45

Arg Leu Glu Ala Phe Leu Thr Gln Lys Gln Lys Val Gly Glu Leu Lys
50 55 60

Asp Asp Asp Phe Glu Lys Ile Ser Glu Leu Gly Ala Gly Asn Gly Gly
65 70 75 80

Val Val Phe Lys Val Ser His Lys Pro Ser Gly Leu Val Met Ala Arg
85 90 95

Lys Leu Ile His Leu Glu Ile Lys Pro Ala Ile Arg Asn Gln Ile Ile
100 105 110

Arg Glu Leu Gln Val Leu His Glu Cys Asn Ser Pro Tyr Ile Val Gly
115 120 125

Phe Tyr Gly Ala Phe Tyr Ser Asp Gly Glu Ile Ser Ile Cys Met Glu
130 135 140

His Met Asp Gly Gly Ser Leu Asp Gln Val Leu Lys Lys Ala Gly Arg
145 150 155 160

Ile Pro Glu Gln Ile Leu Gly Lys Val Ser Ile Ala Val Ile Lys Gly
165 170 175

Leu Thr Tyr Leu Arg Glu Lys His Lys Ile Met His Arg Asp Val Lys
180 185 190

Pro Ser Asn Ile Leu Val Asn Ser Arg Gly Glu Ile Lys Leu Cys Asp
195 200 205

Phe Gly Val Ser Gly Gln Leu Ile Asp Ser Met Ala Asn Ser Phe Val
210 215 220

Gly Thr Arg Ser Tyr Met Ser Pro Glu Arg Leu Gln Gly Thr His Tyr
225 230 235 240

Ser Val Gln Ser Asp Ile Trp Ser Met Gly Leu Ser Leu Val Glu Met
245 250 255

Ala Val Gly Arg Tyr Pro Ile Pro Pro Pro Asp Ala Lys Glu Leu Glu
260 265 270

Leu Leu Phe Gly Cys His Val Glu Gly Asp Ala Ala Glu Thr Pro Pro
275 280 285

Arg Pro Arg Thr Pro Gly Arg Pro Leu Ser Ser Tyr Gly Met Asp Ser
290 295 300

Arg Pro Pro Met Ala Ile Phe Glu Leu Leu Asp Tyr Ile Val Asn Glu
305 310 315 320

Pro Pro Pro Lys Leu Pro Ser Gly Val Phe Ser Leu Glu Phe Gln Asp
325 330 335

Phe Val Asn Lys Cys Leu Ile Lys Asn Pro Ala Glu Arg Ala Asp Leu 340 345 350

Lys Gln Leu Met Val His Ala Phe Ile Lys Arg Ser Asp Ala Glu Glu
355 360 365

Val Asp Phe Ala Gly Trp Leu Cys Ser Thr Ile Gly Leu Asn Gln Pro
370 375 380

Ser Thr Pro Thr His Ala Ala Ser Ile
385 390

<210> SEQ ID NO 69
<211> LENGTH: 1182
<212> TYPE: DNA
<213> ORGANISM: Oryctolagus cuniculus

<400> SEQUENCE: 69
atgccaaaga agaagcccac ccccatccag ctgaatcctg cccctgacgg ctcggcggtg 60
aatggtacca gctcggcgga gaccaacctg gaggccttgc agaagaagct ggaggagctg 120
gagcttgacg agcagcagcg gaagcgcctg gaggccttcc tcacccagaa gcagaaagtg 180
ggagagctga aggacgatga cttcgagaag atcagtgagc tgggagccgg caacggcggc 240
gtggtgttca aggtctccca caagcccagt ggcctggtga tggccagaaa gcttattcac 300
ctggagatca aacctgctat ccggaaccag atcataaggg agctgcaggt tctgcacgag 360
tgcaactccc cgtacatcgt gggcttctac ggggcattct acagcgatgg cgagatcagc 420
atctgcatgg agcacatgga cgggggttcc ttggatcaag tcctgaagaa agctggacgg 480
attcccgagc aaattttggg gaaagttagc attgctgtga tcaagggcct gacgtatctg 540
agggagaagc acaagatcat gcacagagat gtgaagccct ccaacatcct ggtcaactcc 600
cgcggggaga tcaagctctg tgacttcggg gtcagtgggc agctcatcga ctccatggcc 660
aactccttcg tgggcaccag gtcttatatg tcgcccgaga gactccaggg gacacactac 720
tctgtgcagt cggacatctg gagcatgggg ctgtccctgg tggagatggc ggtggggcgg 780
taccccatcc cgccccccga cgccaaggag ctggagctga tgtttgggtg ccaggtggag 840
ggcgatgcgg ccgagactcc gcccaggccc aggacccctg ggcggcccct cagctcgtat 900
ggaatggata gccggcctcc catggcgatt tttgagctgc tggattacat cgtcaatgag 960
cctcctccga aactccccag cgcagtcttc agcctggagt ttcaagattt tgtgaataaa 1020
tgcttaataa aaaaccccgc cgagagagca gacttgaagc agctcatggt tcatgctttt 1080
atcaagaggt ctgatgccga ggaggtggat tttgctggtt ggctgtgctc caccatcggc 1140
cttaaccagc ccagcacgcc gacgcacgcg gccggtgtgt ga 1182

<210> SEQ ID NO 70
<211> LENGTH: 393
<212> TYPE: PRT
<213> ORGANISM: Oryctolagus cuniculus

<400> SEQUENCE: 70

Met Pro Lys Lys Lys Pro Thr Pro Ile Gln Leu Asn Pro Ala Pro Asp
1 5 10 15

Gly Ser Ala Val Asn Gly Thr Ser Ser Ala Glu Thr Asn Leu Glu Ala
20 25 30

Leu Gln Lys Lys Leu Glu Glu Leu Glu Leu Asp Glu Gln Gln Arg Lys
35 40 45

Arg Leu Glu Ala Phe Leu Thr Gln Lys Gln Lys Val Gly Glu Leu Lys
50 55 60

-continued

```
Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Ala Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390
```

<210> SEQ ID NO 71
<211> LENGTH: 1872
<212> TYPE: DNA
<213> ORGANISM: Cavia porcellus

<400> SEQUENCE: 71

```
cgtgtcttcg tcgggaccgc cctcctcctt gagtcctccc cccaccggga cggccgagtg      60

gagaggccgg acgaaggcgg cggccccggc ggcggctttt cctcggcttc gctgtgcagc     120

gtgcgcggcg aggttgaccg cccgcgagcg cccgtgactg agggaacagg gagagagctc     180

gggcggccga gcgcgcagcc ctccgtgggc attgccgcct ggacctcccg gaaggcaccc     240
```

```
cgggccgcgg ccgccacccg tcccgccctc gttcggagct gagacgccgt cgccgcgcaa    300

gatgcccaag aagaagccga cgcccatcca gctgaacccg gcccccgacg gctcggcggt    360

gaacgggacc agctcggccg agaccaacct agaggctttg cagaagaagc tggaggagct    420

ggagctggat gagcagcagc ggaagcgcct cgaagctttc ctgacacaga agcagaaggt    480

gggcgagctg aaggacgatg actttgagaa gatcagtgag ctgggtgccg gcaatggcgg    540

tgtggtgttc aaggtctccc acaagccatc tggcctggtc atggcccgaa agcttatcca    600

cctggagatc aagccagcca tccgcaatca gatcatccgt gagctgcagg ttctgcacga    660

gtgcaactcg ccctacattg tgggcttcta tggggccttc tacagtgatg gcgagatcag    720

catctgcatg gagcacatgg atggaggttc cttggatcaa gtcctgaaga aagctggaag    780

aattcctgag caaattttag gaaaagttag cattgctgtg atcaaaggcc tgacatacct    840

gagggagaag cacaagatta tgcacagaga tgtcaagccc tccaacatcc tggtcaactc    900

ccgcggggag atcaagctct gtgactttgg ggtcagcggg cagctcatcg attccatggc    960

caactccttc gtgggcaccc ggtcctacat gtcgccagag agactgcagg gcacacacta   1020

ctcagtgcag tcggacatct ggagcatggg actgtcactg gtggagatgg cggttgggag   1080

gtaccccatc ccccctccag atgccaagga gctggagctg gtgttcgggt gccaggtgga   1140

aggagatgca gctgagatgc cgcccaggcc caggaccccc ggaagacccc tgagctcata   1200

tggaatggac agccggcctc ccatggcgat tttcgagctg ttggattaca tagtcaacga   1260

gccacctccc aaactgccca gtggagtctt cagtctggaa ttccaggact ttgtaaataa   1320

atgcttaata aagaaccctg cggagagagc agacttgaag cagctcatgg ttcatgcctt   1380

catcaagcgc tctgatgctg aggaggtgga cttcgcaggt tggctctgtg ccaccatcgg   1440

ccttaaccag cccagtaccc cgacccacgt ggccagcatc tgagctgcgg cccggcccag   1500

acgtgctctg ccagcagccg ctatgctctg gcctctccct cgcttctctt cagacgtgcg   1560

tttcacctcc gaccagggtg cagacacagc atgtgccaag ctgtatttgt gttccttttc   1620

agtctttatt gccaccgtgt cacccgagtg gatttgcttt gtgcttaggg ctgtttgtgc   1680

tgatgatcac acacacgctg agctgaacag tgacacttgg tgatgtggtt gtcactgttc   1740

tcactccatg tggctggcct gttgcctcca gtgtctccag acttggggat gtctggtggc   1800

acttcccctg ccagggcatc tcctcagcag agagggaggc ctctgggccc ttgtccttgg   1860

cagtgcaagt ga                                                       1872
```

<210> SEQ ID NO 72
<211> LENGTH: 393
<212> TYPE: PRT
<213> ORGANISM: Cavia porcellus

<400> SEQUENCE: 72

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80
```

-continued

```
Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Val Phe Gly Cys Gln Val Glu Gly Asp Ala Ala Glu Met Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ala Thr Ile Gly Leu Asn Gln Pro
    370                 375                 380

Ser Thr Pro Thr His Val Ala Ser Ile
385                 390
```

<210> SEQ ID NO 73
<211> LENGTH: 1257
<212> TYPE: DNA
<213> ORGANISM: Canis familiaris

<400> SEQUENCE: 73

```
ggagagcgag acacgggccg ctctccgctc ggagccggac gcgccttccc gcgtccaaaa     60

tgcccaagaa gaagccgacg cccatccagc tgaacccggc ccccgacggc tcggcggtga    120

acgggaccag ctcggcggag accaacctgg aggccttgca gaagaagctg gaggagctgg    180

agcttgatga gcagcagcgg aagcgccttg aggcctttct cacccagaag cagaaggtcg    240

gggaactgaa ggatgacgac ttcgagaaga tcagtgagct gggtgctggc aacggtggcg    300

tggtgttcaa ggtctcccac aagccgtccg gcctagtcat ggccagaaag ctaattcacc    360
```

```
tggagatcaa acctgcaatc cggaaccaga tcataaggga gctacaggtt ctacatgagt    420

gcaactcccc gtacatcgtg ggcttctatg gtgcattcta cagcgatggc gagatcagta    480

tctgcatgga gcacatggat gggggttcct tggatcaagt cctgaagaaa gctggaagaa    540

ttcctgaaca aattctagga aaagttagca tcgctgtaat aaaaggtctg acatacctga    600

gagagaagca caagattatg cacagagatg tcaagccttc caacatcctc gtgaactccc    660

gtggggagat caagctctgt gactttgggg tcagcgggca gctcattgac tccatggcca    720

actccttcgt gggcacaagg tcctacatgt cgccagaaag actccagggg actcattact    780

ccgtgcagtc ggacatctgg agcatggggc tctctctggt ggagatggca gttgggaggt    840

atcccatccc tcctccggat gccaaggagc tggagctgat gtttgggtgc caagtggagg    900

gagacgtggc tgagacccca cccagaccaa ggaccccggg aagacccctt agctcttatg    960

gaatggacag ccgaccgccc atggcaattt ttgagctgtt ggattacata gtcaacgagc   1020

cccctccaaa actgcccagt ggagtattca gtctggaatt tcaagatttt gtgaataaat   1080

gcttaataaa aaacccagca gagagagcag atctgaagca actcatggtt catgccttca   1140

tcaagagatc tgacggtgaa gaagtggatt ttgcaggttg gctctgctcc ccccattggc   1200

cttaaccagc ccagcacgcc gacccacgca gctggcgtct aactcgagtc tagagat      1257
```

<210> SEQ ID NO 74
<211> LENGTH: 381
<212> TYPE: PRT
<213> ORGANISM: Canis familiaris

<400> SEQUENCE: 74

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
```

-continued

```
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Met Phe Gly Cys Gln Val Glu Gly Asp Val Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Gly Glu Glu
        355                 360                 365

Val Asp Phe Ala Gly Trp Leu Cys Ser Pro His Trp Pro
    370                 375                 380


<210> SEQ ID NO 75
<211> LENGTH: 2095
<212> TYPE: DNA
<213> ORGANISM: Felis catus

<400> SEQUENCE: 75

agccggcaag gagttgagcg tgcggggtgc ataggcgcgg gtcgtgggag atgaagctgg     60

agaggaccaa cctggaggcc ttgcagaaga agctggagga gctggagctc gatgagcagc    120

aacggaagcg cctggaggcc tttcttaccc agaagcagaa ggtcggggaa ttgaaggatg    180

acgacttcga gaagatcagc gagctgggcg ctggcaacgg tggtgtggtg ttcaaggtct    240

cccataagcc gtctggcctg gtcatggcca gaaagctaat tcacctggag atcaaacctg    300

caatccggaa ccagatcata agggagctgc aggttctaca tgagtgcaac tccccataca    360

tcgtgggctt ctatggcgcg ttctacagcg acggcgagat cagtatctgt atggagcaca    420

tggatggggg ttccttggat caagtcctga agaaagctgg aagaattcct gaacaaattt    480

taggaaaagt tagcattgct gtaataaaag gtctgacata cctgagggag aagcacaaga    540

ttatgcacag agatgtcaag ccttccaaca tcctagtgaa ctctcgtggg gagatcaagc    600

tctgtgactt tggggtcagc gggcagctca tcgactccat ggccaactcc ttcgtgggca    660

caaggtccta catgtcgcca gaaagactcc aggggactca ttactccgtg cagtcggaca    720

tctggagcat ggggctatct ctggttgaga tggcagtcgg gaggtatccc atccctcctc    780

ccgatgccaa ggagctggag ctgatgtttg ggtgccaagt ggagggagat gcggctgaga    840

cgccacccag gccgaggacc cccggaaggc ccctcagctc gtatggaatg gacagccgac    900

ctcccatggc aatttttgag ttgttggatt acatagtcaa cgagcctcct ccaaagctgc    960

ccagtggagt attcagtctg gaatttcaag attttgtgaa taaatgcctc ataaaaaacc   1020

cagcagagag agcagatctg aaacaactca tggttcatgc ctttatcaag agatctgatg   1080

gtgaggaagt ggattttgca ggttggctct gctccaccat cggccttaac cagcccagca   1140

caccgaccca cgcggccggc gtctaagtat ctgggaagca gcaaagagcg agtcccctgc   1200
```

```
ccagtggtgt gccattgtcg ctttcaggcc tctttgccat gcctgtctcc gttcagacgt   1260

gcatttcgcc tacgacaaag gatgaagaac acagcatgtg ccaaaattct atttgtgtct   1320

tttttaatat tactgtcatt tattctgtta tttccctaag tggattggct ttgtgcttgg   1380

ggctattttt gtgtatgttg atccaaacat gcgcaacgtt cagttacagt gaaaccttgg   1440

tgactgtggg tagtcattct tactgaaaat tgcactgctc ttcccccacc gtgactggct   1500

agctgcctgt agttttggga ttcttttgac acttggtggt actgcattct tgccgggcgc   1560

accttccttc tgttggggta ggagccttgt aagatccttc acaggcactg catgtgaagc   1620

atgctttgct gctatgaaaa agaacatcag aaagtataga tcttgttatt ttattatatt   1680

tttgcttttg gtgtagaatg aagcaatttc tgtcaaaatc tagccagagc ccttcactgc   1740

cacgatagct ggggcttcac cagtctgtct actgtgatga tttgtagact tctggttgta   1800

tttctatatt tattttaaaa tatattatgt gggatattta gtggtatgtg tctctttaag   1860

tttgaattag tgtttctaaa atgatggtta ctttgaatgt tacaaatgga tcaaggcatt   1920

aaaatgtatg agatttatct ttccccaaat ccaagtaccg atgctattgt aaacaacagt   1980

gtgtatagtg cctaagaatt gtatgaaaat ccttttaacc atttcaaccc agatgtttaa   2040

caaatctaat ctcttattct aataaatata ctatcaagtt aaaaggatga aaaaa        2095
```

<210> SEQ ID NO 76
<211> LENGTH: 371
<212> TYPE: PRT
<213> ORGANISM: Felis catus

<400> SEQUENCE: 76

```
Met Lys Leu Glu Arg Thr Asn Leu Glu Ala Leu Gln Lys Lys Leu Glu
1               5                   10                  15

Glu Leu Glu Leu Asp Glu Gln Gln Arg Lys Arg Leu Glu Ala Phe Leu
            20                  25                  30

Thr Gln Lys Gln Lys Val Gly Glu Leu Lys Asp Asp Asp Phe Glu Lys
        35                  40                  45

Ile Ser Glu Leu Gly Ala Gly Asn Gly Gly Val Val Phe Lys Val Ser
    50                  55                  60

His Lys Pro Ser Gly Leu Val Met Ala Arg Lys Leu Ile His Leu Glu
65                  70                  75                  80

Ile Lys Pro Ala Ile Arg Asn Gln Ile Ile Arg Glu Leu Gln Val Leu
                85                  90                  95

His Glu Cys Asn Ser Pro Tyr Ile Val Gly Phe Tyr Gly Ala Phe Tyr
            100                 105                 110

Ser Asp Gly Glu Ile Ser Ile Cys Met Glu His Met Asp Gly Gly Ser
        115                 120                 125

Leu Asp Gln Val Leu Lys Lys Ala Gly Arg Ile Pro Glu Gln Ile Leu
    130                 135                 140

Gly Lys Val Ser Ile Ala Val Ile Lys Gly Leu Thr Tyr Leu Arg Glu
145                 150                 155                 160

Lys His Lys Ile Met His Arg Asp Val Lys Pro Ser Asn Ile Leu Val
                165                 170                 175

Asn Ser Arg Gly Glu Ile Lys Leu Cys Asp Phe Gly Val Ser Gly Gln
            180                 185                 190

Leu Ile Asp Ser Met Ala Asn Ser Phe Val Gly Thr Arg Ser Tyr Met
        195                 200                 205

Ser Pro Glu Arg Leu Gln Gly Thr His Tyr Ser Val Gln Ser Asp Ile
```

```
    210                 215                 220

Trp Ser Met Gly Leu Ser Leu Val Glu Met Ala Val Gly Arg Tyr Pro
225                 230                 235                 240

Ile Pro Pro Pro Asp Ala Lys Glu Leu Glu Leu Met Phe Gly Cys Gln
                245                 250                 255

Val Glu Gly Asp Ala Ala Glu Thr Pro Pro Arg Pro Arg Thr Pro Gly
            260                 265                 270

Arg Pro Leu Ser Ser Tyr Gly Met Asp Ser Arg Pro Pro Met Ala Ile
        275                 280                 285

Phe Glu Leu Leu Asp Tyr Ile Val Asn Glu Pro Pro Pro Lys Leu Pro
    290                 295                 300

Ser Gly Val Phe Ser Leu Glu Phe Gln Asp Phe Val Asn Lys Cys Leu
305                 310                 315                 320

Ile Lys Asn Pro Ala Glu Arg Ala Asp Leu Lys Gln Leu Met Val His
                325                 330                 335

Ala Phe Ile Lys Arg Ser Asp Gly Glu Glu Val Asp Phe Ala Gly Trp
            340                 345                 350

Leu Cys Ser Thr Ile Gly Leu Asn Gln Pro Ser Thr Pro Thr His Ala
        355                 360                 365

Ala Gly Val
    370


<210> SEQ ID NO 77
<211> LENGTH: 2405
<212> TYPE: DNA
<213> ORGANISM: Bos taurus

<400> SEQUENCE: 77

ccggttgact gagggagagt gggagggaat cccgggctgc cgagctgcgc cggcggggaa     60

gcccttcggt tccctgtgca ctgagcaagt gggccggggg gttcccccag accgccactg    120

gccctttggc cctgacggga ccgcgcaggg cgcgcccccc gaaggcagcc ttcgggcttg    180

cggcccagac ttggccccgc gaggccggcg cggggcagct cagagggagg aagctagagg    240

ggccgccctc agagttggga gcgcctttcc tgggtccaaa atgcccaaga agaagccgac    300

gcccatccag ctgaacccgg ccccggacgg ctccgcggtt aacgggacca gctcggcgga    360

gaccaacctg gaggccttgc agaagaagct ggaggagctg gagctcgatg aacagcagcg    420

gaagcgcctc gaggcctttc tgacccagaa gcagaaggtg ggggaactga aggatgatga    480

ctttgagaag atcagtgagc tgggtgccgg caatggaggt gtggtgttca aggtctccca    540

caagccgtcc ggacttgtta tggccagaaa gctaattcac ctggagatca aacctgccat    600

ccggaaccag atcataaggg agctgcaggt tctccatgag tgcaactcgc cttatatcgt    660

gggcttctac ggggcgttct acagcgacgg cgagatcagc atctgcatgg agcacatgga    720

tgggggttcc ttggatcaag ttctgaagaa agctggaaga attcctgaac aaattttagg    780

aaaagttagc attgctgtaa taaaaggcct gacatacctg agggagaagc acaagattat    840

gcacagagat gtcaagccgt ccaacatcct agtgaacagc cgtggagaga tcaagctctg    900

tgactttggg gtcagcgggc agctcatcga ctccatggcc aactccttcg tgggcaccag    960

gtcctacatg tcgccagagc gactccaggg gacccattac tccgtgcagt cggacatctg   1020

gagcatgggg ctctctctgg ttgagatggc tgtcgggagg tatcccatcc ctcctccaga   1080

tgccaaggag ctggagctga tgtttgggtg ccaggtggag ggagatgcgg ctgagacccc   1140

gcccaggcca aggacccccg ggaggcccct cagctcttat ggaatggaca gccgacctcc   1200
```

```
aatggcaatt tttgagttgt tggattacat agtcaatgag cctcctccaa aactgcccag   1260

tggagtattc agtctggaat ttcaagattt tgtgaataaa tgcttaataa aaaaccccgc   1320

agagagagca gatttgaagc aactcatggt tcatgctttt atcaagagat ctgatgctga   1380

ggaagtggat tttgcaggtt ggctctgctc caccatcggc cttaaccaac ccagcacacc   1440

cacccatgcg gctggcgtct aagtggttgg gaagcagcag tccctgccca agggcatgca   1500

ctgttgcttc cgggcagcct tcccatgcct gtctctgttc agacgtgcat ttcacctatg   1560

acaaaggatg aagaacacag catgtgccaa aattctattt gtgtcatttt caatattatc   1620

atctttactc ttattactat tgttattccc ctaagtggat tggctttgtg cttggggcta   1680

tttttgtgta tattgatgat gaagacatgt gcaatgtaga attacagtga aactctggtg   1740

actgtgggta gtcattctta ctgaaaactg cactgctttc ccacaccatg aactggctgg   1800

tcgcctctat tttcgggatt ctttgacact tggtggtact tcattcttgc caggcatacc   1860

ttctaactga gtaggaagga gccttgtaag atccttcaca ggcagtgcat gtgaagcatg   1920

ctttgctgct ataaaaatga gcatcagaaa gtgtgtatca tgttatttta ttatgttctt   1980

gcttttggtg tagaattcag caaattttca tcaaaatcta gccagagccc ttcactgcca   2040

tgatagctgg ggcttcacca gtctgtctac tgtgatgatt tgtagacttc tggttgtatt   2100

tctgtattta tttttaaatc taccgtgtgg atatttagtg ctatgtctct ttaagtttgg   2160

attagtgttt ctaaaatggt ggagttgctc tgaatgttac aaatggatca aggcattaaa   2220

atgaatgaga tctacctttc accaagtact gatgctattg taaacaacag tgtgtatagt   2280

gcctaacaac tgtatgaaaa tccttttacc attttaatcc agatgtttaa caagcctaat   2340

ctcttactct aataaatata ctatcaaatt caaaggaaaa aaaaaaaaaa aaaaaaaaaa   2400

aaaaa                                                               2405
```

```
<210> SEQ ID NO 78
<211> LENGTH: 393
<212> TYPE: PRT
<213> ORGANISM: Bos taurus

<400> SEQUENCE: 78

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
```

-continued

```
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390


<210> SEQ ID NO 79
<211> LENGTH: 2146
<212> TYPE: DNA
<213> ORGANISM: Equus caballus

<400> SEQUENCE: 79

caagtgggaa agcttgggat gcgtggagga gccagctact agtttagtgt gctgggtgcg      60

tcggtgcagg tcgcaggaga tgaagccgga gaggaccaac ctggaggcct tgcagaagaa     120

gctggaggag ctggagctcg atgaacagca gcgaaagcgc cttgaggcct ttcttactca     180

gaagcagaag gttggggaac tgaaggatga tgactttgag aagatcagtg agctgggtgc     240

tggcaatggt ggtgtggtat tcaaggttgc ccacaaaccg tctggtttgg tcatggccag     300

aaagctaatt cacctggaga tcaagcctgc aatccggaac cagatcataa gggagctgca     360

ggttctacat gagtgcaact ccccatatat tgtgggcttc tatggcgcat tctacagcga     420

tggtgagatc agcatctgca tggagcacat ggatgggggt tccttggatc aagtcctaaa     480

gaaagctgga agaattcctg agcaaatttt aggaaaagtt agcattgctg taataaaagg     540

cctgacgtat ctgagggaga agcacaagat tatgcacaga gatgtcaagc cctccaacat     600

cctagtgaac tcccgtgggg agatcaagct gtgtgatttt ggggtcagcg ggcagctcat     660

cgactccatg gccaactcct tcgtgggcac aaggtcttac atgtcgccgg aaagactcca     720
```

-continued

```
ggggactcat tattcagtgc agtcggacat ctggagcatg gggctctctc tggttgagat    780

ggcggtcggg aggtatccca tccctcctcc agatgccaag gagctggagc tgatgtttgg    840

gtgccaagtg gagggagatg cggctgagac tccgcctagg ccaaggaccc ctggaagacc    900

cctcagctct tatggaatgg acagccgacc tcctatggca atttttgagt tactggatta    960

catagtcaac gagcctcctc ccaagctgcc cagtggagta ttcagtctgg aatttcagga   1020

ttttgtgaat aaatgcttaa tcaaaaaccc tgcagagaga gcagatttga agcaactcat   1080

ggttcacgct tttatcaaga gatctgatgc cgaggaagtg gattttgcag gttggctctg   1140

ctccaccatt ggccttaacc agcccagcac accaacccac gcggctggcg tctaagcgtt   1200

tgggaagcag caaaaagcga gccccctgcc gcgtggtgtg ccatgttgct ttcgggcctc   1260

cttcccatgc ctgtctgttc acacgtgcat ttcacctgtg acaaaggatg aagaacacag   1320

catgtgccaa aattctattt gtgtcatttt taatagtact gtctttattc ttattactat   1380

tgttattccc ctaagtggat tggctttgtg cttgggacta ttttgtgtat gttgatgatc   1440

aaaacatgcg caatgttgaa ttaccgtgaa actggtgact gtgggtagtc cttcttattg   1500

aaaattgcac tgctcttccc tccctgtcac tggctggctg cctgtatttc tggggttctt   1560

tgacacttgg tggtacttca ttcttgcagg gcatacctcc tattcgagta ggaaggagcc   1620

tttaagatcc ttcacaggca gtgcatgtga agcatgcttt gctgctatga aaatgagcat   1680

cagaaagtgt atatcatgtt attttattat tattatgttt ttgcttttgg tgtagaattc   1740

agcaatttcc atcaagatct agccagagcc cttcactgcc atgatagctg ggcttcacc    1800

agtctgccta ctgtgatgat ttgtagactt ctggttgtat ttctatattt atttttaaat   1860

atactgtgtg ggatatttag tggtatatgt ctctctaagt ttggagtggt gtttctaaaa   1920

tggagttact ttgaatgtta tagatggatc aaggcataaa atgtatgaga tttatttttc   1980

cccaaatcca aatactgatg ctattgtaaa caacaaacag tgtgtatagt gcctaaaaat   2040

tgtatgaaag tccttttaac cattttaatc cagatgttta acaaatctaa tctcttattc   2100

taataaatat actatcaagt taaacggaca aaagatttct actttc                  2146
```

```
<210> SEQ ID NO 80
<211> LENGTH: 371
<212> TYPE: PRT
<213> ORGANISM: Equus caballus

<400> SEQUENCE: 80

Met Lys Pro Glu Arg Thr Asn Leu Glu Ala Leu Gln Lys Lys Leu Glu
1               5                   10                  15

Glu Leu Glu Leu Asp Glu Gln Gln Arg Lys Arg Leu Glu Ala Phe Leu
            20                  25                  30

Thr Gln Lys Gln Lys Val Gly Glu Leu Lys Asp Asp Asp Phe Glu Lys
        35                  40                  45

Ile Ser Glu Leu Gly Ala Gly Asn Gly Gly Val Val Phe Lys Val Ala
    50                  55                  60

His Lys Pro Ser Gly Leu Val Met Ala Arg Lys Leu Ile His Leu Glu
65                  70                  75                  80

Ile Lys Pro Ala Ile Arg Asn Gln Ile Ile Arg Glu Leu Gln Val Leu
                85                  90                  95

His Glu Cys Asn Ser Pro Tyr Ile Val Gly Phe Tyr Gly Ala Phe Tyr
            100                 105                 110

Ser Asp Gly Glu Ile Ser Ile Cys Met Glu His Met Asp Gly Gly Ser
        115                 120                 125
```

```
Leu Asp Gln Val Leu Lys Lys Ala Gly Arg Ile Pro Glu Gln Ile Leu
    130                 135                 140

Gly Lys Val Ser Ile Ala Val Ile Lys Gly Leu Thr Tyr Leu Arg Glu
145                 150                 155                 160

Lys His Lys Ile Met His Arg Asp Val Lys Pro Ser Asn Ile Leu Val
                165                 170                 175

Asn Ser Arg Gly Glu Ile Lys Leu Cys Asp Phe Gly Val Ser Gly Gln
            180                 185                 190

Leu Ile Asp Ser Met Ala Asn Ser Phe Val Gly Thr Arg Ser Tyr Met
        195                 200                 205

Ser Pro Glu Arg Leu Gln Gly Thr His Tyr Ser Val Gln Ser Asp Ile
    210                 215                 220

Trp Ser Met Gly Leu Ser Leu Val Glu Met Ala Val Gly Arg Tyr Pro
225                 230                 235                 240

Ile Pro Pro Pro Asp Ala Lys Glu Leu Glu Leu Met Phe Gly Cys Gln
                245                 250                 255

Val Glu Gly Asp Ala Ala Glu Thr Pro Pro Arg Pro Arg Thr Pro Gly
            260                 265                 270

Arg Pro Leu Ser Ser Tyr Gly Met Asp Ser Arg Pro Pro Met Ala Ile
        275                 280                 285

Phe Glu Leu Leu Asp Tyr Ile Val Asn Glu Pro Pro Pro Lys Leu Pro
    290                 295                 300

Ser Gly Val Phe Ser Leu Glu Phe Gln Asp Phe Val Asn Lys Cys Leu
305                 310                 315                 320

Ile Lys Asn Pro Ala Glu Arg Ala Asp Leu Lys Gln Leu Met Val His
                325                 330                 335

Ala Phe Ile Lys Arg Ser Asp Ala Glu Glu Val Asp Phe Ala Gly Trp
            340                 345                 350

Leu Cys Ser Thr Ile Gly Leu Asn Gln Pro Ser Thr Pro Thr His Ala
        355                 360                 365

Ala Gly Val
    370
```

<210> SEQ ID NO 81
<211> LENGTH: 2274
<212> TYPE: DNA
<213> ORGANISM: Gallus gallus

<400> SEQUENCE: 81

```
ctaaccaggc gggagctgtc ggtgcggagc tcggtgtcgc tccgccgggc aggccgggtc      60

gacggccgcg ctgtgccgga gcggcagcgt cgcgggctcg gctccttctc ggggaggcgg     120

ccgcgcgctg ctccggcgct gaggggcggc cccgaagttt gcttcgcgtc gggaagtccg     180

tcggacctgg ccgaagtggg gccgcggccg ctccgtccgt cacgctctgc gctggccggg     240

gggcaacatg cccaagaaga agccagggcc gatccagctc aaccccgctc cggatggctc     300

cgccgtcaac gggaccagct ctgccgagac aaacttggaa gctcttcaga agaagctgga     360

agagctagag ctggatgaac agcaaaggaa gcgccttgaa gctttcctta cccagaaaca     420

aaaagttggg gagctgaagg atgatgactt cgagaagatc agtgagctgg gagcagggaa     480

tggcggggtg gtgttcaaag tatctcacaa gccttctggc ctcatcatgg caagaaaatt     540

gattcatcta gaaatcaagc cagctattcg aaaccagatc atccgtgagc tgcaggttct     600

acatgagtgc aattcaccat acatagtggg cttttatgga gctttttaca gtgatgggga     660
```

```
aatcagcatt tgcatggaac acatggatgg tggctcattg gatcaagtgc tgaaaaaggc    720

tggaagaatt ccagagcaga tactgggcaa agtcagcatt gcagtaataa aaggactcac    780

atatctgaga gaaaagcata aaataatgca cagagatgtt aaaccatcta acatcttggt    840

aaactctaga ggtgagatca agctttgtga ttttggtgtc agtggacaac tgatagattc    900

tatggcaaac tcatttgttg gcacgcgctc ctacatgtct ccggaaagac tgcagggaac    960

tcattattca gtgcagtcag atatatggag tatggggctg tctctggtag aaatggccat   1020

tggcagatac ccgattcctc ctcctgactc taaggagctc gagttgatgt ttggctgccc   1080

ggtagaggga gattctccag tcacagagac ctcacccagg caaagaacac ctggtcgacc   1140

aatgagctcc tatggaccag acagcagacc cccgatggca atctttgaac ttctggatta   1200

catcgtcaat gagccacctc caaaactgcc caatggtgtc tttggttctg aatttcaaga   1260

ttttgttaac aaatgtttaa ttaaaaatcc tgctgagaga gctgatttga agcagctgat   1320

gattcacgct ttcattaaga gatctgaagc agaggaggtg gattttgcag gatggctttg   1380

ctcaaccata ggccttaacc aaccgagtac acccacgcat gctgctggag tctgaatgtg   1440

gaagagcaaa tcctgtcccg tacatctgtt aacagcgcta ctttggtcct atttcctaag   1500

cttgtacctg ttcaaacatg tatttcacct cttaaggaag aatgtcttta tagcatgtgc   1560

caaattgttt tcaattttgt catcaactaa ttggtattgt actgggttac atttgtttgc   1620

tgaccaaaat gtaaaatgtt taagttacag tgcttgctga ttttaagtga ttatggaatt   1680

atggatattc tttcttaatg aaaatatcac tggggggg aa tttacccctg gattgtttga   1740

actttatcaa gactctttgt aaactgttgg tacttcagtc atgcttacct aatctcccat   1800

gcaaaaaaag gggtagggat gctccaaaac tgtatctgtt gagcatgctt ttgctgctgc   1860

caaactgtat cttggaagtt aggcctaatg gttccaattt ggtgttgtgt agagatcact   1920

ctttccaggt aaagaaggta agagctctgc attccttggg atggacaggg cagtatccta   1980

cttgtagact tgttcatatt tctatattta tttttaaaat gtatcatcat acttggattt   2040

agtgatatat gtctttccaa ttgattttta aaggttagct ctcagaagcg tcctacagaa   2100

tcatgacaaa gatctgggct ttcttttaac cttaagattc atgacagctg tgtttggtgt   2160

ctaaaatgta tgaagatcct ctattgtttt attctctcag atgtttagca atggtttctc   2220

ttaataaata tattatcaag taaaaaaaaa aaaaaaataa aaaaaaaaaa aaaa         2274

<210> SEQ ID NO 82
<211> LENGTH: 395
<212> TYPE: PRT
<213> ORGANISM: Gallus gallus

<400> SEQUENCE: 82

Met Pro Lys Lys Lys Pro Gly Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Ile Met Ala Arg
                85                  90                  95
```

-continued

```
Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Ile Gly Arg Tyr Pro Ile Pro Pro Pro Asp Ser Lys Glu Leu Glu
            260                 265                 270

Leu Met Phe Gly Cys Pro Val Glu Gly Asp Ser Pro Val Thr Glu Thr
        275                 280                 285

Ser Pro Arg Gln Arg Thr Pro Gly Arg Pro Met Ser Ser Tyr Gly Pro
    290                 295                 300

Asp Ser Arg Pro Pro Met Ala Ile Phe Glu Leu Leu Asp Tyr Ile Val
305                 310                 315                 320

Asn Glu Pro Pro Pro Lys Leu Pro Asn Gly Val Phe Gly Ser Glu Phe
                325                 330                 335

Gln Asp Phe Val Asn Lys Cys Leu Ile Lys Asn Pro Ala Glu Arg Ala
            340                 345                 350

Asp Leu Lys Gln Leu Met Ile His Ala Phe Ile Lys Arg Ser Glu Ala
        355                 360                 365

Glu Glu Val Asp Phe Ala Gly Trp Leu Cys Ser Thr Ile Gly Leu Asn
    370                 375                 380

Gln Pro Ser Thr Pro Thr His Ala Ala Gly Val
385                 390                 395
```